(12) United States Patent
Alvey et al.

(10) Patent No.: US 11,339,166 B2
(45) Date of Patent: May 24, 2022

(54) COMPOUNDS AND PHARMACEUTICAL COMPOSITIONS THEREOF FOR THE TREATMENT OF DISEASES

(71) Applicant: Galapagos NV, Mechelen (BE)

(72) Inventors: Luke Jonathan Alvey, Romainville (FR); Denis Maurice Annoot, Romainville (FR); Florence Marie-Emilie Bonnaterre, Romainville (FR); Denis Bucher, Rheinfelden (CH); Béranger Duthion, Romainville (FR); Hélène Marie Jary, Romainville (FR); Christophe Peixoto, Romainville (FR); Taoues Temal-Laib, Romainville (FR); Amynata Tirera, Romainville (FR); Nicolas Desroy, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 16/768,825

(22) PCT Filed: Nov. 26, 2018

(86) PCT No.: PCT/EP2018/082537
§ 371 (c)(1),
(2) Date: Jun. 1, 2020

(87) PCT Pub. No.: WO2019/105886
PCT Pub. Date: Jun. 6, 2019

(65) Prior Publication Data
US 2021/0101903 A1 Apr. 8, 2021

(30) Foreign Application Priority Data

Dec. 2, 2017 (GB) .................. 1720101
Oct. 25, 2018 (GB) .................. 1817343

(51) Int. Cl.
| | | |
|---|---|---|
| *C07D 487/04* | (2006.01) |
| *C07D 401/04* | (2006.01) |
| *C07D 403/04* | (2006.01) |
| *C07D 403/14* | (2006.01) |
| *C07D 413/04* | (2006.01) |
| *C07D 471/04* | (2006.01) |
| *C07D 491/10* | (2006.01) |
| *C07D 495/10* | (2006.01) |

(52) U.S. Cl.
CPC ......... *C07D 487/04* (2013.01); *C07D 401/04* (2013.01); *C07D 403/04* (2013.01); *C07D 403/14* (2013.01); *C07D 413/04* (2013.01); *C07D 471/04* (2013.01); *C07D 491/10* (2013.01); *C07D 495/10* (2013.01)

(58) Field of Classification Search
CPC .. C07D 487/04; C07D 401/04; C07D 403/04; C07D 403/14; C07D 413/04; C07D 471/04; C07D 491/10; C07D 495/10
See application file for complete search history.

(56) References Cited

FOREIGN PATENT DOCUMENTS

| WO | 2009014620 A1 | 1/2009 |
| WO | 2009150240 A1 | 12/2009 |

(Continued)

OTHER PUBLICATIONS

Surprising finding provides more support for Alzheimer's being an autoimmune disease, https://www.j-alz.com/content/surprising-finding-provides-more-support-alzheimer%E2%80%99s-being-autoimmune-disease, Mar. 10, 2015. (Year: 2015).*
Fu, Yong, et al., "HG-9-91-01 Attenuates Murine Experimental Colitis by Promoting Interleukin-10 Production in Colonic Macrophages through the SIK/CRTC3 Pathway," Inflammatory Bowel Diseases, Crohn's & Colitis Foundation, May 14, 2021, pp. 1-11.
Nishimori, Shigeki, et al., "PTHrP targets salt-inducible kinases, HDAC4 and HDAC5, to repress chondrocyte hypertrophy in the growth plate," Bone 142, 2021, 115709, pp. 1-6.
Darling, Nicola J., et al., "Salt-inducible kinases are required for the IL-33-dependent secretion of cytokines and chemokines in mast cells," JBC Research Article, Jan. 28, 2021, 296, 100428, pp. 1-12.
Hutchinson, Luke D., et al., "Salt-inducible kinases (SIKs) regulate TGFB-mediated transcriptional and apoptotic Yesponses," Cell Death & Disease, 2020, 11:49, pp. 1-17.

(Continued)

*Primary Examiner* — Laura L Stockton
(74) *Attorney, Agent, or Firm* — ArentFox Schiff LLP

(57) ABSTRACT

The present invention discloses compounds according to Formula I:

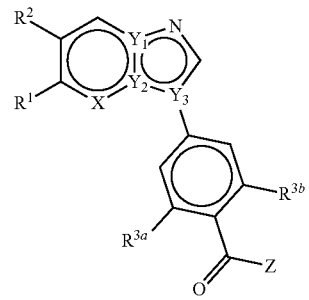

wherein $R^1$, $R^2$, $R^{3a}$, $R^{3b}$, X, $Y_1$, $Y_2$, $Y_3$, and Z are as defined herein.

The present invention relates to compounds, methods for their production, pharmaceutical compositions comprising the same, and methods of treatment using the same, for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases by administering the compound of the invention.

20 Claims, 1 Drawing Sheet

(56) References Cited

FOREIGN PATENT DOCUMENTS

| | | |
|---|---|---|
| WO | 2014093383 A1 | 6/2014 |
| WO | 2017040993 A1 | 3/2017 |

OTHER PUBLICATIONS

Hu, Jinxiu, et al., "Role of SIK1 in the transition of acute kidney injury into chronic kidney disease," Journal of Translational Medicine, 2021, 19:69, pp. 1-18.

Armouti, Marah, et al. "Salt-inducible Kinases are Critical Determinants of Female Fertility," Endocrinology, Jul. 2020, 161(7), pp. 1-13.

Antonio, Tatiana, et al., "The role of salt-inducible kinases on the modulation of renal and intestinal Na+, K+-ATPase activity during short- and long-term high-salt intake," European Journal of Pharmacology, Apr. 30, 2021, 30 pages.

Ahmed et al., "SIK2 Is a Centrosome Kinase Required for Bipolar Mitotic Spindle Formation that Provides a Potential Target for Therapy in Ovarian Cancer", Cancer Cell, (2010), vol. 18, pp. 109-121.

Charoenfuprasert et al., "Identification of Salt-Inducible Kinase 3 as a Novel Tumor Antigen Associated with Tumorigenesis of Ovarian Cancer", Oncogene, (2011), vol. 30, pp. 3570-3584.

Clark et al., "Phosphorylation of CRTC3 by the Salt-Inducible Kinases Controls the Interconversion of Classically Activated and Regulatory Macrophages", Proceedings of the National Academy of Sciences of the United States of America, (2012), vol. 109 no. 42, pp. 16986-16991.

Darling et al., "Inhibition of SIK2 and SIK3 During Differentiation Enhances the Anti-Inflammatory Phenotype of Macrophages", Biochemical Journal, (2017), vol. 474, pp. 521-537.

Katoh et al., "Salt-Inducible Kinase (SIK) Isoforms: Their Involvement in Steroidogenesis and Adipogenesis", Molecular and Cellular Endocrinology, (2004), vol. 217, No. 1-2, pp. 109-112.

Kumagai et al., "A Potent Inhibitor of SIK2, 3, 3', 7-Trihydroxy-4'-Methoxyflavon (4'-0-Methylfisetin), Promotes Melanogenesis in B16F10 Melanoma Cells", PLoS ONE, (2011), vol. 6, No. 10, pp. e26148.

Nixon et al., "Skeletal Muscle Salt Inducible Kinase 1 Promotes Insulin Resistance in Obesity", Molecular Metabolism, (2015), vol. 5, pp. 34-46.

Ozanne et al., "The Clinically Approved Drugs Dasatinib and Bosutinib Induce Anti-Inflammatory Macrophages by Inhibiting the Salt-Inducible Kinases", Biochemical Journal, (2015), vol. 465, pp. 271-279.

Sasaki et al., "SIK2 Is a Key Regulator for Neuronal Survival after Ischemia via TORC1-CREB", Neuron, (2011), vol. 39, pp. 106-119.

Sina et al., "G Protein-Coupled Receptor 43 is Essential for Neutrophil Recruitment During Intestinal Inflammation", The Journal of Immunology, (2009), vol. 183, pp. 7514-7522.

Sundberg et al., "Small-Molecule Screening Identifies Inhibition of Salt-Inducible Kinases as a Therapeutic Strategy to Enhance Immunoregulatory Functions of Dendritic Cells", Proceedings of the National Academy of Sciences of the United States of America, (2014), vol. 111, No. 34, pp. 12468-12473.

Wein et al., "SIKs Control Osteocyte Responses To Parathyroid Hormone", Nature Communications, (2016), vol. 7, No. 13176, pp. 1-19.

Wirtz et al., "Chemically Induced Mouse Models of Intestinal Inflammation", Nature Protocols, (2007), vol. 2, No. 3, pp. 541-546.

Yu et al., Salt-Inducible Kinase 1 is Involved in High Glucose-Induced Mesangial Cell Proliferation Mediated by the ALK5 Signaling Pathway, International Journal of Molecular Medicine, (2013), vol. 32, pp. 151-157.

Bush et al., "Reduction of Joint Inflammation and Bone Erosion in Rat Adjuvant Arthritis by Treatment with Interleukin-17 Receptor IgG1 Fc Fusion Protein", Arthritis & Rheumatism, (2002), vol. 46, No. 3, pp. 802-805.

Van der Fits L et al., "Imiquimod-Induced Psoriasis-Like Skin Inflammation in Mice is Mediated via the IL-23/IL-17 Axis", The Journal of Immunology, (2009), vol. 182, pp. 5836-5845.

Jou et al., "Thrombospondin 1 as an Effective Gene Therapeutic Strategy in Collagen-Induced Arthritis", Arthritis & Rheumatism, (2005), vol. 52, No. 1, pp. 339-344.

Nishida et al., "Histone Deacetylase Inhibitor Suppression of Autoantibody-Mediated Arthritis in Mice via Regulation of p16INK4a and p21WAF1/Cip1 Expression", Arthritis & Rheumatism, (2004), vol. 50, No. 10, pp. 3365-3376.

Rizzo et al., "IL-23-Mediated Psoriasis-Like Epidermal Hyperplasia Is Dependent on IL-17A", The Journal of Immunology, (2011), vol. 186, pp. 1495-1502.

Salvemini et al., "Amelioration of Joint Disease in a Rat Model of Collagen-Induced Arthritis by M40403, a Superoxide Dismutase Mimetic", Arthritis & Rheumatism, (2001), vol. 44, No. 12, pp. 2909-2921.

Sherlock et al. "IL-23 Induces Spondyloarthropathy by Acting on ROR-γt+ CD3+CD4-CD8- Entheseal Resident T Dells", Nature Medicine, (2012), vol. 18, No. 7, pp. 1069-1077.

Sims et al., "Targeting Osteoclasts with Zoledronic Acid Prevents Bone Destruction in Collagen-Induced Arthritis", Arthritis & Rheumatism, (2004), vol. 50, No. 7, pp. 2338-2346.

Yokogawa et al., "Epicutaneous Application of Toll-like Receptor 7 Agonists Leads to Systemic Autoimmunity in Wild-Type Mice: A New Model of Systemic Lupus Erythematosus", Arthritis & Rheumatism, (2014), vol. 66, No. 3, pp. 394-706.

International Search Report and Written Opinion for PCT/EP2018/082537 dated Jan. 30, 2019.

Argilés et al., "Catabolic Proinflammatory Cytokines", Current Opinion in Clinical Nutrition & Metabolic Care, (1998), vol. 1, pp. 245-251.

Khachigian, "Collagen Antibody-Induced Arthritis," Nature Protocols, (2006), vol. 1, No. 5, pp. 2512-2516.

Lin et al., "Anti-Rheumatic Activities of Histone Deacetylase (HDAC) Inhibitors in vivo in Collagen-Induced Arthritis in Rodents", British Journal of Pharmacology, (2007), vol. 150, pp. 862-872.

Liu et al., "Dense Genotyping of Immune-Related Disease Regions Identifies Nine New Risk Loci For Primary Sclerosing Cholangitis," Nature Genetics, (2013), vol. 45, No. 6, pp. 670-675.

Rall et al., "Rheumatoid Cachexia: Metabolic Abnormalities, Mechanisms and Interventions," Rheumatology, (2004), vol. 43, No. 10, pp. 1219-1223.

Shelton et al., "Nerve Growth Factor Mediates Hyperalgesia and Cachexia in Auto-Immune Arthritis," Pain, (2005), vol. 116, pp. 8-16.

Nalsmith et al., "Tumor Necrosis Factor-Alpha Production is Associated with Less Body Cell Mass in Women with Rheumatoid Arthritis," The Journal of Rheumatology, (2004), vol. 31, No. 1, pp. 23-29.

Kao et al., "Prostaglandin E2 promotes Th1 Differentiation via Synergistic Amplification of IL-12 Signalling by cAMP and PI3-Kinase," Nature Communications, (2013), vol. 4, No. 1685, pp. 1-13.

Morman, "The Use of Salt-Inducible Kinase Inhibitors to Treat Autoimmune and Inflammatory Diseases: Evaluation of WO201 3136070," Expert Opinion on Therapeutic Patents, (2014), vol. 24, No. 8, pp. 943-946.

Jin et al., "High-Throughput Implementation of the NanoBRET Target Engagement Intracellular Kinase Assay to Reveal Differential Compound Engagement by SIK2/3 Isoforms," SLAS Discovery, (2019), pp. 1-8.

* cited by examiner

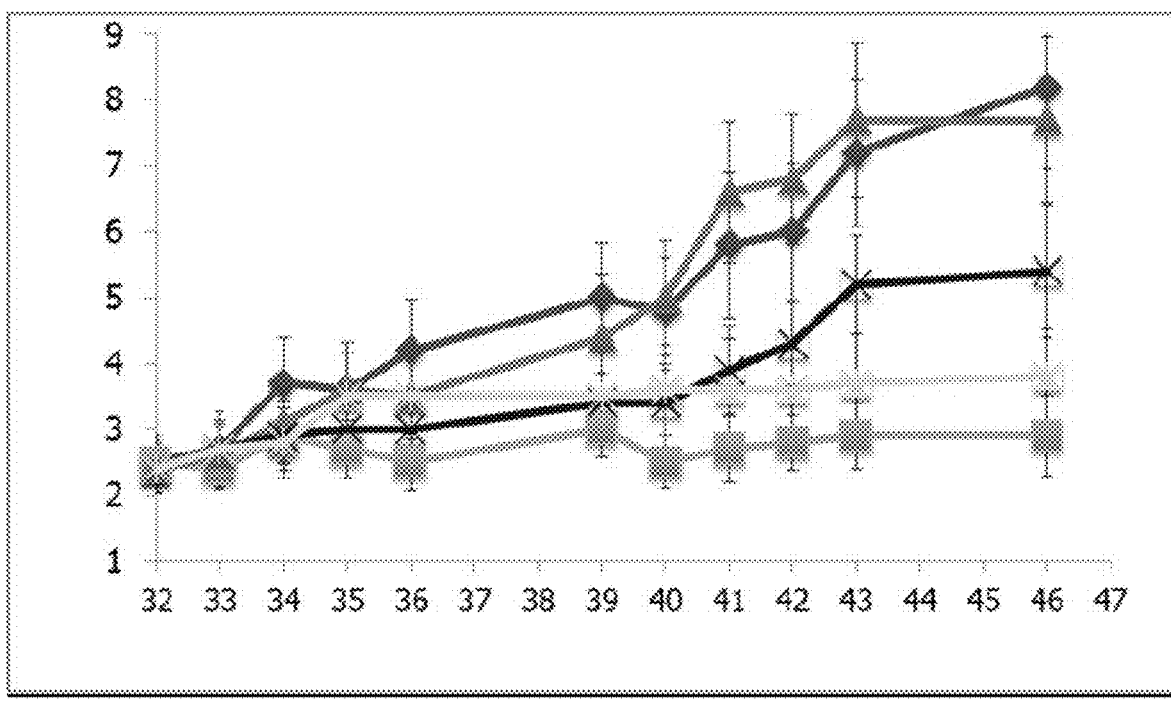

COMPOUNDS AND PHARMACEUTICAL COMPOSITIONS THEREOF FOR THE TREATMENT OF DISEASES

CROSS-REFERENCE TO RELATED APPLICATIONS

This application is a National Stage Entry of PCT/EP2018/082537, filed Nov. 26, 2018, which claims foreign priority to GB Patent Application No. 1720101.3 filed on Dec. 2, 2017 and GB Patent Application No. 1817343.5 filed on Oct. 25, 2018.

FIELD OF THE INVENTION

The present invention relates to compounds, methods for the production of the compounds of the invention, pharmaceutical compositions comprising the compounds of the invention, uses and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases by administering the compounds of the invention. In particular, the compounds of the invention may inhibit Salt-Inducible Kinases ('SIK' kinases).

BACKGROUND OF THE INVENTION

Protein kinases belong to a large family of structurally related enzymes which are responsible for the control of a wide variety of cellular signal transduction processes. In particular, they have been shown to be key regulators in cellular functions including for example proliferation, metabolism, and apoptosis. Consequently, defective control of protein phosphorylation which leads to uncontrolled signaling is involved in a number of diseases, including for example, inflammation, allergies, cancer, autoimmune diseases, CNS disorders, angiogenesis.

In healthy individuals inflammation is self-limiting, and resolution is controlled by the release of anti-inflammatory mediators and cytokines, such as interleukin-10 (IL-10), produced by cells called 'suppressive' or 'regulatory' which are produced as part of a negative feedback loop.

Indeed, in the normal process of inflammation in the body, an initial pro-inflammatory response is followed by a pro-resolution response which turns the inflammation off after the insult has been resolved, leading to the reduction of pro-inflammatory cytokines such as TNFα and IL-12, coupled with increased levels of anti-inflammatory cytokines such as IL-10 and TGF-β, resulting in the generation of a so-called tolerogenic environment.

Adenosine Monophosphate-activated Protein Kinases (AMPK) belongs to the protein kinase family, which comprises Salt-Inducible Kinases (SIKs), a family of serine/threonine kinases widely expressed in the body, and involved in particular in cellular energy homeostasis. Three SIK isoforms have been identified, named SIK1 (also referred as SNF1-Like Kinase (SNF1LK) or Myocardial Snf1-like Kinase (MSK)), SIK2 (SNF1LK2 or KIAA0781) and SIK3 (KIAA0999) (Katoh et al. 2004).

The SIKs play a number of roles in different cell types have been found to phosphorylate a number of substrates including CREB-responsive transcriptional co-activator (CRTC) proteins, and also Histone de-acetylase (HDAC) proteins, thereby regulating the transcription of a number of different genes. One of the roles of CRTC signalling relates to control of the phenotype of macrophage, in particular polarisation of macrophage through phosphorylation of CRTC3 as measured by decreased proinflammatory cytokine IL-12 secretion and concomitant increased pro-resolution cytokine IL-10 secretion (Clark et al. 2012; Ozanne et al. 2015).

SIK1 has recently been shown to be involved in mouse in skeletal muscle sensitivity in obese individuals, and may be an interesting target to prevent type II diabetes (Nixon et al. 2016), and diabetic nephropathy (Yu et al. 2013).

SIK2 and SIK3 have recently been identified to play a role in inflammation through the secretion of high levels of anti-inflammatory cytokines, in particular Interleukin-10 (IL-10) and very low levels of pro-inflammatory cytokines such as TNF-α (Darling et al. 2017).

A role for SIK2 in T helper (Th)1 cell differentiation has recently been described through the regulation of IFNγ and IL-12 signaling, suggesting SIK2 may be an interesting target for inflammatory diseases (Yao et al. 2013).

Recently, it has also been shown that like PTH, small molecule SIK inhibitors cause decreased phosphorylation and increased nuclear translocation of HDAC4/5 and CRTC2. Treatment with the small molecule SIK inhibitor YKL-05-099 increased bone formation and bone mass in mice (Wein et al. 2016), confirming the relevance of SIK inhibition in the treatment of bone turnover diseases.

Furthermore, it was shown that inhibition of SIK2 after oxygen-glucose deprivation enhances neuron survival (Sasaki et al. 2011) or promotes melanogenesis in melanoma cells (Kumagai et al. 2011). In this context, since therapeutic strategies are needed to modulate the stress cellular response, such as during ischaemia and post reperfusion of tissue, in the chronic phase of cardiac remodelling, in diabetes and neurodegenerative conditions, the rapid activation or degradation of the SIK proteins, following multiple kinds of stresses, makes them interesting targets in inflammatory, cardiac or metabolic diseases and neurodegenerative disorders. SIK inhibition might also have application in cosmetology or pigmentation-related diseases to induce melanogenesis.

The regulation of ALK5 by SIK1 (Yu et al. 2013) and the identification of the SIK2 gene as a risk locus for primary sclerosing cholangitis (Liu et al. 2013) suggest a role for SIK proteins in fibrotic diseases.

Besides the pivotal function in cellular energy homeostasis, the SIK proteins have also been involved in the regulation of the cell cycle. Higher expression of SIK2 significantly correlated with poor survival in patients with high-grade serous ovarian cancers (Ashour Ahmed et al. 2010), moreover, expression of SIK3 was elevated in ovarian cancers, particularly in the serous subtype and at later stages (Charoenfuprasert et al. 2011). Therefore SIK inhibition may be useful in the treatment of cancer.

Despite great advances over the past two decades in the treatments of patients affected by auto-immune disorders, based on antibodies targeting pro-inflammatory cytokines such as anti-TNFα, a significant proportion of patients do not respond to these therapies or experience serious adverse events such as opportunistic infections. Therefore a large unmet medical need still exist for the treatment of these disease, and new agents for the prophylaxis and/or treatment of the above mentioned diseases are required.

DESCRIPTION OF THE FIGURES

FIGURE refers to Example 4.2 and shows the evolution of the clinical score in the CIA mouse model for the vehicle (filled diamonds), Enbrel (filled squares), Cpd 53 dosed at 2 mg/kg bid (filled triangles), Cpd 53 dosed at 5 mg/kg bid (crosses) and Cpd 53 dosed at 30 mg/kg bid (asterisks) [x-axis: protocol day, y-axis: clinical score].

SUMMARY OF THE INVENTION

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, and more particularly SIK1, SIK2 and/or SIK3 inhibitors. The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having a Formula (I):

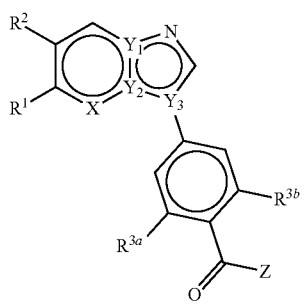

I wherein,
X is N or $CR^4$;
one of $Y_1$, $Y_2$ and $Y_3$ is N and the other two are C;
Z is
—$NR^{5a}R^{5b}$,
—$NR^{5c}$—, wherein the N atom and $R^{3b}$ together with the atoms onto which they are attached form a fused 5-6 membered heterocycloalkenyl comprising one double bond and further comprising zero, one, or two additional heteroatoms independently selected from N, O, and S, or
N-linked 4-7 membered heterocycloalkyl further comprising zero, one, or two additional heteroatoms independently selected from N, O, and S, optionally substituted with one, two or three independently selected $R^6$ groups;
$R^1$ is H, halo, $C_{1-4}$ alkyl, or $C_{1-4}$ alkoxy optionally substituted with $C_{1-4}$ alkoxy, phenyl, —CN, —C(=O)OH, or —C(=O)—$C_{1-4}$ alkoxy;
$R^2$ is 5-6 membered monocyclic heteroaryl comprising one, two or three heteroatoms independently selected from N, O, and S, which heteroaryl is optionally substituted with one or more independently selected $R^7$ groups;
$R^{3a}$ and $R^{3b}$ are independently selected from
halo,
$C_{1-4}$ alkyl,
$C_{1-4}$ alkoxy optionally substituted with one or more independently selected halo, —OH or $C_{1-4}$ alkoxy,
—$NR^{8a}R^{8b}$, and
—OH;
$R^4$ is H or $C_{1-4}$ alkyl;
$R^{5a}$ is H or $C_{1-4}$ alkyl;
$R^{5b}$ is selected from
$C_{1-6}$ alkyl optionally substituted with one or more independently selected $R^9$,
$C_{3-7}$ cycloalkyl optionally substituted with one or more independently selected $R^{10}$,
4-7 membered monocyclic heterocycloalkyl comprising one, two or three heteroatoms independently selected from N, O, and S, which heterocycloalkyl is optionally substituted with one or more oxo, and
5-6 membered monocyclic heteroaryl comprising one, two or three heteroatoms independently selected from N, O, and S, which heteroaryl is optionally substituted with one or more independently selected $C_{1-4}$ alkyl;
$R^{5c}$ is selected from $C_{3-7}$ cycloalkyl, and $C_{1-6}$ alkyl optionally substituted with one or more independently selected halo;
each $R^6$ is independently selected from
oxo,
halo,
—CN,
—OH,
—$NR^{11a}R^{11b}$,
phenyl,
$C_{3-7}$ cycloalkyl,
$C_{2-4}$ alkynyl,
—C(=O)—$C_{1-4}$ alkoxy,
$C_{1-4}$ alkoxy optionally substituted with one or more halo or phenyl,
$C_{1-4}$ alkyl optionally substituted with one or more halo, —OH, or $C_{1-4}$ alkoxy, and
4-7 membered monocyclic heterocycloalkyl comprising one, two or three heteroatoms independently selected from N, O, and S;
each $R^7$ is selected from
halo,
—CN,
$C_{1-6}$ alkyl optionally substituted with one or more independently selected
halo,
—CN,
—OH, C$_{1-4}$ alkoxy optionally substituted with one or more independently selected halo,
—NR$^{11c}$R$^{11d}$,
—C(=O)R$^{12}$, or
4-6 membered monocyclic heterocycloalkyl comprising one, two or three heteroatoms independently selected from N, O, and S,
C$_{1-4}$ alkoxy,
C$_{3-7}$ cycloalkyl,
4-6 membered monocyclic heterocycloalkyl comprising one, two or three heteroatoms independently selected from N, O, and S, which heterocycloalkyl is optionally substituted with —C(=O)C$_{1-4}$ alkoxy or C$_{1-4}$ alkyl optionally substituted with —CN,
—NR$^{13a}$R$^{13b}$, and
—C(=O)NR$^{13c}$R$^{13d}$;
each R$^{8a}$ and R$^{8b}$ is independently selected from H and C$_{1-4}$ alkyl optionally substituted with one —OH or C$_{1-4}$ alkoxy;
each R$^9$ is independently selected from
halo,
—CN,
—NR$^{11e}$R$^{11f}$,
—OH,
C$_{1-4}$ alkoxy,
—S(=O)$_2$—C$_{1-4}$ alkyl,
4-7 membered monocyclic heterocycloalkyl comprising one, two or three heteroatoms independently selected from N, O, and S, and
5-6 membered monocyclic heteroaryl comprising one, two or three heteroatoms independently selected from N, O, and S, which heteroaryl is optionally substituted with one or more independently selected C$_{1-4}$ alkyl;
each R$^{10}$ is independently selected from
halo,
C$_{1-4}$ alkyl optionally substituted with one or more independently selected halo, —OH, or C$_{1-4}$ alkoxy,
—OH,
C$_{1-4}$ alkoxy, and
—NR$^{11g}$R$^{11h}$;
each R$^{11a}$, R$^{11b}$, R$^{11c}$, R$^{11d}$, R$^{11e}$, R$^{11f}$, R$^{11g}$, and R$^{11h}$ is independently selected from H and C$_{1-4}$ alkyl;
each R$^{12}$ is
—NR$^{14a}$R$^{14b}$, wherein each R$^{14a}$ and R$^{14b}$ is independently selected from H and C$_{1-4}$ alkyl,
—OH,
C$_{1-4}$ alkoxy optionally substituted with one or more independently selected C$_{3-7}$ cycloalkyl, halo, —NR$^{15a}$R$^{15b}$, or 4-6 membered monocyclic heterocycloalkyl comprising one, two or three heteroatoms independently selected from N, O, and S,
—O-(4-6 membered monocyclic heterocycloalkyl comprising one, two or three heteroatoms independently selected from N, O, and S), or
—O—(C$_{3-7}$ monocyclic cycloalkyl);
each R$^{13a}$, R$^{13b}$, R$^{13c}$, and R$^{13d}$ is independently selected from H and C$_{1-4}$ alkyl;
each R$^{15a}$ and R$^{15b}$ is independently selected from H and C$_{1-4}$ alkyl.

In a particular aspect, the compounds of the invention are provided for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

Furthermore, it has also been unexpectedly demonstrated that the compounds of the invention exhibit potency against the SIK kinase family, which may result in a tolerogenic therapy (i.e. reduction of pro-inflammatory cytokines such as TNFα and IL-12, coupled with increased levels of anti-inflammatory cytokines such as IL-10 and TGF-β).

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—$CH_3$), ethyl (—$CH_2$—$CH_3$), n-propyl (—$CH_2$—$CH_2$—$CH_3$), isopropyl (—CH($CH_3$)$_2$), n-butyl (—$CH_2$—$CH_2$—$CH_2$—$CH_3$), tert-butyl (—$CH_2$—C($CH_3$)$_3$), sec-butyl (—$CH_2$—CH($CH_3$)$_2$), n-pentyl (—$CH_2$—$CH_2$—$CH_2$—$CH_2$—$CH_3$), n-hexyl (—$CH_2$—$CH_2$—$CH_2$—$CH_2$—$CH_2$—$CH_3$), and 1,2-dimethylbutyl (—CHCH$_3$)—C(CH$_3$)H$_2$—$CH_2$—$CH_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=$CH_2$), n-propenyl (—$CH_2$CH=$CH_2$), isopropenyl (—C($CH_3$)=$CH_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—$CH_2$—), ethylene (—$CH_2$—$CH_2$—), or —CH($CH_3$)— and the like.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as —C≡C—, —$CH_2$—C≡C—, and —C($CH_3$)H—C≡CH—.

'Alkoxy' refers to the group O-alkyl, where the alkyl group has the number of carbon atoms specified. In particular the term refers to the group —O—$C_{1-6}$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —$NH_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, isobenzoxazolyl, benzisoxazolyl, benzothiazolyl, benzoisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

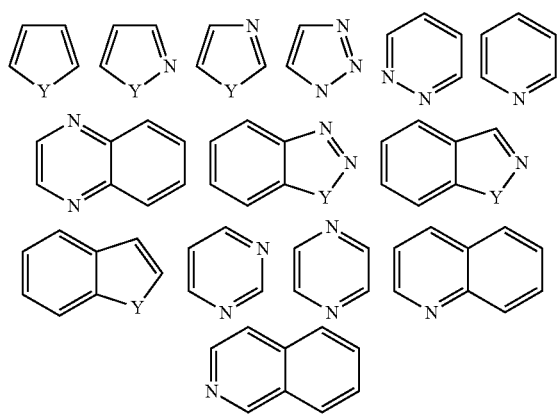

wherein each Y is selected from >C=O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), tetrahydrofuranyl (e.g. 1-tetrahydrofuranyl, 2-tetrahydrofuranyl and 3-tetrahydrofuranyl), tetrahydrothiophenyl (e.g. 1-tetrahydrothiophenyl, 2-tetrahydrothiophenyl and 3-tetrahydrothiophenyl), piperidinyl (e.g. 1-piperidinyl, 2-piperidinyl, 3-piperidinyl and 4-piperidinyl), tetrahydropyranyl (e.g. 4-tetrahydropyranyl), tetrahydrothiopyranyl (e.g. 4-tetrahydrothiopyranyl), morpholinyl, thiomorpholinyl, dioxanyl, or piperazinyl.

As used herein, the term 'heterocycloalkenyl' means a 'heterocycloalkyl', which comprises at least one double bond. Particular examples of heterocycloalkenyl groups are shown in the following illustrative examples:

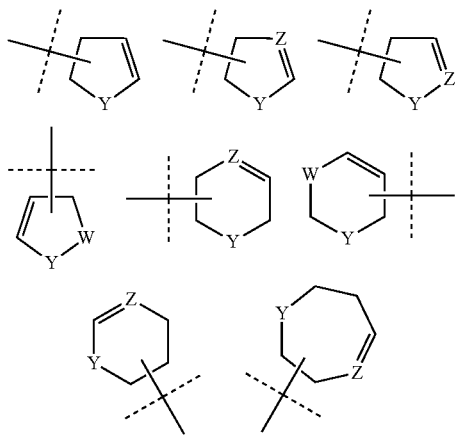

wherein each W is selected from $CH_2$, NH, O and S; each Y is selected from NH, O, C(=O), $SO_2$, and S; and each Z is selected from N or CH.

Particular examples of monocyclic rings are shown in the following illustrative examples:

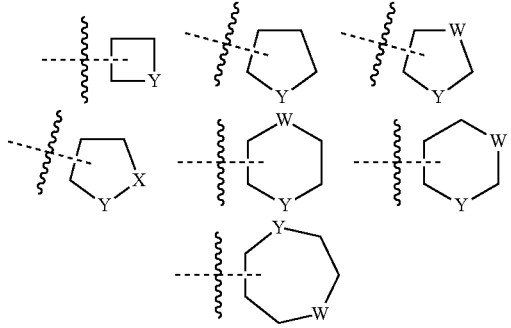

wherein each W and Y is independently selected from $-CH_2-$, $-NH-$, $-O-$ and $-S-$.

Particular examples of fused bicyclic rings are shown in the following illustrative examples:

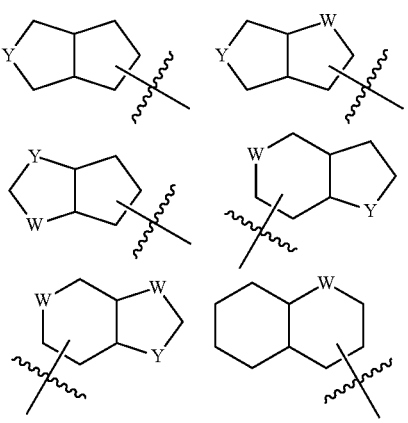

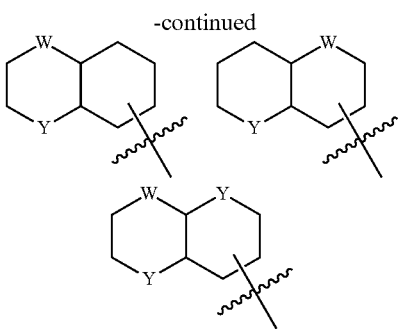

wherein each W and Y is independently selected from —CH$_2$—, —NH—, —O— and —S—.

Particular examples of bridged bicyclic rings are shown in the following illustrative examples:

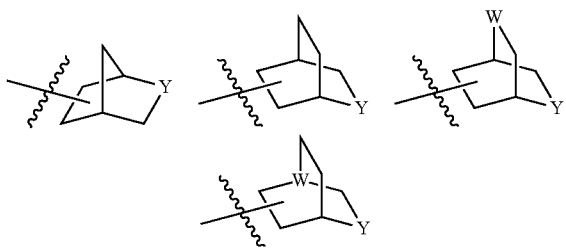

wherein each W and Y is independently selected from —CH$_2$—, —NH—, —O— and —S—.

Particular examples of spirocyclic rings are shown in the following illustrative examples:

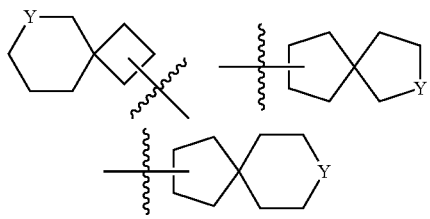

wherein each Y is selected from —CH$_2$—, —NH—, —O— and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —S-alkyl where the alkyl group has the number of carbon atoms specified. In particular the term refers to the group —S—C$_{1-6}$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethyl-thiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, 'treating' or 'treatment' relates to slowing the progression of the disease.

As used herein the term 'inflammatory disease(s)' refers to the group of conditions including, rheumatoid arthritis, osteoarthritis, juvenile idiopathic arthritis, psoriasis, psoriatic arthritis, ankylosing spondylitis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, chronic obstructive pulmonary disease (COPD) and inflammatory bowel diseases As used herein the term 'autoinflammatory diseases(s)' refers to the group of diseases including Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease.

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, autoimmune liver diseases (e.g. autoimmune hepatitis, primary sclerosing cholangitis, and primary biliary cirrhosis), Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term 'fibrotic disease(s)' refers to diseases characterized by excessive scarring due to excessive production, deposition, and contraction of extracellular matrix, and that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak syndrome, tuberous sclerosis, neurofibromatosis, metabolic storage diseases, familial interstitial lung disease); radiation induced fibrosis; chronic obstructive pulmonary disease; scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; diabetic nephropathy, focal segmental glomerular sclerosis; IgA nephropathy; hypertension; Alport syndrome; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; Duchenne muscular dystrophy (DMD) associated musculoskeletal fibrosis, vascular restenosis; atherosclerosis; arteriosclerosis; Wegener's granulomatosis; Peyronie's disease, or chronic lymphocytic. More particularly, the term 'fibrotic diseases' refers to idiopathic pulmonary fibrosis (IPF), Dupuytren disease, nonalcoholic steatohepatitis (NASH), systemic sclerosis, renal fibrosis, and cutaneous fibrosis.

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'diseases involving impairment of bone turnover' includes conditions such as osteoporosis (including postmenopausal osteoporosis, male osteoporosis, glucocorticosteroid induced osteoporosis and juvenile osteoporosis), osteoporosis caused through neoplastic bone marrow disorders, osteopenia, hormone deficiency (vitamin D deficiency, male and female hypogonadism), hormone excess (hyperprolactinaemia, excess glucocorticoid, hyperthyroidism, hyperparathyroidism), Paget's disease, osteoarthritis, renal bone disease, osteogenesis imperfecta, hypophosphatasia.

As used herein the term 'disease(s) associated with hypersecretion of IL-6' includes conditions such as Castleman's disease, multiple myeloma, psoriasis, Kaposi's sarcoma and/or mesangial proliferative glomerulonephritis.

As used herein the term 'disease(s) associated with hypersecretion of TNFα, interferons, IL-12 and/or IL-23 includes conditions such as systemic and cutaneous lupus erythematosis, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease.

As used herein, the term 'respiratory disease' refers to diseases affecting the organs that are involved in breathing, such as the nose, throat, larynx, eustachian tubes, trachea, bronchi, lungs, related muscles (e.g., diaphragm and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity and/or diabetes type II.

As used herein the term 'cardiovascular disease' refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. More particularly, cardiovascular disease refers to atherosclerosis.

As used herein the term 'dermatological disease(s)' refers to a skin disorder. In particular, dermatological disorders include proliferative or inflammatory disorders of the skin such as, atopic dermatitis, bullous disorders, collagenoses, psoriasis, psoriatic lesions, dermatitis, contact dermatitis, eczema, vitiligo, pruritus, urticaria, rosacea, scleroderma, wound healing, scarring, hypertrophic scarring, keloids, Kawasaki disease, rosacea, Sjögren-Larsson syndrome, or urticaria.

As used herein the term 'abnormal angiogenesis associated disease' refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and $(C_{6-10}$ aryl)-$(C_{1-4}$ alkyl) esters of the compounds of the invention.

The present disclosure includes all isotopic forms of the compounds of the invention provided herein, whether in a form (i) wherein all atoms of a given atomic number have a mass number (or mixture of mass numbers) which predominates in nature (referred to herein as the 'natural isotopic form') or (ii) wherein one or more atoms are replaced by atoms having the same atomic number, but a mass number different from the mass number of atoms which predominates in nature (referred to herein as an 'unnatural variant isotopic form'). It is understood that an atom may naturally exists as a mixture of mass numbers. The term 'unnatural variant isotopic form' also includes embodiments in which the proportion of an atom of given atomic number having a mass number found less commonly in nature (referred to herein as an 'uncommon isotope') has been increased relative to that which is naturally occurring e.g. to the level of >20%, >50%, >75%, >90%, >95% or >99% by number of the atoms of that atomic number (the latter embodiment referred to as an 'isotopically enriched variant form'). The term 'unnatural variant isotopic form' also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, and more particularly SIK1, SIK2 and/or SIK3 inhibitors.

The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having Formula I:

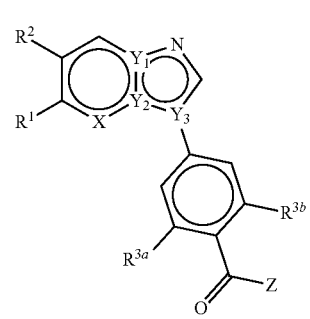

wherein,

X is N or CR$^4$;

one of Y$_1$, Y$_2$ and Y$_3$ is N and the other two are C;

Z is
- —NR$^{5a}$R$^{5b}$,
- —NR$^{5c}$—, wherein the N atom and R$^{3b}$ together with the atoms onto which they are attached form a fused 5-6 membered heterocycloalkenyl comprising one double bond and further comprising zero, one, or two additional heteroatoms independently selected from N, O, and S, or
- N-linked 4-7 membered heterocycloalkyl further comprising zero, one, or two additional heteroatoms independently selected from N, O, and S, optionally substituted with one, two or three independently selected R$^6$ groups;

R$^1$ is H, halo, C$_{1-4}$ alkyl, or C$_{1-4}$ alkoxy optionally substituted with C$_{1-4}$ alkoxy, phenyl, —CN, —C(═O)OH, or —C(═O)—C$_{1-4}$ alkoxy;

R$^2$ is 5-6 membered monocyclic heteroaryl comprising one, two or three heteroatoms independently selected from N, O, and S, which heteroaryl is optionally substituted with one or more independently selected R$^7$ groups;

R$^{3a}$ and R$^{3b}$ are independently selected from
- halo,
- C$_{1-4}$ alkyl,
- C$_{1-4}$ alkoxy optionally substituted with one or more independently selected halo, —OH or C$_{1-4}$ alkoxy,
- —NR$^{8a}$R$^{8b}$, and
- —OH;

R$^4$ is H or C$_{1-4}$ alkyl;

R$^{5a}$ is H or C$_{1-4}$ alkyl;

$R^{5b}$ is selected from
- $C_{1-6}$ alkyl optionally substituted with one or more independently selected $R^9$,
- $C_{3-7}$ cycloalkyl optionally substituted with one or more independently selected $R^{10}$,
- 4-7 membered monocyclic heterocycloalkyl comprising one, two or three heteroatoms independently selected from N, O, and S, which heterocycloalkyl is optionally substituted with one or more oxo, and
- 5-6 membered monocyclic heteroaryl comprising one, two or three heteroatoms independently selected from N, O, and S, which heteroaryl is optionally substituted with one or more independently selected $C_{1-4}$ alkyl;

$R^{5c}$ is selected from $C_{3-7}$ cycloalkyl, and $C_{1-6}$ alkyl optionally substituted with one or more independently selected halo;

each $R^6$ is independently selected from
- oxo,
- halo,
- —CN,
- —OH,
- —NR$^{11a}$R$^{11b}$,
- phenyl,
- $C_{3-7}$ cycloalkyl,
- $C_{2-4}$ alkynyl,
- —C(=O)—$C_{1-4}$ alkoxy,
- $C_{1-4}$ alkoxy optionally substituted with one or more halo or phenyl,
- $C_{1-4}$ alkyl optionally substituted with one or more halo, —OH, or $C_{1-4}$ alkoxy, and
- 4-7 membered monocyclic heterocycloalkyl comprising one, two or three heteroatoms independently selected from N, O, and S;

each $R^7$ is selected from
- halo,
- —CN,
- $C_{1-6}$ alkyl optionally substituted with one or more independently selected
  - halo,
  - —CN,
  - —OH,
  - $C_{1-4}$ alkoxy optionally substituted with one or more independently selected halo,
  - —NR$^{11c}$R$^{11d}$,
  - —C(=O)R$^{12}$, or
  - 4-6 membered monocyclic heterocycloalkyl comprising one, two or three heteroatoms independently selected from N, O, and S,
- $C_{1-4}$ alkoxy,
- $C_{3-7}$ cycloalkyl,
- 4-6 membered monocyclic heterocycloalkyl comprising one, two or three heteroatoms independently selected from N, O, and S, which heterocycloalkyl is optionally substituted with —C(=O)$C_{1-4}$ alkoxy or $C_{1-4}$ alkyl optionally substituted with —CN,
- —NR$^{13a}$R$^{13b}$, and
- —C(=O)NR$^{13c}$R$^{13d}$;

each $R^{8a}$ and $R^{8b}$ is independently selected from H and $C_{1-4}$ alkyl optionally substituted with one —OH or $C_{1-4}$ alkoxy;

each $R^9$ is independently selected from
- halo,
- —CN,
- —NR$^{11e}$R$^{11f}$,
- —OH,
- $C_{1-4}$ alkoxy,
- —S(=O)$_2$—$C_{1-4}$ alkyl,
- 4-7 membered monocyclic heterocycloalkyl comprising one, two or three heteroatoms independently selected from N, O, and S, and
- 5-6 membered monocyclic heteroaryl comprising one, two or three heteroatoms independently selected from N, O, and S, which heteroaryl is optionally substituted with one or more independently selected $C_{1-4}$ alkyl;

each $R^{10}$ is independently selected from
- halo,
- $C_{1-4}$ alkyl optionally substituted with one or more independently selected halo, —OH, or $C_{1-4}$ alkoxy,
- —OH,
- $C_{1-4}$ alkoxy, and
- —NR$^{11g}$R$^{11h}$;

each $R^{11a}$, $R^{11b}$, $R^{11c}$, $R^{11d}$, $R^{11e}$, $R^{11f}$, $R^{11g}$, and $R^{11h}$ is independently selected from H and $C_{1-4}$ alkyl;

each $R^{12}$ is
- —NR$^{14a}$R$^{14b}$, wherein each $R^{14a}$ and $R^{14b}$ is independently selected from H and $C_{1-4}$ alkyl,
- —OH,
- $C_{1-4}$ alkoxy optionally substituted with one or more independently selected $C_{3-7}$ cycloalkyl, halo, —NR$^{15a}$R$^{15b}$, or 4-6 membered monocyclic heterocycloalkyl comprising one, two or three heteroatoms independently selected from N, O, and S,
- —O-(4-6 membered monocyclic heterocycloalkyl comprising one, two or three heteroatoms independently selected from N, O, and S), or
- —O—($C_{3-7}$ monocyclic cycloalkyl);

each $R^{13a}$, $R^{13b}$, $R^{13c}$, and $R^{13d}$ is independently selected from H and $C_{1-4}$ alkyl;

each $R^{15a}$ and $R^{15b}$ is independently selected from H and $C_{1-4}$ alkyl.

In one embodiment, the compound of the invention is according to Formula I, wherein X is CR$^4$ and R$^4$ is H.

In one embodiment, the compound of the invention is according to Formula I, wherein X is CR$^4$ and R$^4$ is $C_{1-4}$ alkyl. In a particular embodiment, R$^4$ is —CH$_3$, —CH$_2$CH$_3$, or —CH(CH$_3$)$_2$. In a more particular embodiment, R$^4$ is —CH$_3$.

In one embodiment, the compound of the invention is according to Formula IIa, IIb, IIc, IId, IIe, or IIf:

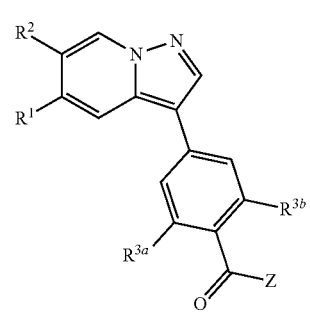

IIa

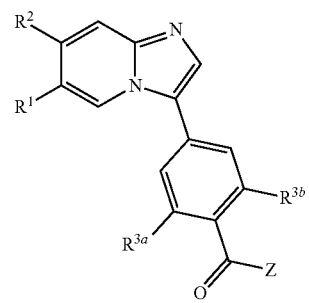

IIb

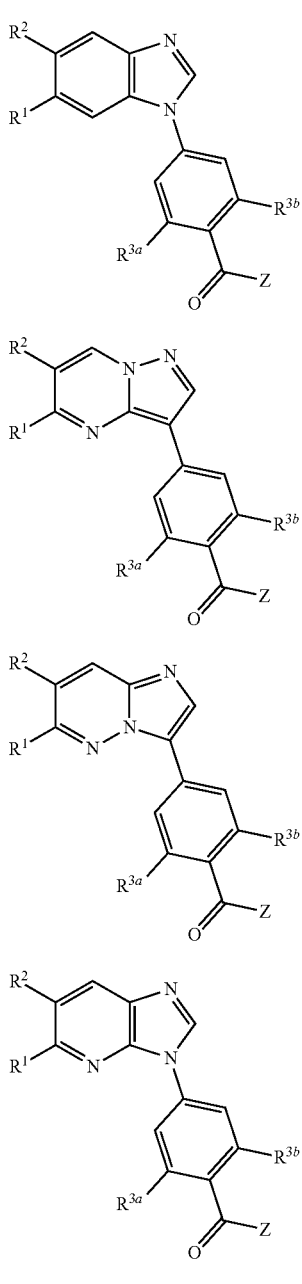

wherein $R^1$, $R^2$, $R^{3a}$, $R^{3b}$, and Z are as described above.

In one embodiment, the compound of the invention is according to any one of Formulae I-IIf, wherein $R^1$ is H.

In one embodiment, the compound of the invention is according to any one of Formulae I-IIf, wherein $R^1$ is halo. In a particular embodiment, $R^1$ is F, Cl, or Br.

In one embodiment, the compound of the invention is according to any one of Formulae I-IIf, wherein $R^1$ is $C_{1-4}$ alkyl. In a particular embodiment, $R^1$ is —$CH_3$, —$CH_2CH_3$, or —$CH(CH_3)_2$. In a more particular embodiment, $R^1$ is —$CH_3$.

In one embodiment, the compound of the invention is according to any one of Formulae I-IIf, wherein $R^1$ is $C_{1-4}$ alkoxy. In a particular embodiment, $R^1$ is —O—$CH_3$, —O—$CH_2CH_3$, or —O—$CH(CH_3)_2$. In a more particular embodiment, $R^1$ is —O—$CH_3$.

In one embodiment, the compound of the invention is according to any one of Formulae I-IIf, wherein $R^1$ is $C_{1-4}$ alkoxy substituted with $C_{1-4}$ alkoxy, phenyl, —CN, —C(=O)OH, or —C(=O)—$C_{1-4}$ alkoxy. In a particular embodiment, $R^1$ is —O—$CH_2CH_3$ or —O—$CH(CH_3)_2$, substituted with $C_{1-4}$ alkoxy, phenyl, —CN, —C(=O)OH, or —C(=O)—$C_{1-4}$ alkoxy. In another particular embodiment, $R^1$ is $C_{1-4}$ alkoxy substituted with —O—$CH_3$ or —O—$CH_2CH_3$, phenyl, —CN, —C(=O)OH, or —C(=O)—O—$CH_2CH_3$. In a more particular embodiment, $R^1$ is —O—$CH_2CH_2$—O—$CH_3$, benzyloxy, —O—CH(CN)$CH_3$, —O—$CH_2$—C(=O)OH, —O—CH($CH_3$)—C(=O)OH, —O—$CH_2$—C(=O)—O—$CH_2CH_3$, or —O—CH($CH_3$)—C(=O)—O—$CH_2CH_3$.

In one embodiment, the compound of the invention is according to any one of Formulae I-IIf, wherein $R^1$ is $C_{1-4}$ alkoxy substituted with $C_{1-4}$ alkoxy. In a particular embodiment, $R^1$ is —O—$CH_2CH_3$ or —O—$CH(CH_3)_2$, substituted with $C_{1-4}$ alkoxy. In another particular embodiment, $R^1$ is $C_{1-4}$ alkoxy substituted with —O—$CH_3$ or —O—$CH_2CH_3$. In a more particular embodiment, $R^1$ is —O—$CH_2CH_2$—O—$CH_3$.

In one embodiment, the compound of the invention is according to Formula IIIa, IIIb, IIIc, IIId, IIIe, or IIIf:

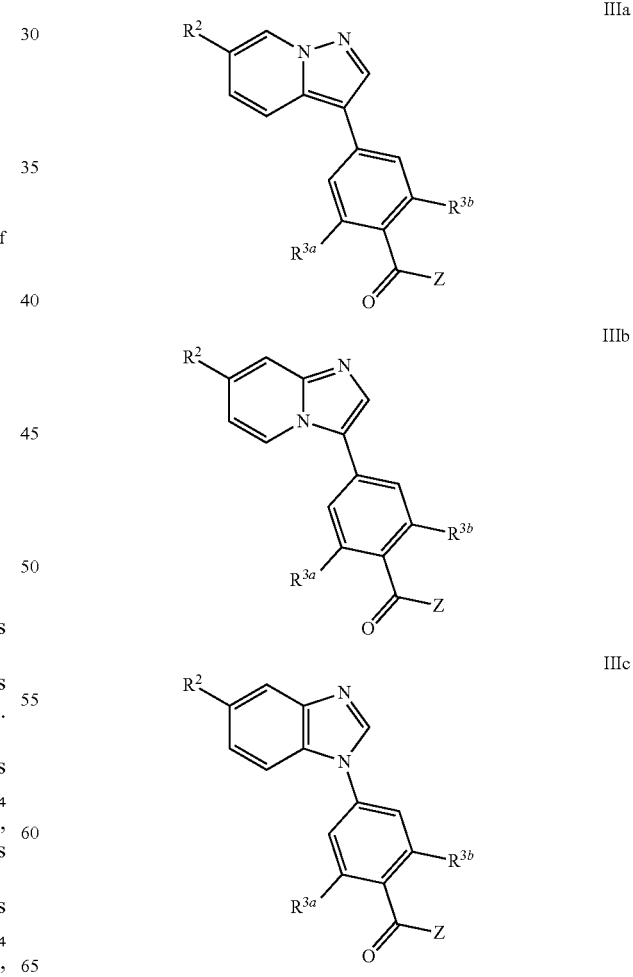

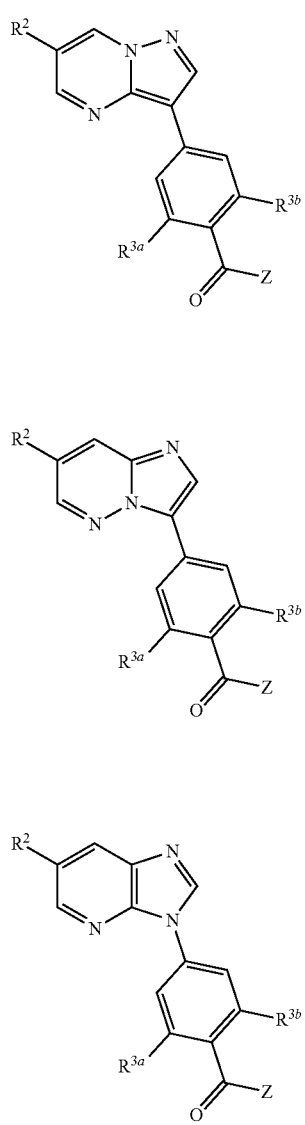

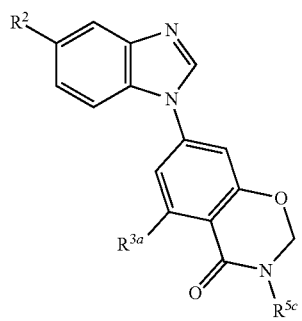

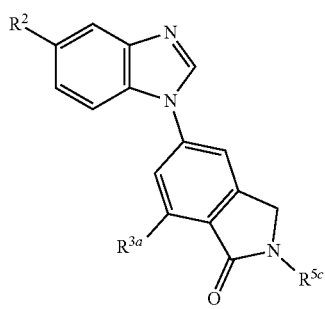

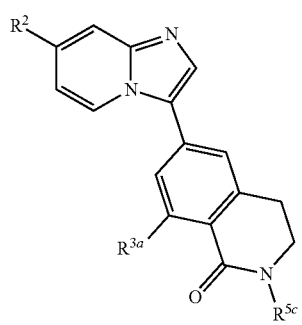

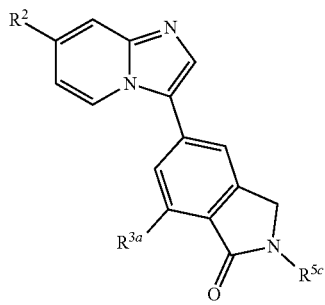

wherein $R^2$, $R^{3a}$, $R^{3b}$ and Z are as described above.

In one embodiment, the compound of the invention is according to any one of Formulae I-IIIf, wherein Z is —$NR^{5c}$—, wherein the N atom and $R^{3b}$ together with the atoms onto which they are attached form a fused 5-6 membered heterocycloalkenyl comprising one double bond and further comprising zero, one, or two additional heteroatoms independently selected from N, O, and S, and $R^{5c}$ is as previously described. In a particular embodiment, Z is —$NR^{5c}$—, wherein the N atom and $R^{3b}$ together with the atoms onto which they are attached form a fused 3,4-dihydro-2H-1,3-oxazine, 1,2,3,4-tetrahydropyrimidine, 3-pyrroline, 1,2,3,6-tetrahydropyridine, or 3,4-dihydro-2H-1,3-thiazine. In a more particular embodiment, Z is —$NR^{5c}$—, wherein the N atom and $R^{3b}$ together with the atoms onto which they are attached form a fused 3,4-dihydro-2H-1,3-oxazine, 3-pyrroline, or 1,2,3,6-tetrahydropyridine.

In one embodiment, the compound of the invention is according to Formula IVa, IVb, IVc, or IVd:

wherein $R^2$, $R^{3a}$, and $R^{5c}$ are as described above.

In one embodiment, the compound of the invention is according to any one of Formulae I-IVd, wherein $R^{5c}$ is $C_{3-7}$ cycloalkyl. In a particular embodiment, $R^{5c}$ is cyclopropyl, cyclobutyl, or cyclopentyl. In a more particular embodiment, $R^{5c}$ is cyclopropyl.

In one embodiment, the compound of the invention is according to any one of Formulae I-IVd, wherein $R^{5c}$ is $C_{1-6}$ alkyl. In a particular embodiment, $R^{5c}$ is —$CH_3$, —$CH_2CH_3$, —$CH_2CH_2CH_3$, —$CH(CH_3)_2$, or —$C(CH_3)_3$. In a more particular embodiment, $R^{5c}$ is —$CH_2CH_3$.

In one embodiment, the compound of the invention is according to any one of Formulae I-IVd, wherein $R^{5c}$ is $C_{1-6}$ alkyl substituted with one or more independently selected halo. In a particular embodiment, $R^{5c}$ is —$CH_3$, —$CH_2CH_3$, —CH$_2$CH$_2$CH$_3$, —CH(CH$_3$)$_2$, or —C(CH$_3$)$_3$, each of which is substituted with one or more independently selected halo. In another particular embodiment, R$^{5c}$ is C$_{1-6}$ alkyl substituted with one, two, or three independently selected halo. In yet another particular embodiment, R$^{5c}$ is C$_{1-6}$ alkyl substituted with one or more independently selected F or Cl. In a more particular embodiment, R$^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one, two, or three independently selected halo. In another more particular embodiment, R$^{5c}$ is C$_{1-6}$ alkyl substituted with one, two, or three independently selected F or Cl. In yet another more particular embodiment, R$^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one or more independently selected F or Cl. In a further more particular embodiment, R$^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one, two, or three independently selected F or Cl. In another further more particular embodiment, R$^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one or more F. In yet another further more particular embodiment, R$^{5c}$ is C$_{1-6}$ alkyl substituted with one, two, or three independently selected F. In a most particular embodiment, R$^{5c}$ is —CH$_2$CH$_3$ substituted with one, two, or three F.

In one embodiment, the compound of the invention is according to any one of Formulae I-IVd, wherein R$^2$ is 5-6 membered monocyclic heteroaryl comprising one, two or three heteroatoms independently selected from N, O, and S. In a particular embodiment, R$^2$ is imidazolyl, pyrazolyl, triazolyl, thiazolyl, oxazolyl, isoxazolyl, oxadiazolyl, pyridinyl, pyridazinyl, pyrimidinyl, or pyrazinyl. In a more particular embodiment, R$^2$ is pyrazolyl.

In one embodiment, the compound of the invention is according to any one of Formulae I-IVd, wherein R$^2$ is 5-6 membered monocyclic heteroaryl comprising one, two or three heteroatoms independently selected from N, O, and S, which heteroaryl is substituted with one or more independently selected R$^7$ groups. In a particular embodiment, R$^2$ is 5-6 membered monocyclic heteroaryl comprising one, two or three heteroatoms independently selected from N, O, and S, which heteroaryl is substituted with one, two, or three independently selected R$^7$ groups. In another particular embodiment, R$^2$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more independently selected R$^7$ groups. In a more particular embodiment, R$^2$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one R$^7$ group. In a most particular embodiment, R$^2$ is pyrazolyl substituted with one R$^7$ group.

In one embodiment, the compound of the invention is according to any one of Formulae I-IVd, wherein R$^2$ is 5-6 membered monocyclic heteroaryl comprising one, two or three heteroatoms independently selected from N, O, and S, which heteroaryl is substituted with one or more independently selected R$^7$ groups and R$^7$ is halo or —CN. In a particular embodiment, R$^7$ is F, Cl, Br or —CN. In a more particular embodiment, R$^7$ is F or —CN.

In one embodiment, the compound of the invention is according to any one of Formulae I-IVd, wherein R$^2$ is 5-6 membered monocyclic heteroaryl comprising one, two or three heteroatoms independently selected from N, O, and S, which heteroaryl is substituted with one or more independently selected R$^7$ groups and R$^7$ is C$_{1-4}$ alkoxy. In a particular embodiment, R$^7$ is —O—CH$_3$, —O—CH$_2$CH$_3$, or —O—CH(CH$_3$)$_2$. In a more particular embodiment, R$^7$ is —O—CH$_3$ or —O—CH$_2$CH$_3$.

In one embodiment, the compound of the invention is according to any one of Formulae I-IVd, wherein R$^2$ is 5-6 membered monocyclic heteroaryl comprising one, two or three heteroatoms independently selected from N, O, and S, which heteroaryl is substituted with one or more independently selected R$^7$ groups, R$^7$ is —NR$^{13a}$R$^{13b}$ and each R$^{13a}$ and R$^{13b}$ is as previously described. In a particular embodiment, R$^{13a}$ and R$^{13b}$ are both H. In another particular embodiment, one of R$^{13a}$ and R$^{13b}$ is H, and the other is C$_{1-4}$ alkyl. In yet another particular embodiment, R$^{13a}$ and R$^{13b}$ are both C$_{1-4}$ alkyl. In a further more particular embodiment, each R$^{13a}$ and R$^{13b}$ is independently selected H, —CH$_3$, —CH$_2$CH$_3$, or —CH(CH$_3$)$_2$. In a more particular embodiment, one of R$^{13a}$ and R$^{13b}$ is H, and the other is —CH$_3$, —CH$_2$CH$_3$, or —CH(CH$_3$)$_2$. In a most particular embodiment, R$^7$ is —NH$_2$ or —N(CH$_3$)$_2$.

In one embodiment, the compound of the invention is according to any one of Formulae I-IVd, wherein R$^2$ is 5-6 membered monocyclic heteroaryl comprising one, two or three heteroatoms independently selected from N, O, and S, which heteroaryl is substituted with one or more independently selected R$^7$ groups, R$^7$ is —C(=O)NR$^{13c}$R$^{13d}$, and each R$^{13c}$ and R$^{13d}$ is as previously described. In a particular embodiment, R$^{13c}$ and R$^{13d}$ are both H. In another particular embodiment, one of R$^{13c}$ and R$^{13d}$ is H, and the other is C$_{1-4}$ alkyl. In yet another particular embodiment, R$^{13c}$ and R$^{13d}$ are both C$_{1-4}$ alkyl. In a more particular embodiment, one of R$^{13c}$ and R$^{13d}$ is H, and the other is —CH$_3$, —CH$_2$CH$_3$, or —CH(CH$_3$)$_2$. In a more particular embodiment, each R$^{13c}$ and R$^{13d}$ is independently selected H, —CH$_3$, —CH$_2$CH$_3$, or —CH(CH$_3$)$_2$. In another more particular embodiment, R$^{13c}$ and R$^{13d}$ are —CH$_3$, —CH$_2$CH$_3$, or —CH(CH$_3$)$_2$.

In one embodiment, the compound of the invention is according to Formula Va, Vb, Vc, Vd, Ve, or Vf:

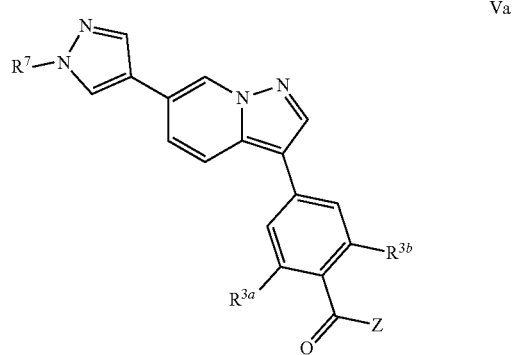

Va

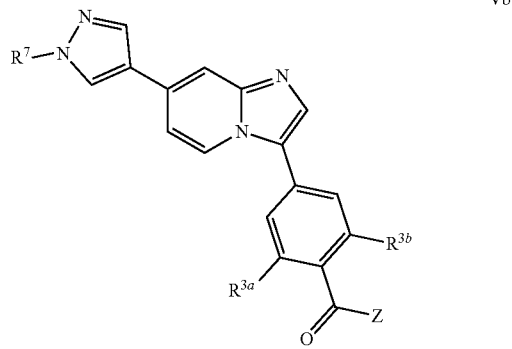

Vb

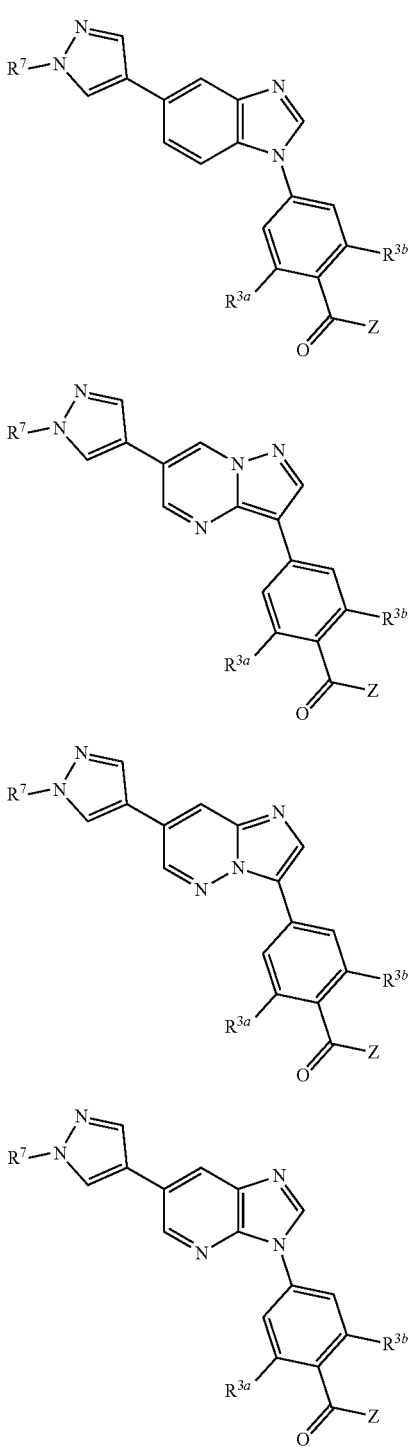

wherein R³ᵃ, R³ᵇ, R⁷ and Z are as described above.

In one embodiment, the compound of the invention is according to any one of Formulae I-Vf, wherein R⁷ is $C_{1-6}$ alkyl. In a particular embodiment, R⁷ is —CH₃, —CH₂CH₃, —CH₂CH₂CH₃, —CH(CH₃)₂, —CH₂CH(CH₃)₂, —C(CH₃)₃, —CH(CH₃)CH₂CH₃, —CH(CH₃)CH(CH₃)₂, —CH₂CH(CH₃)CH₂CH₃, or —CH₂CH₂CH(CH₃)₂. In a more particular embodiment, R⁷ is —CH₃ or —CH₂CH₃. In a most particular embodiment, R⁷ is —CH₃.

In one embodiment, the compound of the invention is according to any one of Formulae I-Vf, wherein R⁷ is $C_{1-4}$ alkyl. In a particular embodiment, R⁷ is —CH₃, —CH₂CH₃, or —CH(CH₃)₂. In a more particular embodiment, R⁷ is —CH₃ or —CH₂CH₃. In a most particular embodiment, R⁷ is —CH₃.

In one embodiment, the compound of the invention is according to any one of Formulae I-Vf, wherein R⁷ is $C_{1-6}$ alkyl substituted with one or more independently selected halo, —CN, —OH, $C_{1-4}$ alkoxy optionally substituted with one or more independently selected halo, —NR¹¹ᶜR¹¹ᵈ, —C(=O)R¹², or 4-6 membered monocyclic heterocycloalkyl comprising one, two or three heteroatoms independently selected from N, O, and S. In a particular embodiment, R⁷ is —CH₃, —CH₂CH₃, —CH₂CH₂CH₃, —CH(CH₃)₂, —CH₂CH(CH₃)₂, —C(CH₃)₃, —CH(CH₃)CH₂CH₃, —CH(CH₃)CH(CH₃)₂, —CH₂CH(CH₃)CH₂CH₃, or —CH₂CH₂CH(CH₃)₂, each of which is substituted with one or more independently selected halo, —CN, —OH, $C_{1-4}$ alkoxy optionally substituted with one or more independently selected halo, —NR¹¹ᶜR¹¹ᵈ, —C(=O)R¹², or 4-6 membered monocyclic heterocycloalkyl comprising one, two or three heteroatoms independently selected from N, O, and S. In another particular embodiment, R⁷ is $C_{1-6}$ alkyl substituted with one, two, or three independently selected halo, —CN, —OH, $C_{1-4}$ alkoxy optionally substituted with one or more independently selected halo, —NR¹¹ᶜR¹¹ᵈ, —C(=O)R¹², or 4-6 membered monocyclic heterocycloalkyl comprising one, two or three heteroatoms independently selected from N, O, and S. In yet another particular embodiment, R⁷ is $C_{1-6}$ alkyl substituted with one or more independently selected F, Cl, —CN, —OH, —O—CH₃, —O—CH₂CH₃, —O—CH(CH₃)₂, —O—CHF₂, —O—CF₃, —O—CH₂CHF₂, —NR¹¹ᶜR¹¹ᵈ, —C(=O)R¹², azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, R⁷ is —CH₃, —CH₂CH₃, —CH₂CH₂CH₃, —CH(CH₃)₂, —CH₂CH(CH₃)₂, —CH(CH₃)CH₂CH₃, —CH(CH₃)CH(CH₃)₂, —CH₂CH(CH₃)CH₂CH₃, or —CH₂CH₂CH(CH₃)₂, each of which is substituted with one, two or three independently selected halo, —CN, —OH, $C_{1-4}$ alkoxy optionally substituted with one or more independently selected halo, —NR¹¹ᶜR¹¹ᵈ, —C(=O)R¹², or 4-6 membered monocyclic heterocycloalkyl comprising one, two or three heteroatoms independently selected from N, O, and S. In another more particular embodiment, R⁷ is $C_{1-6}$ alkyl substituted with one, two, or three independently selected F, Cl, —CN, —OH, —O—CH₃, —O—CH₂CH₃, —O—CH(CH₃)₂, —O—CHF₂, —O—CF₃, —O—CH₂CHF₂, —NR¹¹ᶜR¹¹ᵈ, or —C(=O)R¹². In yet another more particular embodiment, R⁷ is $C_{1-6}$ alkyl substituted with one azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a further more particular embodiment, R⁷ is —CH₃, —CH₂CH₃, —CH₂CH₂CH₃, —CH(CH₃)₂, —CH₂CH(CH₃)₂, or —CH₂CH₂CH(CH₃)₂, each of which is substituted with one, two or three independently selected F, Cl, —CN, —OH, —O—CH₃, —O—CH₂CH₃, —O—CH(CH₃)₂, —O—CHF₂, —O—CF₃, —O—CH₂CHF₂, —NR¹¹ᶜR¹¹ᵈ, or —C(=O)R¹². In another further more particular embodiment, R⁷ is —CH₃ or —CH₂CH₃, each of which is substituted with one azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a most particular embodiment, $R^7$ is —$CH_3$, —$CH_2CH_3$, —$CH_2CH_2CH_3$, —$CH(CH_3)_2$, —$CH_2CH(CH_3)_2$, or —$CH_2CH_2CH(CH_3)_2$, each of which is substituted with one, two or three independently selected F, —CN, —OH, —O—$CH_3$, or —C(=O)$R^{12}$. In another most particular embodiment, $R^7$ is —$CH_3$ or —$CH_2CH_3$, each of which is substituted with one tetrahydrofuranyl or morpholinyl.

In one embodiment, the compound of the invention is according to any one of Formulae I-Vf, wherein $R^7$ is $C_{1-4}$ alkyl substituted with one or more independently selected halo, —CN, —OH, $C_{1-4}$ alkoxy optionally substituted with one or more independently selected halo, —$NR^{11c}R^{11d}$, —C(=O)$R^{12}$, or 4-6 membered monocyclic heterocycloalkyl comprising one, two or three heteroatoms independently selected from N, O, and S. In a particular embodiment, $R^7$ is —$CH_3$, —$CH_2CH_3$, —$CH_2CH_2CH_3$, or —$CH(CH_3)_2$, each of which is substituted with one or more independently selected halo, —CN, —OH, $C_{1-4}$ alkoxy optionally substituted with one or more independently selected halo, —$NR^{11c}R^{11d}$, —C(=O)$R^{12}$, or 4-6 membered monocyclic heterocycloalkyl comprising one, two or three heteroatoms independently selected from N, O, and S. In another particular embodiment, $R^7$ is $C_{1-4}$ alkyl substituted with one, two, or three independently selected halo, —CN, —OH, $C_{1-4}$ alkoxy optionally substituted with one or more independently selected halo, —$NR^{11c}R^{11d}$, —C(=O)$R^{12}$, or 4-6 membered monocyclic heterocycloalkyl comprising one, two or three heteroatoms independently selected from N, O, and S. In yet another particular embodiment, $R^7$ is $C_{1-4}$ alkyl substituted with one or more independently selected F, Cl, —CN, —OH, —O—$CH_3$, —O—$CH_2CH_3$, —O—$CH(CH_3)_2$, —O—$CHF_2$, —O—$CF_3$, —O—$CH_2CHF_2$, —$NR^{11c}R^{11d}$, —C(=O) $R^{12}$, azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^7$ is —$CH_3$, —$CH_2CH_3$, or —$CH_2CH_2CH_3$, each of which is substituted with one, two or three independently selected halo, —CN, —OH, $C_{1-4}$ alkoxy optionally substituted with one or more independently selected halo, —$NR^{11c}R^{11d}$, —C(=O)$R^{12}$, or 4-6 membered monocyclic heterocycloalkyl comprising one, two or three heteroatoms independently selected from N, O, and S. In another more particular embodiment, $R^7$ is $C_{1-4}$ alkyl substituted with one, two, or three independently selected F, Cl, —CN, —OH, —O—$CH_3$, —O—$CH_2CH_3$, —O—$CH(CH_3)_2$, —O—$CHF_2$, —O—$CF_3$, —O—$CH_2CHF_2$, —$NR^{11c}R^{11d}$, or —C(=O) $R^{12}$. In yet another more particular embodiment, $R^7$ is $C_{1-4}$ alkyl substituted with one azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a further more particular embodiment, $R^7$ is —$CH_3$, —$CH_2CH_3$, or —$CH_2CH_2CH_3$, each of which is substituted with one, two or three independently selected F, Cl, —CN, —OH, —O—$CH_3$, —O—$CH_2CH_3$, —O—CH$(CH_3)_2$, —O—$CHF_2$, —O—$CF_3$, —O—$CH_2CHF_2$, —$NR^{11c}R^{11d}$, or —C(=O)$R^{12}$. In another further more particular embodiment, $R^7$ is —$CH_3$ or —$CH_2CH_3$, each of which is substituted with one azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a most particular embodiment, $R^7$ is —$CH_3$, —$CH_2CH_3$, or —$CH_2CH_2CH_3$, each of which is substituted with one, two or three independently selected F, —CN, —OH, —O—$CH_3$, or —C(=O)$R^2$. In another most particular embodiment, $R^7$ is —$CH_3$ or —$CH_2CH_3$, each of which is substituted with one tetrahydrofuranyl or morpholinyl.

In one embodiment, the compound of the invention is according to any one of Formulae I-Vf, wherein $R^7$ is $C_{1-6}$ alkyl substituted with one or more independently selected—$NR^{11c}R^{11d}$, and $R^{11c}$ and $R^{11d}$ are both H. In another embodiment, one of $R^{11c}$ and $R^{11d}$ is H, and the other is $C_{1-4}$ alkyl. In yet another embodiment, $R^{11c}$ and $R^{11d}$ are both $C_{1-4}$ alkyl. In a particular embodiment, one of $R^{11c}$ and $R^{11d}$ is H, and the other is —$CH_3$, —$CH_2CH_3$, or —$CH(CH_3)_2$. In another more particular embodiment, $R^{11c}$ and $R^{11d}$ are —$CH_3$, —$CH_2CH_3$, or —$CH(CH_3)_2$.

In one embodiment, the compound of the invention is according to any one of Formulae I-Vf, wherein $R^7$ is $C_{1-4}$ alkyl substituted with one or more independently selected—$NR^{11c}R^{11d}$, and $R^{11c}$ and $R^{11d}$ are both H. In another embodiment, one of $R^{11c}$ and $R^{11d}$ is H, and the other is $C_{1-4}$ alkyl. In yet another embodiment, $R^{11c}$ and $R^{11d}$ are both $C_{1-4}$ alkyl. In a particular embodiment, one of $R^{11c}$ and $R^{11d}$ is H, and the other is —$CH_3$, —$CH_2CH_3$, or —$CH(CH_3)_2$. In another more particular embodiment, $R^{11c}$ and $R^{11d}$ are —$CH_3$, —$CH_2CH_3$, or —$CH(CH_3)_2$.

In one embodiment, the compound of the invention is according to any one of Formulae I-Vf, wherein $R^7$ is $C_{1-6}$ alkyl substituted with one or more independently selected—C(=O)$R^{12}$, $R^{12}$ is —$NR^{14a}R^{14b}$, and each $R^{14a}$ and $R^{14b}$ is as previously described. In a particular embodiment, $R^{14a}$ and $R^{14b}$ are both H. In another particular embodiment, one of $R^{14a}$ and $R^{14b}$ is H, and the other is $C_{1-4}$ alkyl. In yet another particular embodiment, $R^{14a}$ and $R^{14b}$ are both $C_{1-4}$ alkyl. In a more particular embodiment, one of $R^{14a}$ and $R^{14b}$ is H, and the other is —$CH_3$, —$CH_2CH_3$, or —$CH(CH_3)_2$. In another more particular embodiment, $R^{14a}$ and $R^{14b}$ are —$CH_3$, —$CH_2CH_3$, or —$CH(CH_3)_2$.

In one embodiment, the compound of the invention is according to any one of Formulae I-Vf, wherein $R^7$ is $C_{1-4}$ alkyl substituted with one or more independently selected—C(=O)$R^{12}$, $R^{12}$ is —$NR^{14a}R^{14b}$, and each $R^{14a}$ and $R^{14b}$ is as previously described. In a particular embodiment, $R^{14a}$ and $R^{14b}$ are both H. In another particular embodiment, one of $R^{14a}$ and $R^{14b}$ is H, and the other is $C_{1-4}$ alkyl. In yet another particular embodiment, $R^{14a}$ and $R^{14b}$ are both $C_{1-4}$ alkyl. In a more particular embodiment, one of $R^{14a}$ and $R^{14b}$ is H, and the other is —$CH_3$, —$CH_2CH_3$, or —$CH(CH_3)_2$. In another more particular embodiment, $R^{14a}$ and $R^{14b}$ are —$CH_3$, —$CH_2CH_3$, or —$CH(CH_3)_2$.

In one embodiment, the compound of the invention is according to any one of Formulae I-Vf, wherein $R^7$ is $C_{1-6}$ alkyl substituted with one or more independently selected—C(=O)$R^{12}$, and $R^{12}$ is —OH.

In one embodiment, the compound of the invention is according to any one of Formulae I-Vf, wherein $R^7$ is $C_{1-4}$ alkyl substituted with one or more independently selected—C(=O)$R^{12}$, and $R^{12}$ is —OH.

In one embodiment, the compound of the invention is according to any one of Formulae I-Vf, wherein $R^7$ is $C_{1-6}$ alkyl substituted with one or more independently selected—C(=O)$R^{12}$, and $R^{12}$ is $C_{1-4}$ alkoxy. In a particular embodiment, $R^{12}$ is —O—$CH_3$, —O—$CH_2CH_3$, —O—$CH(CH_3)_2$, or —O—C$(CH_3)_3$.

In one embodiment, the compound of the invention is according to any one of Formulae I-Vf, wherein $R^7$ is $C_{1-4}$ alkyl substituted with one or more independently selected—C(=O)$R^{12}$, and $R^{12}$ is $C_{1-4}$ alkoxy. In a particular embodiment, $R^{12}$ is —O—$CH_3$, —O—$CH_2CH_3$, —O—$CH(CH_3)_2$, or —O—C$(CH_3)_3$.

In one embodiment, the compound of the invention is according to any one of Formulae I-Vf, wherein $R^7$ is $C_{1-6}$ alkyl substituted with one or more independently selected—$C(=O)R^{12}$, and $R^{12}$ is $C_{1-4}$ alkoxy substituted with one or more independently selected $C_{3-7}$ cycloalkyl, halo, —$NR^{15a}R^{15b}$, or 4-6 membered monocyclic heterocycloalkyl comprising one, two or three heteroatoms independently selected from N, O, and S. In a particular embodiment, $R^{12}$ is —O—$CH_3$, —O—$CH_2CH_3$, or —O—$CH(CH_3)_2$, each of which is substituted with one or more independently selected $C_{3-7}$ cycloalkyl, halo, —$NR^{15a}R^{15b}$, or 4-6 membered monocyclic heterocycloalkyl comprising one, two or three heteroatoms independently selected from N, O, and S. In another particular embodiment, $R^{12}$ is $C_{1-4}$ alkoxy substituted with one, two, or three independently selected $C_{3-7}$ cycloalkyl, halo, —$NR^{15a}R^{15b}$, or 4-6 membered monocyclic heterocycloalkyl comprising one, two or three heteroatoms independently selected from N, O, and S. In yet another particular embodiment, $R^{12}$ is $C_{1-4}$ alkoxy substituted with one or more independently selected cyclopropyl, cyclobutyl, cyclopentyl, F, Cl, —$NR^{15a}R^{15b}$, azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{12}$ is —O—$CH_3$ or —O—$CH_2CH_3$, each of which is substituted with one, two, or three $C_{3-7}$ cycloalkyl, halo, —$NR^{15a}R^{15b}$, or 4-6 membered monocyclic heterocycloalkyl comprising one, two or three heteroatoms independently selected from N, O, and S. In another more particular embodiment, $R^{12}$ is $C_{1-4}$ alkoxy substituted with one, two, or three cyclopropyl, cyclobutyl, or cyclopentyl, F, —$NR^{15a}R^{15b}$, or tetrahydrofuranyl. In a most particular embodiment, $R^{12}$ is —O—$CH_3$ or —O—$CH_2CH_3$, each of which is substituted with one, two, or three F. In another most particular embodiment, $R^{12}$ is —O—$CH_3$ or —O—$CH_2CH_3$, each of which is substituted with one cyclopropyl, cyclobutyl, cyclopentyl, —$NR^{15a}R^{15b}$, or tetrahydrofuranyl.

In one embodiment, the compound of the invention is according to any one of Formulae I-Vf, wherein $R^7$ is $C_{1-6}$ alkyl substituted with one or more independently selected—$C(=O)R^{12}$, $R^{12}$ is $C_{1-4}$ alkoxy substituted with one or more independently selected—$NR^{15a}R^{15b}$, and each $R^{15a}$ and $R^{15b}$ is as previously described. In a particular embodiment, $R^{15a}$ and $R^{15b}$ are both H. In another particular embodiment, one of $R^{15a}$ and $R^{15b}$ is H, and the other is $C_{1-4}$ alkyl. In yet another particular embodiment, both $R^{15a}$ and $R^{15b}$ are $C_{1-4}$ alkyl. In a more particular embodiment, one of $R^{15a}$ and $R^{15b}$ is H, and the other is —$CH_3$, —$CH_2CH_3$, or —$CH(CH_3)_2$. In another more particular embodiment, both $R^{15a}$ and $R^{15b}$ are —$CH_3$, —$CH_2CH_3$, or —$CH(CH_3)_2$. In a most particular embodiment, both $R^{15a}$ and $R^{15b}$ are —$CH_2CH_3$.

In one embodiment, the compound of the invention is according to any one of Formulae I-Vf, wherein $R^7$ is $C_{1-4}$ alkyl substituted with one or more independently selected—$C(=O)R^{12}$, and $R^{12}$ is $C_{1-4}$ alkoxy substituted with one or more independently selected $C_{3-7}$ cycloalkyl or halo. In a particular embodiment, $R^{12}$ is —O—$CH_3$, —O—$CH_2CH_3$, or —O—$CH(CH_3)_2$, each of which is substituted with one or more independently selected $C_{3-7}$ cycloalkyl or halo. In another particular embodiment, $R^{12}$ is $C_{1-4}$ alkoxy substituted with one, two, or three independently selected $C_{3-7}$ cycloalkyl or halo. In yet another particular embodiment, $R^{12}$ is $C_{1-4}$ alkoxy substituted with one or more independently selected cyclopropyl, cyclobutyl, cyclopentyl, F, or Cl. In a more particular embodiment, $R^{12}$ is —O—$CH_3$ or —O—$CH_2CH_3$, each of which is substituted with one, two, or three $C_{3-7}$ cycloalkyl or halo. In another more particular embodiment, $R^{12}$ is $C_{1-4}$ alkoxy substituted with one, two, or three cyclopropyl, cyclobutyl, or cyclopentyl or F. In a most particular embodiment, $R^{12}$ is —O—$CH_3$ or —O—$CH_2CH_3$, each of which is substituted with one, two, or three F. In another most particular embodiment, $R^{12}$ is —O—$CH_3$ or —O—$CH_2CH_3$, each of which is substituted with one cyclopropyl, cyclobutyl, or cyclopentyl.

In one embodiment, the compound of the invention is according to any one of Formulae I-Vf, wherein $R^7$ is $C_{1-6}$ alkyl substituted with one or more independently selected—$C(=O)R^{12}$, and $R^{12}$ is —O-(4-6 membered monocyclic heterocycloalkyl comprising one, two or three heteroatoms independently selected from N, O, and S). In a particular embodiment, $R^{12}$ is —O-azetidinyl, —O-oxetanyl, —O-pyrrolidinyl, —O-tetrahydrofuranyl, —O-piperidinyl, —O-tetrahydropyranyl, —O-tetrahydrothiopyranyl, —O-morpholinyl, —O-thiomorpholinyl, —O-dioxanyl, or —O-piperazinyl. In a more particular embodiment, $R^{12}$ is —O-tetrahydrofuranyl.

In one embodiment, the compound of the invention is according to any one of Formulae I-Vf, wherein $R^7$ is $C_{1-6}$ alkyl substituted with one or more independently selected—$C(=O)R^{12}$, and $R^{12}$ is —O—($C_{3-7}$ monocyclic cycloalkyl). In a particular embodiment, $R^{12}$ is —O-cyclopropyl, —O-cyclobutyl, or —O-cyclopentyl. In a more particular embodiment, $R^{12}$ is —O-cyclopropyl.

In one embodiment, the compound of the invention is according to any one of Formulae I-Vf, wherein $R^7$ is $C_{3-7}$ cycloalkyl. In a particular embodiment, $R^7$ is cyclopropyl, cyclobutyl, cyclopentyl, or cyclohexyl. In a more particular embodiment, $R^7$ is cyclopropyl.

In one embodiment, the compound of the invention is according to any one of Formulae I-Vf, wherein $R^7$ is 4-6 membered monocyclic heterocycloalkyl comprising one, two or three heteroatoms independently selected from N, O, and S. In a particular embodiment, $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^7$ is azetidinyl, pyrrolidinyl, tetrahydrofuranyl, piperidinyl, tetrahydropyranyl, morpholinyl, or piperazinyl.

In one embodiment, the compound of the invention is according to any one of Formulae I-Vf, wherein $R^7$ is 4-6 membered monocyclic heterocycloalkyl comprising one, two or three heteroatoms independently selected from N, O, and S, substituted with —$C(=O)C_{1-4}$ alkoxy or $C_{1-4}$ alkyl optionally substituted with —CN. In a particular embodiment, $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with —$C(=O)C_{1-4}$ alkoxy or $C_{1-4}$ alkyl optionally substituted with —CN. In another particular embodiment, $R^7$ is 4-6 membered monocyclic heterocycloalkyl comprising one, two or three heteroatoms independently selected from N, O, and S, substituted with —$C(=O)$—O—$CH_3$, —$C(=O)$—O—$CH_2CH_3$, —$C(=O)$—O—$CH(CH_3)_2$, —$C(=O)$—O—$C(CH_3)_3$, —$CH_3$, —$CH_2CH_3$, —CH ($CH_3)_2$, —$CH_2$—CN, —$CH_2CH_2$—CN, —$CH_2CH(CH_3)$—CN, or —$CH(CH_3)CH_2$—CN. In a more particular embodiment, $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with —$C(=O)$—O—$CH_3$, —$C(=O)$—O—$CH_2CH_3$, —$C(=O)$—O—$CH(CH_3)_2$, —$C(=O)$—O—$C(CH_3)_3$, —$CH_3$, —$CH_2CH_3$, —CH ($CH_3)_2$, —$CH_2$—CN, —CH$_2$CH$_2$—CN, —CH$_2$CH(CH$_3$)—CN, or —CH(CH$_3$)CH$_2$—CN. In a further more particular embodiment, R$^7$ is azetidinyl, pyrrolidinyl, piperidinyl, or piperazinyl, each of which is substituted with —C(=O)—O—CH$_3$, —C(=O)—O—CH$_2$CH$_3$, —C(=O)—O—CH(CH$_3$)$_2$, —C(=O)—O—C(CH$_3$)$_3$, —CH$_3$, —CH$_2$CH$_3$, —CH (CH$_3$)$_2$, —CH$_2$—CN, —CH$_2$CH$_2$—CN, —CH$_2$CH(CH$_3$)—CN, or —CH(CH$_3$)CH$_2$—CN. In another further more particular embodiment, R$^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with —C(=O)—O—C(CH$_3$)$_3$, —CH$_3$, —CH$_2$—CN, or —CH$_2$CH$_2$—CN. In a most particular embodiment, R$^7$ is azetidinyl, pyrrolidinyl, piperidinyl, or piperazinyl, each of which is substituted with —C(=O)—O—C(CH$_3$)$_3$, —CH$_3$, —CH$_2$—CN, or —CH$_2$CH$_2$—CN.

In one embodiment, the compound of the invention is according to any one of Formulae I-IIIf, and Va-Vf, wherein R$^{3b}$ is halo or —OH. In a particular embodiment, R$^{3b}$ is F, Cl, or —OH.

In one embodiment, the compound of the invention is according to anyone of Formulae I-IIIf, and Va-f, wherein R$^{3b}$ is C$_{1-4}$ alkyl. In a particular embodiment, R$^{3b}$ is —CH$_3$, —CH$_2$CH$_3$, or —CH(CH$_3$)$_2$. In a more particular embodiment, R$^{3b}$ is —CH$_3$, or —CH$_2$CH$_3$. In a most particular embodiment, R$^{3b}$ is —CH$_3$.

In one embodiment, the compound of the invention is according to any one of Formulae I-IIIf, and Va-f, wherein R$^{3b}$ is C$_{1-4}$ alkoxy. In a particular embodiment, R$^{3b}$ is —O—CH$_3$, —O—CH$_2$CH$_3$, or —O—CH(CH$_3$)$_2$. In a more particular embodiment, R$^{3b}$ is —O—CH$_3$ or —O—CH(CH$_3$)$_2$. In a most particular embodiment, R$^{3b}$ is —O—CH$_3$.

In one embodiment, the compound of the invention is according to any one of Formulae I-IIIf, and Va-f, wherein R$^{3b}$ is C$_{1-4}$ alkoxy substituted with one or more independently selected halo, —OH or C$_{1-4}$ alkoxy. In a particular embodiment, R$^{3b}$ is —O—CH$_3$, —O—CH$_2$CH$_3$, or —O—CH(CH$_3$)$_2$, each of which is substituted with one or more independently selected halo, —OH or C$_{1-4}$ alkoxy. In another particular embodiment, R$^{3b}$ is C$_{1-4}$ alkoxy substituted with one, two, or three independently selected halo, —OH or C$_{1-4}$ alkoxy. In yet another particular embodiment, R$^{3b}$ is C$_{1-4}$ alkoxy substituted with one or more independently selected F, Cl, —OH, —O—CH$_3$, —O—CH$_2$CH$_3$, or —O—CH(CH$_3$)$_2$. In more a particular embodiment, R$^{3b}$ is —O—CH$_3$ or —O—CH$_2$CH$_3$, each of which is substituted with one or more independently selected halo, —OH or C$_{1-4}$ alkoxy. In another more particular embodiment, R$^{3b}$ is C$_{1-4}$ alkoxy substituted with one, two, or three F or Cl. In yet another more particular embodiment, R$^{3b}$ is C$_{1-4}$ alkoxy substituted with one —OH, —O—CH$_3$, —O—CH$_2$CH$_3$, or —O—CH(CH$_3$)$_2$. In a further more particular embodiment, R$^{3b}$ is C$_{1-4}$ alkoxy substituted with one or more independently selected F, —OH, or —O—CH$_3$. In an even more particular embodiment, R$^{3b}$ is —O—CH$_3$ or —O—CH$_2$CH$_3$, each of which is substituted with one, two, or three F. In another even more particular embodiment, R$^3$ is —O—CH$_3$ or —O—CH$_2$CH$_3$, each of which is substituted with one —OH or —O—CH$_3$. In a most particular embodiment, R$^{3b}$ is —O—CHF$_2$.

In one embodiment, the compound of the invention is according to any one of Formulae I-IIIf, and Va-f, wherein R$^{3b}$ is —NR$^{8a}$R$^{8b}$, and each R$^{8a}$ and R$^{8b}$ is as previously described. In a particular embodiment, R$^{8a}$ and R$^{8b}$ are both H. In another particular embodiment, one of R$^{8a}$ and R$^{8b}$ is H, and the other is C$_{1-4}$ alkyl optionally substituted with one —OH or C$_{1-4}$ alkoxy. In yet another particular embodiment, R$^{8a}$ and R$^{8b}$ are both C$_{1-4}$ alkyl optionally substituted with one —OH or C$_{1-4}$ alkoxy. In a more particular embodiment, one of R$^{8a}$ and R$^{8b}$ is H, and the other is —CH$_3$, —CH$_2$CH$_3$, or —CH(CH$_3$)$_2$. In another more particular embodiment, one of R$^{8a}$ and R$^{8b}$ is H, and the other is —CH$_3$, —CH$_2$CH$_3$, or —CH(CH$_3$)$_2$, each of which is substituted with one —OH, —O—CH$_3$, —O—CH$_2$CH$_3$, or —O—CH(CH$_3$)$_2$. In a most particular embodiment, R$^{3b}$ is —NH—CH$_3$, —NH—CH(CH$_3$)$_2$, or —NH—CH$_2$CH$_2$—OH.

In one embodiment, the compound of the invention is according to Formula VIa, VIb, VIc, VId, VIe, or VIf:

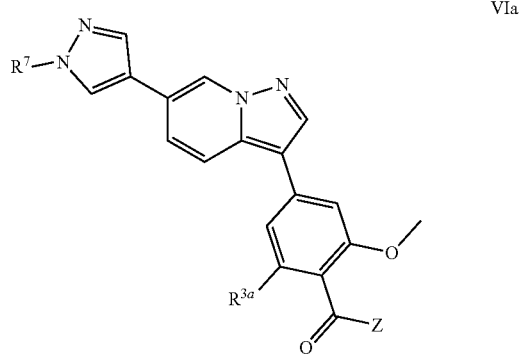

VIa

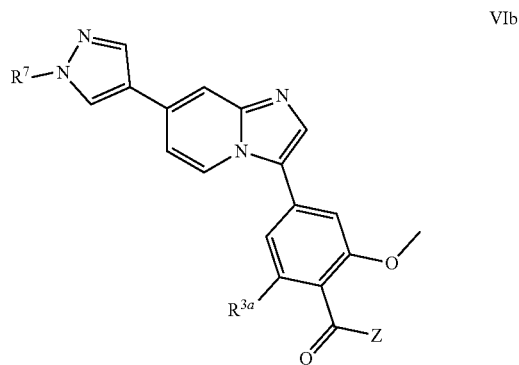

VIb

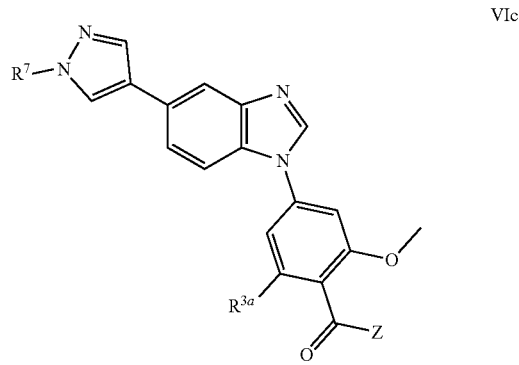

VIc

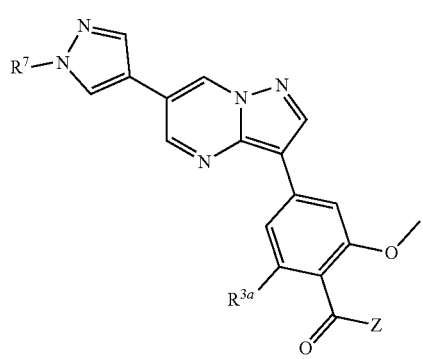

VId

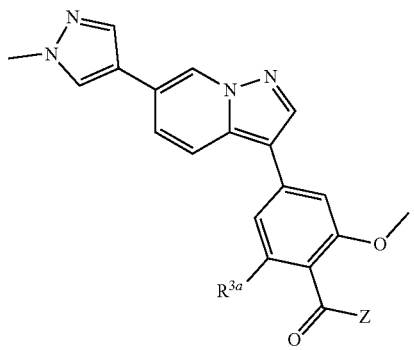

VIIa

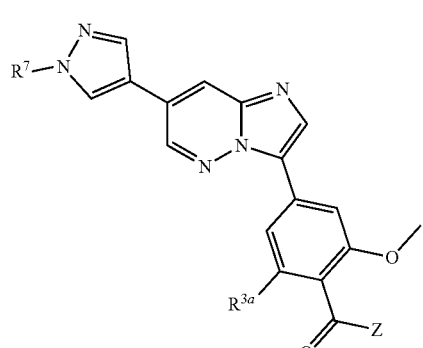

VIe

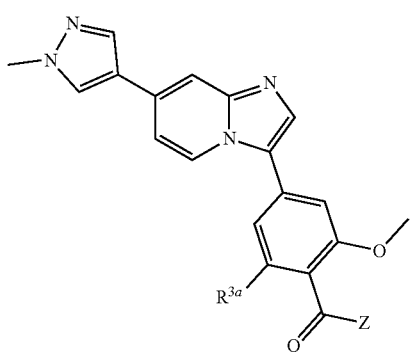

VIIb

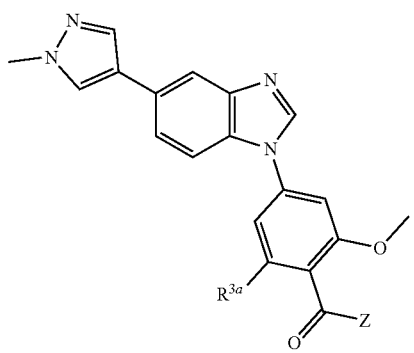

VIIc

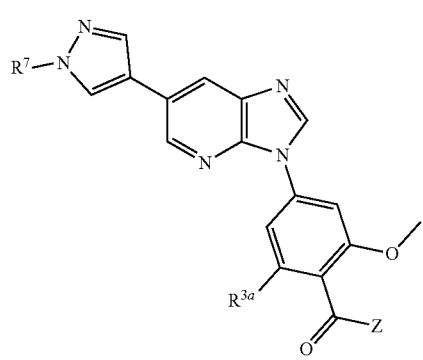

VIf wherein $R^{3a}$, $R^7$ and Z are as described above.

In one embodiment, the compound of the invention is according to any one of Formulae VIa-f, wherein $R^7$ is $C_{1-4}$ alkyl. In a particular embodiment, $R^7$ is —$CH_3$, —$CH_2CH_3$, or —$CH(CH_3)_2$. In a more particular embodiment, $R^7$ is —$CH_3$ or —$CH_2CH_3$. In a most particular embodiment, $R^7$ is —$CH_3$.

In one embodiment, the compound of the invention is according to Formula VIIa, VIIb, VIIc, VIId, VIe, or VIIf:

VIId

-continued

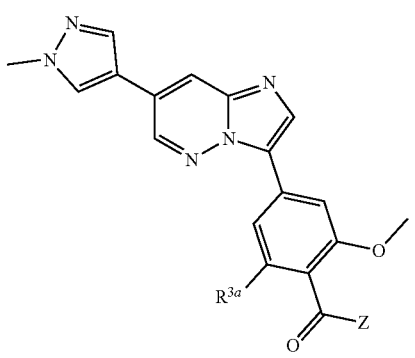

VIIe

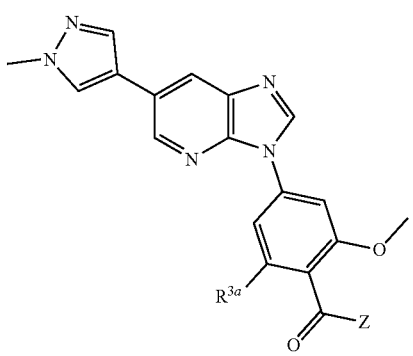

VIIf wherein R$^{3a}$ and Z are as described above.

In one embodiment, the compound of the invention is according to any one of Formulae I-VIIf, wherein R$^{3a}$ is halo or —OH. In a particular embodiment, R$^{3a}$ is F, Cl, or —OH.

In one embodiment, the compound of the invention is according to any one of Formulae I-VIIf, wherein R$^{3a}$ is C$_{1-4}$ alkyl. In a particular embodiment, R$^{3a}$ is —CH$_3$, —CH$_2$CH$_3$, or —CH(CH$_3$)$_2$. In a more particular embodiment, R$^{3a}$ is —CH$_3$, or —CH$_2$CH$_3$. In a most particular embodiment, R$^{3a}$ is —CH$_3$.

In one embodiment, the compound of the invention is according to any one of Formulae I-VIIf, wherein R$^{3a}$ is C$_{1-4}$ alkoxy. In a particular embodiment, R$^{3a}$ is —O—CH$_3$, —O—CH$_2$CH$_3$, or —O—CH(CH$_3$)$_2$. In a more particular embodiment, R$^{3a}$ is —O—CH$_3$ or —O—CH(CH$_3$)$_2$. In a most particular embodiment, R$^{3a}$ is —O—CH$_3$.

In one embodiment, the compound of the invention is according to any one of Formulae I-VIIf, wherein R$^{3a}$ is C$_{1-4}$ alkoxy substituted with one or more independently selected halo, —OH or C$_{1-4}$ alkoxy. In a particular embodiment, R$^{3a}$ is —O—CH$_3$, —O—CH$_2$CH$_3$, or —O—CH(CH$_3$)$_2$, each of which is substituted with one or more independently selected halo, —OH or C$_{1-4}$ alkoxy. In another particular embodiment, R$^{3a}$ is C$_{1-4}$ alkoxy substituted with one, two, or three independently selected halo, —OH or C$_{1-4}$ alkoxy. In yet another particular embodiment, R$^{3a}$ is C$_{1-4}$ alkoxy substituted with one or more independently selected F, Cl, —OH, —O—CH$_3$, —O—CH$_2$CH$_3$, or —O—CH(CH$_3$)$_2$. In more a particular embodiment, R$^{3a}$ is —O—CH$_3$ or —O—CH$_2$CH$_3$, each of which is substituted with one or more independently selected halo, —OH or C$_{1-4}$ alkoxy. In another more particular embodiment, R$^{3a}$ is C$_{1-4}$ alkoxy substituted with one, two, or three F or Cl. In yet another more particular embodiment, R$^{3a}$ is C$_{1-4}$ alkoxy substituted with one —OH, —O—CH$_3$, —O—CH$_2$CH$_3$, or —O—CH(CH$_3$)$_2$. In a further more particular embodiment, R$^{3a}$ is C$_{1-4}$ alkoxy substituted with one or more independently selected F, —OH, or —O—CH$_3$. In an even more particular embodiment, R$^{3a}$ is —O—CH$_3$ or —O—CH$_2$CH$_3$, each of which is substituted with one, two, or three F. In another even more particular embodiment, R$^{3a}$ is —O—CH$_3$ or —O—CH$_2$CH$_3$, each of which is substituted with one —OH or —O—CH$_3$. In a most particular embodiment, R$^{3a}$ is —O—CHF$_2$.

In one embodiment, the compound of the invention is according to any one of Formulae I-VIIf, wherein R$^{3a}$ is —NR$^{8a}$R$^{8b}$, and each R$^{8a}$ and R$^{8b}$ is as previously described. In a particular embodiment, R$^{8a}$ and R$^{8b}$ are both H. In another particular embodiment, one of R$^{8a}$ and R$^{8b}$ is H, and the other is C$_{1-4}$ alkyl optionally substituted with one —OH or C$_{1-4}$ alkoxy. In yet another particular embodiment, R$^{8a}$ and R$^{8b}$ are both C$_{1-4}$ alkyl optionally substituted with one —OH or C$_4$ alkoxy. In a more particular embodiment, one of R$^{8a}$ and R$^{8b}$ is H, and the other is —CH$_3$, —CH$_2$CH$_3$, or —CH(CH$_3$)$_2$. In another more particular embodiment, one of R$^{8a}$ and R$^{8b}$ is H, and the other is —CH$_3$, —CH$_2$CH$_3$, or —CH(CH$_3$)$_2$, each of which is substituted with one —OH, —O—CH$_3$, —O—CH$_2$CH$_3$, or —O—CH(CH$_3$)$_2$. In a most particular embodiment, R$^{3a}$ is —NH—CH$_3$, —NH—CH(CH$_3$)$_2$, or —NH—CH$_2$CH$_2$—OH.

In one embodiment, the compound of the invention is according to Formula VIIIa, VIIIb, VIIIc, or VIIId:

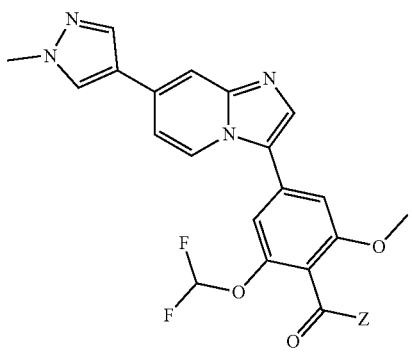

VIIIa

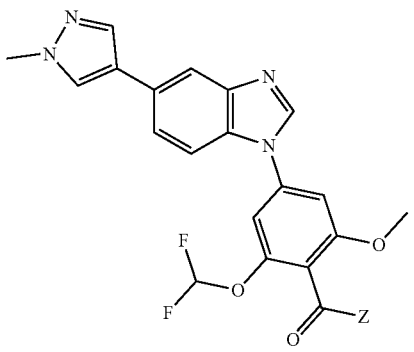

VIIIb

-continued

VIIIc

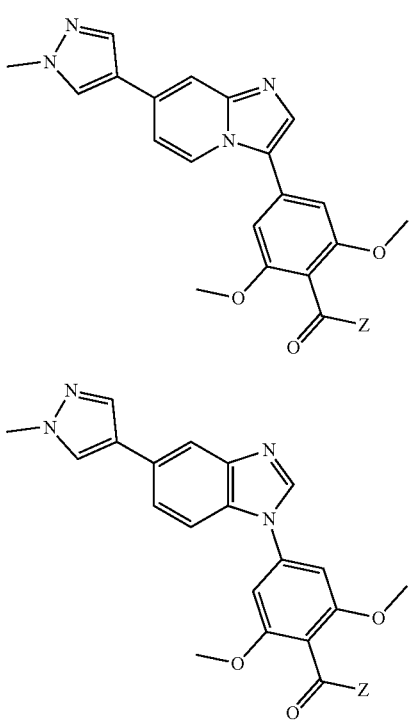

VIIId wherein Z is as described above.

In one embodiment, the compound of the invention is according to any one of Formulae I-IIIf, and Va-VIIId, wherein Z is —NR$^{5a}$R$^{5b}$, and R$^{5a}$ and R$^{5b}$ are as previously described. In a particular embodiment, R$^{5a}$ is H. In another particular embodiment, R$^{5a}$ is C$_{1-4}$ alkyl. In a more particular embodiment, R$^{5a}$ is —CH$_3$, —CH$_2$CH$_3$, or —CH(CH$_3$)$_2$. In a most particular embodiment, R$^{5a}$ is —CH$_3$.

In one embodiment, the compound of the invention is according to any one of Formulae I-IIIf, and Va-VIIId, wherein Z is —NR$^{5a}$R$^{5b}$, R$^{5a}$ is as previously described, and R$^{5b}$ is C$_{1-6}$ alkyl. In a particular embodiment, R$^{5b}$ is —CH$_3$, —CH$_2$CH$_3$, —CH$_2$CH$_2$CH$_3$, —CH(CH$_3$)$_2$, —CH$_2$CH(CH$_3$)$_2$, —C(CH$_3$)$_3$, —CH(CH$_3$)CH$_2$CH$_3$, or —CH(CH$_3$)CH(CH$_3$)$_2$. In a more particular embodiment, R$^{5b}$ is —CH$_3$, —CH$_2$CH$_3$, —CH$_2$CH$_2$CH$_3$, —CH(CH$_3$)$_2$, or —CH(CH$_3$)CH(CH$_3$)$_2$. In a most particular embodiment, R$^{5b}$ is —CH$_2$CH$_3$.

In one embodiment, the compound of the invention is according to any one of Formulae I-IIIf, and Va-VIIId, wherein Z is —NR$^{5a}$R$^{5b}$, R$^{5a}$ is as previously described, and R$^{5b}$ is C$_{1-6}$ alkyl substituted with one or more independently selected R$^9$. In a particular embodiment, R$^{5b}$ is —CH$_3$, —CH$_2$CH$_3$, —CH$_2$CH$_2$CH$_3$, —CH(CH$_3$)$_2$, —CH$_2$CH(CH$_3$)$_2$, —C(CH$_3$)$_3$, —CH(CH$_3$)CH$_2$CH$_3$, or —CH(CH$_3$)CH(CH$_3$)$_2$, each of which is substituted with one or more independently selected R$^9$. In another particular embodiment, R$^{5b}$ is C$_{1-6}$ alkyl substituted with one, two, or three independently selected R$^9$. In a more particular embodiment, R$^{5b}$ is —CH$_3$, —CH$_2$CH$_3$, —CH$_2$CH$_2$CH$_3$, —CH(CH$_3$)$_2$, —C(CH$_3$)$_3$, or —CH(CH$_3$)CH(CH$_3$)$_2$, each of which is substituted with one or more independently selected R$^9$. In another more particular embodiment, R$^{5b}$ is —CH$_3$, —CH$_2$CH$_3$, —CH$_2$CH$_2$CH$_3$, —CH(CH$_3$)$_2$, —CH$_2$CH(CH$_3$)$_2$, —C(CH$_3$)$_3$, —CH(CH$_3$)CH$_2$CH$_3$, or —CH(CH$_3$)CH(CH$_3$)$_2$, each of which is substituted with one, two, or three independently selected R$^9$. In yet another more particular embodiment, R$^{5b}$ is C$_{1-6}$ alkyl substituted with one R$^9$. In an even more particular embodiment, R$^{5b}$ is —CH$_3$, —CH$_2$CH$_3$, —CH$_2$CH$_2$CH$_3$, —CH(CH$_3$)$_2$, —C(CH$_3$)$_3$, or —CH(CH$_3$)CH(CH$_3$)$_2$, each of which is substituted with one, two, or three independently selected R$^9$. In another even more particular embodiment, R$^{5b}$ is —CH$_3$, —CH$_2$CH$_3$, —CH$_2$CH$_2$CH$_3$, —CH(CH$_3$)$_2$, —CH$_2$CH(CH$_3$)$_2$, —C(CH$_3$)$_3$, —CH(CH$_3$)CH$_2$CH$_3$, or —CH(CH$_3$)CH(CH$_3$)$_2$, each of which is substituted with one R$^9$. In a most particular embodiment, R$^{5b}$ is —CH$_3$, —CH$_2$CH$_3$, —CH$_2$CH$_2$CH$_3$, —CH(CH$_3$)$_2$, —C(CH$_3$)$_3$, or —CH(CH$_3$)CH(CH$_3$)$_2$, each of which is substituted with one R$^9$.

In one embodiment, the compound of the invention is according to anyone of Formulae I-IIIf, and Va-VIIId, wherein Z is —NR$^{5a}$R$^{5b}$, R$^{5a}$ is as previously described, R$^{5b}$ is C$_{1-6}$ alkyl substituted with one or more independently selected R$^9$, and R$^9$ is halo, —CN, —OH, C$_{1-4}$ alkoxy, or —S(=O)$_2$—C$_{1-4}$ alkyl. In a particular embodiment, each R$^9$ is independently F, Cl, —CN, —OH, —O—CH$_3$, —O—CH$_2$CH$_3$, —O—CH(CH$_3$)$_2$, —S(=O)$_2$—CH$_3$, —S(=O)$_2$—CH$_2$CH$_3$, or —S(=O)$_2$—CH(CH$_3$)$_2$. In a more particular embodiment, each R$^9$ is independently F, —CN, —OH, —O—CH$_3$, or —S(=O)$_2$—CH$_3$.

In one embodiment, the compound of the invention is according to anyone of Formulae I-IIIf, and Va-VIIId, wherein Z is —NR$^{5a}$R$^{5b}$, R$^{5a}$ is as previously described, R$^{5b}$ is C$_{1-6}$ alkyl substituted with one or more independently selected R$^9$, and R$^9$ is —NR$^{11e}$R$^{11f}$, and each R$^{11e}$ and R$^{11f}$ is as previously described. In a particular embodiment, R$^{11e}$ and R$^{11f}$ are both H. In another particular embodiment, one of R$^{11e}$ and R$^{11f}$ is H, and the other is C$_{1-4}$ alkyl. In yet another particular embodiment, R$^{11e}$ and R$^{11f}$ are both C$_{1-4}$ alkyl. In a more particular embodiment, one of R$^{11e}$ and R$^{11f}$ is H, and the other is —CH$_3$, —CH$_2$CH$_3$, or —CH(CH$_3$)$_2$. In another more particular embodiment, R$^{11e}$ and R$^{11f}$ are —CH$_3$, —CH$_2$CH$_3$, or —CH(CH$_3$)$_2$. In a most particular embodiment, R$^{11e}$ and R$^{11f}$ are —CH$_3$.

In one embodiment, the compound of the invention is according to anyone of Formulae I-IIIf, and Va-VIIId, wherein Z is —NR$^{5a}$R$^{5b}$, R$^{5a}$ is as previously described, R$^{5b}$ is C$_{1-6}$ alkyl substituted with one or more independently selected R$^9$, and R$^9$ is 4-7 membered monocyclic heterocycloalkyl comprising one, two or three heteroatoms independently selected from N, O, and S. In a particular embodiment, R$^9$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, R$^9$ is dioxanyl.

In one embodiment, the compound of the invention is according to any one of Formulae I-IIIf, and Va-VIIId, wherein Z is —NR$^{5a}$R$^{5b}$, R$^{5a}$ is as previously described, R$^{5b}$ is C$_{1-6}$ alkyl substituted with one or more independently selected R$^9$, and R$^9$ is 5-6 membered monocyclic heteroaryl comprising one, two or three heteroatoms independently selected from N, O, and S. In a particular embodiment, R$^9$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, R$^9$ is imidazolyl, pyrazolyl, or pyridinyl. In a most particular embodiment, R$^9$ is pyridinyl.

In one embodiment, the compound of the invention is according to any one of Formulae I-IIIf, and Va-VIIId, wherein Z is —NR$^{5a}$R$^{5b}$, R$^{5a}$ is as previously described, R$^{5b}$ is C$_{1-6}$ alkyl substituted with one or more independently selected R$^9$, and R$^9$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected $C_{1-4}$ alkyl. In another particular embodiment, $R^9$ is 5-6 membered monocyclic heteroaryl comprising one, two or three heteroatoms independently selected from N, O, and S, which heteroaryl is substituted with one $C_{1-4}$ alkyl. In yet another particular embodiment, $R^9$ is 5-6 membered monocyclic heteroaryl comprising one, two or three heteroatoms independently selected from N, O, and S, which heteroaryl is substituted with one or more independently selected —$CH_3$, —$CH_2CH_3$, or —$CH(CH_3)_2$. In a more particular embodiment, $R^9$ is imidazolyl or pyrazolyl, each of which is substituted with one or more independently selected $C_{1-4}$ alkyl. In another more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one $C_{1-4}$ alkyl. In yet another more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected—$CH_3$, —$CH_2CH_3$, or —$CH(CH_3)_2$. In a further more particular embodiment, $R^9$ is 5-6 membered monocyclic heteroaryl comprising one, two or three heteroatoms independently selected from N, O, and S, which heteroaryl is substituted with one —$CH_3$, —$CH_2CH_3$, or —$CH(CH_3)_2$. In yet a further more particular embodiment, $R^9$ is 5-6 membered monocyclic heteroaryl comprising one, two or three heteroatoms independently selected from N, O, and S, which heteroaryl is substituted with one or more —$CH_3$. In an even more particular embodiment, $R^9$ is imidazolyl or pyrazolyl, each of which is substituted with one $C_{1-4}$ alkyl. In another even more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one —$CH_3$, —$CH_2CH_3$, or —$CH(CH_3)_2$. In yet another even more particular embodiment, $R^9$ is 5-6 membered monocyclic heteroaryl comprising one, two or three heteroatoms independently selected from N, O, and S, which heteroaryl is substituted with one —$CH_3$. In a most particular embodiment, $R^9$ is imidazolyl or pyrazolyl, each of which is substituted with one —$CH_3$.

In one embodiment, the compound of the invention is according to anyone of Formulae I-IIIf, and Va-VIIId, wherein Z is —$NR^{5a}R^{5b}$, $R^{5a}$ is as previously described, and $R^{5b}$ is $C_{3-7}$ cycloalkyl. In a particular embodiment, $R^{5b}$ is cyclopropyl, cyclobutyl, cyclopentyl, or cyclohexyl. In a more particular embodiment, $R^{5b}$ is cyclopropyl, cyclobutyl, cyclopentyl. In a most particular embodiment, $R^{5b}$ is cyclopropyl.

In one embodiment, the compound of the invention is according to any one of Formulae I-IIIf, and Va-VIIId, wherein Z is —$NR^{5a}R^{5b}$, $R^{5a}$ is as previously described, and $R^{5b}$ is $C_{3-7}$ cycloalkyl substituted with one or more independently selected $R^{10}$. In a particular embodiment, $R^{5b}$ is cyclopropyl, cyclobutyl, cyclopentyl, or cyclohexyl, each of which is substituted with one or more independently selected $R^{10}$. In another particular embodiment, $R^{5b}$ is $C_{3-7}$ cycloalkyl substituted with one, two, or three independently selected $R^{10}$. In a more particular embodiment, $R^{5b}$ is cyclopropyl, cyclobutyl, cyclopentyl, or cyclohexyl, each of which is substituted with one, two, or three independently selected $R^{10}$. In another more particular embodiment, $R^{5b}$ is $C_{3-7}$ cycloalkyl substituted with one $R^{10}$. In a most particular embodiment, $R^{5b}$ is cyclopropyl, cyclobutyl, cyclopentyl, or cyclohexyl, each of which is substituted with one $R^{10}$.

In one embodiment, the compound of the invention is according to any one of Formulae I-IIIf, and Va-VIIId, wherein Z is —$NR^{5a}R^{5b}$, $R^{5a}$ is as previously described, $R^{5b}$ is $C_{3-7}$ cycloalkyl substituted with one or more independently selected $R^{10}$, and $R^{10}$ is halo, —OH, or $C_{1-4}$ alkoxy. In a particular embodiment, $R^{10}$ is F, Cl, —OH, —O—$CH_3$, —O—$CH_2CH_3$, or —O—$CH(CH_3)_2$. In a more particular embodiment, $R^{10}$ is F, —OH, or —O—$CH_3$.

In one embodiment, the compound of the invention is according to anyone of Formulae I-IIIf, and Va-VIIId, wherein Z is —$NR^{5a}R^{5b}$, $R^{5a}$ is as previously described, $R^{5b}$ is $C_{3-7}$ cycloalkyl substituted with one or more independently selected $R^{10}$, and $R^{10}$ is $C_{1-4}$ alkyl. In a particular embodiment, $R^{10}$ is —$CH_3$, —$CH_2CH_3$, or —$CH(CH_3)_2$. In a more particular embodiment, $R^{10}$ is —$CH_3$.

In one embodiment, the compound of the invention is according to anyone of Formulae I-IIIf, and Va-VIIId, wherein Z is —$NR^{5a}R^{5b}$, $R^{5a}$ is as previously described, $R^{5b}$ is $C_{3-7}$ cycloalkyl substituted with one or more independently selected $R^{10}$, and $R^{10}$ is $C_{1-4}$ alkyl substituted with one or more independently selected halo, —OH, or $C_{1-4}$ alkoxy. In a particular embodiment, $R^1$ is —$CH_3$, —$CH_2CH_3$, or —$CH(CH_3)_2$, each of which is substituted with one or more independently selected halo, —OH, or $C_{1-4}$ alkoxy. In another particular embodiment, $R^{10}$ is $C_{1-4}$ alkyl substituted with one, two, or three independently selected halo, —OH, or $C_{1-4}$ alkoxy. In yet another particular embodiment, $R^{10}$ is $C_{1-4}$ alkyl substituted with one or more F, Cl, —OH, —O—$CH_3$, —O—$CH_2CH_3$, or —O—$CH(CH_3)_2$. In a more particular embodiment, $R^{10}$ is —$CH_3$ substituted with one or more independently selected halo, —OH, or $C_{1-4}$ alkoxy. In another more particular embodiment, $R^{10}$ is $C_{1-4}$ alkyl substituted with one halo, —OH, or $C_{1-4}$ alkoxy. In yet another more particular embodiment, $R^{10}$ is $C_{1-4}$ alkyl substituted with one or more independently selected F or —OH. In a further more particular embodiment, $R^{10}$ is —$CH_3$, —$CH_2CH_3$, or —$CH(CH_3)_2$, each of which is substituted with one, two, or three independently selected halo, —OH, or $C_{1-4}$ alkoxy. In yet a further more particular embodiment, $R^{10}$ is $C_{1-4}$ alkyl substituted with one, two, or three independently selected F, Cl, —OH, —O—$CH_3$, —O—$CH_2CH_3$, or —O—$CH(CH_3)_2$. In a most particular embodiment, $R^{10}$ is —$CH_2F$, —$CHF_2$, —$CF_3$, or —$CH_2$—OH.

In one embodiment, the compound of the invention is according to any one of Formulae I-IIIf, and Va-VIIId, wherein Z is —$NR^{5a}R^{5b}$, $R^{5a}$ is as previously described, $R^{5b}$ is $C_{3-7}$ cycloalkyl substituted with one or more independently selected $R^{10}$, and $R^{10}$ is —$NR^{11g}R^{11h}$, and each $R^{11g}$ and $R^{11h}$ is as previously described. In a particular embodiment, $R^{11g}$ and $R^{11h}$ are both H. In another particular embodiment, one of $R^{11g}$ and $R^{11h}$ is H, and the other is $C_{1-4}$ alkyl. In yet another particular embodiment, $R^{11g}$ and $R^{11h}$ are both $C_{1-4}$ alkyl. In a more particular embodiment, one of $R^{11g}$ and $R^{11h}$ is H, and the other is —$CH_3$, —$CH_2CH_3$, or —$CH(CH_3)_2$. In another more particular embodiment, $R^{11g}$ and $R^{11h}$ are —$CH_3$, —$CH_2CH_3$, or —$CH(CH_3)_2$. In a most particular embodiment, $R^{11g}$ and $R^{11h}$ are —$CH_3$.

In one embodiment, the compound of the invention is according to any one of Formulae I-IIIf, and Va-VIIId, wherein Z is —NR$^{5a}$R$^{5b}$, R$^{5a}$ is as previously described, and R$^{5b}$ is 4-7 membered monocyclic heterocycloalkyl comprising one, two or three heteroatoms independently selected from N, O, and S. In a particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl. In a more particular embodiment, R$^{5b}$ is oxetanyl, thietanyl, or tetrahydrothiopyranyl. In a most particular embodiment, R$^{5b}$ is oxetanyl.

In one embodiment, the compound of the invention is according to anyone of Formulae I-IIIf, and Va-VIIId, wherein Z is —NR$^{5a}$R$^{5b}$, R$^{5a}$ is as previously described, and R$^{5b}$ is 4-7 membered monocyclic heterocycloalkyl comprising one, two or three heteroatoms independently selected from N, O, and S, which heterocycloalkyl is substituted with one or more oxo. In a particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl, each of which is substituted with one or more oxo. In another particular embodiment, R$^{5b}$ is 4-7 membered monocyclic heterocycloalkyl comprising one, two or three heteroatoms independently selected from N, O, and S, which heterocycloalkyl is substituted with one oxo. In a more particular embodiment, R$^{5b}$ is thietanyl or tetrahydrothiophenyl, each of which is substituted with one or more oxo. In another more particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl, each of which is substituted with one oxo. In a most particular embodiment, R$^{5b}$ is thietanyl or tetrahydrothiophenyl, each of which is substituted with two oxo.

In one embodiment, the compound of the invention is according to anyone of Formulae I-IIIf, and Va-VIIId, wherein Z is —NR$^{5a}$R$^{5b}$, R$^{5a}$ is as previously described, and R$^{5b}$ is 5-6 membered monocyclic heteroaryl comprising one, two or three heteroatoms independently selected from N, O, and S. In a particular embodiment, R$^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl. In a more particular embodiment, R$^{5b}$ is imidazolyl, pyrazolyl, isoxazolyl, or pyrimidinyl. In a most particular embodiment, R$^{5b}$ is isoxazolyl.

In one embodiment, the compound of the invention is according to anyone of Formulae I-IIIf, and Va-VIIId, wherein Z is —NR$^{5a}$R$^{5b}$, R$^{5a}$ is as previously described, and R$^{5b}$ is 5-6 membered monocyclic heteroaryl comprising one, two or three heteroatoms independently selected from N, O, and S, which heteroaryl is substituted with one or more independently selected C$_{1-4}$ alkyl. In a particular embodiment, R$^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more independently selected C$_{1-4}$ alkyl. In another particular embodiment, R$^{5b}$ is 5-6 membered monocyclic heteroaryl comprising one, two or three heteroatoms independently selected from N, O, and S, which heteroaryl is substituted with one C$_{1-4}$ alkyl. In yet another particular embodiment, R$^{5b}$ is 5-6 membered monocyclic heteroaryl comprising one, two or three heteroatoms independently selected from N, O, and S, which heteroaryl is substituted with one or more independently selected—CH$_3$, —CH$_2$CH$_3$, or —CH(CH$_3$)$_2$. In a more particular embodiment, R$^{5b}$ is imidazolyl, pyrazolyl, or pyrimidinyl, each of which is substituted with one or more independently selected C$_{1-4}$ alkyl. In another more particular embodiment, R$^{5b}$ is 5-6 membered monocyclic heteroaryl comprising one, two or three heteroatoms independently selected from N, O, and S, which heteroaryl is substituted with one —CH$_3$. In yet another more particular embodiment, R$^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one C$_{1-4}$ alkyl. In a further more particular embodiment, R$^{5b}$ is 5-6 membered monocyclic heteroaryl comprising one, two or three heteroatoms independently selected from N, O, and S, which heteroaryl is substituted with one —CH$_3$, —CH$_2$CH$_3$, or —CH(CH$_3$)$_2$. In an even more particular embodiment, R$^{5b}$ is imidazolyl, pyrazolyl, or pyrimidinyl, each of which is substituted with one C$_{1-4}$ alkyl. In another even more particular embodiment, R$^{5b}$ is R$^{5b}$ is imidazolyl, pyrazolyl, or pyrimidinyl, each of which is substituted with one or more —CH$_3$, —CH$_2$CH$_3$, or —CH(CH$_3$)$_2$. In yet another even more particular embodiment, R$^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more —CH$_3$. In a further even more particular embodiment, R$^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one —CH$_3$, —CH$_2$CH$_3$, or —CH(CH$_3$)$_2$. In yet a further even more particular embodiment, R$^{5b}$ is 5-6 membered monocyclic heteroaryl comprising one, two or three heteroatoms independently selected from N, O, and S, which heteroaryl is substituted with one —CH$_3$. In a most particular embodiment, R$^{5b}$ is imidazolyl, pyrazolyl, or pyrimidinyl, each of which is substituted with one —CH$_3$.

In one embodiment, the compound of the invention is according to any one of Formulae I-IIIf, and Va-VIIId, wherein Z is —NR$^{5a}$R$^{5b}$, R$^{5a}$ is H, and R$^{5b}$ is —CH$_2$CH$_3$, —CH$_2$CF$_3$, —CH(CH$_3$)CF$_3$, or cyclopropyl.

In one embodiment, the compound of the invention is according to anyone of Formulae I-IIIf, and Va-VIIId, wherein Z is N-linked 4-7 membered heterocycloalkyl further comprising zero, one, or two additional heteroatoms independently selected from N, O, and S. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, Z is azetidinyl, pyrrolidinyl, piperidinyl, 2-oxa-6-azaspiro[3.3]heptanyl, or 2-thia-6-azaspiro[3.3]heptanyl.

In one embodiment, the compound of the invention is according to anyone of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected R$^6$ groups. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two or three independently selected R$^6$ groups. In a more particular embodiment, Z is azetidinyl, pyrrolidinyl, piperidinyl, or 2-thia-6-azaspiro[3.3]heptanyl, each of which is substituted with one, two or three independently selected R$^6$ groups.

In one embodiment, the compound of the invention is according to anyone of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is oxo, halo, —CN, —OH, phenyl, $C_{3-7}$ cycloalkyl, $C_{2-4}$ alkynyl, or —C(=O)—$C_{1-4}$ alkoxy. In a particular embodiment, $R^6$ is oxo, F, Cl, —CN, —OH, phenyl, cyclopropyl, cyclobutyl, cyclopentyl, —C≡CH, —C(=O)—O—$CH_3$, —C(=O)—O—$CH_2CH_3$, or —C(=O)—O—CH($CH_3$)$_2$. In a more particular embodiment, $R^6$ is oxo, F, —CN, —OH, phenyl, cyclopropyl, —C≡CH, or —C(=O)—O—$CH_3$.

In one embodiment, the compound of the invention is according to any one of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is —$NR^{11a}R^{11b}$, and each $R^{11a}$ and $R^{11b}$ is as previously described. In a particular embodiment, $R^{11a}$ and $R^{11b}$ are both H. In another particular embodiment, one of $R^{11a}$ and $R^{11b}$ is H, and the other is $C_{1-4}$ alkyl. In yet another embodiment, $R^{11a}$ and $R^{11b}$ are both $C_{1-4}$ alkyl. In a more particular embodiment, one of $R^{11a}$ and $R^{11b}$ is H, and the other is —$CH_3$, —$CH_2CH_3$, or —CH($CH_3$)$_2$. In another more particular embodiment, $R^{11a}$ and $R^{11b}$ bare —$CH_3$, —$CH_2CH_3$, or —CH($CH_3$)$_2$. In a most particular embodiment, $R^{11a}$ and $R^{11b}$ are —$CH_3$.

In one embodiment, the compound of the invention is according to any one of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkoxy. In a particular embodiment, $R^6$ is —O—$CH_3$, —O—$CH_2CH_3$, or —O—CH($CH_3$)$_2$. In a more particular embodiment, $R^6$ is —O—$CH_3$.

In one embodiment, the compound of the invention is according to any one of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkoxy substituted with one or more halo or phenyl. In a particular embodiment, $R^6$ is —O—$CH_3$, —O—$CH_2CH_3$, or —O—CH($CH_3$)$_2$, each of which is substituted with one or more halo or phenyl. In another particular embodiment, $R^6$ is $C_{1-4}$ alkoxy substituted with one, two, or three halo or phenyl. In yet another particular embodiment, $R^6$ is $C_{1-4}$ alkoxy substituted with one or more F, Cl or phenyl. In a more particular embodiment, $R^6$ is —O—$CH_3$, —O—$CH_2CH_3$, or —O—CH($CH_3$)$_2$, each of which is substituted with one or more F, Cl, or phenyl. In another more particular embodiment, $R^6$ is $C_{1-4}$ alkoxy substituted with one, two, or three F, Cl, or phenyl. In yet another more particular embodiment, $R^6$ is —O—$CH_3$ substituted with one, two, or three halo or phenyl. In a most particular embodiment, $R^6$ is —O—$CH_3$ substituted with one, two, or three F. In another most particular embodiment, $R^6$ is —O—$CH_3$ substituted with one phenyl.

In one embodiment, the compound of the invention is according to anyone of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkyl. In a particular embodiment, $R^6$ is —$CH_3$, —$CH_2CH_3$, or —CH($CH_3$)$_2$. In a more particular embodiment, $R^6$ is —$CH_3$ or —$CH_2CH_3$.

In one embodiment, the compound of the invention is according to any one of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkyl substituted with one or more halo, —OH, or $C_{1-4}$ alkoxy. In a particular embodiment, $R^6$ is —$CH_3$, —$CH_2CH_3$, or —CH($CH_3$)$_2$ substituted with one or more halo, —OH, or $C_{1-4}$ alkoxy. In another particular embodiment, $R^6$ is $C_{1-4}$ alkyl substituted with one, two, or three halo, —OH, or $C_{1-4}$ alkoxy. In yet another particular embodiment, $R^6$ is $C_{1-4}$ alkyl substituted with one or more F, Cl, —OH, —O—$CH_3$, —O—$CH_2CH_3$, or —O—CH($CH_3$)$_2$. In a more particular embodiment, $R^6$ is —$CH_3$ substituted with one, two, or three halo, —OH, or $C_{1-4}$ alkoxy. In another more particular embodiment, $R^6$ is $C_{1-4}$ alkyl substituted with one, two, or three F, Cl, —OH, —O—$CH_3$, —O—$CH_2CH_3$, or —O—CH($CH_3$)$_2$. In a further more particular embodiment, $R^6$ is —$CH_3$, —$CH_2CH_3$, or —CH($CH_3$)$_2$, each of which is substituted with one, two, or three F, Cl, —OH, —O—$CH_3$, —O—$CH_2CH_3$, or —O—CH($CH_3$)$_2$. In a most particular embodiment, $R^6$ is —$CH_3$ substituted with one, two, or three F, or —OH.

In one embodiment, the compound of the invention is according to any one of Formulae I-IIIf, and Va-VIIId, wherein Z is N-linked 4-7 membered heterocycloalkyl further comprising zero, one, or two additional heteroatoms independently selected from N, O, and S, substituted with one, two or three independently selected $R^6$ groups, and $R^6$ is 4-7 membered monocyclic heterocycloalkyl comprising one, two or three heteroatoms independently selected from N, O, and S. In a particular embodiment, $R^6$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^6$ is tetrahydropyranyl or morpholinyl.

In one embodiment, the compound of the invention is according to anyone of Formulae I-IIIf, and Va-VIIId, wherein Z is

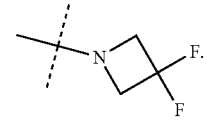

In one embodiment, the compound of the invention is according to Formula I, wherein the compound is selected from:
N-ethyl-4-[5-(1-ethylpyrazol-4-yl)benzimidazol-1-yl]-2,6-dimethoxy-benzamide,
N-ethyl-2,6-dimethoxy-4-[5-(3-pyridyl)benzimidazol-1-yl] benzamide,
N-ethyl-2,6-dimethoxy-4-[5-(6-morpholino-3-pyridyl)benzimidazol-1-yl]benzamide,
N-ethyl-2,6-dimethoxy-4-[5-[1-(2-morpholinoethyl)pyrazol-4-yl]benzimidazol-1-yl]benzamide,
4-[5-(1-ethylpyrazol-4-yl)benzimidazol-1-yl]-N-(2-hydroxyethyl)-2,6-dimethoxy-benzamide,
4-[5-(1-ethylpyrazol-4-yl)benzimidazol-1-yl]-2,6-dimethoxy-N-methyl-benzamide,
N-ethyl-2,6-dimethoxy-4-[5-(1-methylpyrazol-4-yl)benzimidazol-1-yl]benzamide, 4-[5-(1,3-dimethylpyrazol-4-yl)benzimidazol-1-yl]-N-ethyl-2,6-dimethoxy-benzamide,
N-ethyl-4-[6-(1-ethylpyrazol-4-yl)pyrazolo[1,5-a]pyrimidin-3-yl]-2,6-dimethoxy-benzamide,
4-[5-(1-ethylpyrazol-4-yl)benzimidazol-1-yl]-N-(2-fluoroethyl)-2,6-dimethoxy-benzamide,
N-(2,2-difluoroethyl)-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2,2,2-trifluoroethyl)benzamide,
N-ethyl-2,6-dimethoxy-4-[5-[1-(2-methoxyethyl)pyrazol-4-yl]benzimidazol-1-yl]benzamide,
N-ethyl-2,6-dimethoxy-4-[5-(1-tetrahydropyran-4-yl)pyrazol-4-yl)benzimidazol-1-yl]benzamide,
4-[5-[1-(cyanomethyl)pyrazol-4-yl]benzimidazol-1-yl]-N-ethyl-2,6-dimethoxy-benzamide,
N-ethyl-4-[5-[1-(2-hydroxyethyl)pyrazol-4-yl]benzimidazol-1-yl]-2,6-dimethoxy-benzamide,
2-(difluoromethoxy)-N-ethyl-4-[5-(1-ethylpyrazol-4-yl)benzimidazol-1-yl]-6-methoxy-benzamide,
4-[5-[1-(2-amino-2-oxo-ethyl)pyrazol-4-yl]benzimidazol-1-yl]-N-ethyl-2,6-dimethoxy-benzamide,
N-cyclopropyl-4-[5-(1-ethylpyrazol-4-yl)benzimidazol-1-yl]-2,6-dimethoxy-benzamide,
4-[6-(1-ethylpyrazol-4-yl)pyrazolo[1,5-a]pyrimidin-3-yl]-2,6-dimethoxy-N-(2,2,2-trifluoroethyl)benzamide,
N-(2,2-difluoroethyl)-4-[6-(1-ethylpyrazol-4-yl)pyrazolo[1,5-a]pyrimidin-3-yl]-2,6-dimethoxy-benzamide,
4-[5-(1-ethylpyrazol-4-yl)benzimidazol-1-yl]-2,6-dimethoxy-N-propyl-benzamide,
N-ethyl-4-[5-(1-ethylpyrazol-4-yl)benzimidazol-1-yl]-2-hydroxy-6-methoxy-benzamide,
N-(2,2-difluoroethyl)-2,6-dimethoxy-4-[6-(1-methylpyrazol-4-yl)pyrazolo[1,5-a]pyrimidin-3-yl]benzamide,
2,6-dimethoxy-4-[5-(1-methylpyrazol-4-yl)benzimidazol-1-yl]-N-(2,2,2-trifluoroethyl)benzamide,
N-cyclobutyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2-methoxyethyl)-N-methyl-benzamide,
4-[5-(1-ethylpyrazol-4-yl)benzimidazol-1-yl]-N-isobutyl-2,6-dimethoxy-N-methyl-benzamide,
4-[6-(1-ethylpyrazol-4-yl)imidazo[4,5-b]pyridin-3-yl]-2,6-dimethoxy-N-(2,2,2-trifluoroethyl)benzamide,
N-cyclopropyl-4-[5-(1-ethylpyrazol-4-yl)benzimidazol-1-yl]-2,6-dimethoxy-N-methyl-benzamide,
N-(cyanomethyl)-4-[5-(1-ethylpyrazol-4-yl)benzimidazol-1-yl]-2,6-dimethoxy-N-methyl-benzamide,
2,6-dimethoxy-4-[5-(6-morpholino-3-pyridyl)benzimidazol-1-yl]-N-(2,2,2-trifluoroethyl)benzamide,
4-[5-[1-(2-hydroxyethyl)pyrazol-4-yl]benzimidazol-1-yl]-2,6-dimethoxy-N-(2,2,2-trifluoroethyl)benzamide,
2,6-dimethoxy-4-[5-(6-pyrrolidin-1-yl-3-pyridyl)benzimidazol-1-yl]-N-(2,2,2-trifluoroethyl)benzamide,
2,6-dimethoxy-4-[5-(5-methoxy-3-pyridyl)benzimidazol-1-yl]-N-(2,2,2-trifluoroethyl)benzamide,
4-[5-(6-cyano-3-pyridyl)benzimidazol-1-yl]-2,6-dimethoxy-N-(2,2,2-trifluoroethyl)benzamide,
4-[5-[6-(dimethylamino)-3-pyridyl]benzimidazol-1-yl]-2,6-dimethoxy-N-(2,2,2-trifluoroethyl)benzamide,
4-[5-(6-amino-3-pyridyl)benzimidazol-1-yl]-2,6-dimethoxy-N-(2,2,2-trifluoroethyl)benzamide,
2,6-dimethoxy-4-[5-(3-pyridyl)benzimidazol-1-yl]-N-(2,2,2-trifluoroethyl)benzamide,
4-[5-[1-(cyanomethyl)pyrazol-4-yl]benzimidazol-1-yl]-2,6-dimethoxy-N-(2,2,2-trifluoroethyl)benzamide,
2,6-dimethoxy-4-[5-[1-(2-morpholinoethyl)pyrazol-4-yl]benzimidazol-1-yl]-N-(2,2,2-trifluoroethyl)benzamide,
2,6-dimethoxy-4-[5-[1-(4-piperidyl)pyrazol-4-yl]benzimidazol-1-yl]-N-(2,2,2-trifluoroethyl)benzamide,
N-tert-butyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(3,3,3-trifluoropropyl)benzamide,
N-cyclopentyl-4-[5-(1-ethylpyrazol-4-yl)benzimidazol-1-yl]-2,6-dimethoxy-benzamide,
2,6-dimethoxy-4-[5-[1-(1-methyl-4-piperidyl)pyrazol-4-yl]benzimidazol-1-yl]-N-(2,2,2-trifluoroethyl)benzamide,
2,6-dimethoxy-4-[5-(1H-pyrazol-4-yl)benzimidazol-1-yl]-N-(2,2,2-trifluoroethyl)benzamide,
2-(difluoromethoxy)-N-ethyl-6-methoxy-4-[5-(1-methylpyrazol-4-yl)benzimidazol-1-yl]benzamide,
4-[5-(1-ethylpyrazol-4-yl)benzimidazol-1-yl]-2,6-dimethoxy-N-[(2R)-2-methylcyclopropyl]benzamide,
N-(cyanomethyl)-4-[5-(1-ethylpyrazol-4-yl)benzimidazol-1-yl]-2,6-dimethoxy-benzamide,
4-(5-isoxazol-4-ylbenzimidazol-1-yl)-2,6-dimethoxy-N-(2,2,2-trifluoroethyl)benzamide,
2,6-dimethoxy-4-[6-(1-methylpyrazol-4-yl)pyrazolo[1,5-a]pyrimidin-3-yl]-N-(2,2,2-trifluoroethyl)benzamide,
N-cyclopropyl-2-(difluoromethoxy)-6-methoxy-4-[5-(1-methylpyrazol-4-yl)benzimidazol-1-yl]benzamide,
N-cyclopropyl-2-(difluoromethoxy)-4-[5-(1-ethylpyrazol-4-yl)benzimidazol-1-yl]-6-methoxy-benzamide,
4-[5-[1-(cyanomethyl)pyrazol-4-yl]benzimidazol-1-yl]-N-cyclopropyl-2-(difluoromethoxy)-6-methoxy-benzamide,
N-cyclopropyl-2-(difluoromethoxy)-6-methoxy-4-[5-[1-(2-morpholinoethyl)pyrazol-4-yl]benzimidazol-1-yl]benzamide,
2-(difluoromethoxy)-N-ethyl-6-methoxy-4-[5-[1-(2-morpholinoethyl)pyrazol-4-yl]benzimidazol-1-yl]benzamide,
2,6-dimethoxy-4-[5-(1-methylpyrazol-4-yl)benzimidazol-1-yl]-N-[(1R)-2,2,2-trifluoro-1-methyl-ethyl]benzamide,
N-(2-cyanoethyl)-2,6-dimethoxy-4-[5-(1-methylpyrazol-4-yl)benzimidazol-1-yl]benzamide,
2,6-dimethoxy-N-(3-methoxypropyl)-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1-methylpyrazol-3-yl)methyl]benzamide,
2,6-dimethoxy-4-[5-(1-methylpyrazol-4-yl)benzimidazol-1-yl]-N-(2-pyridylmethyl)benzamide,
N-(3-hydroxypropyl)-2,6-dimethoxy-4-[5-(1-methylpyrazol-4-yl)benzimidazol-1-yl]benzamide,
N-(1,1-dioxothietan-3-yl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2-methylsulfonylethyl)benzamide,
N-(1,1-dioxothiolan-3-yl)-2,6-dimethoxy-4-[5-(1-methylpyrazol-4-yl)benzimidazol-1-yl]benzamide,
N-[[(2R)-1,4-dioxan-2-yl]methyl]-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2,2,2-trifluoro-1,1-dimethyl-ethyl)benzamide,
N-[[(2S)-1,4-dioxan-2-yl]methyl]-2,6-dimethoxy-4-[5-(1-methylpyrazol-4-yl)benzimidazol-1-yl]benzamide,
2,6-dimethoxy-N-(5-methylpyrazin-2-yl)-4-[5-(1-methylpyrazol-4-yl)benzimidazol-1-yl]benzamide,
2,6-dimethoxy-N-[(1-methylimidazol-2-yl)methyl]-4-[5-(1-methylpyrazol-4-yl)benzimidazol-1-yl]benzamide,
N-isoxazol-3-yl-2,6-dimethoxy-4-[5-(1-methylpyrazol-4-yl)benzimidazol-1-yl]benzamide,
2,6-dimethoxy-N-(2-methylpyrazol-3-yl)-4-[5-(1-methylpyrazol-4-yl)benzimidazol-1-yl]benzamide, N-(cyanomethyl)-2,6-dimethoxy-N-methyl-4-[5-(1-methylpyrazol-4-yl)benzimidazol-1-yl]benzamide,
N-(cyanomethyl)-2,6-dimethoxy-4-[5-(1-methylpyrazol-4-yl)benzimidazol-1-yl]benzamide,
N-tert-butyl-2,6-dimethoxy-4-[5-(1-methylpyrazol-4-yl)benzimidazol-1-yl]benzamide,
N-cyclobutyl-2,6-dimethoxy-4-[5-(1-methylpyrazol-4-yl)benzimidazol-1-yl]benzamide,
N-(2,2-difluoroethyl)-2,6-dimethoxy-4-[5-(1-methylpyrazol-4-yl)benzimidazol-1-yl]benzamide,
N-(2-fluoroethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1S)-2,2,2-trifluoro-1-methyl-ethyl]benzamide,
2,6-dimethoxy-N-(1-methylpyrazol-3-yl)-4-[5-(1-methylpyrazol-4-yl)benzimidazol-1-yl]benzamide,
2,6-dimethoxy-N-(1-methylimidazol-4-yl)-4-[5-(1-methylpyrazol-4-yl)benzimidazol-1-yl]benzamide,
2,6-dimethoxy-N-(1-methylpyrazol-4-yl)-4-[5-(1-methylpyrazol-4-yl)benzimidazol-1-yl]benzamide,
2,6-dimethoxy-4-[5-[1-(2-methoxyethyl)pyrazol-4-yl]benzimidazol-1-yl]-N-(2,2,2-trifluoroethyl)benzamide,
2,6-dimethoxy-4-[5-[1-(oxetan-3-yl)pyrazol-4-yl]benzimidazol-1-yl]-N-(2,2,2-trifluoroethyl)benzamide,
N-cyclopropyl-2,6-dimethoxy-4-[5-(1-methylpyrazol-4-yl)benzimidazol-1-yl]benzamide,
N-(1-cyanoethyl)-2,6-dimethoxy-4-[5-(1-methylpyrazol-4-yl)benzimidazol-1-yl]benzamide,
2,6-dimethoxy-4-[7-(1-methylpyrazol-4-yl)imidazo[1,2-a]pyridin-3-yl]-N-(2,2,2-trifluoroethyl)benzamide,
2,6-dimethoxy-4-[5-(1-methylpyrazol-3-yl)benzimidazol-1-yl]-N-(2,2,2-trifluoroethyl)benzamide,
N-(2,2-difluorocyclopentyl)-2,6-dimethoxy-4-[5-(1-methylpyrazol-4-yl)benzimidazol-1-yl]benzamide,
N-(2,2-difluoro-1-methyl-ethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(oxetan-3-yl)benzamide,
2,6-dimethoxy-4-(5-pyridazin-4-ylbenzimidazol-1-yl)-N-(2,2,2-trifluoroethyl)benzamide,
4-[5-[1-(azetidin-3-yl)pyrazol-4-yl]benzimidazol-1-yl]-2,6-dimethoxy-N-(2,2,2-trifluoroethyl)benzamide,
4-[5-(1-isopropylpyrazol-4-yl)benzimidazol-1-yl]-2,6-dimethoxy-N-(2,2,2-trifluoroethyl)benzamide,
4-[5-(1-cyclopropylpyrazol-4-yl)benzimidazol-1-yl]-2,6-dimethoxy-N-(2,2,2-trifluoroethyl)benzamide,
4-[5-[1-(difluoromethyl)pyrazol-4-yl]benzimidazol-1-yl]-2,6-dimethoxy-N-(2,2,2-trifluoroethyl)benzamide,
2,6-dimethoxy-4-[5-[1-(1-methylazetidin-3-yl)pyrazol-4-yl]benzimidazol-1-yl]-N-(2,2,2-trifluoroethyl)benzamide,
2,6-dimethoxy-4-[6-(1-methylpyrazol-4-yl)pyrazolo[1,5-a]pyridin-3-yl]-N-(2,2,2-trifluoroethyl)benzamide,
4-[5-[1-[1-(cyanomethyl)azetidin-3-yl]pyrazol-4-yl]benzimidazol-1-yl]-2,6-dimethoxy-N-(2,2,2-trifluoroethyl)benzamide,
2,6-dimethoxy-4-[5-(3-methyl-1H-pyrazol-5-yl)benzimidazol-1-yl]-N-(2,2,2-trifluoroethyl)benzamide,
N-cyclopropyl-2,6-dimethoxy-4-[7-(1-methylpyrazol-4-yl)imidazo[1,2-a]pyridin-3-yl]benzamide,
2,6-dimethoxy-4-[5-(1-propylpyrazol-4-yl)benzimidazol-1-yl]-N-(2,2,2-trifluoroethyl)benzamide,
2,6-dimethoxy-4-(5-pyrimidin-5-ylbenzimidazol-1-yl)-N-(2,2,2-trifluoroethyl)benzamide,
2,6-dimethoxy-4-[5-(2-methoxypyrimidin-5-yl)benzimidazol-1-yl]-N-(2,2,2-trifluoroethyl)benzamide,
2,6-dimethoxy-4-[5-(2-methoxy-4-pyridyl)benzimidazol-1-yl]-N-(2,2,2-trifluoroethyl)benzamide,
2,6-dimethoxy-4-[7-(1-methylpyrazol-4-yl)imidazo[1,2-b]pyridazin-3-yl]-N-(2,2,2-trifluoroethyl)benzamide,
2,6-dimethoxy-4-[5-(3-methylisoxazol-4-yl)benzimidazol-1-yl]-N-(2,2,2-trifluoroethyl)benzamide,
2,6-dimethoxy-4-[5-(3-methylisoxazol-5-yl)benzimidazol-1-yl]-N-(2,2,2-trifluoroethyl)benzamide,
4-[5-(1-isobutylpyrazol-4-yl)benzimidazol-1-yl]-2,6-dimethoxy-N-(2,2,2-trifluoroethyl)benzamide,
2,6-dimethoxy-4-[5-[1-(tetrahydrofuran-2-ylmethyl)pyrazol-4-yl]benzimidazol-1-yl]-N-(2,2,2-trifluoroethyl)benzamide,
N-cyclopropyl-2,6-dimethoxy-4-[7-(1-methylpyrazol-4-yl)imidazo[1,2-b]pyridazin-3-yl]benzamide,
N-isobutyl-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-sec-butyl-benzamide,
N-isopropyl-2,6-dimethoxy-4-[5-(1-methylpyrazol-4-yl)benzimidazol-1-yl]benzamide,
2-(difluoromethoxy)-N-ethyl-6-methoxy-4-[7-(1-methylpyrazol-4-yl)imidazo[1,2-a]pyridin-3-yl]benzamide,
2-(difluoromethoxy)-N-ethyl-6-methoxy-4-[6-(1-methylpyrazol-4-yl)pyrazolo[1,5-a]pyridin-3-yl]benzamide,
2-(difluoromethoxy)-N-ethyl-6-methoxy-4-[7-(1-methylpyrazol-4-yl)imidazo[1,2-b]pyridazin-3-yl]benzamide,
N-cyclopropyl-2-isopropoxy-6-methoxy-4-[5-(1-methylpyrazol-4-yl)benzimidazol-1-yl]benzamide,
2,6-dimethoxy-4-[5-[2-(4-methylpiperazin-1-yl)-4-pyridyl]benzimidazol-1-yl]-N-(2,2,2-trifluoroethyl)benzamide,
2,6-dimethoxy-4-[5-(6-methylpyridazin-4-yl)benzimidazol-1-yl]-N-(2,2,2-trifluoroethyl)benzamide,
N-(cyanomethyl)-2,6-dimethoxy-4-[7-(1-methylpyrazol-4-yl)imidazo[1,2-a]pyridin-3-yl]benzamide,
2-(difluoromethoxy)-N-ethyl-6-methoxy-4-[7-(3-methylisoxazol-5-yl)imidazo[1,2-a]pyridin-3-yl]benzamide,
N-cyclopropyl-2-(difluoromethoxy)-6-methoxy-4-[7-(1-methylpyrazol-4-yl)imidazo[1,2-a]pyridin-3-yl]benzamide,
N-(3,3-difluorocyclobutyl)-2,6-dimethoxy-4-[5-(1-methylpyrazol-4-yl)benzimidazol-1-yl]benzamide,
2,6-dimethoxy-4-[5-(5-methyl-1,2,4-oxadiazol-3-yl)benzimidazol-1-yl]-N-(2,2,2-trifluoroethyl)benzamide,
2,6-dimethoxy-4-[5-(5-methyl-4H-1,2,4-triazol-3-yl)benzimidazol-1-yl]-N-(2,2,2-trifluoroethyl)benzamide,
2,6-dimethoxy-4-(5-pyrazin-2-ylbenzimidazol-1-yl)-N-(2,2,2-trifluoroethyl)benzamide,
N-isobutyl-2,6-dimethoxy-4-[7-(1-methylpyrazol-4-yl)imidazo[1,2-a]pyridin-3-yl]benzamide,
N-(1,1-dioxothietan-3-yl)-2,6-dimethoxy-4-[7-(i-methylpyrazol-4-yl)imidazo[1,2-a]pyridin-3-yl]benzamide,
2,6-dimethoxy-N-(2-methoxyethyl)-N-methyl-4-[7-(1-methylpyrazol-4-yl)imidazo[1,2-a]pyridin-3-yl]benzamide,
2,6-dimethoxy-4-[7-(1-methylpyrazol-4-yl)imidazo[1,2-a]pyridin-3-yl]-N-[(1S)-2,2,2-trifluoro-1-methyl-ethyl]benzamide,
N-(2,2-difluoroethyl)-2,6-dimethoxy-4-[7-(1-methylpyrazol-4-yl)imidazo[1,2-a]pyridin-3-yl]benzamide,
2,6-dimethoxy-4-[5-(1-methylimidazol-2-yl)benzimidazol-1-yl]-N-(2,2,2-trifluoroethyl)benzamide,
2,6-dimethoxy-4-[5-(3-methylimidazol-4-yl)benzimidazol-1-yl]-N-(2,2,2-trifluoroethyl)benzamide,
2-(difluoromethoxy)-N-ethyl-6-methoxy-4-[5-(5-methyl-1,2,4-oxadiazol-3-yl)benzimidazol-1-yl]benzamide, 2,6-dimethoxy-4-[5-(1-methylimidazol-4-yl)benzimidazol-1-yl]-N-(2,2,2-trifluoroethyl)benzamide,
4-[5-(2,3-dimethylimidazol-4-yl)benzimidazol-1-yl]-2,6-dimethoxy-N-(2,2,2-trifluoroethyl)benzamide,
N-[(1R,2R)-2-aminocyclohexyl]-2,6-dimethoxy-4-[5-(1-methylpyrazol-4-yl)benzimidazol-1-yl]benzamide,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-hydroxycyclopentyl]-2,6-dimethoxy-4-[5-(1-methylpyrazol-4-yl)benzimidazol-1-yl]benzamide,
(3,3-difluoroazetidin-1-yl)-[2,6-dimethoxy-4-[5-(1-methylpyrazol-4-yl)benzimidazol-1-yl]phenyl]methanone,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-fluorocyclopropyl]-2,6-dimethoxy-4-[5-(1-methylpyrazol-4-yl)benzimidazol-1-yl]benzamide,
2-(difluoromethoxy)-N-ethyl-6-methoxy-4-(7-pyridazin-4-ylimidazo[1,2-a]pyridin-3-yl)benzamide,
4-[7-(6-cyano-3-pyridyl)imidazo[1,2-a]pyridin-3-yl]-2-(difluoromethoxy)-N-ethyl-6-methoxy-benzamide,
tert-butyl 4-[4-[3-[3-(difluoromethoxy)-4-(ethylcarbamoyl)-5-methoxy-phenyl]imidazo[1,2-a]pyridin-7-yl]pyrazol-1-yl]piperidine-1-carboxylate,
2-(difluoromethoxy)-N-ethyl-6-methoxy-4-[7-[1-(1-methyl-4-piperidyl)pyrazol-4-yl]imidazo[1,2-a]pyridin-3-yl]benzamide,
2-(difluoromethoxy)-N-ethyl-6-methoxy-4-[7-[1-(4-piperidyl)pyrazol-4-yl]imidazo[1,2-a]pyridin-3-yl]benzamide,
2-(difluoromethoxy)-N-ethyl-6-methoxy-4-[5-(5-methyl-4H-1,2,4-triazol-3-yl)benzimidazol-1-yl]benzamide,
2-(difluoromethoxy)-4-[7-[1-(difluoromethyl)pyrazol-4-yl]imidazo[1,2-a]pyridin-3-yl]-N-ethyl-6-methoxy-benzamide,
2,6-dimethoxy-4-[5-(2-methyl-1H-imidazol-5-yl)benzimidazol-1-yl]-N-(2,2,2-trifluoroethyl)benzamide,
4-[5-(1H-imidazol-4-yl)benzimidazol-1-yl]-2,6-dimethoxy-N-(2,2,2-trifluoroethyl)benzamide,
2,6-dimethoxy-4-[5-(3-methylpyrazol-1-yl)benzimidazol-1-yl]-N-(2,2,2-trifluoroethyl)benzamide,
2,6-dimethoxy-4-[5-(4-methylimidazol-1-yl)benzimidazol-1-yl]-N-(2,2,2-trifluoroethyl)benzamide,
N-[(1R,2R)-2-(hydroxymethyl)cyclopropyl]-2,6-dimethoxy-4-[5-(1-methylpyrazol-4-yl)benzimidazol-1-yl]benzamide,
N-[(1R,2R)-2-(difluoromethyl)cyclopropyl]-2,6-dimethoxy-4-[5-(1-methylpyrazol-4-yl)benzimidazol-1-yl]benzamide,
N-[(1R,2S)-2-(difluoromethyl)cyclopropyl]-2,6-dimethoxy-4-[5-(1-methylpyrazol-4-yl)benzimidazol-1-yl]benzamide,
N-[(1R,2R)-2-hydroxycyclobutyl]-2,6-dimethoxy-4-[5-(1-methylpyrazol-4-yl)benzimidazol-1-yl]benzamide,
2,6-dimethoxy-4-[5-(1-methyltriazol-4-yl)benzimidazol-1-yl]-N-(2,2,2-trifluoroethyl)benzamide,
2,6-dimethoxy-N-(2-methoxycyclohexyl)-4-[5-(1-methylpyrazol-4-yl)benzimidazol-1-yl]benzamide,
azetidin-1-yl-[2,6-dimethoxy-4-[5-(1-methylpyrazol-4-yl)benzimidazol-1-yl]phenyl]methanone,
N-(2-aminoethyl)-2,6-dimethoxy-4-[5-(1-methylpyrazol-4-yl)benzimidazol-1-yl]benzamide,
N-[(1S,2S)-2-hydroxycyclohexyl]-2,6-dimethoxy-4-[5-(1-methylpyrazol-4-yl)benzimidazol-1-yl]benzamide,
4-[5-(3,5-dimethylpyrazol-1-yl)benzimidazol-1-yl]-2,6-dimethoxy-N-(2,2,2-trifluoroethyl)benzamide,
2,6-dimethoxy-4-[5-(3-methyl-1,2,4-triazol-1-yl)benzimidazol-1-yl]-N-(2,2,2-trifluoroethyl)benzamide,
2,6-dimethoxy-4-[5-(5-methyl-1,3,4-oxadiazol-2-yl)benzimidazol-1-yl]-N-(2,2,2-trifluoroethyl)benzamide,
4-[5-(4,5-dimethyl-1,2,4-triazol-3-yl)benzimidazol-1-yl]-2,6-dimethoxy-N-(2,2,2-trifluoroethyl)benzamide,
2,6-dimethoxy-4-[5-(3-methyl-1,2,4-oxadiazol-5-yl)benzimidazol-1-yl]-N-(2,2,2-trifluoroethyl)benzamide,
N-[(1S,2S)-2-hydroxycyclobutyl]-2,6-dimethoxy-4-[7-(1-methylpyrazol-4-yl)imidazo[1,2-a]pyridin-3-yl]benzamide,
N-isopropyl-2,6-dimethoxy-4-[7-(1-methylpyrazol-4-yl)imidazo[1,2-a]pyridin-3-yl]benzamide,
N-[(1S,2S)-2-(difluoromethyl)cyclopropyl]-2,6-dimethoxy-4-[7-(1-methylpyrazol-4-yl)imidazo[1,2-a]pyridin-3-yl]benzamide,
(3,3-difluoroazetidin-1-yl)-[2,6-dimethoxy-4-[7-(1-methylpyrazol-4-yl)imidazo[1,2-a]pyridin-3-yl]phenyl]methanone,
2,6-dimethoxy-4-[7-(1-methylpyrazol-4-yl)imidazo[1,2-a]pyridin-3-yl]-N-[(1R)-2,2,2-trifluoro-1-methyl-ethyl]benzamide,
2-ethyl-7-fluoro-5-[5-(1-methylpyrazol-4-yl)benzimidazol-1-yl]isoindolin-1-one,
2-ethyl-7-methoxy-5-[7-(1-methylpyrazol-4-yl)imidazo[1,2-a]pyridin-3-yl]isoindolin-1-one,
2-(difluoromethoxy)-N-ethyl-6-methoxy-4-[6-(1-methylpyrazol-4-yl)imidazo[4,5-b]pyridin-3-yl]benzamide,
2-(difluoromethoxy)-N-ethyl-6-methoxy-4-[7-(1-methylimidazol-4-yl)imidazo[1,2-a]pyridin-3-yl]benzamide,
[2,6-dimethoxy-4-[5-(1-methylpyrazol-4-yl)benzimidazol-1-yl]phenyl]-(3,3-dimethylazetidin-1-yl)methanone,
[2,6-dimethoxy-4-[5-(1-methylpyrazol-4-yl)benzimidazol-1-yl]phenyl]-(3-phenylazetidin-1-yl)methanone,
[2,6-dimethoxy-4-[5-(1-methylpyrazol-4-yl)benzimidazol-1-yl]phenyl]-(2,4-dimethylazetidin-1-yl)methanone,
[2,6-dimethoxy-4-[5-(1-methylpyrazol-4-yl)benzimidazol-1-yl]phenyl]-(2-methylazetidin-1-yl)methanone,
[2,6-dimethoxy-4-[5-(1-methylpyrazol-4-yl)benzimidazol-1-yl]phenyl]-[3-(hydroxymethyl)azetidin-1-yl]methanone,
[2,6-dimethoxy-4-[5-(1-methylpyrazol-4-yl)benzimidazol-1-yl]phenyl]-(3-hydroxyazetidin-1-yl)methanone,
[2,6-dimethoxy-4-[5-(1-methylpyrazol-4-yl)benzimidazol-1-yl]phenyl]-[3-(dimethylamino)azetidin-1-yl]methanone,
(3-benzyloxyazetidin-1-yl)-[2,6-dimethoxy-4-[5-(1-methylpyrazol-4-yl)benzimidazol-1-yl]phenyl]methanone,
[2,6-dimethoxy-4-[5-(1-methylpyrazol-4-yl)benzimidazol-1-yl]phenyl]-(2-phenylazetidin-1-yl)methanone,
[2,6-dimethoxy-4-[5-(1-methylpyrazol-4-yl)benzimidazol-1-yl]phenyl]-(3-morpholinoazetidin-1-yl)methanone,
[2,6-dimethoxy-4-[5-(1-methylpyrazol-4-yl)benzimidazol-1-yl]phenyl]-(2,2,4-trimethylazetidin-1-yl)methanone,
[2,6-dimethoxy-4-[5-(1-methylpyrazol-4-yl)benzimidazol-1-yl]phenyl]-(3-methoxyazetidin-1-yl)methanone,
[2,6-dimethoxy-4-[5-(1-methylpyrazol-4-yl)benzimidazol-1-yl]phenyl]-(3-tetrahydropyran-4-ylazetidin-1-yl)methanone,
1-[2,6-dimethoxy-4-[5-(1-methylpyrazol-4-yl)benzimidazol-1-yl]benzoyl]azetidine-3-carbonitrile,
[2,6-dimethoxy-4-[5-(1-methylpyrazol-4-yl)benzimidazol-1-yl]phenyl]-[2-(hydroxymethyl)azetidin-1-yl]methanone,
[2,6-dimethoxy-4-[5-(1-methylpyrazol-4-yl)benzimidazol-1-yl]phenyl]-(2-oxa-6-azaspiro[3.3]heptan-6-yl)methanone,

[2,6-dimethoxy-4-[5-(1-methylpyrazol-4-yl)benzimidazol-1-yl]phenyl]-(2,2-dioxo-2λ$^6$-thia-6-azaspiro[3.3]heptan-6-yl)methanone,

[2,6-dimethoxy-4-[5-(1-methylpyrazol-4-yl)benzimidazol-1-yl]phenyl]-(3-phenylpyrrolidin-1-yl)methanone,

[2,6-dimethoxy-4-[5-(1-methylpyrazol-4-yl)benzimidazol-1-yl]phenyl]-(4-fluoro-1-piperidyl)methanone,

[2,6-dimethoxy-4-[5-(1-methylpyrazol-4-yl)benzimidazol-1-yl]phenyl]-[4-(trifluoromethoxy)-1-piperidyl]methanone, N-tert-butyl-2-(difluoromethoxy)-6-methoxy-4-[5-(1-methylpyrazol-4-yl)benzimidazol-1-yl]benzamide, 2,6-dimethoxy-4-[7-(1-methylpyrazol-4-yl)imidazo[1,2-a]pyridin-3-yl]-N-[2-methyl-1-(trifluoromethyl)propyl]benzamide, 2-ethyl-7-(2-hydroxyethylamino)-5-[7-(1-methylpyrazol-4-yl)imidazo[1,2-a]pyridin-3-yl]isoindolin-1-one, 2-ethyl-7-(2-hydroxyethylamino)-5-[5-(1-methylpyrazol-4-yl)benzimidazol-1-yl]isoindolin-1-one, 2-fluoro-6-methoxy-4-[7-(1-methylpyrazol-4-yl)imidazo[1,2-a]pyridin-3-yl]-N-(2,2,2-trifluoroethyl)benzamide, 2-methoxy-6-(methylamino)-4-[7-(1-methylpyrazol-4-yl)imidazo[1,2-a]pyridin-3-yl]-N-(2,2,2-trifluoroethyl)benzamide, 2-(2-hydroxyethylamino)-6-methoxy-4-[7-(1-methylpyrazol-4-yl)imidazo[1,2-a]pyridin-3-yl]-N-(2,2,2-trifluoroethyl)benzamide, 2-methoxy-6-methyl-4-[7-(1-methylpyrazol-4-yl)imidazo[1,2-a]pyridin-3-yl]-N-(2,2,2-trifluoroethyl)benzamide, 2-chloro-6-methoxy-4-[7-(1-methylpyrazol-4-yl)imidazo[1,2-a]pyridin-3-yl]-N-(2,2,2-trifluoroethyl)benzamide,

[2,6-dimethoxy-4-[7-(1-methylpyrazol-4-yl)imidazo[1,2-a]pyridin-3-yl]phenyl]-(3,3-dimethylazetidin-1-yl)methanone, 1-[2,6-dimethoxy-4-[7-(1-methylpyrazol-4-yl)imidazo[1,2-a]pyridin-3-yl]benzoyl]azetidine-3-carbonitrile, 1-[2,6-dimethoxy-4-[7-(1-methylpyrazol-4-yl)imidazo[1,2-a]pyridin-3-yl]benzoyl]pyrrolidine-3-carbonitrile, (3,3-difluoropyrrolidin-1-yl)-[2,6-dimethoxy-4-[7-(1-methylpyrazol-4-yl)imidazo[1,2-a]pyridin-3-yl]phenyl]methanone, (4,4-difluoro-1-piperidyl)-[2,6-dimethoxy-4-[7-(1-methylpyrazol-4-yl)imidazo[1,2-a]pyridin-3-yl]phenyl]methanone,

[2,6-dimethoxy-4-[7-(1-methylpyrazol-4-yl)imidazo[1,2-a]pyridin-3-yl]phenyl]-[3-(trifluoromethyl)azetidin-1-yl]methanone, 8-methoxy-6-[7-(1-methylpyrazol-4-yl)imidazo[1,2-a]pyridin-3-yl]-3,4-dihydro-2H-isoquinolin-1-one, 2,6-dimethoxy-4-[7-(1-methylimidazol-4-yl)imidazo[1,2-a]pyridin-3-yl]-N-[(1R)-2,2,2-trifluoro-1-methyl-ethyl]benzamide, 2,6-dimethoxy-4-[7-(1-methylimidazol-4-yl)imidazo[1,2-a]pyridin-3-yl]-N-[(1S)-2,2,2-trifluoro-1-methyl-ethyl]benzamide,

[2,6-dimethoxy-4-[5-(1-methylpyrazol-4-yl)benzimidazol-1-yl]phenyl]-(3-hydroxy-3-methyl-azetidin-1-yl)methanone,

[2,6-dimethoxy-4-[5-(1-methylpyrazol-4-yl)benzimidazol-1-yl]phenyl]-(3-ethyl-3-hydroxy-azetidin-1-yl)methanone,

[2,6-dimethoxy-4-[5-(1-methylpyrazol-4-yl)benzimidazol-1-yl]phenyl]-[3-hydroxy-3-(trifluoromethyl)azetidin-1-yl]methanone, (3-cyclopropyl-3-hydroxy-azetidin-1-yl)-[2,6-dimethoxy-4-[5-(1-methylpyrazol-4-yl)benzimidazol-1-yl]phenyl]methanone,

[2,6-dimethoxy-4-[5-(1-methylpyrazol-4-yl)benzimidazol-1-yl]phenyl]-(3-ethynyl-3-hydroxy-azetidin-1-yl)methanone, 2,6-dimethoxy-4-[7-(1H-pyrazol-4-yl)imidazo[1,2-a]pyridin-3-yl]-N-[(1R)-2,2,2-trifluoro-1-methyl-ethyl]benzamide, 2,6-dimethoxy-4-[7-(3-methylisoxazol-5-yl)imidazo[1,2-a]pyridin-3-yl]-N-[(1R)-2,2,2-trifluoro-1-methyl-ethyl]benzamide, 2,6-dimethoxy-4-[7-(3-methylisoxazol-5-yl)imidazo[1,2-a]pyridin-3-yl]-N-[(1S)-2,2,2-trifluoro-1-methyl-ethyl]benzamide, 8-methoxy-6-[7-(1-methylpyrazol-4-yl)imidazo[1,2-a]pyridin-3-yl]-2-(2,2,2-trifluoroethyl)-3,4-dihydroisoquinolin-1-one, methyl 1-[2,6-dimethoxy-4-[7-(1-methylpyrazol-4-yl)imidazo[1,2-a]pyridin-3-yl]benzoyl]azetidine-3-carboxylate, 2,6-dimethoxy-4-[7-(1H-pyrazol-4-yl)imidazo[1,2-a]pyridin-3-yl]-N-(2,2,2-trifluoroethyl)benzamide, 2-[4-[3-[3,5-dimethoxy-4-(2,2,2-trifluoroethylcarbamoyl)phenyl]imidazo[1,2-a]pyridin-7-yl]pyrazol-1-yl]acetic acid, tert-butyl 2-[4-[3-[3,5-dimethoxy-4-(2,2,2-trifluoroethylcarbamoyl)phenyl]imidazo[1,2-a]pyridin-7-yl]pyrazol-1-yl]acetate, ethyl 2-[4-[3-[3,5-dimethoxy-4-(2,2,2-trifluoroethylcarbamoyl)phenyl]imidazo[1,2-a]pyridin-7-yl]pyrazol-1-yl]acetate, isopropyl 2-[4-[3-[3,5-dimethoxy-4-(2,2,2-trifluoroethylcarbamoyl)phenyl]imidazo[1,2-a]pyridin-7-yl]pyrazol-1-yl]acetate, 2,6-dimethoxy-4-[7-(3-methylisoxazol-5-yl)imidazo[1,2-a]pyridin-3-yl]-N-(2,2,2-trifluoroethyl)benzamide, 2-hydroxy-6-methoxy-4-[7-(1-methylpyrazol-4-yl)imidazo[1,2-a]pyridin-3-yl]-N-(2,2,2-trifluoroethyl)benzamide, cyclopropyl 2-[4-[3-[3,5-dimethoxy-4-(2,2,2-trifluoroethylcarbamoyl)phenyl]imidazo[1,2-a]pyridin-7-yl]pyrazol-1-yl]acetate, 2-fluoroethyl 2-[4-[3-[3,5-dimethoxy-4-(2,2,2-trifluoroethylcarbamoyl)phenyl]imidazo[1,2-a]pyridin-7-yl]pyrazol-1-yl]acetate, methyl 2-[4-[3-[3,5-dimethoxy-4-(2,2,2-trifluoroethylcarbamoyl)phenyl]imidazo[1,2-a]pyridin-7-yl]pyrazol-1-yl]acetate, tetrahydrofuran-3-yl 2-[4-[3-[3,5-dimethoxy-4-(2,2,2-trifluoroethylcarbamoyl)phenyl]imidazo[1,2-a]pyridin-7-yl]pyrazol-1-yl]acetate, cyclobutylmethyl 2-[4-[3-[3,5-dimethoxy-4-(2,2,2-trifluoroethylcarbamoyl)phenyl]imidazo[1,2-a]pyridin-7-yl]pyrazol-1-yl]acetate, 2,6-dimethoxy-4-[7-(6-methoxy-3-pyridyl)imidazo[1,2-a]pyridin-3-yl]-N-(2,2,2-trifluoroethyl)benzamide, 4-[7-(6-cyano-3-pyridyl)imidazo[1,2-a]pyridin-3-yl]-2,6-dimethoxy-N-(2,2,2-trifluoroethyl)benzamide, 2,6-dimethoxy-4-[7-(2-methoxypyrimidin-5-yl)imidazo[1,2-a]pyridin-3-yl]-N-(2,2,2-trifluoroethyl)benzamide, 2,6-dimethoxy-4-(7-pyrimidin-5-ylimidazo[1,2-a]pyridin-3-yl)-N-(2,2,2-trifluoroethyl)benzamide, tert-butyl 2-[4-[3-[3,5-dimethoxy-4-(2,2,2-trifluoroethylcarbamoyl)phenyl]imidazo[1,2-a]pyridin-7-yl]pyrazol-1-yl]propanoate, methyl 2-[4-[3-[3,5-dimethoxy-4-(2,2,2-trifluoroethylcarbamoyl)phenyl]imidazo[1,2-a]pyridin-7-yl]pyrazol-1-yl]propanoate, 2,6-dimethoxy-4-[7-(5-methoxy-3-pyridyl)imidazo[1,2-a]pyridin-3-yl]-N-(2,2,2-trifluoroethyl)benzamide, 4-[7-(2-aminopyrimidin-5-yl)imidazo[1,2-a]pyridin-3-yl]-2,6-dimethoxy-N-(2,2,2-trifluoroethyl)benzamide,
2,6-dimethoxy-4-(7-pyridazin-4-ylimidazo[1,2-a]pyridin-3-yl)-N-(2,2,2-trifluoroethyl)benzamide,
4-[7-(5-ethoxy-3-pyridyl)imidazo[1,2-a]pyridin-3-yl]-2,6-dimethoxy-N-(2,2,2-trifluoroethyl)benzamide,
2,6-dimethoxy-4-[7-[1-methyl-3-(trifluoromethyl)pyrazol-4-yl]imidazo[1,2-a]pyridin-3-yl]-N-(2,2,2-trifluoroethyl)benzamide,
2,6-dimethoxy-4-[7-(2-methoxy-3-pyridyl)imidazo[1,2-a]pyridin-3-yl]-N-(2,2,2-trifluoroethyl)benzamide,
2,6-dimethoxy-4-[7-(6-morpholino-3-pyridyl)imidazo[1,2-a]pyridin-3-yl]-N-(2,2,2-trifluoroethyl)benzamide,
2,6-dimethoxy-4-[7-(6-methylpyridazin-4-yl)imidazo[1,2-a]pyridin-3-yl]-N-(2,2,2-trifluoroethyl)benzamide,
4-[7-(4-isopropylpyrimidin-5-yl)imidazo[1,2-a]pyridin-3-yl]-2,6-dimethoxy-N-(2,2,2-trifluoroethyl)benzamide,
2-[4-[3-[3,5-dimethoxy-4-(2,2,2-trifluoroethylcarbamoyl)phenyl]imidazo[1,2-a]pyridin-7-yl]pyrazol-1-yl]propanoic acid,
4-[4-[3-[3,5-dimethoxy-4-(2,2,2-trifluoroethylcarbamoyl)phenyl]imidazo[1,2-a]pyridin-7-yl]pyrazol-1-yl]butanoic acid,
methyl 4-[4-[3-[3,5-dimethoxy-4-(2,2,2-trifluoroethylcarbamoyl)phenyl]imidazo[1,2-a]pyridin-7-yl]pyrazol-1-yl]butanoate,
ethyl 4-[4-[3-[3,5-dimethoxy-4-(2,2,2-trifluoroethylcarbamoyl)phenyl]imidazo[1,2-a]pyridin-7-yl]pyrazol-1-yl]butanoate,
4-[7-(4-cyano-3-pyridyl)imidazo[1,2-a]pyridin-3-yl]-2,6-dimethoxy-N-(2,2,2-trifluoroethyl)benzamide,
3-[3-[3,5-dimethoxy-4-(2,2,2-trifluoroethylcarbamoyl)phenyl]imidazo[1,2-a]pyridin-7-yl]pyridine-4-carboxamide,
tert-butyl 3-[4-[3-[3,5-dimethoxy-4-(2,2,2-trifluoroethylcarbamoyl)phenyl]imidazo[1,2-a]pyridin-7-yl]pyrazol-1-yl]azetidine-1-carboxylate,
7-methoxy-5-[7-(1-methylpyrazol-4-yl)imidazo[1,2-a]pyridin-3-yl]-2-(2,2,2-trifluoroethyl)isoindolin-1-one,
2-cyclopropyl-8-methoxy-6-[7-(1-methylpyrazol-4-yl)imidazo[1,2-a]pyridin-3-yl]-3,4-dihydroisoquinolin-1-one,
ethyl 2-[4-[3-[3,5-dimethoxy-4-(2,2,2-trifluoroethylcarbamoyl)phenyl]imidazo[1,2-a]pyridin-7-yl]pyrazol-1-yl]propanoate,
4-[7-[1-[1-(2-cyanoethyl)azetidin-3-yl]pyrazol-4-yl]imidazo[1,2-a]pyridin-3-yl]-2,6-dimethoxy-N-(2,2,2-trifluoroethyl)benzamide,
4-[7-[1-[1-(cyanomethyl)azetidin-3-yl]pyrazol-4-yl]imidazo[1,2-a]pyridin-3-yl]-2,6-dimethoxy-N-(2,2,2-trifluoroethyl)benzamide,
4-[7-(1-methylpyrazol-4-yl)imidazo[1,2-a]pyridin-3-yl]-2,6-bis(trideuteriomethoxy)-N-(2,2,2-trifluoroethyl)benzamide,
N-cyclopropyl-2-(difluoromethoxy)-6-methoxy-4-[7-(6-methoxy-3-pyridyl)imidazo[1,2-a]pyridin-3-yl]benzamide,
4-[7-(2-cyano-3-pyridyl)imidazo[1,2-a]pyridin-3-yl]-2,6-dimethoxy-N-(2,2,2-trifluoroethyl)benzamide,
2,6-dimethoxy-4-[7-(6-methylpyridazin-3-yl)imidazo[1,2-a]pyridin-3-yl]-N-(2,2,2-trifluoroethyl)benzamide,
N-cyclopropyl-2-(difluoromethoxy)-6-methoxy-4-[7-(3-methylisoxazol-5-yl)imidazo[1,2-a]pyridin-3-yl]benzamide,
2,6-difluoro-4-[7-(1-methylpyrazol-4-yl)imidazo[1,2-a]pyridin-3-yl]-N-(2,2,2-trifluoroethyl)benzamide,
N-cyclopropyl-2-(difluoromethoxy)-6-methoxy-4-[7-(6-methylpyridazin-4-yl)imidazo[1,2-a]pyridin-3-yl]benzamide,
N-cyclopropyl-2-(difluoromethoxy)-6-methoxy-4-[7-(6-methylpyridazin-3-yl)imidazo[1,2-a]pyridin-3-yl]benzamide,
N-cyclopropyl-2-(difluoromethoxy)-6-methoxy-4-[7-(3-methylimidazol-4-yl)imidazo[1,2-a]pyridin-3-yl]benzamide,
8-methoxy-6-[7-(6-methylpyridazin-3-yl)imidazo[1,2-a]pyridin-3-yl]-2-(2,2,2-trifluoroethyl)-3,4-dihydroisoquinolin-1-one,
N-cyclopropyl-2-fluoro-6-methoxy-4-[7-(1-methylpyrazol-4-yl)imidazo[1,2-a]pyridin-3-yl]benzamide,
N-cyclopropyl-2-(isopropylamino)-6-methoxy-4-[7-(1-methylpyrazol-4-yl)imidazo[1,2-a]pyridin-3-yl]benzamide,
N-cyclopropyl-2-methoxy-6-(2-methoxyethoxy)-4-[7-(1-methylpyrazol-4-yl)imidazo[1,2-a]pyridin-3-yl]benzamide,
N-cyclopropyl-2-(2-hydroxyethoxy)-6-methoxy-4-[7-(1-methylpyrazol-4-yl)imidazo[1,2-a]pyridin-3-yl]benzamide,
N-cyclopropyl-2-(difluoromethoxy)-6-methoxy-4-[7-(6-methoxypyridazin-3-yl)imidazo[1,2-a]pyridin-3-yl]benzamide,
N-cyclopropyl-2-(difluoromethoxy)-6-methoxy-4-[7-[6-(trifluoromethyl)pyridazin-3-yl]imidazo[1,2-a]pyridin-3-yl]benzamide,
4-[7-(6-cyanopyridazin-3-yl)imidazo[1,2-a]pyridin-3-yl]-N-cyclopropyl-2-(difluoromethoxy)-6-methoxy-benzamide,
N-cyclopropyl-2-(difluoromethoxy)-4-[7-[6-(dimethylamino)pyridazin-3-yl]imidazo[1,2-a]pyridin-3-yl]-6-methoxy-benzamide,
ethyl 2-[4-[3-[4-(cyclopropylcarbamoyl)-3-(difluoromethoxy)-5-methoxy-phenyl]imidazo[1,2-a]pyridin-7-yl]pyrazol-1-yl]acetate,
N-cyclopropyl-4-[7-(6-cyclopropylpyridazin-3-yl)imidazo[1,2-a]pyridin-3-yl]-2-(difluoromethoxy)-6-methoxy-benzamide,
N-cyclopropyl-2-(difluoromethoxy)-6-methoxy-4-[7-(6-morpholinopyridazin-3-yl)imidazo[1,2-a]pyridin-3-yl]benzamide,
7-[5-(5-fluoro-3-pyridyl)benzimidazol-1-yl]-5-methoxy-2,3-dihydro-1,3-benzoxazin-4-one,
5-methoxy-7-[5-(5-methoxy-3-pyridyl)benzimidazol-1-yl]-2,3-dihydro-1,3-benzoxazin-4-one,
7-[5-(3-fluoro-2-pyridyl)benzimidazol-1-yl]-5-methoxy-2,3-dihydro-1,3-benzoxazin-4-one,
7-[5-(2-isopropylthiazol-4-yl)benzimidazol-1-yl]-5-methoxy-2,3-dihydro-1,3-benzoxazin-4-one,
ethyl 3-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
ethyl 2-[[4-[3-[3,5-dimethoxy-4-(2,2,2-trifluoroethylcarbamoyl)phenyl]imidazo[1,2-a]pyridin-7-yl]pyrazol-1-yl]methyl]-3-methyl-butanoate,
ethyl 2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
ethyl 2-[4-[3-[3,5-dimethoxy-4-(2,2,2-trifluoroethylcarbamoyl)phenyl]imidazo[1,2-a]pyridin-7-yl]pyrazol-1-yl]-3-methyl-butanoate,
tetrahydrofuran-2-ylmethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
ethyl 2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxyacetate, 2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxyacetic acid,
4-[6-benzyloxy-7-(1-methylpyrazol-4-yl)imidazo[1,2-a]pyridin-3-yl]-N-cyclopropyl-2-(difluoromethoxy)-6-methoxy-benzamide,
4-[6-(1-cyanoethoxy)-7-(1-methylpyrazol-4-yl)imidazo[1,2-a]pyridin-3-yl]-N-cyclopropyl-2-(difluoromethoxy)-6-methoxy-benzamide,
ethyl 2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxypropanoate,
2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxypropanoic acid,
2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoic acid,
2-(diethylamino)ethyl 2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
N-cyclopropyl-2-(difluoromethoxy)-6-methoxy-4-[5-(1H-pyrazol-4-yl)benzimidazol-1-yl]benzamide, and
N-cyclopropyl-2-(difluoromethoxy)-6-methoxy-4-[7-(1H-pyrazol-4-yl)imidazo[1,2-a]pyridin-3-yl]benzamide.

In one embodiment, the compound of the invention is according to Formula I, wherein the compound is selected from:
N-ethyl-4-[5-(1-ethylpyrazol-4-yl)benzimidazol-1-yl]-2,6-dimethoxy-benzamide,
N-ethyl-2,6-dimethoxy-4-[5-(3-pyridyl)benzimidazol-1-yl]benzamide,
N-ethyl-2,6-dimethoxy-4-[5-(6-morpholino-3-pyridyl)benzimidazol-1-yl]benzamide,
N-ethyl-2,6-dimethoxy-4-[5-[1-(2-morpholinoethyl)pyrazol-4-yl]benzimidazol-1-yl]benzamide,
4-[5-(1-ethylpyrazol-4-yl)benzimidazol-1-yl]-N-(2-hydroxyethyl)-2,6-dimethoxy-benzamide,
4-[5-(1-ethylpyrazol-4-yl)benzimidazol-1-yl]-2,6-dimethoxy-N-methyl-benzamide,
N-ethyl-2,6-dimethoxy-4-[5-(1-methylpyrazol-4-yl)benzimidazol-1-yl]benzamide,
4-[5-(1,3-dimethylpyrazol-4-yl)benzimidazol-1-yl]-N-ethyl-2,6-dimethoxy-benzamide,
N-ethyl-4-[6-(1-ethylpyrazol-4-yl)pyrazolo[1,5-a]pyrimidin-3-yl]-2,6-dimethoxy-benzamide,
4-[5-(1-ethylpyrazol-4-yl)benzimidazol-1-yl]-N-(2-fluoroethyl)-2,6-dimethoxy-benzamide,
N-(2,2-difluoroethyl)-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2,2,2-trifluoroethyl)benzamide,
N-ethyl-2,6-dimethoxy-4-[5-[1-(2-methoxyethyl)pyrazol-4-yl]benzimidazol-1-yl]benzamide,
N-ethyl-2,6-dimethoxy-4-[5-(1-tetrahydropyran-4-ylpyrazol-4-yl)benzimidazol-1-yl]benzamide,
4-[5-[1-(cyanomethyl)pyrazol-4-yl]benzimidazol-1-yl]-N-ethyl-2,6-dimethoxy-benzamide,
N-ethyl-4-[5-[1-(2-hydroxyethyl)pyrazol-4-yl]benzimidazol-1-yl]-2,6-dimethoxy-benzamide,
2-(difluoromethoxy)-N-ethyl-4-[5-(1-ethylpyrazol-4-yl)benzimidazol-1-yl]-6-methoxy-benzamide,
4-[5-[1-(2-amino-2-oxo-ethyl)pyrazol-4-yl]benzimidazol-1-yl]-N-ethyl-2,6-dimethoxy-benzamide,
N-cyclopropyl-4-[5-(1-ethylpyrazol-4-yl)benzimidazol-1-yl]-2,6-dimethoxy-benzamide,
4-[6-(1-ethylpyrazol-4-yl)pyrazolo[1,5-a]pyrimidin-3-yl]-2,6-dimethoxy-N-(2,2,2-trifluoroethyl)benzamide,
N-(2,2-difluoroethyl)-4-[6-(1-ethylpyrazol-4-yl)pyrazolo[1,5-a]pyrimidin-3-yl]-2,6-dimethoxy-benzamide,
4-[5-(1-ethylpyrazol-4-yl)benzimidazol-1-yl]-2,6-dimethoxy-N-propyl-benzamide,
N-ethyl-4-[5-(1-ethylpyrazol-4-yl)benzimidazol-1-yl]-2-hydroxy-6-methoxy-benzamide,
N-(2,2-difluoroethyl)-2,6-dimethoxy-4-[6-(1-methylpyrazol-4-yl)pyrazolo[1,5-a]pyrimidin-3-yl]benzamide,
2,6-dimethoxy-4-[5-(1-methylpyrazol-4-yl)benzimidazol-1-yl]-N-(2,2,2-trifluoroethyl)benzamide,
N-cyclobutyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2-methoxyethyl)-N-methyl-benzamide,
4-[5-(1-ethylpyrazol-4-yl)benzimidazol-1-yl]-N-isobutyl-2,6-dimethoxy-N-methyl-benzamide,
4-[6-(1-ethylpyrazol-4-yl)imidazo[4,5-b]pyridin-3-yl]-2,6-dimethoxy-N-(2,2,2-trifluoroethyl)benzamide,
N-cyclopropyl-4-[5-(1-ethylpyrazol-4-yl)benzimidazol-1-yl]-2,6-dimethoxy-N-methyl-benzamide,
N-(cyanomethyl)-4-[5-(1-ethylpyrazol-4-yl)benzimidazol-1-yl]-2,6-dimethoxy-N-methyl-benzamide,
2,6-dimethoxy-4-[5-(6-morpholino-3-pyridyl)benzimidazol-1-yl]-N-(2,2,2-trifluoroethyl)benzamide,
4-[5-[1-(2-hydroxyethyl)pyrazol-4-yl]benzimidazol-1-yl]-2,6-dimethoxy-N-(2,2,2-trifluoroethyl)benzamide,
2,6-dimethoxy-4-[5-(6-pyrrolidin-1-yl-3-pyridyl)benzimidazol-1-yl]-N-(2,2,2-trifluoroethyl)benzamide,
2,6-dimethoxy-4-[5-(5-methoxy-3-pyridyl)benzimidazol-1-yl]-N-(2,2,2-trifluoroethyl)benzamide,
4-[5-(6-cyano-3-pyridyl)benzimidazol-1-yl]-2,6-dimethoxy-N-(2,2,2-trifluoroethyl)benzamide,
4-[5-[6-(dimethylamino)-3-pyridyl]benzimidazol-1-yl]-2,6-dimethoxy-N-(2,2,2-trifluoroethyl)benzamide,
4-[5-(6-amino-3-pyridyl)benzimidazol-1-yl]-2,6-dimethoxy-N-(2,2,2-trifluoroethyl)benzamide,
2,6-dimethoxy-4-[5-(3-pyridyl)benzimidazol-1-yl]-N-(2,2,2-trifluoroethyl)benzamide,
4-[5-[1-(cyanomethyl)pyrazol-4-yl]benzimidazol-1-yl]-2,6-dimethoxy-N-(2,2,2-trifluoroethyl)benzamide,
2,6-dimethoxy-4-[5-[1-(2-morpholinoethyl)pyrazol-4-yl]benzimidazol-1-yl]-N-(2,2,2-trifluoroethyl)benzamide,
2,6-dimethoxy-4-[5-[1-(4-piperidyl)pyrazol-4-yl]benzimidazol-1-yl]-N-(2,2,2-trifluoroethyl)benzamide,
N-tert-butyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(3,3,3-trifluoropropyl)benzamide,
N-cyclopentyl-4-[5-(1-ethylpyrazol-4-yl)benzimidazol-1-yl]-2,6-dimethoxy-benzamide,
2,6-dimethoxy-4-[5-[1-(1-methyl-4-piperidyl)pyrazol-4-yl]benzimidazol-1-yl]-N-(2,2,2-trifluoroethyl)benzamide,
2,6-dimethoxy-4-[5-(1H-pyrazol-4-yl)benzimidazol-1-yl]-N-(2,2,2-trifluoroethyl)benzamide,
2-(difluoromethoxy)-N-ethyl-6-methoxy-4-[5-(1-methylpyrazol-4-yl)benzimidazol-1-yl]benzamide,
4-[5-(1-ethylpyrazol-4-yl)benzimidazol-1-yl]-2,6-dimethoxy-N-[(2R)-2-methylcyclopropyl]benzamide,
N-(cyanomethyl)-4-[5-(1-ethylpyrazol-4-yl)benzimidazol-1-yl]-2,6-dimethoxy-benzamide,
4-(5-isoxazol-4-ylbenzimidazol-1-yl)-2,6-dimethoxy-N-(2,2,2-trifluoroethyl)benzamide,
2,6-dimethoxy-4-[6-(1-methylpyrazol-4-yl)pyrazolo[1,5-a]pyrimidin-3-yl]-N-(2,2,2-trifluoroethyl)benzamide, N-cyclopropyl-2-(difluoromethoxy)-6-methoxy-4-[5-(1-methylpyrazol-4-yl)benzimidazol-1-yl]benzamide,
N-cyclopropyl-2-(difluoromethoxy)-4-[5-(1-ethylpyrazol-4-yl)benzimidazol-1-yl]-6-methoxy-benzamide,
4-[5-[1-(cyanomethyl)pyrazol-4-yl]benzimidazol-1-yl]-N-cyclopropyl-2-(difluoromethoxy)-6-methoxy-benzamide,
N-cyclopropyl-2-(difluoromethoxy)-6-methoxy-4-[5-[1-(2-morpholinoethyl)pyrazol-4-yl]benzimidazol-1-yl]benzamide,
2-(difluoromethoxy)-N-ethyl-6-methoxy-4-[5-[1-(2-morpholinoethyl)pyrazol-4-yl]benzimidazol-1-yl]benzamide,
2,6-dimethoxy-4-[5-(1-methylpyrazol-4-yl)benzimidazol-1-yl]-N-[(1R)-2,2,2-trifluoro-1-methyl-ethyl]benzamide,
N-(2-cyanoethyl)-2,6-dimethoxy-4-[5-(1-methylpyrazol-4-yl)benzimidazol-1-yl]benzamide,
2,6-dimethoxy-N-(3-methoxypropyl)-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1-methylpyrazol-3-yl)methyl]benzamide,
2,6-dimethoxy-4-[5-(1-methylpyrazol-4-yl)benzimidazol-1-yl]-N-(2-pyridylmethyl)benzamide,
N-(3-hydroxypropyl)-2,6-dimethoxy-4-[5-(1-methylpyrazol-4-yl)benzimidazol-1-yl]benzamide,
N-(1,1-dioxothietan-3-yl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2-methylsulfonylethyl)benzamide,
N-(1,1-dioxothiolan-3-yl)-2,6-dimethoxy-4-[5-(1-methylpyrazol-4-yl)benzimidazol-1-yl]benzamide,
N-[[(2R)-1,4-dioxan-2-yl]methyl]-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2,2,2-trifluoro-1,1-dimethyl-ethyl)benzamide,
N-[[(2S)-1,4-dioxan-2-yl]methyl]-2,6-dimethoxy-4-[5-(1-methylpyrazol-4-yl)benzimidazol-1-yl]benzamide,
2,6-dimethoxy-N-(5-methylpyrazin-2-yl)-4-[5-(1-methylpyrazol-4-yl)benzimidazol-1-yl]benzamide,
2,6-dimethoxy-N-[(1-methylimidazol-2-yl)methyl]-4-[5-(1-methylpyrazol-4-yl)benzimidazol-1-yl]benzamide,
N-isoxazol-3-yl-2,6-dimethoxy-4-[5-(1-methylpyrazol-4-yl)benzimidazol-1-yl]benzamide,
2,6-dimethoxy-N-(2-methylpyrazol-3-yl)-4-[5-(1-methylpyrazol-4-yl)benzimidazol-1-yl]benzamide,
N-(cyanomethyl)-2,6-dimethoxy-N-methyl-4-[5-(1-methylpyrazol-4-yl)benzimidazol-1-yl]benzamide,
N-(cyanomethyl)-2,6-dimethoxy-4-[5-(1-methylpyrazol-4-yl)benzimidazol-1-yl]benzamide,
N-tert-butyl-2,6-dimethoxy-4-[5-(1-methylpyrazol-4-yl)benzimidazol-1-yl]benzamide,
N-cyclobutyl-2,6-dimethoxy-4-[5-(1-methylpyrazol-4-yl)benzimidazol-1-yl]benzamide,
N-(2,2-difluoroethyl)-2,6-dimethoxy-4-[5-(1-methylpyrazol-4-yl)benzimidazol-1-yl]benzamide,
N-(2-fluoroethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1S)-2,2,2-trifluoro-1-methyl-ethyl]benzamide,
2,6-dimethoxy-N-(1-methylpyrazol-3-yl)-4-[5-(1-methylpyrazol-4-yl)benzimidazol-1-yl]benzamide,
2,6-dimethoxy-N-(1-methylimidazol-4-yl)-4-[5-(1-methylpyrazol-4-yl)benzimidazol-1-yl]benzamide,
2,6-dimethoxy-N-(1-methylpyrazol-4-yl)-4-[5-(1-methylpyrazol-4-yl)benzimidazol-1-yl]benzamide,
2,6-dimethoxy-4-[5-[1-(2-methoxyethyl)pyrazol-4-yl]benzimidazol-1-yl]-N-(2,2,2-trifluoroethyl)benzamide,
2,6-dimethoxy-4-[5-[1-(oxetan-3-yl)pyrazol-4-yl]benzimidazol-1-yl]-N-(2,2,2-trifluoroethyl)benzamide,
N-cyclopropyl-2,6-dimethoxy-4-[5-(1-methylpyrazol-4-yl)benzimidazol-1-yl]benzamide,
N-(1-cyanoethyl)-2,6-dimethoxy-4-[5-(1-methylpyrazol-4-yl)benzimidazol-1-yl]benzamide,
2,6-dimethoxy-4-[7-(1-methylpyrazol-4-yl)imidazo[1,2-a]pyridin-3-yl]-N-(2,2,2-trifluoroethyl)benzamide,
2,6-dimethoxy-4-[5-(1-methylpyrazol-3-yl)benzimidazol-1-yl]-N-(2,2,2-trifluoroethyl)benzamide,
N-(2,2-difluorocyclopentyl)-2,6-dimethoxy-4-[5-(1-methylpyrazol-4-yl)benzimidazol-1-yl]benzamide,
N-(2,2-difluoro-1-methyl-ethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(oxetan-3-yl)benzamide,
2,6-dimethoxy-4-(5-pyridazin-4-ylbenzimidazol-1-yl)-N-(2,2,2-trifluoroethyl)benzamide,
4-[5-[1-(azetidin-3-yl)pyrazol-4-yl]benzimidazol-1-yl]-2,6-dimethoxy-N-(2,2,2-trifluoroethyl)benzamide,
4-[5-(1-isopropylpyrazol-4-yl)benzimidazol-1-yl]-2,6-dimethoxy-N-(2,2,2-trifluoroethyl)benzamide,
4-[5-(1-cyclopropylpyrazol-4-yl)benzimidazol-1-yl]-2,6-dimethoxy-N-(2,2,2-trifluoroethyl)benzamide,
4-[5-[1-(difluoromethyl)pyrazol-4-yl]benzimidazol-1-yl]-2,6-dimethoxy-N-(2,2,2-trifluoroethyl)benzamide,
2,6-dimethoxy-4-[5-[1-(1-methylazetidin-3-yl)pyrazol-4-yl]benzimidazol-1-yl]-N-(2,2,2-trifluoroethyl)benzamide,
2,6-dimethoxy-4-[6-(1-methylpyrazol-4-yl)pyrazolo[1,5-a]pyridin-3-yl]-N-(2,2,2-trifluoroethyl)benzamide,
4-[5-[1-[1-(cyanomethyl)azetidin-3-yl]pyrazol-4-yl]benzimidazol-1-yl]-2,6-dimethoxy-N-(2,2,2-trifluoroethyl)benzamide,
2,6-dimethoxy-4-[5-(3-methyl-1H-pyrazol-5-yl)benzimidazol-1-yl]-N-(2,2,2-trifluoroethyl)benzamide,
N-cyclopropyl-2,6-dimethoxy-4-[7-(1-methylpyrazol-4-yl)imidazo[1,2-a]pyridin-3-yl]benzamide,
2,6-dimethoxy-4-[5-(1-propylpyrazol-4-yl)benzimidazol-1-yl]-N-(2,2,2-trifluoroethyl)benzamide,
2,6-dimethoxy-4-(5-pyrimidin-5-ylbenzimidazol-1-yl)-N-(2,2,2-trifluoroethyl)benzamide,
2,6-dimethoxy-4-[5-(2-methoxypyrimidin-5-yl)benzimidazol-1-yl]-N-(2,2,2-trifluoroethyl)benzamide,
2,6-dimethoxy-4-[5-(2-methoxy-4-pyridyl)benzimidazol-1-yl]-N-(2,2,2-trifluoroethyl)benzamide,
2,6-dimethoxy-4-[7-(1-methylpyrazol-4-yl)imidazo[1,2-b]pyridazin-3-yl]-N-(2,2,2-trifluoroethyl)benzamide,
2,6-dimethoxy-4-[5-(3-methylisoxazol-4-yl)benzimidazol-1-yl]-N-(2,2,2-trifluoroethyl)benzamide,
2,6-dimethoxy-4-[5-(3-methylisoxazol-5-yl)benzimidazol-1-yl]-N-(2,2,2-trifluoroethyl)benzamide,
4-[5-(1-isobutylpyrazol-4-yl)benzimidazol-1-yl]-2,6-dimethoxy-N-(2,2,2-trifluoroethyl)benzamide,
2,6-dimethoxy-4-[5-[i-(tetrahydrofuran-2-ylmethyl)pyrazol-4-yl]benzimidazol-1-yl]-N-(2,2,2-trifluoroethyl)benzamide,
N-cyclopropyl-2,6-dimethoxy-4-[7-(1-methylpyrazol-4-yl)imidazo[1,2-b]pyridazin-3-yl]benzamide,
N-isobutyl-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-sec-butyl-benzamide,
N-isopropyl-2,6-dimethoxy-4-[5-(1-methylpyrazol-4-yl)benzimidazol-1-yl]benzamide,
2-(difluoromethoxy)-N-ethyl-6-methoxy-4-[7-(1-methylpyrazol-4-yl)imidazo[1,2-a]pyridin-3-yl]benzamide,
2-(difluoromethoxy)-N-ethyl-6-methoxy-4-[6-(1-methylpyrazol-4-yl)pyrazolo[1,5-a]pyridin-3-yl]benzamide, 2-(difluoromethoxy)-N-ethyl-6-methoxy-4-[7-(1-methylpyrazol-4-yl)imidazo[1,2-b]pyridazin-3-yl]benzamide,
N-cyclopropyl-2-isopropoxy-6-methoxy-4-[5-(1-methylpyrazol-4-yl)benzimidazol-1-yl]benzamide,
2,6-dimethoxy-4-[5-[2-(4-methylpiperazin-1-yl)-4-pyridyl]benzimidazol-1-yl]-N-(2,2,2-trifluoroethyl)benzamide,
2,6-dimethoxy-4-[5-(6-methylpyridazin-4-yl)benzimidazol-1-yl]-N-(2,2,2-trifluoroethyl)benzamide,
N-(cyanomethyl)-2,6-dimethoxy-4-[7-(1-methylpyrazol-4-yl)imidazo[1,2-a]pyridin-3-yl]benzamide,
2-(difluoromethoxy)-N-ethyl-6-methoxy-4-[7-(3-methylisoxazol-5-yl)imidazo[1,2-a]pyridin-3-yl]benzamide,
N-cyclopropyl-2-(difluoromethoxy)-6-methoxy-4-[7-(1-methylpyrazol-4-yl)imidazo[1,2-a]pyridin-3-yl]benzamide,
N-(3,3-difluorocyclobutyl)-2,6-dimethoxy-4-[5-(1-methylpyrazol-4-yl)benzimidazol-1-yl]benzamide,
2,6-dimethoxy-4-[5-(5-methyl-1,2,4-oxadiazol-3-yl)benzimidazol-1-yl]-N-(2,2,2-trifluoroethyl)benzamide,
2,6-dimethoxy-4-[5-(5-methyl-4H-1,2,4-triazol-3-yl)benzimidazol-1-yl]-N-(2,2,2-trifluoroethyl)benzamide,
2,6-dimethoxy-4-(5-pyrazin-2-ylbenzimidazol-1-yl)-N-(2,2,2-trifluoroethyl)benzamide,
N-isobutyl-2,6-dimethoxy-4-[7-(1-methylpyrazol-4-yl)imidazo[1,2-a]pyridin-3-yl]benzamide,
N-(1,1-dioxothietan-3-yl)-2,6-dimethoxy-4-[7-(1-methylpyrazol-4-yl)imidazo[1,2-a]pyridin-3-yl]benzamide,
2,6-dimethoxy-N-(2-methoxyethyl)-N-methyl-4-[7-(1-methylpyrazol-4-yl)imidazo[1,2-a]pyridin-3-yl]benzamide,
2,6-dimethoxy-4-[7-(1-methylpyrazol-4-yl)imidazo[1,2-a]pyridin-3-yl]-N-[(1S)-2,2,2-trifluoro-1-methyl-ethyl]benzamide,
N-(2,2-difluoroethyl)-2,6-dimethoxy-4-[7-(1-methylpyrazol-4-yl)imidazo[1,2-a]pyridin-3-yl]benzamide,
2,6-dimethoxy-4-[5-(1-methylimidazol-2-yl)benzimidazol-1-yl]-N-(2,2,2-trifluoroethyl)benzamide,
2,6-dimethoxy-4-[5-(3-methylimidazol-4-yl)benzimidazol-1-yl]-N-(2,2,2-trifluoroethyl)benzamide,
2-(difluoromethoxy)-N-ethyl-6-methoxy-4-[5-(5-methyl-1,2,4-oxadiazol-3-yl)benzimidazol-1-yl]benzamide,
2,6-dimethoxy-4-[5-(1-methylimidazol-4-yl)benzimidazol-1-yl]-N-(2,2,2-trifluoroethyl)benzamide,
4-[5-(2,3-dimethylimidazol-4-yl)benzimidazol-1-yl]-2,6-dimethoxy-N-(2,2,2-trifluoroethyl)benzamide,
N-[(1R,2R)-2-aminocyclohexyl]-2,6-dimethoxy-4-[5-(1-methylpyrazol-4-yl)benzimidazol-1-yl]benzamide,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-hydroxycyclopentyl]-2,6-dimethoxy-4-[5-(1-methylpyrazol-4-yl)benzimidazol-1-yl]benzamide,
(3,3-difluoroazetidin-1-yl)-[2,6-dimethoxy-4-[5-(1-methylpyrazol-4-yl)benzimidazol-1-yl]phenyl]methanone,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-fluorocyclopropyl]-2,6-dimethoxy-4-[5-(1-methylpyrazol-4-yl)benzimidazol-1-yl]benzamide,
2-(difluoromethoxy)-N-ethyl-6-methoxy-4-(7-pyridazin-4-ylimidazo[1,2-a]pyridin-3-yl)benzamide,
4-[7-(6-cyano-3-pyridyl)imidazo[1,2-a]pyridin-3-yl]-2-(difluoromethoxy)-N-ethyl-6-methoxy-benzamide,
tert-butyl 4-[4-[3-[3-(difluoromethoxy)-4-(ethylcarbamoyl)-5-methoxy-phenyl]imidazo[1,2-a]pyridin-7-yl]pyrazol-1-yl]piperidine-1-carboxylate,
2-(difluoromethoxy)-N-ethyl-6-methoxy-4-[7-[1-(1-methyl-4-piperidyl)pyrazol-4-yl]imidazo[1,2-a]pyridin-3-yl]benzamide,
2-(difluoromethoxy)-N-ethyl-6-methoxy-4-[7-[1-(4-piperidyl)pyrazol-4-yl]imidazo[1,2-a]pyridin-3-yl]benzamide,
2-(difluoromethoxy)-N-ethyl-6-methoxy-4-[5-(5-methyl-4H-1,2,4-triazol-3-yl)benzimidazol-1-yl]benzamide,
2-(difluoromethoxy)-4-[7-[1-(difluoromethyl)pyrazol-4-yl]imidazo[1,2-a]pyridin-3-yl]-N-ethyl-6-methoxy-benzamide,
2,6-dimethoxy-4-[5-(2-methyl-1H-imidazol-5-yl)benzimidazol-1-yl]-N-(2,2,2-trifluoroethyl)benzamide,
4-[5-(1H-imidazol-4-yl)benzimidazol-1-yl]-2,6-dimethoxy-N-(2,2,2-trifluoroethyl)benzamide,
2,6-dimethoxy-4-[5-(3-methylpyrazol-1-yl)benzimidazol-1-yl]-N-(2,2,2-trifluoroethyl)benzamide,
2,6-dimethoxy-4-[5-(4-methylimidazol-1-yl)benzimidazol-1-yl]-N-(2,2,2-trifluoroethyl)benzamide,
N-[(1R,2R)-2-(hydroxymethyl)cyclopropyl]-2,6-dimethoxy-4-[5-(1-methylpyrazol-4-yl)benzimidazol-1-yl]benzamide,
N-[(1R,2R)-2-(difluoromethyl)cyclopropyl]-2,6-dimethoxy-4-[5-(1-methylpyrazol-4-yl)benzimidazol-1-yl]benzamide,
N-[(1R,2S)-2-(difluoromethyl)cyclopropyl]-2,6-dimethoxy-4-[5-(1-methylpyrazol-4-yl)benzimidazol-1-yl]benzamide,
N-[(1R,2R)-2-hydroxycyclobutyl]-2,6-dimethoxy-4-[5-(1-methylpyrazol-4-yl)benzimidazol-1-yl]benzamide,
2,6-dimethoxy-4-[5-(1-methyltriazol-4-yl)benzimidazol-1-yl]-N-(2,2,2-trifluoroethyl)benzamide,
2,6-dimethoxy-N-(2-methoxycyclohexyl)-4-[5-(1-methylpyrazol-4-yl)benzimidazol-1-yl]benzamide,
azetidin-1-yl-[2,6-dimethoxy-4-[5-(1-methylpyrazol-4-yl)benzimidazol-1-yl]phenyl]methanone,
N-(2-aminoethyl)-2,6-dimethoxy-4-[5-(1-methylpyrazol-4-yl)benzimidazol-1-yl]benzamide,
N-[(1S,2S)-2-hydroxycyclohexyl]-2,6-dimethoxy-4-[5-(1-methylpyrazol-4-yl)benzimidazol-1-yl]benzamide,
4-[5-(3,5-dimethylpyrazol-1-yl)benzimidazol-1-yl]-2,6-dimethoxy-N-(2,2,2-trifluoroethyl)benzamide,
2,6-dimethoxy-4-[5-(3-methyl-1,2,4-triazol-1-yl)benzimidazol-1-yl]-N-(2,2,2-trifluoroethyl)benzamide,
2,6-dimethoxy-4-[5-(5-methyl-1,3,4-oxadiazol-2-yl)benzimidazol-1-yl]-N-(2,2,2-trifluoroethyl)benzamide,
4-[5-(4,5-dimethyl-1,2,4-triazol-3-yl)benzimidazol-1-yl]-2,6-dimethoxy-N-(2,2,2-trifluoroethyl)benzamide,
2,6-dimethoxy-4-[5-(3-methyl-1,2,4-oxadiazol-5-yl)benzimidazol-1-yl]-N-(2,2,2-trifluoroethyl)benzamide,
N-[(1S,2S)-2-hydroxycyclobutyl]-2,6-dimethoxy-4-[7-(1-methylpyrazol-4-yl)imidazo[1,2-a]pyridin-3-yl]benzamide,
N-isopropyl-2,6-dimethoxy-4-[7-(1-methylpyrazol-4-yl)imidazo[1,2-a]pyridin-3-yl]benzamide,
N-[(1S,2S)-2-(difluoromethyl)cyclopropyl]-2,6-dimethoxy-4-[7-(1-methylpyrazol-4-yl)imidazo[1,2-a]pyridin-3-yl]benzamide,
(3,3-difluoroazetidin-1-yl)-[2,6-dimethoxy-4-[7-(1-methylpyrazol-4-yl)imidazo[1,2-a]pyridin-3-yl]phenyl]methanone,
2,6-dimethoxy-4-[7-(1-methylpyrazol-4-yl)imidazo[1,2-a]pyridin-3-yl]-N-[(1R)-2,2,2-trifluoro-1-methyl-ethyl]benzamide,
2-ethyl-7-fluoro-5-[5-(1-methylpyrazol-4-yl)benzimidazol-1-yl]isoindolin-1-one,
2-ethyl-7-methoxy-5-[7-(1-methylpyrazol-4-yl)imidazo[1,2-a]pyridin-3-yl]isoindolin-1-one,
2-(difluoromethoxy)-N-ethyl-6-methoxy-4-[6-(1-methylpyrazol-4-yl)imidazo[4,5-b]pyridin-3-yl]benzamide, 2-(difluoromethoxy)-N-ethyl-6-methoxy-4-[7-(1-methyl-imidazol-4-yl)imidazo[1,2-a]pyridin-3-yl]benzamide,
[2,6-dimethoxy-4-[5-(1-methylpyrazol-4-yl)benzimidazol-1-yl]phenyl]-(3,3-dimethylazetidin-1-yl)methanone,
[2,6-dimethoxy-4-[5-(1-methylpyrazol-4-yl)benzimidazol-1-yl]phenyl]-(3-phenylazetidin-1-yl)methanone,
[2,6-dimethoxy-4-[5-(1-methylpyrazol-4-yl)benzimidazol-1-yl]phenyl]-(2,4-dimethylazetidin-1-yl)methanone,
[2,6-dimethoxy-4-[5-(1-methylpyrazol-4-yl)benzimidazol-1-yl]phenyl]-(2-methylazetidin-1-yl)methanone,
[2,6-dimethoxy-4-[5-(1-methylpyrazol-4-yl)benzimidazol-1-yl]phenyl]-[3-(hydroxymethyl)azetidin-1-yl]methanone,
[2,6-dimethoxy-4-[5-(1-methylpyrazol-4-yl)benzimidazol-1-yl]phenyl]-(3-hydroxyazetidin-1-yl)methanone,
[2,6-dimethoxy-4-[5-(1-methylpyrazol-4-yl)benzimidazol-1-yl]phenyl]-[3-(dimethylamino)azetidin-1-yl]methanone,
(3-benzyloxyazetidin-1-yl)-[2,6-dimethoxy-4-[5-(1-methylpyrazol-4-yl)benzimidazol-1-yl]phenyl]methanone,
[2,6-dimethoxy-4-[5-(1-methylpyrazol-4-yl)benzimidazol-1-yl]phenyl]-(2-phenylazetidin-1-yl)methanone,
[2,6-dimethoxy-4-[5-(1-methylpyrazol-4-yl)benzimidazol-1-yl]phenyl]-(3-morpholinoazetidin-1-yl)methanone,
[2,6-dimethoxy-4-[5-(1-methylpyrazol-4-yl)benzimidazol-1-yl]phenyl]-(2,2,4-trimethylazetidin-1-yl)methanone,
[2,6-dimethoxy-4-[5-(1-methylpyrazol-4-yl)benzimidazol-1-yl]phenyl]-(3-methoxyazetidin-1-yl)methanone,
[2,6-dimethoxy-4-[5-(1-methylpyrazol-4-yl)benzimidazol-1-yl]phenyl]-(3-tetrahydropyran-4-ylazetidin-1-yl)methanone,
1-[2,6-dimethoxy-4-[5-(1-methylpyrazol-4-yl)benzimidazol-1-yl]benzoyl]azetidine-3-carbonitrile,
[2,6-dimethoxy-4-[5-(1-methylpyrazol-4-yl)benzimidazol-1-yl]phenyl]-[2-(hydroxymethyl)azetidin-1-yl]methanone,
[2,6-dimethoxy-4-[5-(1-methylpyrazol-4-yl)benzimidazol-1-yl]phenyl]-(2-oxa-6-azaspiro[3.3]heptan-6-yl)methanone,
[2,6-dimethoxy-4-[5-(1-methylpyrazol-4-yl)benzimidazol-1-yl]phenyl]-(2,2-dioxo-2$\lambda^6$-thia-6-azaspiro[3.3]heptan-6-yl)methanone,
[2,6-dimethoxy-4-[5-(1-methylpyrazol-4-yl)benzimidazol-1-yl]phenyl]-(3-phenylpyrrolidin-1-yl)methanone,
[2,6-dimethoxy-4-[5-(1-methylpyrazol-4-yl)benzimidazol-1-yl]phenyl]-(4-fluoro-1-piperidyl)methanone,
[2,6-dimethoxy-4-[5-(1-methylpyrazol-4-yl)benzimidazol-1-yl]phenyl]-[4-(trifluoromethoxy)-1-piperidyl]methanone,
N-tert-butyl-2-(difluoromethoxy)-6-methoxy-4-[5-(1-methylpyrazol-4-yl)benzimidazol-1-yl]benzamide,
2,6-dimethoxy-4-[7-(1-methylpyrazol-4-yl)imidazo[1,2-a]pyridin-3-yl]-N-[2-methyl-1-(trifluoromethyl)propyl]benzamide,
2-ethyl-7-(2-hydroxyethylamino)-5-[7-(1-methylpyrazol-4-yl)imidazo[1,2-a]pyridin-3-yl]isoindolin-1-one,
2-ethyl-7-(2-hydroxyethylamino)-5-[5-(1-methylpyrazol-4-yl)benzimidazol-1-yl]isoindolin-1-one,
2-fluoro-6-methoxy-4-[7-(1-methylpyrazol-4-yl)imidazo[1,2-a]pyridin-3-yl]-N-(2,2,2-trifluoroethyl)benzamide,
2-methoxy-6-(methylamino)-4-[7-(1-methylpyrazol-4-yl)imidazo[1,2-a]pyridin-3-yl]-N-(2,2,2-trifluoroethyl)benzamide,
2-(2-hydroxyethylamino)-6-methoxy-4-[7-(1-methylpyrazol-4-yl)imidazo[1,2-a]pyridin-3-yl]-N-(2,2,2-trifluoroethyl)benzamide,
2-methoxy-6-methyl-4-[7-(1-methylpyrazol-4-yl)imidazo[1,2-a]pyridin-3-yl]-N-(2,2,2-trifluoroethyl)benzamide,
2-chloro-6-methoxy-4-[7-(1-methylpyrazol-4-yl)imidazo[1,2-a]pyridin-3-yl]-N-(2,2,2-trifluoroethyl)benzamide,
[2,6-dimethoxy-4-[7-(1-methylpyrazol-4-yl)imidazo[1,2-a]pyridin-3-yl]phenyl]-(3,3-dimethylazetidin-1-yl)methanone,
1-[2,6-dimethoxy-4-[7-(1-methylpyrazol-4-yl)imidazo[1,2-a]pyridin-3-yl]benzoyl]azetidine-3-carbonitrile,
1-[2,6-dimethoxy-4-[7-(1-methylpyrazol-4-yl)imidazo[1,2-a]pyridin-3-yl]benzoyl]pyrrolidine-3-carbonitrile,
(3,3-difluoropyrrolidin-1-yl)-[2,6-dimethoxy-4-[7-(1-methylpyrazol-4-yl)imidazo[1,2-a]pyridin-3-yl]phenyl]methanone,
(4,4-difluoro-1-piperidyl)-[2,6-dimethoxy-4-[7-(1-methylpyrazol-4-yl)imidazo[1,2-a]pyridin-3-yl]phenyl]methanone,
[2,6-dimethoxy-4-[7-(1-methylpyrazol-4-yl)imidazo[1,2-a]pyridin-3-yl]phenyl]-[3-(trifluoromethyl)azetidin-1-yl]methanone,
8-methoxy-6-[7-(1-methylpyrazol-4-yl)imidazo[1,2-a]pyridin-3-yl]-3,4-dihydro-2H-isoquinolin-1-one,
2,6-dimethoxy-4-[7-(1-methylimidazol-4-yl)imidazo[1,2-a]pyridin-3-yl]-N-[(1R)-2,2,2-trifluoro-1-methyl-ethyl]benzamide,
2,6-dimethoxy-4-[7-(1-methylimidazol-4-yl)imidazo[1,2-a]pyridin-3-yl]-N-[(1S)-2,2,2-trifluoro-1-methyl-ethyl]benzamide,
[2,6-dimethoxy-4-[5-(1-methylpyrazol-4-yl)benzimidazol-1-yl]phenyl]-(3-hydroxy-3-methyl-azetidin-1-yl)methanone,
[2,6-dimethoxy-4-[5-(1-methylpyrazol-4-yl)benzimidazol-1-yl]phenyl]-(3-ethyl-3-hydroxy-azetidin-1-yl)methanone,
[2,6-dimethoxy-4-[5-(1-methylpyrazol-4-yl)benzimidazol-1-yl]phenyl]-[3-hydroxy-3-(trifluoromethyl)azetidin-1-yl]methanone,
(3-cyclopropyl-3-hydroxy-azetidin-1-yl)-[2,6-dimethoxy-4-[5-(1-methylpyrazol-4-yl)benzimidazol-1-yl]phenyl]methanone,
[2,6-dimethoxy-4-[5-(1-methylpyrazol-4-yl)benzimidazol-1-yl]phenyl]-(3-ethynyl-3-hydroxy-azetidin-1-yl)methanone,
2,6-dimethoxy-4-[7-(1H-pyrazol-4-yl)imidazo[1,2-a]pyridin-3-yl]-N-[(1R)-2,2,2-trifluoro-1-methyl-ethyl]benzamide,
2,6-dimethoxy-4-[7-(3-methylisoxazol-5-yl)imidazo[1,2-a]pyridin-3-yl]-N-[(1R)-2,2,2-trifluoro-1-methyl-ethyl]benzamide,
2,6-dimethoxy-4-[7-(3-methylisoxazol-5-yl)imidazo[1,2-a]pyridin-3-yl]-N-[(1S)-2,2,2-trifluoro-1-methyl-ethyl]benzamide,
8-methoxy-6-[7-(1-methylpyrazol-4-yl)imidazo[1,2-a]pyridin-3-yl]-2-(2,2,2-trifluoroethyl)-3,4-dihydroisoquinolin-1-one,
methyl 1-[2,6-dimethoxy-4-[7-(1-methylpyrazol-4-yl)imidazo[1,2-a]pyridin-3-yl]benzoyl]azetidine-3-carboxylate,
2,6-dimethoxy-4-[7-(1H-pyrazol-4-yl)imidazo[1,2-a]pyridin-3-yl]-N-(2,2,2-trifluoroethyl)benzamide,
2-[4-[3-[3,5-dimethoxy-4-(2,2,2-trifluoroethylcarbamoyl)phenyl]imidazo[1,2-a]pyridin-7-yl]pyrazol-1-yl]acetic acid,
tert-butyl 2-[4-[3-[3,5-dimethoxy-4-(2,2,2-trifluoroethylcarbamoyl)phenyl]imidazo[1,2-a]pyridin-7-yl]pyrazol-1-yl]acetate, ethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
isopropyl 2-[4-[3-[3,5-dimethoxy-4-(2,2,2-trifluoroethylcarbamoyl)phenyl]imidazo[1,2-a]pyridin-7-yl]pyrazol-1-yl]acetate,
2,6-dimethoxy-4-[7-(3-methylisoxazol-5-yl)imidazo[1,2-a]pyridin-3-yl]-N-(2,2,2-trifluoroethyl)benzamide,
2-hydroxy-6-methoxy-4-[7-(1-methylpyrazol-4-yl)imidazo[1,2-a]pyridin-3-yl]-N-(2,2,2-trifluoroethyl)benzamide,
cyclopropyl 2-[4-[3-[3,5-dimethoxy-4-(2,2,2-trifluoroethylcarbamoyl)phenyl]imidazo[1,2-a]pyridin-7-yl]pyrazol-1-yl]acetate,
2-fluoroethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
methyl 2-[4-[3-[3,5-dimethoxy-4-(2,2,2-trifluoroethylcarbamoyl)phenyl]imidazo[1,2-a]pyridin-7-yl]pyrazol-1-yl]acetate,
tetrahydrofuran-3-yl 2-[4-[3-[3,5-dimethoxy-4-(2,2,2-trifluoroethylcarbamoyl)phenyl]imidazo[1,2-a]pyridin-7-yl]pyrazol-1-yl]acetate,
cyclobutylmethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
2,6-dimethoxy-4-[7-(6-methoxy-3-pyridyl)imidazo[1,2-a]pyridin-3-yl]-N-(2,2,2-trifluoroethyl)benzamide,
4-[7-(6-cyano-3-pyridyl)imidazo[1,2-a]pyridin-3-yl]-2,6-dimethoxy-N-(2,2,2-trifluoroethyl)benzamide,
2,6-dimethoxy-4-[7-(2-methoxypyrimidin-5-yl)imidazo[1,2-a]pyridin-3-yl]-N-(2,2,2-trifluoroethyl)benzamide,
2,6-dimethoxy-4-(7-pyrimidin-5-ylimidazo[1,2-a]pyridin-3-yl)-N-(2,2,2-trifluoroethyl)benzamide,
tert-butyl 2-[4-[3-[3,5-dimethoxy-4-(2,2,2-trifluoroethylcarbamoyl)phenyl]imidazo[1,2-a]pyridin-7-yl]pyrazol-1-yl]propanoate,
methyl 2-[4-[3-[3,5-dimethoxy-4-(2,2,2-trifluoroethylcarbamoyl)phenyl]imidazo[1,2-a]pyridin-7-yl]pyrazol-1-yl]propanoate,
2,6-dimethoxy-4-[7-(5-methoxy-3-pyridyl)imidazo[1,2-a]pyridin-3-yl]-N-(2,2,2-trifluoroethyl)benzamide,
4-[7-(2-aminopyrimidin-5-yl)imidazo[1,2-a]pyridin-3-yl]-2,6-dimethoxy-N-(2,2,2-trifluoroethyl)benzamide,
2,6-dimethoxy-4-(7-pyridazin-4-ylimidazo[1,2-a]pyridin-3-yl)-N-(2,2,2-trifluoroethyl)benzamide,
4-[7-(5-ethoxy-3-pyridyl)imidazo[1,2-a]pyridin-3-yl]-2,6-dimethoxy-N-(2,2,2-trifluoroethyl)benzamide,
2,6-dimethoxy-4-[7-[1-methyl-3-(trifluoromethyl)pyrazol-4-yl]imidazo[1,2-a]pyridin-3-yl]-N-(2,2,2-trifluoroethyl)benzamide,
2,6-dimethoxy-4-[7-(2-methoxy-3-pyridyl)imidazo[1,2-a]pyridin-3-yl]-N-(2,2,2-trifluoroethyl)benzamide,
2,6-dimethoxy-4-[7-(6-morpholino-3-pyridyl)imidazo[1,2-a]pyridin-3-yl]-N-(2,2,2-trifluoroethyl)benzamide,
2,6-dimethoxy-4-[7-(6-methylpyridazin-4-yl)imidazo[1,2-a]pyridin-3-yl]-N-(2,2,2-trifluoroethyl)benzamide,
4-[7-(4-isopropylpyrimidin-5-yl)imidazo[1,2-a]pyridin-3-yl]-2,6-dimethoxy-N-(2,2,2-trifluoroethyl)benzamide,
2-[4-[3-[3,5-dimethoxy-4-(2,2,2-trifluoroethylcarbamoyl)phenyl]imidazo[1,2-a]pyridin-7-yl]pyrazol-1-yl]propanoic acid,
4-[4-[3-[3,5-dimethoxy-4-(2,2,2-trifluoroethylcarbamoyl)phenyl]imidazo[1,2-a]pyridin-7-yl]pyrazol-1-yl]butanoic acid,
methyl 4-[4-[3-[3,5-dimethoxy-4-(2,2,2-trifluoroethylcarbamoyl)phenyl]imidazo[1,2-a]pyridin-7-yl]pyrazol-1-yl]butanoate,
ethyl 4-[4-[3-[3,5-dimethoxy-4-(2,2,2-trifluoroethylcarbamoyl)phenyl]imidazo[1,2-a]pyridin-7-yl]pyrazol-1-yl]butanoate,
4-[7-(4-cyano-3-pyridyl)imidazo[1,2-a]pyridin-3-yl]-2,6-dimethoxy-N-(2,2,2-trifluoroethyl)benzamide,
3-[3-[3,5-dimethoxy-4-(2,2,2-trifluoroethylcarbamoyl)phenyl]imidazo[1,2-a]pyridin-7-yl]pyridine-4-carboxamide,
tert-butyl 3-[4-[3-[3,5-dimethoxy-4-(2,2,2-trifluoroethylcarbamoyl)phenyl]imidazo[1,2-a]pyridin-7-yl]pyrazol-1-yl]azetidine-1-carboxylate,
7-methoxy-5-[7-(1-methylpyrazol-4-yl)imidazo[1,2-a]pyridin-3-yl]-2-(2,2,2-trifluoroethyl)isoindolin-1-one,
2-cyclopropyl-8-methoxy-6-[7-(1-methylpyrazol-4-yl)imidazo[1,2-a]pyridin-3-yl]-3,4-dihydroisoquinolin-1-one,
ethyl 2-[4-[3-[3,5-dimethoxy-4-(2,2,2-trifluoroethylcarbamoyl)phenyl]imidazo[1,2-a]pyridin-7-yl]pyrazol-1-yl]propanoate,
4-[7-[1-[1-(2-cyanoethyl)azetidin-3-yl]pyrazol-4-yl]imidazo[1,2-a]pyridin-3-yl]-2,6-dimethoxy-N-(2,2,2-trifluoroethyl)benzamide,
4-[7-[1-[1-(cyanomethyl)azetidin-3-yl]pyrazol-4-yl]imidazo[1,2-a]pyridin-3-yl]-2,6-dimethoxy-N-(2,2,2-trifluoroethyl)benzamide,
4-[7-(1-methylpyrazol-4-yl)imidazo[1,2-a]pyridin-3-yl]-2,6-bis(trideuteriomethoxy)-N-(2,2,2-trifluoroethyl)benzamide,
N-cyclopropyl-2-(difluoromethoxy)-6-methoxy-4-[7-(6-methoxy-3-pyridyl)imidazo[1,2-a]pyridin-3-yl]benzamide,
4-[7-(2-cyano-3-pyridyl)imidazo[1,2-a]pyridin-3-yl]-2,6-dimethoxy-N-(2,2,2-trifluoroethyl)benzamide,
2,6-dimethoxy-4-[7-(6-methylpyridazin-3-yl)imidazo[1,2-a]pyridin-3-yl]-N-(2,2,2-trifluoroethyl)benzamide,
N-cyclopropyl-2-(difluoromethoxy)-6-methoxy-4-[7-(3-methylisoxazol-5-yl)imidazo[1,2-a]pyridin-3-yl]benzamide,
2,6-difluoro-4-[7-(1-methylpyrazol-4-yl)imidazo[1,2-a]pyridin-3-yl]-N-(2,2,2-trifluoroethyl)benzamide,
N-cyclopropyl-2-(difluoromethoxy)-6-methoxy-4-[7-(6-methylpyridazin-4-yl)imidazo[1,2-a]pyridin-3-yl]benzamide,
N-cyclopropyl-2-(difluoromethoxy)-6-methoxy-4-[7-(6-methylpyridazin-3-yl)imidazo[1,2-a]pyridin-3-yl]benzamide,
N-cyclopropyl-2-(difluoromethoxy)-6-methoxy-4-[7-(3-methylimidazol-4-yl)imidazo[1,2-a]pyridin-3-yl]benzamide,
8-methoxy-6-[7-(6-methylpyridazin-3-yl)imidazo[1,2-a]pyridin-3-yl]-2-(2,2,2-trifluoroethyl)-3,4-dihydroisoquinolin-1-one,
N-cyclopropyl-2-fluoro-6-methoxy-4-[7-(1-methylpyrazol-4-yl)imidazo[1,2-a]pyridin-3-yl]benzamide,
N-cyclopropyl-2-(isopropylamino)-6-methoxy-4-[7-(1-methylpyrazol-4-yl)imidazo[1,2-a]pyridin-3-yl]benzamide,
N-cyclopropyl-2-methoxy-6-(2-methoxyethoxy)-4-[7-(1-methylpyrazol-4-yl)imidazo[1,2-a]pyridin-3-yl]benzamide,
N-cyclopropyl-2-(2-hydroxyethoxy)-6-methoxy-4-[7-(1-methylpyrazol-4-yl)imidazo[1,2-a]pyridin-3-yl]benzamide,
N-cyclopropyl-2-(difluoromethoxy)-6-methoxy-4-[7-(6-methoxypyridazin-3-yl)imidazo[1,2-a]pyridin-3-yl]benzamide,
N-cyclopropyl-2-(difluoromethoxy)-6-methoxy-4-[7-[6-(trifluoromethyl)pyridazin-3-yl]imidazo[1,2-a]pyridin-3-yl]benzamide, 4-[7-(6-cyanopyridazin-3-yl)imidazo[1,2-a]pyridin-3-yl]-N-cyclopropyl-2-(difluoromethoxy)-6-methoxy-benzamide, N-cyclopropyl-2-(difluoromethoxy)-4-[7-[6-(dimethylamino)pyridazin-3-yl]imidazo[1,2-a]pyridin-3-yl]-6-methoxy-benzamide, ethyl 2-[4-[3-[4-(cyclopropylcarbamoyl)-3-(difluoromethoxy)-5-methoxy-phenyl]imidazo[1,2-a]pyridin-7-yl]pyrazol-1-yl]acetate, N-cyclopropyl-4-[7-(6-cyclopropylpyridazin-3-yl)imidazo[1,2-a]pyridin-3-yl]-2-(difluoromethoxy)-6-methoxy-benzamide, N-cyclopropyl-2-(difluoromethoxy)-6-methoxy-4-[7-(6-morpholinopyridazin-3-yl)imidazo[1,2-a]pyridin-3-yl]benzamide, 7-[5-(5-fluoro-3-pyridyl)benzimidazol-1-yl]-5-methoxy-2,3-dihydro-1,3-benzoxazin-4-one, 5-methoxy-7-[5-(5-methoxy-3-pyridyl)benzimidazol-1-yl]-2,3-dihydro-1,3-benzoxazin-4-one, 7-[5-(3-fluoro-2-pyridyl)benzimidazol-1-yl]-5-methoxy-2,3-dihydro-1,3-benzoxazin-4-one, and 7-[5-(2-isopropylthiazol-4-yl)benzimidazol-1-yl]-5-methoxy-2,3-dihydro-1,3-benzoxazin-4-one.

In one embodiment, the compound of the invention is according to Formula I, wherein the compound is N-cyclopropyl-2-(difluoromethoxy)-6-methoxy-4-[5-(1-methylpyrazol-4-yl)benzimidazol-1-yl]benzamide.

In one embodiment, the compound of the invention is according to Formula I, wherein the compound is not N-cyclopropyl-2-(difluoromethoxy)-6-methoxy-4-[5-(1-methylpyrazol-4-yl)benzimidazol-1-yl]benzamide.

In one embodiment, the present invention provides a compound for the preparation of the compounds of the invention according to Formula A:

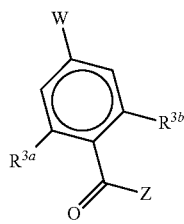

A wherein,
W is Cl, Br, I, —NH$_2$, —B(OH)$_2$, or 4,4,5,5-tetramethyl-1,3,2-dioxaborolan-2-yl;
Z is
—NR$^{5a}$R$^{5b}$, or
N-linked 4-7 membered heterocycloalkyl further comprising zero, one, or two additional heteroatoms independently selected from N, O, and S, optionally substituted with one, two or three independently selected R$^6$ groups;
R$^{3a}$ and R$^{3b}$ are independently selected C$_{1-4}$ alkoxy optionally substituted with one or more independently selected halo, —OH or C$_{1-4}$ alkoxy;
R$^{5a}$ is H or C$_{1-4}$ alkyl;
R$^{5b}$ is selected from
C$_{1-6}$ alkyl optionally substituted with one or more independently selected R$^9$,
C$_{3-7}$ cycloalkyl optionally substituted with one or more independently selected R$^{10}$, 4-7 membered monocyclic heterocycloalkyl comprising one, two or three heteroatoms independently selected from N, O, and S, which heterocycloalkyl is optionally substituted with one or more oxo, and
5-6 membered monocyclic heteroaryl comprising one, two or three heteroatoms independently selected from N, O, and S, which heteroaryl is optionally substituted with one or more independently selected C$_{1-4}$ alkyl;
each R$^6$ is independently selected from
oxo,
halo,
—CN,
—OH,
—NR$^{11a}$R$^{11b}$,
phenyl,
C$_{3-7}$ cycloalkyl,
C$_{2-4}$ alkynyl,
—C(=O)—C$_{1-4}$ alkoxy,
C$_{1-4}$ alkoxy optionally substituted with one or more halo or phenyl,
C$_{1-4}$ alkyl optionally substituted with one or more halo, —OH, or C$_{1-4}$ alkoxy, and
4-7 membered monocyclic heterocycloalkyl comprising one, two or three heteroatoms independently selected from N, O, and S;
each R$^9$ is independently selected from
halo,
—CN,
—NR$^{11e}$R$^{11f}$,
—OH,
C$_{1-4}$ alkoxy,
—S(=O)$_2$—C$_{1-4}$ alkyl,
4-7 membered monocyclic heterocycloalkyl comprising one, two or three heteroatoms independently selected from N, O, and S, and
5-6 membered monocyclic heteroaryl comprising one, two or three heteroatoms independently selected from N, O, and S, which heteroaryl is optionally substituted with one or more independently selected C$_{1-4}$ alkyl;
each R$^{10}$ is independently selected from
halo,
C$_{1-4}$ alkyl optionally substituted with one or more independently selected halo, —OH, or C$_{1-4}$ alkoxy,
—OH,
C$_{1-4}$ alkoxy, and
—NR$^{11g}$R$^{11h}$;
each R$^{11a}$, R$^{11b}$, R$^{11e}$, R$^{11f}$, R$^{11g}$, and R$^{11h}$ is independently selected from H and C$_{1-4}$ alkyl.

In a further embodiment, the present invention provides a compound for the preparation of the compounds of the invention according to Formula A, wherein In a further embodiment, the present invention provides a compound for the preparation of the compounds of the invention according to Formula A, wherein R$^{3a}$ is halo or —OH. In a particular embodiment, R$^{3a}$ is F, Cl, or —OH.

In a further embodiment, the present invention provides a compound for the preparation of the compounds of the invention according to Formula A, wherein R$^{3a}$ is C$_{1-4}$ alkyl. In a particular embodiment, R$^{3a}$ is —CH$_3$, —CH$_2$CH$_3$, or —CH(CH$_3$)$_2$. In a more particular embodiment, R$^{3a}$ is —CH$_3$, or —CH$_2$CH$_3$. In a most particular embodiment, R$^{3a}$ is —CH$_3$.

In a further embodiment, the present invention provides a compound for the preparation of the compounds of the invention according to Formula A, wherein R$^{3a}$ is C$_{1-4}$ alkoxy. In a particular embodiment, R$^{3a}$ is —O—CH$_3$, —O—CH$_2$CH$_3$, or —O—CH(CH$_3$)$_2$. In a more particular embodiment, $R^{3a}$ is —O—CH$_3$ or —O—CH(CH$_3$)$_2$. In a most particular embodiment, $R^{3a}$ is —O—CH$_3$.

In a further embodiment, the present invention provides a compound for the preparation of the compounds of the invention according to Formula A, wherein $R^{3a}$ is C$_{1-4}$ alkoxy substituted with one or more independently selected halo, —OH or C$_{1-4}$ alkoxy. In a particular embodiment, $R^{3a}$ is —O—CH$_3$, —O—CH$_2$CH$_3$, or —O—CH(CH$_3$)$_2$, each of which is substituted with one or more independently selected halo, —OH or C$_{1-4}$ alkoxy. In another particular embodiment, $R^{3a}$ is C$_{1-4}$ alkoxy substituted with one, two, or three independently selected halo, —OH or C$_{1-4}$ alkoxy. In yet another particular embodiment, $R^{3a}$ is C$_{1-4}$ alkoxy substituted with one or more independently selected F, Cl, —OH, —O—CH$_3$, —O—CH$_2$CH$_3$, or —O—CH(CH$_3$)$_2$. In more a particular embodiment, $R^{3a}$ is —O—CH$_3$ or —O—CH$_2$CH$_3$, each of which is substituted with one or more independently selected halo, —OH or C$_{1-4}$ alkoxy. In another more particular embodiment, $R^{3a}$ is C$_{1-4}$ alkoxy substituted with one, two, or three F or Cl. In yet another more particular embodiment, $R^{3a}$ is C$_{1-4}$ alkoxy substituted with one —OH, —O—CH$_3$, —O—CH$_2$CH$_3$, or —O—CH(CH$_3$)$_2$. In a further more particular embodiment, $R^{3a}$ is C$_{1-4}$ alkoxy substituted with one or more independently selected F, —OH, or —O—CH$_3$. In an even more particular embodiment, $R^{3a}$ is —O—CH$_3$ or —O—CH$_2$CH$_3$, each of which is substituted with one, two, or three F. In another even more particular embodiment, $R^{3a}$ is —O—CH$_3$ or —O—CH$_2$CH$_3$, each of which is substituted with one —OH or —O—CH$_3$. In a most particular embodiment, $R^{3a}$ is —O—CHF$_2$.

In a further embodiment, the present invention provides a compound for the preparation of the compounds of the invention according to Formula A, wherein $R^{3a}$ is —NR$^{8a}$R$^{8b}$, and each R$^{8a}$ and R$^{8b}$ is as previously described. In a particular embodiment, R$^{8a}$ and R$^{8b}$ are both H. In another particular embodiment, one of R$^{8a}$ and R$^{8b}$ is H, and the other is C$_{1-4}$ alkyl optionally substituted with one —OH or C$_{1-4}$ alkoxy. In yet another particular embodiment, R$^{8a}$ and R$^{8b}$ are both C$_{1-4}$ alkyl optionally substituted with one —OH or C$_{1-4}$ alkoxy. In a more particular embodiment, one of R$^{8a}$ and R$^{8b}$ is H, and the other is —CH$_3$, —CH$_2$CH$_3$, or —CH(CH$_3$)$_2$. In another more particular embodiment, one of R$^{8a}$ and R$^{8b}$ is H, and the other is —CH$_3$, —CH$_2$CH$_3$, or —CH(CH$_3$)$_2$, each of which is substituted with one —OH, —O—CH$_3$, —O—CH$_2$CH$_3$, or —O—CH(CH$_3$)$_2$. In a most particular embodiment, $R^{3a}$ is —NH—CH$_3$, —NH—CH(CH$_3$)$_2$, or —NH—CH$_2$CH$_2$—OH.

In a further embodiment, the present invention provides a compound for the preparation of the compounds of the invention according to Formula A, wherein $R^{3b}$ is halo or —OH. In a particular embodiment, $R^{3b}$ is F, Cl, or —OH.

In a further embodiment, the present invention provides a compound for the preparation of the compounds of the invention according to Formula A, wherein $R^{3b}$ is C$_{1-4}$ alkyl. In a particular embodiment, $R^{3b}$ is —CH$_3$, —CH$_2$CH$_3$, or —CH(CH$_3$)$_2$. In a more particular embodiment, $R^{3b}$ is —CH$_3$, or —CH$_2$CH$_3$. In a most particular embodiment, $R^{3b}$ is —CH$_3$.

In a further embodiment, the present invention provides a compound for the preparation of the compounds of the invention according to Formula A, wherein $R^{3b}$ is C$_{1-4}$ alkoxy. In a particular embodiment, $R^{3b}$ is —O—CH$_3$, —O—CH$_2$CH$_3$, or —O—CH(CH$_3$)$_2$. In a more particular embodiment, $R^{3b}$ is —O—CH$_3$ or —O—CH(CH$_3$)$_2$. In a most particular embodiment, $R^{3b}$ is —O—CH$_3$.

In a further embodiment, the present invention provides a compound for the preparation of the compounds of the invention according to Formula A, wherein $R^{3b}$ is C$_{1-4}$ alkoxy substituted with one or more independently selected halo, —OH or C$_{1-4}$ alkoxy. In a particular embodiment, $R^{3b}$ is —O—CH$_3$, —O—CH$_2$CH$_3$, or —O—CH(CH$_3$)$_2$, each of which is substituted with one or more independently selected halo, —OH or C$_{1-4}$ alkoxy. In another particular embodiment, $R^{3b}$ is C$_{1-4}$ alkoxy substituted with one, two, or three independently selected halo, —OH or C$_{1-4}$ alkoxy. In yet another particular embodiment, $R^{3b}$ is C$_{1-4}$ alkoxy substituted with one or more independently selected F, Cl, —OH, —O—CH$_3$, —O—CH$_2$CH$_3$, or —O—CH(CH$_3$)$_2$. In more a particular embodiment, $R^{3b}$ is —O—CH$_3$ or —O—CH$_2$CH$_3$, each of which is substituted with one or more independently selected halo, —OH or C$_{1-4}$ alkoxy. In another more particular embodiment, $R^{3b}$ is C$_{1-4}$ alkoxy substituted with one, two, or three F or Cl. In yet another more particular embodiment, $R^{3b}$ is C$_{1-4}$ alkoxy substituted with one —OH, —O—CH$_3$, —O—CH$_2$CH$_3$, or —O—CH(CH$_3$)$_2$. In a further more particular embodiment, $R^{3b}$ is C$_{1-4}$ alkoxy substituted with one or more independently selected F, —OH, or —O—CH$_3$. In an even more particular embodiment, $R^{3b}$ is —O—CH$_3$ or —O—CH$_2$CH$_3$, each of which is substituted with one, two, or three F. In another even more particular embodiment, $R^{3b}$ is —O—CH$_3$ or —O—CH$_2$CH$_3$, each of which is substituted with one —OH or —O—CH$_3$. In a most particular embodiment, $R^{3b}$ is —O—CHF$_2$.

In a further embodiment, the present invention provides a compound for the preparation of the compounds of the invention according to Formula A, wherein $R^{3b}$ is —NR$^{8a}$R$^{8b}$, and each R$^{8a}$ and R$^{8b}$ is as previously described. In a particular embodiment, R$^{8a}$ and R$^{8b}$ are both H. In another particular embodiment, one of R$^{8a}$ and R$^{8b}$ is H, and the other is C$_{1-4}$ alkyl optionally substituted with one —OH or C$_{1-4}$ alkoxy. In yet another particular embodiment, R$^{8a}$ and R$^{8b}$ are both C$_{1-4}$ alkyl optionally substituted with one —OH or C$_{1-4}$ alkoxy. In a more particular embodiment, one of R$^{8a}$ and R$^{8b}$ is H, and the other is —CH$_3$, —CH$_2$CH$_3$, or —CH(CH$_3$)$_2$. In another more particular embodiment, one of R$^{8a}$ and R$^{8b}$ is H, and the other is —CH$_3$, —CH$_2$CH$_3$, or —CH(CH$_3$)$_2$, each of which is substituted with one —OH, —O—CH$_3$, —O—CH$_2$CH$_3$, or —O—CH(CH$_3$)$_2$. In a most particular embodiment, $R^{3b}$ is —NH—CH$_3$, —NH—CH(CH$_3$)$_2$, or —NH—CH$_2$CH$_2$—OH.

In a further embodiment, the present invention provides a compound for the preparation of the compounds of the invention according to Formula A, wherein Z is —NR$^{5a}$R$^{5b}$, and R$^{5a}$ and R$^{5b}$ are as previously described. In a particular embodiment, R$^{5a}$ is H. In another particular embodiment, R$^{5a}$ is C$_{1-4}$ alkyl. In a more particular embodiment, R$^{5a}$ is —CH$_3$, —CH$_2$CH$_3$, or —CH(CH$_3$)$_2$. In a most particular embodiment, R$^{5a}$ is —CH$_3$.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is C$_{1-6}$ alkyl. In a particular embodiment, R$^{5b}$ is —CH$_3$, —CH$_2$CH$_3$, —CH$_2$CH$_2$CH$_3$, —CH(CH$_3$)$_2$, —CH$_2$CH(CH$_3$)$_2$, —C(CH$_3$)$_3$, —CH(CH$_3$)CH$_2$CH$_3$, or —CH(CH$_3$)CH(CH$_3$)$_2$. In a more particular embodiment, R$^{5b}$ is —CH$_3$, —CH$_2$CH$_3$, —CH$_2$CH$_2$CH$_3$, —CH(CH$_3$)$_2$, or —CH$_2$CH(CH$_3$)$_2$. In a most particular embodiment, R$^{5b}$ is —CH$_2$CH$_3$.

In a further embodiment, the present invention provides a compound for the preparation of the compounds of the invention according to Formula A, wherein Z is —NR$^{5a}$R$^{5b}$, $R^{5a}$ is as previously described, and $R^{5b}$ is $C_{1-6}$ alkyl substituted with one or more independently selected $R^9$. In a particular embodiment, $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one or more independently selected $R^9$. In another particular embodiment, $R^{5b}$ is $C_{1-6}$ alkyl substituted with one, two, or three independently selected $R^9$. In a more particular embodiment, $R^{5b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one or more independently selected $R^9$. In another more particular embodiment, $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one, two, or three independently selected $R^9$. In yet another more particular embodiment, $R^{5b}$ is $C_{1-6}$ alkyl substituted with one $R^9$. In an even more particular embodiment, $R^{5b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one, two, or three independently selected $R^9$. In another even more particular embodiment, $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one $R^9$. In a most particular embodiment, $R^{5b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one $R^9$.

In a further embodiment, the present invention provides a compound for the preparation of the compounds of the invention according to Formula A, wherein Z is —$NR^{5a}R^{5b}$, $R^{5a}$ is as previously described, $R^{5b}$ is $C_{1-6}$ alkyl substituted with one or more independently selected $R^9$, and $R^9$ is halo, —CN, —OH, $C_{1-4}$ alkoxy, or —$S(=O)_2$—$C_{1-4}$ alkyl. In a particular embodiment, each $R^9$ is independently F, Cl, —CN, —OH, —O—$CH_3$, —O—$CH_2CH_3$, —O—$CH(CH_3)_2$, —$S(=O)_2$—$CH_3$, —$S(=O)_2$—$CH_2CH_3$, or —$S(=O)_2$—$CH(CH_3)_2$. In a more particular embodiment, each $R^9$ is independently F, —CN, —OH, —O—$CH_3$, or —$S(=O)_2$—$CH_3$.

In a further embodiment, the present invention provides a compound for the preparation of the compounds of the invention according to Formula A, wherein Z is —$NR^{5a}R^{5b}$, $R^{5a}$ is as previously described, $R^{5b}$ is $C_{1-6}$ alkyl substituted with one or more independently selected $R^9$, and $R^9$ is —$NR^{11e}R^{11f}$, and each $R^{11e}$ and $R^{11f}$ is as previously described. In a particular embodiment, $R^{11e}$ and $R^{11f}$ are both H. In another particular embodiment, one of $R^{11e}$ and $R^{11f}$ is H, and the other is $C_{1-4}$ alkyl. In yet another particular embodiment, $R^{11e}$ and $R^{11f}$ are both $C_{1-4}$ alkyl. In a more particular embodiment, one of $R^{11e}$ and $R^{11f}$ is H, and the other is —$CH_3$, —$CH_2CH_3$, or —$CH(CH_3)_2$. In another more particular embodiment, $R^{11e}$ and $R^{11f}$ are —$CH_3$, —$CH_2CH_3$, or —$CH(CH_3)_2$. In a most particular embodiment, $R^{11e}$ and $R^{11f}$ are —$CH_3$.

In a further embodiment, the present invention provides a compound for the preparation of the compounds of the invention according to Formula A, wherein Z is —$NR^{5a}R^{5b}$, $R^{5a}$ is as previously described, $R^{5b}$ is $C_{1-6}$ alkyl substituted with one or more independently selected $R^9$, and $R^9$ is 4-7 membered monocyclic heterocycloalkyl comprising one, two or three heteroatoms independently selected from N, O, and S. In a particular embodiment, $R^9$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^9$ is dioxanyl.

In a further embodiment, the present invention provides a compound for the preparation of the compounds of the invention according to Formula A, wherein Z is —$NR^{5a}R^{5b}$, $R^{5a}$ is as previously described, $R^{5b}$ is $C_{1-6}$ alkyl substituted with one or more independently selected $R^9$, and $R^9$ is 5-6 membered monocyclic heteroaryl comprising one, two or three heteroatoms independently selected from N, O, and S. In a particular embodiment, $R^9$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, $R^9$ is imidazolyl, pyrazolyl, or pyridinyl. In a most particular embodiment, $R^9$ is pyridinyl.

In a further embodiment, the present invention provides a compound for the preparation of the compounds of the invention according to Formula A, wherein Z is —$NR^{5a}R^{5b}$, $R^{5a}$ is as previously described, $R^{5b}$ is $C_{1-6}$ alkyl substituted with one or more independently selected $R^9$, and $R^9$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected $C_{1-4}$ alkyl. In another particular embodiment, $R^9$ is 5-6 membered monocyclic heteroaryl comprising one, two or three heteroatoms independently selected from N, O, and S, which heteroaryl is substituted with one $C_{1-4}$ alkyl. In yet another particular embodiment, $R^9$ is 5-6 membered monocyclic heteroaryl comprising one, two or three heteroatoms independently selected from N, O, and S, which heteroaryl is substituted with one or more independently selected —$CH_3$, —$CH_2CH_3$, or —$CH(CH_3)_2$. In a more particular embodiment, $R^9$ is imidazolyl or pyrazolyl, each of which is substituted with one or more independently selected $C_{1-4}$ alkyl. In another more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one $C_{1-4}$ alkyl. In yet another more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected —$CH_3$, —$CH_2CH_3$, or —$CH(CH_3)_2$. In a further more particular embodiment, $R^9$ is 5-6 membered monocyclic heteroaryl comprising one, two or three heteroatoms independently selected from N, O, and S, which heteroaryl is substituted with one —$CH_3$, —$CH_2CH_3$, or —$CH(CH_3)_2$. In yet a further more particular embodiment, $R^9$ is 5-6 membered monocyclic heteroaryl comprising one, two or three heteroatoms independently selected from N, O, and S, which heteroaryl is substituted with one or more —$CH_3$. In an even more particular embodiment, $R^9$ is imidazolyl or pyrazolyl, each of which is substituted with one $C_{1-4}$ alkyl. In another even more particular embodiment, $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one —CH$_3$, —CH$_2$CH$_3$, or —CH(CH$_3$)$_2$. In yet another even more particular embodiment, R$^9$ is 5-6 membered monocyclic heteroaryl comprising one, two or three heteroatoms independently selected from N, O, and S, which heteroaryl is substituted with one —CH$_3$. In a most particular embodiment, R$^9$ is imidazolyl or pyrazolyl, each of which is substituted with one —CH$_3$.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is C$_{3-7}$ cycloalkyl. In a particular embodiment, R$^{5b}$ is cyclopropyl, cyclobutyl, cyclopentyl, or cyclohexyl. In a more particular embodiment, R$^{5b}$ is cyclopropyl, cyclobutyl, cyclopentyl. In a most particular embodiment, R$^{5b}$ is cyclopropyl.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is C$_{3-7}$ cycloalkyl substituted with one or more independently selected R$^{10}$. In a particular embodiment, R$^{5b}$ is cyclopropyl, cyclobutyl, cyclopentyl, or cyclohexyl, each of which is substituted with one or more independently selected R$^{10}$. In another particular embodiment, R$^{5b}$ is C$_{3-7}$ cycloalkyl substituted with one, two, or three independently selected R$^{10}$. In a more particular embodiment, R$^{5b}$ is cyclopropyl, cyclobutyl, cyclopentyl, or cyclohexyl, each of which is substituted with one, two, or three independently selected R$^{10}$. In another more particular embodiment, R$^{5b}$ is C$_{3-7}$ cycloalkyl substituted with one R$^{10}$. In a most particular embodiment, R$^{5b}$ is cyclopropyl, cyclobutyl, cyclopentyl, or cyclohexyl, each of which is substituted with one R$^{10}$.

In a further embodiment, the present invention provides a compound for the preparation of the compounds of the invention according to Formula A, wherein Z is —NR$^{5a}$R$^{5b}$, R$^{5a}$ is as previously described, R$^{5b}$ is C$_{3-7}$ cycloalkyl substituted with one or more independently selected R$^{10}$, and R$^{10}$ is halo, —OH, or C$_{1-4}$ alkoxy. In a particular embodiment, R$^{10}$ is F, Cl, —OH, —O—CH$_3$, —O—CH$_2$CH$_3$, or —O—CH(CH$_3$)$_2$. In a more particular embodiment, R$^{10}$ is F, —OH, or —O—CH$_3$.

In a further embodiment, the present invention provides a compound for the preparation of the compounds of the invention according to Formula A, wherein Z is —NR$^{5a}$R$^{5b}$, R$^{5a}$ is as previously described, R$^{5b}$ is C$_{3-7}$ cycloalkyl substituted with one or more independently selected R$^{10}$, and R$^{10}$ is C$_{1-4}$ alkyl. In a particular embodiment, R$^{10}$ is —CH$_3$, —CH$_2$CH$_3$, or —CH(CH$_3$)$_2$. In a more particular embodiment, R$^{10}$ is —CH$_3$.

In a further embodiment, the present invention provides a compound for the preparation of the compounds of the invention according to Formula A, wherein Z is —NR$^{5a}$R$^{5b}$, R$^{5a}$ is as previously described, R$^{5b}$ is C$_{3-7}$ cycloalkyl substituted with one or more independently selected R$^{10}$, and R$^{10}$ is C$_{1-4}$ alkyl substituted with one or more independently selected halo, —OH, or C$_{1-4}$ alkoxy. In a particular embodiment, R$^{10}$ is —CH$_3$, —CH$_2$CH$_3$, or —CH(CH$_3$)$_2$, each of which is substituted with one or more independently selected halo, —OH, or C$_{1-4}$ alkoxy. In another particular embodiment, R$^{10}$ is C$_{1-4}$ alkyl substituted with one, two, or three independently selected halo, —OH, or C$_{1-4}$ alkoxy. In yet another particular embodiment, R$^{10}$ is C$_{1-4}$ alkyl substituted with one or more F, Cl, —OH, —O—CH$_3$, —O—CH$_2$CH$_3$, or —O—CH(CH$_3$)$_2$. In a more particular embodiment, R$^{10}$ is —CH$_3$ substituted with one or more independently selected halo, —OH, or C$_{1-4}$ alkoxy. In another more particular embodiment, R$^{10}$ is C$_{1-4}$ alkyl substituted with one halo, —OH, or C$_{1-4}$ alkoxy. In yet another more particular embodiment, R$^{10}$ is C$_{1-4}$ alkyl substituted with one or more independently selected F or —OH. In a further more particular embodiment, R$^1$ is —CH$_3$, —CH$_2$CH$_3$, or —CH(CH$_3$)$_2$, each of which is substituted with one, two, or three independently selected halo, —OH, or C$_{1-4}$ alkoxy. In yet a further more particular embodiment, R$^{10}$ is C$_{1-4}$ alkyl substituted with one, two, or three independently selected F, Cl, —OH, —O—CH$_3$, —O—CH$_2$CH$_3$, or —O—CH(CH$_3$)$_2$. In a most particular embodiment, R$^{10}$ is —CH$_2$F, —CHF$_2$, —CF$_3$, or —CH$_2$—OH.

In a further embodiment, the present invention provides a compound for the preparation of the compounds of the invention according to Formula A, wherein Z is —NR$^{5a}$R$^{5b}$, R$^{5a}$ is as previously described, R$^{5b}$ is C$_{3-7}$ cycloalkyl substituted with one or more independently selected R$^{10}$, and R$^{10}$ is —NR$^{11g}$R$^{11h}$, and each R$^{11g}$ and R$^{11h}$ is as previously described. In a particular embodiment, R$^{11g}$ and R$^{11h}$ are both H. In another particular embodiment, one of R$^{11g}$ and R$^{11h}$ is H, and the other is C$_{1-4}$ alkyl. In yet another particular embodiment, R$^{11g}$ and R$^{11h}$ are both C$_{1-4}$ alkyl. In a more particular embodiment, one of R$^{11g}$ and R$^{11h}$ is H, and the other is —CH$_3$, —CH$_2$CH$_3$, or —CH(CH$_3$)$_2$. In another more particular embodiment, R$^{11g}$ and R$^{11h}$ are —CH$_3$, —CH$_2$CH$_3$, or —CH(CH$_3$)$_2$. In a most particular embodiment, R$^{11g}$ and R$^{11h}$ are —CH$_3$.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is 4-7 membered monocyclic heterocycloalkyl comprising one, two or three heteroatoms independently selected from N, O, and S. In a particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl. In a more particular embodiment, R$^{5b}$ is oxetanyl, thietanyl, or tetrahydrothiopyranyl. In a most particular embodiment, R$^{5b}$ is oxetanyl.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is 4-7 membered monocyclic heterocycloalkyl comprising one, two or three heteroatoms independently selected from N, O, and S, which heterocycloalkyl is substituted with one or more oxo. In a particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl, each of which is substituted with one or more oxo. In another particular embodiment, R$^{5b}$ is 4-7 membered monocyclic heterocycloalkyl comprising one, two or three heteroatoms independently selected from N, O, and S, which heterocycloalkyl is substituted with one oxo. In a more particular embodiment, R$^{5b}$ is thietanyl or tetrahydrothiophenyl, each of which is substituted with one or more oxo. In another more particular embodiment, R$^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl, each of which is substituted with one oxo. In a most particular embodiment, R$^{5b}$ is thietanyl or tetrahydrothiophenyl, each of which is substituted with two oxo.

In a further embodiment, the present invention provides a compound for the preparation of the compounds of the invention according to Formula A, wherein Z is —NR$^{5a}$R$^{5b}$, R$^{5a}$ is as previously described, and R$^{5b}$ is 5-6 membered monocyclic heteroaryl comprising one, two or three heteroatoms independently selected from N, O, and S. In a particular embodiment, $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl. In a more particular embodiment, $R^{5b}$ is imidazolyl, pyrazolyl, isoxazolyl, or pyrimidinyl. In a most particular embodiment, $R^{5b}$ is isoxazolyl.

In a further embodiment, the present invention provides a compound for the preparation of the compounds of the invention according to Formula A, wherein Z is —$NR^{5a}R^{5b}$, $R^{5a}$ is as previously described, and $R^{5b}$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more independently selected $C_{1-4}$ alkyl. In another particular embodiment, $R^{5b}$ is 5-6 membered monocyclic heteroaryl comprising one, two or three heteroatoms independently selected from N, O, and S, which heteroaryl is substituted with one $C_{1-4}$ alkyl. In yet another particular embodiment, $R^{5b}$ is 5-6 membered monocyclic heteroaryl comprising one, two or three heteroatoms independently selected from N, O, and S, which heteroaryl is substituted with one or more independently selected—$CH_3$, —$CH_2CH_3$, or —$CH(CH_3)_2$. In a more particular embodiment, $R^{5b}$ is imidazolyl, pyrazolyl, or pyrimidinyl, each of which is substituted with one or more independently selected $C_{1-4}$ alkyl. In another more particular embodiment, $R^{5b}$ is 5-6 membered monocyclic heteroaryl comprising one, two or three heteroatoms independently selected from N, O, and S, which heteroaryl is substituted with one —$CH_3$. In yet another more particular embodiment, $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one $C_{1-4}$ alkyl. In a further more particular embodiment, $R^{5b}$ is 5-6 membered monocyclic heteroaryl comprising one, two or three heteroatoms independently selected from N, O, and S, which heteroaryl is substituted with one —$CH_3$, —$CH_2CH_3$, or —$CH(CH_3)_2$. In an even more particular embodiment, $R^{5b}$ is imidazolyl, pyrazolyl, or pyrimidinyl, each of which is substituted with one $C_4$ alkyl. In another even more particular embodiment, $R^{5b}$ is $R^{5b}$ is imidazolyl, pyrazolyl, or pyrimidinyl, each of which is substituted with one or more —$CH_3$, —$CH_2CH_3$, or —$CH(CH_3)_2$. In yet another even more particular embodiment, $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more —$CH_3$. In a further even more particular embodiment, $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one —$CH_3$, —$CH_2CH_3$, or —$CH(CH_3)_2$. In yet a further even more particular embodiment, $R^{5b}$ is 5-6 membered monocyclic heteroaryl comprising one, two or three heteroatoms independently selected from N, O, and S, which heteroaryl is substituted with one —$CH_3$. In a most particular embodiment, $R^{5b}$ is imidazolyl, pyrazolyl, or pyrimidinyl, each of which is substituted with one —$CH_3$.

In a further embodiment, the present invention provides a compound for the preparation of the compounds of the invention according to Formula A, wherein Z is —$NR^{5a}R^{5b}$, $R^{5a}$ is H, and $R^{5b}$ is —$CH_2CH_3$, —$CH_2CF_3$, —$CH(CH_3)CF_3$, or cyclopropyl.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, Z is azetidinyl, pyrrolidinyl, piperidinyl, 2-oxa-6-azaspiro[3.3]heptanyl, or 2-thia-6-azaspiro[3.3]heptanyl.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two or three independently selected $R^6$ groups. In a more particular embodiment, Z is azetidinyl, pyrrolidinyl, piperidinyl, or 2-thia-6-azaspiro[3.3]heptanyl, each of which is substituted with one, two or three independently selected $R^6$ groups.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is oxo, halo, —CN, —OH, phenyl, $C_{3-7}$ cycloalkyl, $C_{2-4}$ alkynyl, or —C(=O)—$C_{L}4$ alkoxy. In a particular embodiment, $R^6$ is oxo, F, Cl, —CN, —OH, phenyl, cyclopropyl, cyclobutyl, cyclopentyl, —C≡CH, —C(=O)—O—$CH_3$, —C(=O)—O—$CH_2CH_3$, or —C(=O)—O—$CH(CH_3)_2$. In a more particular embodiment, $R^6$ is oxo, F, —CN, —OH, phenyl, cyclopropyl, —C≡CH, or —C(=O)—O—$CH_3$.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is —$NR^{11a}R^{11b}$, and each $R^{11a}$ and $R^{11b}$ is as previously described. In a particular embodiment, $R^{11a}$ and $R^{11b}$ are both H. In another particular embodiment, one of $R^{11a}$ and $R^{11b}$ is H, and the other is $C_{1-4}$ alkyl. In yet another particular embodiment, $R^{11a}$ and $R^{11b}$ are both $C_{1-4}$ alkyl. In a more particular embodiment, one of $R^{11a}$ and $R^{11b}$ is H, and the other is —$CH_3$, —$CH_2CH_3$, or —$CH(CH_3)_2$. In another more particular embodiment, $R^{11a}$ and $R^{11b}$ are —$CH_3$, —$CH_2CH_3$, or —$CH(CH_3)_2$. In a most particular embodiment, $R^{11a}$ and $R^{11b}$ are —$CH_3$.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkoxy. In a particular embodiment, $R^6$ is —O—$CH_3$, —O—$CH_2CH_3$, or —O—$CH(CH_3)_2$. In a more particular embodiment, $R^6$ is —O—$CH_3$.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkoxy substituted with one or more halo or phenyl. In a particular embodiment, $R^6$ is —O—$CH_3$, —O—$CH_2CH_3$, or —O—$CH(CH_3)_2$, each of which is substituted with one or more halo or phenyl. In another particular embodiment, $R^6$ is $C_{1-4}$ alkoxy substituted with one, two, or three halo or phenyl. In yet another particular embodiment, $R^6$ is $C_{1-4}$ alkoxy substituted with one or more F, Cl or phenyl. In a more particular embodiment, $R^6$ is —O—$CH_3$, —O—$CH_2CH_3$, or —O—$CH(CH_3)_2$, each of which is substituted with one or more F, Cl, or phenyl. In another more particular embodiment, $R^6$ is $C_{1-4}$ alkoxy substituted with one, two, or three F, Cl, or phenyl. In yet another more particular embodiment, $R^6$ is —O—$CH_3$ substituted with one, two, or three halo or phenyl. In a most particular embodiment, $R^6$ is —O—$CH_3$ substituted with one, two, or three F. In another most particular embodiment, $R^6$ is —O—$CH_3$ substituted with one phenyl.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkyl. In a particular embodiment, $R^6$ is —$CH_3$, —$CH_2CH_3$, or —$CH(CH_3)_2$. In a more particular embodiment, $R^6$ is —$CH_3$ or —$CH_2CH_3$.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is $C_{1-4}$ alkyl substituted with one or more halo, —OH, or $C_{1-4}$ alkoxy. In a particular embodiment, $R^6$ is —$CH_3$, —$CH_2CH_3$, or —$CH(CH_3)_2$ substituted with one or more halo, —OH, or $C_{1-4}$ alkoxy. In another particular embodiment, $R^6$ is $C_{1-4}$ alkyl substituted with one, two, or three halo, —OH, or $C_{1-4}$ alkoxy. In yet another particular embodiment, $R^6$ is $C_{1-4}$ alkyl substituted with one or more F, Cl, —OH, —O—$CH_3$, —O—$CH_2CH_3$, or —O—$CH(CH_3)_2$. In a more particular embodiment, $R^6$ is —$CH_3$ substituted with one, two, or three halo, —OH, or $C_{1-4}$ alkoxy. In another more particular embodiment, $R^6$ is $C_{1-4}$ alkyl substituted with one, two, or three F, Cl, —OH, —O—$CH_3$, —O—$CH_2CH_3$, or —O—$CH(CH_3)_2$. In a further more particular embodiment, $R^6$ is —$CH_3$, —$CH_2CH_3$, or —$CH(CH_3)_2$, each of which is substituted with one, two, or three F, Cl, —OH, —O—$CH_3$, —O—$CH_2CH_3$, or —O—$CH(CH_3)_2$. In a most particular embodiment, $R^6$ is —$CH_3$ substituted with one, two, or three F, or —OH.

In a further embodiment, the present invention provides a compound for the preparation of the compounds of the invention according to Formula A, wherein Z is N-linked 4-7 membered heterocycloalkyl further comprising zero, one, or two additional heteroatoms independently selected from N, O, and S, substituted with one, two or three independently selected $R^6$ groups, and $R^6$ is 4-7 membered monocyclic heterocycloalkyl comprising one, two or three heteroatoms independently selected from N, O, and S. In a particular embodiment, $R^6$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^6$ is tetrahydropyranyl or morpholinyl.

In a further embodiment, the present invention provides a compound for the preparation of the compounds of the invention according to Formula A, wherein Z is

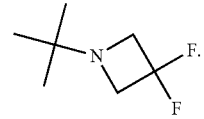

In one embodiment, the present invention provides a compound for the preparation of the compounds of the invention according to Formula A wherein $R^{3a}$ is —O—$CH_3$, $R^{3b}$ is —O—$CHF_2$, W is Br, Z is —$NR^{5a}R^{5b}$, $R^{5a}$ is H, and $R^{5b}$ is cyclopropyl.

In one embodiment, the present invention provides a compound for the preparation of the compounds of the invention according to Formula A wherein $R^{3a}$ and $R^{3b}$ are —O—$CH_3$, W is Br, Z is —$NR^{5a}R^{5b}$, $R^{5a}$ is H, and $R^{5b}$ is —$CH_2CF_3$.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the C1 to C8 alkyl, C2-C8 alkenyl, aryl, C7-C12 substituted aryl, and C7-C12 arylalkyl esters of the compounds of the invention.

Clauses

1. A compound according to Formula I:

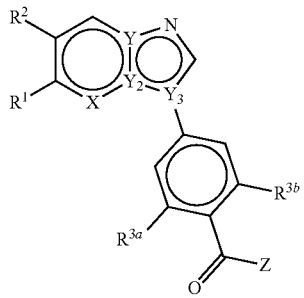

I wherein,
X is N or $CR^4$;
one of $Y_1$, $Y_2$ and $Y_3$ is N and the other two are C;
Z is
  $-NR^{5a}R^{5b}$,
  $-NR^{5c}-$, wherein the N atom and $R^{3b}$ together with the atoms onto which they are attached form a fused 5-6 membered heterocycloalkenyl comprising one double bond and further comprising zero, one, or two additional heteroatoms independently selected from N, O, and S, or
  N-linked 4-7 membered heterocycloalkyl further comprising zero, one, or two additional heteroatoms independently selected from N, O, and S, optionally substituted with one, two or three independently selected $R^6$ groups;
$R^1$ is H, halo, $C_{1-4}$ alkyl, or $C_{1-4}$ alkoxy optionally substituted with $C_{1-4}$ alkoxy, phenyl, $-CN$, $-C(=O)OH$, or $-C(=O)-C_{1-4}$ alkoxy;
$R^2$ is 5-6 membered monocyclic heteroaryl comprising one, two or three heteroatoms independently selected from N, O, and S, which heteroaryl is optionally substituted with one or more independently selected $R^7$ groups;
$R^{3a}$ and $R^{3b}$ are independently selected from
  halo,
  $C_{1-4}$ alkyl,
  $C_{1-4}$ alkoxy optionally substituted with one or more independently selected halo, $-OH$ or $C_{1-4}$ alkoxy,
  $-NR^{8a}R^{8b}$, and
  $-OH$;
$R^4$ is H or $C_{1-4}$ alkyl;
$R^{5a}$ is H or $C_{1-4}$ alkyl;
$R^{5b}$ is selected from
  $C_{1-6}$ alkyl optionally substituted with one or more independently selected $R^9$,
  $C_{3-7}$ cycloalkyl optionally substituted with one or more independently selected $R^{10}$,
  4-7 membered monocyclic heterocycloalkyl comprising one, two or three heteroatoms independently selected from N, O, and S, which heterocycloalkyl is optionally substituted with one or more oxo, and
  5-6 membered monocyclic heteroaryl comprising one, two or three heteroatoms independently selected from N, O, and S, which heteroaryl is optionally substituted with one or more independently selected $C_{1-4}$ alkyl;
$R^{5c}$ is selected from $C_{3-7}$ cycloalkyl, and $C_{1-6}$ alkyl optionally substituted with one or more independently selected halo;
each $R^6$ is independently selected from
  oxo,
  halo,
  $-CN$,
  $-OH$,
  $-NR^{11a}R^{11b}$,
  phenyl,
  $C_{3-7}$ cycloalkyl,
  $C_{2-4}$ alkynyl,
  $-C(=O)-C_{1-4}$ alkoxy,
  $C_{1-4}$ alkoxy optionally substituted with one or more halo or phenyl,
  $C_{1-4}$ alkyl optionally substituted with one or more halo, $-OH$, or $C_{1-4}$ alkoxy, and
  4-7 membered monocyclic heterocycloalkyl comprising one, two or three heteroatoms independently selected from N, O, and S;
each $R^7$ is selected from
  halo,
  $-CN$,
  $C_{1-6}$ alkyl optionally substituted with one or more independently selected
    halo,
    $-CN$,
    $-OH$,
    $C_{1-4}$ alkoxy optionally substituted with one or more independently selected halo,
    $-NR^{11c}R^{11d}$,
    $-C(=O)R^{12}$, or
    4-6 membered monocyclic heterocycloalkyl comprising one, two or three heteroatoms independently selected from N, O, and S,
  $C_{1-4}$ alkoxy,
  $C_{3-7}$ cycloalkyl,
  4-6 membered monocyclic heterocycloalkyl comprising one, two or three heteroatoms independently selected from N, O, and S, which heterocycloalkyl is optionally substituted with $-C(=O)C_{1-4}$ alkoxy or $C_{1-4}$ alkyl optionally substituted with $-CN$,
  $-NR^{13a}R^{13b}$, and
  $-C(=O)NR^{13c}R^{13d}$;
each $R^{8a}$ and $R^{8b}$ is independently selected from H and $C_{1-4}$ alkyl optionally substituted with one $-OH$ or $C_{1-4}$ alkoxy;
each $R^9$ is independently selected from halo,
—CN,
—NR$^{11e}$R$^{11f}$,
—OH,
C$_{1-4}$ alkoxy,
—S(=O)$_2$—C$_{1-4}$ alkyl,
4-7 membered monocyclic heterocycloalkyl comprising one, two or three heteroatoms independently selected from N, O, and S, and
5-6 membered monocyclic heteroaryl comprising one, two or three heteroatoms independently selected from N, O, and S, which heteroaryl is optionally substituted with one or more independently selected C$_{1-4}$ alkyl;
each R$^{10}$ is independently selected from
halo,
C$_{1-4}$ alkyl optionally substituted with one or more independently selected halo, —OH, or C$_{1-4}$ alkoxy,
—OH,
C$_{1-4}$ alkoxy, and
—NR$^{11g}$R$^{11h}$,
each R$^{11a}$, R$^{11b}$, R$^{11c}$, R$^{11d}$, R$^{11e}$, R$^{11f}$, R$^{11g}$, and R$^{11h}$ is independently selected from H and C$_{1-4}$ alkyl;
each R$^{12}$ is
—NR$^{14a}$R$^{14b}$, wherein each R$^{14a}$ and R$^{14b}$ is independently selected from H and C$_{1-4}$ alkyl,
—OH,
C$_{1-4}$ alkoxy optionally substituted with one or more independently selected C$_{3-7}$ cycloalkyl, halo, —NR$^{15a}$R$^{15b}$, or 4-6 membered monocyclic heterocycloalkyl comprising one, two or three heteroatoms independently selected from N, O, and S,
—O-(4-6 membered monocyclic heterocycloalkyl comprising one, two or three heteroatoms independently selected from N, O, and S), or
—O—(C$_{3-7}$ monocyclic cycloalkyl);
each R$^{13a}$, R$^{13b}$, R$^{13c}$, and R$^{13a}$ is independently selected from H and C$_{1-4}$ alkyl;
each R$^{15a}$ and R$^{15b}$ is independently selected from H and C$_{1-4}$ alkyl; or a pharmaceutically acceptable salt, solvate, or salt of the solvate thereof.

2. A compound or pharmaceutically acceptable salt thereof, according to clause 1, wherein X is CR$^4$ and R$^4$ is H.

3. A compound or pharmaceutically acceptable salt thereof, according to clause 1, wherein X is CR$^4$ and R$^4$ is —CH$_3$, —CH$_2$CH$_3$, or —CH(CH$_3$)$_2$.

4. A compound or pharmaceutically acceptable salt thereof, according to clause 1, wherein the compound is according to any one of Formulae IIa-IIf:

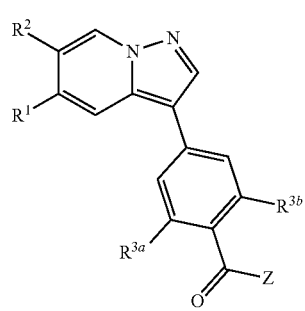
IIa

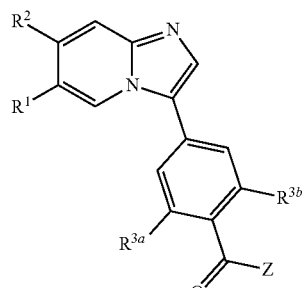
IIb

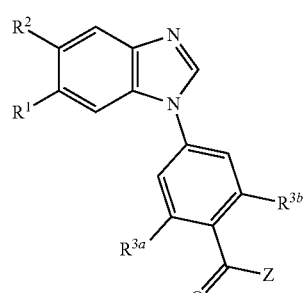
IIc

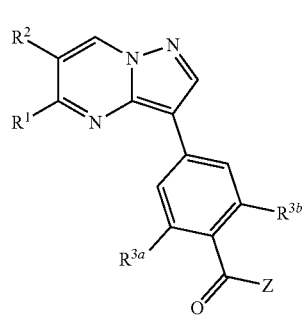
IId

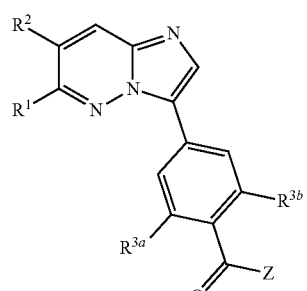
IIe

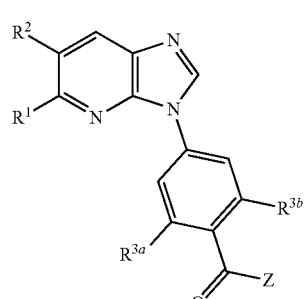
IIf

5. A compound or pharmaceutically acceptable salt thereof, according to any one of clauses 1-4, wherein R$^1$ is H.

6. A compound or pharmaceutically acceptable salt thereof, according to any one of clauses 1-4, wherein R$^1$ is F, Cl, or Br.

7. A compound or pharmaceutically acceptable salt thereof, according to any one of clauses 1-4, wherein $R^1$ is —CH$_3$, —CH$_2$CH$_3$, or —CH(CH$_3$)$_2$.

8. A compound or pharmaceutically acceptable salt thereof, according to any one of clauses 1-4, wherein $R^1$ is —CH$_3$.

9. A compound or pharmaceutically acceptable salt thereof, according to any one of clauses 1-4, wherein $R^1$ is —O—CH$_3$, —O—CH$_2$CH$_3$, or —O—CH(CH$_3$)$_2$.

10. A compound or pharmaceutically acceptable salt thereof, according to any one of clauses 1-4, wherein $R^1$ is —O—CH$_3$.

11. A compound or pharmaceutically acceptable salt thereof, according to any one of clauses 1-4, wherein $R^1$ is —O—CH$_2$CH$_3$ or —O—CH(CH$_3$)$_2$, substituted with C alkoxy.

12. A compound or pharmaceutically acceptable salt thereof, according to any one of clauses 1-4, wherein $R^1$ is —O—CH$_2$CH$_2$—O—CH$_3$.

13. A compound or pharmaceutically acceptable salt thereof, according to clause 1, wherein the compound is according to any one of Formulae IIIa-IIIf:

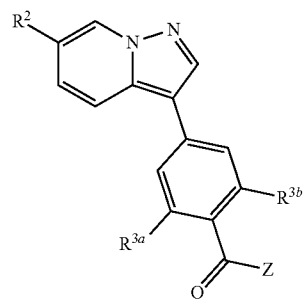

IIIa

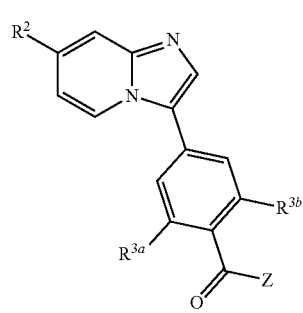

IIIb

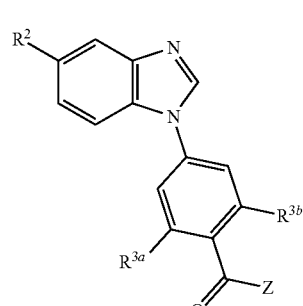

IIIc

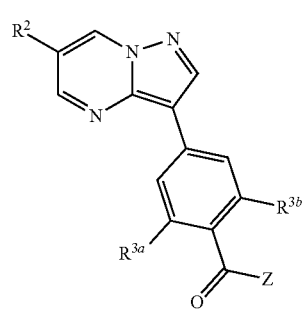

IIId

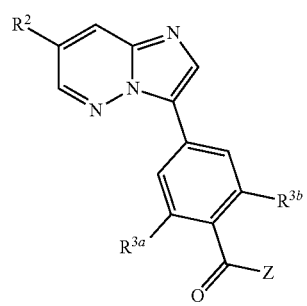

IIIe

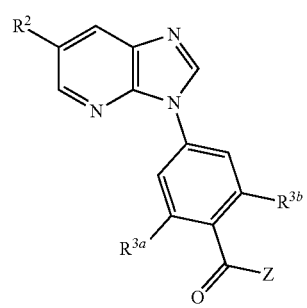

IIIf

14. A compound or pharmaceutically acceptable salt thereof, according to anyone of clauses 1-13, wherein Z is —NR$^{5c}$—, wherein the N atom and R$^{3b}$ together with the atoms onto which they are attached form a fused 3,4-dihydro-2H-1,3-oxazine, 1,2,3,4-tetrahydropyrimidine, 3-pyrroline, 1,2,3,6-tetrahydropyridine, or 3,4-dihydro-2H-1,3-thiazine.

15. A compound or pharmaceutically acceptable salt thereof, according to any one of clauses 1-13, wherein Z is —NR$^{5c}$—, wherein the N atom and R$^{3b}$ together with the atoms onto which they are attached form a fused 3,4-dihydro-2H-1,3-oxazine, 3-pyrroline, or 1,2,3,6-tetrahydropyridine.

16. A compound or pharmaceutically acceptable salt thereof, according to clause 1, wherein the compound is according to any one of Formulae Va-f:

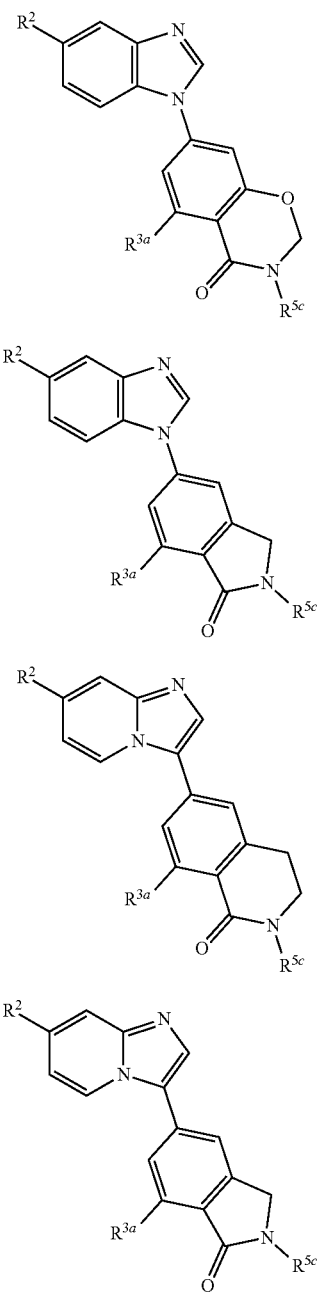

IVa

IVb

IVc

IVd

17. A compound or pharmaceutically acceptable salt thereof, according to clause 1 or 16, wherein $R^{5c}$ is $C_{3-7}$ cycloalkyl.

18. A compound or pharmaceutically acceptable salt thereof, according to clause 1 or 16, wherein $R^{5c}$ is cyclopropyl, cyclobutyl, or cyclopentyl.

19. A compound or pharmaceutically acceptable salt thereof, according to clause 1 or 16, wherein $R^{5c}$ is —CH$_3$, —CH$_2$CH$_3$, —CH$_2$CH$_2$CH$_3$, —CH(CH$_3$)$_2$, or —C(CH$_3$)$_3$.

20. A compound or pharmaceutically acceptable salt thereof, according to clause 1 or 16, wherein $R^{5c}$ is —CH$_2$CH$_3$.

21. A compound or pharmaceutically acceptable salt thereof, according to clause 1 or 16, wherein $R^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one, two, or three independently selected halo.

22. A compound or pharmaceutically acceptable salt thereof, according to clause 1 or 16, wherein $R^{5c}$ is —CH$_3$, —CH$_2$CH$_3$, —CH$_2$CH$_2$CH$_3$, —CH(CH$_3$)$_2$, or —C(CH$_3$)$_3$, each of which is substituted with one, two, or three independently selected F or Cl.

23. A compound or pharmaceutically acceptable salt thereof, according to clause 1 or 16, wherein $R^{5c}$ is —CH$_2$CH$_3$ substituted with one, two, or three F.

24. A compound or pharmaceutically acceptable salt thereof, according to any one of clauses 1-23, wherein $R^2$ is imidazolyl, pyrazolyl, triazolyl, thiazolyl, oxazolyl, isoxazolyl, oxadiazolyl, pyridinyl, pyridazinyl, pyrimidinyl, or pyrazinyl.

25. A compound or pharmaceutically acceptable salt thereof, according to any one of clauses 1-23, wherein $R^2$ is pyrazolyl.

26. A compound or pharmaceutically acceptable salt thereof, according to any one of clauses 1-23, wherein $R^2$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more independently selected $R^7$ groups.

27. A compound or pharmaceutically acceptable salt thereof, according to any one of clauses 1-23, wherein $R^2$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one $R^7$ group.

28. A compound or pharmaceutically acceptable salt thereof, according to any one of clauses 1-23, wherein $R^2$ is pyrazolyl substituted with one $R^7$ group.

29. A compound or pharmaceutically acceptable salt thereof, according to any one of clauses 1, 26-28, wherein $R^7$ is F, Cl, Br or —CN.

30. A compound or pharmaceutically acceptable salt thereof, according to any one of clauses 1, 26-28, wherein $R^7$ is F or —CN.

31. A compound or pharmaceutically acceptable salt thereof, according to any one of clauses 1, 26-28, wherein $R^7$ is —O—CH$_3$, —O—CH$_2$CH$_3$, or —O—CH(CH$_3$)$_2$.

32. A compound or pharmaceutically acceptable salt thereof, according to any one of clauses 1, 26-28, wherein $R^7$ is —O—CH$_3$ or —O—CHCH$_3$.

33. A compound or pharmaceutically acceptable salt thereof, according to any one of clauses 1, 26-28, wherein $R^7$ is 34. A compound or pharmaceutically acceptable salt thereof, according to any one of clauses 1, 26-28, wherein $R^7$ is —NR$^{13a}$R$^{13b}$ and each R$^{13a}$ and R$^{13b}$ is independently selected H, —CH$_3$, —CH$_2$CH$_3$, or —CH(CH$_3$)$_2$.

35. A compound or pharmaceutically acceptable salt thereof, according to any one of clauses 1, 26-28, wherein $R^7$ is —NH$_2$ or —N(CH$_3$)$_2$.

36. A compound or pharmaceutically acceptable salt thereof, according to any one of clauses 1, 26-28, wherein $R^7$ is —C(=O)NR$^{13c}$R$^{13d}$, and each R$^{13c}$ and R$^{13b}$ is independently selected H, —CH$_3$, —CH$_2$CH$_3$, or —CH(CH$_3$)$_2$.

37. A compound or pharmaceutically acceptable salt thereof, according to any one of clauses 1, 26-28, wherein $R^7$ is —C(=O)NR$^{13c}$R$^{13d}$, and one of R$^{13c}$ and R$^{13d}$ is H, and the other is —CH$_3$, —CH$_2$CH$_3$, or —CH(CH$_3$)$_2$.

38. A compound or pharmaceutically acceptable salt thereof, according to clause 1, wherein the compound is according to any one of Formulae Va-Vf:

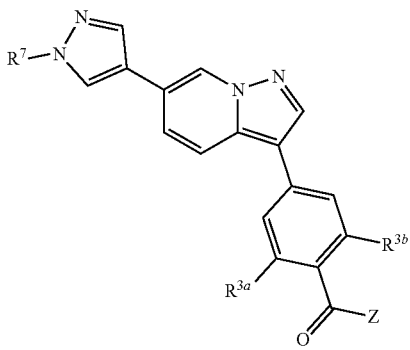

Va

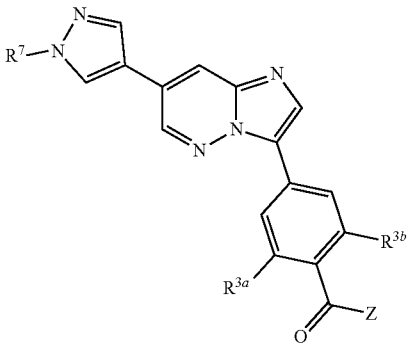

Ve

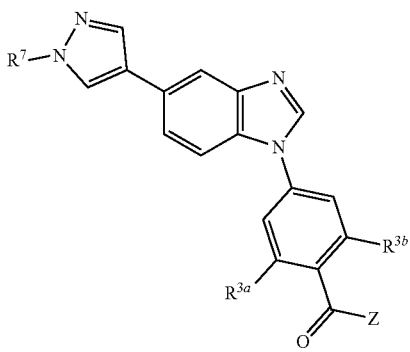

Vb

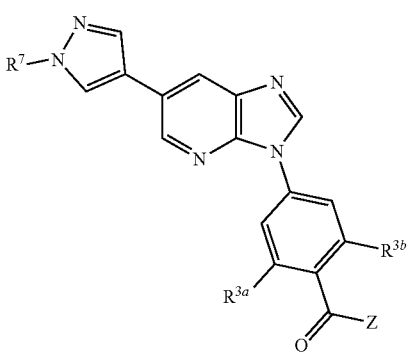

Vf

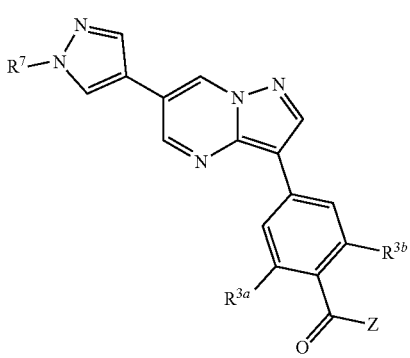

Vc

Vd

39. A compound or pharmaceutically acceptable salt thereof, according to any one of clauses 1-13, 24-28, and 38, wherein $R^7$ is —CH$_3$, —CH$_2$CH$_3$, or —CH(CH$_3$)$_2$.

40. A compound or pharmaceutically acceptable salt thereof, according to any one of clauses 1-13, 24-28, and 38, wherein $R^7$ is —CH$_2$CH$_3$.

41. A compound or pharmaceutically acceptable salt thereof, according to any one of clauses 1-13, 24-28, and 38, wherein $R^7$ is —CH$_3$.

42. A compound or pharmaceutically acceptable salt thereof, according to any one of clauses 1-13, 24-28, and 38, wherein $R^7$ is —CH$_3$, —CHCH$_3$, —CH$_2$CH$_2$CH$_3$, or —CH(CH$_3$)$_2$, each of which is substituted with one or more independently selected halo, —CN, —OH, C$_{1-4}$ alkoxy optionally substituted with one or more independently selected halo, —NR$^{11c}$R$^{11d}$, —C(=O)R$^{12}$, or 4-6 membered monocyclic heterocycloalkyl comprising one, two or three heteroatoms independently selected from N, O, and S.

43. A compound or pharmaceutically acceptable salt thereof, according to any one of clauses 1-13, 24-28, and 38, wherein $R^7$ is C$_{1-4}$ alkyl substituted with one or more independently selected F, Cl, —CN, —OH, —O—CH$_3$, —O—CH$_2$CH$_3$, —O—CH(CH$_3$)$_2$, —O—CHF$_2$, —O—CF$_3$, —O—CH$_2$CHF$_2$, —NR$^{11c}$R$^{11d}$, —C(=O)R$^{12}$, azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl.

44. A compound or pharmaceutically acceptable salt thereof, according to any one of clauses 1-13, 24-28, and 38, wherein $R^7$ is —CH$_3$ or —CH$_2$CH$_3$, each of which is substituted with one tetrahydrofuranyl or morpholinyl.

45. A compound or pharmaceutically acceptable salt thereof, according to clauses 42 and 43, wherein one of $R^{11c}$ and $R^{11d}$ is H, and the other is C$_{1-4}$ alkyl.

46. A compound or pharmaceutically acceptable salt thereof, according to clauses 42 and 43, wherein $R^{11c}$ and Ria are —CH$_3$, —CH$_2$CH$_3$, or —CH(CH$_3$)$_2$.

47. A compound or pharmaceutically acceptable salt thereof, according to clauses 42 and 43, wherein $R^{12}$ is $-NR^{14a}R^{14b}$, and one of $R^{14a}$ and $R^{14b}$ is H, and the other is $C_{1-4}$ alkyl.
48. A compound or pharmaceutically acceptable salt thereof, according to clauses 42 and 43, wherein $R^{12}$ is $-NR^{14a}R^{14b}$, and $R^{14a}$ and $R^{14b}$ are $-CH_3$, $-CH_2CH_3$, or $-CH(CH_3)_2$.
49. A compound or pharmaceutically acceptable salt thereof, according to clauses 42 and 43, wherein $R^{12}$ is $-OH$.
50. A compound or pharmaceutically acceptable salt thereof, according to clauses 42 and 43, wherein $R^{12}$ is $-O-CH_3$, $-O-CH_2CH_3$, $-O-CH(CH_3)_2$, or $-O-C(CH_3)_3$.
51. A compound or pharmaceutically acceptable salt thereof, according to clauses 42 and 43, wherein $R^{12}$ is $-O-CH_3$ or $-O-CH_2CH_3$, each of which is substituted with one, two, or three $C_{3-7}$ cycloalkyl or halo.
52. A compound or pharmaceutically acceptable salt thereof, according to clauses 42 and 43, wherein $R^{12}$ is $R^{12}$ is $-O-CH_3$ or $-O-CH_2CH_3$, each of which is substituted with one, two, or three F.
53. A compound or pharmaceutically acceptable salt thereof, according to clauses 42 and 43, wherein $R^{12}$ is $R^{12}$ is $-O-CH_3$ or $-O-CH_2CH_3$, each of which is substituted with one cyclopropyl, cyclobutyl, or cyclopentyl.
54. A compound or pharmaceutically acceptable salt thereof, according to any one of clauses 1-13, 24-28, and 38, wherein $R^7$ is cyclopropyl, cyclobutyl, cyclopentyl, or cyclohexyl.
55. A compound or pharmaceutically acceptable salt thereof, according to any one of clauses 1-13, 24-28, and 38, wherein $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl.
56. A compound or pharmaceutically acceptable salt thereof, according to any one of clauses 1-13, 24-28, and 38, wherein $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with $-C(=O)$ $C_{1-4}$ alkoxy or $C_{1-4}$ alkyl optionally substituted with $-CN$.
57. A compound or pharmaceutically acceptable salt thereof, according to any one of clauses 1-13, 24-28, and 38, wherein $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with $-C(=O)-O-C(CH_3)_3$, $-CH_3$, $-CH_2-CN$, or $-CH_2CH_2-CN$.
58. A compound or pharmaceutically acceptable salt thereof, according to any one of clauses 1-13, 24-28, and 38, wherein $R^7$ is azetidinyl, pyrrolidinyl, piperidinyl, or piperazinyl, each of which is substituted with $-C(=O)-O-C(CH_3)_3$, $-CH_3$, $-CH_2-CN$, or $-CH_2CH_2-CN$.
59. A compound or pharmaceutically acceptable salt thereof, according to any one of clauses 1-13, and 24-59, wherein $R^{3b}$ is $-O-CH_3$, $-O-CH_2CH_3$, or $-O-CH(CH_3)_2$.
60. A compound or pharmaceutically acceptable salt thereof, according to any one of clauses 1-13, and 24-59, wherein $R^{3b}$ is $-O-CH_3$.
61. A compound or pharmaceutically acceptable salt thereof, according to any one of clauses 1-13, and 24-59, wherein $R^{3b}$ is $-O-CH_3$, $-O-CH_2CH_3$, or $-O-CH(CH_3)_2$, each of which is substituted with one or more independently selected halo, $-OH$ or $C_{1-4}$ alkoxy.
62. A compound or pharmaceutically acceptable salt thereof, according to any one of clauses 1-13, and 24-59, wherein $R^{3b}$ is $C_{1-4}$ alkoxy substituted with one or more independently selected F, Cl, $-OH$, $-O-CH_3$, $-O-CH_2CH_3$, or $-O-CH(CH_3)_2$.
63. A compound or pharmaceutically acceptable salt thereof, according to any one of clauses 1-13, and 24-59, wherein $R^{3b}$ is $-O-CHF_2$.
64. A compound or pharmaceutically acceptable salt thereof, according to any one of clauses 1-13, and 24-59, wherein $R^{3b}$ is $-NR^{8a}R^{8b}$, and $R^{8a}$ and $R^{8b}$ are both H.
65. A compound or pharmaceutically acceptable salt thereof, according to any one of clauses 1-13, and 24-59, wherein $R^{3b}$ is $-NR^{8a}R^{8b}$, and $R^{8a}$ and $R^{8b}$ is H, and the other is $C_{1-4}$ alkyl optionally substituted with one $-OH$ or $C_{1-4}$ alkoxy.
66. A compound or pharmaceutically acceptable salt thereof, according to any one of clauses 1-13, and 24-59, wherein $R^{3b}$ is $-NH-CH_3$, $-NH-CH(CH_3)_2$, or $-NH-CH_2CH_2-OH$.
67. A compound or pharmaceutically acceptable salt thereof, according to clause 1, wherein the compound is according to any one of Formulae VIa-VIf:

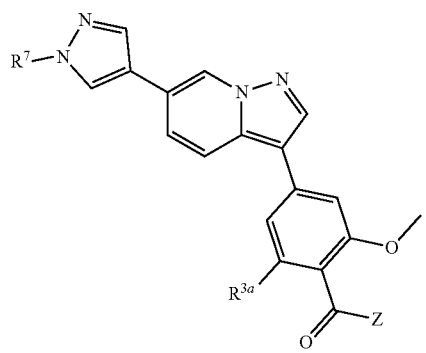

VIa

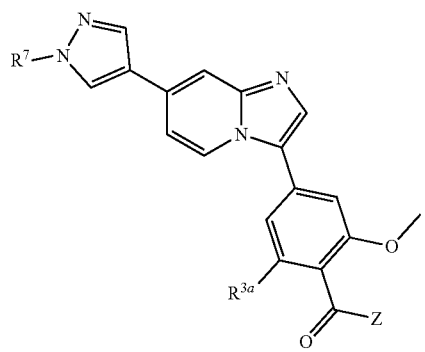

VIb

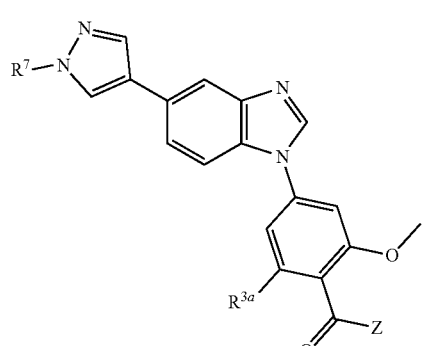
VIc
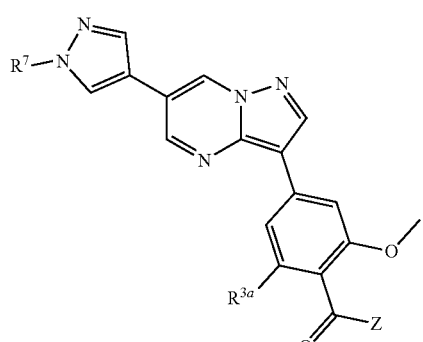
VId
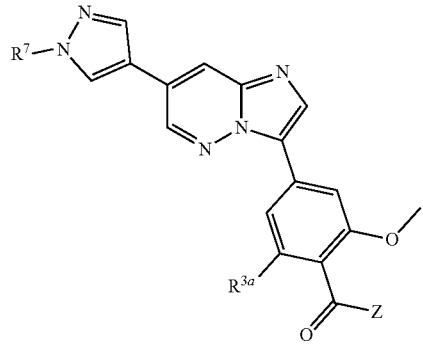
VIe
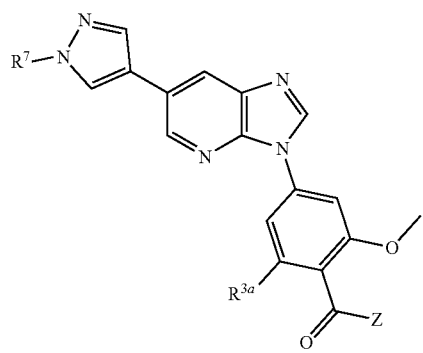
VIf
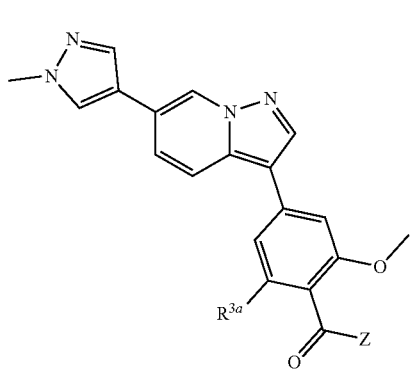
VIIa
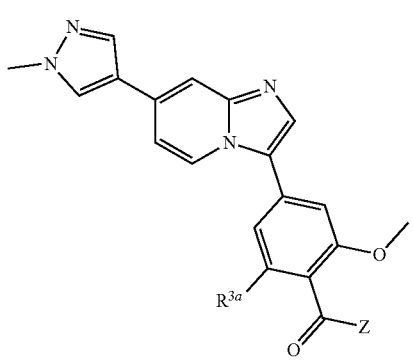
VIIb
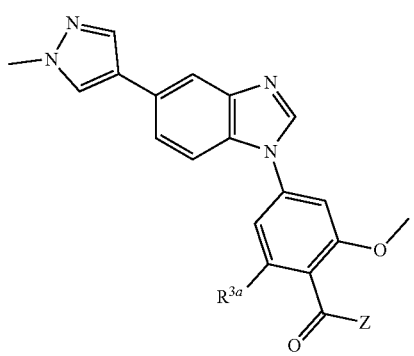
VIIc
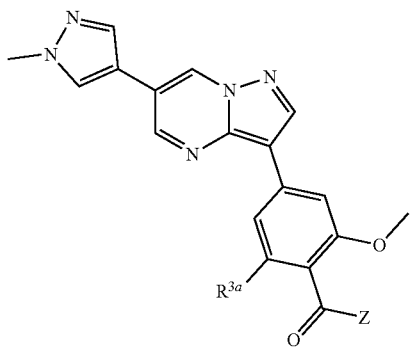
VIId
68. A compound or pharmaceutically acceptable salt thereof, according to any one of clauses 1-13, and 24-67, wherein $R^7$ is —$CH_3$, —$CH_2CH_3$, or —$CH(CH_3)_2$.
69. A compound or pharmaceutically acceptable salt thereof, according to clauses 1, wherein the compound is according to any one of Formulae VIIa-f:

-continued

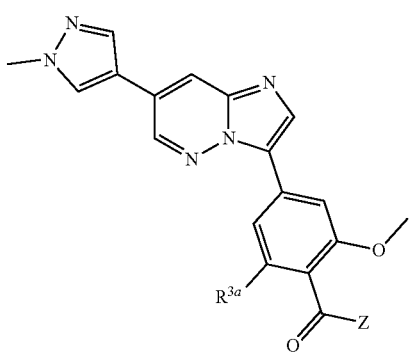
VIIe

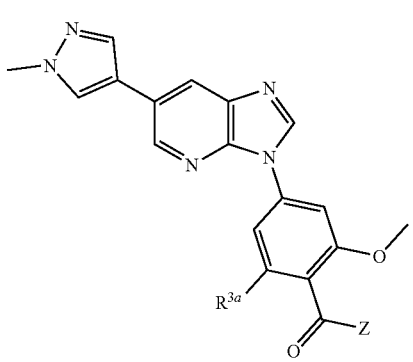
VIIf

70. A compound or pharmaceutically acceptable salt thereof, according to any one of clauses 1-69, wherein $R^{3a}$ is F, Cl, or —OH.
71. A compound or pharmaceutically acceptable salt thereof, according to any one of clauses 1-69, wherein $R^{3a}$ is —CH$_3$, —CH$_2$CH$_3$, or —CH(CH$_3$)$_2$.
72. A compound or pharmaceutically acceptable salt thereof, according to any one of clauses 1-69, wherein $R^{3a}$ is —O—CH$_3$, —O—CH$_2$CH$_3$, or —O—CH(CH$_3$)$_2$.
73. A compound or pharmaceutically acceptable salt thereof, according to any one of clauses 1-69, wherein $R^{3a}$ is —O—CH$_3$.
74. A compound or pharmaceutically acceptable salt thereof, according to any one of clauses 1-69, wherein $R^{3a}$ is —O—CH$_3$, —O—CH$_2$CH$_3$, or —O—CH(CH$_3$)$_2$, each of which is substituted with one or more independently selected halo, —OH or $C_{1-4}$ alkoxy.
75. A compound or pharmaceutically acceptable salt thereof, according to any one of clauses 1-69, wherein $R^{3a}$ is $C_{1-4}$ alkoxy substituted with one, two, or three F or Cl.
76. A compound or pharmaceutically acceptable salt thereof, according to any one of clauses 1-69, wherein $R^{3a}$ is —O—CH$_3$ or —O—CH$_2$CH$_3$, each of which is substituted with one —OH or —O—CH$_3$.
77. A compound or pharmaceutically acceptable salt thereof, according to any one of clauses 1-69, wherein $R^{3a}$ is —O—CHF$_2$.
78. A compound or pharmaceutically acceptable salt thereof, according to any one of clauses 1-69, wherein $R^{3a}$ is —NR$^{8a}$R$^{8b}$, and R$^{8a}$ and R$^{8b}$ are both H.
79. A compound or pharmaceutically acceptable salt thereof, according to any one of clauses 1-69, wherein $R^{3a}$ is —NR$^{8a}$R$^{8b}$, and one of R$^{8a}$ and R$^{8b}$ is H, and the other is $C_{1-4}$ alkyl optionally substituted with one —OH or $C_{1-4}$ alkoxy.
80. A compound or pharmaceutically acceptable salt thereof, according to any one of clauses 1-69, wherein $R^{3a}$ is —NH—CH$_3$, —NH—CH(CH$_3$)$_2$, or —NH—CH$_2$CH$_2$—OH.

81. A compound or pharmaceutically acceptable salt thereof, according to clause 1, wherein the compound is according to any one of Formulae VIIIa-VIIId:

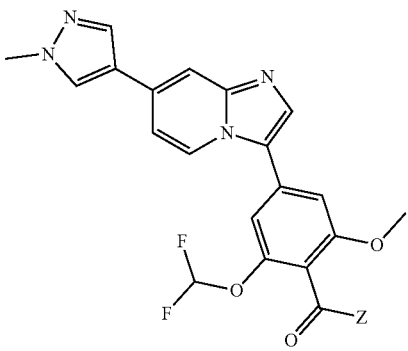
VIIIa

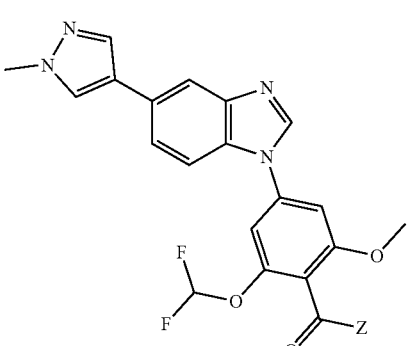
VIIIb

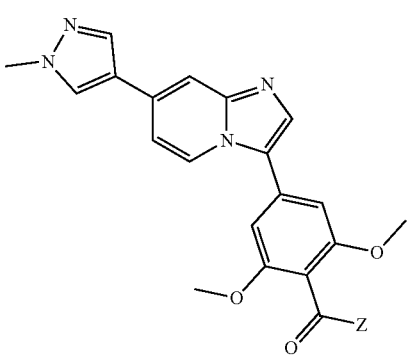
VIIIc

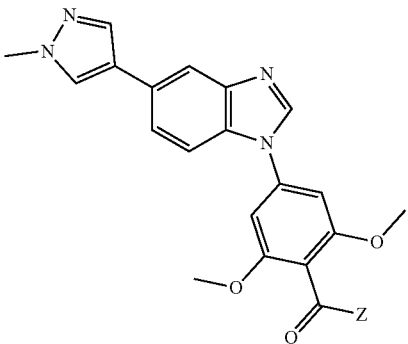
VIIId

82. A compound or pharmaceutically acceptable salt thereof, according to any one of clauses 1-13, and 24-81 wherein Z is —NR$^{5a}$R$^{5b}$.
83. A compound or pharmaceutically acceptable salt thereof, according to clause 82, wherein R$^{5a}$ is H.

84. A compound or pharmaceutically acceptable salt thereof, according to clause 82, wherein $R^{5a}$ is —$CH_3$, —$CH_2CH_3$, or —$CH(CH_3)_2$.
85. A compound or pharmaceutically acceptable salt thereof, according to clause 82, wherein $R^{5a}$ is —$CH_3$.
86. A compound or pharmaceutically acceptable salt thereof, according to clause 82, wherein $R^{5a}$ is —$CH_2CH_3$.
87. A compound or pharmaceutically acceptable salt thereof, according to any one of clauses 82-86 wherein $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$.
88. A compound or pharmaceutically acceptable salt thereof, according to any one of clauses 82-86, wherein $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one or more independently selected $R^9$.
89. A compound or pharmaceutically acceptable salt thereof, according to any one of clauses 82-86, wherein $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted one, two, or three independently selected $R^9$.
90. A compound or pharmaceutically acceptable salt thereof, according to any one of clauses 82-86, wherein $R^{5b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted one $R^9$.
91. A compound or pharmaceutically acceptable salt thereof, according to any one of clauses 88-90, wherein each $R^9$ is independently F, Cl, —CN, —OH, —O—$CH_3$, —O—$CH_2CH_3$, —O—$CH(CH_3)_2$, —$S(=O)_2$—$CH_3$, —$S(=O)_2$—$CH_2CH_3$, or —$S(=O)_2$—$CH(CH_3)_2$.
92. A compound or pharmaceutically acceptable salt thereof, according to any one of clauses 88-90, wherein $R^9$ is F, —CN, —OH, —O—$CH_3$, or —$S(=O)_2$—$CH_3$.
93. A compound or pharmaceutically acceptable salt thereof, according to any one of clauses 88-90, wherein $R^9$ is —$NR^{11e}R^{11f}$, and $R^{11e}$ and $R^{11f}$ are both H.
94. A compound or pharmaceutically acceptable salt thereof, according to any one of clauses 88-90, wherein $R^9$ is $NR^{11e}R^{11f}$, and $R^{11e}$ and $R^{11f}$ is H, and the other is —$CH_3$, —$CH_2CH_3$, or —$CH(CH_3)_2$.
95. A compound or pharmaceutically acceptable salt thereof, according to any one of clauses 88-90, wherein $R^9$ is —$N(CH_3)_2$.
96. A compound or pharmaceutically acceptable salt thereof, according to any one of clauses 88-90, wherein $R^9$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl.
97. A compound or pharmaceutically acceptable salt thereof, according to any one of clauses 88-90, wherein $R^9$ is dioxanyl.
98. A compound or pharmaceutically acceptable salt thereof, according to any one of clauses 88-90, wherein $R^9$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl
99. A compound or pharmaceutically acceptable salt thereof, according to any one of clauses 88-90, wherein $R^9$ is imidazolyl, pyrazolyl, or pyridinyl.
100. A compound or pharmaceutically acceptable salt thereof, according to any one of clauses 88-90, wherein $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected $C_4$ alkyl.
101. A compound or pharmaceutically acceptable salt thereof, according to any one of clauses 88-90, wherein $R^9$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected—$CH_3$, —$CH_2CH_3$, or —$CH(CH_3)_2$.
102. A compound or pharmaceutically acceptable salt thereof, according to any one of clauses 82-86, wherein $R^{5b}$ is cyclopropyl, cyclobutyl, cyclopentyl, or cyclohexyl.
103. A compound or pharmaceutically acceptable salt thereof, according to any one of clauses 82-86, wherein $R^{5b}$ is cyclopropyl.
104. A compound or pharmaceutically acceptable salt thereof, according to any one of clauses 82-86, wherein $R^{5b}$ is cyclopropyl, cyclobutyl, cyclopentyl, or cyclohexyl, each of which is substituted with one, two, or three independently selected $R^{10}$.
105. A compound or pharmaceutically acceptable salt thereof, according to any one of clauses 82-86, wherein $R^{5b}$ is cyclopropyl, cyclobutyl, cyclopentyl, or cyclohexyl, each of which is substituted with one $R^{10}$.
106. A compound or pharmaceutically acceptable salt thereof, according to clause 104 or 105, wherein $R^{10}$ is halo, —OH, or $C_{1-4}$ alkoxy.
107. A compound or pharmaceutically acceptable salt thereof, according to clause 104 or 105, wherein $R^{10}$ is F, Cl, —OH, —O—$CH_3$, —O—$CH_2CH_3$, or —O—$CH(CH_3)_2$.
108. A compound or pharmaceutically acceptable salt thereof, according to clause 104 or 105, wherein $R^{10}$ is —$CH_3$, —$CH_2CH_3$, or —$CH(CH_3)_2$.
109. A compound or pharmaceutically acceptable salt thereof, according to clause 104 or 105, wherein $R^{10}$ is —$CH_3$, —$CH_2CH_3$, or —$CH(CH_3)_2$, each of which is substituted with one, two, or three independently selected halo, —OH, or $C_{1-4}$ alkoxy.
110. A compound or pharmaceutically acceptable salt thereof, according to clause 104 or 105, wherein $R^{10}$ is —$CH_2F$, —$CHF_2$, —$CF_3$, or —$CH_2$—OH.
111. A compound or pharmaceutically acceptable salt thereof, according to clause 104 or 105, wherein $R^{10}$ is —$NR^{11g}R^{11h}$.
112. A compound or pharmaceutically acceptable salt thereof, according to clause 111, wherein $R^{11g}$ and $R^{11h}$ are independently, H, —$CH_3$, —$CH_2CH_3$, or —$CH(CH_3)_2$.
113. A compound or pharmaceutically acceptable salt thereof, according to clause 104 or 105, wherein $R^{10}$ is —$N(CH_3)_2$.
114. A compound or pharmaceutically acceptable salt thereof, according to any one of clauses 82-86, wherein $R^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl. In a more particular embodiment, $R^{5b}$ is oxetanyl, thietanyl, or tetrahydrothiopyranyl.
115. A compound or pharmaceutically acceptable salt thereof, according to any one of clauses 82-86, wherein $R^{5b}$ is oxetanyl.

116. A compound or pharmaceutically acceptable salt thereof, according to any one of clauses 82-86, wherein $R^{5b}$ is azetidinyl, oxetanyl, thietanyl, pyrrolidinyl, tetrahydrofuranyl, tetrahydrothiophenyl, piperidinyl, tetrahydropyranyl, or tetrahydrothiopyranyl, each of which is substituted with one or more oxo.

117. A compound or pharmaceutically acceptable salt thereof, according to any one of clauses 82-86, wherein $R^{5b}$ is thietanyl or tetrahydrothiophenyl, each of which is substituted with two oxo.

118. A compound or pharmaceutically acceptable salt thereof, according to any one of clauses 82-86, wherein $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl.

119. A compound or pharmaceutically acceptable salt thereof, according to any one of clauses 82-86, wherein $R^{5b}$ is imidazolyl, pyrazolyl, isoxazolyl, or pyrimidinyl.

120. A compound or pharmaceutically acceptable salt thereof, according to any one of clauses 82-86, wherein $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one or more independently selected $C_4$ alkyl.

121. A compound or pharmaceutically acceptable salt thereof, according to any one of clauses 82-86, wherein $R^{5b}$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is substituted with one —$CH_3$, —$CH_2CH_3$, or —$CH(CH_3)_2$.

122. A compound or pharmaceutically acceptable salt thereof, according to any one of clauses 82-86, wherein $R^{5b}$ is imidazolyl, pyrazolyl, or pyrimidinyl, each of which is substituted with one —$CH_3$.

123. A compound or pharmaceutically acceptable salt thereof, according to clause 82 wherein $R^{5a}$ is H, and $R^{5b}$ is —$CH_2CH_3$, —$CH_2CF_3$, —$CH(CH_3)CF_3$, or cyclopropyl.

124. A compound or pharmaceutically acceptable salt thereof, according to any one of clauses 1-13, and 24-81 wherein Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, Z is azetidinyl, pyrrolidinyl, piperidinyl, 2-oxa-6-azaspiro[3.3]heptanyl, or 2-thia-6-azaspiro[3.3]heptanyl.

125. A compound or pharmaceutically acceptable salt thereof, according to any one of clauses 1-13, and 24-81 wherein Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two or three independently selected $R^6$ groups.

126. A compound or pharmaceutically acceptable salt thereof, according to any one of clauses 1-13, and 24-81 wherein Z is azetidinyl, pyrrolidinyl, piperidinyl, or 2-thia-6-azaspiro[3.3]heptanyl, each of which is substituted with one, two or three independently selected $R^6$ groups.

127. A compound or pharmaceutically acceptable salt thereof, according to clauses 125 or 126, wherein $R^6$ is oxo, F, Cl, —CN, —OH, phenyl, cyclopropyl, cyclobutyl, cyclopentyl, —C≡CH, —C(=O)—O—$CH_3$, —C(=O)—O—$CH_2CH_3$, or —C(=O)—O—$CH(CH_3)_2$.

128. A compound or pharmaceutically acceptable salt thereof, according to clauses 125 or 126, wherein $R^6$ is —$NR^{11a}R^{11b}$ and each $R^{11a}$ and $R^{11b}$ is independently selected from H, —$CH_3$, —$CH_2CH_3$, and —$CH(CH_3)_2$.

129. A compound or pharmaceutically acceptable salt thereof, according to clauses 125 or 126, wherein $R^6$ is —$N(CH_3)_2$.

130. A compound or pharmaceutically acceptable salt thereof, according to clauses 125 or 126, wherein $R^6$ is —O—$CH_3$, —O—$CH_2CH_3$, or —O—$CH(CH_3)_2$.

131. A compound or pharmaceutically acceptable salt thereof, according to clauses 125 or 126, wherein $R^6$ is —O—$CH_3$, —O—$CH_2CH_3$, or —O—$CH(CH_3)_2$, each of which is substituted with one or more F, Cl, or phenyl.

132. A compound or pharmaceutically acceptable salt thereof, according to clauses 125 or 126, wherein R is —$CH_3$, —$CH_2CH_3$, or —$CH(CH_3)_2$.

133. A compound or pharmaceutically acceptable salt thereof, according to clauses 125 or 126, wherein R is —$CH_3$, —$CH_2CH_3$, or —$CH(CH_3)_2$, each of which is substituted with one, two, or three F, Cl, —OH, —O—$CH_3$, —O—$CH_2CH_3$, or —O—$CH(CH_3)_2$.

134. A compound or pharmaceutically acceptable salt thereof, according to clauses 125 or 126, wherein $R^6$ is —$CH_3$ substituted with one, two, or three F, or —OH.

135. A compound or pharmaceutically acceptable salt thereof, according to clauses 125 or 126, wherein $R^6$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl.

136. A compound or pharmaceutically acceptable salt thereof, according to clauses 125 or 126, wherein R is tetrahydropyranyl or morpholinyl 137. A compound or pharmaceutically acceptable salt thereof, according to any one of clauses 1-13, and 24-81 wherein Z is 138. A compound or pharmaceutically acceptable salt thereof, according to clause 1, wherein the compound is selected from Table III.

139. A pharmaceutical composition comprising a pharmaceutically acceptable carrier and a pharmaceutically effective amount of a compound according to any one of clauses 1-138.

140. A pharmaceutical composition according to clause 138 comprising a further therapeutic agent.

141. A compound or pharmaceutically acceptable salt thereof, according to any one of clause 1-138, or a pharmaceutical composition according to clause 139 or 140 for use in medicine.

142. A compound or pharmaceutically acceptable salt thereof, according to any one of clause 1-138, or a pharmaceutical composition according to clause 139 or 140 for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

143. A compound or pharmaceutically acceptable salt thereof, according to any one of clause 1-138, or a pharmaceutical composition according to clause 139 or 140, wherein said compound or pharmaceutical composition is administered in combination with a further therapeutic agent.

144. The pharmaceutical composition according to clause 140, or the use according to clause 143, wherein the further therapeutic agent is an agent for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration or stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine.

In one embodiment, the present invention provides compounds of the invention or pharmaceutical compositions comprising a compound of the invention, for use in the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In another embodiment, the present invention provides the use of compounds of the invention or pharmaceutical compositions comprising a compound of the invention in the manufacture of a medicament for the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides pharmaceutical compositions comprising a compound of the invention, and another therapeutic agent. In a particular embodiment, the other therapeutic agent is a inflammatory diseases treatment agent. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides compounds of the invention or pharmaceutical compositions comprising a compound of the invention, for use in the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In another embodiment, the present invention provides the use of compounds of the invention or pharmaceutical compositions comprising a compound of the invention in the manufacture of a medicament for the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In additional method of treatment aspects, this invention provides methods of prophylaxis and/or treatment of a mammal afflicted with autoinflammatory diseases, which methods comprise the administration of an effective amount of a compound of the invention or one or more of the pharmaceutical compositions herein described for the treatment or prophylaxis of said condition. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides pharmaceutical compositions comprising a compound of the invention, and another therapeutic agent. In a particular embodiment, the other therapeutic agent is a autoinflammatory diseases treatment agent. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides compounds of the invention or pharmaceutical compositions comprising a compound of the invention, for use in the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In another embodiment, the present invention provides the use of compounds of the invention or pharmaceutical compositions comprising a compound of the invention in the manufacture of a medicament for the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In one embodiment, the present invention provides pharmaceutical compositions comprising a compound of the invention, and another therapeutic agent. In a particular embodiment, the other therapeutic agent is a autoimmune diseases treatment agent. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In another embodiment, the present invention provides the use of compounds of the invention or pharmaceutical compositions comprising a compound of the invention in the manufacture of a medicament for the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides pharmaceutical compositions comprising a compound of the invention, and another therapeutic agent. In a particular embodiment, the other therapeutic agent is a proliferative diseases treatment agent. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides compounds of the invention or pharmaceutical compositions comprising a compound of the invention, for use in the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In another embodiment, the present invention provides the use of compounds of the invention or pharmaceutical compositions comprising a compound of the invention in the manufacture of a medicament for the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides pharmaceutical compositions comprising a compound of the invention, and another therapeutic agent. In a particular embodiment, the other therapeutic agent is a fibrotic diseases treatment agent. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides compounds of the invention or pharmaceutical compositions comprising a compound of the invention, for use in the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to a graft-versus-host disease.

In another embodiment, the present invention provides the use of compounds of the invention or pharmaceutical compositions comprising a compound of the invention in the manufacture of a medicament for the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to a graft-versus-host disease.

In additional method of treatment aspects, this invention provides methods of prophylaxis and/or treatment of a mammal afflicted with transplantation rejection, which methods comprise the administration of an effective amount of a compound of the invention or one or more of the pharmaceutical compositions herein described for the treatment or prophylaxis of said condition. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to a graft-versus-host disease.

In one embodiment, the present invention provides pharmaceutical compositions comprising a compound of the invention, and another therapeutic agent. In a particular embodiment, the other therapeutic agent is a transplantation rejection treatment agent. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to a graft-versus-host disease.

In one embodiment, the present invention provides compounds of the invention or pharmaceutical compositions comprising a compound of the invention, for use in the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In another embodiment, the present invention provides the use of compounds of the invention or pharmaceutical compositions comprising a compound of the invention in the manufacture of a medicament for the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In additional method of treatment aspects, this invention provides methods of prophylaxis and/or treatment of a mammal afflicted with diseases involving impairment of cartilage turnover, which methods comprise the administration of an effective amount of a compound of the invention or one or more of the pharmaceutical compositions herein described for the treatment or prophylaxis of said condition. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides pharmaceutical compositions comprising a compound of the invention, and another therapeutic agent. In a particular embodiment, the other therapeutic agent is a diseases involving impairment of cartilage turnover treatment agent. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides compounds of the invention or pharmaceutical compositions comprising a compound of the invention, for use in the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In another embodiment, the present invention provides the use of compounds of the invention or pharmaceutical compositions comprising a compound of the invention in the manufacture of a medicament for the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In additional method of treatment aspects, this invention provides methods of prophylaxis and/or treatment of a mammal afflicted with congenital cartilage malformation, which methods comprise the administration of an effective amount of a compound of the invention or one or more of the pharmaceutical compositions herein described for the treatment or prophylaxis of said condition. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides pharmaceutical compositions comprising a compound of the invention, and another therapeutic agent. In a particular embodiment, the other therapeutic agent is a congenital cartilage malformation treatment agent. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides compounds of the invention or pharmaceutical compositions comprising a compound of the invention, for use in the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In another embodiment, the present invention provides the use of compounds of the invention or pharmaceutical compositions comprising a compound of the invention in the manufacture of a medicament for the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In additional method of treatment aspects, this invention provides methods of prophylaxis and/or treatment of a mammal afflicted with diseases involving impairment of bone turnover, which methods comprise the administration of an effective amount of a compound of the invention or one or more of the pharmaceutical compositions herein described for the treatment or prophylaxis of said condition. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides pharmaceutical compositions comprising a compound of the invention, and another therapeutic agent. In a particular embodiment, the other therapeutic agent is a diseases involving impairment of bone turnover treatment agent. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides compounds of the invention or pharmaceutical compositions comprising a compound of the invention, for use in the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In another embodiment, the present invention provides the use of compounds of the invention or pharmaceutical compositions comprising a compound of the invention in the manufacture of a medicament for the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In additional method of treatment aspects, this invention provides methods of prophylaxis and/or treatment of a mammal afflicted with diseases associated with hypersecretion of IL-6, which methods comprise the administration of an effective amount of a compound of the invention or one or more of the pharmaceutical compositions herein described for the treatment or prophylaxis of said condition. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides pharmaceutical compositions comprising a compound of the invention, and another therapeutic agent. In a particular embodiment, the other therapeutic agent is a diseases associated with hypersecretion of IL-6 treatment agent. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides compounds of the invention or pharmaceutical compositions comprising a compound of the invention, for use in the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In another embodiment, the present invention provides the use of compounds of the invention or pharmaceutical compositions comprising a compound of the invention in the manufacture of a medicament for the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In additional method of treatment aspects, this invention provides methods of prophylaxis and/or treatment of a mammal afflicted with diseases associated with hypersecretion of TNFα, interferons, IL-12 and/or IL-23, which methods comprise the administration of an effective amount of a compound of the invention or one or more of the pharmaceutical compositions herein described for the treatment or prophylaxis of said condition. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides pharmaceutical compositions comprising a compound of the invention, and another therapeutic agent. In a particular embodiment, the other therapeutic agent is a diseases associated with hypersecretion of TNFα, interferons, IL-12 and/or IL-23 treatment agent. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides compounds of the invention or pharmaceutical compositions comprising a compound of the invention, for use in the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In another embodiment, the present invention provides the use of compounds of the invention or pharmaceutical compositions comprising a compound of the invention in the manufacture of a medicament for the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In additional method of treatment aspects, this invention provides methods of prophylaxis and/or treatment of a mammal afflicted with respiratory diseases, which methods comprise the administration of an effective amount of a compound of the invention or one or more of the pharmaceutical compositions herein described for the treatment or prophylaxis of said condition. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides pharmaceutical compositions comprising a compound of the invention, and another therapeutic agent. In a particular embodiment, the other therapeutic agent is a respiratory diseases treatment agent. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides compounds of the invention or pharmaceutical compositions comprising a compound of the invention, for use in the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or diabetes type II.

In another embodiment, the present invention provides the use of compounds of the invention or pharmaceutical compositions comprising a compound of the invention in the manufacture of a medicament for the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or diabetes type II.

In additional method of treatment aspects, this invention provides methods of prophylaxis and/or treatment of a mammal afflicted with endocrine and/or metabolic diseases, which methods comprise the administration of an effective amount of a compound of the invention or one or more of the pharmaceutical compositions herein described for the treatment or prophylaxis of said condition. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or diabetes type II.

In one embodiment, the present invention provides pharmaceutical compositions comprising a compound of the invention, and another therapeutic agent. In a particular embodiment, the other therapeutic agent is a endocrine and/or metabolic diseases treatment agent. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or diabetes type II.

In one embodiment, the present invention provides compounds of the invention or pharmaceutical compositions comprising a compound of the invention, for use in the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. More particularly, the term refers to atherosclerosis.

In another embodiment, the present invention provides the use of compounds of the invention or pharmaceutical compositions comprising a compound of the invention in the manufacture of a medicament for the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. More particularly, the term refers to atherosclerosis.

In additional method of treatment aspects, this invention provides methods of prophylaxis and/or treatment of a mammal afflicted with cardiovascular diseases, which methods comprise the administration of an effective amount of a compound of the invention or one or more of the pharmaceutical compositions herein described for the treatment or prophylaxis of said condition. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. More particularly, the term refers to atherosclerosis.

In one embodiment, the present invention provides pharmaceutical compositions comprising a compound of the invention, and another therapeutic agent. In a particular embodiment, the other therapeutic agent is a cardiovascular diseases treatment agent. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. More particularly, the term refers to atherosclerosis.

In one embodiment, the present invention provides compounds of the invention or pharmaceutical compositions comprising a compound of the invention, for use in the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, urticaria, rosacea, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In another embodiment, the present invention provides the use of compounds of the invention or pharmaceutical compositions comprising a compound of the invention in the manufacture of a medicament for the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, urticaria, rosacea, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In additional method of treatment aspects, this invention provides methods of prophylaxis and/or treatment of a mammal afflicted with dermatological diseases, which methods comprise the administration of an effective amount of a compound of the invention or one or more of the pharmaceutical compositions herein described for the treatment or prophylaxis of said condition. In particular, the term dermatological diseases refers to atopic dermatitis, bullous disorders, collagenoses, psoriasis, psoriatic lesions, dermatitis, contact dermatitis, eczema, vitiligo, pruritus, urticaria, rosacea, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In one embodiment, the present invention provides pharmaceutical compositions comprising a compound of the invention, and another therapeutic agent. In a particular embodiment, the other therapeutic agent is a dermatological diseases treatment agent. In particular, the term dermatological diseases refers to atopic dermatitis, bullous disorders, collagenoses, psoriasis, psoriatic lesions, dermatitis, contact dermatitis, eczema, vitiligo, pruritus, urticaria, rosacea, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In one embodiment, the present invention provides compounds of the invention or pharmaceutical compositions comprising a compound of the invention, for use in the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In another embodiment, the present invention provides the use of compounds of the invention or pharmaceutical compositions comprising a compound of the invention in the manufacture of a medicament for the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In additional method of treatment aspects, this invention provides methods of prophylaxis and/or treatment of a mammal afflicted with abnormal angiogenesis associated diseases, which methods comprise the administration of an effective amount of a compound of the invention or one or more of the pharmaceutical compositions herein described for the treatment or prophylaxis of said condition. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In one embodiment, the present invention provides pharmaceutical compositions comprising a compound of the invention, and another therapeutic agent. In a particular embodiment, the other therapeutic agent is a abnormal angiogenesis associated diseases treatment agent. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leucovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin®), capecitabine, raloxifene hydrochloride, EGFR inhibitors (e.g. Iressa®, Tarceva®, Erbitux®), VEGF inhibitors (e.g. Avastin®), proteasome inhibitors (e.g. Velcade®), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracylines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. cetirizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

CHEMICAL SYNTHETIC PROCEDURES

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts & Greene 2006).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 µm), normal phase Interchim® 15 m spherical silica columns, or with Biotage® SNAP KP-NH or Biotage® SNAP Ultra flash chromatography cartridges. Thin layer chromatography is carried out using pre-coated silica gel F-254 plates (thickness 0.25 mm). $^1$H NMR spectra are recorded on a Bruker DPX 400 NMR spectrometer (400 MHz or a Bruker Advance 300 NMR spectrometer (300 MHz). Chemical shifts (δ) for $^1$H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintet (quin), multiplet (m) and broad (br). Electrospray MS spectra are obtained on a Waters platform LC/MS spectrometer or with Waters Acquity H-Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra MS 5 µm C18, 100×4.6 mm. The methods are using either $ACN/H_2O$ gradients ($H_2O$ contains either 0.1% TFA or 0.1% $NH_3$) or $MeOH/H_2O$ gradients ($H_2O$ contains 0.05% TFA). Microwave heating is performed with a Biotage Initiator.

TABLE I

List of abbreviations used in the experimental section:

| Abbreviation | Definition |
| --- | --- |
| µL | microliter |
| AcOH | acetic acid |
| AcOK | potassium acetate |
| ACN | acetonitrile |
| aq. | aqueous |
| ATP | adenosine 5'-triphosphate |
| BBBPY | 4,4'-di-tert-butyl-2,2'-dipyridyl |
| Boc | tert-butyloxy-carbonyl |
| $B_2pin_2$ | 4,4,5,5-tetramethyl-2-(4,4,5,5-tetramethyl-1,3,2-dioxaborolan-2-yl)-1,3,2-dioxaborolane |
| broad s | broad singlet |
| BrettPhos | 2-(Dicyclohexylphosphino)3,6-dimethoxy-2',4',6'-triisopropyl-1,1'-biphenyl |
| Calcd | calculated |
| d | doublet |
| DBU | 1,8-diazabicyclo[5.4.0]undec-7-ene |
| dd | doublet of doublet |
| DCM | dichloromethane |
| DIPEA | N,N-diisopropylethylamine |
| DMAC | dimethylacetamide |
| DMF | N,N-dimethylformamide |
| DMSO | Dimethylsulfoxide |
| DPPF | 1,1'-bis(diphenylphosphino)ferrocene |
| $Et_2O$ | diethyl ether |
| EtOAc | ethyl acetate |
| EtOH | ethanol |
| eq. | equivalent |
| g | gram |
| h | hour |
| HATU | 1-[bis(dimethylamino)methylene]-1H-1,2,3-triazolo[4,5-b]pyridinium 3-oxid hexafluorophosphate |
| HPLC | high-performance liquid chromatography |
| i-PrOH | isopropanol |
| [Ir(OMe)(COD)]$_2$ | (1,5-cyclooctadiene)(methoxy)iridium(I) dimer |
| LiHMDS | lithium hexamethyldisilazane |
| LCMS | Liquid Chromatography-Mass Spectrometry |
| m | multiplet |
| MeOH | methanol |
| MeONa | sodium methoxide |
| mg | milligram |
| min | minute |
| mL | milliliter |
| mmol | millimole |
| MS | mass spectrometry |
| MTBE | methyl tert-butyl ether |
| MW | molecular weight |
| MW (obs) | molecular weight observed |
| MW (calc) | molecular weight calculated |
| NA | not available |
| n-BuOH | butan-1-ol |
| NMP | N-methyl-2-pyrrolidone |

TABLE I-continued

List of abbreviations used in the experimental section:

| Abbreviation | Definition |
|---|---|
| obsd | observed |
| Pd(dppf)Cl$_2$•DCM | 1,1'-bis(diphenylphosphino)ferroceneldichloropalladium(II), complex with dichloromethane |
| Pd(OAc)$_2$ | palladium(II) acetate |
| Pd(PPh$_3$)$_4$ | tetrakis(triphenylphosphine)palladium(0) |
| Pd$_2$(dba)$_3$ | tris(dibenzylideneacetone)dipalladium(0) |
| ppm | part-per-million |
| q | quadruplet |
| RT | room temperature |
| s | singlet |
| sat. | saturated |
| SM | starting material |
| t | triplet |
| t-BuXPhos | 2-di-tert-butylphosphino-2',4',6'-triisopropylbiphenyl |
| Et$_3$N | triethylamine |
| TFA | trifluoroacetic acid |
| THF | tetrahydrofuran |
| TLC | thin layer chromatography |
| XantPhos | 4,5-bis(diphenylphosphino)-9,9-dimethylxanthene |

Synthetic Preparation of the Compounds of the Invention

Example 1. General Synthetic Methods 1.1. Synthetic Methods Overview

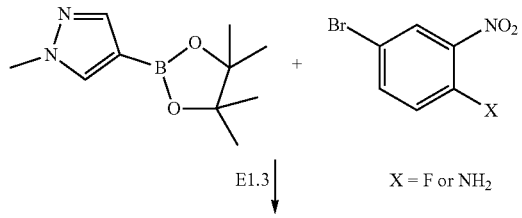

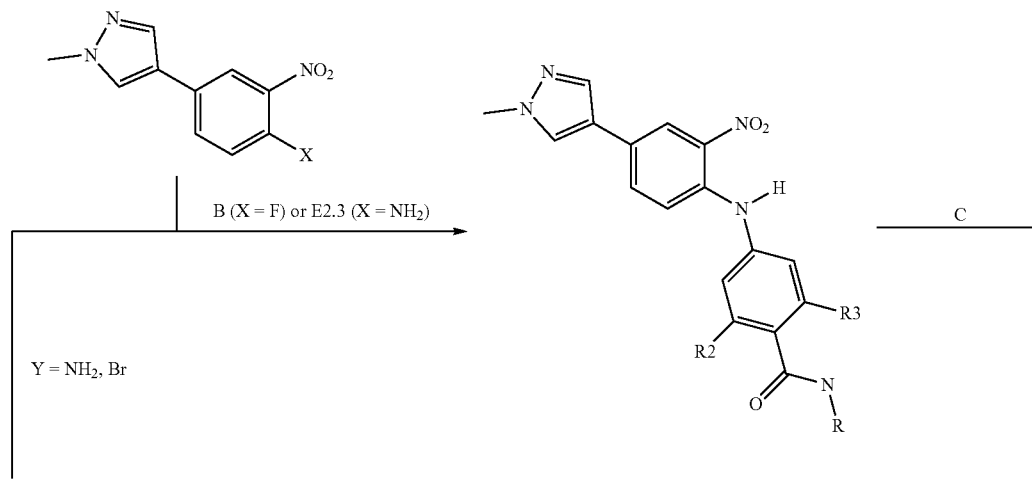

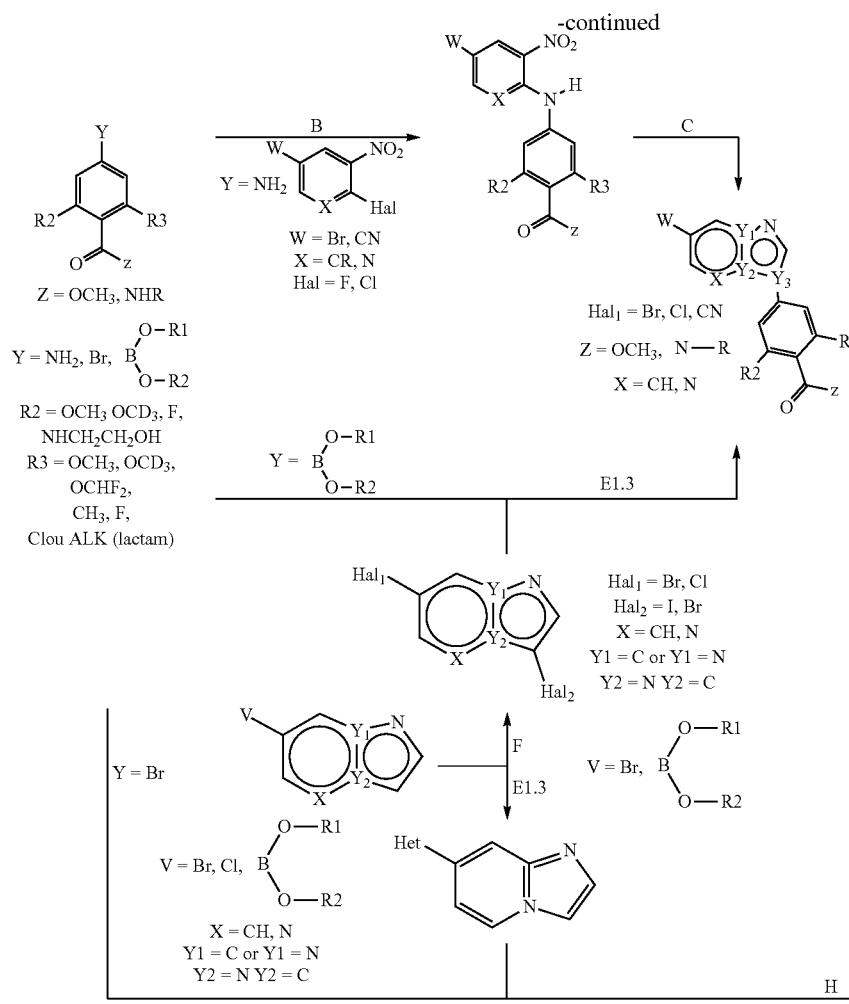
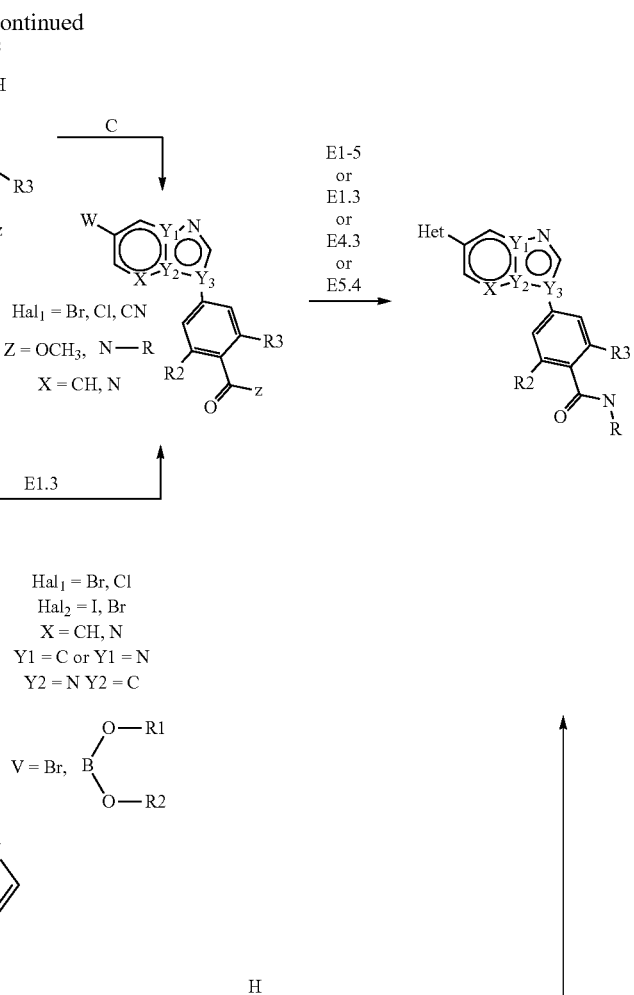

General Methods B: $S_NAr$ of Trisubstituted Aniline on Halogeno Nitro Phenyl or Pyridine Derivative
  Method B1: $S_NAr$ of disubstituted amino benzoate on halogeno nitro phenyl derivative
  Method B2: $S_NAr$ of disubstituted amino benzamide on halogeno nitro phenyl derivative
  Method B3: $S_NAr$ of disubstituted amino benzamide or benzoate on halogeno nitro pyridine derivative
General Methods C: Reduction and Cyclisation Process
  Method C1: $SnCl_2$, $2H_2O/SnCl_2$/trimethyl orthoformate
  Method C2: Zn/AcOH/HC(OCH3)3
General Methods E: Aryl Coupling with Peptide Coupling
  Method E1: Suzuki reaction process (3 steps with interchangeable order)
  Method E2: Buchwald reaction process (3 steps)
  Method E3: Copper amination process (3 steps)
  Method E4: Borylation then Suzuki reaction (3 steps)
  Method E5: Cyanation then ring formation process (4 steps)
General Methods F: Iodination of Heteroaryl Compound
General Methods H: C—H Activation
General Methods I: Phenol Deprotection (Demethylation)
General Methods J: Phenol Alkylation
  Method J1: $K_2CO_3$/Alkyl iodide
  Method J2: KOH/diethyl (bromodifluoromethyl)phosphonate
General Methods K: Amine Deprotection
General Methods L: Amine Functionalization
  Method L1: Reductive amination
  Method L2: N-alkylation of amine
General Methods M: $S_NAr$
  Method M1: $S_NAr$ with amine
  Method M2: $S_NAr$ with alcohol
General Methods N: Pyrazole Alkylation
  Method N1: Alkylation with alkyl halide
  Method N2: Alkylation with halogenoacetate
General Methods O: Amide Alkylation
General Methods P: Cleavage of Tert-Butyl Ester
General Methods Q: Esterification of Carboxylic Acid
  Method Q1: HATU
  Method Q2: $SOCl_2$
  Method Q3: Alkyl bromide/$Cs_2CO_3$
General Methods R: Transesterification of Tert-Butyl Ester 1.2. General Methods 1.2.1. Methods B: $S_NAr$ of Trisubstituted Aniline on Halogeno Nitro Phenyl or Pyridine Derivative 1.2.1.1. Method B1: $S_NAr$ of Disubstituted Amino Benzoate on Halogeno Nitro Phenyl Derivative A solution of methyl 4-amino-2,6-dimethoxy-benzoate (1 eq.) and 4-bromo-1-fluoro-2-nitro-benzene (1 eq.) in THF is cooled at 0° C. under N$_2$. LiHMDS (1 M solution in THF, 2.3 eq.) is then added dropwise over 2 h. The reaction is quenched with water. THF is evaporated, and the rest of the reaction mixture is left stirred at 3° C. overnight. To the reaction mixture 2 M HCl is added slowly while rapidly stirred and the mixture is stirred for 1 h at 3° C. The precipitate is filtered off then dried in a vacuum oven at 45° C. and 20 mbar for 5 h to afford the expected intermediate.

Illustrative Synthesis of Int 59

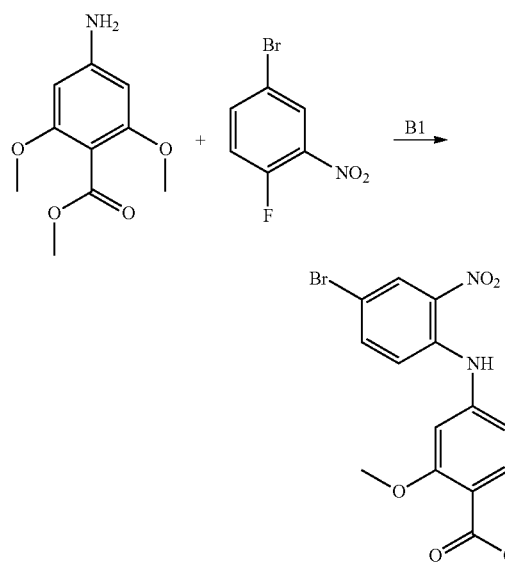

A solution of methyl 4-amino-2,6-dimethoxy-benzoate (40 g, 189.4 mmol, 1 eq.) and 4-bromo-1-fluoro-2-nitro-benzene (23.3 mL, 189.4 mmol, 1 eq.) in THF (1000 mL) is cooled at 0° C. under N$_2$. LiHMDS (1 M solution in THF, 435.6 mL, 435.6 mmol, 2.3 eq.) is then added dropwise over 2 h. The reaction is quenched with water (800 mL). THF is evaporated, and the rest of the reaction mixture is left stirred at 3° C. overnight. To the reaction mixture 2 M HCl (600 mL) is added slowly while rapidly stirred and the mixture is stirred for 1 h at 3° C. The precipitate is filtered off then dried in a vacuum oven at 45° C. and 20 mbar for 5 h to afford the expected compound.

1.2.1.2. Method B2: S$_N$Ar of Disubstituted Amino Benzamide on Halogeno Nitro Phenyl Derivative

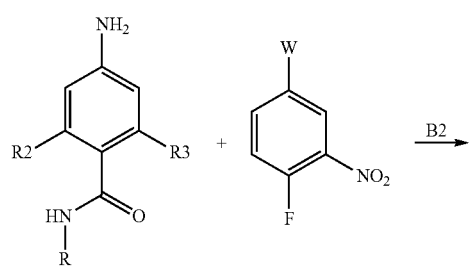

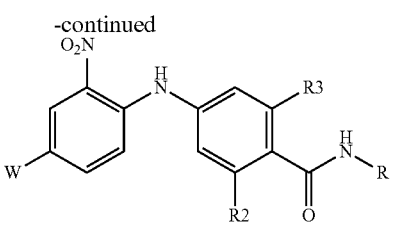

To a solution of disubstituted amino benzamide (1 to 1.1 eq.) in anhydrous THF or DMF (DMF used for case of CN substituent), placed under argon atmosphere is added fluoro nitro derivative (1 to 1.7 eq.). The mixture is cooled at 0° C. and NaH (3 eq.) is added portionwise. The mixture is stirred at 0° C. for 10 min then at RT overnight or heated to 100° C. for 3 h (when W=—CN). The mixture is cooled to 0° C., quenched with water or a saturated NH$_4$Cl solution, diluted with EtOAc or DCM and water, a saturated NH$_4$Cl solution or brine, extracted with EtOAc or DCM. The combined organic layers are dried or washed with brine then dried (Na$_2$SO$_4$ or MgSO$_4$), filtered and concentrated in vacuo. Purification by flash chromatography on silica gel affords the desired compound Illustrative Synthesis of Int 61

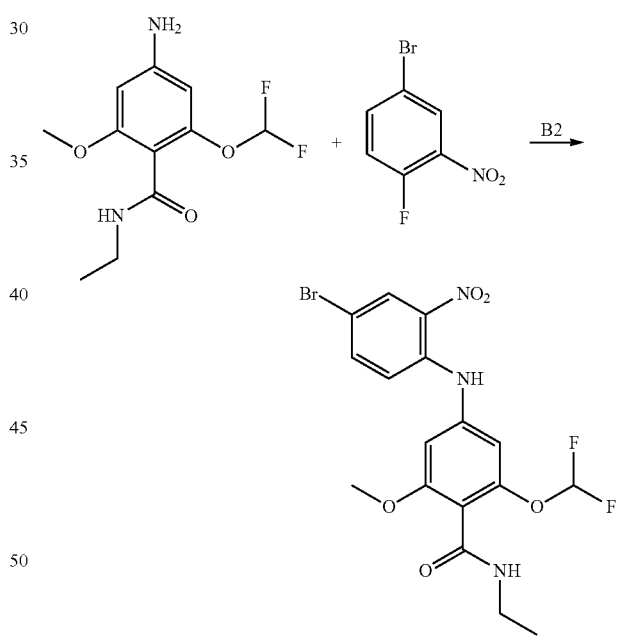

To a solution Int 12 (3.90 g, 14.98 mmol, 1 eq.) in anhydrous THF (30 mL), degassed with N$_2$ then placed under argon atmosphere is added 4-bromo-1-fluoro-2-nitro-benzene (3.95 g, 17.97 mmol, 1.2 eq.). The mixture is cooled at 0° C. and NaH (1.79 g, 44.94 mmol, 3 eq.) is added portionwise. The mixture is warmed to RT and stirred at RT overnight. The mixture is cooled to 0° C., quenched with cold water, diluted with EtOAc, water and a saturated NH$_4$Cl solution, extracted with EtOAc. The combined organic layers are dried, filtered and concentrated in vacuo. The residue is purified by flash chromatography on silica gel (eluting with DCM/MeOH 95/5) to afford the expected product.

Illustrative Synthesis of 4-(4-cyano-2-nitro-anilino)-2-(difluoromethoxy)-N-ethyl-6-methoxy-benzamide

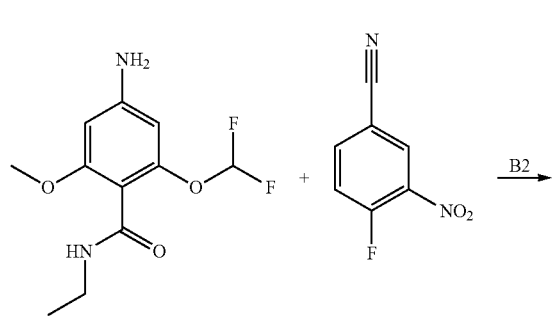

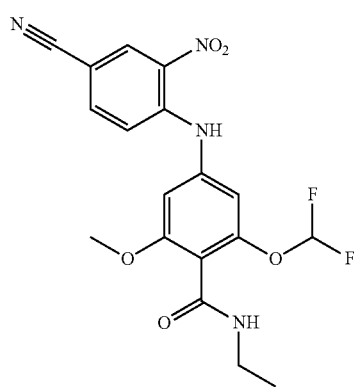

To a stirred solution Int 12 (1.00 g, 3.84 mmol, 1 eq.) and fluoro-nitro derivative (0.79 g, 4.77 mmol, 1.1 eq.) in anhydrous DMF (15 mL) cooled to 0° C. is added NaH (0.46 g, 11.52 mmol, 3 eq.). The mixture is stirred at 0° C. for 1 h, then at RT for 1 h, then at 100° C. for 3 h. The mixture is carefully added to an ice/water mixture. Brine is added and the aqueous layer is extracted with EtOAc The combined organic layers are dried over MgSO$_4$, filtered and concentrated in vacuo. The residue is purified by flash chromatography on silica gel (eluting with DCM/MeOH 100/0 to 98/2) to afford the expected product.

LCMS: MW (calcd): 406.3; m/z MW (obsd): 407.3 (M+H).

1.2.1.3. Method B3: S$_N$Ar of Disubstituted Amino Benzamide or Benzoate on Halogeno Nitro Pyridine Derivative

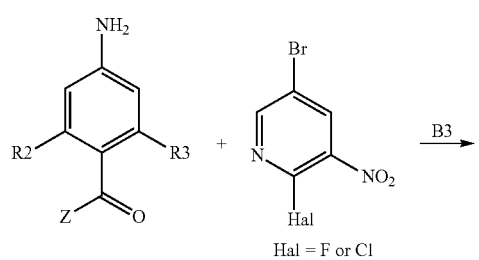

Hal = F or Cl

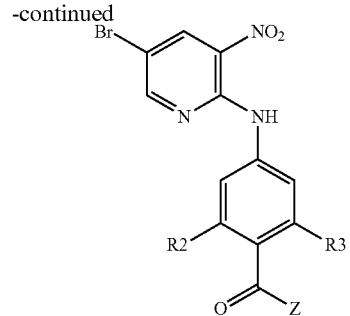

To a room temperature or heated to 80° C. solution of aniline (1 to 1.2 eq.) and Chloro or Fluoro-Nitro pyridine derivative (1 to 1.2 eq.) in anhydrous DMSO or DMF is added Et$_3$N (5 eq.). The mixture is stirred to 80° C. overnight. After cooling to RT, the mixture is concentrated in vacuo (reaction with DMF as solvent only), diluted with EtOAc or DCM, water or NaCl solution, extracted with EtOAc or DCM. The combined organic layers are dried, filtered or dried by filtration over hydrophobic column and concentrated in vacuo. The residue is purified by flash chromatography on silica gel to afford the expected product.

Illustrative Synthesis of Int 73

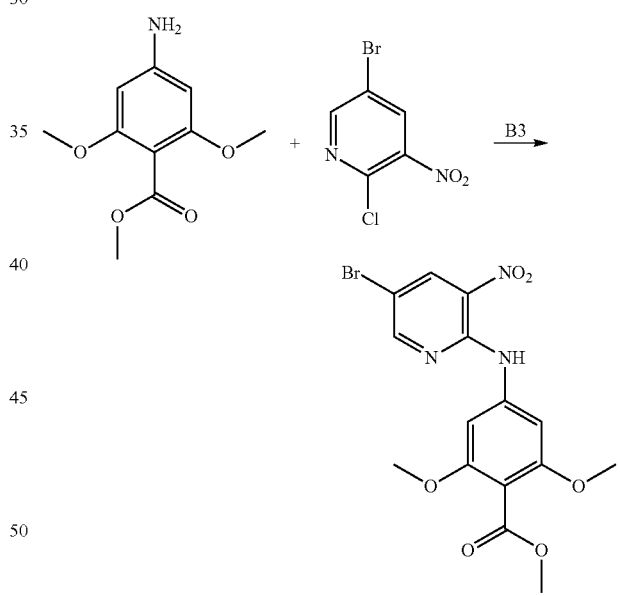

Int-073

To a solution of methyl 4-amino-2,6-dimethoxy-benzoate (232 mg, 1.1 mmol, 1.2 eq.) and 5-bromo-2-chloro-3-nitro-pyridine (250 mg, 0.914 mmol, 1 eq.) in anhydrous DMSO (0.5 mL) stirred to 80° C. for 5 min is added Et$_3$N (0.64 mL, 4.57 mmol, 5 eq.). The mixture is stirred to 80° C. then anhydrous DMSO (1 mL) is added and the mixture is stirred to 80° C. overnight. After cooling to RT, the mixture is diluted with EtOAc, water and brine. The aqueous layer is extracted with EtOAC. The combined organic layers are dried, filtered and concentrated in vacuo. The residue is purified by flash chromatography on silica gel (eluting with heptane/EtOAc 80/20) to afford the expected product.

1.2.2. Method C: Reduction and Cyclisation Process

1.2.2.1. Method C1: SnCl$_2$, 2H$_2$O/SnCl$_2$/Trimethyl Orthoformate

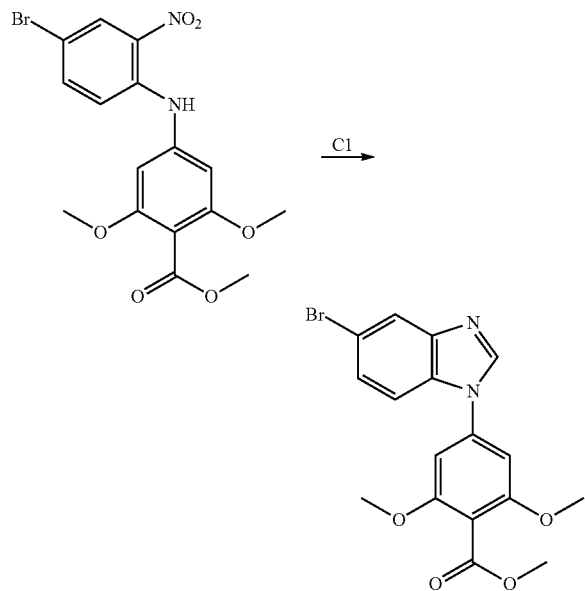

A mixture of nitroaniline derivative (1 eq.), tin(II) chloride dihydrate (2.3 eq.) and tin(II) chloride (1.7 eq.) in EtOH is stirred at reflux for 2 h. After complete reduction to amine showed by UPLC monitoring, trimethyl orthoformate (4 eq.)) is added slowly to the mixture and the stirring continued at reflux for 2 h. The mixture is cooled to RT and concentrated to dryness. The residue is dissolved in EtOAc and washed with 2 M NaOH. The suspension formed (butter of tin) is filtered. The layers are separated. To the organic layer sat. aq. NaHCO$_3$ is added. Again the suspension forms. To the suspension 20% NaOH is added (exothermic). The layers are left to separate overnight. The organic layer is dried over K$_2$CO$_3$ and filtered. All filtration residues are washed with EtOAc, combined with aqueous layers and the layers are separated. The organic layers are combined and concentrated to dryness under reduced pressure. The residue is suspended in Et$_2$O, stirred for 30 min and filtered. The cake is left on the funnel under suction for 20 min to give the expected product.

Illustrative Synthesis of Int 45

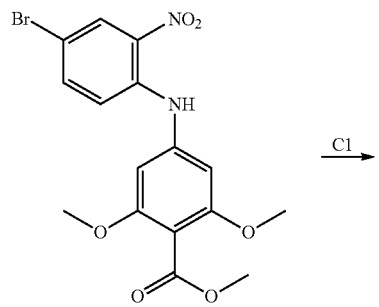

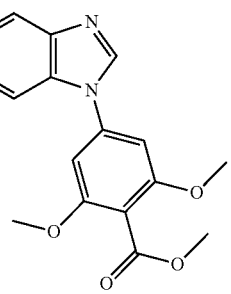

A mixture of Int 59 (148.2 g, 360.4 mmol, 1 eq.), tin(II) chloride dihydrate (188 g, 833.1 mmol, 2.3 eq.) and tin(II) chloride (116.2 g, 612.8 mmol, 1.7 eq.) in EtOH (1800 mL) is stirred at reflux for 2 h. After complete reduction to amine showed by UPLC monitoring, trimethyl orthoformate (157.7 mL, 1441.5 mmol, 4 eq.)) is added slowly to the mixture and the stirring continued at reflux for 2 h. The mixture is cooled to RT and concentrated to dryness. The residue is dissolved in EtOAc (1400 mL) and washed with 2 M NaOH (600 mL). The suspension formed (butter of tin) is filtered (left filtering overnight). The layers are separated. To the organic layer sat. aq. NaHCO$_3$ (1000 mL) is added. Again the suspension forms. To the suspension 20% NaOH (2000 mL) is added (exothermic). The layers are left to separate overnight. The organic layer is dried over K$_2$CO$_3$ and filtered. All filtration residues are washed with EtOAc, combined with aqueous layers and the layers are separated. The organic layers are combined and concentrated to dryness under reduced pressure. The residue is suspended in Et$_2$O (500 mL), stirred for 30 min and filtered. The cake is left on the funnel under suction for 20 min to give the expected product Int 45 (82.1 g).

1.2.2.2. Method C2: Zn/AcOH/HC(OCH3)$_3$

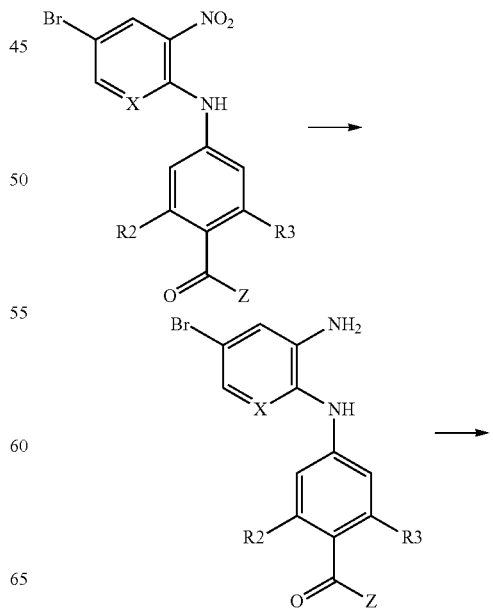

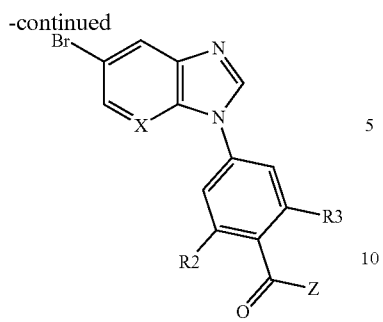

To a solution of nitroamino derivative (1 eq.) in glacial acetic acid stirred at RT or reflux is introduced by portions zinc dust (5 to 11.1 eq.). The resulting mixture is stirred (75° C. or reflux) for 10 min to 1 h. (completion of the reaction is monitored by TLC and/or UPLC-MS)). The reaction mixture is cooled to RT, filtered over Clarcel after dilution in EtOAc or toluene or not diluted, rinsed with EtOAc or toluene or AcOH or EtOAc and toluene. The filtrate is evaporated to dryness and either the diamino derivative is used as such in the next step or the residue is purified by flash chromatography on Biotage® SNAP KP-NH cartridge and used in the next step.

To a solution of diamino derivative (1 eq.) in MeOH is introduced p-Toluenesulfonic acid or p-Toluenesulfonic acid monohydrate (0.2 to 0.6 eq.) or AcOH (0.2 eq.) and trimethyl orthoformate (3 to 5 eq.). The resulting mixture is stirred to 75° C.-reflux (30 min to overnight) and cooled to RT. The reaction mixture is concentrated in vacuo, purified by flash chromatography on silica gel or extracted with water/EtOAc and purified by flash chromatography on silica gel to afford the expected product.

Illustrative Synthesis of Int 42

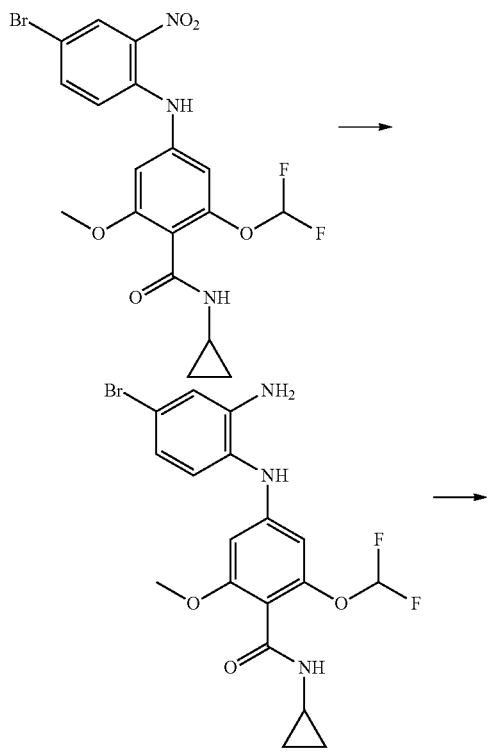

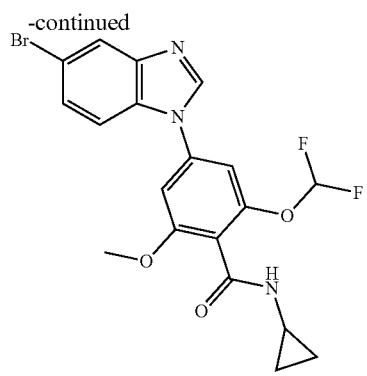

To a solution of Int 60 (313 mg, 0.663 mmol, 1 eq.) in glacial acetic acid stirred to reflux is introduced by portions zinc dust (330 mg, 5.047 mmol, 7.6 eq.). The resulting mixture is stirred to reflux, then zinc dust (150 mg, 2.294 mmol, 3.5 eq.) is added again and the mixture is stirred to reflux (completion monitored by TLC). The reaction mixture is cooled to RT, filtered over Clarcel, rinsed with EtOAc and toluene. The filtrate is concentrated in vacuo and 4-(2-amino-4-bromo-anilino)-N-cyclopropyl-2-(difluoromethoxy)-6-methoxy-benzamide, the o-phenylenediamine derivative is used as such in the next step.

To a solution of o-phenylenediamine derivative (0.663 mmol, 1 eq.) in MeOH (7 mL) is introduced p-toluenesulfonic acid monohydrate (25 mg, 0.133 mmol, 0.2 eq.) and trimethyl orthoformate (218 μL, 1.988 mmol, 3 eq.). The resulting mixture is stirred to 90° C. for 30 min and RT overnight. The reaction mixture is concentrated in vacuo and purified by flash chromatography on silica gel (eluting with DCM/MeOH 100/0 to 90/10) to afford the expected product.

1.2.3. Method E

1.2.3.1. Method E1: Suzuki Reaction Process (3 Steps with Interchangeable Order)

Method E1: Sequence E1.1+E1.2+E1.3

1.2.3.1.1 E1.1: Ester Saponification

A mixture of methyl ester derivative (1 eq.), MeOH/THF mixture or MeOH and 2 M NaOH (2 to 20 eq) or a mixture of methyl ester derivative (1 eq.), MeOH and NaOH pellets (excess) is stirred at 65-90° C. for 5 h to overnight. After cooling to ambient temperature the organic solvents are removed under reduced pressure. The residue is diluted with water, pH is adjusted until acidic pH with HCl (2 N or 6 N). The resulting suspension is filtered, rinsed either with pentane and Et$_2$O or water and dried in a vacuum oven or the suspension is extracted with a CHCl$_3$/n-BuOH mixture (9/1), the combined organic layers are dried, filtered and concentrated in vacuo to afford the expected product.

Illustrative Synthesis of Int 44

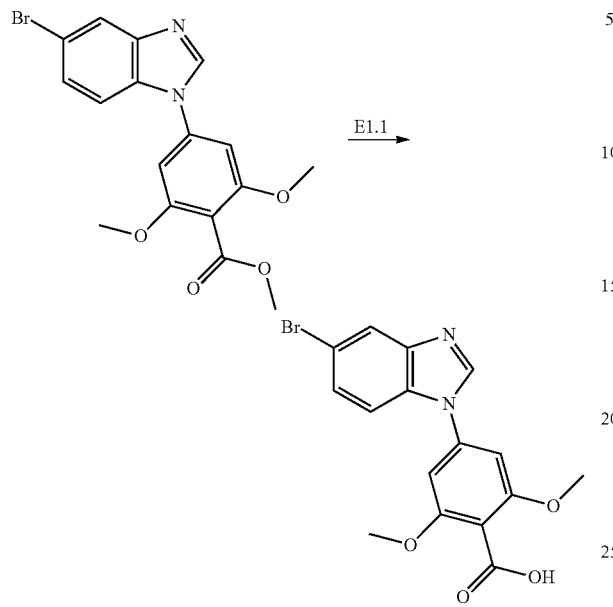

A mixture of methyl 4-(5-bromobenzimidazol-1-yl)-2,6-dimethoxy-benzoate (Int 45) (82.1 g, 209.8 mmol, 1 eq.), MeOH (450 mL), THF (550 mL) and 2 M NaOH (550 mL, 1100 mmol, 5.2 eq.) is stirred at 75° C. overnight. After cooling to ambient temperature the organic solvents are removed under reduced pressure. The residue is diluted with water (800 mL). pH is adjusted from 12.4 to 1.6 with 6 M aq. HCl. The resulting suspension is stirred at 2° C. for 30 min and then filtered. The cake is washed with water (800 mL) and left on the funnel under suction for 20 min to give a dark red solid. The solid is dried in a vacuum oven at 45° C. for 2 h giving 4-(5-bromobenzimidazol-1-yl)-2,6-dimethoxy-benzoic acid in the form of a purple powder.

1.2.3.1.2 E1.2: Peptidic Coupling

A flask is charged with the carboxylic acid derivative (1 eq.), anhydrous DMF, HATU (1.0 to 2 eq.), DIPEA (2 to 10 eq.). The mixture is stirred for 5 to 20 min at RT then the amine or amine hydrochloride (1.2 to 4.8 eq.) is added. The mixture is stirred at RT for 1 h to 96 h. the precipitate is either filtered after addition of water in the mixture and affords the expected amide derivative or the mixture is optionally concentrated in vacuo, water or a saturated NaHCO₃ solution is added followed by extraction with EtOAc, EtOAc/MeOH, EtOAc/i-PrOH, or DCM. The combined organic layers are then either dried over hydrophobic column or washed with HCl 0.1 N then brine or brine only and dried over anhydrous Na₂SO₄ (or MgSO₄), filtered, concentrated in vacuo. The residue is purified by flash chromatography on silica gel or Biotage® SNAP KP-NH cartridge or triturated in ACN or DCM to afford the expected amide derivative. Alternative work-up: the mixture is concentrated in vacuo, purified by flash chromatography on Biotage® SNAP KP-NH cartridge to afford the expected amide derivative.

Illustrative Synthesis of Int 39

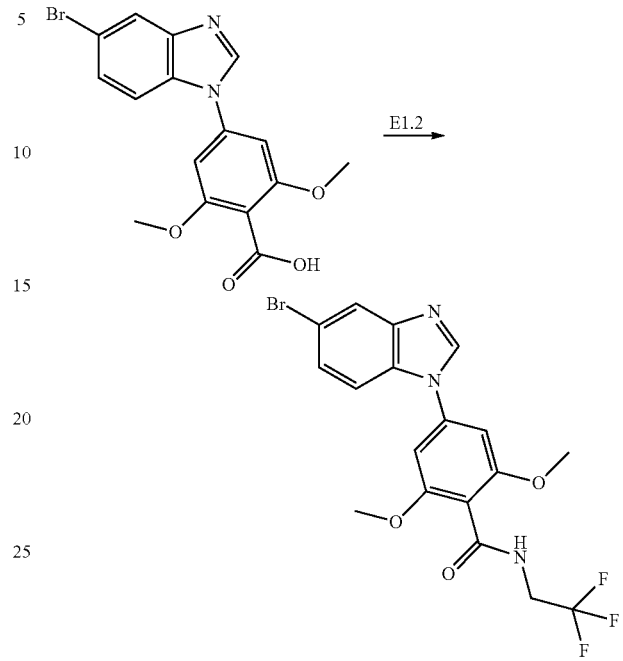

A flask is charged with Int 44 (0.3 g, 0.795 mmol, 1 eq.), HATU (332 mg, 0.874 mmol, 1.1 eq.), anhydrous DMF (9 mL) and DIPEA (0.4 mL, 2.39 mmol, 3 eq.). The mixture is stirred at RT for 10 min then 2,2,2-trifluoroethanamine hydrochloride (216 mg, 1.6 mmol, 2 eq.) is added. The mixture is stirred at RT overnight. After evaporation of the DMF, the residue is partitioned between EtOAc and water. The aqueous layer is extracted with EtOAc. The combined organic layers are dried over anhydrous Na₂SO₄, filtered, concentrated in vacuo and purified by flash chromatography on silica gel (eluting with DCM/MeOH 100/0 to 95/5) to afford Int 39.

1.2.3.1.3 E1.3: Suzuki Reaction

A pressure reactor or an open round bottom flask equipped with a condenser is charged with heteroarylbromide derivative (1 eq.), boronic acid or boronic acid pinacol ester (1.1 to 1.5 eq.), a base (Cs₂CO₃, Na₂CO₃, or KF, 2 to 3 eq.) and dioxane/water solvent mixture: 4/1 or 3/1 or DMF/water solvent mixture: 4/1 or THF/water mixture: 9/1 or DME/water: 10/1). The mixture is either heated to 50° C. or reflux, degassed with N₂ then Pd catalyst (Pd(Ph₃)₄ or Pd(dppf)Cl₂.DCM adduct (0.07 to 0.2 eq.) is added or degassed with N₂ or Ar at RT before addition of the catalyst or the solvent is degassed before being added in the mixture and the catalyst is added at the end. The mixture is stirred to 50° C.-110° C. for 15 min to 20 h. Either the reaction mixture is concentrated in vacuo and the residue is taken up in EtOAc or DCM and water or the reaction mixture is quenched with water or a saturated NaHCO₃ solution. The reaction mixture is then extracted with EtOAc or DCM. The combined organic layers are optionally washed with brine, dried over anhydrous Na₂SO₄ or MgSO₄, filtered, concentrated in vacuo and purified by flash chromatography on silica gel or/and Biotage® SNAP KP-NH cartridge to afford Illustrative Synthesis of Cpd 25

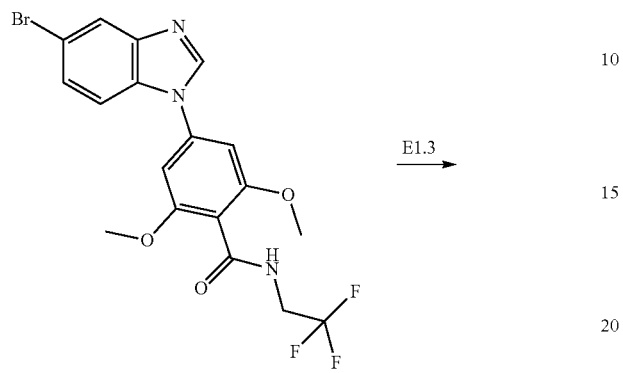

Illustrative Synthesis of Cpd 51

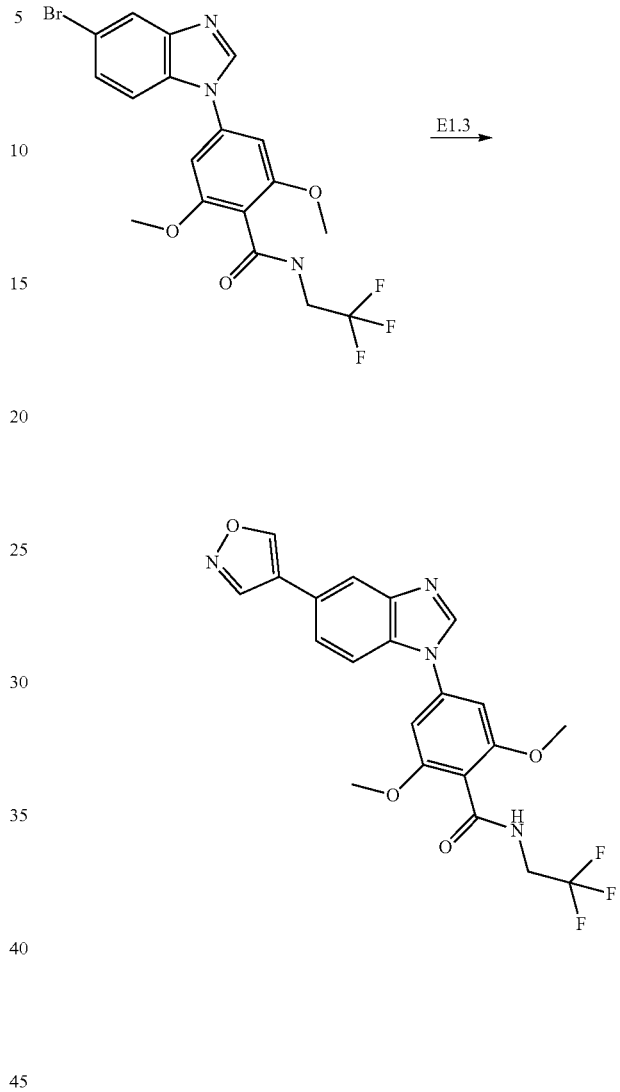

A flask is charged with 4-(5-bromobenzimidazol-1-yl)-2,6-dimethoxy-N-(2,2,2-trifluoroethyl)benzamide, Int 39 (450 mg, 0.982 mmol, 1 eq.), Cs$_2$CO$_3$ (961 mg, 2.95 mmol, 3 eq.) 1-methyl-4-(4,4,5,5-tetramethyl-1,3,2-dioxaborolan-2-yl)pyrazole (CAS #761446-44-0; 306 mg, 1.47 mmol, 1.5 eq.) and dioxane/water solvent mixture: 4/1 (20 mL). The mixture is heated to 100° C., degassed with N$_2$ for 5 min, before Pd(PPh$_3$)$_4$ (173 mg, 0.15 mmol, 0.15 eq.) is added. The mixture is stirred to 100° C. for 2 h. The reaction mixture is concentrated in vacuo. The residue is taken up with in EtOAc and water and the aqueous layer is extracted with EtOAc. The combined organic layers are dried over anhydrous Na$_2$SO$_4$, filtered, concentrated in vacuo and purified by flash chromatography on silica gel (eluting with DCM/MeOH 95/5) to afford the expected compound.

A flask is charged with 4-(5-bromobenzimidazol-1-yl)-2,6-dimethoxy-N-(2,2,2-trifluoroethyl)benzamide (Int 39) (40 mg, 0.09 mmol, 1 eq.), KF (16 mg, 0.27 mmol, 3 eq.), 4-(4,4,5,5-tetramethyl-1,3,2-dioxaborolan-2-yl)isoxazole (CAS #928664-98-6; 26 mg, 0.135 mmol, 1.5 eq.) and DMF/water solvent mixture: 4/1 (2 mL). The mixture is heated to 50° C., degassed with N$_2$ for 3 min, before Pd(dppf)Cl$_2$.DCM (8 mg, 0.009 mmol, 0.1 eq.) is added. The mixture is stirred to 50° C. for 2 h. The mixture is partitioned in EtOAc and water and the aqueous layer is extracted with EtOAc. The combined organic layers are dried over anhydrous Na$_2$SO$_4$, filtered, concentrated in vacuo and purified by flash chromatography on silica gel (eluting with DCM/MeOH 95/5) then preparative HPLC to afford the expected compound.

137
Illustrative Synthesis of Cpd 55

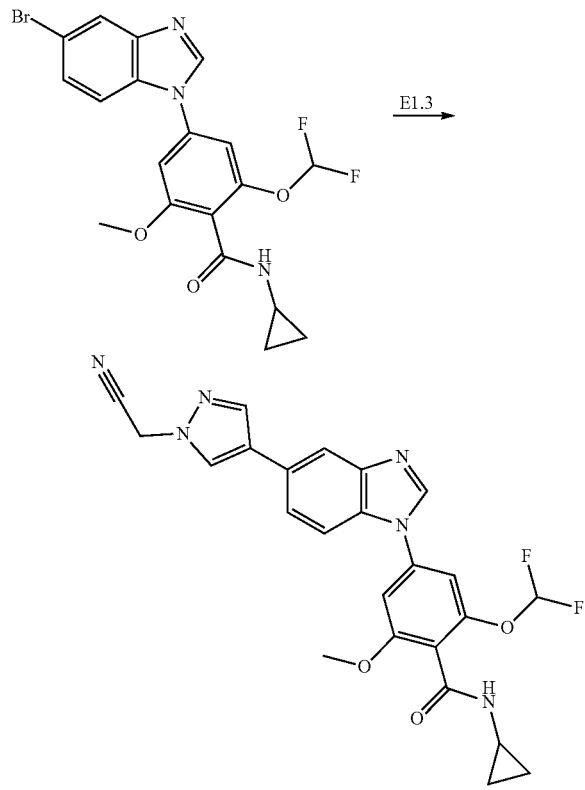

A flask is charged with Int 42 (50 mg, 0.11 mmol, 1 eq.), Cs₂CO₃ (107 mg, 0.33 mmol, 3 eq.) 2-(4-(4,4,5,5-tetramethyl-1,3,2-dioxaborolan-2-yl)-1H-pyrazol-1-yl)acetonitrile (CAS #1093307-35-7; 33 mg, 0.14 mmol, 1.3 eq.) and THF/water solvent mixture: 9/1 (3 mL). The mixture is heated to reflux, degassed with N₂ for 5 min, before Pd(dppf)Cl₂.DCM (9 mg, 0.01 mmol, 0.1 eq.) is added. The mixture is stirred to reflux for 1 h. The mixture is partitioned in DCM and water and the aqueous layer is extracted with DCM. The combined organic layers are dried by filtration over hydrophobic column, concentrated in vacuo and purified by flash chromatography on silica gel (eluting with DCM/MeOH 95/5). A trituration in isopropylic ether and few drops of ACN then filtration affords the expected compound.

Illustrative Synthesis of Cpd 124

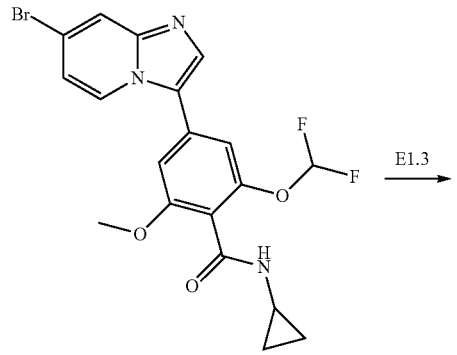

138
-continued

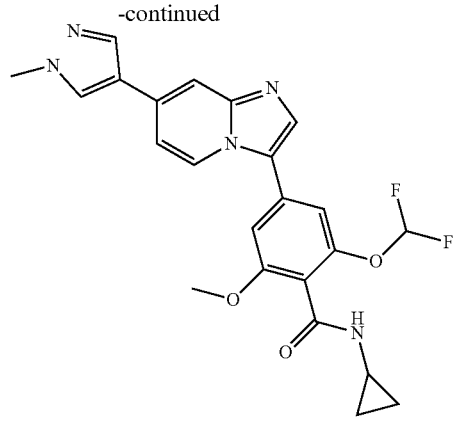

To a previously degassed solution of Int 37 (90 mg, 0.19 mmol, 1 eq.), 1-methyl-4-(4,4,5,5-tetramethyl-1,3,2-dioxaborolan-2-yl)pyrazole (47 mg, 0.23 mmol, 1.2 eq.) are added Cs₂CO₃ (124 mg, 0.38 mmol, 2 eq.) and Pd(dppf)Cl₂.DCM complex (15.5 mg, 0.019 mmol, 0.1 eq.). The solution is stirred to 105-110° C. for 2 h. The reaction mixture is diluted in DCM, washed with water and brine. The organic layer is separated, dried over MgSO₄, filtered, concentrated in vacuo. The residue is purified by flash chromatography on silica gel (eluting with DCM/MeOH 100/0 to 95/5) then triturated in Et₂O and concentrated in vacuo to afford the expected compound.

1.2.3.1.4 E1.3a: Suzuki Reaction Without Water

Illustrative Synthesis of Cpd 284

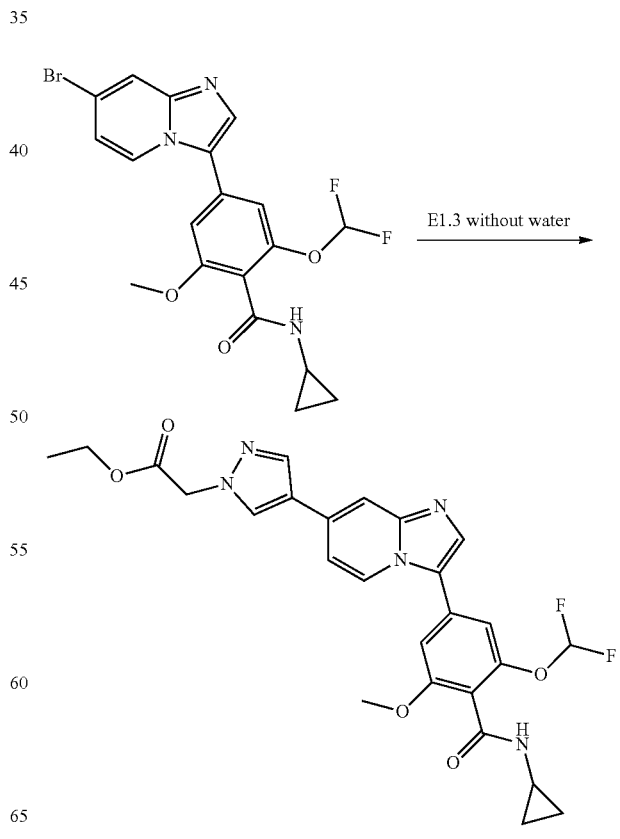

A flask is charged with Int 37 (50 mg, 0.110 mmol, 1 eq.), 1-(ethoxycarbonylmethyl)-1H-pyrazole-4-boronic acid, pinacol ester (CAS #864754-16-5; 34 mg, 0.12 mmol, 1.1 eq.), $Cs_2CO_3$ (72 mg, 0.22 mmol, 2 eq.), dioxane degassed with $N_2$ (1 mL) and Pd(dppf)$Cl_2$.DCM adduct (6.3 mg, 0.008 mmol, 0.07 eq.). The flask is sealed and the mixture is heated to 90° C. for 6.5 h. 1-(ethoxycarbonylmethyl)-1h-pyrazole-4-boronic acid, pinacol ester (CAS #864754-16-5; 10 mg, 0.04 mmol, 0.3 eq.) and Pd(dppf)$Cl_2$.DCM adduct (6.3 mg, 0.008 mmol, 0.07 eq.) are added and the mixture is stirred to 90° C. for 2 h. The solvent is evaporated and the residue is taken up in EtOAc and water, extracted with EtOAc. The combined organic layers are washed with brine, dried over anhydrous $MgSO_4$, filtered, concentrated in vacuo and purified by flash chromatography on silica gel (eluting with heptane/EtOAc 100/0 to 0/100 then EtOAc/MeOH 100/0 to 90/10). After evaporation, ACN is added to the residue and the resulting solid obtained is filtered to afford the expected compound Illustrative Synthesis of Int 3

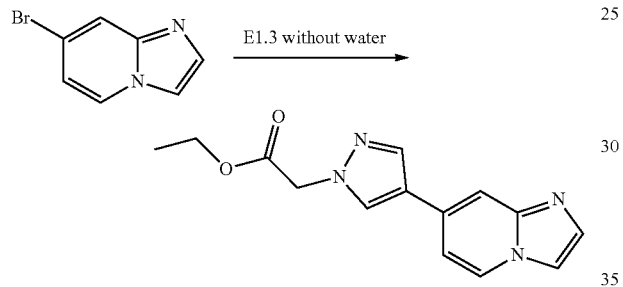

A flask is charged with 7-bromoimidazo[1,2-a]pyridine (476 mg, 2.42 mmol, 1 eq.), dioxane degassed with $N_2$ (15 mL), 1-(Ethoxycarbonylmethyl)-1H-pyrazole-4-boronic acid pinacol ester (CAS #864754-16-5; 745 mg, 2.66 mmol, 1.1 eq.), $Cs_2CO_3$ (1.58 g, 4.84 mmol, 2 eq.) and Pd(dppf)$Cl_2$.DCM adduct (138 mg, 0.17 mmol, 0.07 eq.). The flask is sealed, purged with $N_2$ and the mixture is heated to 90° C. for 3 h. EtOAc, water and brine are added to the mixture, followed by extraction with EtOAc then DCM. The insoluble matter is removed by filtration and the organics layers are separately dried by filtration over hydrophobic column then combined, concentrated in vacuo and purified by flash chromatography on silica gel (eluting with heptane/EtOAc 100/0 to 0/100 then DCM/MeOH 100/0 to 90/10) to afford the expected product.

1.2.3.1.5 E1.3b: Suzuki Reaction with Nitrile Hydrolysis

General method: A flask is charged with appropriate intermediate (1 eq.) and dioxane/water solvent mixture 4/1. The mixture is degassed with $N_2$ then boronic ester (1.2 to 1.5 eq.), $Cs_2CO_3$ (2 eq.), and Pd catalyst (Pd(dppf)$Cl_2$.DCM 0.1 eq., or Pd(PPh$_3$)$_4$ 0.15 eq.) are added. The flask is sealed and the mixture is heated to 90° C.-100° C. for 1 h-1.5 h. The reaction mixture is quenched with water or a saturated $NaHCO_3$ solution, extracted with EtOAc or DCM. The combined organic layers are dried over anhydrous $Na_2SO_4$, filtered or washed with brine and dried by filtration over hydrophobic column then concentrated in vacuo, purified by flash chromatography on silica gel and optionally dissolved in DCM and submitted to SPM32 3-mercaptopropyl ethyl sulfide silica treatment to afford the expected compound.

Illustrative Synthesis of Cpd 259 and Cpd 258

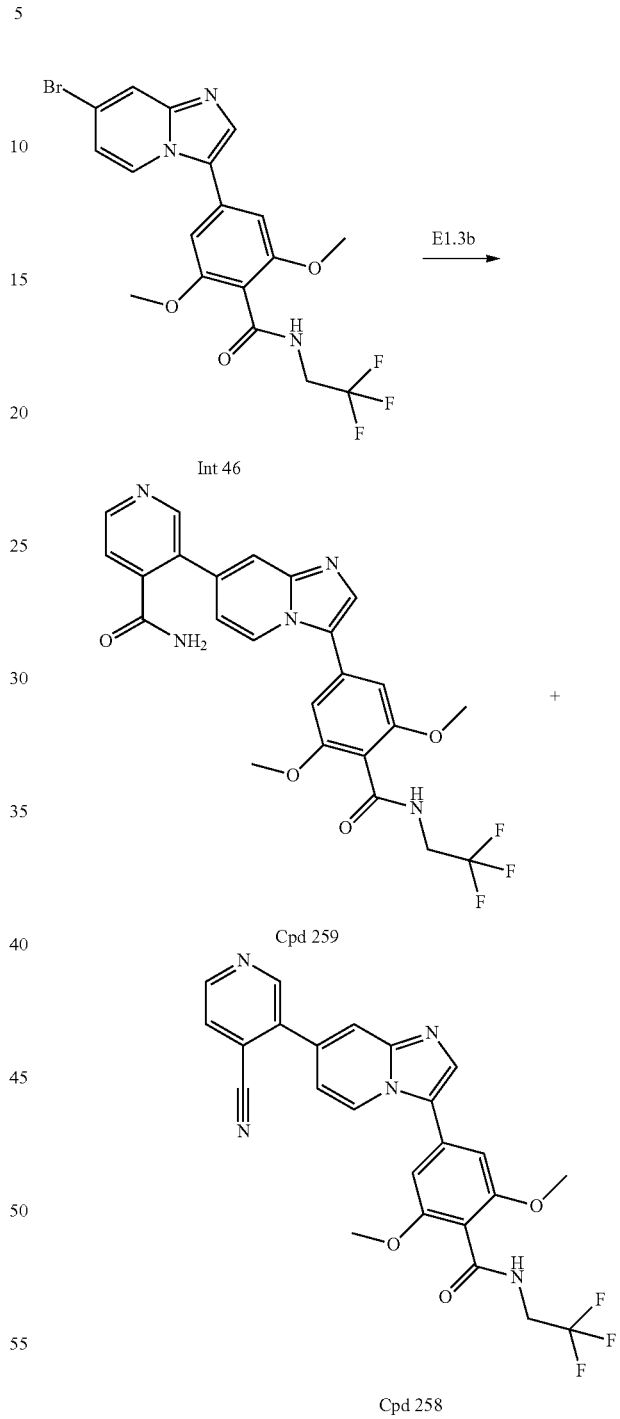

A flask is charged with Int 46 (50 mg, 0.110 mmol, 1 eq.), dioxane/water solvent mixture degassed with $N_2$: 4/1 (1 mL), 3-(4,4,5,5-tetramethyl-1,3,2-dioxaborolan-2-yl)pyridine-4-carbonitrile (CAS #878194-91-3; 38 mg, 0.164 mmol, 1.5 eq.), $Cs_2CO_3$ (83 mg, 0.218 mmol, 2 eq.) and Pd(dppf)$Cl_2$.DCM (9 mg, 0.011 mmol, 0.1 eq.). The flask is sealed and the mixture is heated to 90° C. for 1 h. The reaction mixture is quenched with water, extracted with EtOAc. The combined organic layers are dried over anhydrous Na$_2$SO$_4$, filtered, concentrated in vacuo and purified by flash chromatography on silica gel (eluting with DCM/MeOH 99/1 to 97/3) to afford the expected nitrile compound (Cpd 258) LCMS: MW (calcd): 481.4; m/z MW (obsd): 482.0 (M+H). The elution is pursued from 97/3 to 90/10 to afford the expected carboxamide compound (Cpd 259).

LCMS: MW (calcd): 499.4; m/z MW (obsd): 500.2 (M+H)

1.2.3.1.6 E1.3c: Suzuki Reaction with Ester Cleavage

Illustrative Synthesis of Cpd 255

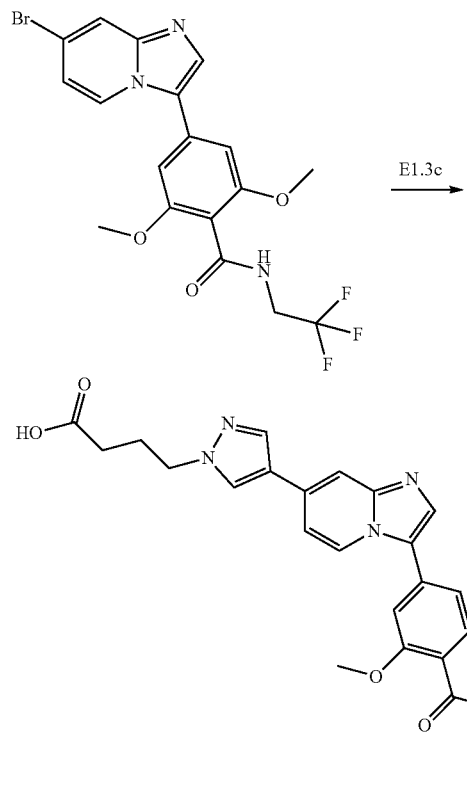

A flask is charged with Int 46 (100 mg, 0.218 mmol, 1 eq.), Cs$_2$CO$_3$ (142 mg, 0.44 mmol, 2 eq.), methyl 4-[4-(4,4,5,5-tetramethyl-1,3,2-dioxaborolan-2-yl)pyrazol-1-yl]butanoate (Int 72) (71 mg, 0.24 mmol, 1.1 eq.) and dioxane/water solvent mixture degassed with N$_2$: 4/1 (4 mL). Pd(dppf)Cl$_2$.DCM (12 mg, 0.015 mmol, 0.07 eq.) is added before the flask is sealed and the mixture is heated to 90° C. for 2 h then to 50° C. overnight. 1 mL of water is added and the mixture is stirred to 90° C. for 4 h. The mixture is concentrated in vacuo and the residue is partitioned between Et$_2$O and water. The organic layer is extracted with water. The combined aqueous layers are acidified to pH 5-6 with HCl 2 N and extracted with EtOAc. The combined organic layers are washed with brine, dried over anhydrous MgSO$_4$, filtered, concentrated in vacuo and purified by flash chromatography on silica gel (eluting with DCM/MeOH 100/0 to 90/10). The precipitate formed during evaporation of the fractions is filtered, rinsed with Et$_2$O to afford the expected compound.

1.2.3.2. Method E1: Sequence E1.1+E1.3+E1.2

1.2.3.2.1 E1.1: Ester Saponification

Cf. E1.1 of Sequence E1.1+E1.2+E1.3

1.2.3.2.2 E1.3: Suzuki Coupling

A flask is charged with the appropriate intermediate (1 eq.), boronic ester (1.3 eq.), Cs$_2$CO$_3$ (3 eq.) and dioxane/water solvent mixture: 4/1. The mixture is degassed with N$_2$ before Pd(PPh$_3$)$_4$ (0.15 eq.) is added. The mixture is stirred to reflux for 2 h then concentrated in vacuo, diluted with EtOAc and water, basified to pH 9-10 with NaOH (2 N). The aqueous phase is separated, acidified to pH 2-3 with HCl (1 N), then a chloroform/n-BuOH mixture: 4/1 is added. The solid formed is filtered, solubilized in DCM/MeOH mixture: 50/50. The solution is dried, filtered, concentrated in vacuo. A trituration in isopropylic ether and ACN, then concentration in vacuo affords the expected compound.

Illustrative Synthesis of Int 50

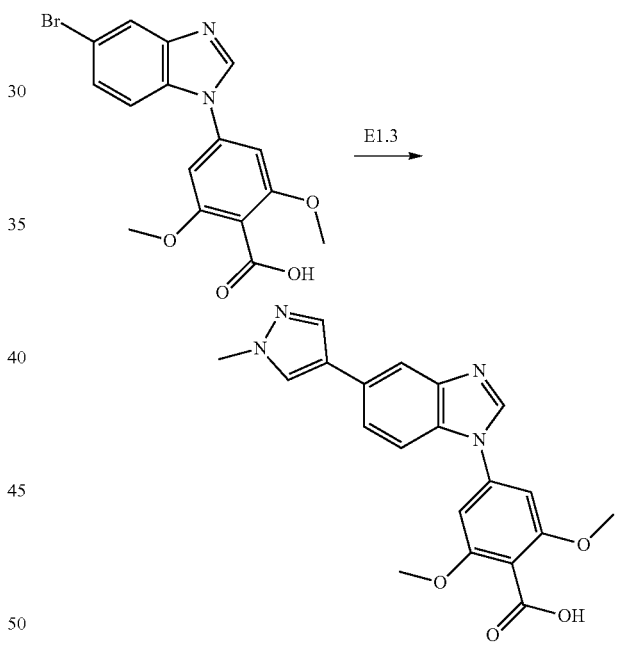

A flask is charged with Int 44 (2.5 g, 6.62 mmol, 1 eq.), 1-methyl-4-(4,4,5,5-tetramethyl-1,3,2-dioxaborolan-2-yl)pyrazole (CAS #761446-44-0; 1.79 g, 8.61 mmol, 1.3 eq.), Cs$_2$CO$_3$ (6.5 g, 19.9 mmol, 3 eq.) and dioxane/water solvent mixture: 4/1 (100 mL). The mixture is degassed with N$_2$ before Pd(PPh$_3$)$_4$ (1.14 g, 0.99 mmol, 0.15 eq.) is added. The mixture is stirred to reflux for 2 h then concentrated in vacuo, diluted with EtOAc and water, basified to pH 9-10 with NaOH (2 N). The aqueous phase is separated, acidified to pH 2-3 with HCl (1 N), then a CHCl$_3$/n-BuOH 4/1 mixture is added. The solid formed is filtered, solubilized in DCM/MeOH mixture: 50/50. The solution is dried, filtered, concentrated in vacuo. A trituration in isopropylic ether and ACN, then concentration in vacuo affords the expected compound.

1.2.3.2.3 E1.2: Peptidic Coupling

A flask is charged with the carboxylic acid derivative (1 eq.), HATU (1.1 to 1.2 eq.), anhydrous DMF or DMSO and DIPEA (3 eq.). The mixture is stirred at RT for 5 min then the amine (3 eq.) is added. The mixture is stirred at RT for 1 h to overnight. The mixture is either purified by preparative LCMS (reaction in DMSO and DMF as solvent) to afford the desired amide or concentrated in vacuo, taken up in EtOAc and water, extracted with EtOAc (reaction in DMF) or diluted in DCM or EtOAc, washed with water and/or brine (reaction in DMF). The combined organic layers are then dried and filtered or dried by filtration on hydrophobic column, concentrated in vacuo and purified by flash chromatography on silica gel to afford the desired amide.

Illustrative Synthesis of Cpd 86

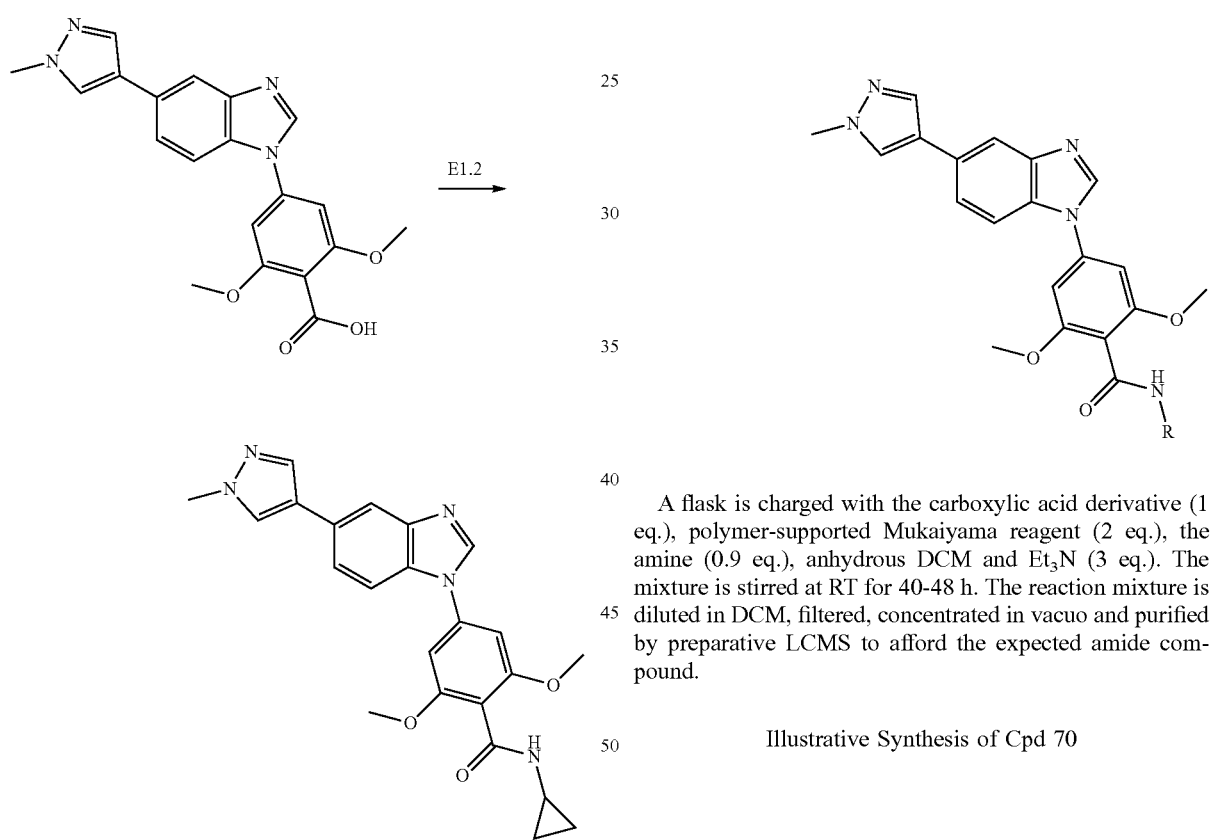

A flask is charged with Int 50 (1.4 g, 3.69 mmol, 1 eq.), HATU (1.54 g, 4.06 mmol, 1.1 eq.), anhydrous DMF (4 mL) and DIPEA (1.92 mL, 11.07 mmol, 3 eq.). The mixture is stirred at RT for 5 min then cyclopropylamine (freebase) (632 mg, 11.07 mmol, 3 eq.) is added. The mixture is stirred at RT for 2 h. The mixture is concentrated in vacuo, the residue is taken up in EtOAc, washed with water then brine. The aqueous layer is extracted with EtOAc. The combined organic layers are dried, filtered, concentrated in vacuo and purified by flash chromatography on silica gel (eluting with DCM/MeOH 100/0 to 95/5) to afford the expected amide derivative.

1.2.3.2.4 E1.2 with Polymer-Supported Mukaiyama Reagent

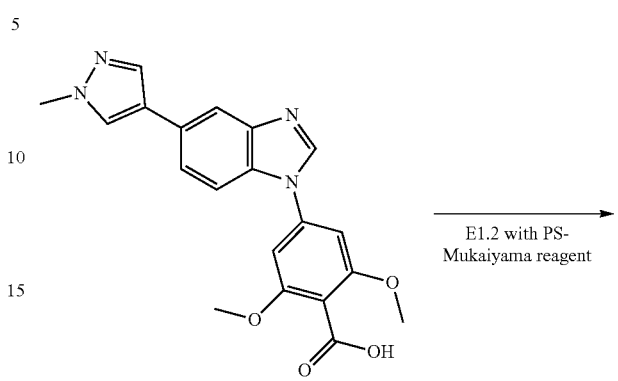

A flask is charged with the carboxylic acid derivative (1 eq.), polymer-supported Mukaiyama reagent (2 eq.), the amine (0.9 eq.), anhydrous DCM and Et$_3$N (3 eq.). The mixture is stirred at RT for 40-48 h. The reaction mixture is diluted in DCM, filtered, concentrated in vacuo and purified by preparative LCMS to afford the expected amide compound.

Illustrative Synthesis of Cpd 70

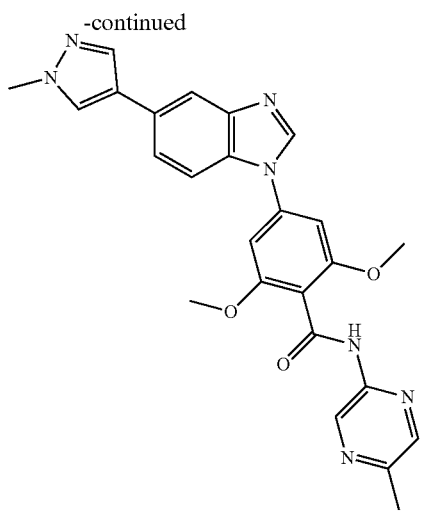

A flask is charged with Int 50 (50 mg, 0.131 mmol, 1 eq.), PS-Mukaiyama reagent (Aldrich, Cat #657182; 223 mg, 1.7-2.5 eq.), 5-methylpyrazin-2-amine (CAS #5521-58-4; 13 mg, 0.118 mmol, 0.9 eq.), Et₃N (55 µL, 0.393 mmol, 3 eq.) and anhydrous DCM (3 mL). The mixture is stirred at RT for 40 h. The reaction mixture is diluted in DCM, filtered, concentrated in vacuo and purified by preparative LCMS to afford the expected amide compound.

1.2.3.3. Method E1: Sequence E1.3+E1.1+E1.2

1.2.3.3.1 E1.3: Suzuki Coupling

Cf. E1.3 of Sequence E1.1+E1.2+E1.3

Illustrative Synthesis of Int 51

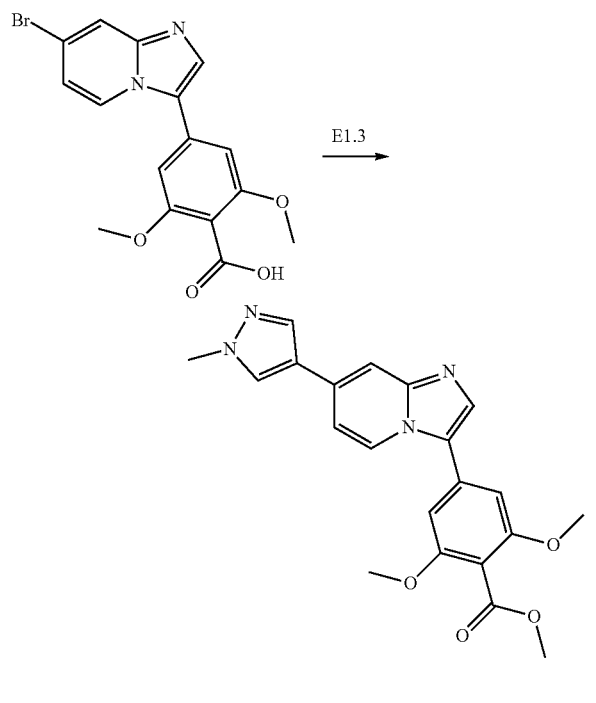

A flask is charged with Int 35 (2.26 g, 0.006 mol., 1 eq.), dioxane/water solvent mixture: 4/1 (25 mL), 1-methyl-4-(4,5,5-tetramethyl-1,3,2-dioxaborolan-2-yl)pyrazole (CAS #761446-44-0; 1.44 g, 0.007 mol., 1.2 eq.), Cs₂CO₃ (3.76 g, 0.012 mol., 2 eq.) and Pd(dppf)Cl₂.DCM (0.47 g, 0.001 mol., 0.1 eq.). The mixture is stirred to 80° C. for 3 h then quenched with water. DCM and a saturated NaHCO₃ solution are added, the aqueous layer is extracted with DCM. The combined organic layers are washed with a saturated NaHCO₃ solution then brine, dried over anhydrous Na₂SO₄, filtered, concentrated in vacuo and purified by flash chromatography on silica gel (eluting with DCM/MeOH 100/0 to 91/9).

Illustrative Synthesis of Int 27

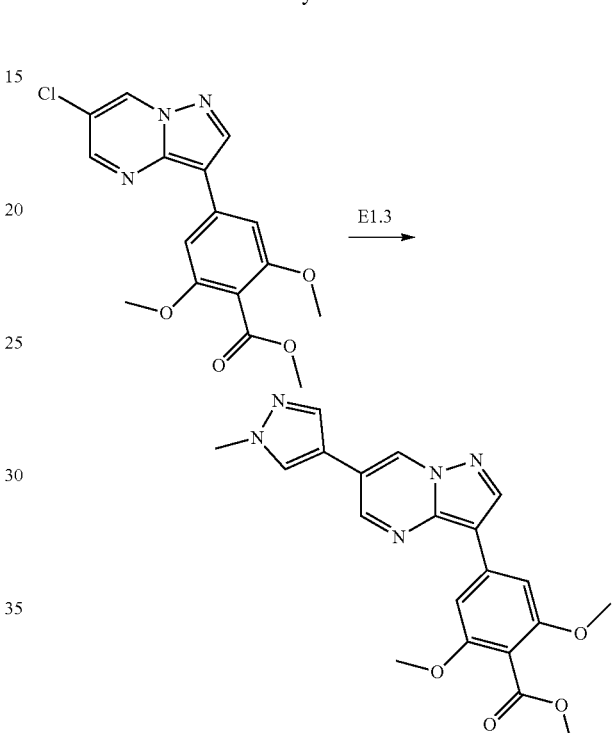

A flask is charged with Int 26 (99 mg, 0.285 mmol, 1 eq.), dioxane/water solvent mixture: 4/1 (25 mL), N₂ is bubbled, 1-methyl-4-(4,4,5,5-tetramethyl-1,3,2-dioxaborolan-2-yl)pyrazole (CAS #761446-44-0; 71 mg, 0.342 mmol, 1.2 eq.), Cs₂CO₃ (186 mg, 0.570 mol., 2 eq.) and Pd(PPh₃)₄ (49 mg, 0.043 mmol, 0.15 eq.) are then added. The mixture is stirred at 100° C. for 3 h then at RT overnight, quenched with a saturated NaHCO₃ solution, extracted with DCM. The combined organic layers are washed with brine, dried over hydrophobic column, concentrated in vacuo and purified by flash chromatography on silica gel (eluting with DCM/MeOH 100/0 to 96/4) to afford the desired intermediate.

1.2.3.3.2 Method E1.3 for Trisubstituted Benzoate or Benzamide Introduction

Illustrative Synthesis of Int 37

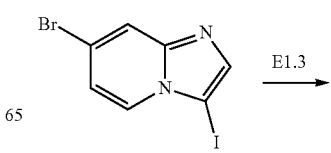

-continued

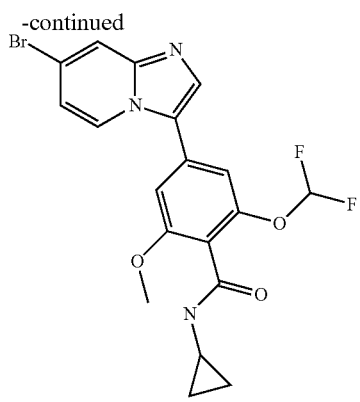

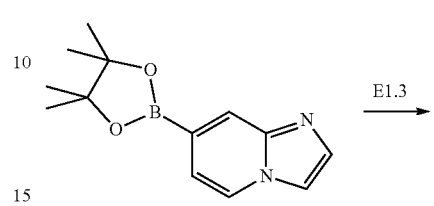

is filtered and the solid is washed with MTBE then dried in vacuo to afford the expected intermediate.

Illustrative Synthesis of Int 2

A flask is charged with 7-bromo-3-iodo-imidazo[1,2-a]pyridine (2 g, 6.19 mmol, 1 eq.), N-cyclopropyl-2-(difluoromethoxy)-6-methoxy-4-(4,4,5,5-tetramethyl-1,3,2-dioxaborolan-2-yl)benzamide (2.37 g, 6.19 mmol, 1 eq.) (Int 17), Cs$_2$CO$_3$ (4.04 g, 12.39 mmol, 2 eq.) and degassed with N$_2$ dioxane/water solvent mixture: 4/1 (70 mL). Pd(PPh$_3$)$_4$ (537 mg, 0.46 mmol, 0.075 eq.) is added and the system is purged with N$_2$ then the mixture is stirred to 90° C. for 20 h. Dioxane is evaporated, water is added and the mixture is extracted with EtOAc or DCM. The combined organic layers are washed with water and brine, dried over anhydrous MgSO$_4$, filtered and concentrated in vacuo until about 100 mL of EtOAc left when a solid precipitates. The solid is filtered, rinsed with EtOAc then Et$_2$O to afford the expected bromoderivative.

1.2.3.3.3 Method E1.3 for Introduction of Heteroaryl

Illustrative Synthesis of Int 1

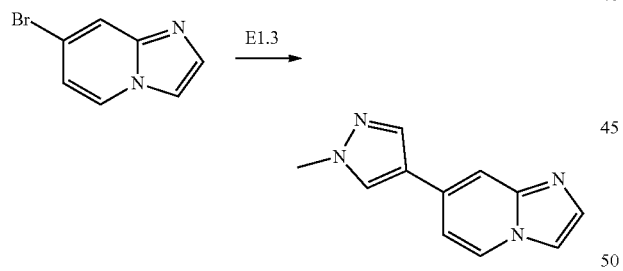

7-bromoimidazo[1,2-a]pyridine (100 g, 507.54 mmol, 1 eq.), 1-methyl-4-(4,4,5,5-tetramethyl-1,3,2-dioxaborolan-2-yl)pyrazole (CAS #761446-44-0; 116.18 g, 558.29 mmol, 1.1 eq.), Na$_2$CO$_3$ (161.37 g, 1522.61 mmol, 3 eq.) are added to a dioxane/water solvent mixture: 3/1 (1 L). The mixture is degassed with N$_2$, then Pd(dppf)Cl$_2$.DCM adduct (2.07 g, 2.54 mmol, 0.005 eq.) is added and the mixture is stirred to 100° C. for 6 h. The mixture is cooled to RT, filtered over Celite®, rinsed with DCM and the filtrate is concentrated in vacuo. The residue is dissolved in DCM/n-BuOH mixture (9/1, 1 L) and water (1 L) is added. The organic layer is separated and the aqueous layer is extracted with DCM (1 L) then DCM/n-BuOH mixture (9/1, 0.5 L). The combined organic layer is washed with brine (0.5 L), dried over anhydrous Na$_2$SO$_4$, filtered and concentrated in vacuo. The residue is triturated in MTBE (0.3 L) at RT, the suspension In a sealed tube is charged with 7-(4,4,5,5-tetramethyl-1,3,2-dioxaboroan-2-yl)imidazo[1,2-a]pyridine (CAS #908268-52-0; 0.5 g, 2.05 mmol, 1 eq.), 3-chloro 6-methyl pyridazine (CAS #1121-79-5; 316 mg, 2.46 mmol, 1.2 eq.), Cs$_2$CO$_3$ (1.34 g, 4.10 mmol, 2 eq.), Pd(dppf)Cl$_2$.DCM (167 mg, 0.20 mmol, 0.1 eq.) and degassed with N$_2$ dioxane/water solvent mixture: 4/1 (10 mL). The system is purged with N$_2$ then the mixture is stirred to 90° C. for 1 h. The reaction mixture is cooled down to RT, diluted in EtOAc, filtered over Celite. The filtrate is concentrated in vacuo and used in the next step without further purification.

1.2.3.3.4 E1.1: Saponfication of Ester cf. E1.1 of Sequence E1.1+E1.2+E1.3

Illustrative Synthesis of Int 52

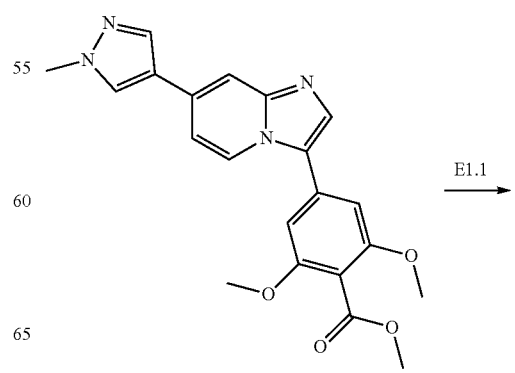

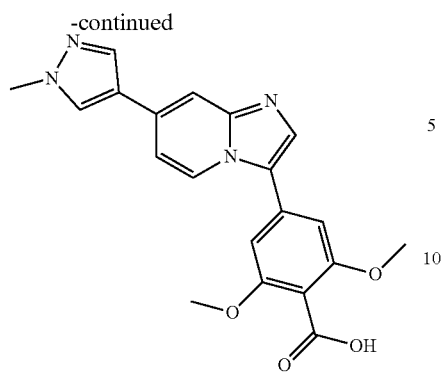

A mixture of Int 51 (1.92 g, 0.005 mol., 1 eq.), MeOH (10 mL), THF (10 mL) and 2 M NaOH (15 mL, 0.029 mol. 6 eq.) is stirred at 70° C. for 18 h. After cooling to ambient temperature the organic solvents are removed under reduced pressure. HCl 2 N is added to the residue, followed by water and ACN, the suspension is triturated, filtered, rinsed with water, then ACN then ACN/DCM mixture to afford Int 52.

Illustrative Synthesis of 2,6-dimethoxy-4-[7-(1-methylimidazol-4-yl)imidazo[1,2-a]pyridin-3-yl] benzoic Acid

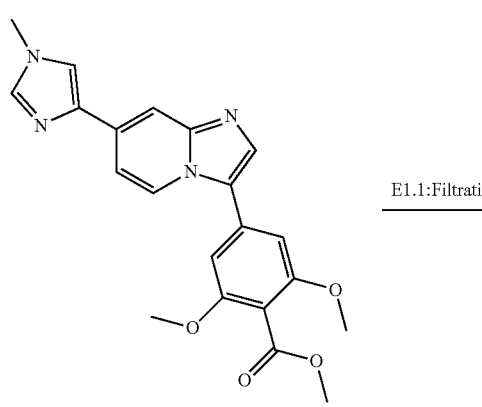

A mixture of methyl 2,6-dimethoxy-4-[7-(1-methylimidazol-4-yl)imidazo[1,2-a]pyridin-3-yl]benzoate (116 mg, 0.296 mmol, 1 eq.), MeOH (5 mL), THF (5 mL) and 2 M NaOH (0.89 mL, 1.774 mmol, 6 eq.) is stirred at 70° C. for 16 h. Then 2 M NaOH (45 μL, 0.090 mmol, 0.3 eq.) is added and the mixture is stirred at 90° C. for 4 h, then RT for 48 h. After cooling to ambient temperature the organic solvents are removed under reduced pressure and HCl 2 N is added to the residue, followed by water. The mixture is concentrated in vacuo, taken up in DCM and small amount of MeOH, filtered. The filtrate is concentrated in vacuo to afford the carboxylic acid compound.

LCMS: MW (calcd): 378.4; m/z MW (obsd): 379.3 (M+H).

Illustrative Synthesis of Int 28

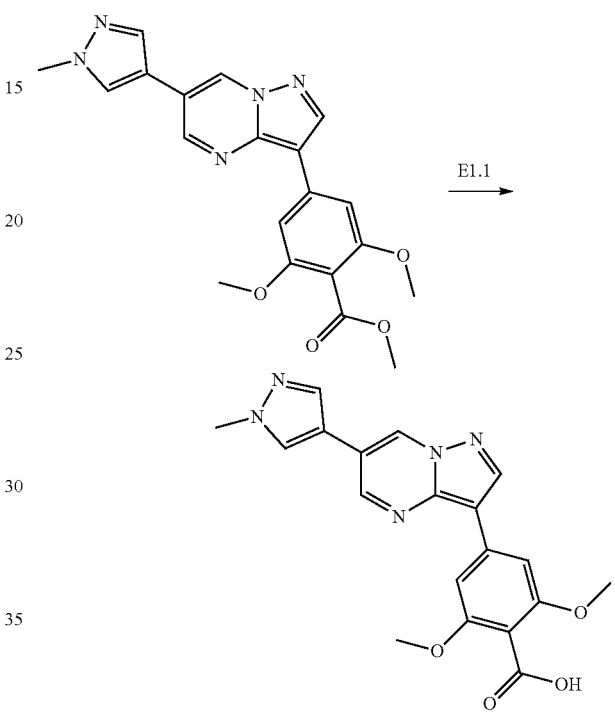

A mixture of Int 27 (43 mg, 0.109 mmol, 1 eq.), MeOH (4 mL), THF (2 mL) and 2 M NaOH (2 mL, 1.088 mmol, 10 eq.) is stirred at 70° C. for 3.5 h, then at 90° C. for 3 h. then RT overnight. The mixture is taken up in DCM and water. The aqueous layer is washed with DCM, then acidified with HCl 2 N and extracted with DCM. The combined organic layers are dried over hydrophobic column and concentrated to afford the carboxylic acid compound.

Illustrative Synthesis of 2-chloro-6-methoxy-4-[7-(1-methylpyrazol-4-yl)imidazo[1,2-a]pyridin-3-yl] benzoic Acid

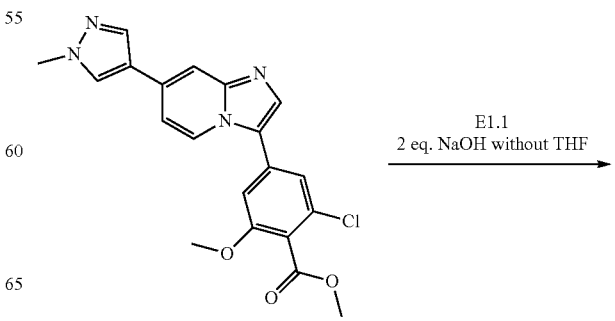

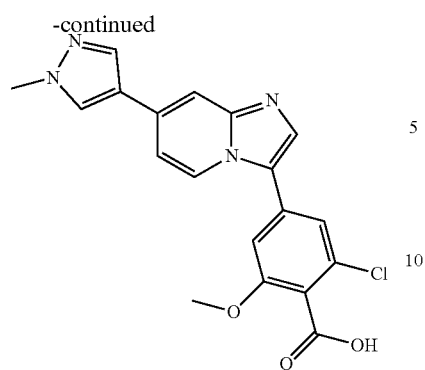

A mixture of methyl 2-chloro-6-methoxy-4-[7-(1-methylpyrazol-4-yl)imidazo[1,2-a]pyridin-3-yl]benzoate (80 mg, 0.20 mmol, 1 eq.), MeOH (2 mL) and 2 N NaOH (200 μL, 0.40 mmol, 2 eq.) is stirred to reflux for 48 h. After cooling to RT, the organic solvents are removed under reduced pressure. The residue is diluted with water. pH is adjusted to 6 with 2 N aq. HCl. The resulting suspension is filtered and dried in vacuo to afford the carboxylic acid derivative.

LCMS: MW (calcd): 382.8; m/z MW (obsd): 383.3-385.2 (M+H).

Illustrative Synthesis of 4-[6-(1-ethylpyrazol-4-yl)imidazo[4,5-b]pyridin-3-yl]-2,6-dimethoxy-benzoic Acid

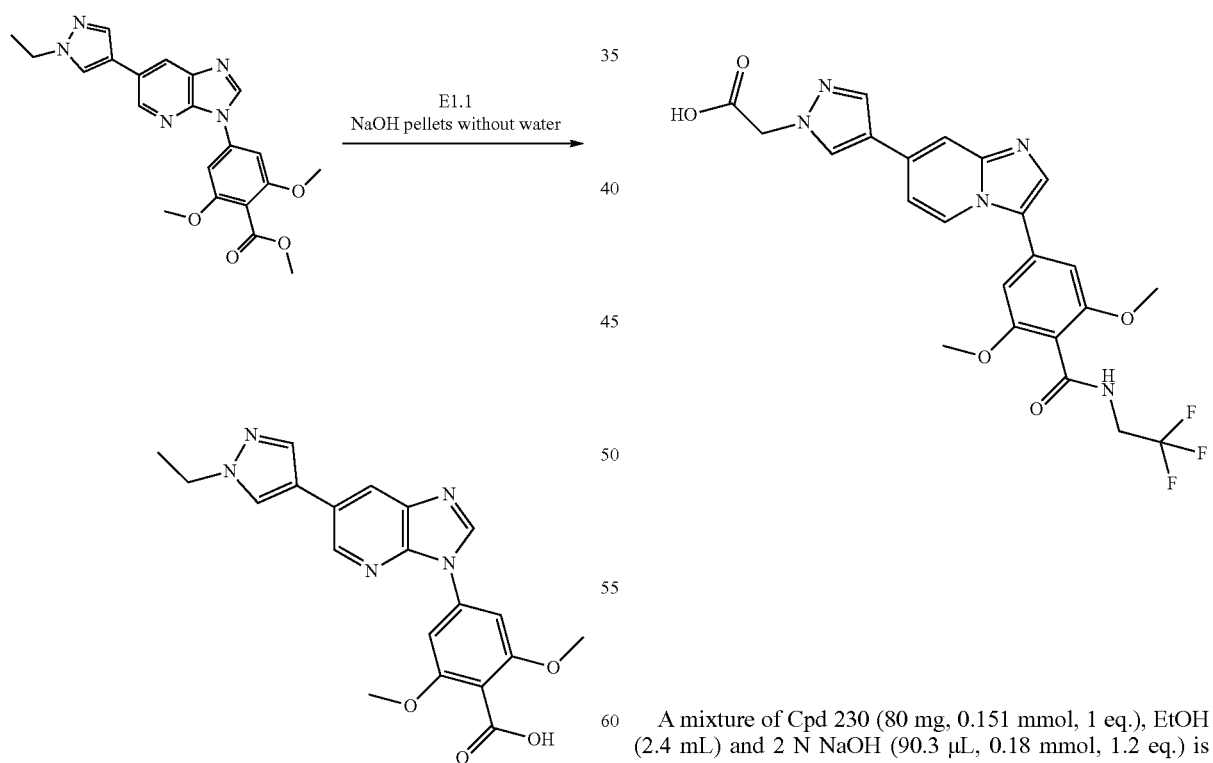

A mixture of methyl 4-[6-(1-ethylpyrazol-4-yl)imidazo[4,5-b]pyridin-3-yl]-2,6-dimethoxy-benzoate (150 mg, 0.368 mmol, 1 eq.), MeOH (5 mL) and NaOH (5 pellets, excess) is stirred to 65° C. overnight. The organic solvents are removed under reduced pressure. The residue is diluted with water. pH is adjusted to 1-2 with 2 N aq. HCl. The resulting mixture is extracted with an n-BuOH/MeOH mixture (9/1), dried, filtered and concentrated in vacuo to afford the carboxylic acid derivative.

LCMS: MW (calcd): 393.4; m/z MW (obsd): 394.4 (M+H).

1.2.3.3.5 Method E1.1 (Pyrazole Acetate Saponification)

Illustrative Synthesis of Cpd 228

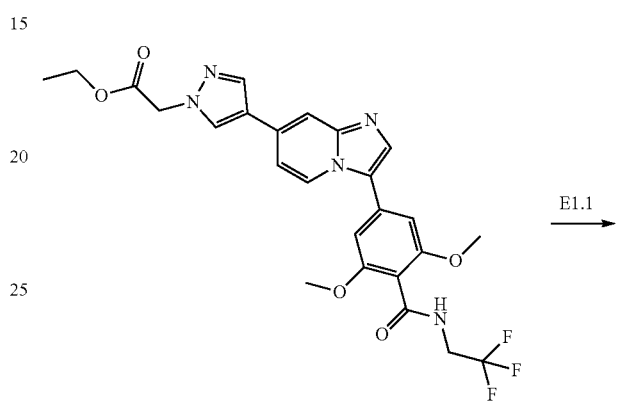

A mixture of Cpd 230 (80 mg, 0.151 mmol, 1 eq.), EtOH (2.4 mL) and 2 N NaOH (90.3 μL, 0.18 mmol, 1.2 eq.) is stirred at 60° C. for 20 min. The organic solvents are removed under vacuum. The residue is diluted with water and Et₂O. The water layer is separated, acidified to pH 5 with 2 N aq. HCl. The suspension formed is stirred, filtered and the solid obtained is purified by preparative HPLC to afford the expected compound.

1.2.3.3.6 E1.2: Peptidic Coupling

Cf. E1.2 from Method E1: Sequence E1.1+E1.2+E1.3

Illustrative Synthesis of Cpd 88

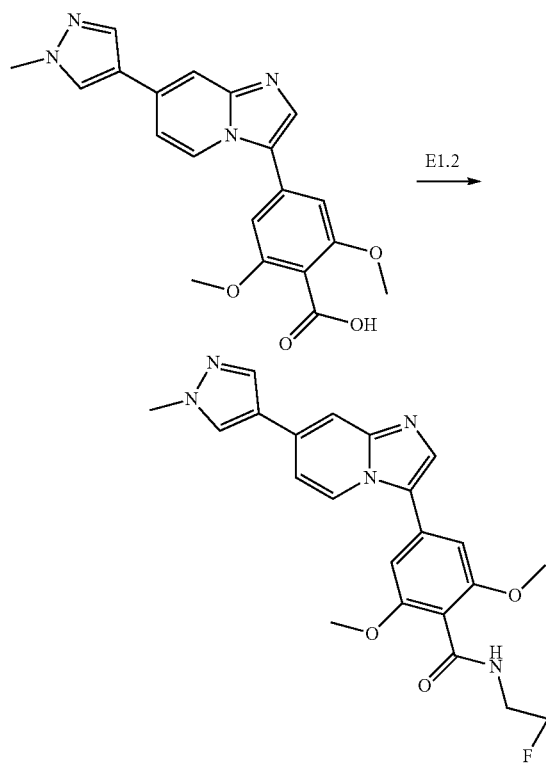

Int 52 (4.66 g, 0.012 mol., 1 eq.) is suspended in anhydrous DMF (45 mL) then HATU (5.62 g, 0.015 mol., 1.2 eq.) and DIPEA (6.44 mL, 0.037 mol., 3 eq.) are added. The mixture is stirred at RT for 5 min then 2,2,2-trifluoroethanamine (CAS #753-90-2; 1.93 mL, 0.025 mol., 2 eq.) is added to the solution. The reaction mixture is stirred at RT for 16 h, quenched with water. EtOAc and a saturated NaHCO₃ solution are added, the aqueous layer is extracted with EtOAc. Brine is added to the combined organic layers and the solid formed is filtered, rinsed with EtOAc and dichloromethane.

The aqueous layer is separated, extracted again with EtOAc. The combined organic layers and the previous ones are dried over anhydrous Na₂SO₄, filtered, concentrated. The residue is taken up in ACN, triturated, sonicated and filtered. The two solids obtained are combined, purified by flash chromatography on silica gel (eluting with DCM/MeOH 100/0 to 96/4) to afford the expected amide derivative.

LCMS: MW (calcd): 459.4; m/z MW (obsd): 460.4 (M+H).

Illustrative Synthesis of Cpd 52

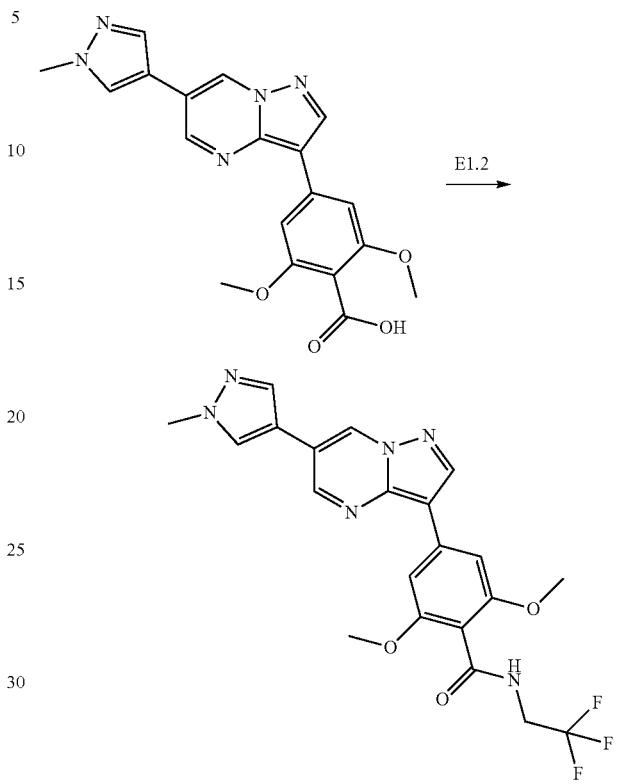

A vial is charged Int 28 (18.5 mg, 0.049 mmol, 1 eq.), anhydrous DMF (1.5 mL) then DIPEA (26 µL, 0.146 mmol, 3 eq.) and HATU (20 mg, 0.054 mmol, 1.1 eq.). The mixture is stirred at RT for 20 min then 2,2,2-trifluoroethanamine hydrochloride (13 mg, 0.098 mol., 2 eq.) is added. The reaction mixture is stirred at RT for 16 h, quenched with a saturated NaHCO₃ solution, extracted with EtOAc. The combined organic layers are dried over hydrophobic column, concentrated in vacuo. The residue is taken up in DCM, ultra-sonicated, filtered, rinsed with Et₂O to afford the desired compound.

Illustrative Synthesis of Cpd 29

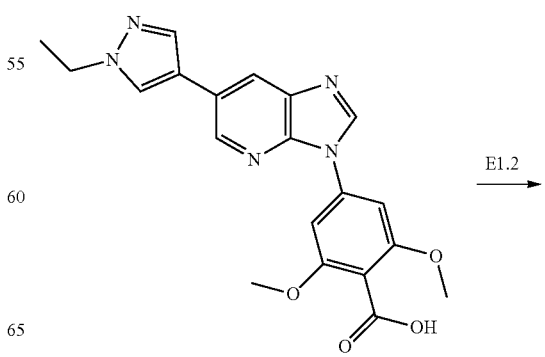

-continued

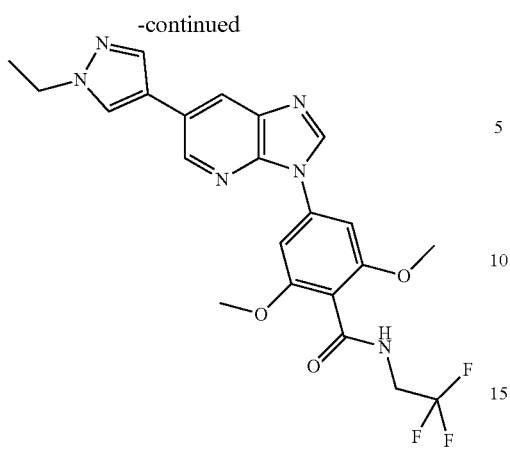

A vial is charged with 4-[6-(1-ethylpyrazol-4-yl)imidazo[4,5-b]pyridin-3-yl]-2,6-dimethoxy-benzoic acid (58 mg, 0.147 mmol, 1 eq.), HATU (61 mg, 0.161 mmol, 1.1 eq.), anhydrous DMF (3 mL) and DIPEA (77 μL, 0.441 mmol, 3 eq.). The mixture is stirred at RT for 10 min then 2,2,2-trifluoroethanamine hydrochloride (60 mg, 0.441 mmol, 3 eq.) is added. The reaction mixture is stirred at RT for 16 h. EtOAc and brine are added, the aqueous layer is extracted with EtOAc. The combined organic layers are dried, filtered, concentrated in vacuo, purified by flash chromatography on silica gel (eluting with DCM/MeOH 100/0 to 95/5) then preparative LCMS to afford the expected amide derivative.

Illustrative Synthesis of Cpd 206

A vial is charged with 2-methoxy-6-methyl-4-[7-(1-methylpyrazol-4-yl)imidazo[1,2-a]pyridin-3-yl]benzoic acid (60 mg, 0.16 mmol, 1 eq.), HATU (69 mg, 0.18 mmol, 1.1 eq.), anhydrous DMF (1 mL) and DIPEA (56 μL, 0.32 mmol, 2 eq.). The mixture is stirred at RT for 10 min then 2,2,2-trifluoroethanamine (15 μL, 0.19 mmol, 1.2 eq.) is added. The reaction mixture is stirred at RT for 96 h. The mixture is concentrated in vacuo, purified by flash chromatography on Biotage® SNAP KP-NH cartridge (eluting with DCM/MeOH 100/0 to 98/2) to afford the expected amide derivative. 1.2.3.4. Method E2: Buchwald reaction process (3 steps)

1.2.3.4.1 E2.1: Saponfication of Ester

Cf. E1.1 of Method E1 Section E1.1+E1.2+E1.3

1.2.3.4.2 E2.2: Peptidic Coupling

Cf. E1.2 of Method E1 Section E1.1+E1.2+E1.3

1.2.3.4.3 E2.3: Buchwald Reaction

To a stirred solution of halogeno aryl derivative (1 eq.) and amine derivative (1.5 eq.) in dioxane previously degassed with $N_2$ are added t-BuOK (3 eq.), t-BuXPhos (0.2 eq.) and $Pd_2(dba)_3$ (0.1 eq.). The mixture is heated to 110° C. overnight, then to 120° C. for 96 h, then purified by preparative LCMS to afford the expected compound.

Illustrative Synthesis of Cpd 154

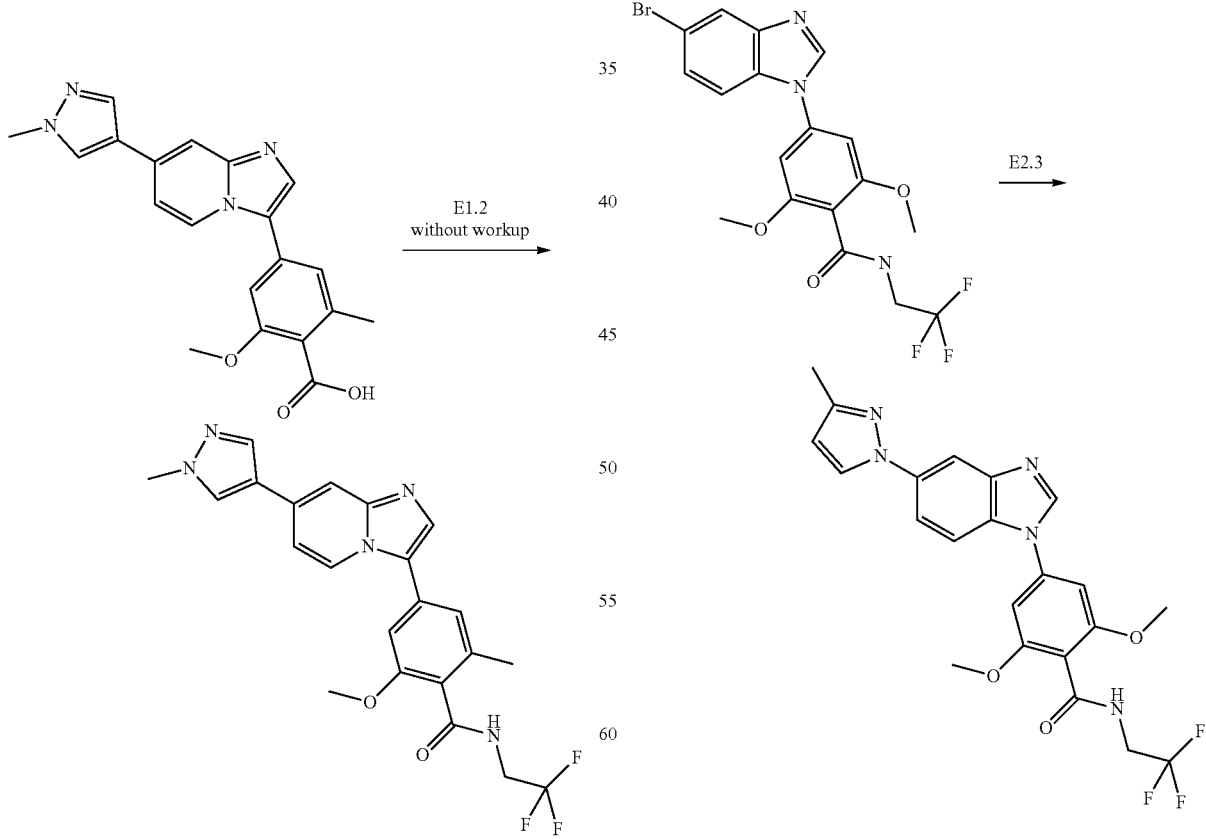

To a stirred solution of Int 39 (46 mg, 0.10 mmol, 1 eq.) and 3-methylpyrazole (CAS #1453-58-3; 12 μL, 0.15 mmol, 1.5 eq.) in dioxane previously degassed with $N_2$ (2 mL) are added t-BuOK (34 mg, 0.30 mmol, 3 eq.), t-BuXPhos (9 mg, 0.02 mmol, 0.2 eq.) and Pd₂(dba)₃ (9 mg, 0.01 mmol, 0.1 eq.). The mixture is heated to 110° C. overnight, then to 120° C. for 96 h, then purified by preparative LCMS to afford the expected compound.

1.2.3.5. Method E3: Copper Amination Process (3 Steps)

1.2.3.5.1 E3.1: Ester Saponification

Cf. E1.1 of Method E1 Section E1.1+E1.2+E1.3

1.2.3.5.2 E3.2: Peptidic Coupling

Cf. E1.2 of Method E1 Section E1.1+E1.2+E1.3

1.2.3.5.3 E3.3: Copper Amination

To a stirred solution of halogeno aryl derivative (1 eq.) and amine derivative (1 eq.) in DMF previously degassed with N₂ are added Cs₂CO₃ (2.5 eq.), CuI (0.4 eq.) and N,N'-dimethylethylenediamine (CAS #110-70-3; 0.2 eq.). The mixture is heated to 140° C. for 20 h, then purified by preparative LCMS to afford the expected compound.

Illustrative Synthesis of Cpd 155

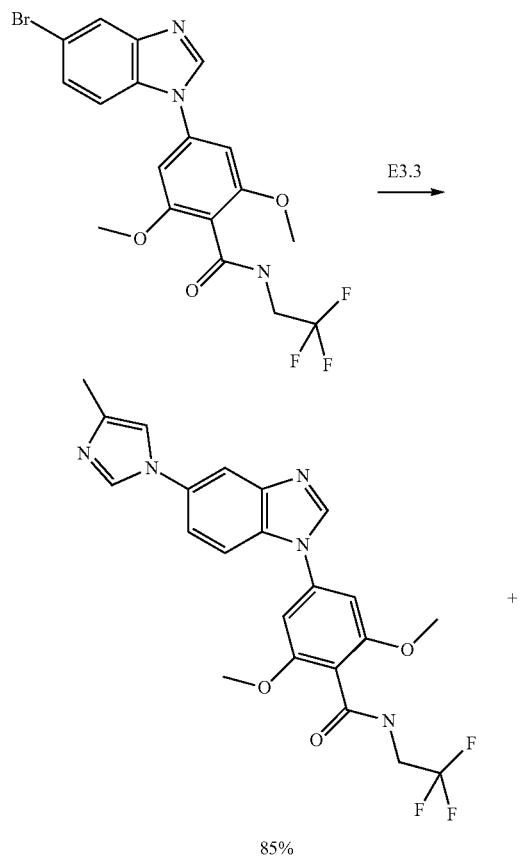

85%

+

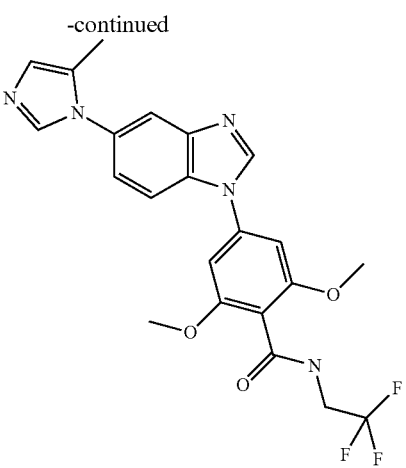

15%

To a stirred solution of Int 39 (92 mg, 0.20 mmol, 1 eq.) and 4(5)-Methylimidazole (CAS #822-36-6; 17 mg, 0.20 mmol, 1 eq.) in DMF previously degassed with N₂ (1 mL) are added Cs₂CO₃ (163 mg, 0.50 mmol, 2.5 eq.), CuI (15 mg, 0.08 mmol, 0.4 eq.) and N,N'-dimethylethylenediamine (CAS #110-70-3; 5 µL, 0.04 mmol, 0.2 eq.). The mixture is heated to 140° C. for 20 h then purified by preparative LCMS to afford the expected compound as a 85/15 regioisomers mixture.

1.2.3.6. Method E4: Borylation then Suzuki Reaction (3 Steps)

1.2.3.6.1 E4.1: Ester Saponification

Cf. E1.1 of Method E1 Section E1.1+E1.2+E1.3

1.2.3.6.2 E4.2: Peptidic Coupling

Cf. E1.2 of Method E1 Section E1.1+E1.2+E1.3

1.2.3.6.3 E4.3: Borylation then Suzuki Reaction

1.2.3.6.3.1. E4.3i:2 Steps in 1 (One Pot)

A flask is charged with halogeno aryl derivative (1 eq.), dioxane previously degassed with N₂, B₂pin₂ (1.1 to 1.5 eq.), potassium acetate (3 to 4 eq.) and Pd(dppf)Cl₂.DCM (0.1 to 0.12 eq.). The mixture is stirred to 90° C.-110° C. for 1.5 h-20 h, cooled to RT or 50° C. and used as such in the Suzuki coupling (cf. E1.3 using from 0.9 to 1.4 eq. of arylbromide or arylchloride).

159

Illustrative Synthesis of Cpd 273

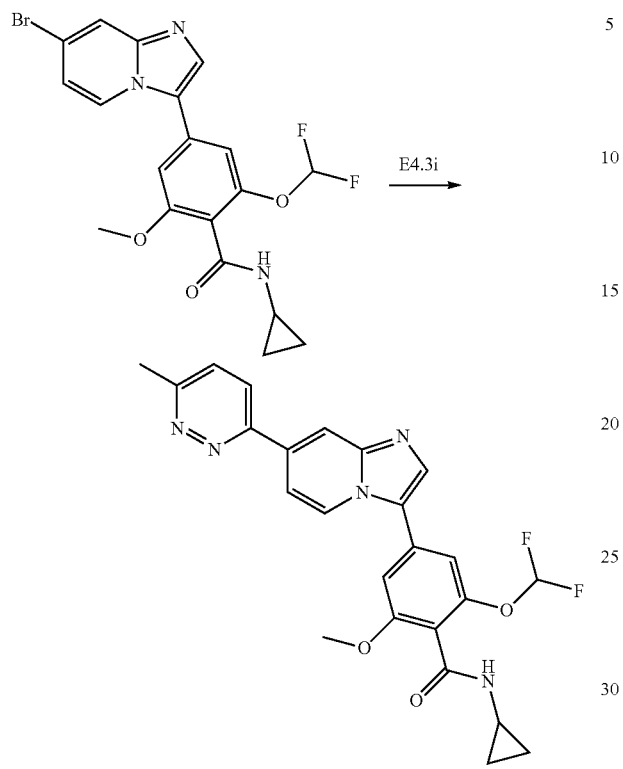

A flask is charged with Int 37 (100 mg, 0.22 mmol, 1 eq.), dioxane previously degassed with $N_2$ (4 mL), $B_2pin_2$ (67 mg, 0.26 mmol, 1.2 eq.), potassium acetate (65 mg, 0.66 mmol, 3 eq.) and Pd(dppf)Cl$_2$.DCM (11 mg, 0.013 mmol, 0.06 eq.). The mixture is stirred to 90° C. for 20 h. Pd(dppf)Cl$_2$.DCM (11 mg, 0.013 mmol, 0.06 eq.), $B_2pin_2$ (17 mg, 0.065 mmol, 0.3 eq.), potassium acetate (22 mg, 0.22 mmol, 1 eq.) are added, the mixture is stirred to 90° C. for 3 h, cooled to RT and used as such in the next step.

Suzuki coupling (equivalent to E1.3 step): the suitable amount of the previous solution of boronic ester/boronic acid mixture (2.1 mL, 0.11 mmol, 1 eq.) is taken and placed into a flask, dioxane and water are added (C=0.037 M, dioxane/water mixture: 4/1) followed by 6-methylchloro-pyridazine (13 mg, 0.099 mmol, 0.9 eq.), Cs$_2$CO$_3$ (72 mg, 0.22 mmol, 2 eq.) and Pd(dppf)Cl$_2$.DCM (4.5 mg, 0.006 mmol, 0.05 eq.). The mixture is stirred to 90° C. for 3 h. Dioxane is evaporated, the remaining aqueous layer is extracted with DCM through SPE separator. The combined organic layers are concentrated in vacuo, purified by preparative LCMS to afford the expected compound.

1.2.3.6.3.2. E4.3ii: 2 Steps

A flask is charged with halogeno aryl derivative (1 eq.), dioxane previously degassed with $N_2$, $B_2pin_2$ (1.5 to 2 eq.), potassium acetate (3 eq.) and Pd(dppf)Cl$_2$.DCM (0.1 to 0.2 eq.). The mixture is degassed with $N_2$ if not previously degassed. The mixture is stirred to 100-110° C. overnight, cooled to RT, either directly concentrated in vacuo or filtered over Clarcel®, rinsed with EtOAc/MeOH and the filtrate is concentrated in vacuo. The residue is taken up either in EtOAc and a saturated NaHCO$_3$ solution or in DCM and

160 water. The mixture is extracted with EtOAc or DCM. The combined organic layers are dried over anhydrous Na$_2$SO$_4$, filtered; concentrated in vacuo and either purified by flash chromatography on silica gel or used as such in the Suzuki coupling (cf. E1.3 using 1 to 1.1 eq. of boronic ester and boronic acid mixture and 1 eq. of arylbromide or arylchloride).

Illustrative Synthesis of Cpd 137

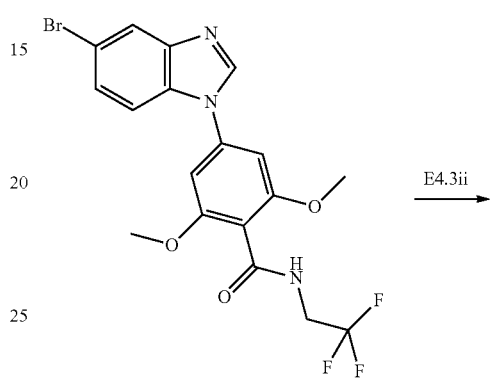

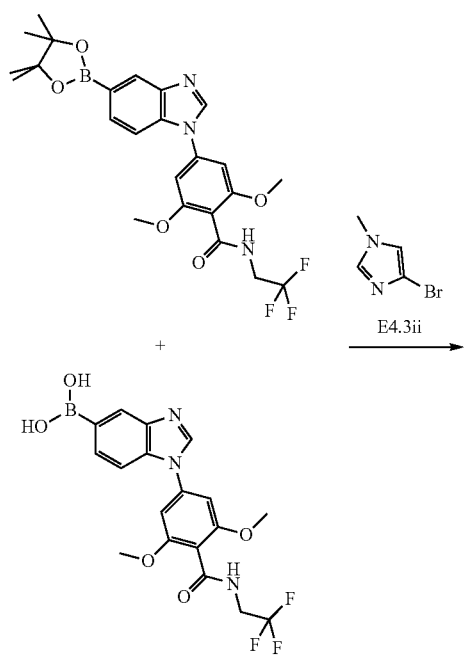

-continued

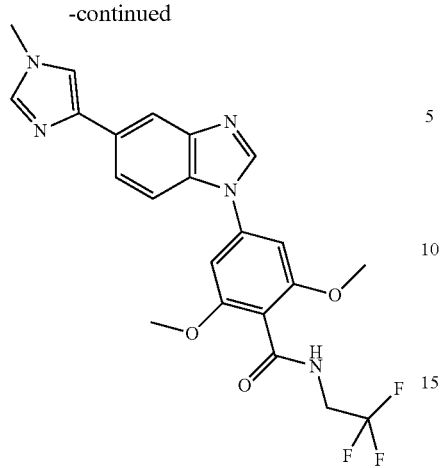

Borylation: A flask is charged with Int 39 (458 mg, 1 mmol, 1 eq.), B₂pin₂ (381 mg, 1.5 mmol, 1.5 eq.), dioxane previously degassed with N₂ (5 mL), potassium acetate (295 mg, 3 mmol, 3 eq.) and Pd(dppf)Cl₂.DCM (82 mg, 0.10 mmol, 0.1 eq.). The mixture is stirred to 100° C. overnight, concentrated in vacuo. The residue is diluted in DCM and water. The organic layer is separated and concentrated in vacuo, purified by flash chromatography on silica gel (eluting with DCM/MeOH 100/0 to 95/5) to afford the expected boronic ester and boronic acid mixture.

LCMS: MW (calcd): 505.3; m/z MW (obsd): 506.3 (M+H).

LCMS: MW (calcd): 423.1; m/z MW (obsd): 424.1 (M+H).

Suzuki coupling: To a stirred solution of boronic ester and boronic acid mixture (51 mg, 0.10 mmol, 1 eq.) and 4-bromo-1-methyl-imidazole (CAS #25676-75-9; 10 µL, 0.10 mmol, 1 eq.) in dioxane (2 mL) is added Cs₂CO₃ (65 mg, 0.20 mmol, 2 eq.), Pd(PPh₃)₄ (12 mg, 0.01 mmol, 0.1 eq.) in water (0.5 mL). The mixture is heated to 90° C. for 1 h then concentrated in vacuo. The residue is diluted in DCM and water. The organic layer is separated and concentrated in vacuo, purified by flash chromatography on Biotage® SNAP KP-NH cartridge (eluting with DCM/MeOH 100/0 to 98/2) to afford the expected compound.

1.2.3.7. Method E5: Cyanation then Ring Formation Process

1.2.3.7.1 E5.1: Saponfication of Ester

Cf. E1.1 of Method E1 Section E1.1+E1.2+E1.3

1.2.3.7.2 E5.2: Peptidic Coupling

Cf. E1.2 of Method E1 Section E1.1+E1.2+E1.3

1.2.3.7.3 E5.3: Cyanation

To a stirred solution of aryl bromide derivative (1 eq.) in degassed N,N-dimethylacetamide is added ZnCN₂ (2 eq.), Pd₂(dba)₃ (0.03 eq.), DPPF (0.07 eq.) and Zn dust (0.04 eq.). The mixture is degassed with argon for 5 min and stirred at 125° C. for 3 h. The reaction mixture is filtered. DCM and water are added. The organic layer is separated and concentrated in vacuo. The residue is purified by flash chromatography on silica gel to afford the expected nitrile intermediate.

Illustrative Synthesis of 4-(5-cyanobenzimidazol-1-yl)-2,6-dimethoxy-N-(2,2,2-trifluoroethyl)benzamide

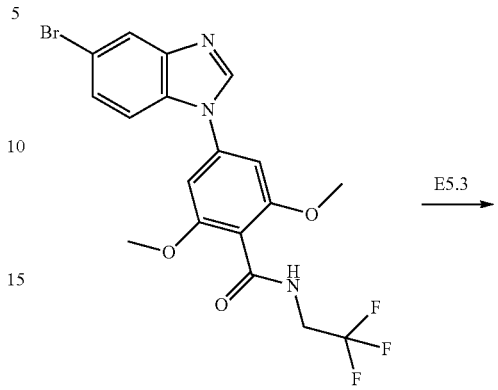

Int 39

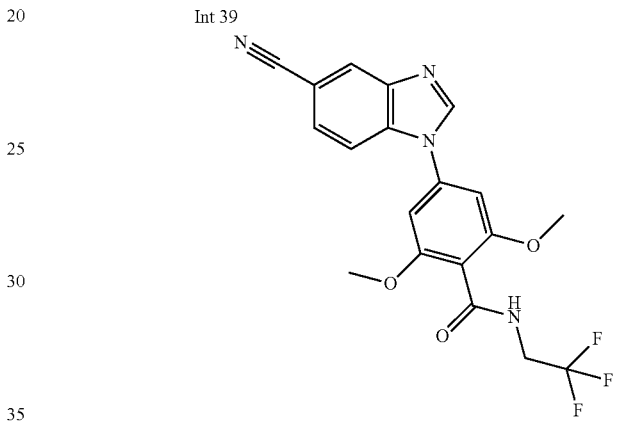

To a stirred solution of Int 39 (458 mg, 1.00 mmol, 1 eq.) in degassed N,N-Dimethylacetamide (5 mL) is added ZnCN₂ (235 mg, 2.00 mmol, 2 eq.), Pd₂(dba)₃ (27 mg, 0.03 mmol, 0.03 eq.), DPPF (39 mg, 0.07 mmol, 0.07 eq.) and Zn dust (3 mg, 0.04 mmol, 0.04 eq.). The mixture is degassed with argon for 5 min and stirred at 125° C. for 3 h. The reaction mixture is filtered. DCM and water are added. The organic layer is separated and concentrated in vacuo. The residue is purified by flash chromatography on silica gel (eluting with DCM/MeOH 100/0 to 96/4) to afford the expected nitrile intermediate.

LCMS: MW (calcd): 404.3; m/z MW (obsd): 405.3 (M+H).

1.2.3.7.4 E5.4: Ring Formation

1.2.3.7.4.1. E5.4i: 1,2,4-Oxadiazole Ring Formation

To a stirred solution of nitrile derivative (1.0 eq.) in EtOH are added Et₃N (3.0 eq.) and hydroxylamine hydrochloride (1.1 eq.). The reaction mixture is stirred at 80° C. (4 to 5 h) and concentrated in vacuo. The residue is either used in the next step without further purification or purified on Biotage® SNAP KP-NH cartridge to afford the N-hydroxycarboximidamide intermediate.

Acetic anhydride is added to N-hydroxycarboximidamide intermediate (1 eq.) and the resulting mixture is stirred for 1 h to 2 h at 100° C. then concentrated in vacuo. The residue is either purified by flash chromatography on silica gel then preparative LCMS or purified on Biotage® SNAP KP-NH cartridge to afford the expected compound.

Illustrative Synthesis of Cpd 126

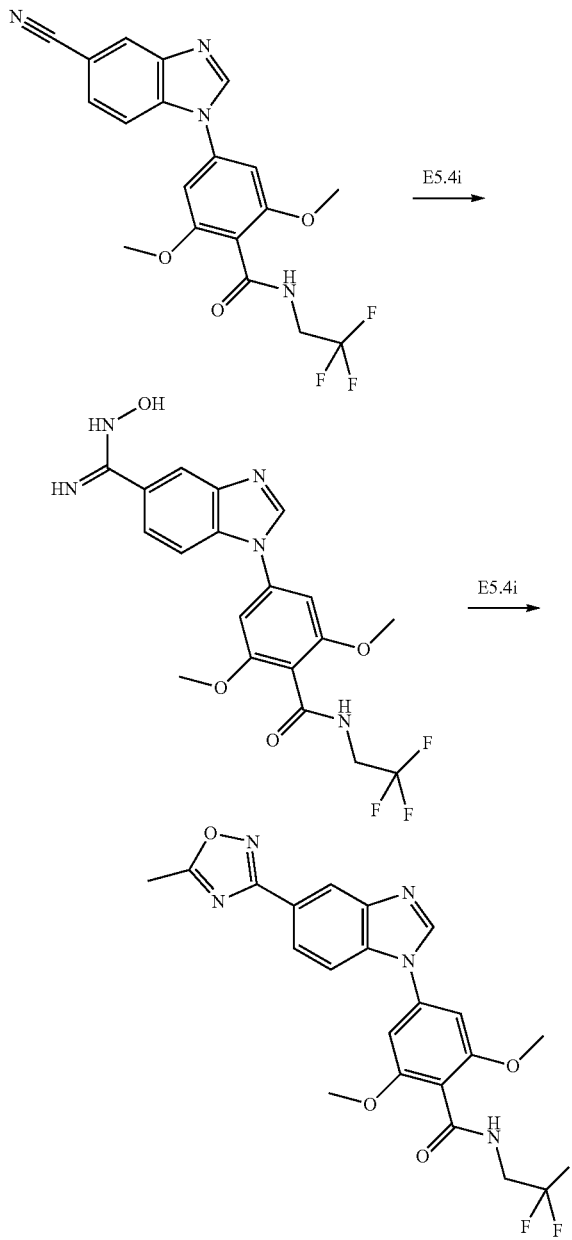

To a stirred solution of 4-(5-cyanobenzimidazol-1-yl)-2,6-dimethoxy-N-(2,2,2-trifluoroethyl)benzamide (37 mg, 0.09 mmol, 1 eq.) in EtOH (2 mL) are added Et$_3$N (37 μL, 0.27 mmol, 3.0 eq.) and hydroxylamine hydrochloride (7 mg, 0.10 mmol, 1.1 eq.). The reaction mixture is stirred to 80° C. for 5 h and concentrated in vacuo. The N-hydroxycarboximidamide intermediate is used in the next step without further purification.

Acetic anhydride (1 mL) is added to N-hydroxycarboximidamide intermediate (39 mg, 0.09 mmol, 1.0 eq.) and the resulting mixture is stirred for 1 h to 100° C. then concentrated in vacuo. The residue is purified by flash chromatography on silica gel (eluting with DCM/MeOH 100/0 to 97/3) to afford the expected compound.

1.2.3.7.4.2. E5.4ii: 1,2,4-triazole Ring Formation

To a stirred solution of nitrile derivative (1.0 eq.) in DMSO are added Copper (I) bromide (0.05 eq.), Cs$_2$CO$_3$ (3.0 eq.) and acetamidine hydrochloride (CAS #124-42-5; 1.5 eq.). The reaction mixture is stirred overnight at 125° C. then purified by preparative LCMS to afford the expected compound.

Illustrative Synthesis of Cpd 127

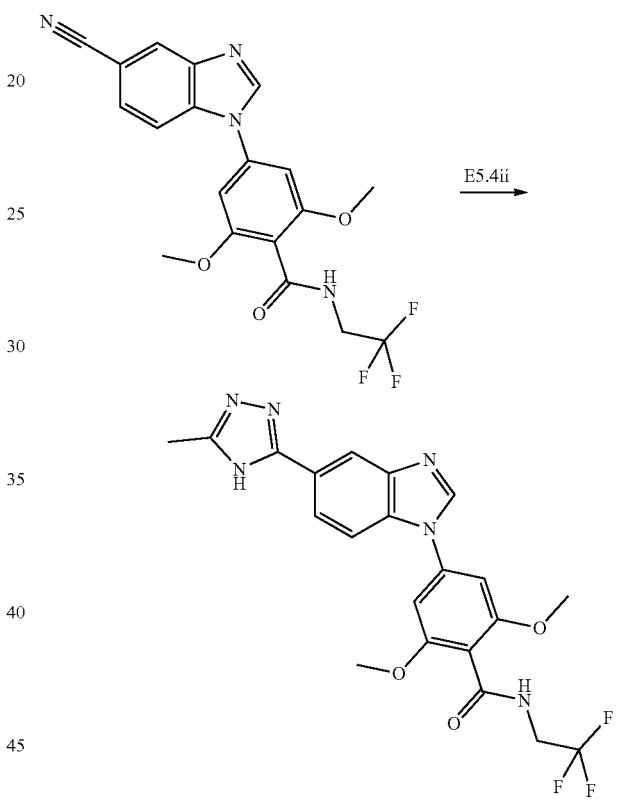

To a stirred solution of 4-(5-cyanobenzimidazol-1-yl)-2,6-dimethoxy-N-(2,2,2-trifluoroethyl)benzamide (41 mg, 0.10 mmol, 1.0 eq.) in DMSO (0.5 mL) are added Copper(I) bromide (1 mg, 0.005 mmol, 0.05 eq.), Cs$_2$CO$_3$ (98 mg, 0.30 mmol, 3.0 eq.) and acetamidine hydrochloride (CAS #124-42-5; 14 mg, 0.15 mmol, 1.5 eq.). The reaction mixture is stirred overnight at 125° C. then purified by preparative LCMS to afford the expected compound.

1.2.4. Method F: Iodination of Bromo Heteroaryl Compound

To a solution of 6-bromopyrazolo[1,5-a]pyridine (CAS #1264193-11-4; 1 eq.) in ACN under N$_2$ atmosphere is introduced N-iodosuccinimide (1.05 eq.). The resulting solution is stirred at RT overnight. The reaction mixture is filtered and the solid is washed with few milliliters of ACN to afford the expected bromo iodo heteroaryl compound.

Illustrative Synthesis of Int 15

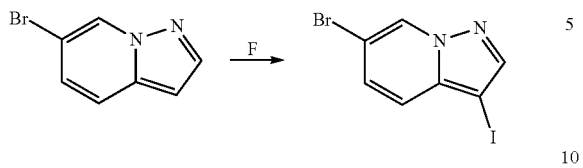

To a solution of 6-bromopyrazolo[1,5-a]pyridine (CAS #1264193-11-4; 650 mg, 3.3 mmol, 1 eq.) in ACN under N$_2$ atmosphere is introduced N-Iodosuccinimide (780 mg, 3.46 mmol, 1.05 eq.). The resulting solution is stirred at RT overnight.

The reaction mixture is filtered and the solid is washed with few milliliters of ACN to afford 6-bromo-3-iodo-pyrazolo[1,5-a]pyridine, which is used as such in the next step.

1.2.5. Method H: C—H Activation

Nitrogen heterocycle (1 eq.) is dissolved in DMAC previously degassed with N$_2$. Aryl bromide (1.0 to 1.6 eq.) and potassium acetate (2 to 3 eq.) are added. The mixture is degassed with N$_2$ then Pd(dppf)Cl$_2$.DCM (0.005 to 0.05 eq.) is added. The mixture is heated to 105-130° C. for 2.5 h to overnight.

Work-up: the mixture is cooled to RT then either diluted in DCM/MeOH mixture, filtered over Celite® and the filtrate is concentrated in vacuo or the reaction mixture is quenched with a saturated NaHCO$_3$ solution, extracted with EtOAc, the combined organic layers are then dried (anhydrous Na$_2$SO$_4$) or washed with water then brine and dried (anhydrous MgSO$_4$), filtered and concentrated in vacuo. The residue obtained by one or the other way is purified by flash chromatography on silica gel or Biotage® SNAP KP-NH cartridge to afford the expected product.

Alternative work-up 1: the mixture is cooled to RT then filtered over Celite®. The solid is triturated in EtOAc and n-BuOH and affords the first batch of crude compound. Water is added to the filtrate and the mixture is extracted with DCM. Water is added to the combined organic layers and the solid formed is filtered leading to the second batch of crude compound. The two batches are combined and triturated with ACN to lead to the expected compound.

Alternative work-up 2: the mixture is cooled to RT, then filtered. Water is added to the filtrate and the suspension is filtered. The solid is washed with water, filtered, then triturated with MTBE. The solid is taken up in water and DCM and the mixture is extracted with DCM. The combined organic layers are washed with water, purified by flash chromatography on silica gel to afford the expected compound.

Illustrative Synthesis of Cpd 275

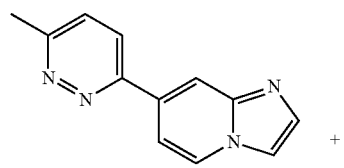

+

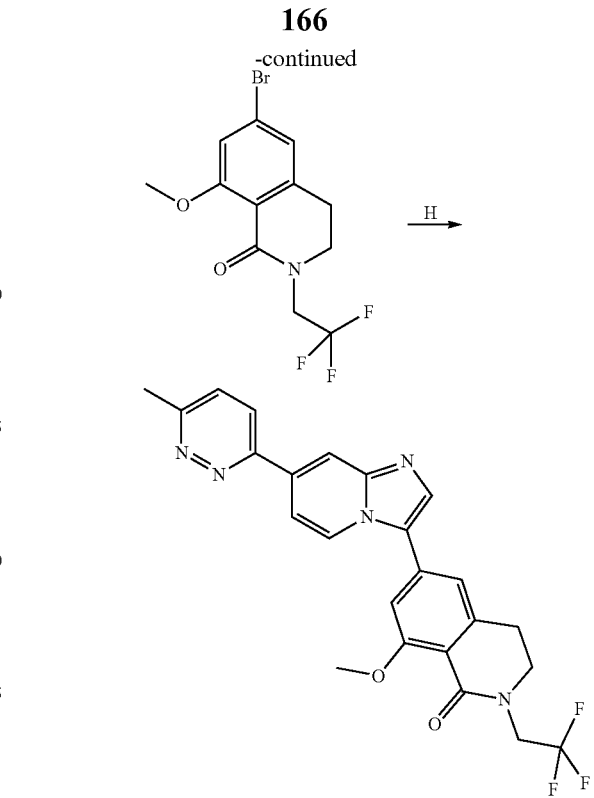

Int 2 (47 mg, 0.22 mmol, 1 eq.) is dissolved in DMAC (2 mL), Int 7 (113 mg, 0.34 mmol, 1.5 eq.), potassium acetate (66 mg, 0.67 mmol, 3 eq.), Pd(dppf)Cl$_2$.DCM (9 mg, 0.01 mmol, 0.05 eq.) are added and the mixture is stirred to 110° C. overnight. The mixture is then cooled to RT, quenched with a saturated NaHCO$_3$ solution, extracted with EtOAc. The combined organic layers are dried over anhydrous Na$_2$SO$_4$, filtered, concentrated in vacuo. The residue is purified twice by flash chromatography over Biotage® SNAP KP-NH cartridge (eluting with DCM/EtOAc 100/0 to 90/10 first, then with heptane/EtOAc 90/10 to 0/100) to afford the expected compound. 1.2.6. Method I: Phenol deprotection (demethylation)

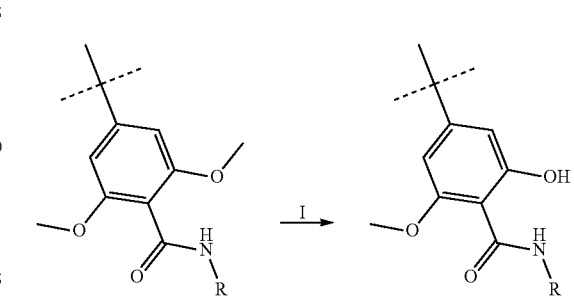

To a stirred mixture of methoxy derivative (1 eq.) in DCM cooled to 0° C.--15° C. is added dropwise BCl$_3$ 1 M in DCM solution (2.2 eq.). The mixture is stirred at 0° C. for 2 h or to 0° C. for 45 min and RT for 3 h. The reaction mixture is poured in ice/water mixture and acidified with HCl (2 N) or poured in HCl (0.1 N)/ice mixture followed by extraction with DCM and few drops of MeOH or with DCM then EtOAc then CHCl$_3$/n-BuOH (90/10 or 80/20 mixture). The combined organic layers are dried (filtration over hydrophobic column or Na$_2$SO$_4$) and concentrated in vacuo. The residue is either used as such in the next step or purified by flash chromatography on silica gel to afford the desired phenol compound.

Illustrative Synthesis of Cpd 233

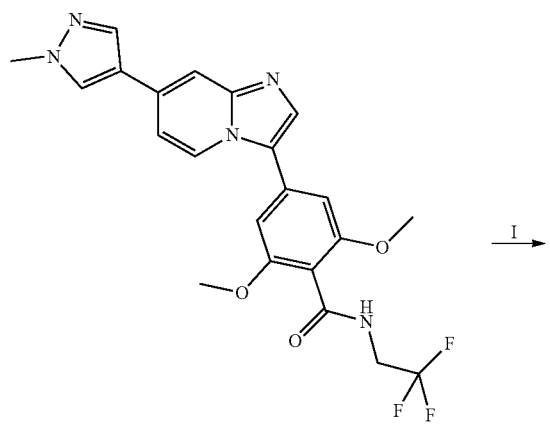

To a stirred mixture of Cpd 88 (100 mg, 0.218 mmol, 1 eq.) in DCM (3 mL) cooled to 0° C. is added dropwise BCl₃ 1 M in DCM solution (479 µL, 0.479 mmol, 2.2 eq.). The mixture is stirred at 0° C. for 2 h. The reaction mixture is poured in a HCl 0.1 N and ice mixture, extracted with DCM and few drops of MeOH then the combined organic layers are dried over hydrophobic column and concentrated in vacuo. The residue is purified by flash chromatography on silica gel (eluting with DCM/MeOH 100/0 to 90/10) to afford the expected compound.

1.2.7. Method J: Phenol Alkylation

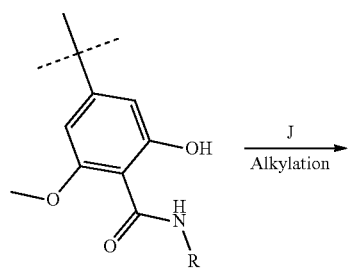

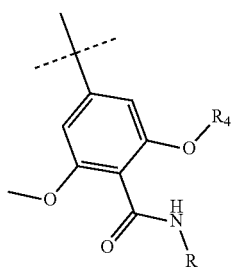

1.2.7.1. Method J1: K₂CO/Alkyl Iodide

To a stirred mixture of phenol derivative (1 eq.) in ACN/THF 1/1 mixture is added dropwise alkyl halide (1.3 eq.). The mixture is stirred at 80° C. for 50 h. The mixture is taken up in DCM and the organic layer is washed with water, dried over hydrophobic column and concentrated in vacuo. The residue is purified by preparative HPLC to afford the expected compound.

Illustrative Synthesis of Cpd 119

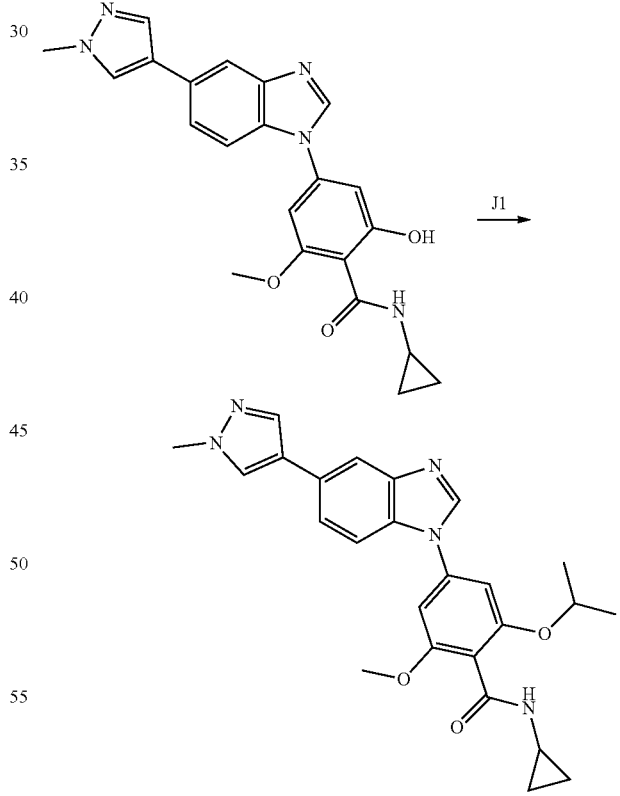

To a stirred mixture of N-cyclopropyl-2-hydroxy-6-methoxy-4-[5-(1-methylpyrazol-4-yl)benzimidazol-1-yl] benzamide (30 mg, 0.074 mmol, 1 eq.) in ACN/THF 1/1 mixture (4 mL) is added dropwise 2-iodopropane (16.3 mg, 0.096 mmol, 1.3 eq.). The mixture is stirred at 80° C. for 50 h. The mixture is taken up in DCM and the organic layer is washed with water, dried over hydrophobic column and concentrated in vacuo. The residue is purified by preparative HPLC to afford the expected compound.

1.2.7.2. Method J2: KOH/diethyl (bromodifluoromethyl)phosphonate

To a stirred mixture of phenol derivative (1 eq.) in ACN/water 1/1 mixture (2 mL) is added KOH pellets (10 eq.). The mixture is stirred to −40° C. for 15 min then diethyl (bromodifluoromethyl)phosphonate (CAS #65094-22-6; 3 eq.) is added. The reaction mixture is stirred to −40° C. for 1 h then warmed to RT and stirred overnight at RT. Further KOH (excess) and diethyl (bromodifluoromethyl)phosphonate are added (3 eq.) and the mixture is stirred at RT for 4 h, then 90° C. for 2 h, then RT for 48 h. The mixture is quenched with a saturated NaHCO₃ solution, extracted with DCM. The combined organic layers are washed with brine, dried by filtration over hydrophobic column and concentrated in vacuo. The residue is purified by flash chromatography on silica gel to afford the expected compound.

Illustrative Synthesis of Cpd 17

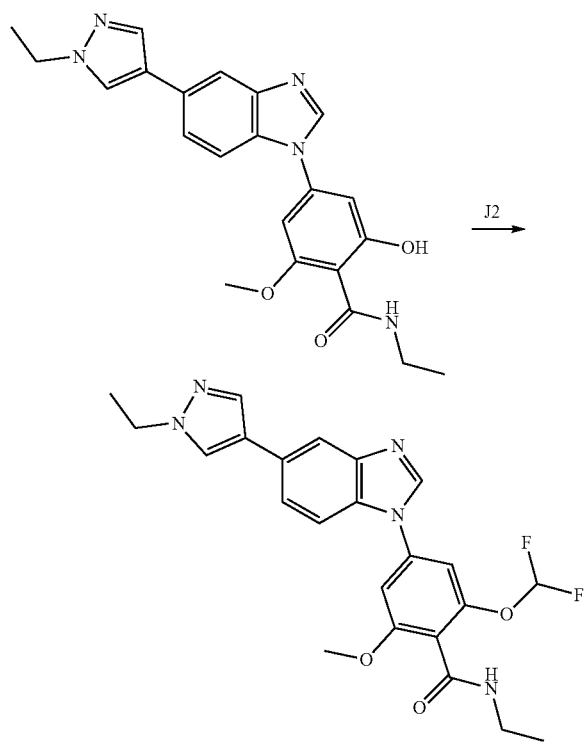

To a stirred mixture of Cpd 23 (36 mg, 0.089 mmol, 1 eq.) in ACN/water 1/1 mixture (2 mL) is added KOH pellets (50 mg, 0.888 mmol, 10 eq.). The mixture is stirred to −40° C. for 15 min then diethyl (bromodifluoromethyl)phosphonate (47 μL, 0.266 mmol, 3 eq.) is added. The reaction mixture is stirred to −40° C. for 1 h then warmed to RT and stirred overnight at RT. Further KOH (excess) and diethyl (bromodifluoromethyl)phosphonate are added (47 μL, 0.266 mmol, 3 eq.) and the mixture is stirred at RT for 4 h, then 90° C. for 2 h, then RT for 48 h. The mixture is quenched with a saturated NaHCO₃ solution, extracted with DCM. The combined organic layers are washed with brine, dried by filtration over hydrophobic column and concentrated in vacuo. The residue is purified by flash chromatography on silica gel (eluting with DCM/MeOH 100/0 to 96/4) to afford the expected compound.

1.2.8. Method K: Amine Deprotection

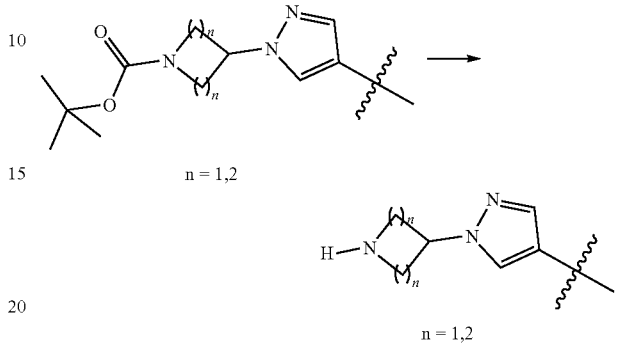

n = 1,2

To a stirred solution of N-Boc protected amine derivative (1 eq.) in DCM is added TFA (DCM/TFA mixture: 90/10 to 50/50). The reaction mixture is stirred at RT for 18 to 72 h. Either the reaction mixture is diluted with DCM, cooled to 0° C., diluted with water, basified with NaOH (2 N) (pH 10-11), extracted, the combined organic layers are dried, filtered and concentrated in vacuo to afford the expected compound or the reaction mixture is diluted in toluene, concentrated in vacuo, diluted with DCM, few drops of MeOH and a saturated Na₂CO₃ solution and the organic layer is separated, washed with brine, dried over anhydrous MgSO₄, filtered, concentrated in vacuo, purified by flash chromatography on Biotage® SNAP KP-NH cartridge to afford the expected compound or the reaction mixture is evaporated to dryness then diluted with DCM and a saturated Na₂CO₃ solution then the organic layer is separated, concentrated in vacuo, purified by flash chromatography on Biotage® SNAP KP-NH cartridge, submitted to activated charcoal treatment and filtered to afford after concentration in vacuo the expected compound or the reaction mixture is concentrated in vacuo, taken up in water, the aqueous layer is washed with EtOAc then basified with NaOH (1 N) to pH 10, extracted with EtOAc and the combined organic layers are dried over anhydrous Na₂SO₄, filtered, concentrated in vacuo. The residue obtained is triturated in Et₂O and filtered to afford the expected compound.

Illustrative Synthesis of Cpd 94

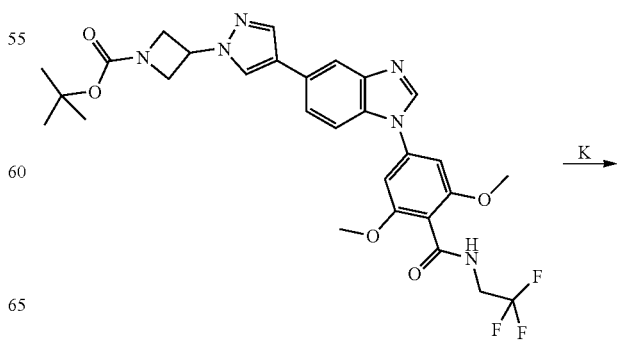

-continued

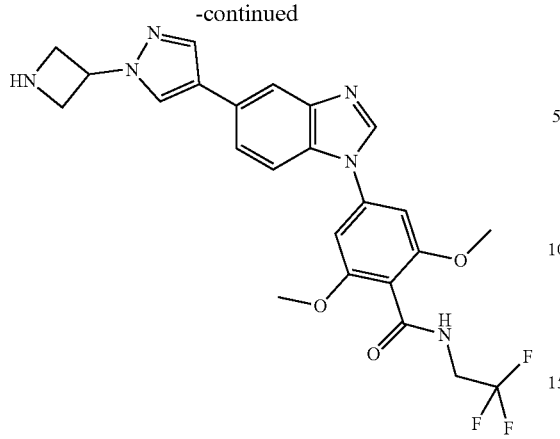

To a stirred solution of tert-butyl 3-[4-[1-[3,5-dimethoxy-4-(2,2,2-trifluoroethylcarbamoyl)phenyl]benzimidazol-5-yl]pyrazol-1-yl]azetidine-1-carboxylate (235 mg, 0.39 mmol, 1 eq.) in DCM (4 mL) is added TFA (0.4 mL). The reaction mixture is stirred at RT for 72 h. The reaction mixture is evaporated to dryness then diluted with DCM and a saturated $Na_2CO_3$ solution. The organic layer is separated and concentrated in vacuo. The residue is purified by flash chromatography on Biotage® SNAP KP-NH cartridge (eluting with DCM/MeOH 100/0 to 97/3), submitted to activated charcoal treatment (50 mg), filtered to afford after concentration in vacuo the expected compound.

1.2.9. Method L: Amine Functionalization

1.2.9.1. Method L1: Reductive Amination

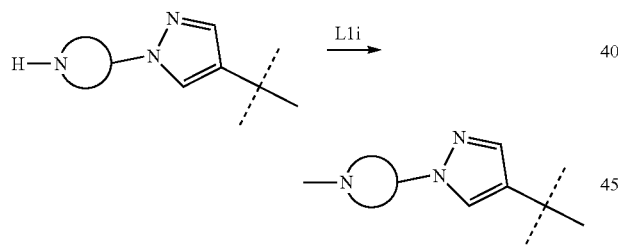

1.2.9.1.1 Method L1i: Reductive Amination Using formaldehyde/NaBH(OAc)$_3$/AcOH To a stirred solution of amine or amine, TFA salt derivative (1 eq.) in ACN or DCM is added formaldehyde (37% in water) (3 eq.) and AcOH (0.1 to 1 eq.). The reaction mixture is stirred at RT and NaBH(OAc)$_3$ (3 eq.) is added. The reaction mixture is stirred overnight at RT. It is either concentrated in vacuo, diluted with DCM and a saturated NaHCO$_3$ solution, the organic layer is then separated, concentrated in vacuo and the residue is purified by flash chromatography on Biotage® SNAP KP-NH cartridge to afford the expected compound, or the reaction mixture is quenched by the addition of a saturated Na$_2$CO$_3$ solution, extracted with DCM and few mL of MeOH, the organic layer is then separated, washed with brine, dried over anhydrous MgSO$_4$, filtered, concentrated in vacuo and the residue is purified by flash chromatography on Biotage® SNAP KP-NH cartridge to afford the expected compound.

Illustrative Synthesis of Cpd 98

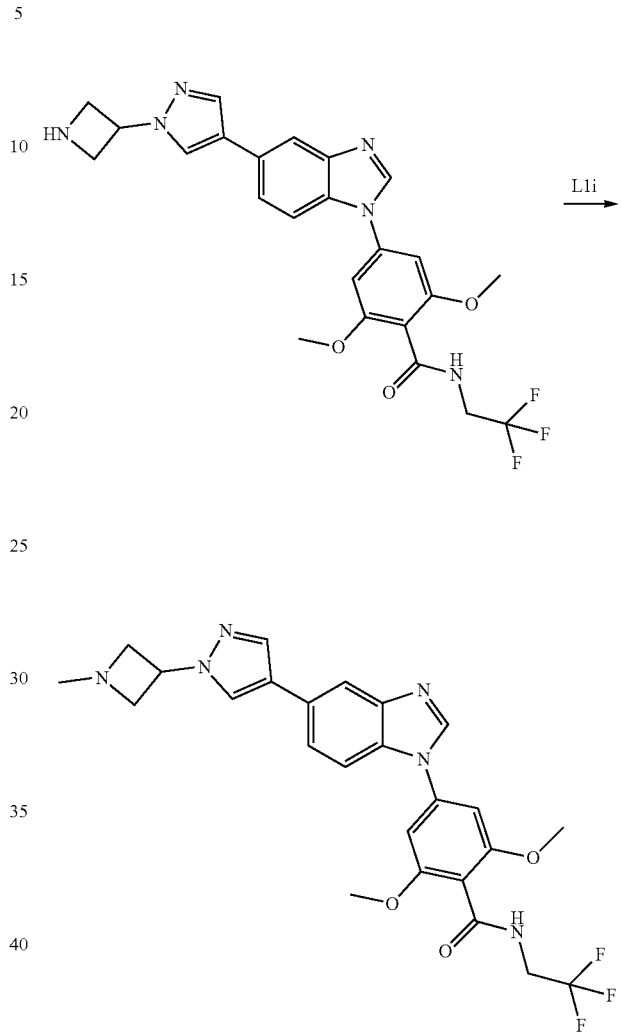

To a stirred solution of Cpd 94 (50 mg, 0.10 mmol, 1 eq.) in ACN (2 mL) is added formaldehyde (37% in water) (24 µL, 0.30 mmol, 3 eq.) and AcOH (12 µL, 0.01 mmol, 0.1 eq.). The reaction mixture is stirred at RT for 5 min and NaBH(OAc)$_3$ (64 mg, 0.30 mmol, 3 eq.) is added. The reaction mixture is stirred overnight at RT, concentrated in vacuo, diluted with DCM and a saturated NaHCO$_3$ solution. The organic layer is separated and concentrated in vacuo. The residue is purified by flash chromatography on a Biotage® SNAP KP-NH cartridge (eluting with DCM/MeOH 100/0 to 97/3) to afford the expected compound.

1.2.9.1.2 Method L1ii: Reductive Amination Using formaldehyde/NaBH$_4$

To a stirred solution of amine derivative (1 eq.) in MeOH at 0° C., under N$_2$ atmosphere, is added formaldehyde (37% in water) (11 eq.) then NaBH$_4$ (20 eq.). The reaction mixture is warmed to RT and stirred for 1 h. A solution of NaOH (2 N) is added, the solid formed is filtered then purified by flash chromatography on silica gel to afford the expected compound.

Illustrative Synthesis of Cpd 46

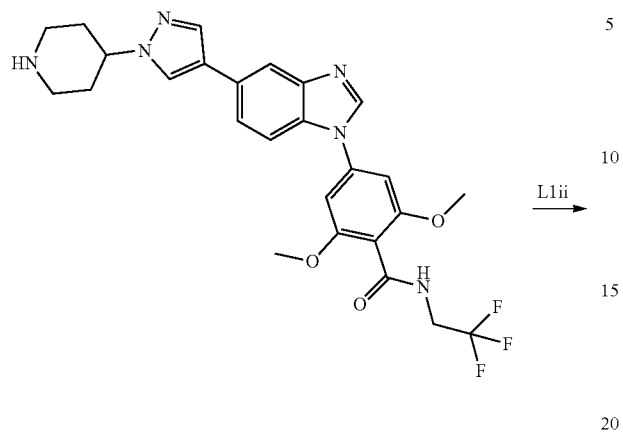

Illustrative Synthesis of Cpd 100

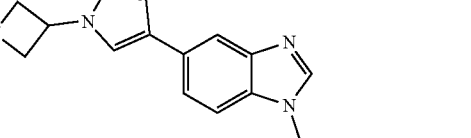

To a stirred solution of Cpd 42 (60 mg, 0.11 mmol, 1 eq.) in MeOH (3 mL) at 0° C., under $N_2$ atmosphere, is added formaldehyde (37% in water) (47 μL, 1.24 mmol, 11 eq.) then $NaBH_4$ (85 mg, 2.26 mmol, 20 eq.). The reaction mixture is warmed to RT and stirred for 1 h. A solution of NaOH (2 N) is added, the solid formed is filtered and purified by flash chromatography on silica gel (eluting with DCM/MeOH 90/10) to afford the expected compound.

1.2.9.2. Method L2: N-alkylation of Amine

1.2.9.2.1 Method L2i: Alkylation Using 2-bromoacetonitrile

To a stirred solution of amine derivative (1 eq.) in ACN are added $K_2CO_3$ (2 eq.) and 2-bromoacetonitrile (1.1 eq.). The reaction mixture is stirred at RT for overnight to 72 h. Either the reaction mixture is concentrated in vacuo, diluted with DCM and water and the organic layer is separated, concentrated in vacuo or a saturated $NaHCO_3$ solution is added and the mixture is extracted with EtOAc, the combined organic layers are dried over anhydrous $Na_2SO_4$, filtered, concentrated in vacuo. The residue obtained by one or the other way is purified by flash chromatography on silica gel to afford the expected compound.

To a stirred solution of Cpd 94 (41 mg, 0.08 mmol, 1 eq.) in ACN (2 mL) are added $K_2CO_3$ (22 mg, 0.16 mmol, 2 eq.) and 2-bromoacetonitrile (6 μL, 0.09 mmol, 1.1 eq.). The reaction mixture is stirred at RT for 72 h. The reaction mixture is concentrated in vacuo, diluted with DCM and water. The organic layer is separated and concentrated in vacuo. The residue is purified by flash chromatography on silica gel (eluting with DCM/MeOH 100/0 to 95/5) to afford the expected compound.

1.2.9.2.2 Method L2ii: Alkylation Using prop-2-enenitrile

To a stirred mixture of amine derivative (1 eq.) in MeOH are added DIPEA (5 eq.) and prop-2-enenitrile (1.1 eq.). The reaction mixture is stirred at RT for 1 h then ACN is added and the mixture is stirred at RT overnight. A solution of saturated $NaHCO_3$ is added and the mixture is extracted with EtOAc. The combined organic layers are dried over $Na_2SO_4$, filtered, concentrated in vacuo, purified by flash chromatography on silica gel to afford the expected compound.

Illustrative Synthesis of Cpd 264

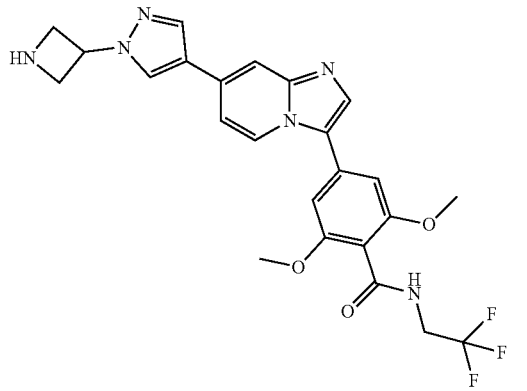

↓ L2ii

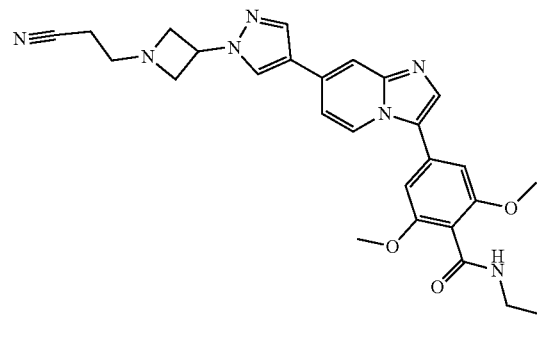

To a stirred mixture of 4-[7-[1-(azetidin-3-yl)pyrazol-4-yl]imidazo[1,2-a]pyridin-3-yl]-2,6-dimethoxy-N-(2,2,2-trifluoroethyl)benzamide (50 mg, 0.10 mmol, 1 eq.) in MeOH (0.5 mL) are added DIPEA (83 μL, 0.50 mmol, 5 eq.) and prop-2-enenitrile (7 μL, 0.11 mmol, 1.1 eq.). The reaction mixture is stirred at RT for 1 h then ACN (0.2 mL) is added and the mixture is stirred at RT overnight. A solution of saturated NaHCO₃ is added and the mixture is extracted with EtOAc. The combined organic layers are dried over Na₂SO₄, filtered, concentrated in vacuo, purified by flash chromatography on silica gel (eluting with DCM/MeOH 99/1 to 95/5) to afford the expected compound.

1.2.10. Method M: S$_N$Ar

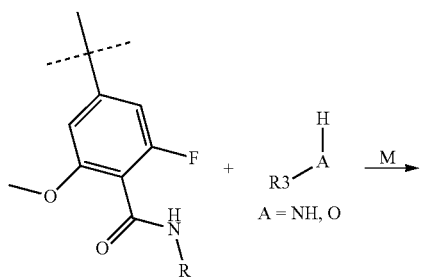

A = NH, O

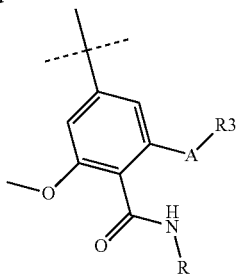

1.2.10.1. Method M1: S$_N$Ar with Amine

In a sealed vial, to a stirred solution of aryl fluoride derivative (1 eq.) in THF are added potassium carbonate (3 eq.) and amine derivative (20 to 50 eq.). The mixture is stirred at 90° C. for 48 h. If completion is not reached at this stage, potassium carbonate (3 eq.) and amine derivative (50 eq.) are added and the mixture is stirred at 90° C., then the mixture is concentrated in vacuo, amine derivative is added (excess) and the mixture is stirred at 90° C. for 18 h, amine derivative (excess) is added again in 3 times and the mixture is stirred at 65° C. for 32 h and at 75° C. for 3 days. The mixture is concentrated in vacuo. Purification by flash chromatography on silica gel or by preparative LCMS affords the desired compound.

Illustrative Synthesis of Cpd 204

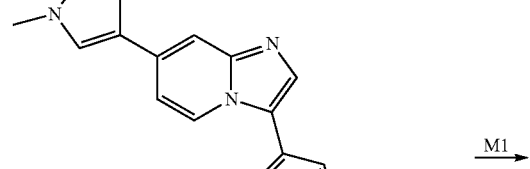

↓ M1

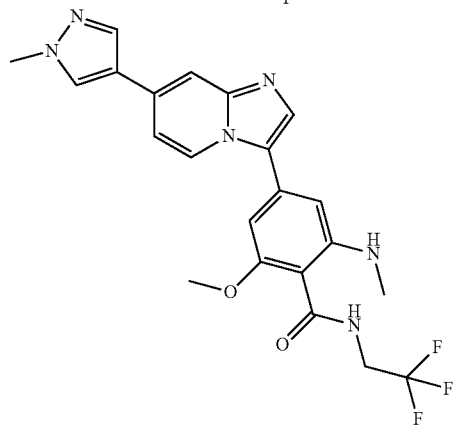

In a sealed vial, to a stirred solution of Cpd 203 (55 mg, 0.12 mmol, 1 eq.) in THF (3 mL) are added potassium carbonate (50 mg, 0.36 mmol, 3 eq.) and a 2 M methylamine solution in THF (1.2 mL, 2.40 mmol, 20 eq.). The mixture is stirred at 90° C. for 48 h. The mixture is concentrated in vacuo. Purification by flash chromatography on silica gel (eluting with 0 to 3% MeOH in DCM) affords the desired compound.

1.2.10.2. Method M2: S$_N$Ar with Alcohol

To a mixture of t-BuOK (3 eq.) and alcohol (excess) stirred for 5 min at RT is added aryl fluoride derivative (1 eq.). The reaction mixture is stirred to 80° C. (2 h to 26 h) and RT for 48 h. If completion is not reached at this stage, t-BuOK (3 eq.) and alcohol (excess) are added and the mixture is stirred to 80° C. for 18 h, then 110° C. for 3 h. The mixture is extracted with DCM and purified by preparative LCMS to afford the expected compound.

Illustrative Synthesis of Cpd 278

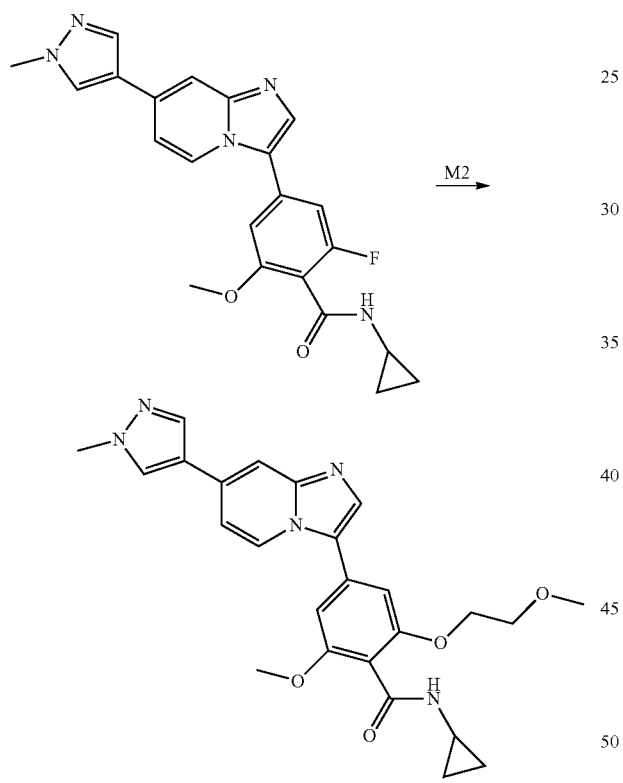

To a mixture of t-BuOK (33 mg, 0.30 mmol, 3 eq.) and 2-methoxyethanol (0.5 mL, excess) stirred for 5 min at RT is added N-cyclopropyl-2-fluoro-6-methoxy-4-[7-(1-methylpyrazol-4-yl)imidazo[1,2-a]pyridin-3-yl]benzamide (Cpd 276) (40 mg, 0.10 mmol, 1 eq.). The reaction mixture is stirred to 80° C. for 2 h and RT for 48 h, extracted with DCM and purified by preparative LCMS to afford the expected compound.

1.2.11. Method N: Pyrazole Alkylation 1.2.11.1. Method N1: Alkylation with Alkyl Halide In a sealed vial, to a stirred solution of pyrazole derivative (1 eq.) in ACN (2 mL) are added K$_2$CO$_3$ (2 eq.) and alkyl halide (1.3 eq.). The reaction mixture is stirred at 60° C. for 2 h and 90° C. overnight or to 90° C. overnight. Further alkyl halide (3.0 eq.) is added and the reaction mixture is stirred at 100° C. (3 h to overnight). The reaction mixture is concentrated in vacuo, diluted with DCM and water. The organic layer is separated and concentrated in vacuo. The residue is purified by flash chromatography on silica gel to afford the expected compound.

Illustrative Synthesis of Cpd 110

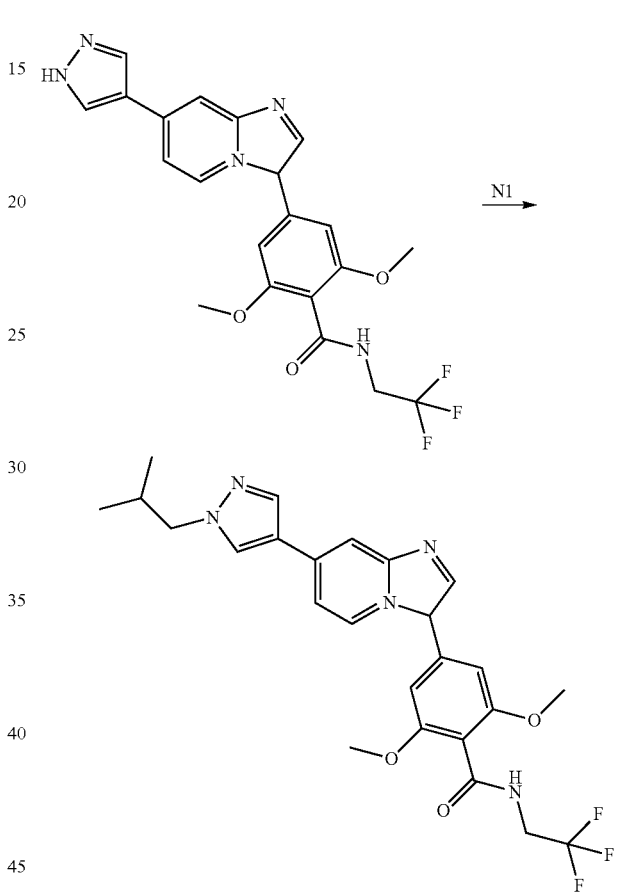

Ina sealed vial, to a stirred solution of Cpd 47 (36 mg, 0.08 mmol, 1 eq.) in ACN (2 mL) are added K$_2$CO$_3$ (22 mg, 0.16 mmol, 2 eq.) and 1-bromo-2-methyl-propane (12 μL, 0.10 mmol, 1.3 eq.). The reaction mixture is stirred at 60° C. for 2 h and at 90° C. overnight. Further 1-bromo-2-methyl-propane (3.0 eq.) is added and the reaction mixture is stirred overnight at 100° C. The reaction mixture is concentrated in vacuo, diluted with DCM and water. The organic layer is separated and concentrated in vacuo. The residue is purified by flash chromatography on silica gel (eluting with DCM/MeOH 100/0 to 95/5) to afford the expected compound.

1.2.11.2. Method N2: Alkylation with Halogenoacetate

To a stirred solution of pyrazole derivative (1 eq.) in DMF are added K$_2$CO$_3$ (1.5 eq.) and halogenoacetate derivative (1.05 eq.). The reaction mixture is stirred at 50° C. for 3 h and at 60° C. for 2 h. The reaction is cooled to RT and water is added. The aqueous layer is extracted with EtOAc and the combined organic layers are washed with brine, dried over MgSO$_4$, filtered, concentrated in vacuo. The residue is purified by filtration over a cake of silica then purified by preparative LCMS then purified by flash chromatography on silica gel to afford the expected compound.

Illustrative Synthesis of Cpd 229

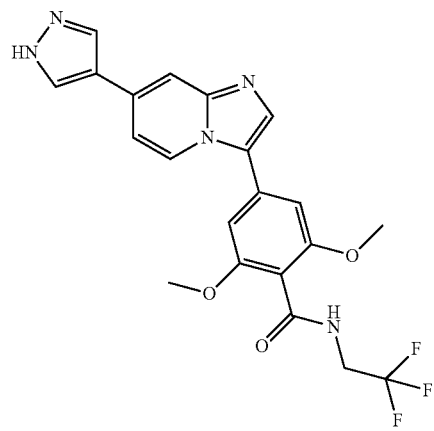

1.2.12. Method O: Amide Alkylation

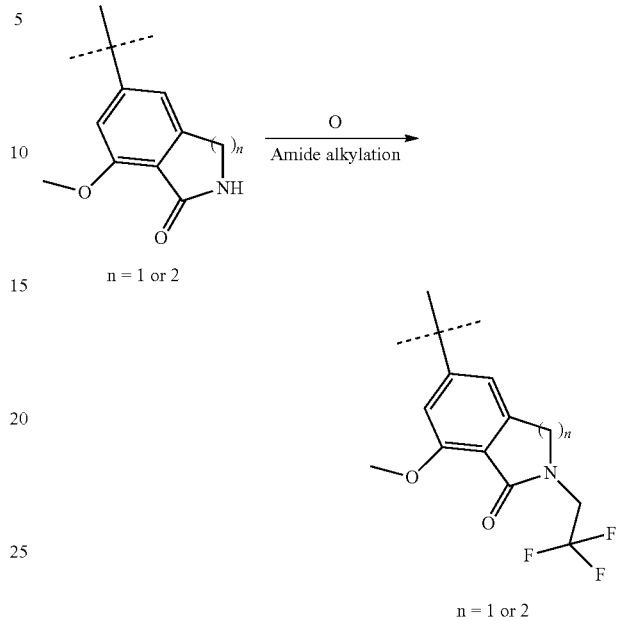

n = 1 or 2

To a stirred mixture of amide derivative (1 eq.) in NMP/THF mixture (1/1) or DMAC at 0° C. is added dropwise a solution of LiHMDS 1N in THF (1.4 to 1.7 eq.). After 15 min of stirring, trifluoromethanesulfonate derivative (1.4 to 1.7 eq.) is added at 0° C. and the reaction mixture is allowed to warm to RT then either stirred at RT overnight and the reaction mixture is quenched by the addition of a saturated NaHCO$_3$ solution, or stirred to 100° C. for 1 h, then to 120° C. for 30 min. In this last case, additional solution of LiHMDS 1 N in THF (1.7 eq.) is added, the reaction mixture is stirred for 15 min, 2,2,2-trifluoroethyl trifluoromethanesulfonate (3.4 eq.) is added and the reaction mixture is stirred to 120° C. for 30 min and the reaction mixture is quenched by the addition of a saturated NaHCO$_3$ solution. The mixture is extracted with EtOAc and the combined organic layers are washed with brine, dried over Na$_2$SO$_4$ or MgSO$_4$, filtered, concentrated in vacuo. The residue is purified by flash chromatography on silica gel and either cristallized in hot ACN or precipitated in Et$_2$O to afford the expected compound.

Illustrative Synthesis of Cpd 225

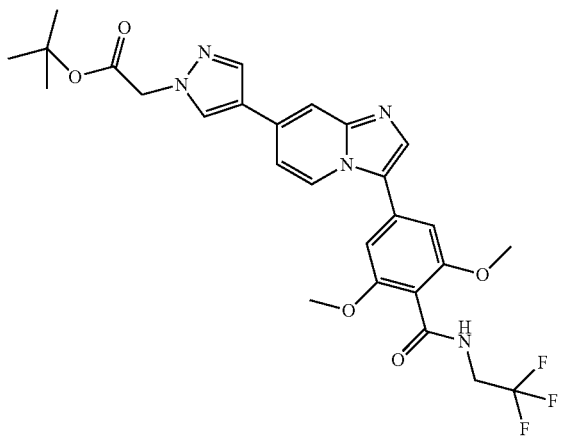

To a stirred solution of Cpd 227 (262 mg, 0.588 mmol, 1 eq.) in DMF (10 mL) are added K$_2$CO$_3$ (122 mg, 0.882 mmol, 1.5 eq.) and tert-butyl 2-chloroacetate (88 µL, 0.618 mmol, 1.05 eq.). The reaction mixture is stirred at 50° C. for 3 h and at 60° C. for 2 h. The reaction is cooled to RT and water is added. The aqueous layer is extracted with EtOAc and the combined organic layers are washed with brine, dried over MgSO$_4$, filtered, concentrated in vacuo. The residue is purified by filtration over a cake of silica (eluting with DCM/MeOH 100/0 to 90/10), then purified by preparative LCMS then purified by flash chromatography on silica gel (eluting with DCM/MeOH 100/0 to 95/5) to afford the expected compound.

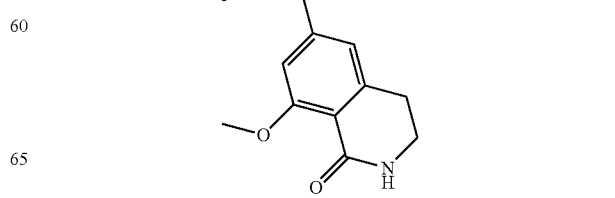

181
-continued

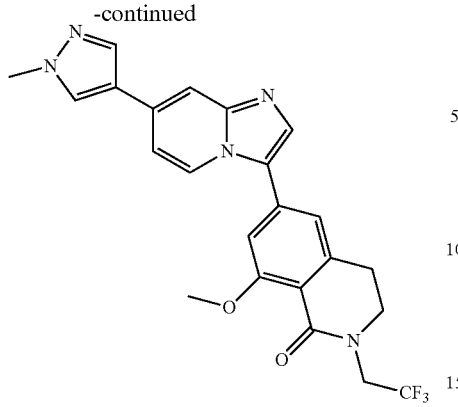

To a stirred mixture of Int 76 (20 mg, 0.054 mmol, 1 eq.) in NMP (2 mL) and THF (1.9 mL) at 0° C. is added dropwise a solution of LiHMDS 1 N in THF (92 µL, 0.093 mmol, 1.7 eq.). After 15 min of stirring, 2,2,2-trifluoroethyl trifluoromethanesulfonate (13.5 µL, 0.093 mmol, 1.7 eq.) is added at 0° C. and the reaction mixture is allowed to warm to RT then stirred to 100° C. for 1 h, then to 120° C. for 30 min. Additional solution of LiHMDS 1 N in THF (92 µL, 0.093 mmol, 1.7 eq.) is added, the reaction mixture is stirred for 15 min and 2,2,2-trifluoroethyl trifluoromethanesulfonate (27 µL, 0.19 mmol, 3.4 eq.) is added. The reaction mixture is stirred to 120° C. for 30 min. The reaction mixture is quenched by the addition of a saturated NaHCO₃ solution, the mixture is extracted with EtOAc and the combined organic layers are washed with brine, dried over Na₂SO₄, filtered, concentrated in vacuo. The residue is purified twice by flash chromatography on silica gel (eluting with DCM/MeOH 100/0 to 95/5) then cristallized in hot ACN to afford the expected compound.

1.2.13. Method P: Cleavage of tert-butyl Ester

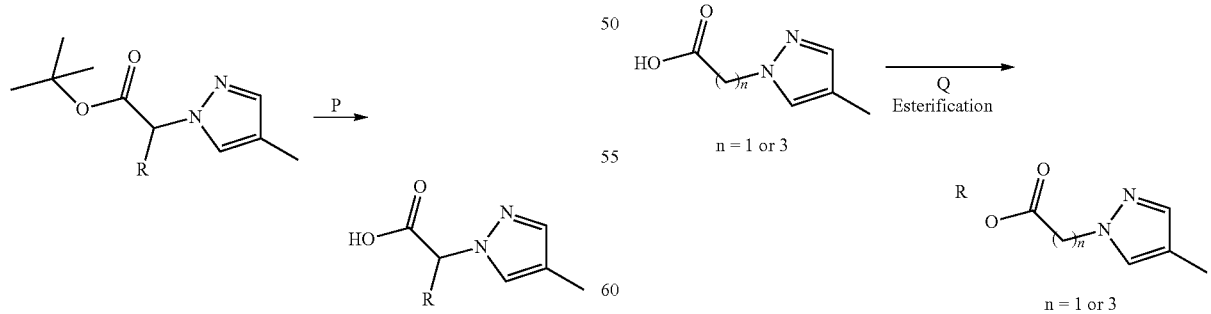

To a stirred solution of tert-butyl ester derivative (1 eq.) in DCM is added a solution of HCl 4 N in dioxane (20 eq.). The reaction mixture is stirred at RT for 48 h and concentrated in vacuo. The solid is taken up in Et₂O, filtered, rinsed with Et₂O to afford the expected compound.

182
Illustrative Synthesis of Cpd 254

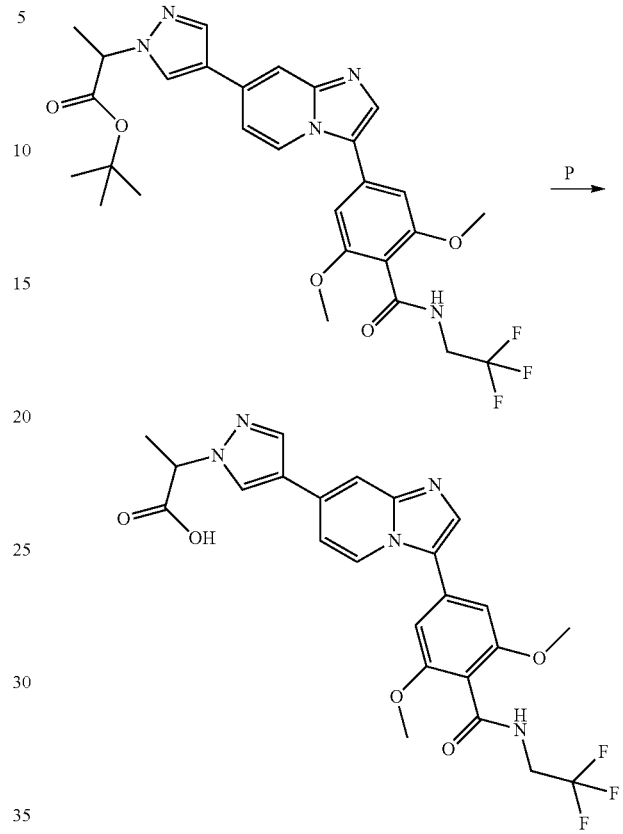

To a stirred solution of Cpd 243 (29 mg, 0.050 mmol, 1 eq.) in DCM (4 mL) is added a solution of HCl 4 N in dioxane (0.25 mL, 0.996 mmol, 20 eq.). The reaction mixture is stirred at RT for 48 h and concentrated in vacuo. The solid is taken up in Et₂O, filtered, rinsed with Et₂O to afford the expected compound.

1.2.14. Method Q: Esterification of Carboxylic Acid

1.2.14.1. Method Q1: HATU

To a stirred solution of carboxylic acid or sodium carboxylate derivative (1 eq.) in DMF is added HATU (1.1 eq.)

and alcohol derivative (2.4 eq.). The reaction mixture is stirred at RT overnight then to 50° C. for 1.5 h. HATU (1.1 eq.) and DIPEA (2 eq.) are added and the reaction mixture is stirred to 50° C. for 4 h. The reaction mixture is purified by preparative LCMS to afford the expected compound.

Illustrative Synthesis of Cpd 235

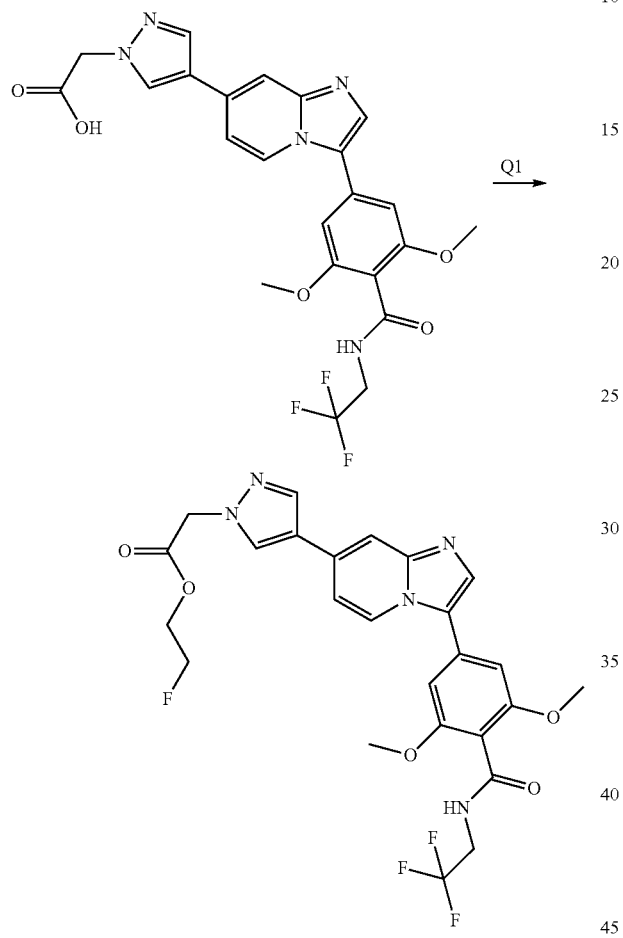

To a stirred solution of Cpd 228 (0.054 mmol, 1 eq.) in DMF (1 mL) is added HATU (23 mg, 0.06 mmol, 1.1 eq.) and 2-fluoroethanol (8 µL, 0.13 mmol, 2.4 eq.). The reaction mixture is stirred at RT overnight then to 50° C. for 1.5 h. HATU (23 mg, 0.06 mmol, 1.1 eq.), DIPEA (19 µL, 0.11 mmol, 2 eq.) are added and the reaction mixture is stirred to 50° C. for 4 h. The reaction mixture is purified by preparative LCMS to afford the expected compound.

1.2.14.2. Method Q2: SOCl$_2$ 1.2.14.2.1 Method Q2i: SOCl$_2$/RT

To a stirred solution of carboxylic acid derivative (1 eq.) in alcohol derivative (1 mL) is added SOCl$_2$ (1.5 to 6 eq., in one or 2 times over 18 h) and the reaction mixture is stirred at RT (18 h to 70 h). The mixture is either concentrated in vacuo, dissolved in DCM/MeOH mixture, neutralized with NaHCO$_3$, purified by flash chromatography on silica gel to afford the expected compound or water and NaHCO$_3$ are added, volatiles are concentrated in vacuo, the mixture is extracted with DCM by filtration over hydrophobic column, concentrated in vacuo. Either the residue is purified by flash chromatography on silica gel to afford the expected compound or ACN is added before complete evaporation, evaporation is kept on going until a small amount of solvent is left and the solid is filtered to afford the expected compound.

Illustrative Synthesis of Cpd 236

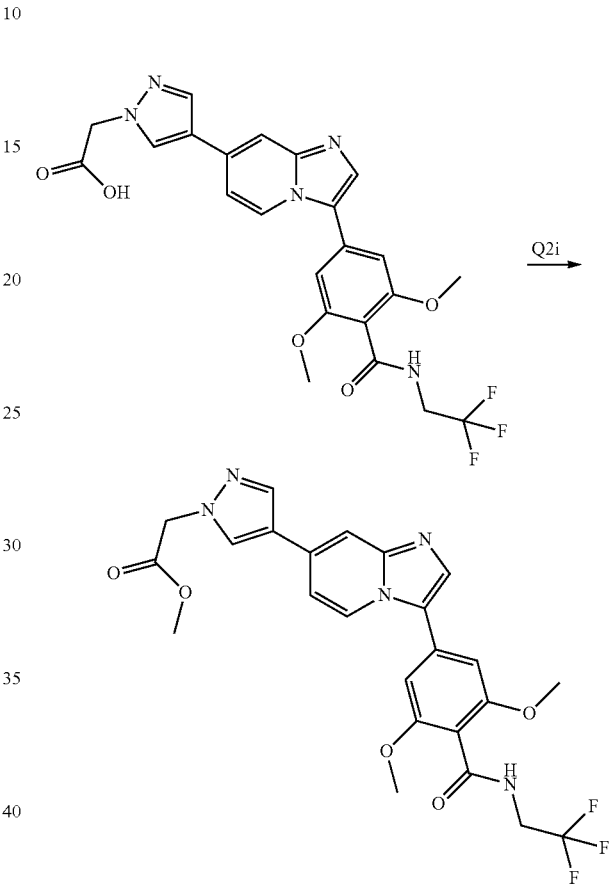

To a stirred solution of Cpd 228 (23 mg, 0.046 mmol, 1 eq.) in MeOH (1 mL) is added SOCl$_2$ (5 µL, 0.068 mmol, 1.5 eq.) and the reaction mixture is stirred at RT overnight. SOCl$_2$ (5 µL, 0.068 mmol, 1.5 eq.) is added and the reaction mixture is stirred at RT for 48 h, concentrated in vacuo, dissolved in DCM/MeOH mixture, neutralized with NaHCO$_3$, purified by flash chromatography on silica gel (eluting with DCM/MeOH 100/0 to 95/5) to afford the expected compound.

1.2.14.2.2 Method Q2ii: SOCl$_2$/60° C.

In a screw cap vial, to a stirred mixture of carboxylic acid derivative (1 eq.) in DCM is added SOCl$_2$ (3 eq.) and alcohol derivative (2 eq.) and the reaction mixture is stirred at RT overnight. Further alcohol derivative (excess) is added and the reaction mixture is stirred to 40° C. for 1 h. DCM is evaporated and SOCl$_2$ (6 eq.) is added in 4 times over 5.5 days while stirring to 60° C. The reaction mixture is concentrated in vacuo, neutralized with NaHCO$_3$, purified by flash chromatography on silica gel, optionally cristallized in DCM/Et$_2$O mixture to afford the expected compound.

Illustrative Synthesis of Cpd 237

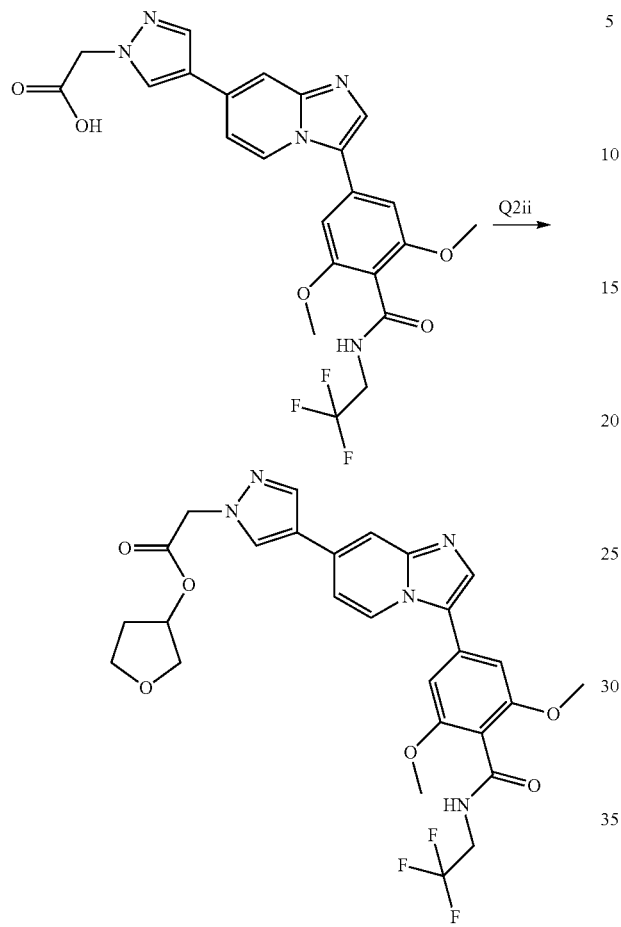

In a screw cap vial, to a stirred mixture of Cpd 228 (20 mg, 0.040 mmol, 1 eq.) in DCM (1 mL) is added SOCl₂ (8.6 µL, 0.12 mmol, 3 eq.) and tetrahydrofuran-3-ol (6.4 µL, 0.08 mmol, 2 eq.) and the reaction mixture is stirred at RT overnight. Further tetrahydrofuran-3-ol (0.2 mL, excess) is added and the reaction mixture is stirred to 40° C. for 1 h. DCM is evaporated, SOCl₂ (4.3 µL, 0.06 mmol, 1.5 eq.) is added and the mixture is stirred to 60° C. for 24 h. SOCl₂ (4.3 µL, 0.06 mmol, 1.5 eq.) is added and the mixture is stirred at 60° C. for 24 h and at RT for 3 days. SOCl₂ (4.3 µL, 0.06 mmol, 1.5 eq.) is added and the mixture is stirred to 50° C. for 4 h. SOCl₂ (4.3 µL, 0.06 mmol, 1.5 eq.) is added and the mixture is stirred to 60° C. for 3 h. The reaction mixture is concentrated in vacuo, neutralized with NaHCO₃, purified by flash chromatography on silica gel (eluting with DCM/MeOH 100/0 to 90/10), cristallized in DCM/Et₂O mixture to afford the expected compound.

1.2.14.3. Method Q3: Alkyl Bromide/Cs₂CO₃

To a stirred mixture of carboxylic acid derivative (1 eq.) in DMF are added Cs₂CO₃ (2 eq.) and alkyl bromide derivative (1.2 eq.). The reaction mixture is stirred to 60° C. for 2 h. Alkyl bromide derivative (1.8 eq.) and Cs₂CO₃ (1 eq.) are added and the reaction mixture is stirred to 60° C. for 20 h. The reaction mixture is purified by preparative LCMS and by flash chromatography on silica gel to afford the expected compound.

Illustrative Synthesis of Cpd 238

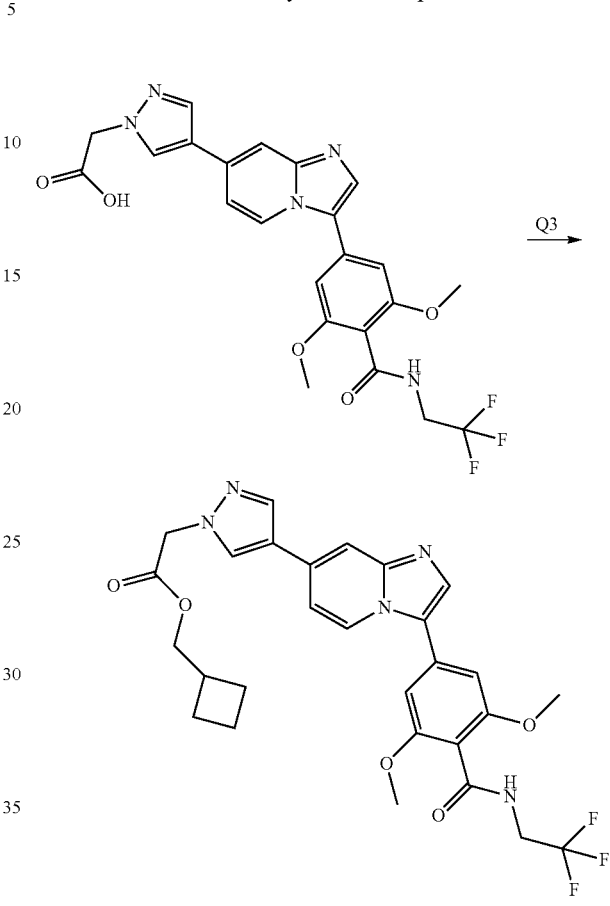

To a stirred mixture of Cpd 228 (24 mg, 0.048 mmol, 1 eq.) in DMF (1 mL) are added Cs₂CO₃ (31 mg, 0.095 mmol, 2 eq.) and bromomethylcyclobutane (6.4 µL, 0.057 mmol, 1.2 eq.). The reaction mixture is stirred to 60° C. for 2 h. Bromomethylcyclobutane (9.6 µL, 0.087 mmol, 1.8 eq.) and Cs₂CO₃ (15 mg, 0.047 mmol, 1 eq.) are added and the reaction mixture is stirred to 60° C. for 20 h. The reaction mixture is purified by preparative LCMS then by flash chromatography on silica gel (eluting with DCM/MeOH 100/0 to 95/5) to afford the expected compound.

1.2.15. Method R: Transesterification of tert-butyl Ester

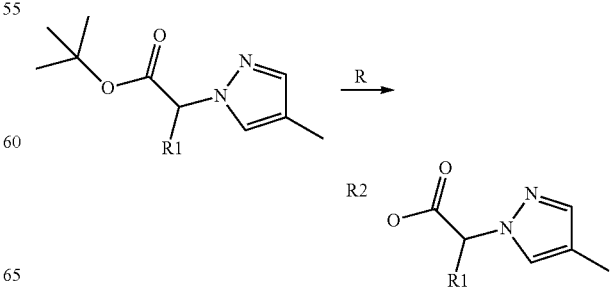

To a stirred solution of tert-butyl ester derivative (1 eq.) in alcohol derivative is added HCl 4 N in dioxane (100 eq.) and the reaction mixture is stirred at RT for 24 h or at 60° C. (0.5 to 1.5 h). The reaction mixture is concentrated in vacuo and either dissolved in DMSO, neutralized by NaHCO₃ and purified by preparative LCMS to afford the expected compound or taken up in DCM and an aqueous solution of NaHCO₃, the mixture is extracted with DCM, dried by filtration over hydrophobic column, concentrated in vacuo, purified by flash chromatography on silica gel to afford the expected compound or taken up in DCM and an aqueous solution of NaHCO₃, the mixture is extracted with DCM, dried by filtration over hydrophobic column, concentrated in vacuo after Et₂O is added and the solid obtained is taken up in Et₂O and filtered to afford the expected compound.

Illustrative Synthesis of Cpd 231

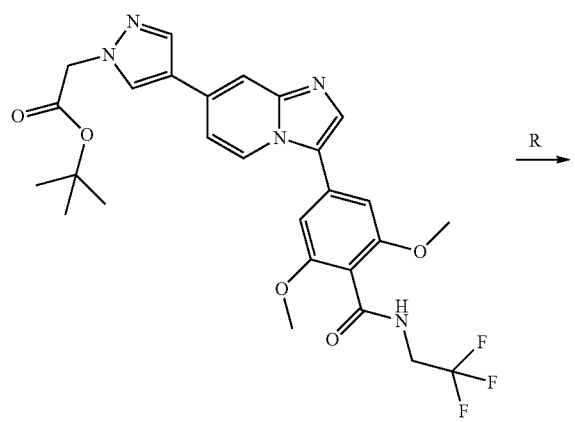

R →

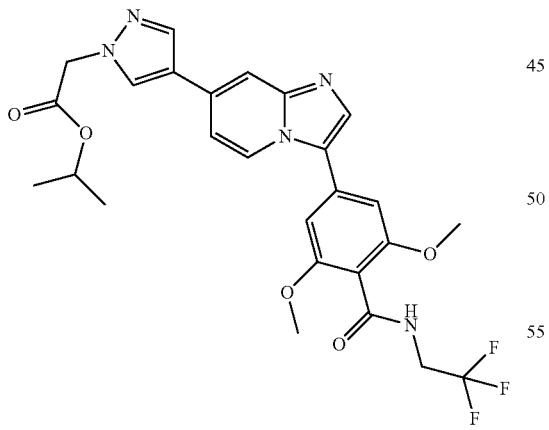

To a stirred solution of Cpd 229 (20 mg, 0.036 mmol, 1 eq.) in propan-2-ol (1 mL) is added HCl 4 N in dioxane (0.89 mL, 3.6 mmol, 100 eq.) and the reaction mixture is stirred to 60° C. for 1.5 h. The reaction mixture is concentrated in vacuo, dissolved in DMSO, neutralized by NaHCO₃ and purified by preparative LCMS to afford the expected compound.

Example 2. Preparation of the Compounds of the Invention 2.1. Int 1

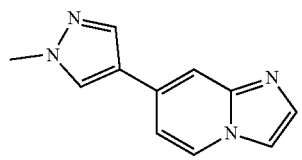

7-bromoimidazo[1,2-a]pyridine (CAS #808744-34-5; 100 g, 507.54 mmol, 1 eq.), 1-methylpyrazole-4-boronic acid pinacol ester (CAS #761446-44-0; 116.18 g, 558.29 mmol, 1.1 eq.), Na₂CO₃ (161.37 g, 1522.61 mmol, 3 eq.) are added to a dioxane/water solvent mixture: 3/1 (1 L). The mixture is degassed with N₂ then Pd(dppf)Cl₂.DCM adduct (2.07 g, 2.54 mmol, 0.005 eq.) is added and the mixture is stirred to 100° C. for 6 h. The mixture is cooled to RT, filtered over Celite®, rinsed with DCM and the filtrate is concentrated in vacuo. The residue is dissolved in DCM/n-BuOH mixture (9/1, 1 L) and water (1 L) is added. The organic layer is separated and the aqueous layer is extracted with DCM (1 L), then with DCM/n-BuOH mixture (9/1, 0.5 L). The combined organic layer is washed with brine (0.5 L), dried over anhydrous Na₂SO₄, filtered and concentrated in vacuo. The residue is triturated in MTBE (0.3 L) at RT, the suspension is filtered and the solid is washed with MTBE, then dried in vacuo to afford the expected intermediate.

2.2. Int 2

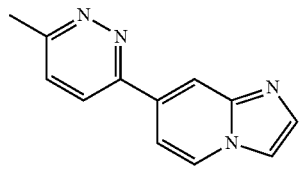 [SMILES: Cc1ccc(-c2ccn3ccnc3c2)nn1]

In a sealed tube is charged 7-(4,4,5,5-tetramethyl-1,3,2-dioxaborolan-2-yl)imidazo[1,2-a]pyridine (CAS #908268-52-0; 0.5 g, 2.05 mmol, 1 eq.), 3-chloro 6-methyl pyridazine (CAS #1121-79-5; 316 mg, 2.46 mmol, 1.2 eq.), Cs₂CO₃ (1.34 g, 4.10 mmol, 2 eq.), Pd(dppf)Cl₂.DCM (167 mg, 0.20 mmol, 0.1 eq.) and a dioxane/water 4/1 solvent mixture (10 mL) degassed with N₂. The system is purged with N₂ then the mixture is stirred at 90° C. for 1 h. The reaction mixture is cooled down to RT, diluted in EtOAc, filtered over Celite®. The filtrate is concentrated in vacuo and used in the next step without further purification.

2.3. Int 4

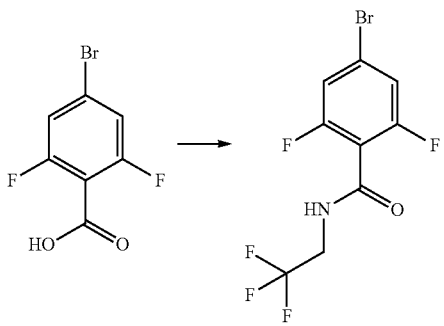 [SMILES: O=C(O)c1c(F)cc(Br)cc1F ; O=C(NCC(F)(F)F)c1c(F)cc(Br)cc1F]

4-bromo-2,6-difluorobenzoic acid (90.5 g, 381.86 mmol, 1.0 eq.) is added to SOCl₂ (181 mL, 2 volumes, 6.5 eq.). The reaction mixture is stirred at reflux. After 6 h of reflux, the heating is stopped and the reaction mixture is cooled down to RT and then concentrated in vacuo. The residue is diluted with toluene (181 mL, 2 volumes) and concentrated to eliminate residual thionyl chloride.

The liquid residue is diluted with DCM (453 mL, 5 volumes). Trifluoro ethylamine hydrochloride (54.34 g, 400.95 mmol, 1.05 eq.) is added to the reaction mixture under N₂ atmosphere and the latter is cooled to 5° C. Et₃N (117.09 mL, 840.08 mmol, 2.2 eq.) is then added dropwise keeping the temperature of the reaction mixture under 27° C. The reaction mixture is then stirred under N₂ at RT for 14 h. The suspension is diluted with DCM (1000 mL, 10 volumes). The organic phase is washed with water (500 mL, 5 volumes) and sat. NaHCO₃ (500 mL, 5 volumes). The organic phase is dried on Na₂SO₄ (100 g), filtered, concentrated and triturated with heptane (500 mL, 6 volumes). The suspension is filtered and washed with heptane (500 mL, 6 volumes) and the solid is dried under reduced pressure to give Int 4.

2.4. Int 5

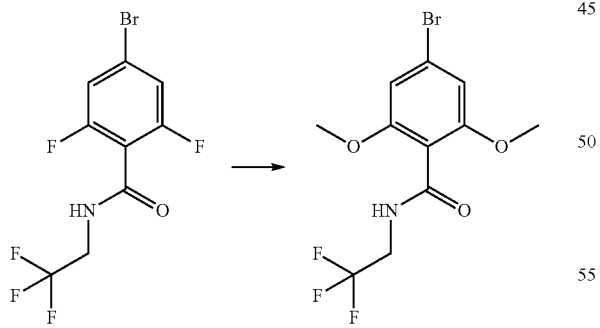

To a solution of Int 4,4-bromo-2,6-difluoro-N-(2,2,2-trifluoroethyl)benzamide (110.20 g, 346.50 mmol, 1.0 eq.) in NMP (551 mL, 5 volumes) under N₂ is added sodium methoxide (56.15 g, 1.04 mol., 3 eq.). The reaction mixture is heated to 90° C. After 1.5 h at 90° C., the reaction mixture is cooled to RT and water (1100 mL, 10 volumes) is added and precipitation occurs. The suspension is filtered and the cake is washed with water (3*1100 mL). The solid is dried at 55° C. under vacuum (3 days) to afford Int 5.

2.5. Int 6

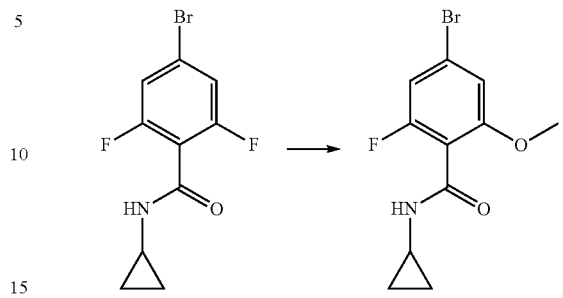

A mixture of Int 62 (1 g, 3.62 mmol, 1 eq.) and sodium methoxide (0.23 g, 4.35 mmol, 1.2 eq.) in DMSO (5 mL) is heated at 60° C. for 24 h. The reaction mixture is cooled down to RT and poured into water (50 mL). The solid formed is filtered, washed with water, and dried to give the expected compound Int 6.

2.6. Int 7

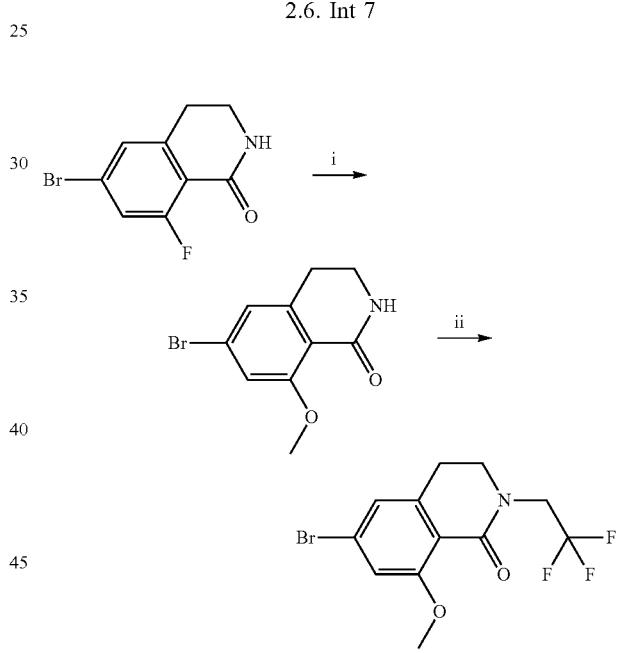

2.6.1. Step i: 6-bromo-8-methoxy-3,4-dihydro-2H-isoquinolin-1-one

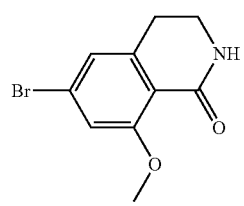

To a stirred solution of 6-bromo-8-fluoro-3,4-dihydro-2H-isoquinolin-1-one (CAS #1242157-15-8; 3 g, 12.29 mmol, 1 eq.) in THF (30 mL) is added dropwise a solution of MeONa 25 w % in MeOH (3.35 mL, 14.75 mmol, 1.2 eq.). Further THF (10 mL) is added during the addition of sodium methylate solution. The reaction mixture is stirred at RT for 2 h, quenched with a saturated aqueous NH$_4$Cl solution and THF is evaporated. The solid obtained in the remaining water is filtered to afford the desired compound LCMS: MW (calcd): 256.1; m/z MW (obsd): 256.1-258.1.

2.6.2. Step ii: 6-bromo-8-methoxy-2-(2,2,2-trifluoroethyl)-3,4-dihydroisoquinolin-1-one

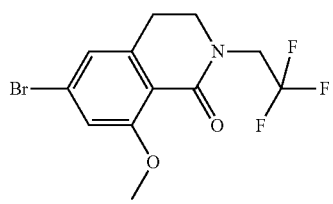 [SMILES: COc1cc(Br)cc2c1C(=O)N(CC(F)(F)F)CC2]

To a stirred solution of 6-bromo-8-methoxy-3,4-dihydro-2H-isoquinolin-1-one (1.95 g, 7.61 mmol, 1 eq.) in THF (45 mL) at 0° C. is added dropwise a solution of LiHMDS 1 N in THF (11.4 mL, 11.4 mmol, 1.5 eq.). The resulting mixture is stirred for 15 min at 0° C. and 2,2,2-trifluoroethyl trifluoromethanesulfonate (1.64 mL, 11.4 mmol, 1.5 eq.) is added at 0° C. The reaction mixture is warmed slowly to RT and stirred at RT overnight then to 65° C. for 2.5 h, then to 80° C. for 2 h. The reaction mixture is quenched with water. THF is evaporated and the aqueous layer is extracted with EtOAc. The combined organic layers are washed with brine, dried over anhydrous Na$_2$SO$_4$, filtered and concentrated in vacuo. The residue is purified by flash chromatography on silica gel (eluting with DCM/MeOH 100/0 to 95/5) to afford Int 7.

2.7. Int 8

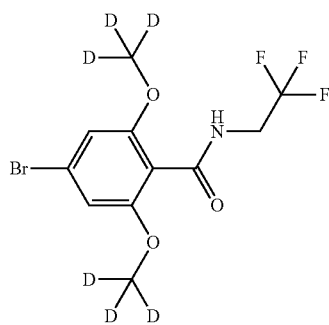 [SMILES: [2H]C([2H])([2H])Oc1cc(Br)cc(OC([2H])([2H])[2H])c1C(=O)NCC(F)(F)F]

To a solution of CD$_3$OD (2.36 mL, 58.00 mmol, 3.0 eq.) in NMP (26.35 mL, 5 volumes) under N$_2$ is cooled to 0° C. with an ice bath and is added by portion NaH (1.99 g, 60% in oil, 3 eq.). The reaction mixture is stirred at RT for 30 min and then Int 4 (5.27 g, 16.57 mmol, 1.0 eq.) is added to the mixture. The reaction mixture is heated to 90° C. for 1.5 h. The reaction mixture is cooled to RT and water (60 mL, 10 volumes) is added. The suspension is filtered and the cake is washed with water (3*60 mL) and heptane (3*60 mL because of the oil from NaH). The solid is dried at 40° C. under vacuum to afford Int 8.

2.8. Int 9

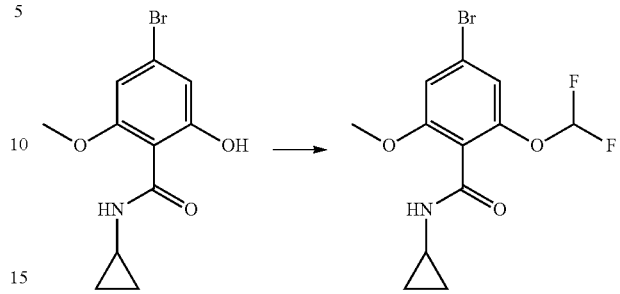

Ina 15 L single jacketed process reactor, potassium hydroxide (10 eq., 243 g) is added to a solution of Int 64 (1 eq., 124 g) in ACN/water (ACN/H$_2$O 1/1, 10 V, 1240 mL). The reaction mixture is cooled to 5° C. (jacket temperature from 20° C. to 0° C. in 40 min). Diethyl (bromodifluoromethyl)phosphonate (2 eq., 154 mL) is added neat over 1 h into the solution at 5° C. (jacket temperature set at 0° C.), while keeping the reaction temperature below 18° C. At the end of the addition, the reaction mixture is warmed up to 20° C. and stirred at 20° C. for 30 min.

The aqueous phase is extracted three times with EtOAc (3*650 mL, 3*5 V). The organic phases are combined and washed once with NaCl 20% (5 V, 650 mL) and concentrated.

The crude is re-slurried in MTBE (3 V/theoretical mass, 400 mL) for 30 min at 20° C. The suspension is filtered and the solid is washed with MTBE (140 mL). The solid is dried to afford Int 9.

Int 9 $^1$H NMR (400 MHz, DMSO-d$_6$) δ ppm 8.31 (1H, broad s), 7.34-6.98 (3H, m), 3.84 (3H, s), 2.74 (1H, m), 0.66 (2H m), 0.43 (2H m).

2.9. Int 10

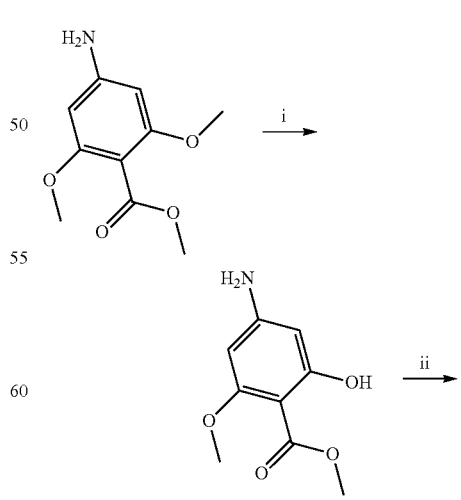

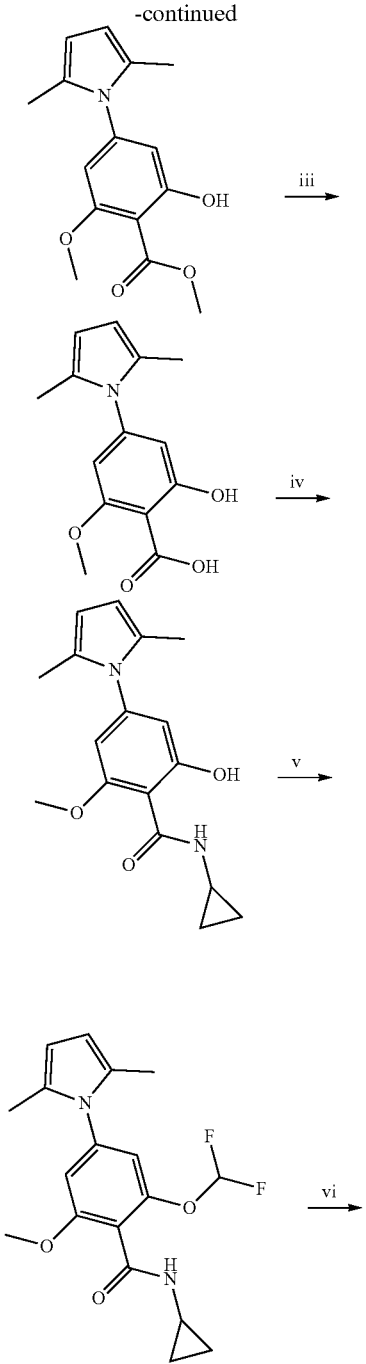

2.9.1. Step i: methyl 4-amino-2-hydroxy-6-methoxy-benzoate

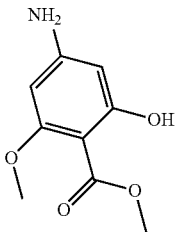

To a solution of methyl 4-amino-2,6-dimethoxy-benzoate (CAS #3956-34-1; 8.75 g, 41 mmol, 1 eq.) in dry DCM (230 mL) under $N_2$ atmosphere is added $BCl_3$ 1 M in DCM (91 mL, 91 mmol, 2.2 eq.) dropwise at 0° C. stirred for 45 min and at RT overnight. HCl 2 N and ice-water is added and the mixture is extracted twice with DCM. The combined organic layers are washed with water, brine, dried over anhydrous $Na_2SO_4$, and evaporated in vacuo to afford the desired product.

LCMS: MW (calcd): 197.1; m/z MW (obsd): 198.2 (M+H).

2.9.2. Step ii: methyl 4-(2,5-dimethylpyrrol-1-yl)-2-hydroxy-6-methoxy-benzoate

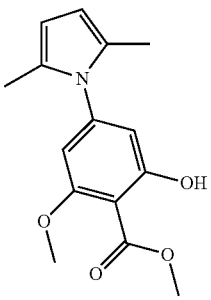 [SMILES: COC(=O)c1c(O)cc(-n2c(C)ccc2C)cc1OC]

To a solution of methyl 4-amino-2-hydroxy-6-methoxy-benzoate (4.72 g, 24 mmol, 1 eq.) in AcOH (100 mL) is added 2.5-hexadione (5.62 mL, 48 mmol, 2 eq.) and is stirred at 110° C. for 15 min then at RT for 1.5 h. The mixture is evaporated in vacuo and is purified by chromatography on silica gel column (heptane/EtOAc, 50/50 v/v) to afford the desired product.

LCMS: MW (calcd): 275.3; m/z MW (obsd): 276.3 (M+H).

2.9.3. Step iii: 4-(2,5-dimethylpyrrol-1-yl)-2-hydroxy-6-methoxy-benzoic Acid

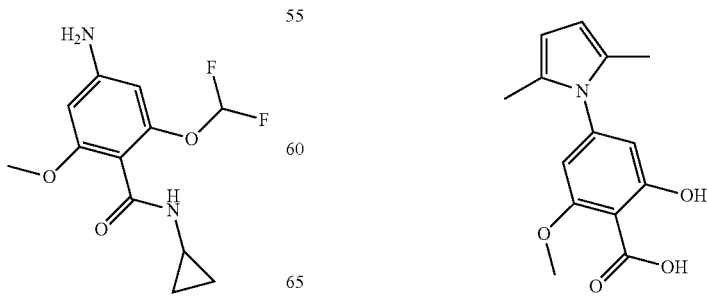

To a solution of methyl 4-(2,5-dimethylpyrrol-1-yl)-2-hydroxy-6-methoxy-benzoate (6.10 g, 22 mmol) in MeOH (100 mL) is added a solution of NaOH 2 N (133 mL, 266 mmol, 12 eq.). Then, the reaction mixture is stirred at 100° C. for 18 h. MeOH is concentrated in vacuo then the aqueous layer is acidified with HCl 2 N (140 mL) and extracted with DCM three times. The combined organic layers are dried over Na₂SO₄, filtered off and concentrated in vacuo to afford the expected product.

LCMS: MW (calcd): 261.2; m/z MW (obsd): 262.2 (M+H).

2.9.4. Step iv: N-cyclopropyl-4-(2,5-dimethylpyrrol-1-yl)-2-hydroxy-6-methoxy-benzamide

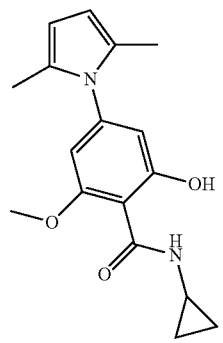 [SMILES: COc1cc(-n2c(C)ccc2C)cc(O)c1C(=O)NC1CC1]

To a stirred solution of 4-(2,5-dimethylpyrrol-1-yl)-2-hydroxy-6-methoxy-benzoic acid (10 g, 38.27 mmol, 1 eq.) and HATU (16.01 g, 42.10 mmol, 1.1 eq.) in anhydrous DMF (200 mL) is added DIPEA (13.34 mL, 76.54 mmol, 2 eq.). The mixture is stirred at RT for 10 min and cyclopropylamine (3.18 mL, 45.92 mmol, 1.2 eq.) is added. The resulting mixture is stirred at RT for 2 h. The reaction mixture is evaporated to dryness and then diluted with EtOAc and water. The organic layer is separated, dried over Na₂SO₄, filtered and concentrated under reduced pressure. The residue is purified by chromatography on silica gel, eluting with 0-30% EtOAc in heptanes. The product fractions ae combined and evaporated to dryness to afford the title compound.

LCMS: MW (calcd): 300.3; m/z MW (obsd): 301.3 (M+H).

2.9.5. Step v: N-cyclopropyl-2-(difluoromethoxy)-4-(2,5-dimethylpyrrol-1-yl)-6-methoxy-benzamide

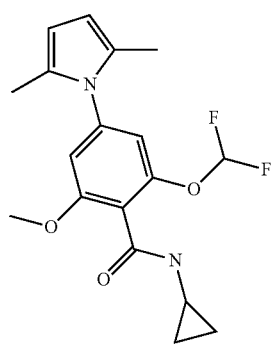 [SMILES: COc1cc(-n2c(C)ccc2C)cc(OC(F)F)c1C(=O)NC1CC1]

To a stirred solution of N-cyclopropyl-4-(2,5-dimethylpyrrol-1-yl)-2-hydroxy-6-methoxy-benzamide (6.33 g, 21.07 mmol, 1 eq.) in ACN (100 mL) at −10° C. is added dropwise KOH (23.65 g, 421.40 mmol, 20 eq.) in H₂O (100 mL). The resulting mixture is stirred at −10° C. for 25 min and diethyl (bromodifluoromethyl)phosphonate (7.49 mL, 44.14 mmol, 2 eq.) in ACN (15 mL) is added dropwise. The mixture is quenched with ice/H₂O and extracted twice with DCM. The organic layers are dried over Na₂SO₄, filtered and concentrated under reduced pressure. The residue is purified on a 2×100 g HP column (Biotage), eluted with 0-2% MeOH in DCM. The product fractions are combined and evaporated to dryness to afford the title compound.

LCMS: MW (calcd): 350.3; m/z MW (obsd): 351.5 (M+H).

2.9.6. Step vi: Int 10

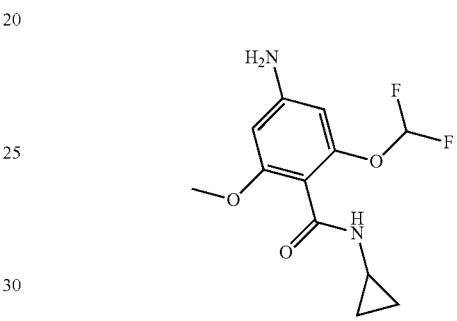

To a stirred solution of N-cyclopropyl-2-(difluoromethoxy)-4-(2,5-dimethylpyrrol-1-yl)-6-methoxy-benzamide (6.78 g, 19.35 mmol, 1 eq.) in EtOH (100 mL) at RT is added hydroxylamine hydrochloride (13.45 g, 193.51 mmol, 10 eq.) in H₂O (50 mL). The resulting mixture is stirred overnight at 110° C. Hydroxylamine hydrochloride (5 eq.) and Et₃N (2 eq.) are added. The resulting mixture is stirred at 110° C. for 3 h 30 min. EtOH is concentrated in vacuo. The aqueous phase is brought to pH 9 with NaOH 2N and extracted twice with EtOAc. The organic layers are dried over Na₂SO₄, filtered and concentrated under reduced pressure. The residue is purified by chromatography on silica gel eluting with 0-5% MeOH in DCM. The product fractions are combined and concentrated in vacuo. The solid is triturated with Et₂O and filtered to afford the title compound LCMS: MW (calcd): 272.2; m/z MW (obsd): 273.2 (M+H).

2.10. Int 11

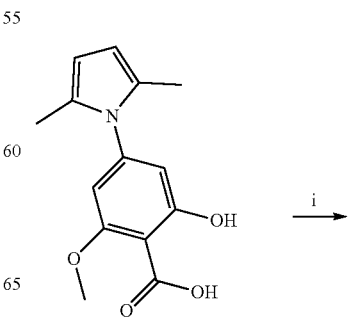

-continued

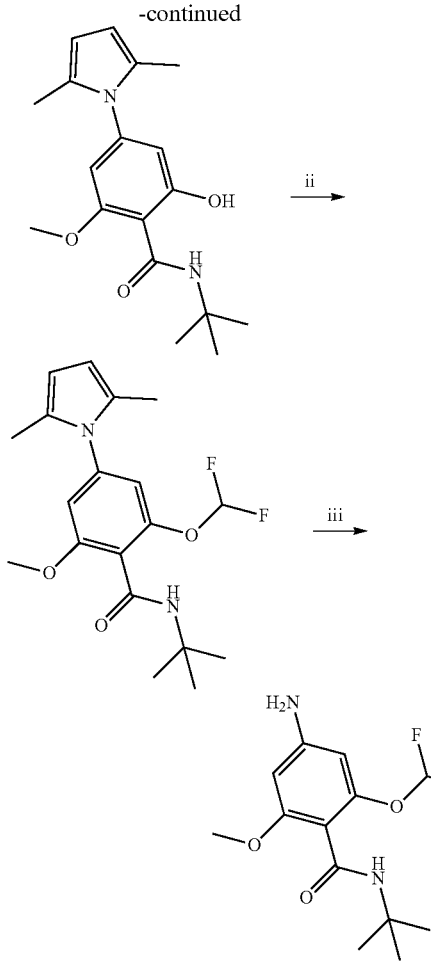

2.10.1. Step i: N-tert-butyl-4-(2,5-dimethylpyrrol-1-yl)-2-hydroxy-6-methoxy-benzamide

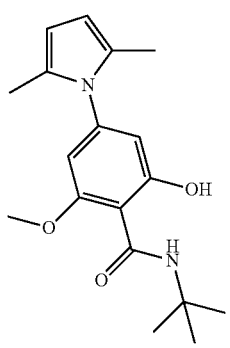 [SMILES: COc1cc(-n2c(C)ccc2C)cc(O)c1C(=O)NC(C)(C)C]

To a stirred solution of 4-(2,5-dimethylpyrrol-1-yl)-2-hydroxy-6-methoxy-benzoic (cf. Int 10 synthesis, Ex. 2.9.3) (5.6 g, 21.4 mmol, 1.0 eq.) and HATU (10.6 g, 27.8 mmol, 1.3 eq.) in anhydrous DMF (25 mL) is added DIPEA (7.3 mL, 42.8 mmol, 2.0 eq.). The mixture is stirred at RT for 10 min and tert-butylamine (4.5 mL, 42.8 mmol, 2.0 eq.) is added. The reaction mixture is evaporated to dryness and then diluted with EtOAc and water. The organic layer is separated, dried over Na$_2$SO$_4$, filtered and concentrated under reduced pressure. Purification by flash chromatography on silica gel (eluting with DCM/heptane 2/1; 4/1; 9/1) affords the desired compound.

LCMS: MW (calcd): 316.4; m/z MW (obsd): 317.7 (M+H).

2.10.2. Step ii: N-tert-butyl-2-(difluoromethoxy)-4-(2,5-dimethylpyrrol-1-yl)-6-methoxy-benzamide

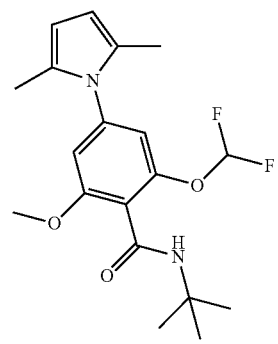 [SMILES: COc1cc(-n2c(C)ccc2C)cc(OC(F)F)c1C(=O)NC(C)(C)C]

To a stirred solution of N-tert-butyl-4-(2,5-dimethylpyrrol-1-yl)-2-hydroxy-6-methoxy-benzamide in ACN (20 mL) at −10° C. is added dropwise KOH (5.3 g, 94.8 mmol, 20 eq.) in H$_2$O (20 mL). The resulting mixture is stirred at −10° C. for 10 min and diethyl (bromodifluoromethyl)phosphonate (1.5 mL, 9.5 mmol, 2.0 eq.) is added dropwise. The mixture is stirred 30 min at 0° C. The mixture is quenched with ice/H$_2$O and extracted twice with DCM. The ACN is concentrated under reduced pressure. The expected product is filtered and washed with water.

LCMS: MW (calcd): 366.4; m/z MW (obsd): 367.8 (M+H).

2.10.3. Step iii: Int 11

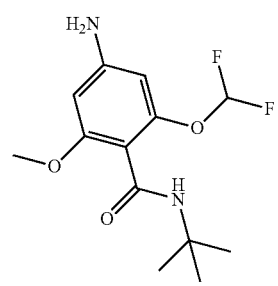 [SMILES: COc1cc(N)cc(OC(F)F)c1C(=O)NC(C)(C)C]

To a stirred solution of N-tert-butyl-2-(difluoromethoxy)-4-(2,5-dimethylpyrrol-1-yl)-6-methoxy-benzamide (1.5 g, 4.1 mmol, 1 eq.) in EtOH (50 mL) and H$_2$O (25 mL) at RT is added Et$_3$N (1.2 mL, 8.2 mmol, 2.0 eq.) and hydroxylamine hydrochloride (2.9 g, 41 mmol, 10 eq.). The resulting mixture is stirred overnight at 100° C. EtOH is evaporated. The aqueous phase is brought to pH 9 with NaOH 2 N and extracted twice with DCM. The organic layers are dried over Na$_2$SO$_4$, filtered and concentrated under reduced pressure. Purification by flash chromatography on silica gel (eluting with DCM then with DCM/MeOH 95/5) affords the desired compound.

2.11. Int 12

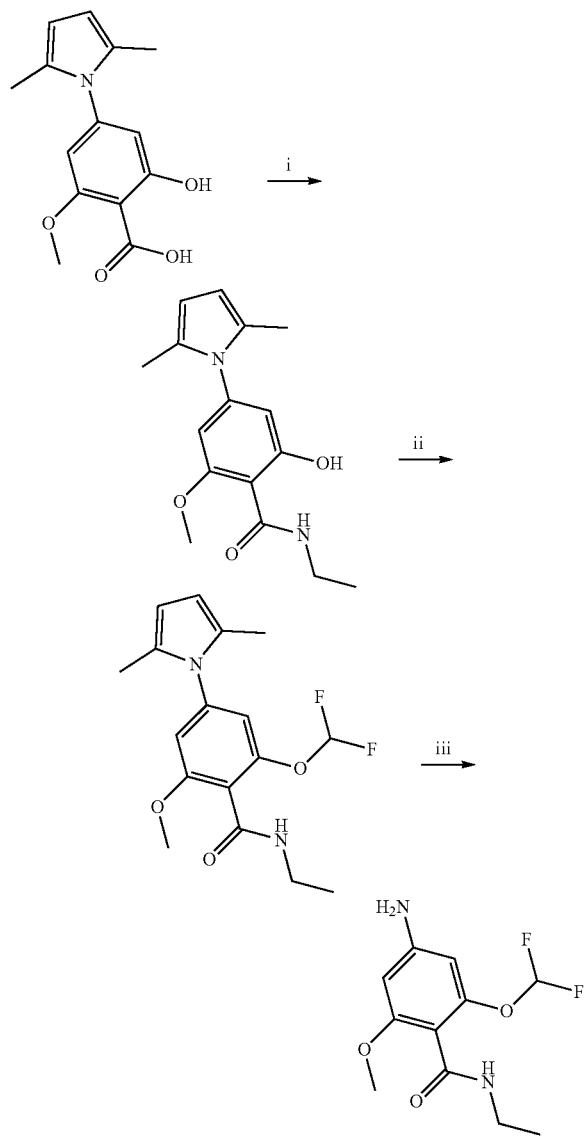

2.11.1. Step i: 4-(2,5-dimethylpyrrol-1-yl)-N-ethyl-2-hydroxy-6-methoxy-benzamide To a solution of 4-(2,5-dimethylpyrrol-1-yl)-2-hydroxy-6-methoxy-benzoic acid (cf. Int 10 synthesis, Ex. 2.9.3) (5.57 g, 21 mmol, 1 eq.) in dry DMF (50 mL) are added HATU (8.92 g, 23 mmol, 1.1 eq.) and DIPEA (29.71 mL, 171 mmol, 8 eq.). The mixture is stirred 30 min at RT then ethylammonium chloride (10.43 g, 128 mmol, 6 eq.) is added and stirred at RT overnight. The reaction mixture is quenched with a solution of sat. $NaHCO_3$ and extracted with EtOAc twice. The combined organic layers are washed with sat. $NaHCO_3$, brine, and dried over $Na_2SO_4$ and evaporated under reduced pressure. The crude is purified by silica gel column chromatography (heptane/EtOAc 80/20) to afford the expected product.

LCMS: MW (calcd): 288.3; m/z MW (obsd): 289.4 (M+H)

2.11.2. Step ii: 2-(difluoromethoxy)-4-(2,5-dimethylpyrrol-1-yl)-N-ethyl-6-methoxy-benzamide To a solution of 4-(2,5-dimethylpyrrol-1-yl)-N-ethyl-2-hydroxy-6-methoxy-benzamide (4.78 g, 17 mmol, 1 eq.) in ACN (100 mL) cooled at −15° C. is added KOH (18.60 g, 332 mmol, 20 eq.) in water (100 mL). Then diethyl (bromodifluoromethyl)phosphonate (5.89 mL, 33 mmol, 2 eq.) solubilised in ACN is slowly added to the mixture and stirred at −10° C. for 45 min. The reaction mixture is quenched with sat. $NaHCO_3$ and ice-water and extracted with DCM twice. The combined organic layers are dried over $Na_2SO_4$ and evaporated under reduced pressure to afford the expected product.

LCMS: MW (calcd): 338.3; m/z MW (obsd): 339.4 (M+H)

2.11.3. Step iii: Int 12

To a stirred solution of 2-(difluoromethoxy)-4-(2,5-dimethylpyrrol-1-yl)-N-ethyl-6-methoxy-benzamide (17 g, 50.2 mmol, 1 eq.) in EtOH (200 mL) at RT is added hydroxylamine hydrochloride (34.9 g, 502.4 mmol, 10 eq.) in $H_2O$ (100 mL) and $Et_3N$ (13.9 mL, 100.5 mmol, 2 eq.). The resulting mixture is stirred overnight at 110° C. EtOH is evaporated. The aqueous phase was brought to pH 9 with NaOH 2N and extracted twice with DCM. The aqueous phase is brought to pH 10 with a sat. Na₂CO₃ aqueous solution and extracted with DCM. The organic layers are combined and dried over Na₂SO₄, filtered and concentrated in vacuo. The solid is triturated with DCM and Et₂O and filtered. Purification by flash chromatography eluting with 0-5% MeOH in DCM affords the expect product.

2.12. Int 13

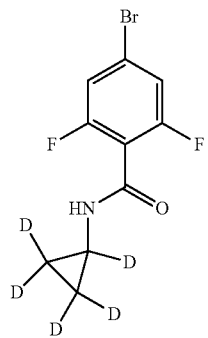 [SMILES: [2H]C1([2H])C([2H])([2H])C1([2H])NC(=O)c1c(F)cc(Br)cc1F]

To a suspension of 4-bromo-2,6-difluorobenzoic acid (2 g, 8.44 mmol, 1.0 eq.) in toluene (5 mL, 2 volumes) is added SOCl₂ (3.08 mL, 42.19 mmol, 5 eq.). The reaction mixture is stirred at reflux. After 4 h of reflux, the reaction shows complete conversion. The heating is stopped and the reaction mixture is cooled down to RT and then concentrated in vacuo. The residue is diluted with toluene (20 mL, 10 volumes) concentrated to eliminate residual thionyl chloride.

The yellow residual liquid is diluted with DCM (5 mL, 5 volumes) under N₂ atmosphere. The reaction mixture is cooled with an iced bath. Et₃N is slowly added followed by cyclopropylamine-d₅. The reaction mixture is then stirred under N₂ at RT overnight. The reaction mixture is then diluted with DCM and water is added. The organic phase is successively washed with aq. NaHCO₃ and 20% NaCl solutions. The organic phase is dried over MgSO₄, filtered and concentrated. The residue is triturated with heptane (500 mL, 6 volumes). The suspension is filtered and washed with heptane (20 mL, 10 volumes) at RT for 30 min. The suspension is filtered and the cake is washed with the minimum of heptane to obtain Int 13.

2.13. Int 14: mixture of methyl 2,6-dimethoxy-4-(4,4,5,5-tetramethyl-1,3,2-dioxaborolan-2-yl)benzoate/(3,5-dimethoxy-4-methoxycarbonyl-phenyl)boronic Acid

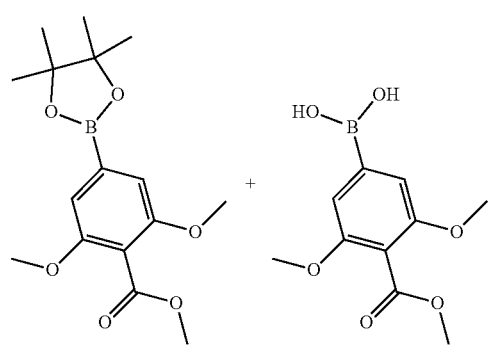

Methyl 2,6-dimethoxybenzoate (CAS #2065-27-2; 96.6 g, 492 mmol, 1 eq.), B₂pin₂ (312.6 g, 1.23 mol, 2.5 eq.), [Ir(OMe)(COD)]2 (6.5 g, 9.8 mmol, 0.02 eq.) and 3,4,7,8-tetramethyl-1,10-phenanthroline (Activate Scientific, Cat #AS21433; 4.7 g, 20 mmol, 0.04 eq.) are dissolved in THF (1 L). The mixture is degassed with nitrogen and then heated to reflux. The reaction mixture is left to stir at 65° C. overnight. The solvent is concentrated in vacuo and the residue is triturated in diisopropyl ether (400 mL). The solid obtained is dried in a vacuum oven at 40° C. overnight to afford the desired compound.

2.14. Int 16

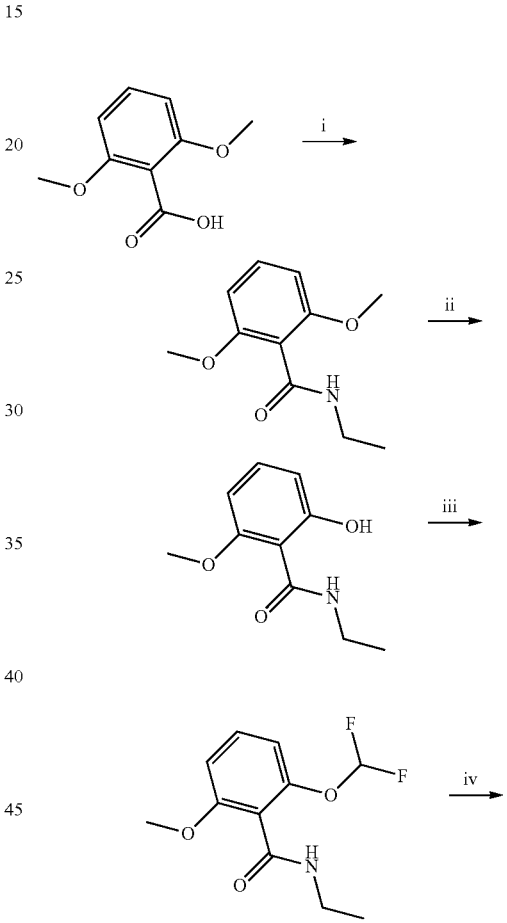

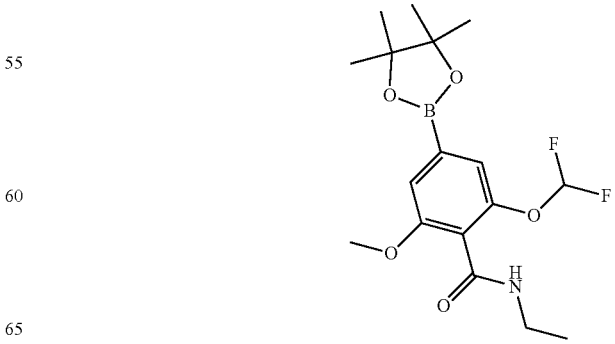

2.14.1. Step i: N-ethyl-2,6-dimethoxy-benzamide

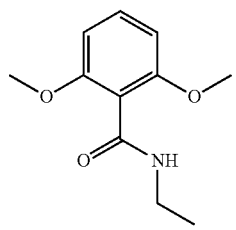

Under an inert atmosphere, 2,6-dimethoxybenzoic acid (2 g, 11 mmol, 1 eq.) is dissolved in DMF (200 mL), then Et$_3$N (31 mL, 220 mmol, 20 eq.) and HATU (6.3 g, 16.47 mmol, 1.5 eq.) are added, stirring at RT during 30 min, then ethylammonium chloride (9 g, 111 mmol, 10 eq.) is added. Reaction time: 18 h at RT. The mixture is concentrated in vacuo. Water and EtOAc are added. The mixture is extracted three times with EtOAc and then the organic phases are combined and dried over Na$_2$SO$_4$, filtered and concentrated in vacuo. Purification by flash chromatography on silica gel (eluting with DCM/MeOH 99/1 to 97/3) affords the desired compound.

LCMS: MW (calcd): 209.2; m/z MW (obsd): 210.4 (M+H)

2.14.2. Step ii: N-ethyl-2-hydroxy-6-methoxy-benzamide

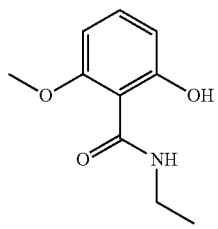

To a solution of N-ethyl-2,6-dimethoxy-benzamide (2.3, 11 mmol, 1 eq.) in DCM (40 mL) at 0° C. is added dropwise boron trichloride (1 M in DCM, 25 mL, 24.15 mmol, 2.2 eq.). The mixture is stirred at 0° C. for 30 min. The crude mixture is poured into ice, water and concentrated ammonium hydroxide. The product is extracted with DCM 3 times. The organic layers are dried on Na$_2$SO$_4$, filtered and concentrated in vacuo. The crude obtained is refluxed for 1 h in aq. HCl 2 N. The compound is extracted with EtOAc 3 times. The organic phases are dried on Na$_2$SO$_4$, filtered and concentrated in vacuo. Purification by flash chromatography on silica gel (eluting with heptane/EtOAc 90/10 to 85/15) affords the desired compound.

LCMS: MW (calcd): 195.2; m/z MW (obsd): 196.4 (M+H)

2.14.3. Step iii: 2-(difluoromethoxy)-N-ethyl-6-methoxy-benzamide

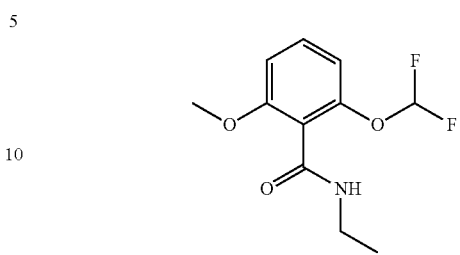

To a solution of N-ethyl-2-hydroxy-6-methoxy-benzamide (300 mg, 1.53 mmol, 1 eq.) in ACN (1.5 mL) are added water (1.5 mL) and KOH (861 mg, 15.3 mmol, 10 eq.). At −40° C., diethyl (bromodifluoromethyl)phosphonate (CAS #65094-22-6; 0.546 mL, 3.06 mmol, 2 eq.) is added dropwise. The mixture is stirred at −40° C. during 10 min then at RT during 30 min. The mixture is cooled down to −40° C. and diethyl (bromodifluoromethyl)phosphonate (0.546 mL, 3.06 mmol, 2 eq.) is added dropwise. The mixture is stirred at −40° C. for 10 min then overnight at RT. Water is added and the compound is extracted with EtOAc 3 times. The combined organic layers are dried on Na$_2$SO$_4$, filtered and concentrated in vacuo. Purification by flash chromatography on silica gel (eluting with heptane/EtOAc 90/10 to 60/40) affords the desired compound.

LCMS: MW (calcd): 245.2; m/z MW (obsd): 246.3 (M+H)

2.14.4. Step iv: Int 16

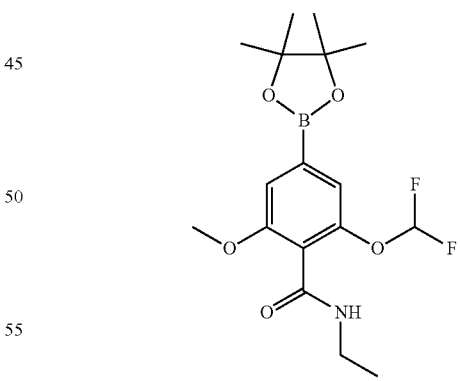

Under an inert atmosphere, 2-(difluoromethoxy)-N-ethyl-6-methoxy-benzamide (690 mg, 2.8 mmol, 1 eq.), B$_2$pin$_2$ (2.15 g, 8.4 mmol, 3 eq.), [Ir(OMe)(COD)]$_2$ (93 mg, 0.1 mmol, 0.05 eq.) and BBBPY (30 mg; 0.11 mmol, 0.04 eq.) are dissolved in THF (12 mL). The mixture is stirred at 70° C. overnight. The mixture is concentrated in vacuo. Purification by flash chromatography on silica gel (eluting with heptane/EtOAc 90/10 to 30/70) affords the desired compound.

2.15. Int 17

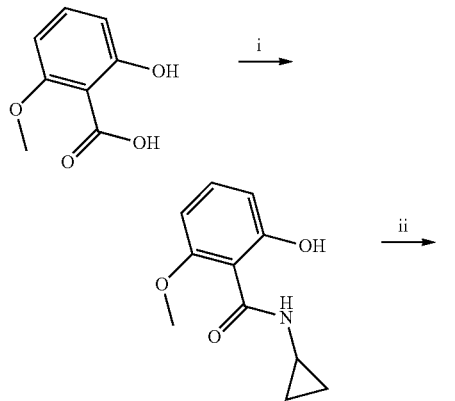

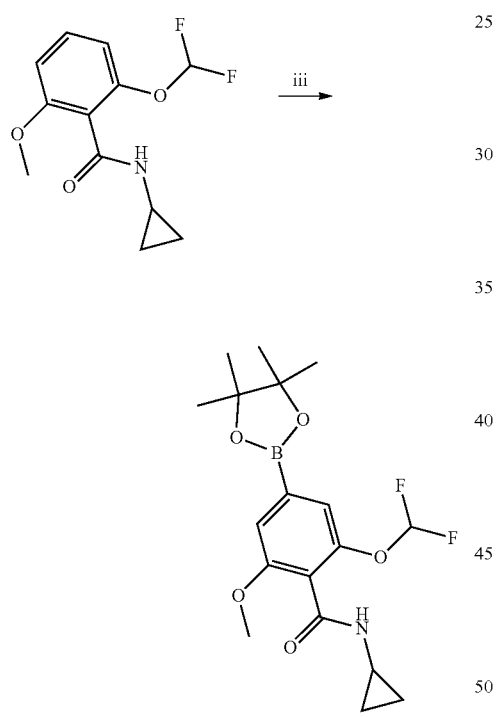

2.15.1. Step i: N-cyclopropyl-2-hydroxy-6-methoxy-benzamide

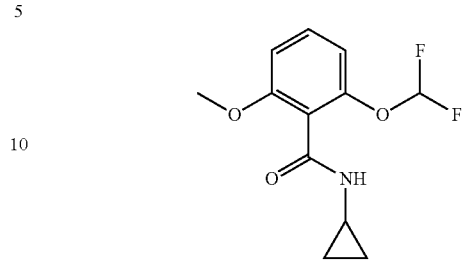

6-methoxysalicyclic acid (CAS #3147-64-6; 10 g, 0.06 mmol, 1 eq.) is dissolved in DMF (50 mL), HATU (33.93 g, 0.09 mmol, 1.5 eq.) is added, followed 15 min later by cyclopropylamine (CAS #765-30-0; 10.18 g, 0.18 mmol, 3 eq.), and DIPEA (34.55 g, 0.26 mmol, 4.5 eq.). The reaction mixture is allowed to stir at RT for 18 h; then 1 eq. of HATU, 2 eq. of cyclopropylamine and 2 eq. of DIPEA are added. The reaction mixture is stirred at RT for 68 h. The reaction mixture is concentrated in vacuo. Purification is performed by flash chromatography on silica gel (eluting with heptane/EtOAc 100/0 to 50/50). The collected fractions are concentrated in vacuo and triturated twice with MeOH/Et$_2$O. The filtrate is concentrated in vacuo to afford the desired product.

LCMS: MW (calcd): 207.2; m/z MW (obsd): 208.4 (M+H)

2.15.2. Step ii: N-cyclopropy-2-(difluoromethoxy)-6-methoxy-benzamide

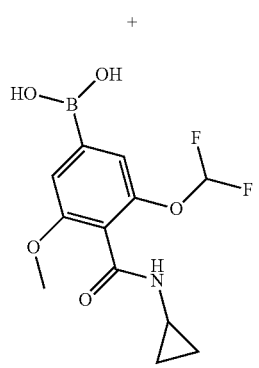

Under an inert atmosphere, N-cyclopropyl-2-hydroxy-6-methoxy-benzamide (2.80 g, 0.013 mmol, 1 eq.) is dissolved in ACN (20 mL) and cooled to −20° C. A solution of KOH (7.57 g, 0.13 mmol, 10 eq.) in water (20 mL) is added and the mixture is stirred for 10 min, then diethyl (bromodifluoromethyl)phosphonate (CAS #65094-22-6; 10.9 g, 0.04 mmol, 3.1 eq.) is added slowly. The reaction mixture is stirred at −20° C. for 30 min then at RT for another 30 min. Water is added and three extractions with EtOAc are performed. The organic layers are dried on Na$_2$SO$_4$, filtered and concentrated in vacuo. Purification by flash chromatography on silica gel (eluting with a gradient heptane/EtOAc 100/0 to 0/100) affords the expected product.

LCMS: MW (calcd): 257.2; m/z MW (obsd): 258.4 (M+H)

2.15.3. Step iii: Int 17: mixture of N-cyclopropyl-2-(difluoromethoxy)-6-methoxy-4-(4,4,5,5-tetramethyl-1,3,2-dioxaborolan-2-yl)benzamide and 4-(cyclopropylcarbamoyl)-3-(difluoromethoxy)-5-methoxyphenylboronic Acid

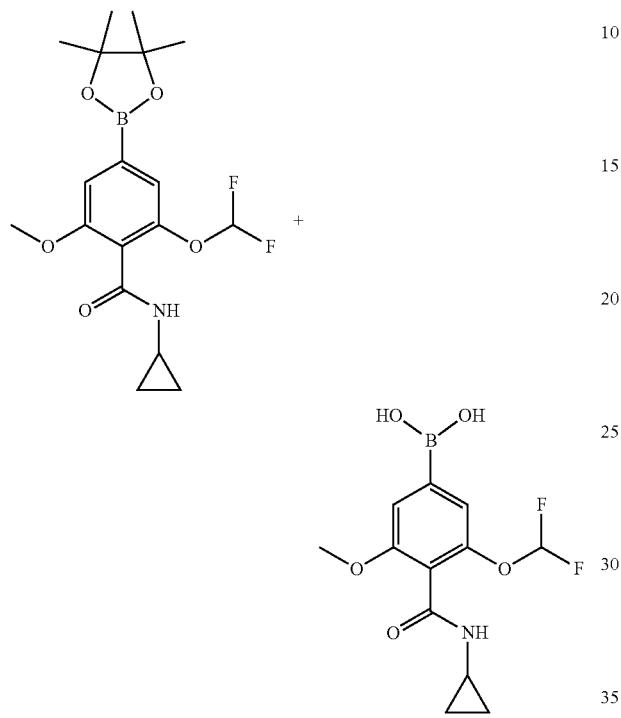

Under an inert atmosphere, N-cyclopropyl-2-(difluoromethoxy)-6-methoxy-benzamide (2.80 g, 10.89 mmol, 1 eq.), B$_2$pin$_2$ (8.30 g, 32.68 mmol, 3 eq.), [Ir(OCH3)(COD)] (360 mg, 0.54 mmol, 0.05 eq.) and BBBPY (120 mg, 0.45 mmol, 0.04 eq.) are dissolved in degassed THF (70 mL). The reaction mixture is stirred at 70° C. under N$_2$ for 3 h then at RT overnight. Purification by flash chromatography on silica gel (eluting with a gradient heptane/EtOAc 100/0 to 30/70) affords the expected product in mixture with the corresponding boronic acid.

2.16. Int 18

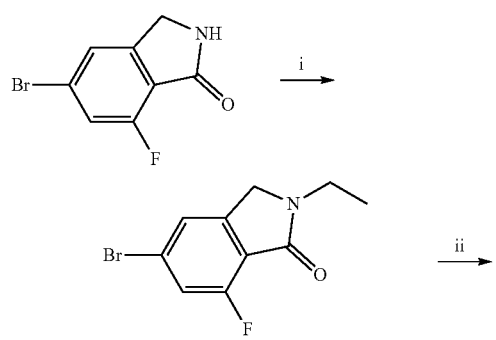

2.16.1. Step i: 5-bromo-2-ethyl-7-fluoro-isoindolin-1-one

To a stirred mixture of 5-bromo-7-fluoro-isoindolin-1-one (CAS #957346-37-1; 0.8 g, 3.48 mmol, 1 eq.) in THF (2 mL) and DMF (25 mL) is added NaH 60% in oil (153 mg, 3.83 mmol, 1.1 eq.). The reaction mixture is stirred at RT for 45 min and iodoethane (308 μL, 3.83 mmol, 1.1 eq.) is added, the reaction mixture is stirred at RT for 1 h. It is then quenched with an aq. NaHCO$_3$ solution, DMF and THF are concentrated, water is added again and the mixture is extracted with EtOAc. The combined organic layers are washed with brine, dried over anhydrous MgSO$_4$, filtered and concentrated in vacuo. The residue is purified by flash chromatography on silica gel (eluting with heptane/EtOAc 100/0 to 50/50) to afford the 5-bromo-2-ethyl-7-fluoro-isoindolin-1-one.

LCMS: MW (calcd): 258.1; m/z MW (obsd): 258.1-260.1

2.16.2. Step ii:
5-bromo-2-ethyl-7-methoxy-isoindolin-1-one

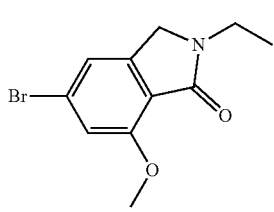

To a stirred solution of 5-bromo-2-ethyl-7-fluoro-isoindolin-1-one (100 mg, 0.387 mmol, 1 eq.) in THF (1 mL) is added a solution of MeONa 25 w % in MeOH (106 µL, 0.465 mmol, 1.2 eq.). The reaction mixture is stirred at RT for 5 min, quenched with a sat. aq. NH₄Cl solution. The mixture is extracted with EtOAc. The combined organic layers are washed with brine, dried over anhydrous MgSO₄, filtered and concentrated in vacuo to afford the 5-bromo-2-ethyl-7-methoxy-isoindolin-1-one.

LCMS: MW (calcd): 270.1; m/z MW (obsd): 270.1-272.1

2.16.3. Step iii: Int 18: mixture of 2-ethyl-7-methoxy-5-(4,4,5,5-tetramethyl-1,3,2-dioxaborolan-2-yl)isoindolin-1-one/(2-ethyl-7-methoxy-1-oxo-isoindolin-5-yl)boronic Acid

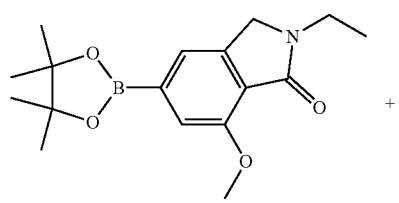

A vial is charged with 5-bromo-2-ethyl-7-methoxy-isoindolin-1-one (0.387 mmol, 1 eq.), B₂pin₂ (118 mg, 0.46 mmol, 1.2 eq.), AcOK (114 mg, 1.16 mmol, 3 eq.), degassed dioxane (2 mL), and Pd(dppf)Cl₂.DCM complex (19 mg, 0.02 mmol, 0.06 eq.). The vial is sealed and the reaction mixture is stirred at 90° C. for 1 h. Water and NaHCO₃ are added and the mixture is extracted with EtOAc. The combined organic layers are washed with brine, dried over anhydrous Na₂SO₄, filtered and concentrated in vacuo. The residue is purified by flash chromatography on silica gel (eluting with DCM/MeOH 100/0 to 90/10) to afford the 2-ethyl-7-methoxy-5-(4,4,5,5-tetramethyl-1,3,2-dioxaborolan-2-yl)isoindolin-1-one/(2-ethyl-7-methoxy-1-oxo-isoindolin-5-yl)boronic acid mixture.

2.17. Int 19

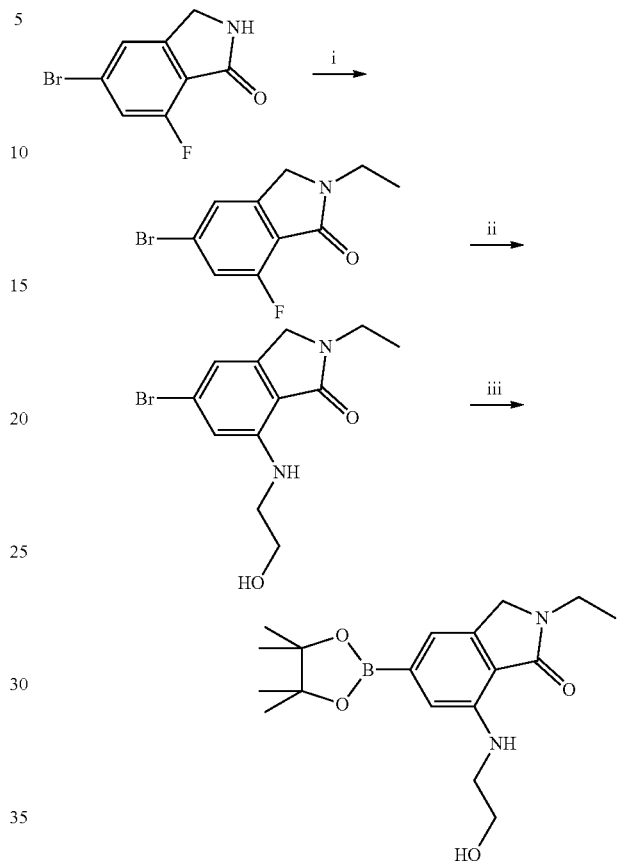

2.17.1. Step i:
5-bromo-2-ethyl-7-fluoro-isoindolin-1-one

Cf. Int 18, Step i

2.17.2. Step ii: 5-bromo-2-ethyl-7-(2-hydroxyethyl-amino)isoindolin-1-one

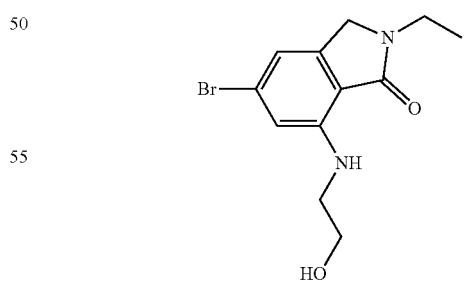

To a stirred solution of 5-bromo-2-ethyl-7-fluoro-isoindolin-1-one (100 mg, 0.387 mmol, 1 eq.) in DMAC (2 mL) are added 2-aminoethanol (70 µL, 1.16 mmol, 3 eq.) and DIPEA (202 µL, 1.16 mmol, 3 eq.). The mixture is stirred at RT for 1 h then at 100° C. for 40 h. The reaction mixture is cooled down, water is added and the mixture is extracted with EtOAc. The combined organic layers are washed with brine, dried over anhydrous MgSO₄, filtered and concentrated in vacuo to afford 5-bromo-2-ethyl-7-(2-hydroxyethylamino)isoindolin-1-one.

LCMS: MW (calcd): 299.2; m/z MW (obsd): 299.3-301.2.

2.17.3. Step iii: Int 19

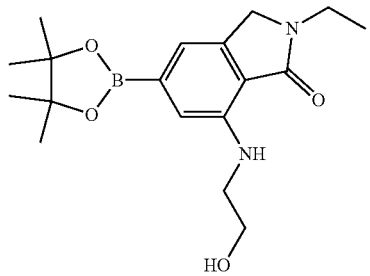 [SMILES: CCN1Cc2cc(B3OC(C)(C)C(C)(C)O3)cc(NCCO)c2C1=O]

A vial is charged with 5-bromo-2-ethyl-7-(2-hydroxyethylamino) isoindolin-1-one (120 mg, 0.387 mmol, 1 eq.), B₂pin₂ (118 mg, 0.46 mmol, 1.2 eq.), AcOK (114 mg, 1.16 mmol, 3 eq.), degassed dioxane (2 mL), and Pd(dppf)Cl₂.DCM complex (19 mg, 0.023 mmol, 0.06 eq.). The vial is sealed and the reaction mixture is stirred at 90° C. for 1 h. Water and NaHCO₃ are added and the mixture is extracted with EtOAc. The combined organic layers are washed with brine, dried over anhydrous MgSO₄, filtered and concentrated in vacuo. The residue is purified by flash chromatography on silica gel (eluting with DCM/MeOH 100/0 to 95/5) to afford 2-ethyl-7-(2-hydroxyethylamino)-5-(4,4,5,5-tetramethyl-1,3,2-dioxaborolan-2-yl)isoindolin-1-one.

2.18. Int 20

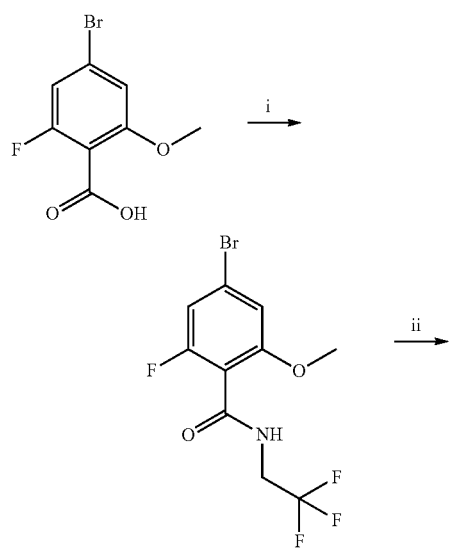

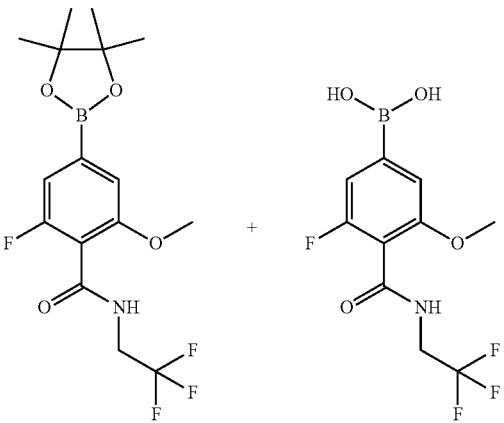

2.18.1. Step i: 4-bromo-2-fluoro-6-methoxy-N-(2,2,2-trifluoroethyl)benzamide

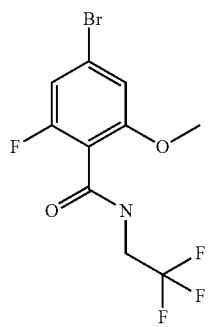 [SMILES: COc1cc(Br)cc(F)c1C(=O)NCC(F)(F)F]

To a stirred solution of 4-bromo-2-fluoro-6-methoxybenzoic acid (500 mg, 2 mmol, 1 eq.) and HATU (841 mg, 2.2 mmol, 1.1 eq.) in anhydrous DMF (5 mL) is added DIPEA (701 μL, 4 mmol, 2 eq.). The mixture is stirred at RT for 10 min and trifluoroethylamine (189 μL, 2.4 mmol, 1.2 eq.) is added. The resulting mixture is stirred overnight at RT. The reaction mixture is concentrated in vacuo. and diluted with DCM and water. The product is extracted with DCM and the organic layers are dried on Na₂SO₄, filtered and concentrated in vacuo. Purification by flash chromatography on silica gel (eluting with DCM) affords the desired compound.

LCMS: MW (calcd): 330.1; m/z MW (obsd): 330.1-332.1 (M+H)

2.18.2. Step ii: Int 20: mixture of 2-fluoro-6-methoxy-4-(4,4,5,5-tetramethyl-1,3,2-dioxaborolan-2-yl)-N-(2,2,2-trifluoroethyl)benzamide and 3-fluoro-5-methoxy-4-[(2,2,2-trifluoroethyl)carbamoyl]phenylboronic Acid

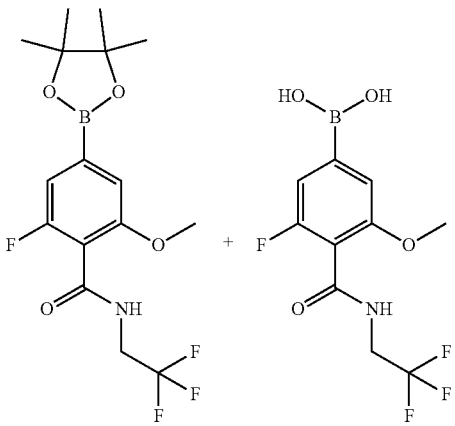 [SMILES: COc1cc(B2OC(C)(C)C(C)(C)O2)cc(F)c1C(=O)NCC(F)(F)F ; COc1cc(B(O)O)cc(F)c1C(=O)NCC(F)(F)F]

To a stirred solution 4-bromo-2-fluoro-6-methoxy-N-(2,2,2-trifluoroethyl)benzamide (165 mg, 0.5 mmol, 1 eq.) and B₂pin₂ (190 mg, 0.75 mmol, 1.5 eq.) in degassed dioxane (2.5 mL) are added KOAc (147 mg, 1.5 mmol, 3 eq.) and Pd(dppf)Cl₂.DCM (41 mg, 0.05 mmol, 0.1 eq.). The reaction mixture is stirred for 2 h at 90° C. The reaction mixture is concentrated in vacuo and then diluted with DCM and water. The organic layer is separated and concentrated under reduced pressure. Purification by flash chromatography on silica gel (eluting with 0-2% MeOH in DCM) affords the desired compound in mixture with the corresponding boronic acid.

2.19. Int 21

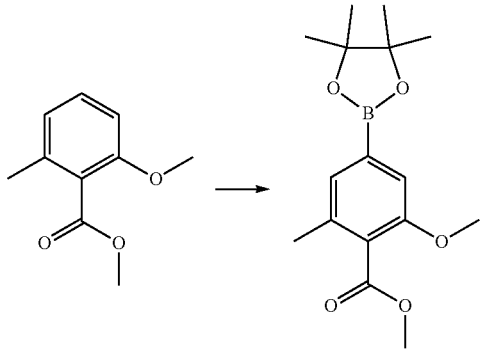

To a stirred solution of methyl 2-methoxy-6-methyl-benzoate (180 mg, 1 mmol, 1 eq.) in degassed THF (3 mL) are added [Ir(OMe)(COD)]₂ (33 mg, 0.05 mmol, 0.05 eq.), BBBPY (13 mg, 0.05 mmol, 0.05 eq.) and B₂pin₂ (330 mg, 1.3 mmol, 1.3 eq.). The reaction mixture is stirred for 2 h at 70° C. More [Ir(OMe)(COD)]₂ (33 mg, 0.05 mmol, 0.05 eq.), BBBPY (13 mg, 0.05 mmol, 0.05 eq.) and B₂pin₂ (330 mg, 1.3 mmol, 1.3 eq.) are added and the reaction mixture is stirred for 4 h at 70° C. The reaction mixture is stirred overnight at 70° C. More [Ir(OMe)(COD)]₂ (33 mg, 0.05 mmol, 0.05 eq.), BBBPY (13 mg, 0.05 mmol, 0.05 eq.) and B₂pin₂ (120 mg, 0.47 mmol, 0.5 eq.) are added and the reaction mixture is stirred for 4 h at 70° C. The reaction mixture is concentrated in vacuo. Purification by flash chromatography on silica gel (eluting with 0-1% MeOH in DCM) affords the desired compound.

2.20. Int 22

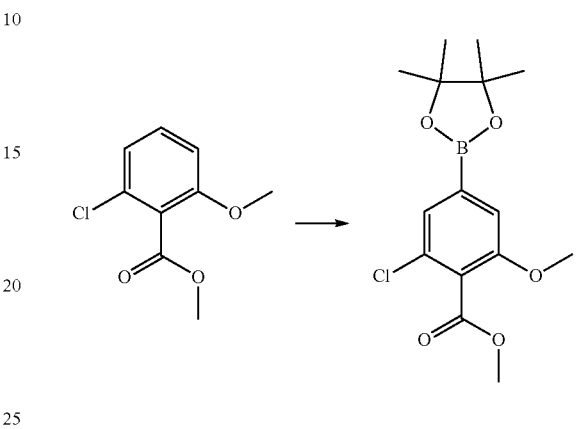

To a stirred solution of methyl 2-chloro-6-methoxy-benzoate (201 mg, 1 mmol, 1 eq.) in degassed THF (3 mL) are added B₂pin₂ (330 mg, 1.3 mmol, 1.3 eq.), BBBPY (13 mg, 0.05 mmol, 0.05 eq.) and [Ir(OMe)(COD)]₂ (33 mg, 0.05 mmol, 0.05 eq.). The reaction mixture is stirred for 1 h at 70° C. The reaction mixture is concentrated in vacuo. Purification by flash chromatography on silica gel (eluting with DCM) affords the desired compound.

2.21. Int 23: mixture of 8-methoxy-6-(4,4,5,5-tetramethyl-1,3,2-dioxaborolan-2-yl)-3,4-dihydro-2H-isoquinolin-1-one and (8-methoxy-1-oxo-3,4-dihydro-2H-isoquinolin-6-yl)boronic Acid

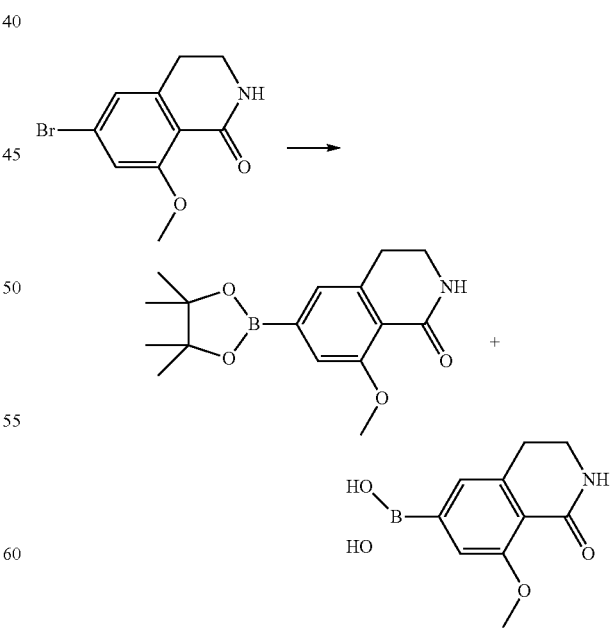

A flask is charged with 6-bromo-8-methoxy-3,4-dihydro-2H-isoquinolin-1-one (100 mg, 0.39 mmol, 1 eq.), B₂pin₂ (119 mg, 0.47 mmol, 1.2 eq.), AcOK (115 mg, 1.17 mmol, 3 eq.), degassed dioxane (2 mL), Pd(dppf)Cl₂.DCM complex (19 mg, 0.023 mmol, 0.06 eq.). The flask is sealed and the reaction mixture is stirred to 90° C. for 1 h, RT overnight and 90° C. for another 1 h. It is then purified by flash chromatography on silica gel (eluting with DCM/MeOH+ 1% of AcOH 100/0/1% to 80/20/1%) to afford the 8-methoxy-6-(4,4,5,5-tetramethyl-1,3,2-dioxaborolan-2-yl)-3,4-dihydro-2H-isoquinolin-1-one/(8-methoxy-1-oxo-3,4-dihydro-2H-isoquinolin-6-yl)boronic acid mixture.

2.22. Int 24

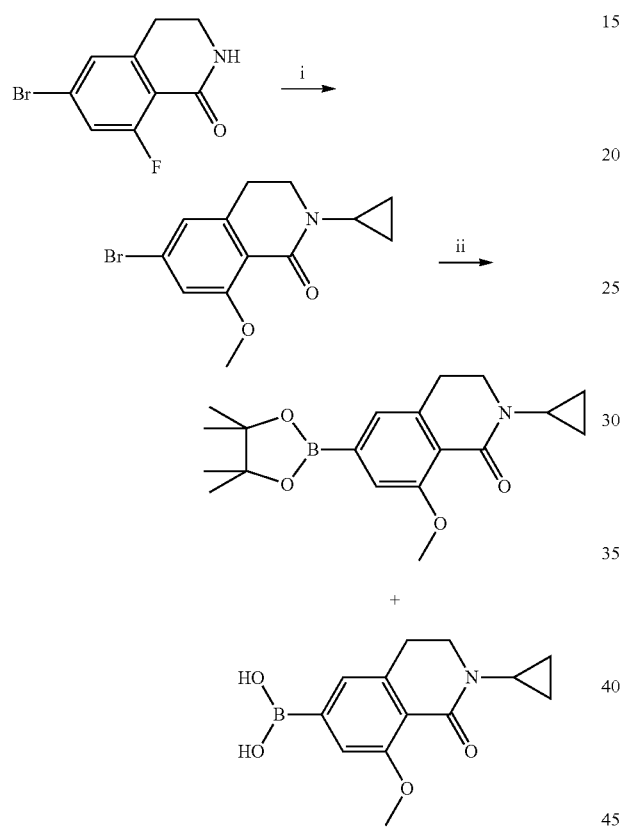

2.22.1. Step i: 6-bromo-2-cyclopropyl-8-methoxy-3,4-dihydroisoquinolin-1-one

To a stirred solution of 6-bromo-8-methoxy-3,4-dihydro-2H-isoquinolin-1-one (223 mg, 0.87 mmol, 1 eq.) in THF (5 mL) at 0° C. is added dropwise a solution of LiHMDS 1 N in THF (1.25 mL, 1.25 mmol, 1.4 eq.). After 15 min of stirring, cyclopropyl trifluoromethanesulfonate (0.15 mL, 1.25 mmol, 1.4 eq.) is added at 0° C. and the reaction mixture is stirred at RT overnight then at 100° C. for 8 h. The reaction mixture is quenched with a sat. NaHCO₃ solution, extracted with EtOAc. The combined organic layers are washed with brine, dried over anhydrous MgSO₄, filtered and concentrated in vacuo. The residue is purified by flash chromatography on silica gel (eluting with heptane/EtOAc 100/0 to 0/100) to afford 6-bromo-2-cyclopropyl-8-methoxy-3,4-dihydroisoquinolin-1-one.

LCMS: MW (calcd): 296.2; m/z MW (obsd): 296.1-298.1.

2.22.2. Step ii: mixture of 2-cyclopropyl-8-methoxy-6-(4,4,5,5-tetramethyl-1,3,2-dioxaborolan-2-yl)-3,4-dihydroisoquinolin-1-one and (2-cyclopropyl-8-methoxy-1-oxo-3,4-dihydroisoquinolin-6-yl)boronic Acid

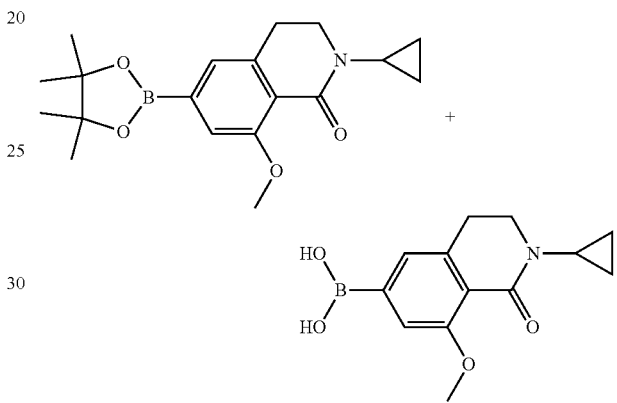

A flask is charged with 6-bromo-2-cyclopropyl-8-methoxy-3,4-dihydroisoquinolin-1-one (106 mg, 0.358 mmol, 1 eq.), B₂pin₂ (109 mg, 0.429 mmol, 1.2 eq.), AcOK (105 mg, 1.074 mmol, 3 eq.), degassed dioxane (2 mL), Pd(dppf)Cl₂.DCM complex (17 mg, 0.021 mmol, 0.06 eq.). The flask is sealed and the reaction mixture is stirred at 90° C. for 2 h. It is then purified by flash chromatography on silica gel (eluting with DCM/MeOH 100/0 to 90/10) to afford the 2-cyclopropyl-8-methoxy-6-(4,4,5,5-tetramethyl-1,3,2-dioxaborolan-2-yl)-3,4-dihydroisoquinolin-1-one/(2-cyclopropyl-8-methoxy-1-oxo-3,4-dihydroisoquinolin-6-yl)boronic acid mixture.

2.23. Int 25

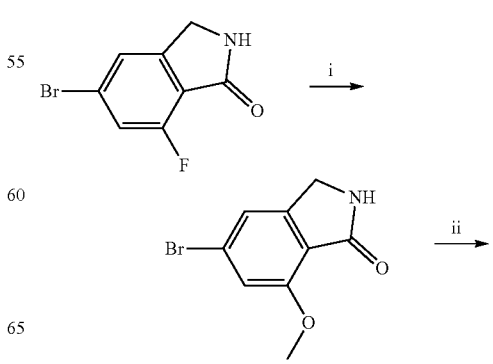

-continued

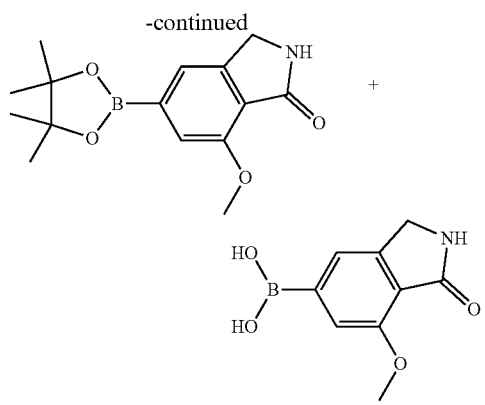

A vial is charged with 5-bromo-7-methoxy-isoindolin-1-one (90 mg, 0.37 mmol, 1 eq.), $B_2pin_2$ (113 mg, 0.45 mmol, 1.2 eq.), AcOK (109 mg, 1.12 mmol, 3 eq.), degassed dioxane (2 mL), and Pd(dppf)Cl$_2$.DCM complex (18 mg, 0.022 mmol, 0.06 eq.). The vial is sealed and the reaction mixture is stirred at 90° C. for 1 h and at RT overnight. It is then purified by flash chromatography on silica gel (eluting with DCM/MeOH 100/0 to 80/20 then DCM/MeOH/AcOH 80/20/2%) to afford the 7-methoxy-5-(4,4,5,5-tetramethyl-1,3,2-dioxaborolan-2-yl)isoindolin-1-one/(7-methoxy-1-oxo-isoindolin-5-yl)boronic acid mixture.

2.24. Int 62

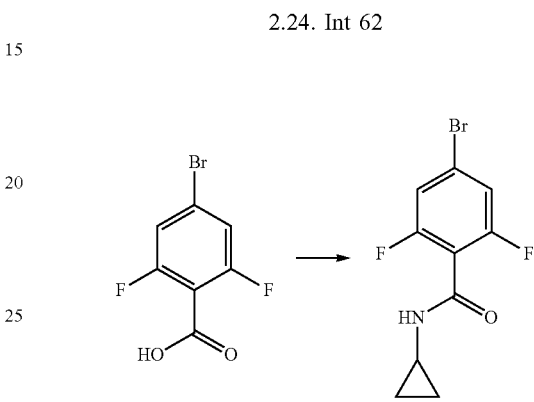

2.23.1. Step i: 5-bromo-7-methoxy-isoindolin-1-one

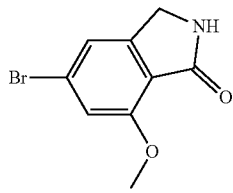

To a stirred mixture of 5-bromo-7-fluoro-isoindolin-1-one (CAS #957346-37-1; 0.5 g, 2.17 mmol, 1 eq.) in THF (5 mL) is added dropwise a solution of MeONa 25 w % in MeOH (0.6 mL, 2.61 mmol, 1.2 eq.). Further THF (5 mL) is added. The reaction mixture is stirred at RT for 24 h, then to 60° C. for 30 min, quenched with a sat. aq. NH$_4$Cl solution, extracted with EtOAc. The combined organic layers are washed with brine, dried over anhydrous MgSO$_4$, filtered and concentrated in vacuo. The residue is purified by flash chromatography on silica gel (eluting with heptane/EtOAc 100/0 to 0/100 then EtOAc/[DCM/MeOH (90/10)] 100/0 to 0/100) to afford 5-bromo-7-methoxy-isoindolin-1-one.

LCMS: MW (calcd): 242.1; m/z MW (obsd): 242.1-244.1

2.23.2. Step ii: Int 25: mixture of 7-methoxy-5-(4,4,5,5-tetramethyl-1,3,2-dioxaborolan-2-yl)isoindolin-1-one and (7-methoxy-1-oxo-isoindolin-5-yl) boronic Acid

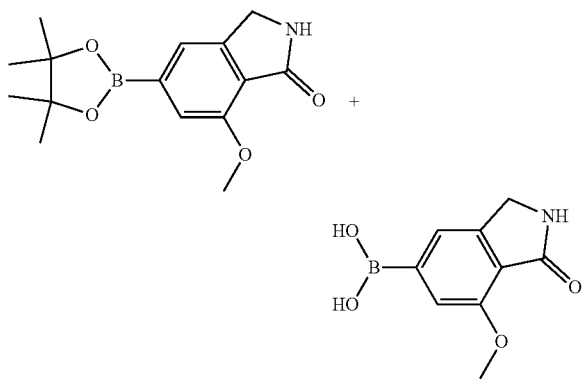

In a 15 L jacketed reactor 4-bromo-2,6-difluorobenzoic acid (900 g, 3.80 mol, 1 eq.) is added to SOCl$_2$ (5 eq., 1385 mL, 19.07 mol, 5 eq.) in toluene (2 V, 1800 mL) under N$_2$ flow at 20° C. (jacket temperature). The suspension is then heated to 80° C. for 17 h (jacket temperature set at 80° C.).

The reaction mixture is cooled to 40° C. and concentrated (200 mL of toluene are used to wash the reactor). Toluene (1 V, 900 mL) is added to the residue and the solution is concentrated.

The liquid residue (940 g) is dissolved in DCM (5 V, 4.5 L) under N$_2$ and placed into the 15 L reactor. The reaction mixture is cooled to 13° C. (jacket temperature: 5° C.) and a mixture of Et$_3$N (582.22 mL, 4.18 mol, 1.1 eq.) and cyclopropylamine (276.21 mL, 3.99 mol, 1.1 eq.) is added over 1.3 h keeping the temperature below 25° C. (jacket temperature set at 5° C. during the addition). The reaction mixture is stirred under N$_2$ at 20° C. for 14 h.

Water (2.2 V, 2 L) is added to the suspension. The biphasic solution is stirred (200 rpm) for 15 min. The organic phase is then successively washed with NaHCO$_3$ 5% (1.1 V, 1 L) and 20% NaCl solution (1.1 V, 1 L). The DCM layer is collected and put into a 15 L reactor.

A solvent exchange is performed in the 15 L reactor: to the DCM layer is added 1 L of heptane. The mixture is heated progressively with the jacket temperature set at 65° C. and DCM is removed between 43° C. and 50° C. After removing 2 L of DCM, 1 L of heptane is added. After removing a total of 4 L of solvent, 1 L of heptane is added and the mixture is cooled to 20° C. in 20 min. Finally 1 L of heptane (a total of 4 L of heptane is added) is added and the mixture is stirred at 20° C. for 45 min.

The suspension is filtered and the cake is washed with 1.5 L of heptane.

The solid is dried at 50 C under vacuum overnight to afford Int 62.

2.25. Int 63

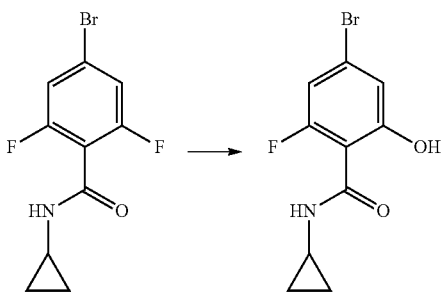 [SMILES: O=C(NC1CC1)c1c(F)cc(Br)cc1F ; O=C(NC1CC1)c1c(O)cc(Br)cc1F]

In a 15 L jacketed reactor, NaOH 4 N (2155 mL, 8.62 mol, 2.5 eq.) is added in one portion to a solution of Int 62 (952 g, 3.45 mol, 1 eq.) in DMSO (2 V, 1.9 L). The suspension is heated to 90° C. (jacket temperature from 50° C. to 90° C. over 20 min then hold at 90° C. for 2 h).

The reaction mixture is then cooled to 25° C. (jacket temperature from 90° C. to 5° C. over 45 min) and HCl 2 N (2.7 L, 5.4 moles, 0.63 eq./NaOH) is added until pH 3 is reached. The temperature is kept below 30° C. during the addition of HCl (addition over 20 min and jacket temperature set at 5° C.). The suspension is stirred at 200 rpm for 2 h while the temperature decreases to 20° C. (jacket temperature set at 5° C.). The suspension is then filtered. The wet cake is washed with water (twice with 2 L, 2*2 V) and the solid is dried on a fritted funnel overnight.

The solid is dried in a vacuum oven at 50° C. for 3 days to afford Int 63.

2.26. Int 64

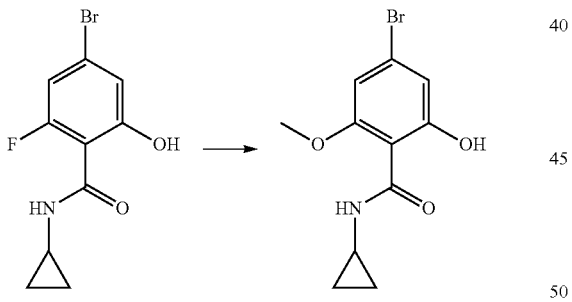

In a 15 L single jacketed process reactor, NaOMe (717 g, 13.27 mol, 3.5 eq.) is added over 20 min to a solution of Int 63 (1040 g, 3.79 mol, 1 eq.) in DMSO (5 V, 5200 mL) under $N_2$ atmosphere. The reaction mixture is heated to 100° C. (jacket temperature from 20° C. to 100° C. over 30 min) and stirred at 250 rpm overnight.

The reaction mixture is cooled to 20° C. (jacket temperature; ramp from 100° C. to 10° C. in 45 min) and HCl 2 N (5.3 L, 10.6 mol, 0.8 eq./NaOMe) is added in 2 h while maintaining internal temperature below 30° C. The suspension is cooled to 20° C., stirred for 15 min and filtered. The cake is washed with water (2*2 L, 2*2 V). The solid is dried in a vacuum oven at 50° C.

In the 15 L reactor, the crude solid (1040 g) is dissolved in acetone (3 L, 3 V). The solution is cooled at 15° C. (jacket temperature from 20° C. to 10° C. in 20 min) and water (3 L, 3 V) is progressively added over 30 min. Crystallization starts after adding 800 mL of water. At the end of the addition, the suspension is cooled down to 15° C. and stirred for 15 min. The suspension is filtered and the cake is washed with water (2*3 L, 2*3 V). The solid is dried in a vacuum oven at 50° C. to afford Int 64.

Int 64 $^1$H NMR (400 MHz, DMSO-$d_6$) δ ppm 13.14 (1H, broad s), 8.38 (1H, broad s), 6.72 (2H, m), 3.86 (3H, s), 2.81 (1H, m), 0.70 (2H, m), 0.59 (2H, m).

2.27. Int 65

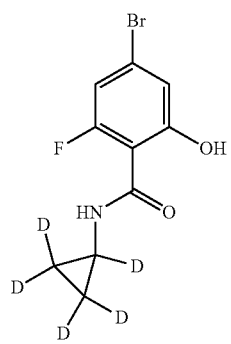 [SMILES: [2H]C1([2H])C([2H])([2H])C1([2H])NC(=O)c1c(O)cc(Br)cc1F]

To a solution of Int 13 (2 g, 7 mmol, 1.0 eq.) in DMSO (4 mL, 2 volumes) is added in one portion an aq. NaOH 4 M solution (4.4 mL). The reaction mixture is stirred at 90° C. After 4 h at 90° C., the reaction mixture is cooled to 25° C. and an aq. HCl 2 M solution (5.7 mL, 11.34 mmol, 0.63 eq./NaOH) is added until pH around 3 while keeping the temperature below 30° C. (addition in 1 min). The suspension is stirred for 30 min while the temperature decreases to 20° C. The suspension is then filtered. The wet cake is washed with water (2*4 mL, 2*2 volumes) and the solid is dried on the fritted funnel overnight to obtain Int 65.

2.28. Int 66

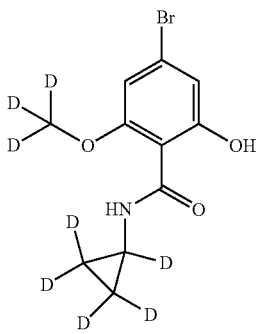 [SMILES: [2H]C([2H])([2H])Oc1cc(Br)cc(O)c1C(=O)NC1([2H])C([2H])([2H])C1([2H])[2H]]

A solution of $CD_3OD$ (0.52 mL, 13.00 mmol, 4.5 eq.) in DMSO (2 mL, 2.5 volumes) under $N_2$ is cooled to 0° C. with an ice bath and NaH is added portionwise (0.310 g, 60% in oil, 4.5 eq.). The reaction mixture is stirred at RT for 30 min. Then a solution of Int 65 (0.8 g, 2.9 mmol, 1.0 eq.) in DMSO (2 mL, 2.5 volumes) is slowly added to the mixture. The reaction mixture is heated to 100° C. for 2.5 h. The reaction mixture is cooled to 20° C. and an aq. HCl 2 M solution (5.2 mL, 10.4 mmol, 0.8 eq./NaOMe) is added. The suspension is stirred for 15 min at 20° C. and then filtered. The cake is washed with water (2*2 mL, 2*2 volumes) to give crude which is dissolved in acetone. The reaction mixture is cooled at 10° C. (ice bath) and water is added. The suspension is left cooling to 10° C. and stirred for 15 min at this temperature. The suspension is filtered and washed with water to afford Int 66.

2.29. Int 67

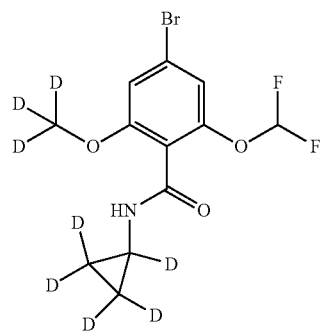 [SMILES: [2H]C([2H])([2H])Oc1cc(Br)cc(OC(F)F)c1C(=O)NC1([2H])C([2H])([2H])C1([2H])[2H]]

Int 66 (1.59 g, 5.40 mmol, 1.0 eq.) is suspended in ACN (8 mL, 5 volumes) at 5° C. KOH (3.03 g, 54.05 mmol, 10.0 eq.) in solution in cold water (8 mL, 5 volumes) is added in 2 min. Diethyl (bromodifluoromethyl)phosphonate (CAS #65094-22-6; 1.34 mL, 7.57 mmol, 1.4 eq.) is added in 1.5 h into the solution at 5° C. by controlling the temperature below 20° C. At the end of the addition (2.2 h), the temperature of the reaction mixture is raised to 20° C. in 10 min. EtOAc (8 mL, 5 volumes) is added to the reaction mixture and then the aqueous phase is extracted. Another extraction is performed with EtOAc (2 mL, 2 volumes). Organic phases are combined and washed once with 20% NaCl (6 mL, 5 volumes) in solution and concentrated. This crude mixture is slurried in MTBE (6 mL, 3 volumes) for 30 min at RT. The suspension is filtered and the solid washed with MTBE (2 mL, 1 volume). The solid is dried at 40° C. in a vacuum oven to give Int 67.

2.30. Int 68

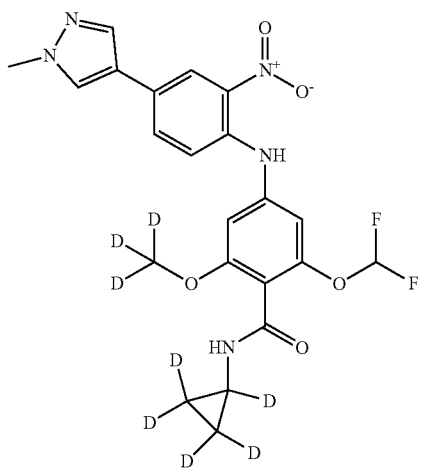 [SMILES: [2H]C([2H])([2H])Oc1cc(Nc2ccc(-c3cnn(C)c3)cc2[N+](=O)[O-])cc(OC(F)F)c1C(=O)NC1([2H])C([2H])([2H])C1([2H])[2H]]

To a solution of Int 67 (1.45 g, 4.21 mmol, 1.0 eq.) and Int 56 (1.01 g, 4.63 mmol, 1.1 eq.) in dioxane (9 mL, 6 volumes) under $N_2$ are added $K_3PO_4$. (1.79 g, 8.43 mmol, 2.0 eq.), $Pd(OAc)_2$ (9.5 mg, 0.04 mmol, 0.010 eq.) and XantPhos (48.8 mg, 0.08 mmol, 0.020 eq.). The reaction mixture is heated at 100° C. for 1 h. The reaction mixture is then cooled to RT. Water (6 mL, 4 volumes) is added to quench the reaction and then further water (12 mL, total of 18 mL, 12 volumes) is added slowly while the reaction temperature decreases. The suspension is stirred for 1 h. The suspension is filtered and the cake is washed with water (9 mL, 6 volumes). The cake is purified on $SiO_2$ column (25 g Biotage® SNAP Ultra, solid deposit), using a gradient of 100% DCM to 98/2 DCM/MeOH to afford Int 68.

2.31. Int 69

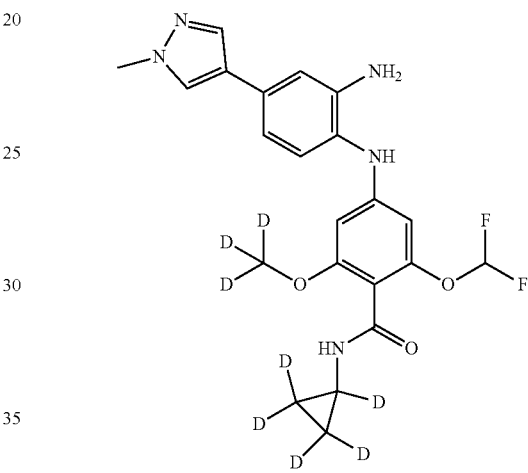

To a solution of Int 68 (1.2 g, 2.49 mmol, 1.0 eq.) and $NH_4Cl$ (0.8 g, 14.95 mmol, 6.0 eq.) in THF/MeOH (4/4 mL, 6 volumes) at 20° C. is added by portions Zn (0.65 g, 9.97 mmol, 4.0 eq.). The reaction mixture is heated to 60° C. for 1 h, then $NH_4Cl$ (70 mg, 1.31 mmol., 0.5 eq) is added. The reaction mixture is cooled to 25° C. and filtered on Dicalite 4158 RE (Carlo Erba Reagents, Cat #P8880017). The cake is washed with THF (10 mL). The filtrate is concentrated. The crude is triturated in EtOAc (6 mL) at RT for 10 min and is filtered. The cake is washed with EtOAc (3 mL). The solid is dried at 45° C. under vacuum overnight to afford Int 69.

2.32. Int 70

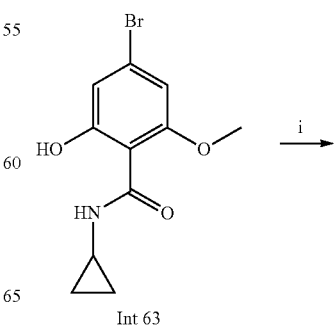

Int 63

223

-continued

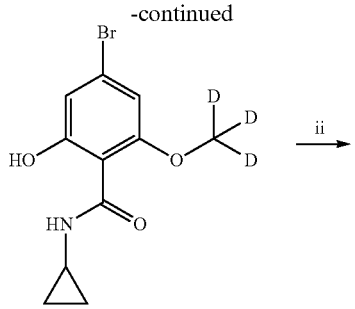

ii →

2.32.1. Step i: 4-bromo-N-cyclopropyl-2-hydroxy-6-(trideuteriomethoxy)benzamide

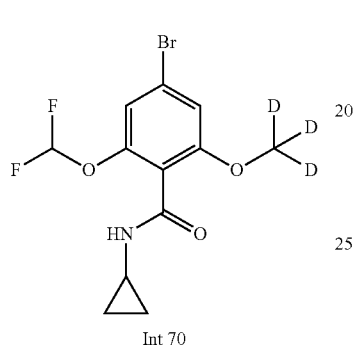

Int 70

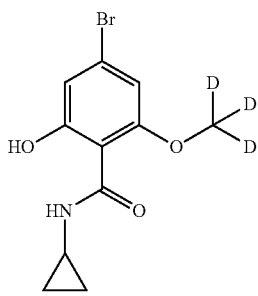 [SMILES: [2H]C([2H])([2H])Oc1cc(Br)cc(O)c1C(=O)NC1CC1]

An oven dried flask (25 mL) under $N_2$ atmosphere is charged with MeOH-$d_4$ (10 g, 12.63 mL). Sodium (1.452 g, 63.15 mmol) is weighed off in heptane and cut into 6 approximately equal portions. The MeOH-$d_4$ is cooled on an ice bath and the sodium is added portionwise over a 40 min period. The mixture is allowed to reach RT over a period of a few hours and subsequently left to stir overnight. The solution is used as such without any further analyses.

Int 63 (1.55 g, 1 eq.) is dissolved in DMSO (8 mL). NaOMe-$d_3$ (3.96 mL, 5 M, 3.5 eq.) is added to the mixture via a syringe and the mixture is heated to 100° C. for 3 h. The mixture is cooled to RT and 2 M HCl (7.92 mL, 2.8 eq.) is added over a 10 min period. The mixture is stirred for 1 h and filtered off. The filter cake is washed with water (2*6 mL) and dried in vacuo at 40° C. overnight to afford 4-bromo-N-cyclopropyl-2-(difluoromethoxy)-6-(trideuteriomethoxy)benzamide.

224

2.32.2. Step ii: Int 70

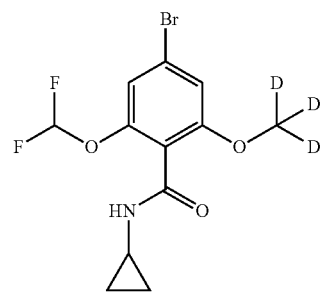

4-bromo-N-cyclopropyl-2-hydroxy-6-(trideuteriomethoxy)benzamide (1.386 g, 1 eq.) is dissolved in ACN (7 mL) and cooled to 0-5° C. A solution of KOH (3.13 mL, 10 eq.) in water (7 mL) is prepared, cooled and added to the mixture resulting in a biphasic mixture. Under stirring is added diethyl (bromodifluoromethyl)phosphonate (CAS #65094-22-6; 1.192 mL, 1.4 eq.), keeping the temperature below 10° C. for 15 min. The mixture is stirred for an additional 15 min and then allowed to reach RT. EtOAc (14 mL) is added, the phases are separated and the aqueous phase is extracted with EtOAc (5 mL). The combined organic layers are washed with brine (5 mL), dried over $Na_2SO_4$ and concentrated in vacuo. The solid is triturated with MTBE (4 mL) for 1 h, filtered off, filter cake washed with MTBE (1.4 mL) and dried in vacuo to afford Int 70.

2.33. Int 72

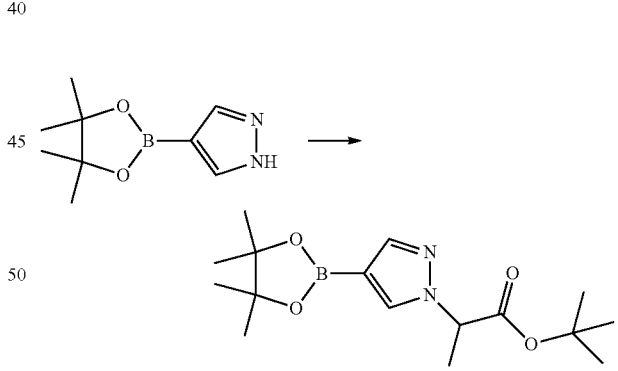

To a stirred solution of 4-(4,4,5,5-tetramethyl-1,3,2-dioxaborolan-2-yl)-1H-pyrazole (CAS #269410-08-4; 200 mg, 1.03 mmol, 1 eq.) in DMF (6 mL) are added tert-butyl 2-bromopropanoate (180 µL, 1.08 mmol, 1.05 eq.), $K_2CO_3$ (150 mg, 1.08 mmol, 1.05 eq.) and the reaction mixture is stirred at RT for 4 h. Tert-butyl 2-bromopropanoate (17 µL, 0.1 mmol, 0.1 eq.), $K_2CO_3$ (14 mg, 0.1 mmol, 0.1 eq.) are added and the reaction mixture is stirred at RT for 4 days. The mixture is concentrated in vacuo, water and DCM are added. The mixture is extracted with DCM, dried by filtration over hydrophobic column and concentrated in vacuo to afford the expected product.

2.34. Int 73

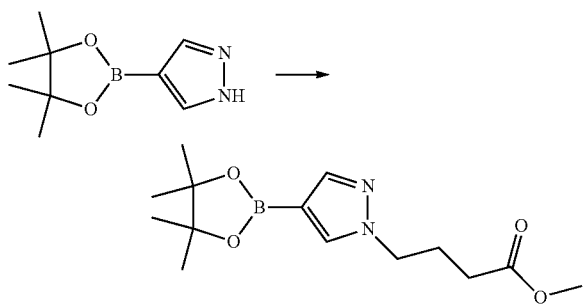

To a stirred solution of 4-(4,4,5,5-tetramethyl-1,3,2-dioxaborolan-2-yl)-1H-pyrazole (200 mg, 1.03 mmol, 1 eq.) in ACN (5 mL) are added methyl 4-bromobutanoate (143 µL, 1.13 mmol, 1.1 eq.), Cs$_2$CO$_3$ (440 mg, 1.33 mmol, 1.3 eq.) and the reaction mixture is stirred at 120° C. for 20 min (microwave heating) then at 130° C. for 10 min. Methyl 4-bromobutanoate (26 µL, 0.21 mmol, 0.2 eq.) is added and the reaction mixture is stirred at 120° C. for 1 h then at RT overnight. The mixture is concentrated in vacuo, water and DCM are added. The mixture is extracted with DCM, dried by filtration over hydrophobic column and concentrated in vacuo to afford the expected product.

2.35. Int 76

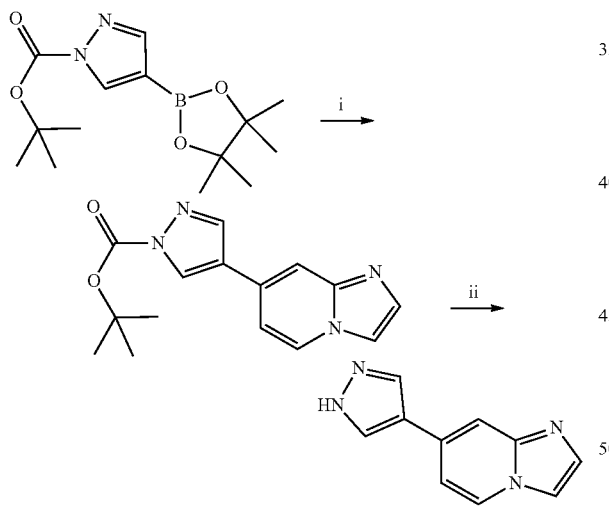

2.35.1. Step i: tert-buty 4-imidazo[1,2-a]pyridin-7-ylpyrazole-1-carboxylate

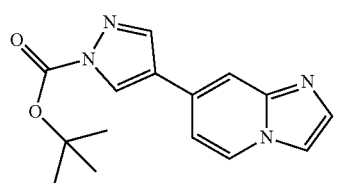 [SMILES: CC(C)(C)OC(=O)n1cc(-c2ccn3ccnc3c2)cn1]

A degassed solution of tert-butyl 4-(4,4,5,5-tetramethyl-1,3,2-dioxaborolan-2-yl)pyrazole-1-carboxylate (CAS #552846-17-0; 1.50 g, 4.99 mmol, 1.10 eq,), potassium phosphate, K$_3$PO (2.91 g, 3.0 eq.), 7-bromoimidazo[1,2-a] pyridine (CAS #808744-34-5; 920 mg, 1.0 eq.) and Pd(dppf) Cl$_2$.DCM complex (190 mg, 0.23 mmol, 0.05 eq.) in dry THF (18 mL) is placed under argon atmosphere and stirred at 70° C. for 3 h. The mixture is cooled to RT and diluted with 100 mL of EtOAc. The organic layer is then washed with 200 mL of water followed by 100 mL of brine. After drying over Na$_2$SO$_4$ and filtration, the solvent is evaporated. The residue is purified by flash chromatography on silica gel (eluting 0 to 50% (10% MeOH in EtOAc) in EtOAc) to afford tert-butyl 4-imidazo[1,2-a]pyridin-7-ylpyrazole-1-carboxylate.

LCMS: MW (calcd): 284.3; m/z MW (obsd): 285.6

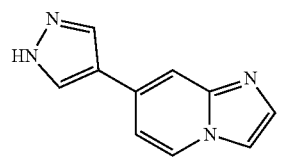

2.35.2. Step ii: Int 76

To a solution of tert-butyl 4-imidazo[1,2-a]pyridin-7-ylpyrazole-1-carboxylate (0.88 g, 2.94 mmol, 1.0 eq) in 40 mL dry DCM is added TFA (4.55 mL, 20.0 eq). The resulting mixture is stirred at RT for 16 h. Volatiles are evaporated and the residue is placed in DCM on a 20 g MeOH-conditioned Agilent Mega BOND-ELUT SCX column, eluted with a NH$_4$OH/MeOH solution and the product is isolated as the free base. Volatiles are evaporated and the residue is triturated with Et$_2$O to afford Int 76.

2.36. Int 77

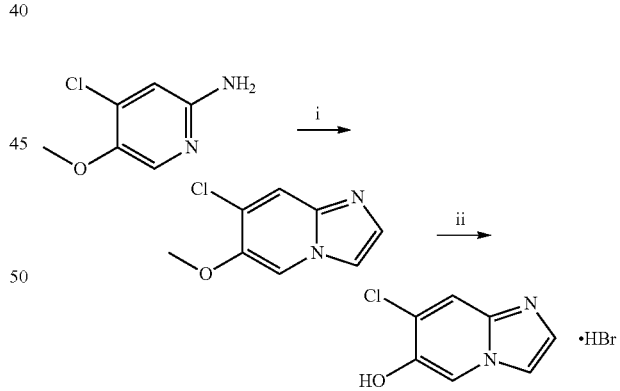

2.36.1. Step i: 7-chloro-6-methoxy-imidazo[1,2-a]pyridine

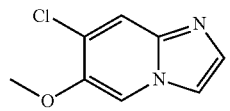

4-chloro-5-methoxy-pyridin-2-amine (CAS #867131-26-8; 1.0 g, 6.1 mmol, 1 eq.) and NaHCO$_3$ (1.04 g, 12.2 mmol, 2 eq.) in EtOH (8 mL) are heated to 60° C. and chloroacetaldehyde (50 w % solution in water, 1.17 mL, 9.2 mmol, 1.5 eq.) is added dropwise. The reaction mixture is then heated to 80° C. for 1 h. The reaction medium is cooled to RT and concentrated to dryness. The residue is poured onto water and extracted with EtOAc. The combined organic layers are dried over MgSO$_4$, filtered and evaporated to dryness. The residue is taken up in 20 mL of a water/aqueous HCl (3N) mixture. The aqueous layer is washed with Et$_2$O before being basified with K$_2$CO$_3$ and extracted with EtOAc. The EtOAc layers are dried over MgSO$_4$, filtered and evaporated to dryness to give the expected product.

LCMS: MW (calcd): 182.6; m/z MW (obsd): 183.0 (M+H)

2.36.2. Step ii: Int 77

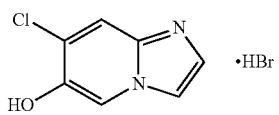

To a solution of 7-chloro-6-methoxy-imidazo[1,2-a]pyridine (445 mg, 2.3 mmol, 1 eq.) in CHCl$_3$ (15 mL) at −15° C. is added dropwise BBr$_3$ (1 N DCM solution, 11.55 mL, 11.5 mmol, 5 eq.). The mixture is allowed to warm up to RT and is stirred for 6 h. The reaction medium is then cooled to 0° C., MeOH (10 mL) is added and the mixture is stirred at RT for 2 h. Volatiles are concentrated and the residue is taken up in EtOH (10 mL). The solvent is evaporated to dryness to afford the expected product.

2.37. Cpd 48

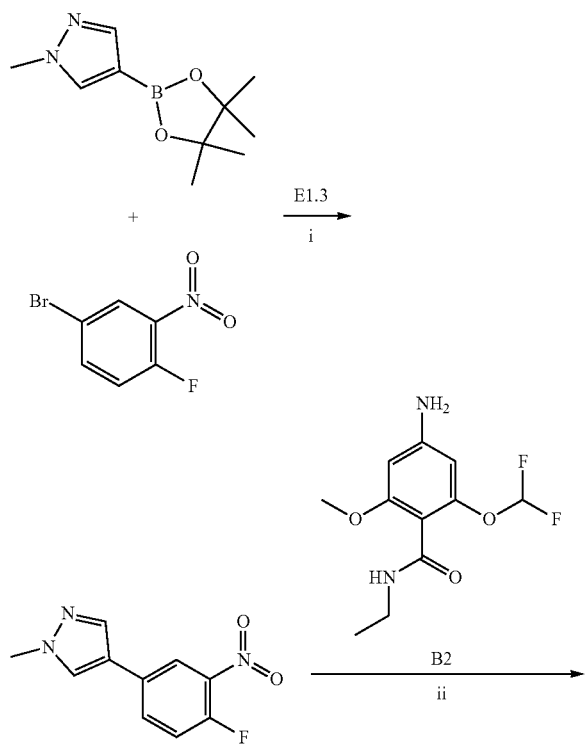

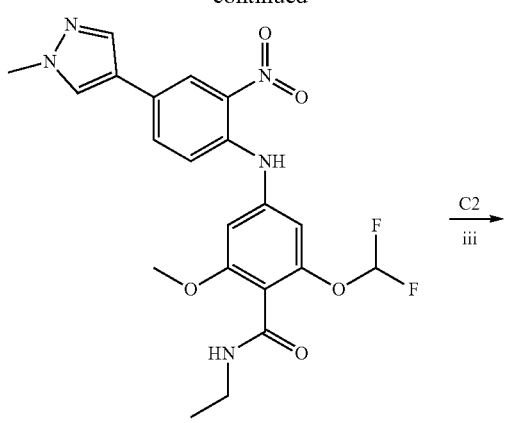

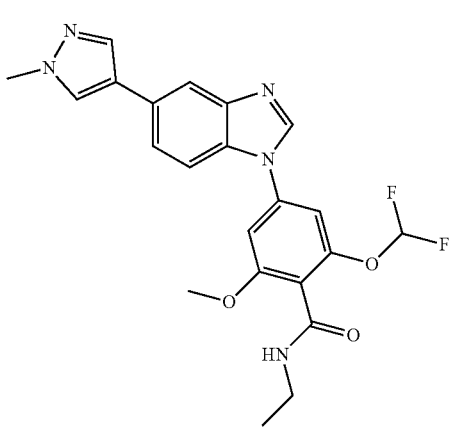

2.37.1. Step i: Method E1.3, Int 58

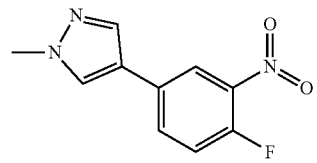 [SMILES: Cn1cc(-c2ccc(F)c([N+](=O)[O-])c2)cn1]

In a round flask are introduced 1-bromo-4-fluoro-3-nitrobenzene (CAS #364-73-8; 10 g, 45.45 mmol, 1 eq.), 1-methyl-4-(4,4,5,5-tetramethyl-1,3,2-dioxaborolan-2-yl)pyrazole (CAS #761446-44-0; 11.34 g, 54.54 mmol, 1.2 eq.), Pd(PPh$_3$)$_4$ (5.3 g, 4.54 mmol, 0.1 eq.), Cs$_2$CO$_3$ (44.5 g, 136.4 mmol, 3 eq.) and a degassed solution of dioxane (100 mL) and water (25 mL). The mixture is stirred at 100° C. for 2 h. The mixture is allowed to cool to RT and the solvents are evaporated in vacuo. Water (200 mL) and brine (50 mL) are added. The mixture is extracted three times with DCM (200 mL, 100 mL, 100 mL). The organic phase is dried over Na$_2$SO$_4$, filtered and concentrated in vacuo. Purification by flash chromatography on silica gel eluting with DCM then DCM/AcOEt 4/1 affords the expected product.

2.37.2. Step ii: Method B2, Int 57

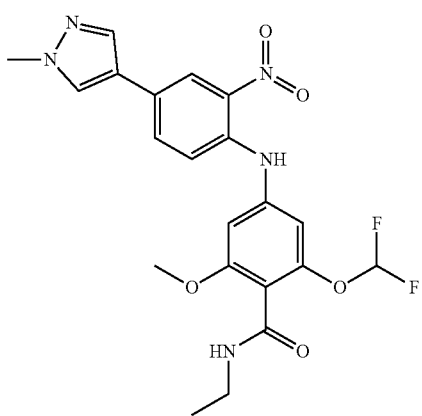 [SMILES: CCNC(=O)c1c(OC)cc(Nc2ccc(-c3cnn(C)c3)cc2[N+](=O)[O-])cc1OC(F)F]

To a stirred solution of Int 12 (7.66 g, 29.4 mmol, 1 eq.) and Int 58 (7.15 g, 32.37 mmol, 1.1 eq.) in anhydrous DMF (75 mL) is added sodium hydride (60% dispersion in mineral oil; 3.53 g, 88.29 mmol, 3 eq.) at 0° C. The reaction mixture is stirred for 1 h at 0° C. and at RT for 1.5 h. The reaction mixture is added carefully on a mixture ice/H$_2$O and the resulting solid is filtered in order to remove remaining Int 12 and DMF. The residue is diluted with EtOAc and washed successively with H$_2$O and brine. The organic layer is dried over Na$_2$SO$_4$, filtered and concentrated in vacuo. Purification by flash chromatography on silica gel (eluting with 0 to 2% MeOH in DCM) affords the desired compound which is triturated with acetone/Et$_2$O and filtered to afford the title Int 57.

2.37.3. Step iii: Method C$_2$, Cpd 48

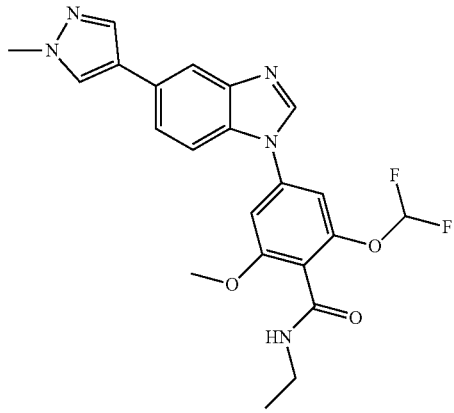 [SMILES: CCNC(=O)c1c(OC)cc(-n2cnc3cc(-c4cnn(C)c4)ccc32)cc1OC(F)F]

To a stirred solution of Int 57 (4 g, 8.66 mmol, 1 eq.) in AcOH (40 mL) at RT is added zinc dust (2.83 g, 43.3 mmol, 5 eq.). The resulting mixture is stirred 1 h at 75° C. The reaction mixture is diluted with EtOAc and filtered over a pad of Dicalite 4158 RE (Carlo Erba Reagents, Cat #P8880017) with EtOAc. The filtrate is concentrated in vacuo. Purification by flash chromatography on silica gel (eluting with 0 to 2% MeOH in DCM) affords the desired compound.

LCMS: MW (calcd): 431.4; m/z MW (obsd): 432.3 (M+H).

The compound obtained (2.91 g, 6.74 mmol, 1 eq.) is solubilized in MeOH (30 mL). Then acetic acid (50 μL) and trimethyl orthoformate (3.68 mL, 33.70 mmol, 5 eq.) are added. The resulting mixture is stirred 1 h at 75° C. The reaction is concentrated in vacuo. Purification by flash chromatography on Biotage® SNAP KP-NH column (eluting with DCM) affords a residue which is again purified by flash chromatography on silica gel (eluting with 0 to 5% MeOH in DCM) to afford the desired compound. Trituration with Et$_2$O (and few drops of MeOH), and a filtration afford the title compound after drying in vacuo.

2.38. Cpd 53

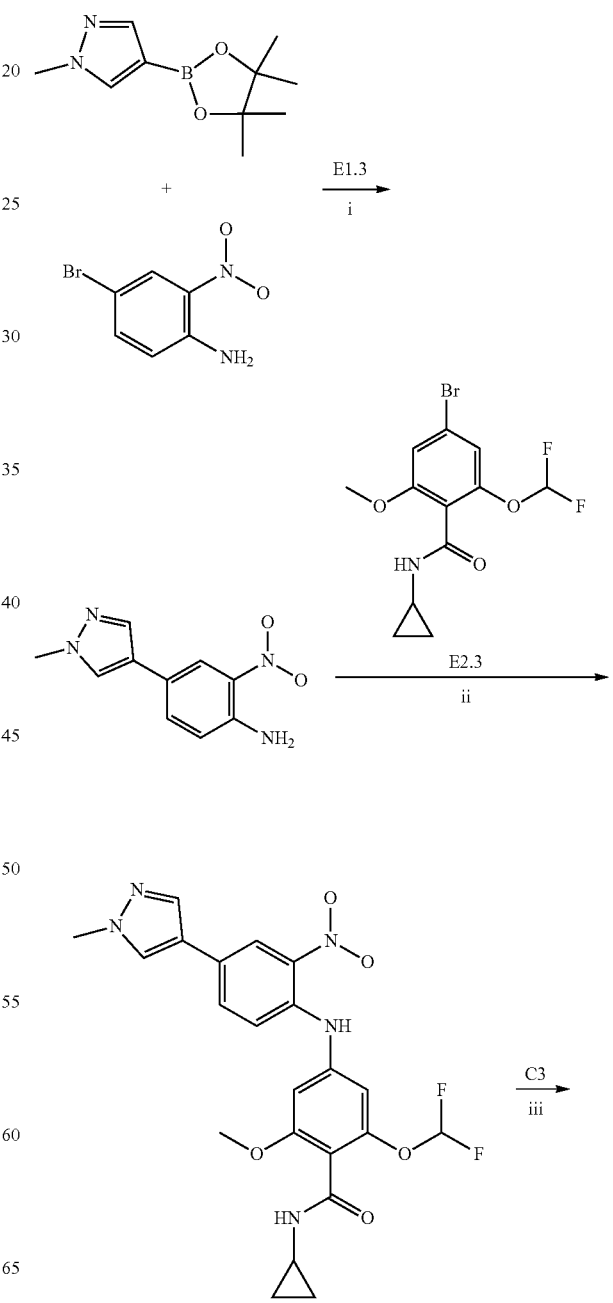

-continued

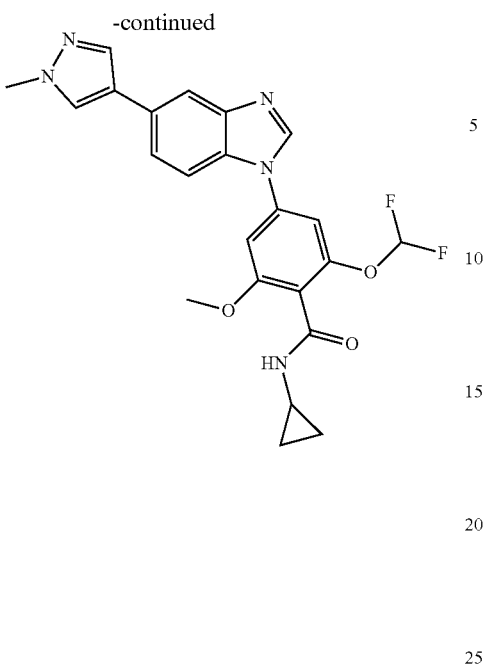

2.38.1. Step i: Method E1.3: 4-(4-fluoro-3-nitro-phenyl)-1-methyl-pyrazole, Int 56

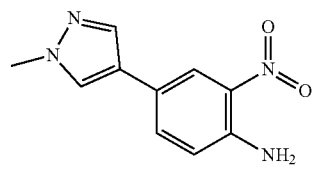 [SMILES: Cn1cc(-c2ccc(N)c([N+](=O)[O-])c2)cn1]

In a 15 L single jacketed process reactor, Na$_2$CO$_3$ (488 g, 2.0 eq.) is added to degassed dioxane/water 4:1 (4 L, 8 V). 1-methyl-4-(4,4,5,5-tetramethyl-1,3,2-dioxaborolan-2-yl) pyrazole (CAS #761446-44-0; 550 g, 1.15 eq.) and 4-bromo-2-nitro-aniline (CAS #875-51-4; 500 g, 1.0 eq.) are successively added to the reaction mixture. Pd(PPh$_3$)$_4$ (26.6 g, 1.0 mol %) is added in one portion and the reaction mixture is heated from 20° C. to 95° C. over 40 min and is then refluxed for 3 h. The reaction mixture is concentrated to remove dioxane and the crude residue is poured into water/ice (4 L, 8 V). The suspension is stirred at RT for 18 h and then filtered. The cake is washed with water (2*2 L, 2*4 V). The crude residue is triturated in i-PrOH (1.5 L, 3 V). The suspension is filtered and the solid is washed with i-PrOH (500 mL, 1 V). The solid is dried in a vacuum oven at 50° C. to give Int 56.

Int 56 $^1$H NMR (400 MHz, DMSO-d$_6$) δ ppm 8.08 (2H, m), 7.80 (1H, s), 7.64 (1H, dd), 7.41 (2H, broad s), 7.04 (1H, d), 3.84 (3H, s).

2.38.2. Step ii: Method E2.3: 2-(difluoromethoxy)-N-ethyl-6-methoxy-4-[4-(1-methylpyrazol-4-yl)-2-nitro-anilino]benzamide, Int 55

Int 55

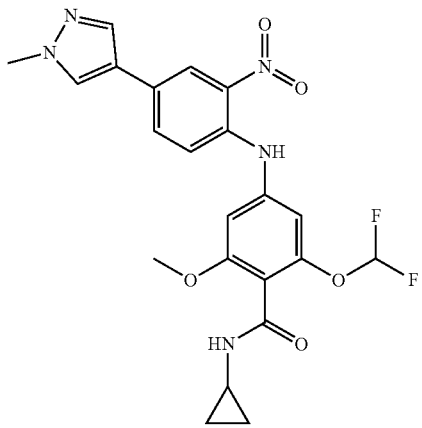

In a 15 L single jacketed process reactor, Pd(OAc)$_2$ (3.6 g, 1.0 mol %) and XantPhos (18.6 g, 2.0 mol %) are added to a solution of Int 9 (540 g, 1.0 eq.), Int 56 (385 g, 1.1 eq.) and K$_3$PO$_4$ (682 g, 2.0 eq.) in dioxane (2.7 L, 5 V) under N$_2$ atmosphere. The reaction mixture is heated at reflux (jacket temperature from 20° C. to 100° C. in 1 h then hold).

After 1 h 20 min at 98-101° C., the jacket temperature is cooled from 100° C. to 15° C. over 1 h. At the beginning of the cooling, water (2 L, 3.7 V) is added to quench the reaction.

The remaining water (3.4 L, total of 5.4 L, 10 V) is then added slowly over 2 h while the reaction temperature decreased from 60° C. to 20° C. Precipitation starts after 3.5 L of water has been added. The bulk of the precipitation occurs when the temperature decreases below 25° C. At the end of the addition, the suspension is aged for 30 min. The suspension is filtered and the solid is washed with water (2 L, 4 V). The solid is dried in a vacuum oven at 60° C. for 2 days.

The crude solid (740 g) is triturated in EtOAc/MTBE (1500/1500 mL, 2 V/2 V) for 1 h. The suspension is filtered and the solid is washed with 700 mL of MTBE (1 V). The solid is dried under vacuum at 50° C. for 4 days to give Int 55.

Int 55 $^1$H NMR (400 MHz, DMSO-d$_6$) δ ppm 9.20 (1H, broad s), 8.24 (3H, broad s), 7.93 (1H, s), 7.82 (1H, dd), 7.44 (1H, d), 7.24 (0.4H, s), 7.06 (0.6H, s), 6.87 (1H, s), 6.70 (1H, s), 3.87 (3H, s), 3.76 (3H, s), 2.77 (1H, m), 0.67 (2H, m), 0.46 (2H, m).

2.38.3. Step iii: Method C3: N-cyclopropyl-2-(difluoromethoxy)-6-methoxy-4-[5-(1-methylpyrazol-4-yl)benzimidazol-1-yl]benzamide (Cpd 53)

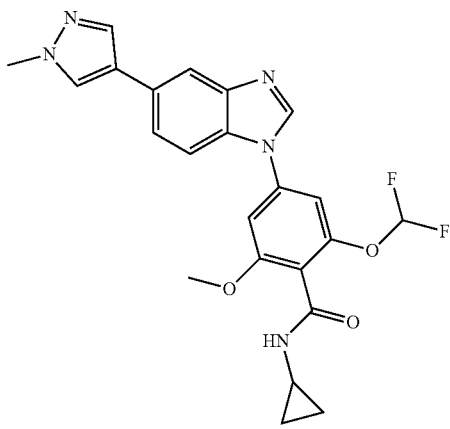 [SMILES: COc1cc(-n2cnc3cc(-c4cnn(C)c4)ccc32)cc(OC(F)F)c1C(=O)NC1CC1]

In a 5 L single jacketed process reactor equipped with baffles, Int 55 (525 g, 1.0 eq.) and ammonium chloride (326 g, 5.5 eq.) are added to a solution of tetrahydrofuran/MeOH 1:1 (2.5 L, 5 V) under N₂ atmosphere. The stirring is set to 300 rpm and zinc dust (<10 μm, 290 g, 4.0 eq.) is added by portions (15 to 40 g) while keeping the reaction temperature below 50° C. (the jacket temperature is set to 20° C. during the additions). The additions are performed over a period of 1 hour.

The reaction mixture is heated at 60° C. (jacket temperature) for 15 min. The reaction mixture is cooled to RT and filtered on Dicalite 4158 RE (Carlo Erba Reagents, Cat #P8880017). The cake is washed with THF (1500 mL, 3 V) and the filtrate is concentrated. When 2 L has been removed, EtOAc (2 L, 4 V) is added to co-evaporate MeOH. At the end of the evaporation, 1 L of EtOAc is added.

The suspension is triturated at RT for 30 min and is filtered. The cake is washed with EtOAc (200 mL). The solid is dried at 45° C. under vacuum overnight to give 4-[2-amino-4-(1-methylpyrazol-4-yl)anilino]-N-cyclopropyl-2-(difluoromethoxy)-6-methoxy-benzamide.

LCMS: MW (calcd): 443.4; m/z MW (obsd): 444.6 (M+H)

¹H NMR (400 MHz, DMSO-d₆) δ ppm 8.04 (1H, d), 7.96 (1H, s), 7.70 (1H, s), 7.57 (1H, s), 7.06-6.69 (3H, m), 6.78 (1H, dd), 6.23 (1H, s), 6.06 (1H, s), 4.79 (2H, broad s), 3.86 (3H, s), 3.66 (3H, s), 2.72 (1H, m), 0.63 (2H, m), 0.44 (2H, m).

In a 5 L single jacketed process reactor, 4-[2-amino-4-(1-methylpyrazol-4-yl)anilino]-N-cyclopropyl-2-(difluoromethoxy)-6-methoxy-benzamide (660 g, 1.0 eq.) is suspended in trimethyl orthoformate (2640 mL, 4 V). The reaction mixture is then refluxed (jacket temperature set at 110° C.) for 1.5 h. The reactor is equipped with a solvent refluxing head and half of the solvents of the reaction mixture are removed (1350 mL of solvents removed in 2.5 h). The reaction temperature increases from 87° C. to 100° C. and precipitation occurs as MeOH is removed. The jacket temperature is programmed to decrease from 110° C. to 20° C. in 1 h. When the reaction temperature reached 60° C., MTBE (1.35 L, 2 V, 1 eq./trimethyl orthoformate) is added slowly. The suspension is stirred at RT overnight.

The suspension is filtered. The cake is washed with MTBE (1 L). The solid is dried at 45° C. under vacuum to give Cpd 53.

2.39. Cpd 165

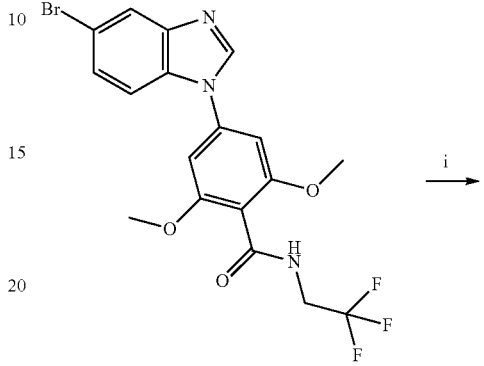

Int 39

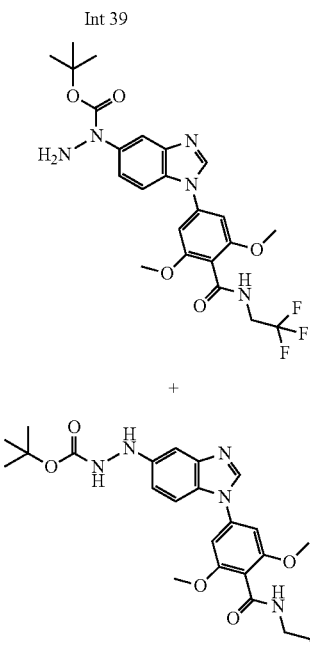

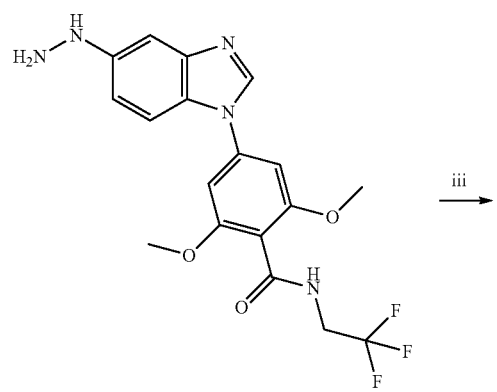

-continued

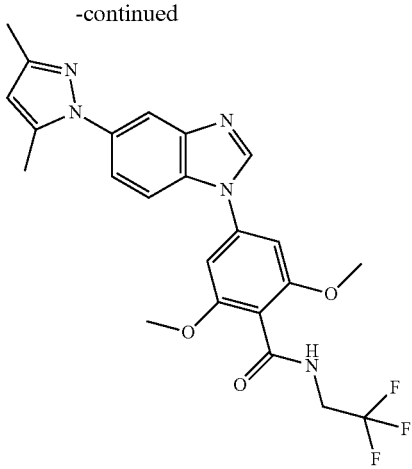

Cpd 165

2.39.1. Step i: mixture of tert-butyl N-amino-N-[1-[3,5-dimethoxy-4-(2,2,2-trifluoroethylcarbamoyl)phenyl]benzimidazol-5-yl]carbamate and tert-butyl N-[[1-[3,5-dimethoxy-4-(2,2,2-trifluoroethylcarbamoyl)phenyl]benzimidazol-5-yl]amino]carbamate

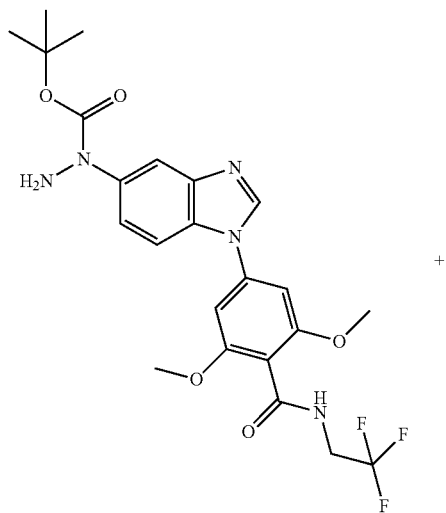

+

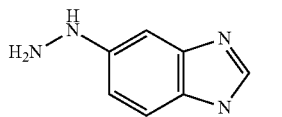

To a stirred solution of Int 39 (92 mg, 0.2 mmol, 1 eq.) and tert-butyl carbazate (CAS #870-46-2; mg, 0.3 mmol, 1.5 eq.) in degassed dioxane (2 mL) are added $Cs_2CO_3$ (196 mg, 0.6 mmol, 3 eq.), BrettPhos (11 mg, 0.02 mmol, 0.1 eq.) and $Pd_2(dba)_3$ (19 mg, 0.02 mmol, 0.1 eq.). The reaction mixture is stirred at 110° C. for 3 h. The reaction mixture is concentrated in vacuo and then diluted with EtOAc and water. The organic phase is separated, dried over $MgSO_4$, filtered and concentrated in vacuo. Purification by flash chromatography on silica gel (eluting 0-5% MeOH in DCM) to afford the expected products (mixture of both regioisomers). Purification by flash chromatography on silica gel (eluting 0-3% MeOH in DCM) to afford the expected regioisomers.

LCMS: Rt=0.64 min, MW (calcd): 509.5; m/z MW (obsd): 510.3 (M+H).

LCMS: Rt=0.58 min. MW (calcd): 509.5: m/z MW (obsd): 510.3 (M+H).

2.39.2. Step ii: 4-(5-hydrazinobenzimidazol-1-yl)-2,6-dimethoxy-N-(2,2,2-trifluoroethyl)benzamide

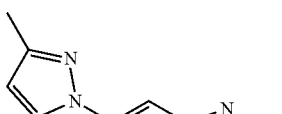

To a stirred solution of one regioisomer of N-Boc protected arylhydrazine (Rt=0.64 min, step i) (40 mg, 0.078 mmol, 1 eq.) in dioxane (2 mL) is added HCl 12 N (65 μL, 0.78 mmol, 10 eq.). The reaction mixture is stirred overnight at RT. The residue is concentrated in vacuo and affords the expected product as hydrochloride salt.

LCMS: MW (calcd): 409.4; m/z MW (obsd): 410.3 (M+H).

2.39.3. Step iii: Cpd 165

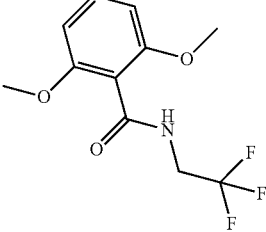

A solution of 4-(5-hydrazinobenzimidazol-1-yl)-2,6-dimethoxy-N-(2,2,2-trifluoroethyl)benzamide (32 mg, 0.078 mmol, 1 eq.) in EtOH (1 mL) is treated with acetylacetone (CAS #123-54-2; 8 μL, 0.078 mmol, 1 eq.) at RT and stirred 1 h at reflux. The reaction mixture is concentrated in vacuo. Purification by flash chromatography on silica gel (eluting 0-1% MeOH in DCM) affords the expected product.

2.40. Cpd 166

2.40.1. Preparation of Ethanimidothioic Acid, Methyl Ester

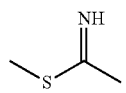

Methyl iodide (249 μL, 4 mmol, 2 eq.) is added dropwise to a solution of thioacetamide (150 mg, 2 mmol, 1 eq.) in acetone (3 mL) at 0° C. The reaction mixture is stirred at RT for 3 h. The reaction mixture is concentrated in vacuo and the residue is filtered and washed with Et$_2$O to afford the title compound.

2.40.2. Cpd 166

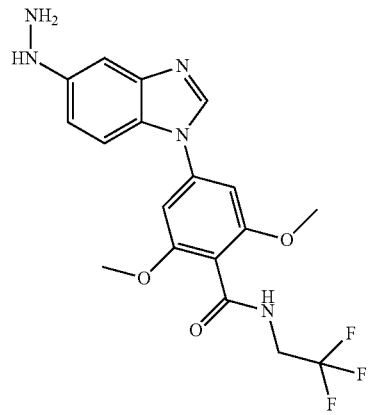

Cpd 166

To a stirred solution of a solution of 4-(5-hydrazinobenzimidazol-1-yl)-2,6-dimethoxy-N-(2,2,2-trifluoroethyl)benzamide (cf. synthesis of Cpd 165 Ex. 2.39, step ii) (30 mg, 0.074 mmol, 1 eq.) in MeOH (1 mL) is added ethanimidothioic acid, methyl ester freshly prepared. The reaction mixture is stirred at RT for 30 min and the solvent is removed under reduced pressure. Toluene (1 mL), trimethyl orthoformate (41 μL, 0.370 mmol, 5 eq.) and pyridine (1 mL) are added, and the reaction mixture is stirred overnight at 110° C. The reaction mixture is concentrated in vacuo. The residue is diluted with a sat. aq. NaHCO$_3$ solution and extracted with DCM on a Biotage® ISOLUTE® phase separator. The organic layer is concentrated in vacuo. Purification by flash chromatography on silica gel (eluting 0-8% MeOH in DCM) to afford the expected product.

2.41. Cpd 167

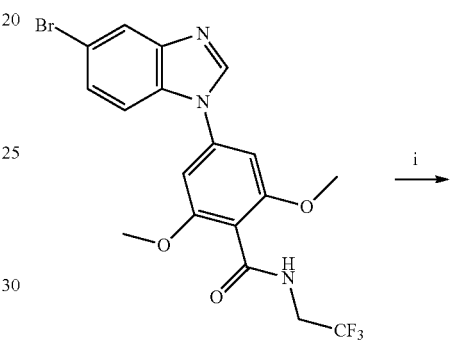

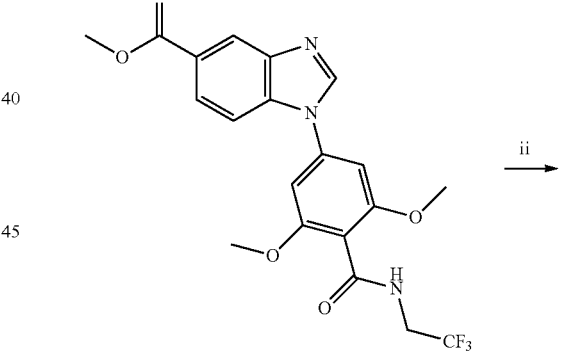

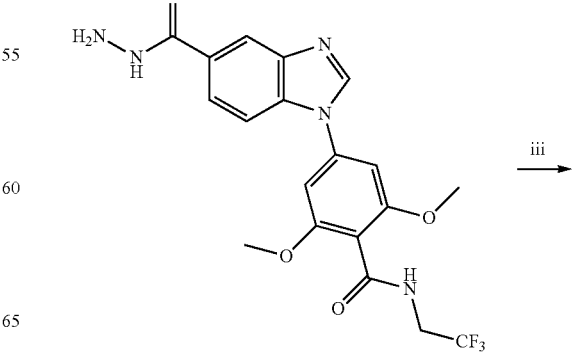

2.41.1. Step i: methyl 1-[3,5-dimethoxy-4-(2,2,2-trifluoroethylcarbamoyl)phenyl]benzimidazole-5-carboxylate

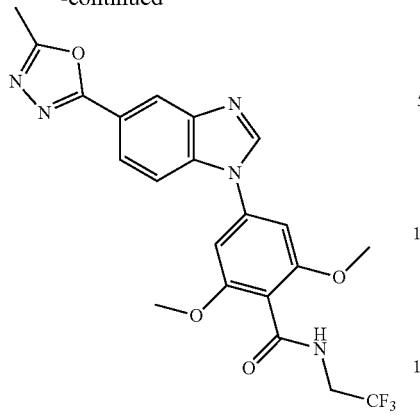

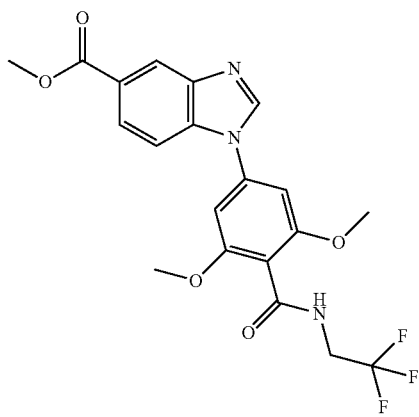 [SMILES: COC(=O)c1ccc2c(c1)ncn2-c1cc(OC)c(C(=O)NCC(F)(F)F)c(OC)c1]

To a stirred solution of Int 39 (92 mg, 0.2 mmol, 1 eq.) in degassed dioxane/MeOH 1/1 (2 mL) are added Mo(CO)$_6$, [(t-Bu)$_3$PH]BF$_4$ (12 mg, 0.04 mmol, 0.2 eq.), Herrmann's catalyst (CAS #172418-32-5; 19 mg, 0.02 mmol, 0.1 eq.) and DBU (45 μL, 0.3 mmol, 0.1 eq.). The reaction mixture is stirred for 1 h at 150° C. under microwave irradiation. The reaction mixture is concentrated in vacuo. Purification by flash chromatography on silica gel (eluting 0-4% MeOH in DCM) to afford the expected product.

LCMS: MW (calcd): 437.4; m/z MW (obsd): 438.5 (M+H)

2.41.2. Step ii: 4-[5-(hydrazinecarbonyl)benzimidazol-1-yl]-2,6-dimethoxy-N-(2,2,2-trifluoroethyl)benzamide

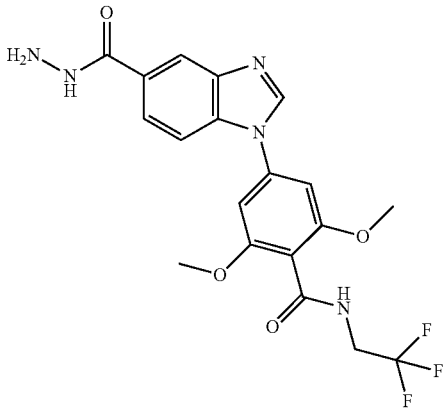 [SMILES: COc1cc(-n2cnc3cc(C(=O)NN)ccc32)cc(OC)c1C(=O)NCC(F)(F)F]

A solution of methyl 1-[3,5-dimethoxy-4-(2,2,2-trifluoroethylcarbamoyl)phenyl]benzimidazole-5-carboxylate (100 mg, 0.23 mmol, 1 eq.) in EtOH (2 mL) is treated with hydrazine hydrate (112 μL, 2.3 mmol, 10 eq.) at RT and stirred 4 h at 120° C. The reaction mixture is stirred twice for 2 h at 150° C. under microwave irradiation. The reaction mixture is concentrated in vacuo. The residue is washed with DCM and then diluted with MeOH. The mixture is filtered and the filtrate is concentrated in vacuo to afford the expected product.

LCMS: MW (calcd): 437.4; m/z MW (obsd): 438.2 (M+H)

2.41.3. Step iii: Cpd 167

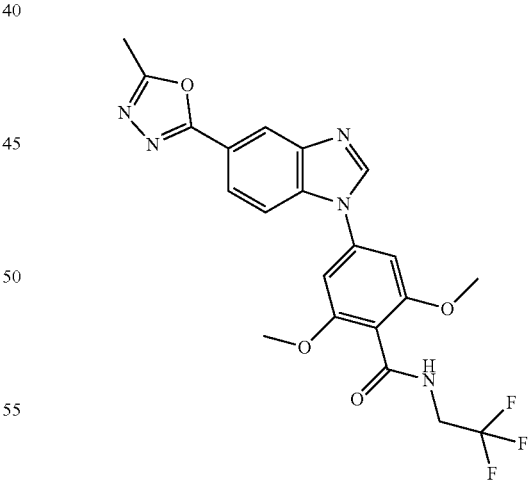

AcOH (1 drop) is added to a solution of 4-[5-(hydrazinecarbonyl)benzimidazol-1-yl]-2,6-dimethoxy-N-(2,2,2-trifluoroethyl)benzamide (50 mg, 0.11 mmol, 1 eq.) in trimethyl orthoacetate (1 mL). The reaction mixture is stirred overnight at 110° C. in sealed vial. The reaction mixture is concentrated in vacuo. Purification by flash chromatography on silica gel (eluting with 0-5% MeOH in DCM) to afford the expected product.

2.42. Cpd 168

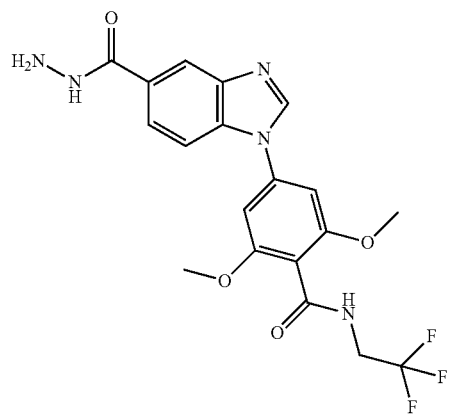

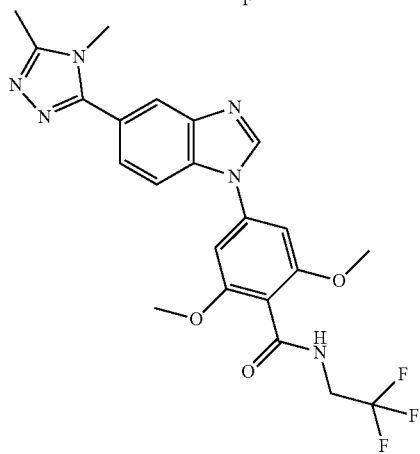

AcOH is added to a solution of 4-[5-(hydrazinecarbonyl)benzimidazol-1-yl]-2,6-dimethoxy-N-(2,2,2-trifluoroethyl)benzamide (cf. Ex. 2.41 Cpd 167, step ii; 50 mg, 0.11 mmol, 1 eq.), trimethyl orthoacetate (44 µL, 0.35 mmol, 1.5 eq.) and methylamine 2 M in THF (345 µL, 0.69 mmol, 3 eq.) in dioxane (1 mL). The reaction mixture is stirred overnight at 120° C. in a sealed vial. The reaction mixture is concentrated in vacuo. Purification by flash chromatography on Biotage® SNAP KP-NH (eluting 0-2% MeOH in DCM) affords the expected product.

2.43. Cpd 169

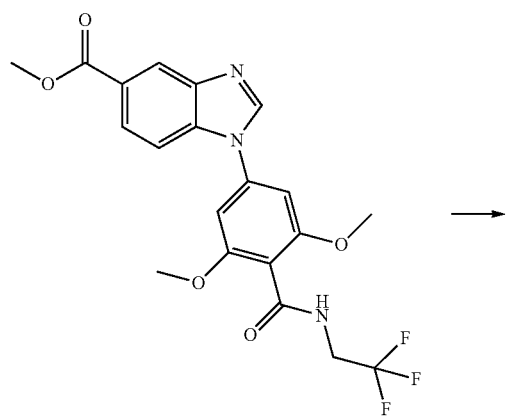

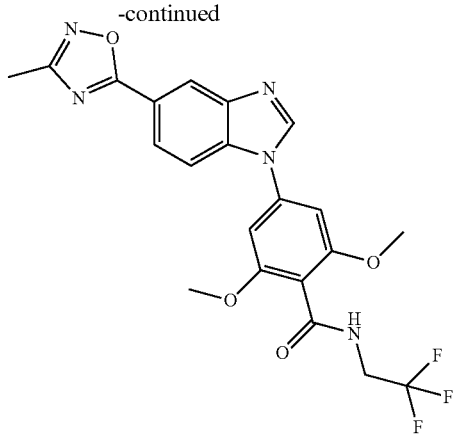

To a stirred solution of N-hydroxyacetamidine (CAS #22059-229; 6 mg, 0.082 mmol, 1.2 eq.) in anhydrous THF (1 mL) under argon is added sodium hydride (60% dispersion in mineral oil) (3 mg, 0.082 mmol, 1 eq.) at RT. The reaction mixture is stirred for 1 h at 60° C. and then cooled to 0° C. before a solution of methyl 1-[3,5-dimethoxy-4-(2,2,2-trifluoroethylcarbamoyl)phenyl]benzimidazole-5-carboxylate (cf. Ex. 2.41 Cpd 167, step i; 30 mg, 0.068 mmol, 1 eq.) in anhydrous THF (1 mL) is added. The reaction mixture is stirred for 1 h at 60° C. A saturated aqueous $NH_4Cl$ solution is added and the aqueous layer is extracted twice with DCM on a Biotage® ISOLUTE® phase separator. The organic layer is concentrated in vacuo. Purification by flash chromatography on silica gel (eluting 0-3% MeOH in DCM) affords the expected product.

2.44. Cpd 173

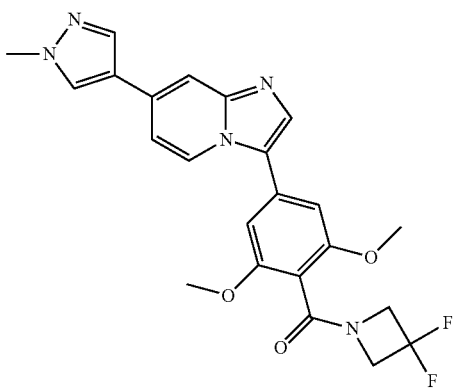 [SMILES: COc1cc(-c2cnc3cc(-c4cnn(C)c4)ccn23)cc(OC)c1C(=O)N1CC(F)(F)C1]

To a suspension of Int 52 (160 mg, 0.42 mmol, 1 eq.) in DMF (1.5 mL) is added HATU (239 mg, 0.63 mmol, 1.5 eq.), then DIPEA (220 µL, 1.26 mmol, 3 eq.) and 3,3-difluoroazetidine hydrochloride (CAS #288315-03-7; 66 mg, 0.51 mmol, 1.2 eq.). The solution is stirred at RT overnight. The mixture is diluted with DCM, washed with water and brine. The organic phase is separated, dried over $MgSO_4$, filtered and concentrated in vacuo. Purification by flash chromatography on silica gel (eluting with 0 to 5% MeOH in DCM). Second purification by flash chromatography on Biotage® SNAP KP-NH column (eluting with 0 to 5% MeOH in DCM) affords the desired compound.

2.45. Cpd 174 (Method E1.2)

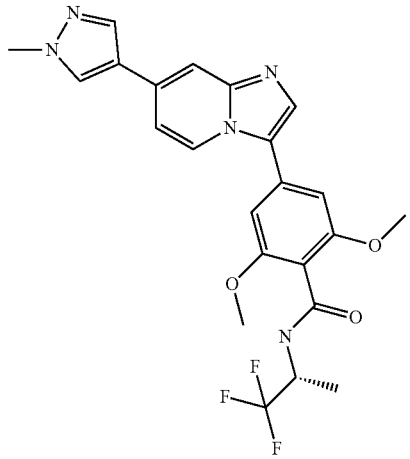

To a suspension of Int 52 (650 mg, 1.72 mmol, 1 eq.) in DMF (5 mL) are added DIPEA (955 μL, 6.87 mmol, 4 eq.), (2R)-1,1,1-trifluoropropan-2-amine (CAS #779303-24-1; 514 mg, 3.44 mmol, 2 eq.) and HATU (718 mg, 1.89 mmol, 1.1 eq.). The mixture is stirred at RT overnight. HATU (460 mg, 0.6 eq.) and (2R)-1,1,1-trifluoropropan-2-amine (0.7 eq.) are added and the mixture is stirred at RT for 3 h. A saturated solution of NaHCO$_3$ and water are added, the mixture is extracted with EtOAc. The combined organic layers are washed with brine, dried over Na$_2$SO$_4$, filtered and concentrated in vacuo. The residue is purified twice by flash chromatography on silica gel (eluting with DCM/MeOH 100/0 to 95/5) to afford the expected compound.

2.46. Cpd 175

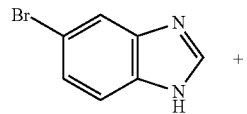

+

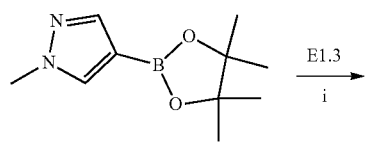

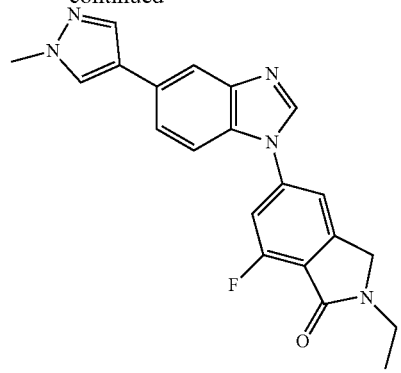

2.46.1. Step i: Method E1.3: 5-(1-Methyl-1H-pyrazol-4-yl)-1H-benzimidazole

A flask equipped with an air condenser is charged with 5-bromo-1 i-benzimidazole (CAS #4887-88-1: 1.052 g, 5.34 mmol, 0.95 eq.), 1-methyl-4-(4,4,5,5-tetramethyl-1,3,2-dioxaborolan-2-yl)pyrazole (CAS #761446-44-0; 1.17 g, 5.62 mmol, 1 eq.), Cs$_2$CO$_3$ (3.67 g, 11.26 mmol, 2 eq.) and a dioxane/water solvent mixture 4/1 (50 mL) degassed with N$_2$. Pd(dppf)Cl$_2$.DCM (344 mg, 0.42 mmol, 0.075 eq.) is added and the system is placed under N$_2$ atmosphere. The reaction mixture is stirred at 115° C. for 2 h, then at RT overnight. The reaction mixture is degassed with N$_2$ then dioxane/water degassed solvent mixture 4/1 (10 mL), 1-methyl-4-(4,4,5,5-tetramethyl-1,3,2-dioxaborolan-2-yl) pyrazole (CAS #761446-44-0; 117 mg, 0.562 mmol, 0.1 eq.), and Pd(dppf)Cl$_2$.DCM (162 mg, 0.198 mmol, 0.035 eq.) are added and the mixture is stirred at 115° C. for 3.5 h. Finally using same protocol, 1-methyl-4-(4,4,5,5-tetramethyl-1,3,2-dioxaborolan-2-yl)pyrazole (CAS #761446-44-0; 117 mg, 0.562 mmol, 0.1 eq.), and Pd(dppf)Cl$_2$.DCM (162 mg, 0.198 mmol, 0.035 eq.) are added and the mixture is stirred to 115° C. for 3 h. The mixture is filtered over Celite®. The filtrate is concentrated in vacuo and purified by flash chromatography on silica gel (eluting with DCM/MeOH 100/0 to 90/10) to afford the expected 5-(1-methyl-1H-pyrazol-4-yl)-1H-benzimidazole.

LCMS: MW (calcd): 198.2; m/z MW (obsd): 199.2 (M+H)

2.46.2. Step ii: Method E2.3: Cpd 175

A microwave vial is charged with 5-(1-methyl-1H-pyrazol-4-yl)-1H-benzimidazole (80 mg, 0.40 mmol, 1 eq.) and K$_3$PO$_4$ (171 mg, 0.81 mmol, 2 eq.). The vial is sealed, then evacuated and filled with argon (this process is repeated 3 times). A degassed solution of anhydrous toluene and anhydrous dioxane (5/1, 0.4 mL) is added via syringe.

A second vial is charged with Pd$_2$dba$_3$ (22 mg, 0.024 mmol, 6% mol.) and Me$_4$t-BuXPhos (CAS #857356-94-6; 23 mg, 0.048 mmol, 12% mol.). The vial is sealed, then evacuated and filled with argon (this process is repeated 3 times). A degassed solution of anhydrous toluene and anhydrous dioxane (5/1, 0.4 mL) is added via syringe. The resulting mixture is stirred to 120° C. for 5 min. Then 5-bromo-2-ethyl-7-fluoro-isoindolin-1-one (cf. Int 19 synthesis, Ex. 2.17, step i; 104 mg, 0.40 mmol, 1 eq.) and the premixed catalyst solution are added to the first vial. The reaction mixture is heated to 120° C. for 18 h.

Water is added and the mixture is extracted with DCM. The combined organic layers are washed with brine, dried over anhydrous MgSO$_4$, filtered and concentrated in vacuo. The residue is purified by flash chromatography on silica gel (eluting with DCM/EtOAc/EtOH 60/35/5 then 60/30/10) and preparative TLC (eluting with DCM/EtOAc/EtOH 60/30/10) to afford Cpd 175.

2.47. Cpd 202

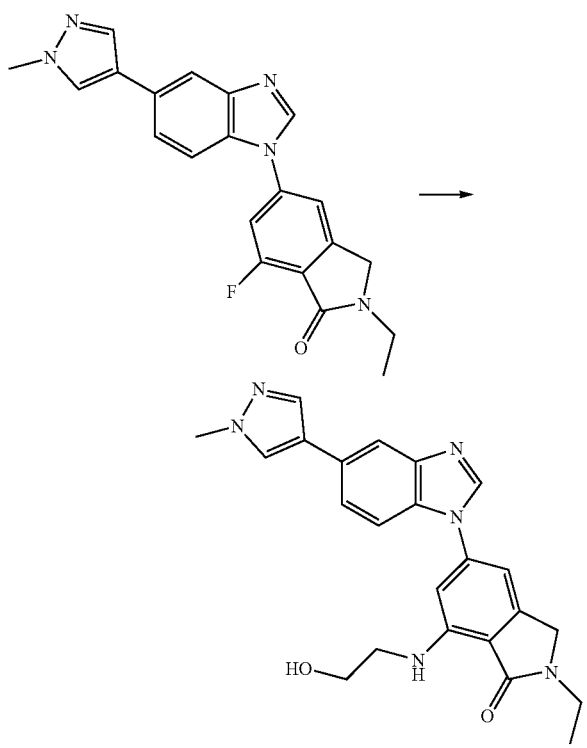

A microwave vial is charged with Cpd 175 (39 mg, 0.104 mmol, 1 eq.), DMAC (0.9 mL), ethanolamine (19 µL, 0.311 mmol, 3 eq.) and DIPEA (54 µL, 0.311 mmol, 3 eq.). The reaction mixture is stirred to 100° C. for 30 h. The mixture is concentrated in vacuo, water and NaHCO$_3$ are added and the mixture is extracted with DCM. The combined organic layers are washed with brine, dried over anhydrous MgSO$_4$, filtered and concentrated in vacuo. The residue is purified by flash chromatography on silica gel (eluting with DCM/MeOH 100/0 to 95/5) to afford Cpd 202.

2.48. Cpd 266 (Method H)

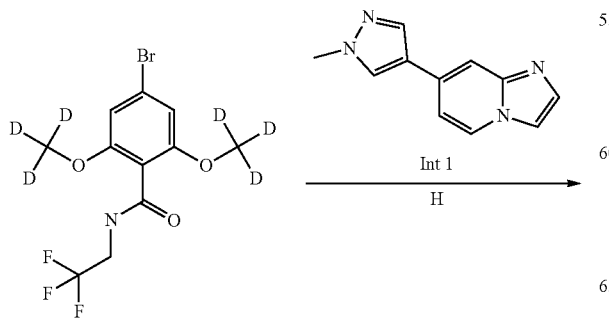

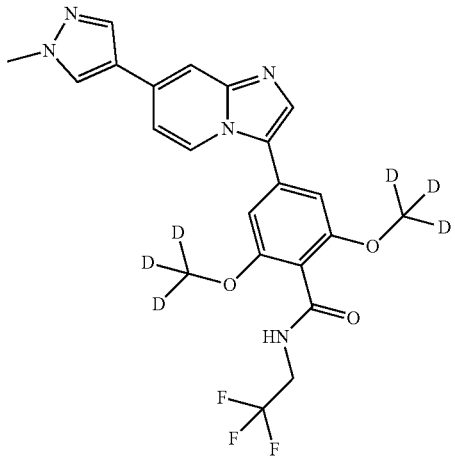

Int 1 (2.5 g, 12.61 mmol, 1.0 eq.), Int 8 (4.32 g, 12.61 mmol, 1.0 eq.), KOAc (2.5 g, 25.22 mmol, 2.0 eq.) and DMAC (25 mL, 10 volumes) are loaded. The reaction mixture is degassed with N$_2$ under stirring. Pd(dppf)Cl$_2$.DCM (0.051 g, 0.063 mmol, 0.005 eq.) is added. The mixture is heated to 130° C. for 21 h. The mixture is cooled to RT, and then filtered. Water (60 mL, 24 volumes) is added to the filtrate and the suspension formed is filtered. The solid is washed with water (60 mL, 24 volumes), filtered, and triturated with MTBE (60 mL, 24 volumes). The solid is taken up in water and DCM and the mixture is extracted with DCM. The combined organic layers are washed with water, purified by flash chromatography on silica gel eluting with DCM/MeOH (100/0 to 95/05) to afford Cpd 266.

2.49. Cpd 291

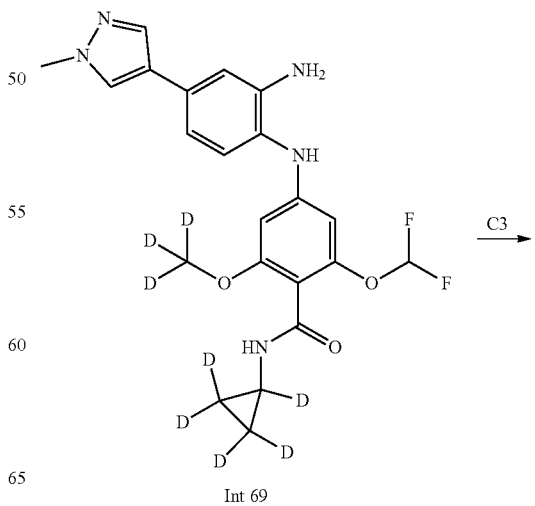

Int 69

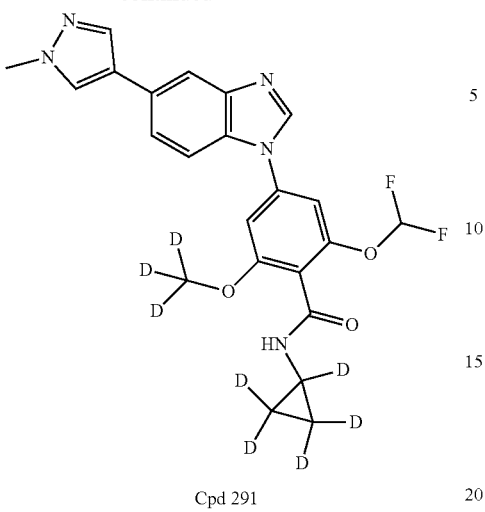

Cpd 291

Int 69 (0.787 g, 1.74 mmol, 1.0 eq.) is suspended in trimethyl orthoformate (3 mL, 4 volumes). The reaction mixture is refluxed (110° C.) for 50 min. The reaction mixture is cooled to 25° C. and then MTBE (3 mL) is added. The reaction mixture is stirred at RT for 1 h. The suspension is filtered. The cake is washed with MTBE (5 mL). The solid is purified on silica gel column, eluting with DCM/ACN until 100% ACN to afford Cpd 291.

2.50. Cpd 292

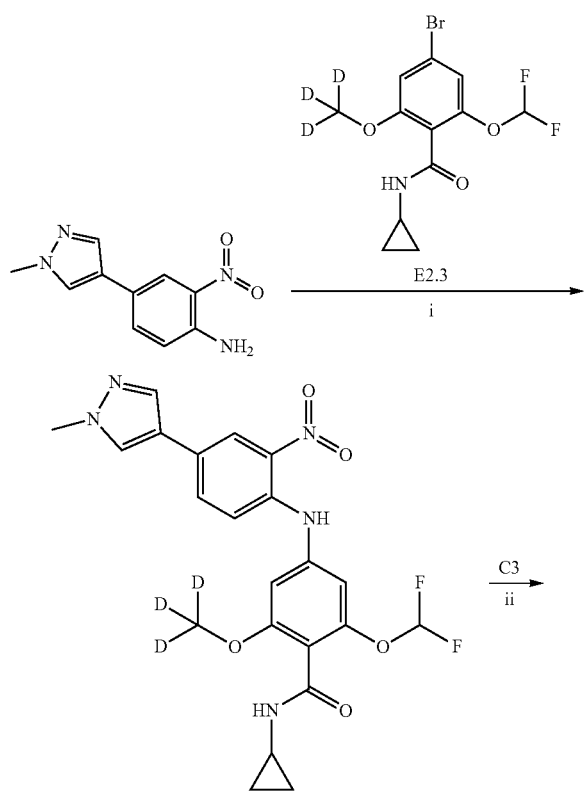

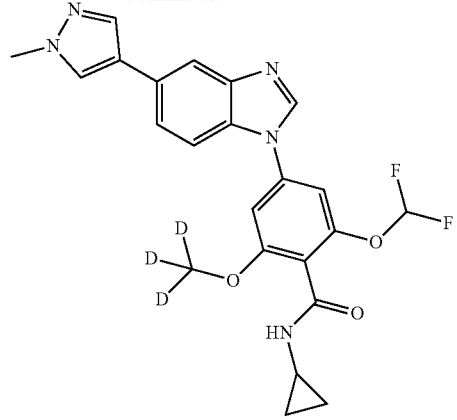

2.50.1. Step i: Method E2.3: N-cyclopropyl-2-(difluoromethoxy)-4-[4-(1-methylpyrazol-4-yl)-2-nitroanilino]-6-(trideuteriomethoxy)benzamide The experiment is performed under oxygen and water free atmosphere (glovebox). Int 70 (1.4 g, 4.13 mmol, 1 eq.), Int 56 (0.99 g, 4.54 mmol, 1.1 eq.), $K_3PO_4$ (1.75 g, 8.26 mmol, 2 eq.), XantPhos (48 mg, 0.083 mmol, 0.02 eq.) and $Pd(OAc)_2$ (9 mg, 0.041 mmol, 0.01 eq.) are suspended in dioxane (5V). The mixture is heated to 100° C. for 90 min. The mixture is cooled to RT. During cooling, water is added to the mixture. The mixture is stirred for 1 h. The mixture is filtered off and the filter cake is washed with water followed by MTBE. The resulting filter cake is dried in vacuo and then suspended in MTBE (10 mL) and triturated overnight. The mixture is filtered off and the filter cake is washed with MTBE (2*5 mL). The resulting solid is dried in vacuo at 50° C. for 3 h to afford the desired nitro anilino compound.
LCMS: MW (calcd): 476.5; m/z MW (obsd): 477.2

2.50.2. Step ii: Method C3: Cpd 292

N-cyclopropyl-2-(difluoromethoxy)-4-[4-(1-methylpyrazol-4-yl)-2-nitro-anilino]-6-(trideuteriomethoxy)benzamide (1.68 g, 1 eq.) is dissolved in THF (9 mL) and MeOH (9 mL). $NH_4Cl$ (2.075 g, 11 eq.) is added, followed by zinc (2.075 g, 9 eq.). The mixture is heated to 30° C. and zinc is added in 0.1 g portions over 15 min maintaining the temperature between 30-40° C. Additional Zn (0.231 g, 1 eq.) and $NH_4Cl$ (0.207 g, 1.1 eq.) is added. The mixture is stirred at 50° C. until it turns from an orange suspension into a pale brown suspension. The mixture is filtered over Celite® and the filter cake is rinsed with THF (3*5 mL) and the filtrate concentrated in vacuo. The resulting solid is suspended in trimethyl orthoformate (7.72 mL, 20 eq.) and heated to reflux for 40 min. The mixture is cooled to 50° C., then MTBE (15 mL) is added and the mixture is further cooled to RT under stirring. EtOAc is added and stirring continued. The mixture is concentrated in vacuo and the crude is purified by flash column chromatography, the residue is evaporated and the resulting solid is triturated in MTBE for 30 min. The mixture is filtered off and the solid is dried in vacuo. The solid is further dissolved in a mixture of i-PrOH and cyclohexane 1:1 (40 mL) under reflux. Upon cooling the mixture is left to stand for 1 h and filtered off. The filtrate is collected and left to stand for 72 h. The mixture is filtered off and the solid dried in vacuo at 40° C. to afford Cpd 292.

2.51. Cpd 293

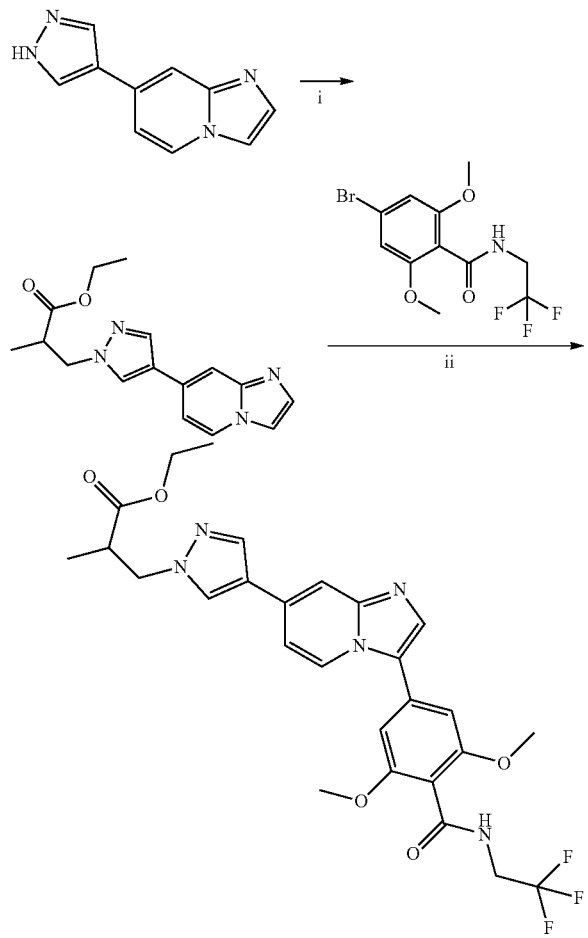

2.51.1. Step i: ethyl 3-(4-imidazo[1,2-a]pyridin-7-ylpyrazol-1-yl)-2-methyl-propanoate

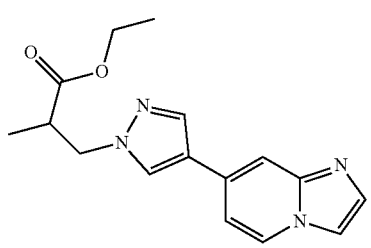 [SMILES: CCOC(=O)C(C)Cn1cc(-c2ccn3ccnc3c2)cn1]

To a suspension of Int 76 (100 mg, 0.52 mmol, 1.0 eq.) in 3 mL of dry ACN are added ethyl methacrylate (327 µL, 5.0 eq.) followed by DBU (40 µL, 0.5 eq). The resulting mixture is stirred at 80° C. in a sealed vial for 16 h. The reaction mixture is cooled to RT and diluted with 20 mL of EtOAc. The organic layers are washed with 2×30 mL of sat. NaHCO₃ water solution followed by 30 mL of brine. After drying over Na₂SO₄ the solvent is evaporated. The residue is purified by flash chromatography on silica gel (eluting 5 to 100% (10% MeOH in EtOAc) in EtOAc) to afford ethyl 3-(4-imidazo[1,2-a]pyridin-7-ylpyrazol-1-yl)-2-methyl-propanoate.

LCMS: MW (calcd): 298.3; m/z MW (obsd): 299.6 (M+H)

2.51.2. Step ii: Cpd 293

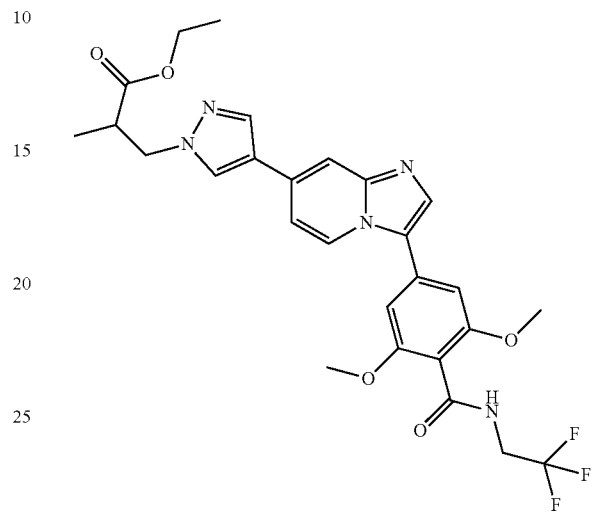

A degassed solution of Int 5 (262 mg, 1.6 eq.), KOAc (138 mg, 3.0 eq.), ethyl 3-(4-imidazo[1,2-a]pyridin-7-ylpyrazol-1-yl)-2-methyl-propanoate (140 mg, 0.464 mmol, 1.0 eq.) and Pd(dppf)Cl₂.DCM (19 mg, 0.05 eq) in dry DMAC (2.0 mL) is placed under argon atmosphere and stirred at 115° C. for 8 h. The reaction mixture is cooled at RT and poured into 30 mL of water. 5 mL of sat. Na₂CO₃ water solution is added. Extraction with 3×15 mL of EtOAc follows. The combined organic layers are washed with 20 mL of brine and dried over Na₂SO₄. After filtration the solvent is evaporated. The residue is purified by flash chromatography on silica gel (eluting 0 to 80% (10% MeOH in DCM) in DCM, then 100% of (10% MeOH in DCM)). After evaporation of the solvent from the gathered fractions, the residue is dissolved in 10 mL of DCM. Evaporation affords the expected product.

2.52. Cpd 294

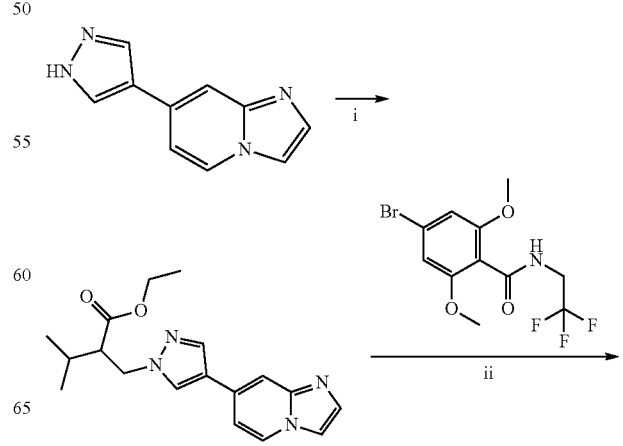

251
-continued

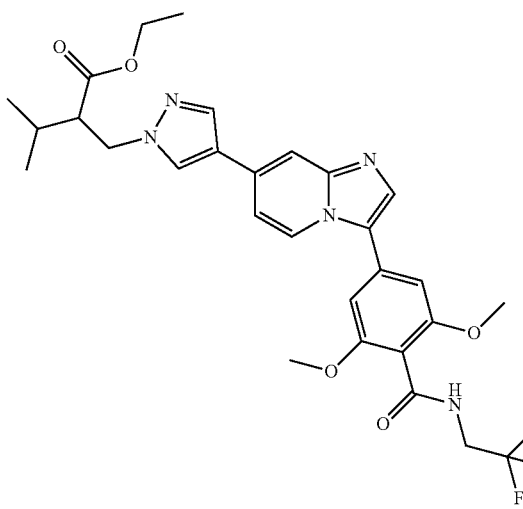

2.52.1. Step i: ethyl 2-[(4-imidazo[1,2-a]pyridin-7-ylpyrazol-1-yl)methyl]-3-methyl-butanoate

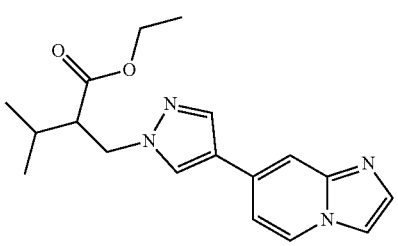 [SMILES: CCOC(=O)C(Cn1cc(-c2ccn3ccnc3c2)cn1)C(C)C]

To a suspension of Int 76 (100 mg, 0.52 mmol, 1.0 eq.) in 3 mL of dry ACN are added ethyl 3-methyl-2-methylene-butanoate (327 µL, 5.0 eq.) followed by DBU (40 µL, 0.5 eq.). The resulting mixture is stirred at 80° C. in a sealed vial for 16 h. The reaction mixture is cooled to RT and diluted with 30 mL of EtOAc. The organic layers are washed with 2×30 mL of sat. NaHCO₃ water solution followed by 30 mL of brine. After drying over Na₂SO₄ the solvent is evaporated. The residue is purified by flash chromatography on silica gel (eluting 5 to 100% (10% MeOH in EtOAc) in EtOAc) to afford ethyl 2-[(4-imidazo[1,2-a]pyridin-7-ylpyrazol-1-yl)methyl]-3-methyl-butanoate.

LCMS: MW (calcd): 326.4; m/z MW (obsd): 327.2 (M+H)

252

2.52.2. Step ii: Cpd 294

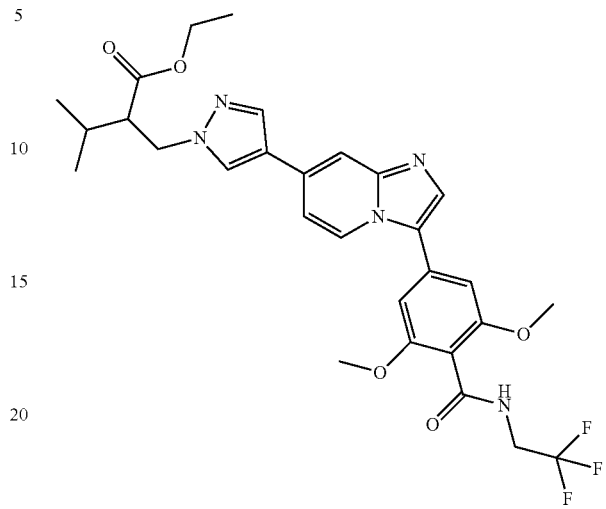

A degassed solution of Int 5 (238 mg, 1.6 eq.), KOAc (138 mg, 3.0 eq.), ethyl 2-[(4-imidazo[1,2-a]pyridin-7-ylpyrazol-1-yl)methyl]-3-methyl-butanoate (145 mg, 0.464 mmol, 1.0 eq.) and Pd(dppf)Cl₂.DCM (18 mg. 0.05 eq) in dry DMAC (2.0 mL) is placed under argon atmosphere and stirred at 115° C. for 8 h. The reaction mixture is cooled at RT and poured into 30 mL of sat. NaHCO₃ water solution. Extraction with 3×15 mL of EtOAc follows. The combined organic layers are washed with 2×20 mL of sat. NaHCO₃ water solution, 20 mL of brine, and dried over Na₂SO₄. After filtration the solvent is evaporated. The residue is purified by flash chromatography on silica gel (eluting 0 to 45% (10% MeOH in DCM) in DCM). After evaporation of the solvent from the gathered fractions, the residue is dissolved in 10 mL of DCM. Evaporation affords the expected product.

2.53. Cpd 295

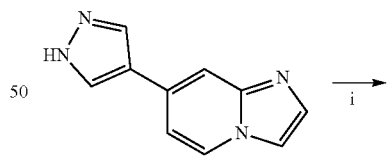

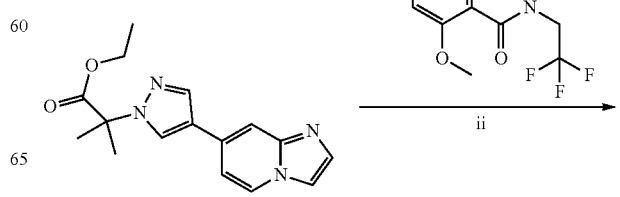

2.53.1. Step i: ethyl 2-(4-imidazo[1,2-a]pyridin-7-ylpyrazol-1-yl)-2-methyl-propanoate

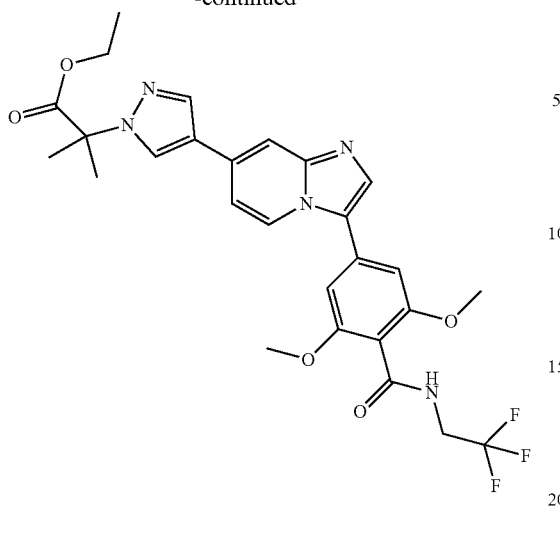

To a suspension of Int 76 (120 mg, 0.585 mmol, 1.0 eq.) and ethyl 2-bromo-2-methyl-propanoate (114 µL, 1.3 eq.) in 2 mL of dry ACN is added $K_2CO_3$ (139 mg, 1.7 eq.). The resulting mixture is stirred at 90° C. in a sealed vial for 16 h. The reaction mixture is cooled to RT and poured in 30 mL of sat. $NaHCO_3$ water solution. Extraction with 2×20 mL of EtOAc follows. The combined organic layers are washed with brine and the solvent is evaporated. The residue is purified by flash chromatography on silica gel (eluting with EtOAc/10% MeOH(DCM), 5-100% of 10% MeOH(DCM)) to afford ethyl 2-(4-imidazo[1,2-a]pyridin-7-ylpyrazol-1-yl)-2-methyl-propanoate.

LCMS: MW (calcd): 298.3; m/z MW (obsd): 299.1 (M+H)

2.53.2. Step ii: Cpd 295

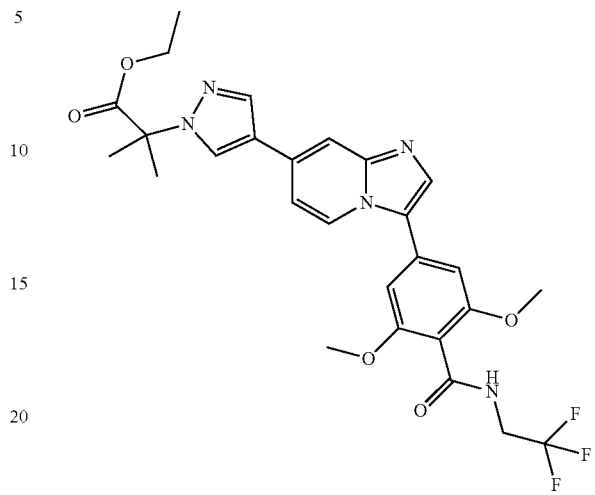

A degassed solution of Int 5 (187 mg, 0.55 mmol, 1.6 eq.), KOAc (98 mg, 3.0 eq.), ethyl 2-(4-imidazo[1,2-a]pyridin-7-ylpyrazol-1-yl)-2-methyl-propanoate (101 mg, 0.331 mmol, 1.0 eq.) and Pd(dppf)Cl$_2$.DCM (15 mg, 0.05 eq) in dry DMAC (2.0 mL) is placed under argon atmosphere and stirred at 115° C. for 4 h. The reaction mixture is cooled at RT and poured into 30 mL of sat. $NaHCO_3$ water solution. Extraction with 3×15 mL of EtOAc follows. The combined organic layers are washed with 2×20 mL of sat. $NaHCO_3$ water solution, 20 mL of brine, and dried over $Na_2SO_4$. After filtration the solvent is evaporated. The residue is purified by flash chromatography on silica gel (eluting 0 to 45% (10% MeOH in DCM) in DCM). After evaporation of the solvent from the gathered fractions, the residue is dissolved in 10 mL of DCM. Evaporation affords the expected product.

2.54. Cpd 296

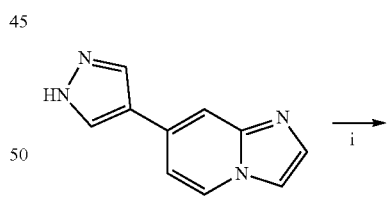

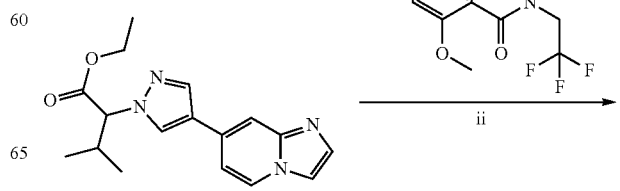

-continued

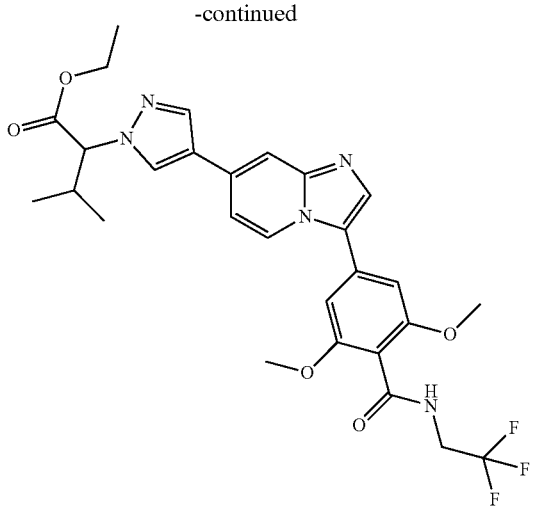

2.54.1. Step i: ethyl 2-(4-imidazo[1,2-a]pyridin-7-ylpyrazol-1-yl)-3-methyl-butanoate

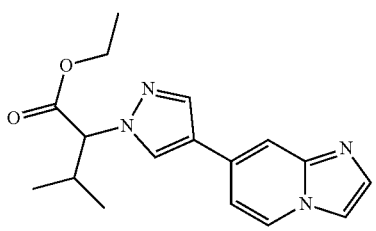 [SMILES: CCOC(=O)C(C(C)C)n1cc(-c2ccn3ccnc3c2)cn1]

To a suspension of Int 76 (120 mg, 0.585 mmol, 1.0 eq.) and ethyl 2-bromo-3-methyl-butanoate (127 µL, 1.3 eq.) in 2 mL of dry DMF is added $K_2CO_3$ (139 mg, 1.7 eq.). The resulting mixture is stirred at 70° C. for 8 h. The reaction mixture is cooled to RT and poured in 30 mL of sat. $NaHCO_3$ water solution. Extraction with 2×20 mL of EtOAc follows. The combined organic layers are washed with brine and the solvent is evaporated. The residue is purified by flash chromatography on silica gel (eluting 0 to 85% of (10% MeOH in DCM) in DCM) to afford ethyl 2-(4-imidazo[1,2-a]pyridin-7-ylpyrazol-1-yl)-3-methyl-butanoate.

LCMS: MW (calcd): 312.4; m/z MW (obsd): 313.2 (M+H)

2.54.2. Step ii: Cpd 296

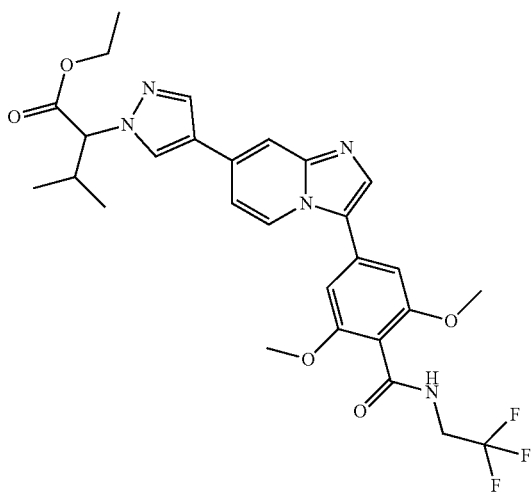 [SMILES: CCOC(=O)C(C(C)C)n1cc(-c2ccn3c(-c4cc(OC)c(C(=O)NCC(F)(F)F)c(OC)c4)cnc3c2)cn1]

A degassed solution of Int 5 (187 mg, 0.55 mmol, 1.6 eq.), KOAc (98 mg, 3.0 eq.), ethyl 2-(4-imidazo[1,2-a]pyridin-7-ylpyrazol-1-yl)-3-methyl-butanoate (105 mg, 0.331 mmol, 1.0 eq.) and Pd(dppf)Cl$_2$.DCM (15 mg, 0.05 eq) in dry DMAC (2.0 mL) is placed under argon atmosphere and stirred at 115° C. for 4 h. The reaction mixture is cooled at RT and poured into 30 mL of sat. $NaHCO_3$ water solution. Extraction with 3×15 mL of EtOAc follows. The combined organic layers are washed with 2×20 mL of sat. $NaHCO_3$ water solution, 20 mL of brine, and dried over $Na_2SO_4$. After filtration the solvent is evaporated. The residue is purified by flash chromatography on silica gel (eluting 0 to 45% of (10% MeOH in DCM) in DCM). After evaporation of the solvent from the gathered fractions, the residue is dissolved in 10 mL of DCM. Evaporation affords the expected product.

2.55. Cpd 297

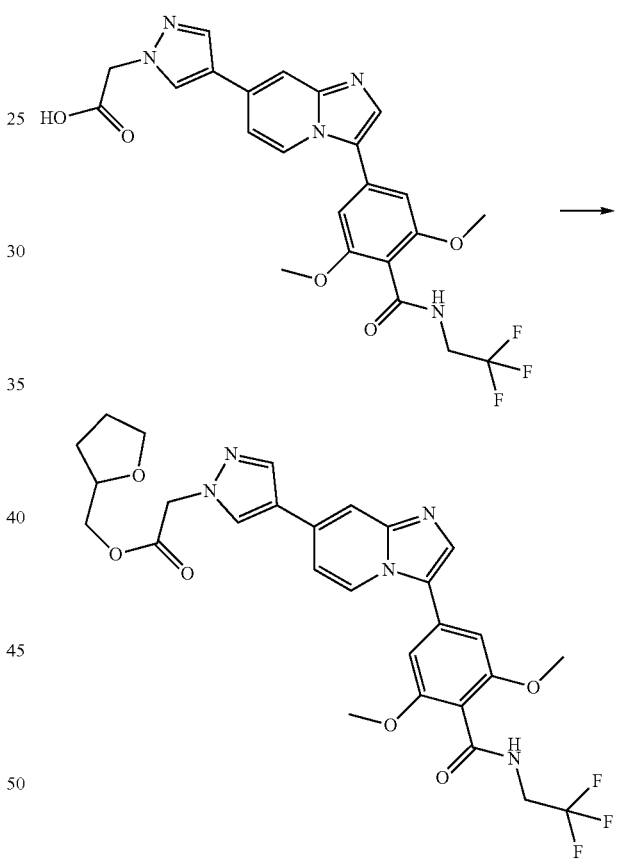

To a solution of Cpd 228 (100 mg, 0.196 mmol, 1.0 eq.) in 1.2 mL of dry DMF is added 1,1'-carbonyldiimidazole (49 mg, 1.5 eq.) and the mixture is stirred at 50° C. for 1 h. Dropwise addition of a mixture of tetrahydrofuran-2-yl-methanol (39 µL, 2.0 eq.) and DBU (45 µL, 1.5 eq.) in 400 µL of dry DMF follows. The mixture is stirred at 50° C. for 2 h and cooled to RT. The mixture is poured into 25 mL of a 5% $NaHCO_3$ water solution. Extraction with 3×15 mL of DCM (10% isopropanol) follows. The combined organic layers are dried over $Na_2SO_4$ and after filtration the solvent is evaporated. The residue is purified by flash chromatography (eluting 0 to 55% of (10% MeOH in DCM) in DCM) to afford the expected product. 2.56. Cpd 298

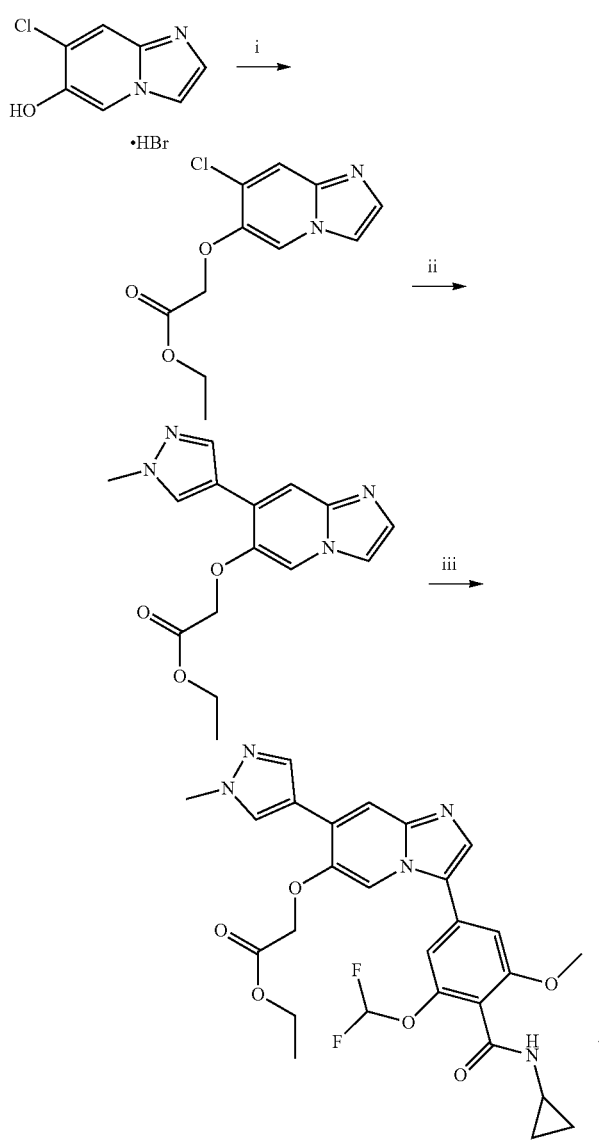

2.56.1. Step i: ethyl 2-(4-imidazo[1,2-a]pyridin-7-ylpyrazol-1-yl)-3-methyl-butanoate

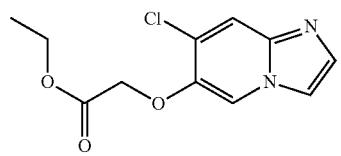 [SMILES: CCOC(=O)COc1cn2ccnc2cc1Cl]

Int 77 (575 mg, 2.3 mmol, 1 eq.) and K₂CO₃ (370 mg, 2.8 mmol, 1.15 eq.) are suspended in DMF (9 mL) and the mixture is heated to 60° C. At this temperature is added dropwise a solution of ethyl bromoacetate (272 μL, 2.43 mmol, 1.05 eq.) in DMF (1 mL). At the end of the addition the suspension is heated at 60° C. for 90 min, then the reaction medium is cooled to RT and is poured into 120 mL of 5% aq. NaHCO₃ solution. The mixture is extracted with EtOAc (3 times) and the combined organic layers are dried over Na₂SO₄, filtered and concentrated. The residue is purified by flash chromatography on silica gel (eluting 0 to 50% (10% MeOH in EtOAc) in MeOH) to afford the expected compound.

LCMS: MW (calcd): 254.7; m/z MW (obsd): 255.3 (M+H)

2.56.2. Step ii: ethyl 2-[7-(1-methylpyrazol-4-yl)imidazo[1,2-a]pyridin-6-yl]oxyacetate

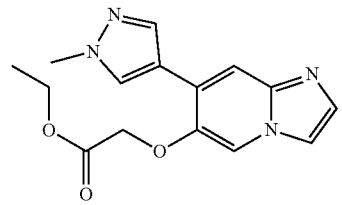 [SMILES: CCOC(=O)COc1cn2ccnc2cc1-c1cnn(C)c1]

A degassed solution of 1-methylpyrazole-4-boronic acid pinacol ester (CAS #761446-44-0; 105 mg, 0.49 mmol, 1.25 eq.), K₃PO₄ (250 mg, 1.2 mmol, 3 eq.), ethyl 2-(7-chloro-imidazo[1,2-a]pyridin-6-yl)oxyacetate (100 mg, 0.39 mmol, 1 eq.) and Pd(dppf)Cl₂.DCM (33 mg, 0.04 mmol, 0.1 eq.) in a mixture of dry 1,4-dioxane and EtOH (2 mL/2 mL) is stirred in a sealed flask at 80° C. under argon for 4 h. The reaction mixture is cooled to RT and is diluted with 50 mL of DCM. The obtained suspension is filtered over celite and the filtrate is concentrated. The residue is purified by flash chromatography on silica gel (eluting 0 to 80% (10% MeOH in DCM) in DCM) to afford the expected product.

LCMS: MW (calcd): 300.3; m/z MW (obsd): 301.1 (M+H)

2.56.3. Step iii: Cpd 298

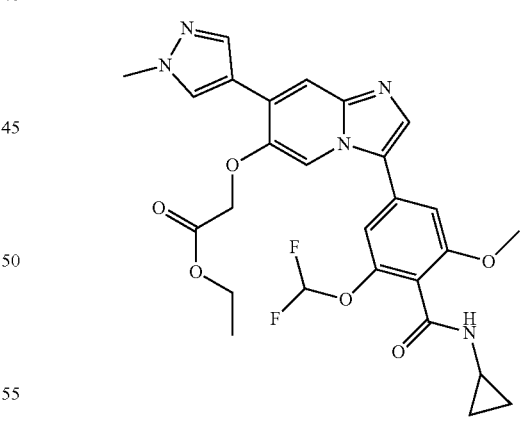

A mixture of Int 9 (128 mg, 0.37 mmol, 1.6 eq.), KOAc (69 mg, 0.69 mmol, 3 eq.), ethyl 2-[7-(1-methylpyrazol-4-yl)imidazo[1,2-a]pyridin-6-yl]oxyacetate (73 mg, 0.23 mmol, 1 eq.) and Pd(dppf)Cl₂.DCM (13 mg, 0.02 mmol, 0.07 eq.) in dry DMAC (1.5 mL) is stirred at 115° C. for 4 h under argon. The reaction medium is then cooled to RT and is poured into 20 mL of 5% aq. NaHCO₃ solution. The mixture is extracted with EtAOc (3 times) and the combined organic layers are washed with a 5% aq. NaHCO₃ solution (2 times) and with brine. The organic layer is dried over Na₂SO₄, filtered and concentrated. The crude mixture is purified by flash chromatography on silica gel (eluting 0 to 80% (10% MeOH in DCM) in DCM) to afford a residue that is dissolved in 10 mL of DCM. Concentration to dryness affords the expected compound.

2.57. Cpd 299

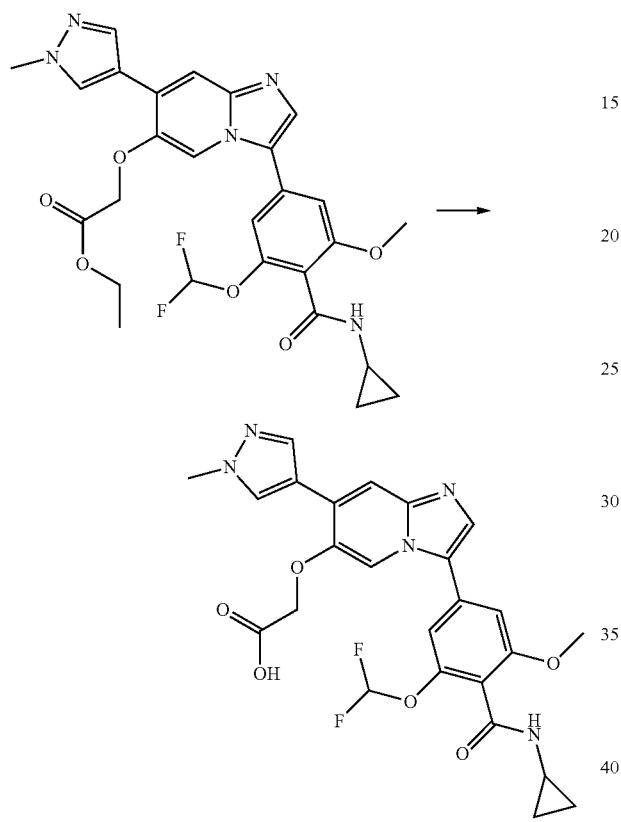

To a solution of Cpd 298 (30 mg, 0.054 mmol, 1 eq.) in a THF/H₂O (2 mL/0.5 mL) solvent mixture is added lithium hydroxide (6.5 mg, 0.27 mmol, 5 eq.) and the reaction mixture is stirred at RT for 1 h. Volatiles are evaporated and the residue is taken up in 10 mL of water and 1.5 mL of 1 N aqueous NaOH solution. The obtained suspension is stirred for 15 min and the pH is adjusted to 3 using a 4 N HCl aq. solution. Precipitation occurs, the solid is collected by filtration and washed with 3 mL of HCl solution at pH=3. Drying of the solid in a vacuum oven at 40° C. for 3 h affords the expected product.

2.58. Cpd 300

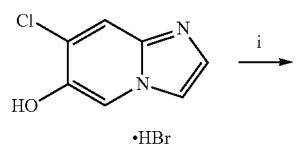

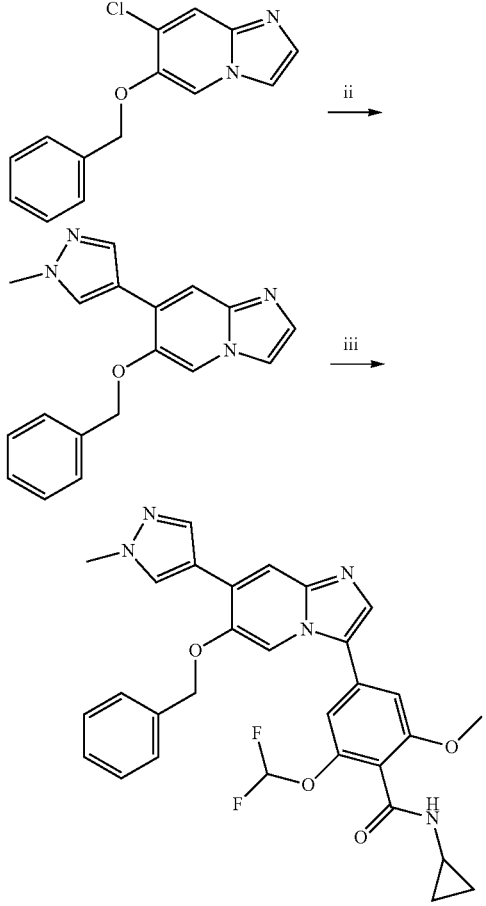

2.58.1. Step i: 6-benzyloxy-7-chloro-imidazo[1,2-a]pyridine

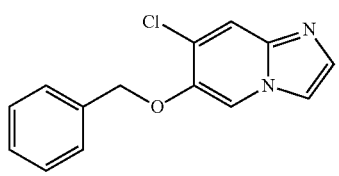 [SMILES: Clc1cc2nccn2cc1OCc1ccccc1]

To a suspension of Int 77 (250 mg, 1 mmol, 1 eq.) and Cs₂CO₃ (653 mg, 2 mmol, 2 eq.) in DMF (3 mL) is added after 5 min stirring benzyl chloride (117 µL, 1 mmol, 1 eq.) and the mixture is stirred at RT for 3 h. The reaction medium is poured into 120 mL of 5% aq. NaHCO₃ and the mixture is extracted with EtOAc. The combined organic layers are dried over Na₂SO₄, filtered and evaporated. The crude mixture is purified by flash chromatography on silica gel (eluting 0 to 50% (10% MeOH in EtOAc) in EtOAc) to afford the expected product.

LCMS: MW (calcd): 258.7; m/z MW (obsd): 259.1 (M+H)

2.58.2. Step ii: 6-benzyloxy-7-(1-methylpyrazol-4-yl)imidazo[1,2-a]pyridine

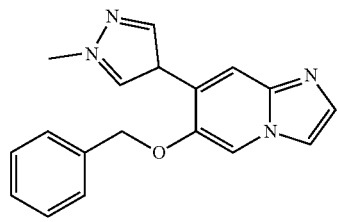

A degassed solution of 1-methylpyrazole-4-boronic acid pinacol ester (CAS #761446-44-0; 96 mg, 0.45 mmol, 1.25 eq.), $K_3PO_4$ (231 mg, 1.1 mmol, 3 eq.), 6-benzyloxy-7-chloro-imidazo[1,2-a]pyridine (105 mg, 0.36 mmol, 1 eq.) and Pd(dppf)Cl$_2$.DCM (30 mg, 0.04 mmol, 0.1 eq.) in a mixture of dry 1,4-dioxane and EtOH (2 mL/2 mL) is stirred in a sealed flask at 80° C. under argon for 4 h. The reaction mixture is cooled to RT and diluted with 50 mL of DCM. The obtained suspension is filtered over celite and the filtrate is concentrated. The residue is purified by flash chromatography on silica gel (eluting 0 to 80% (10% MeOH in DCM) in DCM) to afford the expected product.

LCMS: MW (calcd): 304.4; m/z MW (obsd): 305.2 (M+H)

2.58.3. Step iii: Cpd 300

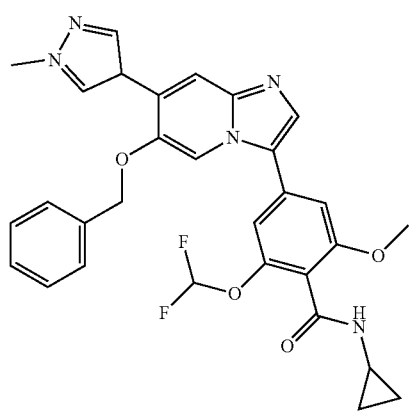

A degassed mixture of Int 9 (81 mg, 0.24 mmol, 1.6 eq.), KOAc (44 mg, 0.44 mmol, 3 eq.), 6-benzyloxy-7-(1-methylpyrazol-4-yl)imidazo[1,2-a]pyridine (47 mg, 0.15 mmol, 1 eq.) and Pd(dppf)Cl$_2$.DCM (8 mg, 0.01 mmol, 0.07 eq.) in dry DMAC (1 mL) is stirred at 115° C. for 4 h under argon. The reaction medium is then cooled to RT and poured into 20 mL of 5% aq. NaHCO$_3$ solution. The mixture is extracted with EtOAc (3 times) and the combined organic layers are washed with a 5% aq. NaHCO$_3$ solution (2 times) and with brine. The organic layer is dried over Na$_2$SO$_4$, filtered and concentrated. The crude mixture is purified by flash chromatography on silica gel (eluting 0 to 80% (10% MeOH in DCM) in DCM) to afford a residue that is dissolved in 10 mL of DCM. Concentration to dryness affords the expected compound.

2.59. Cpd 301

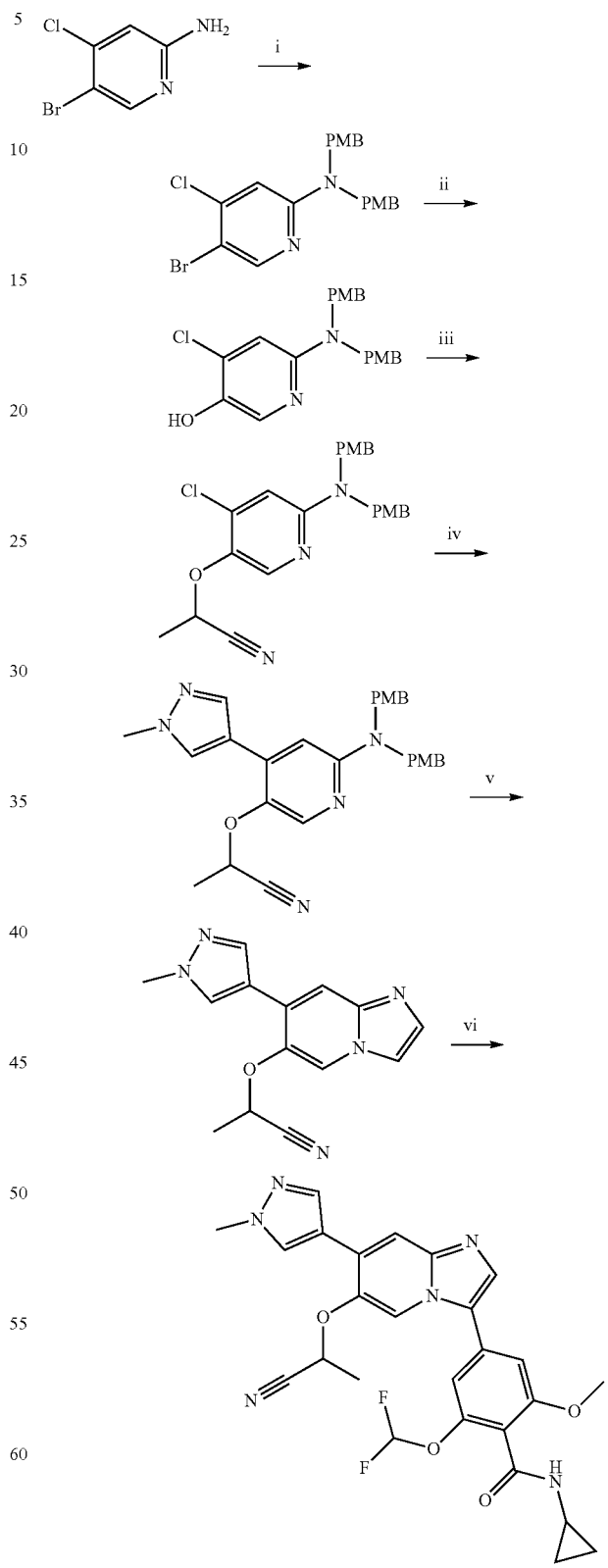

2.59.1. Step i: 5-bromo-4-chloro-N,N-bis[(4-methoxyphenyl)methyl]pyridin-2-amine

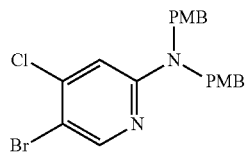

To a solution of 5-bromo-4-chloro-pyridin-2-amine (CAS #942947-94-6; 3.0 g, 14 mmol, 1 eq.) in dry DMF (30 mL) at 0° C. is added sodium hydride (60% dispersion in mineral oil, 1.46 g, 36.5 mmol, 2.6 eq.) and the resulting mixture is stirred at 0° C. for 15 min. Then 1-(chloromethyl)-4-methoxy-benzene (4.08 mL, 29.5 mmol, 2.2 eq.) is added and the mixture is stirred at 0° C. for 90 min. The reaction medium is poured into a Et$_2$O (300 mL)/water (400 mL) mixture and the layers are separated. The aqueous phase is extracted with Et$_2$O (twice) and the combined organic layers are washed with water and brine before being dried over Na$_2$SO$_4$. After filtration, the solvents are concentrated. The residue is purified by flash chromatography on silica gel (eluting 0 to 15% EtOAc in cyclohexane) to afford the expected product.

LCMS: MW (calcd): 447.8; m/z MW (obsd): 447.1/449.1 (M+H)

2.59.2. Step ii: 6-[bis[(4-methoxyphenyl)methyl]amino]-4-chloro-pyridin-3-ol

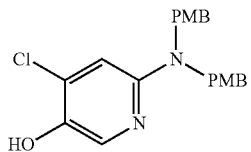

To a solution of 5-bromo-4-chloro-N,N-bis[(4-methoxyphenyl)methyl]pyridin-2-amine (3.2 g, 7.07 mmol, 1 eq.) in dry THF (80 mL) at −78° C. is added dropwise n-butyl lithium (2.5 M in hexanes, 3.54 mL, 8.84 mmol, 1.25 eq.). The mixture is stirred for 90 min at −78° C., then 2-isopropoxy-4,4,5,5-tetramethyl-1,3,2-dioxaborolane (CAS #61676-62-8, 2.94 mL, 14.14 mmol, 2.0 eq.) is added and the reaction is stirred at −78° C. for 45 min. The mixture is left to warm-up to −10° C. in 30 min and hydrogen peroxide (30% water solution, 2.89 mL, 28.28 mmol, 4.0 eq.) is added. The reaction is then stirred at RT for 30 min before being diluted with 250 mL of EtOAc and poured into 250 mL of a water/brine mixture. The layers are separated and the aqueous phase is extracted with EtOAc. The combined organic layers are dried over Na$_2$SO$_4$, filtered and concentrated. The residue is suspended in 400 mL of 1 N NaOH aq. solution and the aqueous phase is washed with Et$_2$O. The pH of the water layer is adjusted to ≈6 using concentrated HCl followed by extraction with EtOAc (3 times). The combined organic layers are dried over Na$_2$SO$_4$, filtered and concentrated to afford the expected product.

LCMS: MW (calcd): 384.9; m/z MW (obsd): 385.2 (M+H)

2.59.3. Step iii: 2-[[6-[bis[(4-methoxyphenyl)methyl]amino]-4-chloro-3-pyridyl]oxy]propanenitrile

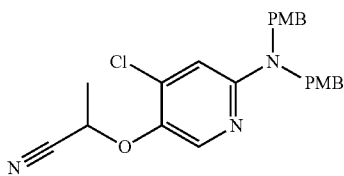

To a suspension of 6-[bis[(4-methoxyphenyl)methyl]amino]-4-chloro-pyridin-3-ol (500 mg, 1.24 mmol, 1.0 eq.) and Cs$_2$CO$_3$ (612 mg, 1.86 mmol, 1.5 eq.) in dry DMF (7 mL) is added 2-bromopropionitrile (133 µL, 1.5 mmol, 1.2 eq.). The resulting mixture is stirred at 75° C. for 45 min and after being cooled down to RT is poured into an EtOAc (70 mL)/water (45 mL)/brine (45 mL) mixture. The layers are separated and the aqueous phase is extracted with EtOAc. The combined organic layers are washed with 50 mL of brine, dried over Na$_2$SO$_4$, filtered and concentrated. The residue is purified by flash chromatography on silica gel (eluting with 0 to 25% EtOAc in cyclohexane) to afford the expected product.

LCMS: MW (calcd): 437.9; m/z MW (obsd): 438.2 (M+H)

2.59.4. Step iv: 2-[[6-[bis[(4-methoxyphenyl)methyl]amino]-4-(1-methylpyrazol-4-yl)-3-pyridyl]oxy]propanenitrile

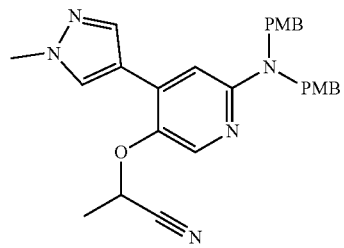

1-methyl-4-(4,4,5,5-tetramethyl-1,3,2-dioxaborolan-2-yl)pyrazole (CAS #761446-44-0; 271 mg, 1.26 mmol, 1.5 eq.), K$_3$PO$_4$ (541 mg, 2.52 mmol, 3 eq.), 2-[[6-[bis[(4-methoxyphenyl)methyl]amino]-4-chloro-3-pyridyl]oxy]propanenitrile (372 mg, 0.84 mmol, 1 eq.) and Pd(dppf)Cl$_2$.DCM (70.8 mg, 0.084 mmol, 0.1 eq.) in dry 1,4-dioxane (6 mL) are stirred in a sealed flask at 115° C. under argon for 16 h. The reaction mixture is cooled to RT and is diluted with 50 mL of EtOAc, 70 mL of water and 50 mL of brine. The layers are separated and the aqueous phase is extracted with EtOAc (2×30 mL). The combined organic layers are washed with brine, filtered over celite and the filtrate is concentrated. The residue is purified by flash chromatography on silica gel (eluting 0 to 35% EtOAc in DCM) to afford the expected product.

LCMS: MW (calcd): 483.6; m/z MW (obsd): 484.3 (M+H)

2.59.5. Step v: 2-[7-(1-methylpyrazol-4-yl)imidazo[1,2-a]pyridin-6-yl]oxypropanenitrile

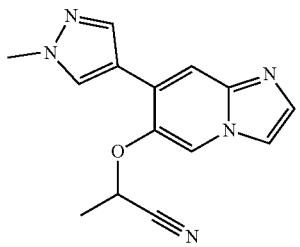 [SMILES: CC(C#N)Oc1cn2ccnc2cc1-c1cnn(C)c1]

To a stirred solution of 2-[[6-[bis[(4-methoxyphenyl)methyl]amino]-4-(1-methylpyrazol-4-yl)-3-pyridyl]oxy]propanenitrile (270 mg, 0.54 mmol, 1 eq.) in dry DCM (7 mL) is added TFA (1.25 mL, 16.1 mmol, 30 eq.) and the mixture is stirred at RT for 16 h. Solvents are then evaporated, the residue is dissolved in DCM (30 mL) and a saturated aq. NaHCO₃ solution (30 mL) is added. The resulting mixture is vigorously stirred for 5 min and the layers are separated. The aqueous phase is extracted with DCM and the combined organic layers are dried over Na₂SO₄, filtered and evaporated. The residue is suspended in EtOH (6 mL), the mixture is heated to 60° C. and 2-chloroacetaldehyde (50% aqueous solution, 0.12 mL, 0.97 mmol, 1.8 eq.) is added dropwise. The reaction medium is stirred at reflux for 3.5 h then volatiles are evaporated and the residue is taken up in DCM (40 mL) and a sat. aq. Na₂CO₃ solution (30 mL). The layers are separated and the aqueous phase is extracted with DCM (twice). The combined organic layers are dried over Na₂SO₄, filtered and concentrated. The residue is purified by flash chromatography on silica gel (eluting 0 to 35% (10% MeOH in DCM) in DCM) to afford the expected product.

LCMS: MW (calcd): 267.3; m/z MW (obsd): 268.1 (M+H)

2.59.6. Step vi: Cpd 301

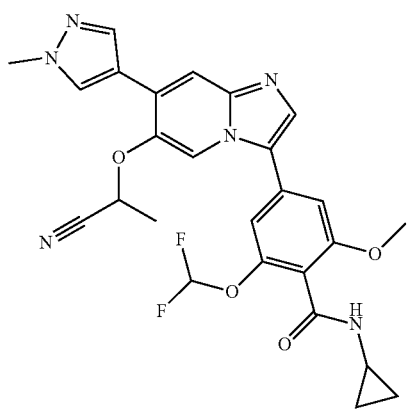

A degassed mixture of Int 9 (99 mg, 0.29 mmol, 1.6 eq.), KOAc (53 mg, 0.54 mmol, 3 eq.), 2-[7-(1-methylpyrazol-4-yl)imidazo[1,2-a]pyridin-6-yl]oxypropanenitrile (50 mg, 0.18 mmol, 1 eq.) and Pd(dppf)Cl₂.DCM (11 mg, 0.01 mmol, 0.07 eq.) in dry DMAC (1.2 mL) is stirred at 119° C. for 2 h under argon. The reaction mixture is then cooled to RT and poured into 20 mL of 5% aq. NaHCO₃ solution. The mixture is extracted with EtOAc (3 times) and the combined organic layers are washed with a 5% aq. NaHCO₃ solution (2 times) and with brine. The organic layer is dried over Na₂SO₄, filtered and concentrated. The crude mixture is purified by flash chromatography on silica gel (eluting 0 to 80% (10% MeOH in DCM) in DCM) to afford a residue that is dissolved in 2 mL of DCM. Concentration to dryness affords the expected compound.

2.60. Cpd 302

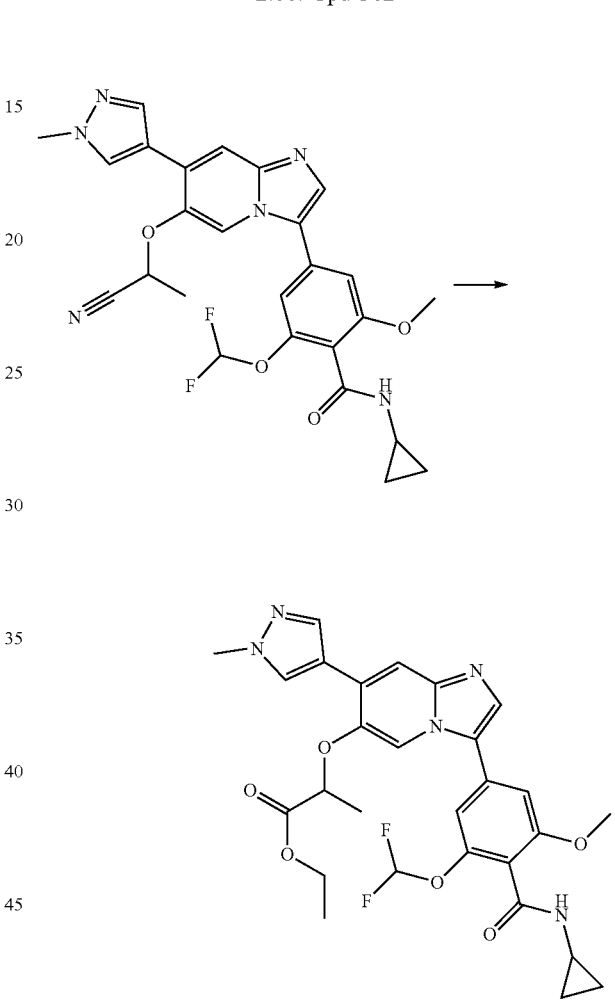

To a solution of Cpd 301 (122 mg, 0.22 mmol, 1 eq.) in dry 1,4-dioxane (2 mL) at −5° C. is added dropwise HCl (1.25 M in EtOH, 1.08 mL, 1.34 mmol, 6 eq.). The resulting mixture is stirred in a sealed vial at 90° C. for 60 h and is then poured on 100 mL of ice. The mixture is stirred for 15 min, diluted with 50 mL of sat. aq. NaHCO₃ solution and extracted with 2×40 mL of EtOAc. The combined organic layers are dried over Na₂SO₄, filtered and concentrated. The crude mixture is purified by flash chromatography on silica gel (eluting 0 to 100% (10% MeOH in EtOAc) in EtOAc) to afford a residue that is dissolved in a DCM/Et₂O mixture. Concentration of solvents affords the expected compound.

2.61. Cpd 303

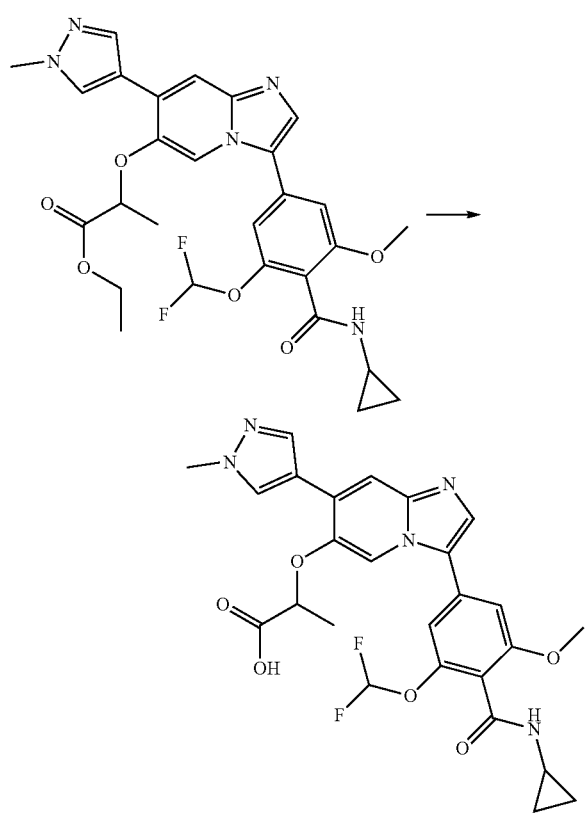

To a solution of Cpd 302 (30 mg, 0.05 mmol, 1 eq.) in a THF/H$_2$O (2 mL/0.7 mL) solvent mixture is added lithium hydroxide (6.1 mg, 0.25 mmol, 5 eq.) and the reaction mixture is stirred at RT for 1 h. Volatiles are evaporated and the residue is taken up in 20 mL of water and 1 mL of 1 N aq NaOH. The solution is washed with Et$_2$O. Then upon stirring the pH of the aqueous phase is adjusted to 3 using a 4 N HCl aq. solution. The obtained solution is extracted with 20% isopropanol in DCM (3×15 mL). The combined organic layers are dried over Na$_2$SO$_4$, passed through a phase separator cartridge and concentrated to afford the expected compound.

2.62. Cpd 304

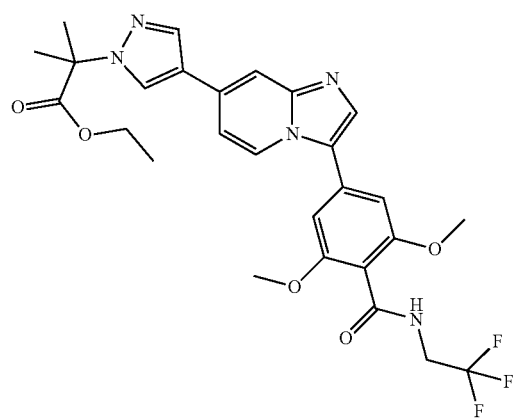

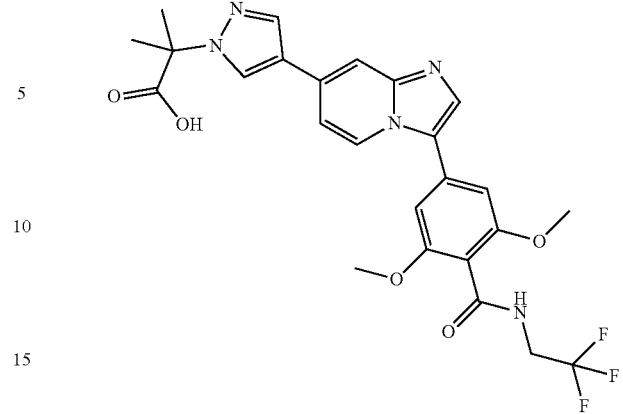

To a stirred suspension of Cpd 295 (22.0 mg, 0.0381 mmol) in 1,4-dioxane (2.0 mL) is slowly added NaOH, 1 N aq. solution (3.00 mL, 3.00 mmol) and the mixture is stirred at RT for 2 h. The mixture is transferred to a flask and 1,4-dioxane is evaporated. The residue is diluted with 3 mL of water. Using a 4 N HCl water solution, the pH of the solution is adjusted to 4. A precipitate forms, which is collected by filtration and washed with 2×3 mL of HCl water solution (pH4). Drying in a vacuum oven at 40° C. for 3 h affords the expected compound.

2.63. Cpd 305

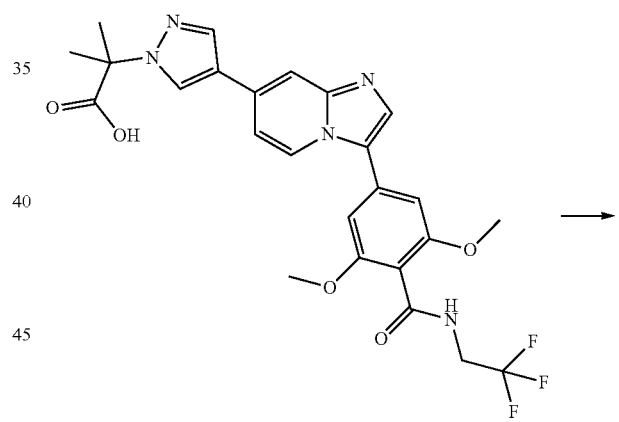

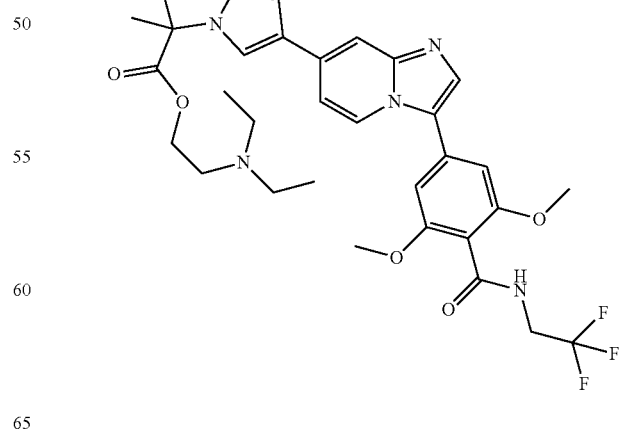

A reaction mixture of Cpd 304 (40.0 mg, 0.0730 mmol), KOAc (50.4 mg, 0.365 mmol) and 2-chloroethyl(diethyl)

ammonium chloride (62.8 mg, 0.365 mmol) is vigorously stirred in a sealed vial at RT for 16 h. The reaction mixture is diluted with 5 mL of EtOAc followed by 5 mL of water and after vigorous shaking is left to separate in two layers. The organic layer is dried over $Na_2SO_4$. After filtration, the solvent is evaporated to afford a crude material which is purified by flash chromatography on silica gel (eluting with 10% isopropanol in DCM then with 10% isopropanol in 1,4-dioxane). Solvent from the gathered fractions is evaporated to afford a residue that is dissolved in a DCM/$Et_2O$ mixture. Concentration of solvents affords the expected compound.

TABLE II

Intermediates used towards the compounds of the invention.

| Int # | Structure | Name | SM | Mtd | MW | MS Mes'd |
|---|---|---|---|---|---|---|
| 1 | 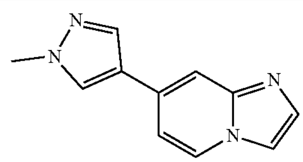 | 7-(1-methylpyrazol-4-yl)imidazo[1,2-a]pyridine | CAS# 808744-34-5 + CAS# 761446-44-0 | E1.3 | 198.2 | 199.0 |
| 2 | 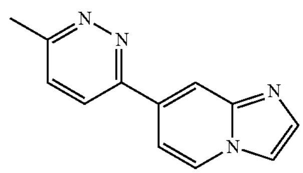 [SMILES: Cc1ccc(-c2ccn3ccnc3c2)nn1] | 7-(6-methylpyridazin-3-yl)imidazo[1,2-a]pyridine | CAS# 908268-52-0 + CAS# 1121-79-5 | E1.3 | 210.2 | 211.2 |
| 3 | 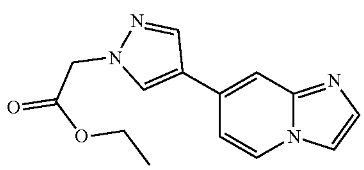 [SMILES: CCOC(=O)Cn1cc(-c2ccn3ccnc3c2)cn1] | ethyl 2-(4-imidazo[1,2-a]pyridin-7-ylpyrazol-1-yl)acetate | CAS# 6188-32-4 + CAS# 864754-16-5 | E1.3a | 270.3 | 271.9 |
| 4 | 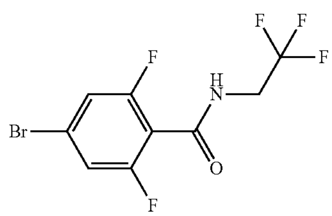 [SMILES: O=C(NCC(F)(F)F)c1c(F)cc(Br)cc1F] | 4-bromo-2,6-difluoro-N-(2,2,2-trifluoroethyl)benzamide | CAS# 183065-68-1 | Ex. 2.3 | 318.0 | 317.8 + 319.8 |
| 5 | 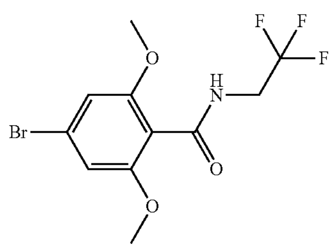 [SMILES: COc1cc(Br)cc(OC)c1C(=O)NCC(F)(F)F] | 4-bromo-2,6-dimethoxy-N-(2,2,2-trifluoroethyl)benzamide | Int 4 | Ex. 2.4 | 342.1 | 341.8 + 343.8 |
| 6 | 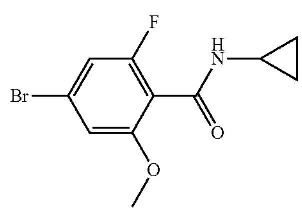 [SMILES: COc1cc(Br)cc(F)c1C(=O)NC1CC1] | 4-bromo-N-cyclopropyl-2-fluoro-6-methoxy-benzamide | Int 62 | Ex. 2.5 | 288.1 | 287.8 + 289.8 |
| 7 | 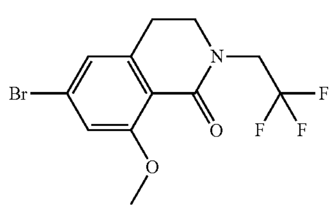 [SMILES: COc1cc(Br)cc2c1C(=O)N(CC(F)(F)F)CC2] | 6-bromo-8-methoxy-2-(2,2,2-trifluoroethyl)-3,4-dihydroisoquinolin-1-one | CAS# 1242157-15-8 | Ex. 2.6 | 338.1 | 338.1 + 340.1 |

TABLE II-continued

Intermediates used towards the compounds of the invention.

| Int # | Structure | Name | SM | Mtd | MW | MS Mes'd |
|---|---|---|---|---|---|---|
| 8 | 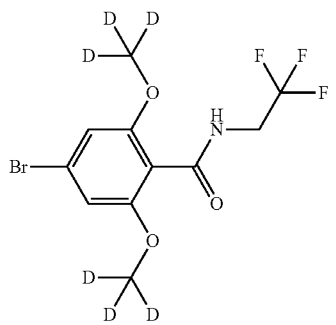 [SMILES: [2H]C([2H])([2H])Oc1cc(Br)cc(OC([2H])([2H])[2H])c1C(=O)NCC(F)(F)F] | 4-bromo-2,6-bis(trideuteriomethoxy)-N-(2,2,2-trifluoroethyl)benzamide | Int 4 | Ex. 2.7 | 348.1 | 347.9 + 349.9 |
| 9 | 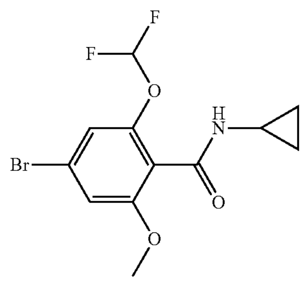 [SMILES: COc1cc(Br)cc(OC(F)F)c1C(=O)NC1CC1] | 4-bromo-N-cyclopropyl-2-(difluoromethoxy)-6-methoxy-benzamide | CAS# 183065-68-1 | Ex. 2.8 | 336.1 | 336.3 + 338.3 |
| 10 | 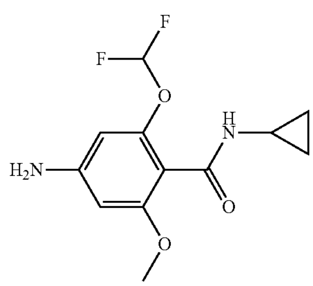 [SMILES: COc1cc(N)cc(OC(F)F)c1C(=O)NC1CC1] | 4-amino-N-cyclopropyl-2-difluoromethoxy)-6-methoxy-benzamide | CAS# 3956-34-1 | Ex. 2.9 | 272.2 | 273.2 |
| 11 | 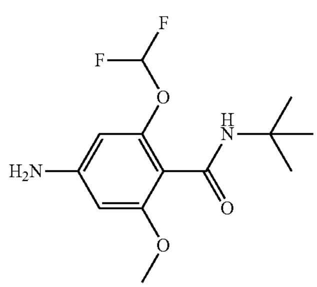 [SMILES: COc1cc(N)cc(OC(F)F)c1C(=O)NC(C)(C)C] | 4-amino-N-tert-butyl-2-(difluoromethoxy)-6-methoxy-benzamide | CAS# 3956-34-1 | Ex. 2.10 | 288.3 | 289.6 |
| 12 | 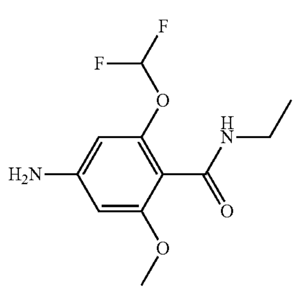 [SMILES: CCNC(=O)c1c(OC)cc(N)cc1OC(F)F] | 4-amino-2-(difluoromethoxy)-N-ethyl-6-methoxy-benzamide | CAS# 3956-34-1 | Ex. 2.11 | 260.2 | 261.2 |

TABLE II-continued

Intermediates used towards the compounds of the invention.

| Int # | Structure | Name | SM | Mtd | MW | MS Mes'd |
|---|---|---|---|---|---|---|
| 13 | 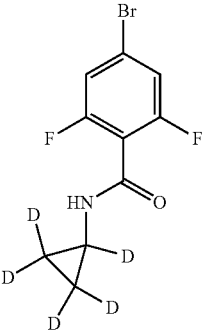 [SMILES: [2H]C1([2H])C([2H])([2H])C1([2H])NC(=O)c1c(F)cc(Br)cc1F] | 4-bromo-2,6-difluoro-N-(1,2,2,3,3-pentadeutericyclopropyl)benzamide | CAS# 183065-68-1 | Ex. 2.12 | 281.1 | 281.3 + 283.3 |
| 14 | 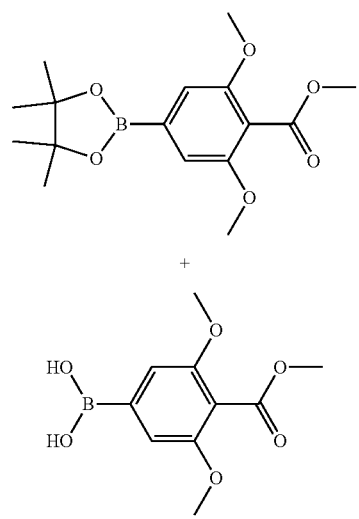 | methyl 2,6-dimethoxy-4-(4,4,5,5-tetramethyl-1,3,2-dioxaborolan-2-yl)benzoate/(3,5-dimethoxy-4-methoxycarbonyl-phenyl)boronic acid mixture | CAS# 2065-27-2 | Ex. 2.13 | 322.2 + 240.0 | 323.1 + 241.1 |
| 15 | 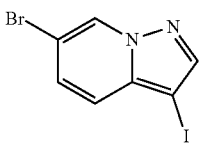 [SMILES: Brc1ccc2c(I)cnn2c1] | 6-bromo-3-iodo-pyrazolo[1,5-a]pyridine | CAS# 1264193-11-4 | F | 322.9 | NA |
| 16 | 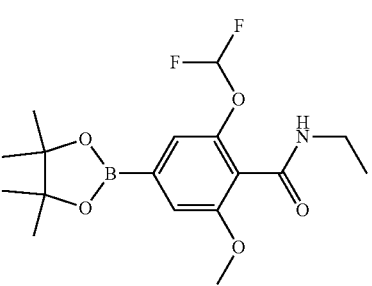 [SMILES: CCNC(=O)c1c(OC)cc(B2OC(C)(C)C(C)(C)O2)cc1OC(F)F] | 2-(difluoromethoxy)-N-ethyl-6-methoxy-4-(4,4,5,5-tetramethyl-1,3,2-dioxaborolan-2-yl)benzamide | CAS# 1466-76-8 | Ex. 2.14 | 371.2 | 372.4 |

TABLE II-continued

Intermediates used towards the compounds of the invention.

| Int # | Structure | Name | SM | Mtd | MW | MS Mes'd |
|---|---|---|---|---|---|---|
| 17 | 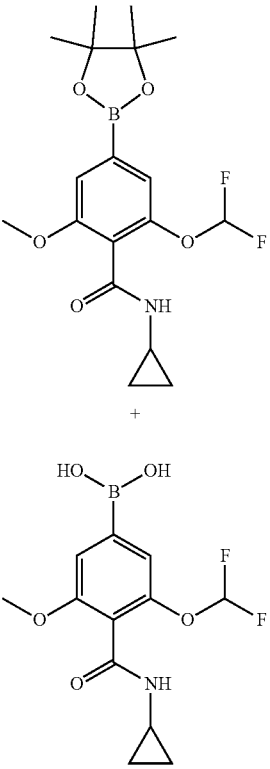 | N-cyclopropyl-2-(difluoromethoxy)-6-methoxy-4-(4,4,5,5-tetramethyl-1,3,2-dioxaborolan-2-yl)benzamide/4-(cyclopropylcarbamoyl)-3-(difluoromethoxy)-5-methoxyphenylboronic acid | CAS# 3147-64-6 | Ex. 2.15 | 383.2 + 301.1 | 384.4 + 302.2 |
| 18 | 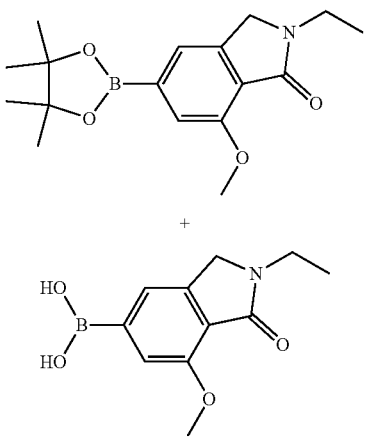 [SMILES: CCN1Cc2cc(B3OC(C)(C)C(C)(C)O3)cc(OC)c2C1=O ; CCN1Cc2cc(B(O)O)cc(OC)c2C1=O] | 2-ethyl-7-methoxy-5-(4,4,5,5-tetramethyl-1,3,2-dioxaborolan-2-yl)isoindolin-1-one/(2-ethyl-7-methoxy-1-oxo-isoindolin-5-yl)boronic acid mixture | CAS# 957346-37-1 | Ex. 2.16 | 317.2 + 235.1 | 318.4 + 236.3 |
| 19 | 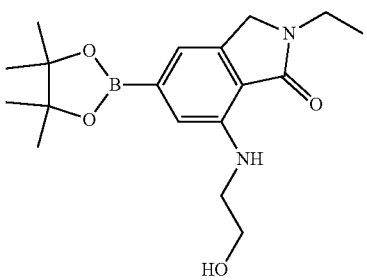 [SMILES: CCN1Cc2cc(B3OC(C)(C)C(C)(C)O3)cc(NCCO)c2C1=O] | 2-ethyl-7-(2-hydroxyethylamino)-5-(4,4,5,5-tetramethyl-1,3,2-dioxaborolan-2-yl)isoindolin-1-one | CAS# 957346-37-1 | Ex. 2.17 | 346.2 | 347.5 |

TABLE II-continued

Intermediates used towards the compounds of the invention.

| Int # | Structure | Name | SM | Mtd | MW | MS Mes'd |
|---|---|---|---|---|---|---|
| 20 | 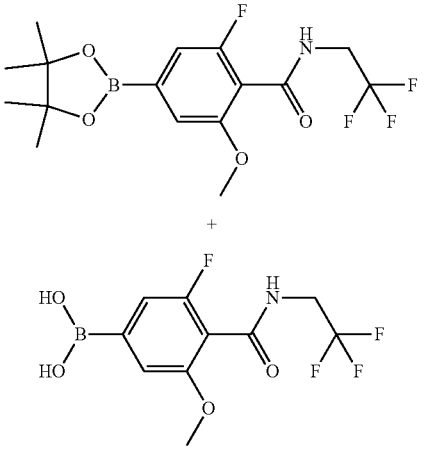 [SMILES: COc1cc(B2OC(C)(C)C(C)(C)O2)cc(F)c1C(=O)NCC(F)(F)F ; COc1cc(B(O)O)cc(F)c1C(=O)NCC(F)(F)F] | 2-fluoro-6-methoxy-4-(4,4,5,5-tetramethyl-1,3,2-dioxaborolan-2-yl)-N-(2,2,2-trifluoroethyl)benzamide/ 3-fluoro-5-methoxy-4-[(2,2,2-trifluoroethyl)carbamoyl]phenyl-boronic acid | CAS# 1472104-49-6 | Ex. 2.18 | 377.1 + 295.0 | 378.4 + 296.1 |
| 21 | 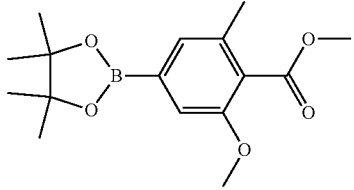 | methyl 2-methoxy-6-methyl-4-(4,4,5,5-tetramethyl-1,3,2-dioxaborolan-2-yl)benzoate | CAS# 79383-44-1 | Ex. 2.19 | 306.2 | 307.3 |
| 22 | 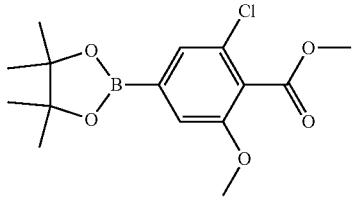 | methyl 2-chloro-6-methoxy-4-(4,4,5,5-tetramethyl-1,3,2-dioxaborolan-2-yl)benzoate | CAS# 936479-46-8 | Ex. 2.20 | 326.6 | 327.2 |
| 23 | 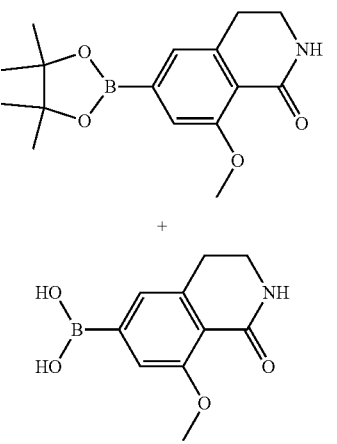 | 8-methoxy-6-(4,4,5,5-dioxaborolan-2-yl)-3,4-dihydro-2H-isoquinolin-1-one/ (8-methoxy-1-oxo-3,4-dihydro-2H-isoquinolin-6-yl)boronic acid mixture | CAS# 1242157-15-8 | Ex. 2.21 | 303.2 + 221.0 | 304.4 + 222.3 |

TABLE II-continued

Intermediates used towards the compounds of the invention.

| Int # | Structure | Name | SM | Mtd | MW | MS Mes'd |
|---|---|---|---|---|---|---|
| 24 | 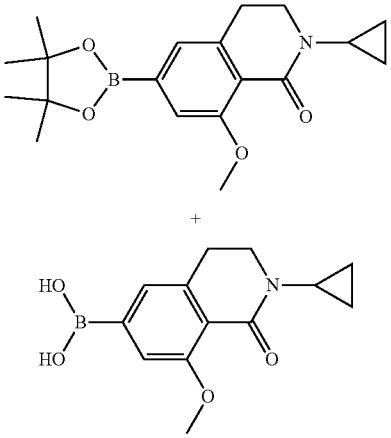 | 2-cyclopropyl-8-methoxy-6-(4,4,5,5-tetramethyl-1,3,2-dioxaborolan-2-yl)-3,4-dihydroisoquinolin-1-one/(2-cyclopropyl-8-methoxy-1-oxo-3,4-dihydroisoquinolin-6-yl)boronic acid mixture | CAS# 1242157-15-8 | Ex. 2.22 | 343.2 + 261.1 | 344.3 + 262.2 |
| 25 | 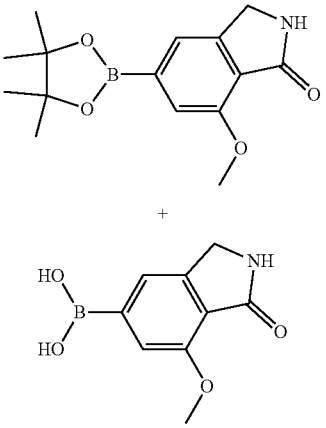 | 7-methoxy-5-(4,4,5,5-tetramethyl-1,3,2-dioxaborolan-2-yl)isoindolin-1-one/(7-methoxy-1-oxo-isoindolin-5-yl)boronic acid mixture | CAS# 957346-37-1 | Ex. 2.23 | 289.1 + 207.0 | 290.3 + 208.3 |
| 26 | 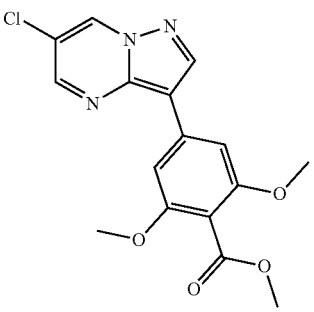 | methyl 5-(6-chloropyrazolo[1,5-a]pyrimidin-3-yl)-2,6-dimethoxy-benzoate | CAS# 1314893-92-9 + Int 14 | E1.3 | 347.8 | 348.3 + 350.3 |
| 27 | 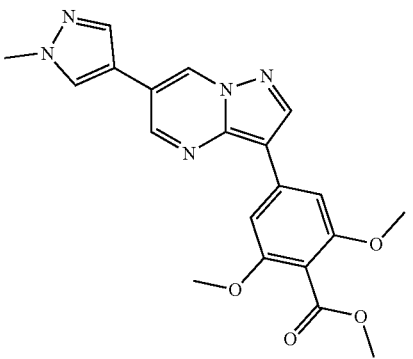 | methyl 2,6-dimethoxy-4-[6-(1-methylpyrazol-4-yl)pyrazolo[1,5-a]pyrimidin-3-yl]benzoate | CAS# 761446-44-0 + Int 26 | E1.3 | 393.4 | 394.2 |

TABLE II-continued

Intermediates used towards the compounds of the invention.

| Int # | Structure | Name | SM | Mtd | MW | MS Mes'd |
|---|---|---|---|---|---|---|
| 28 | 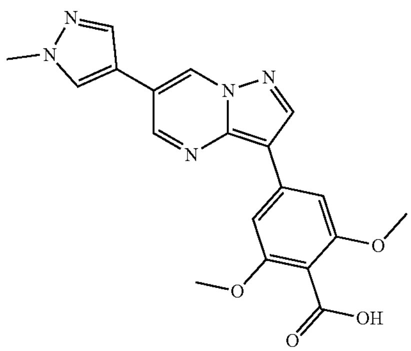 | 2,6-dimethoxy-4-[6-(1-methylpyrazol-4-yl)pyrazolo[1,5-a]pyrimidin-3-yl]benzoic acid | Int 27 | E1.1 | 379.4 | 380.4 |
| 29 | 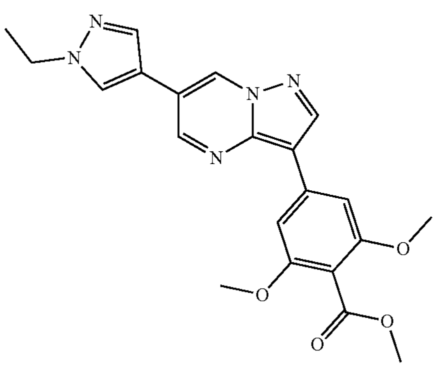 [SMILES: CCn1cc(-c2cnc3c(-c4cc(OC)c(C(=O)OC)c(OC)c4)cnn3c2)cn1] | 4-[6-(1-ethylpyrazol-4-yl)pyrazolo[1,5-a]pyrimidin-3-yl]-2,6-dimethoxybenzoic acid | CAS# 847818-70-6 + Int 26 | E1.3 | 407.4 | 408.4 |
| 30 | 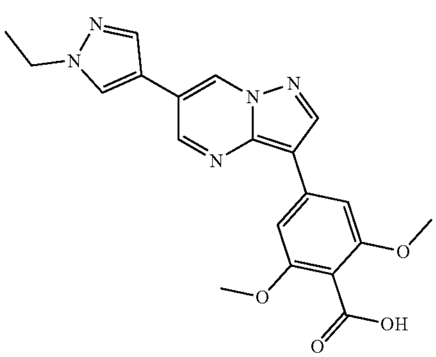 [SMILES: CCn1cc(-c2cnc3c(-c4cc(OC)c(C(=O)O)c(OC)c4)cnn3c2)cn1] | 4-[6-(1-ethylpyrazol-4-yl)pyrazolo[1,5-a]pyrimidin-3-yl]-2,6-dimethoxybenzoic acid | Int 29 | E1.1 | 393.4 | 394.4 |
| 31 | 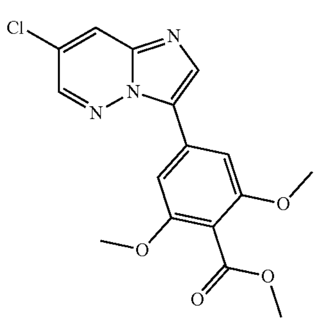 [SMILES: COC(=O)c1c(OC)cc(-c2cnc3cc(Cl)cnn23)cc1OC] | methyl 4-(7-chloroimidazo[1,2-b]pyridazin-3-yl)-2,6-dimethoxybenzoate | CAS# 1383481-13-7 | E1.3 | 347.8 | 348.2 + 350.2 |

TABLE II-continued

Intermediates used towards the compounds of the invention.

| Int # | Structure | Name | SM | Mtd | MW | MS Mes'd |
|---|---|---|---|---|---|---|
| 32 | 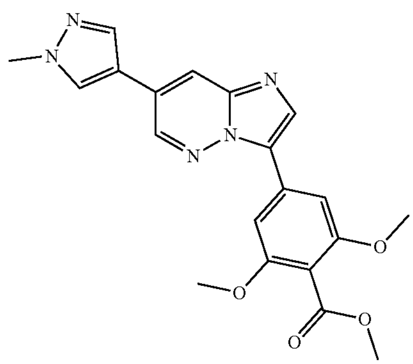 | methyl 2,6-dimethoxy-4-[7-(1-methylpyrazol-4-yl)imidazo[1,2-b]pyridazin-3-yl]benzoate | CAS# 761446-44-0 + Int 31 | E1.3 | 393.4 | 394.4 |
| 33 | 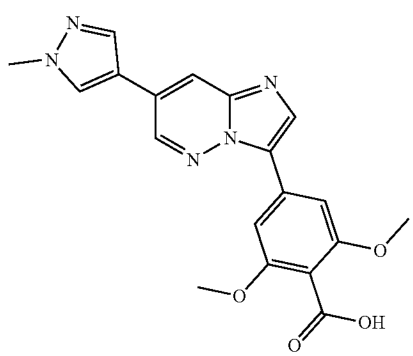 | 2,6-dimethoxy-4-[7-(1-methylpyrazol-4-yl)imidazo[1,2-b]pyridazin-3-yl]benzoic acid | Int 32 | E1.1 | 379.4 | NA |
| 34 | 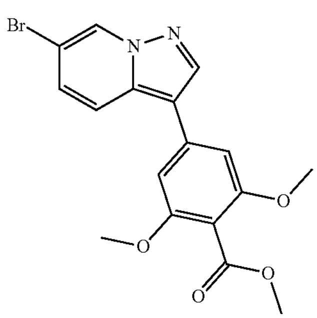 [SMILES: COC(=O)c1c(OC)cc(-c2cnn3cc(Br)ccc23)cc1OC] | methyl 4-(6-bromopyrazolo[1,5-a]pyridin-3-yl)-2,6-dimethoxy-benzoate | Int 15 + Int 14 | E1.3 | 391.2 | 391.1 + 393.0 |
| 35 | 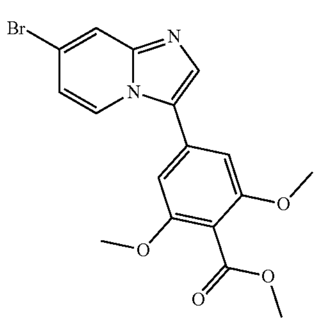 [SMILES: COC(=O)c1c(OC)cc(-c2cnc3cc(Br)ccn23)cc1OC] | methyl 4-(7-bromoimidazol[1,2-a]pyridin-3-yl)-2,6-dimethoxy-benzoate | CAS# 1246184-55-3 + Int 14 | E1.3 | 391.2 | 391.2 + 393.2 |

TABLE II-continued

Intermediates used towards the compounds of the invention.

| Int # | Structure | Name | SM | Mtd | MW | MS Mes'd |
|---|---|---|---|---|---|---|
| 36 | 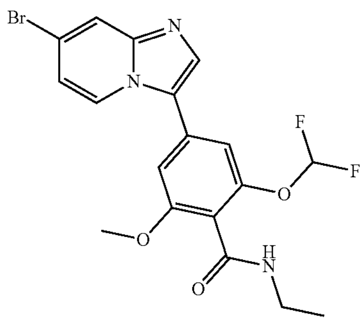 [SMILES: CCNC(=O)c1c(OC)cc(-c2cnc3cc(Br)ccn23)cc1OC(F)F] | 4-(7-bromoimidazo[1,2-a]pyridin-3-yl)-2-(difluoromethoxy)-N-ethyl-6-methoxy-benzamide | CAS# 1246184-55-3 + Int 16 | E1.3 | 440.2 | NA |
| 37 | 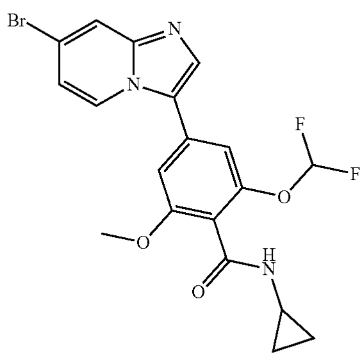 [SMILES: COc1cc(-c2cnc3cc(Br)ccn23)cc(OC(F)F)c1C(=O)NC1CC1] | 4-(7-bromoimidazo[1,2-a]pyridin-3-yl)-N-cyclopropyl-2-(difluoromethoxy)-6-methoxy-benzamide | CAS# 1246184-55-3 + Int 17 | E1.3 | 452.2 | 452.1 + 454.1 |
| 38 | 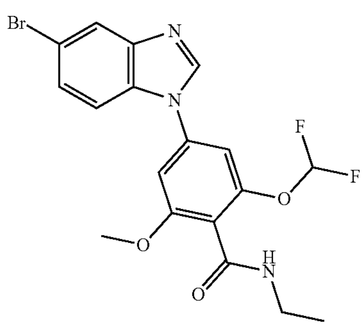 [SMILES: CCNC(=O)c1c(OC)cc(-n2cnc3cc(Br)ccc32)cc1OC(F)F] | 4-(5-bromobenzimidazol-1-yl)-2-(difluoromethoxy)-N-ethyl-6-methoxy-benzamide | CAS# 364-73-8 + Int 12 | B2 + C2 | 440.2 | NA |
| 39 | 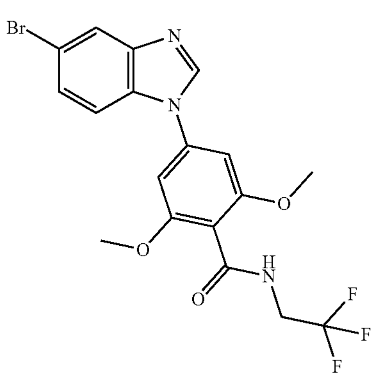 [SMILES: COc1cc(-n2cnc3cc(Br)ccc32)cc(OC)c1C(=O)NCC(F)(F)F] | 4-(5-bromobenzimidazol-1-yl)-2,6-dimethoxy-N-(2,2,2-trifluoroethyl)benzamide | Int 44 | E1.2 | 458.2 | 458.3 + 460.2 |

TABLE II-continued

Intermediates used towards the compounds of the invention.

| Int # | Structure | Name | SM | Mtd | MW | MS Mes'd |
|---|---|---|---|---|---|---|
| 40 | 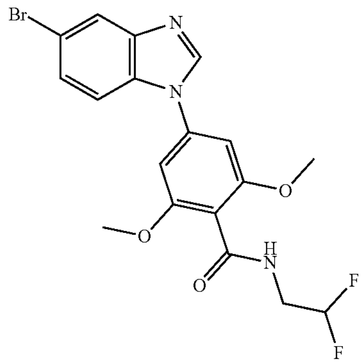 [SMILES: COc1cc(-n2cnc3cc(Br)ccc32)cc(OC)c1C(=O)NCC(F)F] | 4-(5-bromobenzimidazol-1-yl)-N-(2,2-difluoroethyl)-2,6-dimethoxy-benzamide | Int 44 | E1.2 | 440.2 | 438.1 + 440.1 |
| 41 | 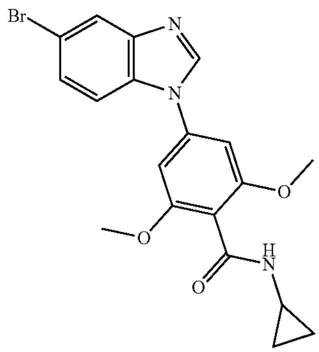 [SMILES: COc1cc(-n2cnc3cc(Br)ccc32)cc(OC)c1C(=O)NC1CC1] | 4-(5-bromobenzimidazol-1-yl)-N-cyclopropyl-2,6-dimethoxy-benzamide | Int 44 | E1.2 | 416.3 | 416.1 + 417.9 |
| 42 | 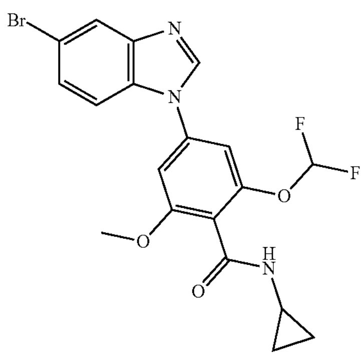 [SMILES: COc1cc(-n2cnc3cc(Br)ccc32)cc(OC(F)F)c1C(=O)NC1CC1] | 4-(7-bromoimidazo[1,2-a]pyridin-3-yl)-N-cyclopropyl-2-(difluoromethoxy)-6-methoxy-benzamide | Int 60 | C2 | 452.2 | 452.4 + 454.4 |
| 43 | 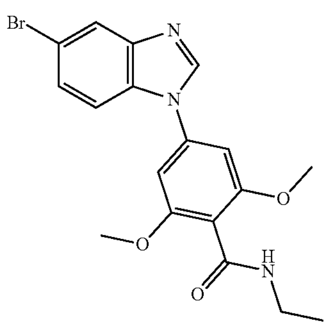 [SMILES: CCNC(=O)c1c(OC)cc(-n2cnc3cc(Br)ccc32)cc1OC] | 4-(5-bromobenzimidazol-1-yl)-N-ethyl-2,6-dimethoxy-benzamide | Int 44 | E1.2 | 404.3 | 404.3 + 406.2 |

TABLE II-continued
Intermediates used towards the compounds of the invention.
| Int # | Structure | Name | SM | Mtd | MW | MS Mes'd |
|---|---|---|---|---|---|---|
| 44 | 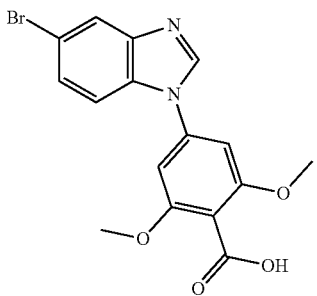 [SMILES: COc1cc(-n2cnc3cc(Br)ccc32)cc(OC)c1C(=O)O] | 4-(5-bromobenzimidazol-1-yl)-2,6-dimethoxy-benzoic acid | Int 45 | E1.1 | 377.2 | 377.0 + 379.0 |
| 45 | 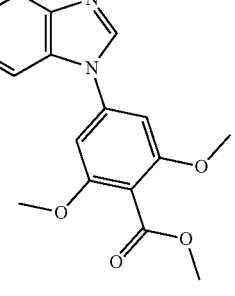 | methyl 4-(5-bromobenzimidazol-1-yl)-2,6-dimethoxy-benzoate | Int 59 | C1 | 391.2 | 391.1 + 393.1 |
| 46 | 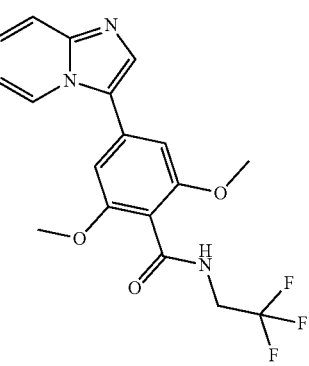 | 4-(7-bromoimidazo[1,2-a]pyridin-3-yl)-2,6-dimethoxy-N-(2,2,2-trifluoroethyl)benzamide | Int 48 | E1.2 | 458.2 | 458.4 + 460.3 |
| 48 | 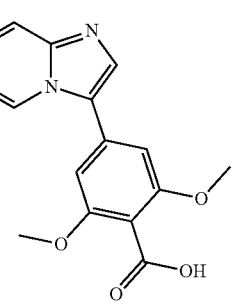 | 4-(7-bromoimidazo[1,2-a]pyridin-3-yl)-2,6-dimethoxy-benzoic acid | Int 35 | E1.1 | 377.2 | 377.2 + 379.2 |

TABLE II-continued

Intermediates used towards the compounds of the invention.

| Int # | Structure | Name | SM | Mtd | MW | MS Mes'd |
|---|---|---|---|---|---|---|
| 50 | 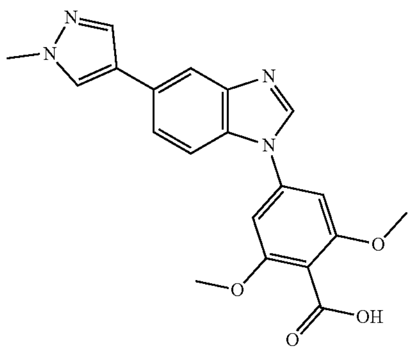 | 2,6-dimethoxy-4-[5-(1-methylpyrazol-4-yl)benzimidazol-1-yl]benzoic acid | Int 44 | E1.3 | 378.4 | 379.5 |
| 51 | 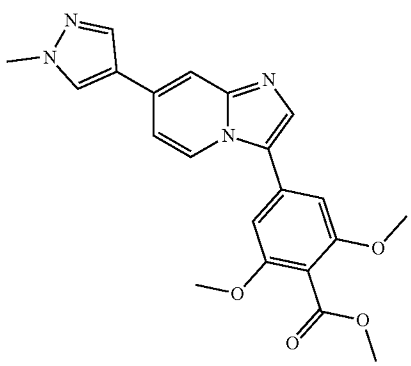 | methyl 2,6-dimethoxy-4-[7-(1-methylpyrazol-4-yl)imidazo[1,2-a]pyridin-3-yl]benzoate | Int 35 | E1.3 | 392.4 | 393.9 |
| 52 | 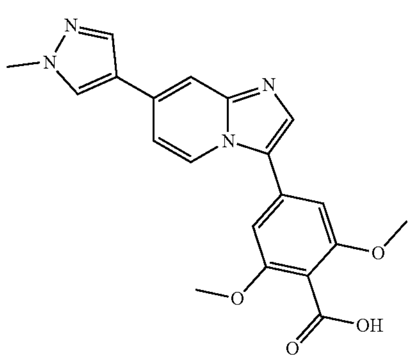 | 2,6-dimethoxy-4-[5-(1-methylpyrazol-4-yl)benzimidazol-1-yl]benzoic acid | Int 51 | E1.1 | 378.4 | 379.3 |
| 53 | 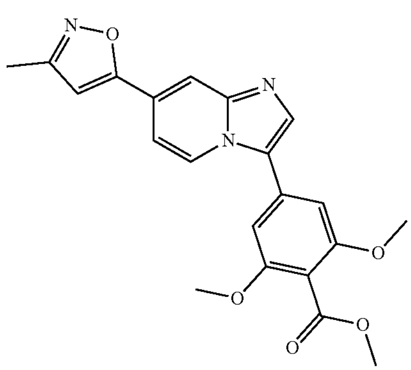 | methyl 2,6-dimethoxy-4-[7-(3-methylisoxazol-5-yl)imidazo[1,2-a]pyridin-3-yl]benzoate | CAS# 1346808-44-3 + Int 35 | E1.3 | 393.4 | 394.3 |

TABLE II-continued

Intermediates used towards the compounds of the invention.

| Int # | Structure | Name | SM | Mtd | MW | MS Mes'd |
|---|---|---|---|---|---|---|
| 54 | 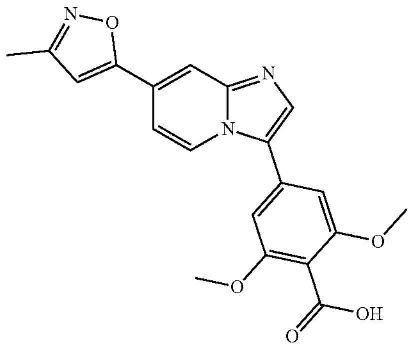 | 2,6-dimethoxy-4-[7-(3-methylisoxazol-5-yl)imidazo[1,2-a]pyridin-3-yl]benzoic acid | Int 53 | E1.1 | 379.4 | 380.3 |
| 55 | 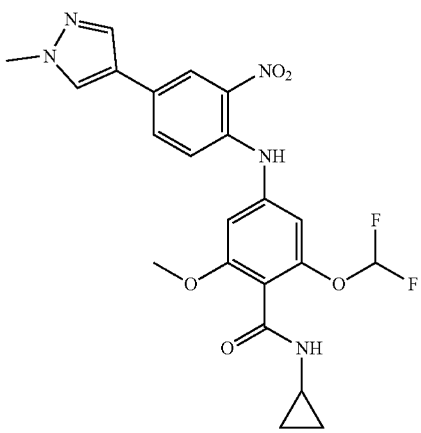 [SMILES: COc1cc(Nc2ccc(-c3cnn(C)c3)cc2[N+](=O)[O-])cc(OC(F)F)c1C(=O)NC1CC1] | N-cyclopropyl-2-(difluoromethoxy)-6-methoxy-4-[4-(1-methylpyrazol-4-yl)-2-nitro-anilino]benzamide | Int 9 + Int 56 | E2.3 | 473.4 | 474.4 |
| 56 | 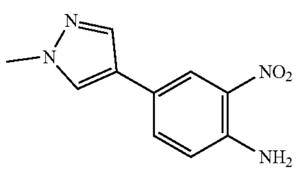 [SMILES: Cn1cc(-c2ccc(N)c([N+](=O)[O-])c2)cn1] | 4-(1-methylpyrazol-4-yl)-2-nito-aniline | CAS# 875-51-4 + CAS# 761446-44-0 | E1.3 | 218.2 | 219.0 |
| 57 | 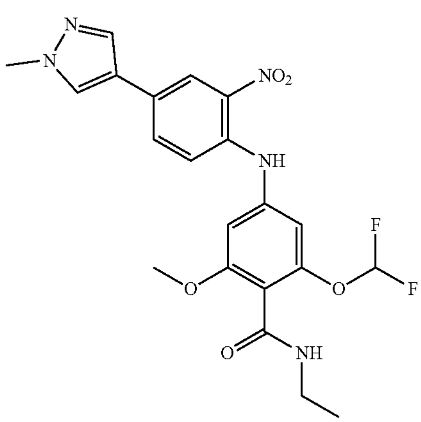 [SMILES: CCNC(=O)c1c(OC)cc(Nc2ccc(-c3cnn(C)c3)cc2[N+](=O)[O-])cc1OC(F)F] | 2-(difluoromethoxy)-N-ethyl-6-methoxy-4-[4-(1-methylpyrazol-4-yl)-2-nitro-anilino]benzamide | Int 58 + Int 12 | B2 | 461.4 | 462.2 |
| 58 | 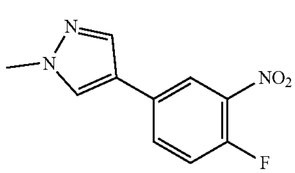 [SMILES: Cn1cc(-c2ccc(F)c([N+](=O)[O-])c2)cn1] | 4-(4-fluoro-3-nitro-phenyl)-1-methyl-pyrazole | CAS# 364-73-8 + CAS# 761446-44-0 | E1.3 | 221.2 | 222.2 |

TABLE II-continued

Intermediates used towards the compounds of the invention.

| Int # | Structure | Name | SM | Mtd | MW | MS Mes'd |
|---|---|---|---|---|---|---|
| 59 | 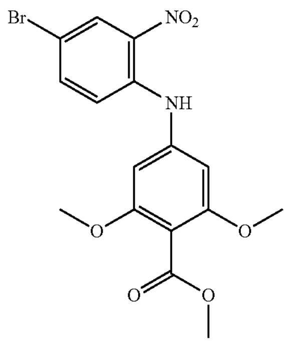 [SMILES: COC(=O)c1c(OC)cc(Nc2ccc(Br)cc2[N+](=O)[O-])cc1OC] | methyl 4-(4-bromo-2-nitro-anilino)-2,6-dimethoxy-benzoate | CAS# 364-73-8 + CAS# 3956-34-1 | B1 | 411.2 | 411.1 + 413.0 |
| 60 | 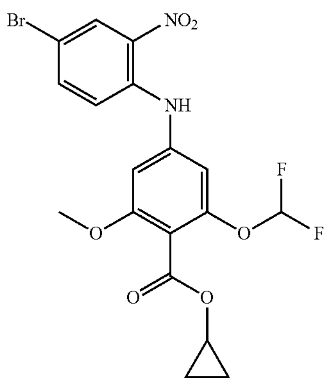 [SMILES: COc1cc(Nc2ccc(Br)cc2[N+](=O)[O-])cc(OC(F)F)c1C(=O)OC1CC1] | 4-(4-bromo-2-nitro-anilino)-N-cyclopropyl-2-(difluoromethoxy)-6-methoxy-benzamide | CAS# 364-73-8 + Int 10 | B2 | 472.3 | 472.1 + 474.0 |
| 61 | 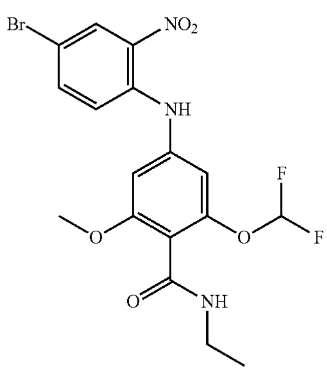 [SMILES: CCNC(=O)c1c(OC)cc(Nc2ccc(Br)cc2[N+](=O)[O-])cc1OC(F)F] | 4-(4-bromo-2-nitro-anilino)-N-cyclopropyl-2-(difluoromethoxy)-6-methoxy-benzamide | CAS# 364-73-8 + Int 12 | B2 | 460.2 | 460.1 + 462.1 |
| 62 | 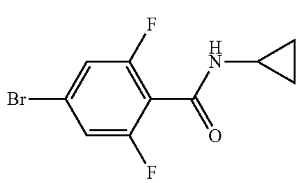 [SMILES: O=C(NC1CC1)c1c(F)cc(Br)cc1F] | 4-bromo-N-cyclopropyl-2,6-difluoro-benzamide | CAS# 183065-68-1 | Ex. 2.24 | 276.1 | 276.1 + 278.1 |
| 63 | 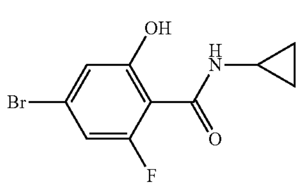 [SMILES: O=C(NC1CC1)c1c(O)cc(Br)cc1F] | 4-bromo-N-cyclopropyl-2-fluoro-6-hydroxy-benzamide | Int 62 | Ex. 2.25 | 274.1 | 273.8 + 275.8 |

TABLE II-continued

Intermediates used towards the compounds of the invention.

| Int # | Structure | Name | SM | Mtd | MW | MS Mes'd |
|---|---|---|---|---|---|---|
| 64 | 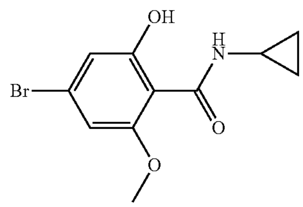 [SMILES: COc1cc(Br)cc(O)c1C(=O)NC1CC1] | 4-bromo-N-cyclopropyl-2-hydroxy-6-methoxy-benzamide | Int 63 | Ex. 2.26 | 286.1 | 286.3 + 288.2 |
| 65 | 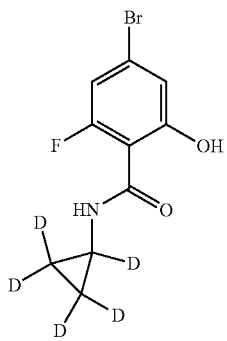 [SMILES: [2H]C1([2H])C([2H])([2H])C1([2H])NC(=O)c1c(O)cc(Br)cc1F] | 4-bromo-2-fluoro-6-hydroxy-N-(1,2,2,3,3-pentadeutericyclopropyl)benzamide | Int 13 | Ex. 2.27 | 279.1 | 279.3 + 281.1 |
| 66 | 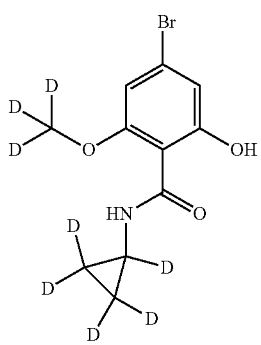 [SMILES: [2H]C([2H])([2H])Oc1cc(Br)cc(O)c1C(=O)NC1([2H])C([2H])([2H])C1([2H])[2H]] | 4-bromo-2-hydroxy-N-(1,2,2,3,3-pentadeutericyclopropyl)-6-(trideuteriomethoxy)benzamide | Int 65 | Ex. 2.28 | 294.1 | 293.9 + 295.9 |
| 67 | 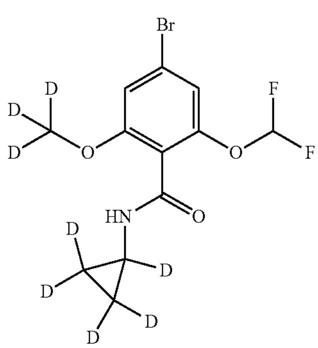 [SMILES: [2H]C([2H])([2H])Oc1cc(Br)cc(OC(F)F)c1C(=O)NC1([2H])C([2H])([2H])C1([2H])[2H]] | 4-bromo-2-(difluoromethoxy)-N-(1,2,2,3,3-pentadeuteriocyclopropyl)-6-(trideuteriomethoxy)benzamide | Int 66 | Ex. 2.29 | 344.2 | 343.9 + 345.9 |

TABLE II-continued

Intermediates used towards the compounds of the invention.

| Int # | Structure | Name | SM | Mtd | MW | MS Mes'd |
|---|---|---|---|---|---|---|
| 68 | 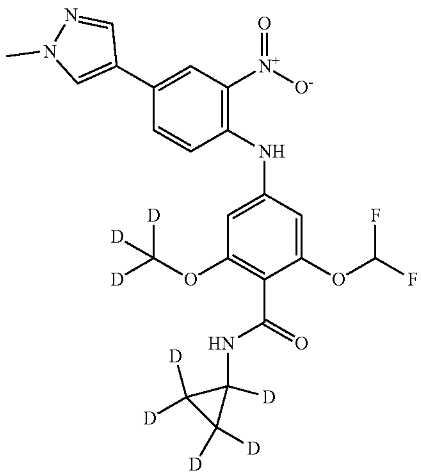 [SMILES: [2H]C([2H])([2H])Oc1cc(Nc2ccc(-c3cnn(C)c3)cc2[N+](=O)[O-])cc(OC(F)F)c1C(=O)NC1([2H])C([2H])([2H])C1([2H])[2H]] | 2-(difluoromethoxy)-4-[4-(1-methylpyrazol-4-yl)-2-nitro-anilino]-N-(1,2,2,3,3-pentadeuteriocyclopropyl)-6-(trideuteriomethoxy)benzamide | Int 56 + Int 67 | E2.3 | 481.5 | 482.1 |
| 69 | 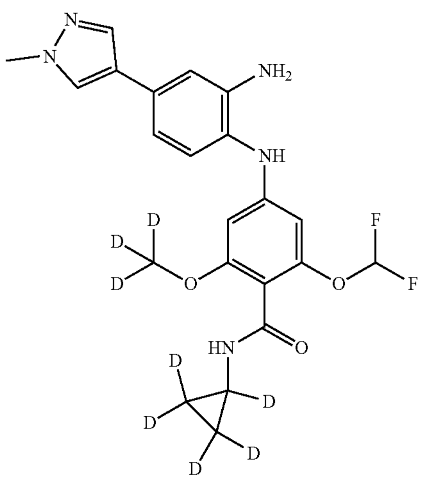 [SMILES: [2H]C([2H])([2H])Oc1cc(Nc2ccc(-c3cnn(C)c3)cc2N)cc(OC(F)F)c1C(=O)NC1([2H])C([2H])([2H])C1([2H])[2H]] | 4-[2-amino-4-(1-methylpyrazol-4-yl)anilino]-2-(difluoromethoxy)-N-(1,2,2,3,3-pentadeuteriocyclopropyl)-6-(trideuteriomethoxy)benzamide | Int 68 | Ex. 2.31 | 451.5 | 452.1 |
| 70 | 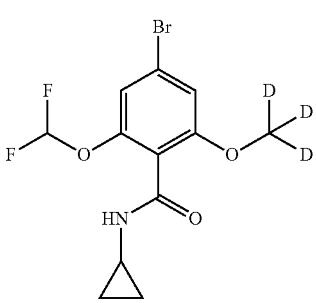 [SMILES: [2H]C([2H])([2H])Oc1cc(Br)cc(OC(F)F)c1C(=O)NC1CC1] | 4-bromo-N-cyclopropyl-2-(difluoromethoxy)-6-(trideuteriomethoxy)benzamide | Int 63 | Ex. 2.32 | 339.1 | 339.0 + 341.0 |
| 71 | 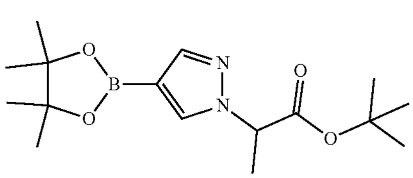 [SMILES: CC(C(=O)OC(C)(C)C)n1cc(B2OC(C)(C)C(C)(C)O2)cn1] | tert-butyl 2-[4-(4,4,5,5-tetramethyl-1,3,2-dioxaborolan-2-yl)pyrazol-1-yl]propanoate | CAS# 269410-08-4 + CAS# 39149-80-9 | Ex. 2.33 | 322.2 | 323.4 |

TABLE II-continued

Intermediates used towards the compounds of the invention.

| Int # | Structure | Name | SM | Mtd | MW | MS Mes'd |
|---|---|---|---|---|---|---|
| 72 | 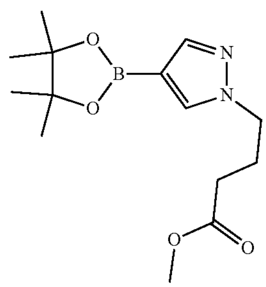 [SMILES: COC(=O)CCCn1cc(B2OC(C)(C)C(C)(C)O2)cn1] | methyl 4-[4-(4,4,5,5-tetramethyl-1,3,2-dioxaborolan-2-yl)pyrazol-1-yl]butanoate | CAS# 269410-08-4 + CAS# 4897-84-1 | Ex. 2.34 | 294.2 | NA |
| 73 | 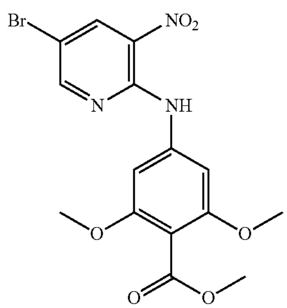 [SMILES: COC(=O)c1c(OC)cc(Nc2ncc(Br)cc2[N+](=O)[O-])cc1OC] | methyl 4-[(5-bromo-3-nitro-2-pyridyl)amino]-2,6-dimethoxy-benzoate | CAS# 67443-38-3 + CAS# 3956-34-1 | B3 | 412.2 | 412.3 + 414.3 |
| 74 | 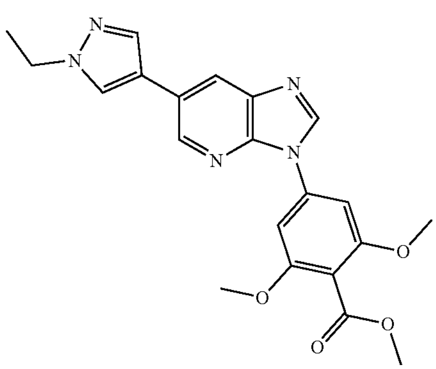 [SMILES: CCn1cc(-c2cnc3c(c2)ncn3-c2cc(OC)c(C(=O)OC)c(OC)c2)cn1] | methyl 4-[6-(1-ethylpyrazol-4-yl)imidazo[4,5-b]pyridin-3-yl]-2,6-dimethoxy-benzoate | Int 74 + CAS# 847818-70-6 | C2 + E1.3 | 407.4 | 408.6 |
| 75 | 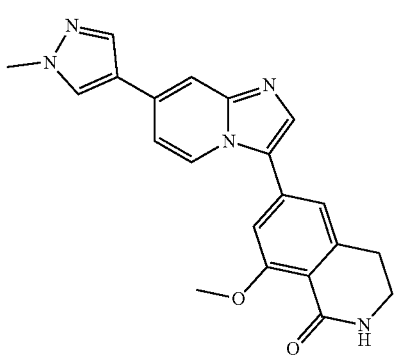 [SMILES: COc1cc(-c2cnc3cc(-c4cnn(C)c4)ccn23)cc2c1C(=O)NCC2] | 8-methoxy-6-[7-(1-methylpyrazol-4-yl)imidazo[1,2-a]pyridin-3-yl]-3,4-dihydro-2H-isoquinolin-1-one | CAS# 1246184-55-3 + Int 23 + CAS# 761446-44-0 | E1.3 + E1.3 | 373.4 | 374.3 |
| 76 | 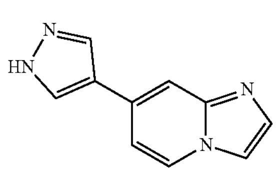 [SMILES: c1cn2ccc(-c3cn[nH]c3)cc2n1] | 7-(1H-pyrazol-4-yl)imidazo[1,2-a]pyridine | CAS# 552846-17-0 + CAS# 808744-34-5 | Ex. 2.35 | 184.2 | 185.5 |

TABLE II-continued

Intermediates used towards the compounds of the invention.

| Int # | Structure | Name | SM | Mtd | MW | MS Mes'd |
|---|---|---|---|---|---|---|
| 77 | (structure: 7-chloroimidazo[1,2-a]pyridin-6-ol·HBr) | 7-chloroimidazo[1,2-a]pyridin-6-ol, hydrobromide salt | CAS# 867131-26-8 | Ex. 2.36 | 158.6 | NA |

SM = Starting Material, Mtd = Method, MS Mes'd = Mesured mass

TABLE III

Illustrative compounds of the invention.

| Cpd # | Structure | Name | SM | Mtd | MW | MS Mes'd |
|---|---|---|---|---|---|---|
| 1 | (structure) | N-ethyl-4-[5-(1-ethylpyrazol-4-yl)benzimidazol-1-yl]-2,6-dimethoxy-benzamide | Int 43 + CAS# 847818-70-6 | E1.3 | 419.5 | 420.5 |
| 2 | (structure) | N-ethyl-2,6-dimethoxy-4-[5-(3-pyridyl)benzimidazol-1-yl]benzamide | Int 43 + CAS# 1692-25-7 | E1.3 | 402.4 | 403.3 |
| 3 | (structure) | N-ethyl-2,6-dimethoxy-4-[5-(6-morpholino-3-pyridyl)benzimidazol-1-yl]benzamide | Int 43 + CAS# 485799-04-0 | E1.3 | 487.6 | 488.4 |

TABLE III-continued

Illustrative compounds of the invention.

| Cpd # | Structure | Name | SM | Mtd | MW | MS Mes'd |
|---|---|---|---|---|---|---|
| 4 | 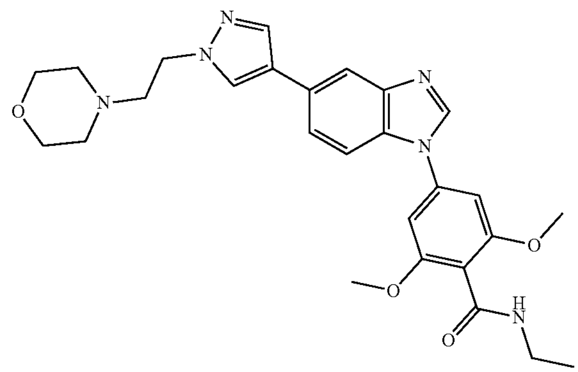 [SMILES: CCNC(=O)c1c(OC)cc(-n2cnc3cc(-c4cnn(CCN5CCOCC5)c4)ccc32)cc1OC] | N-ethyl-2,6-dimethoxy-4-[5-[1-(2-morpholinoethyl)pyrazol-4-yl]benzimidazol-1-yl]benzamide | Int 43 + CAS# 864754-18-7 | E1.3 | 504.6 | 505.4 |
| 5 | 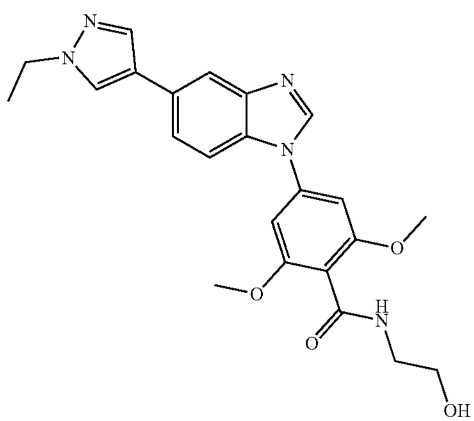 [SMILES: CCn1cc(-c2ccc3c(c2)ncn3-c2cc(OC)c(C(=O)NCCO)c(OC)c2)cn1] | 4-[5-(1-ethylpyrazol-4-yl)benzimidazol-1-yl]-N-(2-hydroxyethyl)-2,6-dimethoxy-benzamide | Int 44 + CAS# 141-43-5 + CAS# 847818-70-6 | E1.2 + E1.3 | 435.5 | 436.4 |
| 6 | 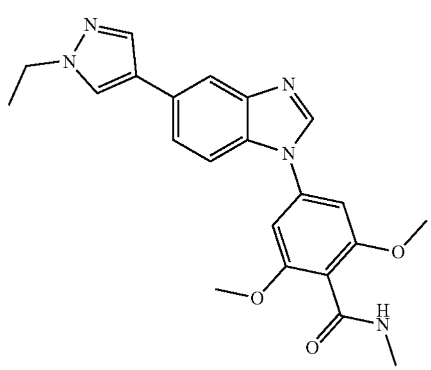 [SMILES: CCn1cc(-c2ccc3c(c2)ncn3-c2cc(OC)c(C(=O)NC)c(OC)c2)cn1] | 4-[5-(1-ethylpyrazol-4-yl)benzimidazol-1-yl]-2,6-dimethoxy-N-methyl-benzamide | Int 44 + methylamine + CAS# 847818-70-6 | E1.2 + E1.3 | 405.4 | 406.5 |
| 7 | 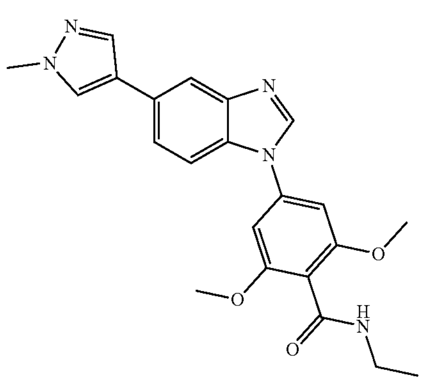 [SMILES: CCNC(=O)c1c(OC)cc(-n2cnc3cc(-c4cnn(C)c4)ccc32)cc1OC] | N-ethyl-2,6-dimethoxy-4-[5-(1-methylpyrazol-4-yl)benzimidazol-1-yl]benzamide | Int 43 + CAS# 761446-44-0 | E1.3 | 405.4 | 406.6 |

TABLE III-continued
Illustrative compounds of the invention.
| Cpd # | Structure | Name | SM | Mtd | MW | MS Mes'd |
|---|---|---|---|---|---|---|
| 8 | 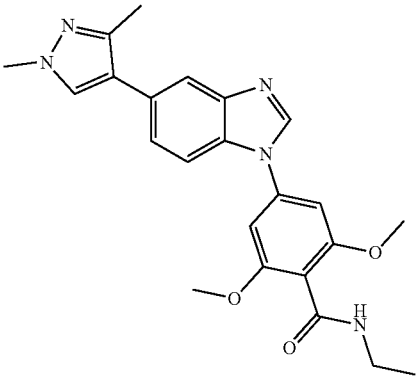 [SMILES: CCNC(=O)c1c(OC)cc(-n2cnc3cc(-c4cn(C)nc4C)ccc32)cc1OC] | 4-[5-(1,3-dimethylpyrazol-4-yl)benzimidazol-1-yl]-N-ethyl-2,6-dimethoxy-benzamide | Int 43 + CAS# 1046832-21-6 | E1.3 | 419.5 | 420.5 |
| 9 | 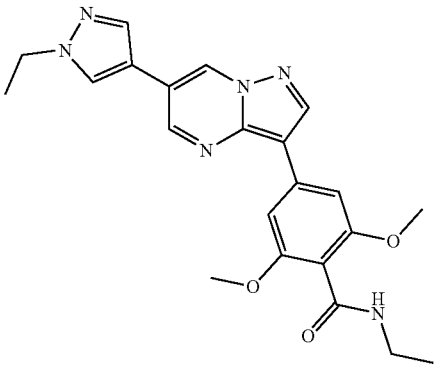 [SMILES: CCNC(=O)c1c(OC)cc(-c2cnn3cc(-c4cnn(CC)c4)cnc23)cc1OC] | N-ethyl-4-[6-(1-ethylpyrazol-4-yl)pyrazolo[1,5-a]pyrimidin-3-yl]-2,6-dimethoxy-benzamide | Int 30 + CAS# 557-66-4 | E1.2 | 420.5 | 421.3 |
| 10 | 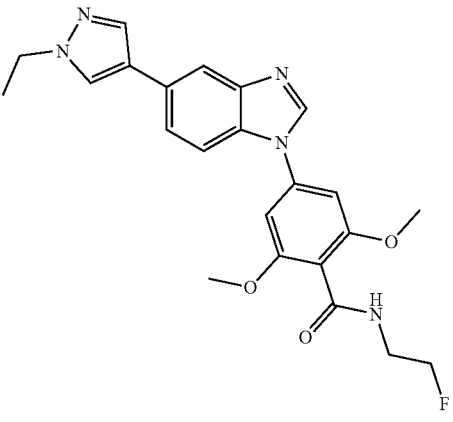 [SMILES: CCn1cc(-c2ccc3c(c2)ncn3-c2cc(OC)c(C(=O)NCCF)c(OC)c2)cn1] | 4-[5-(1-ethylpyrazol-4-yl)benzimidazol-1-yl]-N-(2-fluoroethyl)-2,6-dimethoxy-benzamide | Int 44 + CAS# 460-08-2 + CAS# 847818-70-6 | E1.2 + E1.3 | 437.5 | 438.5 |

TABLE III-continued

Illustrative compounds of the invention.

| Cpd # | Structure | Name | SM | Mtd | MW | MS Mes'd |
|---|---|---|---|---|---|---|
| 11 | 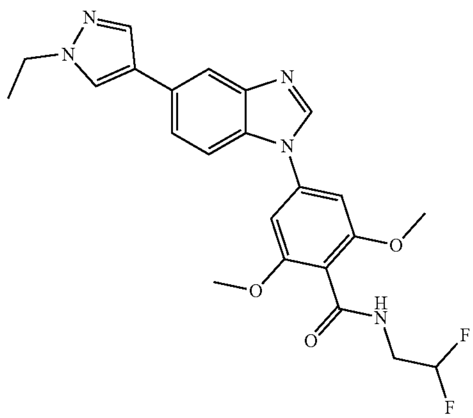 [SMILES: CCn1cc(-c2ccc3c(c2)ncn3-c2cc(OC)c(C(=O)NCC(F)F)c(OC)c2)cn1] | N-(2,2-difluoroethyl)-4-[5-(1-ethylpyrazol-4-yl)benzimidazol-1-yl]-2,6-dimethoxy-benzamide | Int 40 + CAS# 847818-70-6 | E1.3 | 455.5 | 456.4 |
| 12 | 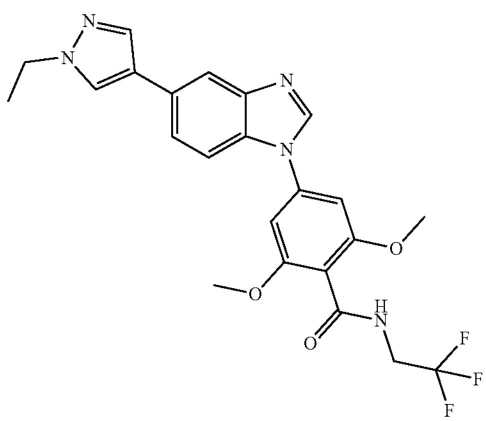 [SMILES: CCn1cc(-c2ccc3c(c2)ncn3-c2cc(OC)c(C(=O)NCC(F)(F)F)c(OC)c2)cn1] | 4-[5-(1-ethylpyrazol-4-yl)benzimidazol-1-yl]-2,6-dimethoxy-N-(2,2,2-trifluoroethyl)benzamide | Int 44 + CAS# 373-88-6 + CAS# 847818-70-6 | E1.2 + E1.3 | 473.4 | 474.6 |
| 13 | 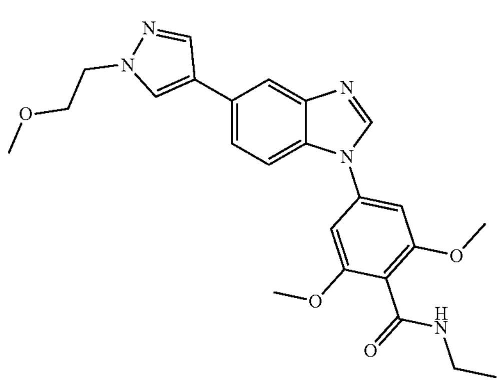 [SMILES: CCNC(=O)c1c(OC)cc(-n2cnc3cc(-c4cnn(CCOC)c4)ccc32)cc1OC] | N-ethyl-2,6-dimethoxy-4-[5-[1-(2-methoxyethyl)pyrazol-4-yl]benzimidazol-1-yl]benzamide | Int 43 + CAS# 847818-71-7 | E1.3 | 449.5 | 450.7 |

TABLE III-continued

Illustrative compounds of the invention.

| Cpd # | Structure | Name | SM | Mtd | MW | MS Mes'd |
|---|---|---|---|---|---|---|
| 14 | 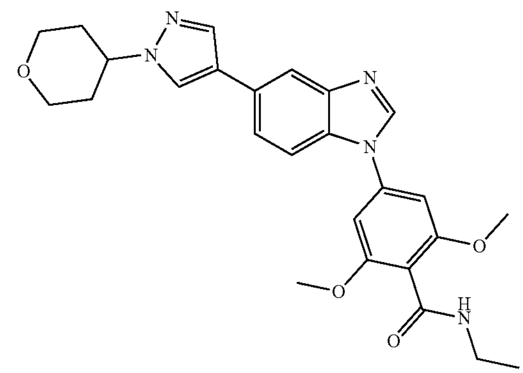 [SMILES: CCNC(=O)c1c(OC)cc(-n2cnc3cc(-c4cnn(C5CCOCC5)c4)ccc32)cc1OC] | N-ethyl-2,6-dimethoxy-4-[5-(1-tetrahydropyran-4-ylpyrazol-4-yl)benzimidazol-1-yl]benzamide | Int 43 + CAS# 1040377-03-4 | E1.3 | 475.5 | 476.3 |
| 15 | 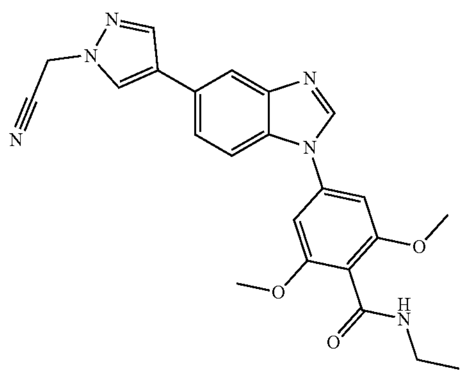 [SMILES: CCNC(=O)c1c(OC)cc(-n2cnc3cc(-c4cnn(CC#N)c4)ccc32)cc1OC] | 4-[5-(1-(cyanomethyl)pyrazol-4-yl]benzimidazol-1-yl]-N-ethyl-2,6-dimethoxy-benzamide | Int 43 + CAS# 1093307-35-7 | E1.3b | 430.5 | 431.2 |
| 16 | 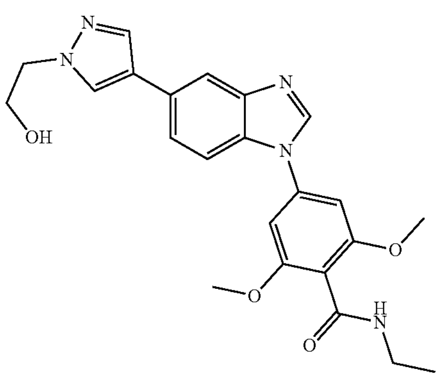 [SMILES: CCNC(=O)c1c(OC)cc(-n2cnc3cc(-c4cnn(CCO)c4)ccc32)cc1OC] | N-ethyl-4-[5-[1-(2-hydroxyethyl)pyrazol-4-yl]benzimidazol-1-yl]-2,6-dimethoxy-benzamide | Int 43 + CAS# 1040377-08-9 | E1.3 | 435.5 | 436.3 |
| 17 | 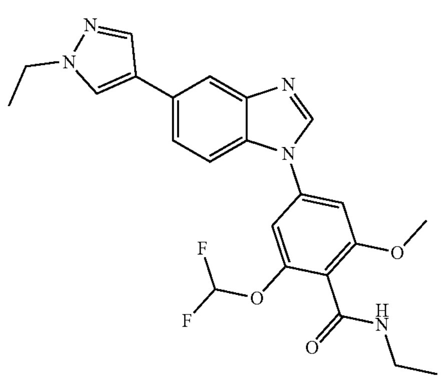 [SMILES: CCNC(=O)c1c(OC)cc(-n2cnc3cc(-c4cnn(CC)c4)ccc32)cc1OC(F)F] | 2-(difluoromethoxy)-N-ethyl-4-[5-(1-ethylpyrazol-4-yl)benzimidazol-1-yl]-6-methoxy-benzamide | Cpd 23 | J2 | 455.5 | 456.2 |

TABLE III-continued

Illustrative compounds of the invention.

| Cpd # | Structure | Name | SM | Mtd | MW | MS Mes'd |
|---|---|---|---|---|---|---|
| 18 | 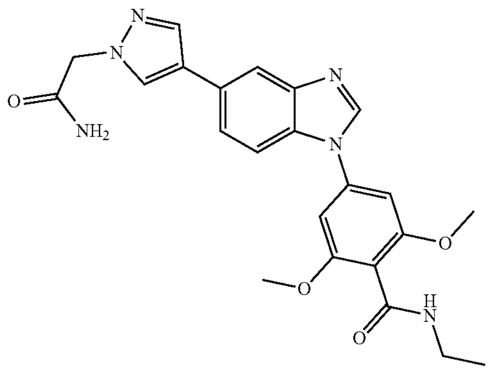 [SMILES: CCNC(=O)c1c(OC)cc(-n2cnc3cc(-c4cnn(CC(N)=O)c4)ccc32)cc1OC] | 4-[5-(1-(2-amino-2-oxo-ethyl)pyrazol-4-yl]benzimidazol-1-yl]-N-ethyl-2,6-dimethoxy-benzamide | Int 43 + CAS# 1093307-35-7 | E1.3b | 448.5 | 449.2 |
| 19 | 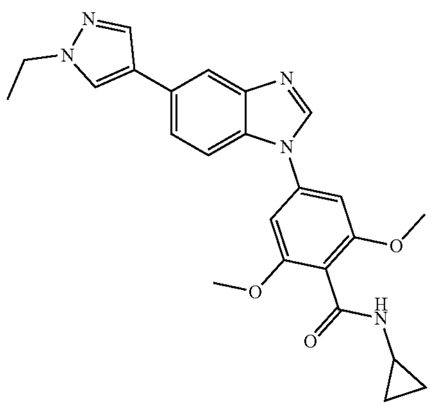 [SMILES: CCn1cc(-c2ccc3c(c2)ncn3-c2cc(OC)c(C(=O)NC3CC3)c(OC)c2)cn1] | N-cyclopropyl-4-[5-(1-ethylpyrazol-4-yl)benzimidazol-1-yl]-2,6-dimethoxy-benzamide | Int 41 + CAS# 847818-70-6 | E1.3 | 431.5 | 432.6 |
| 20 | 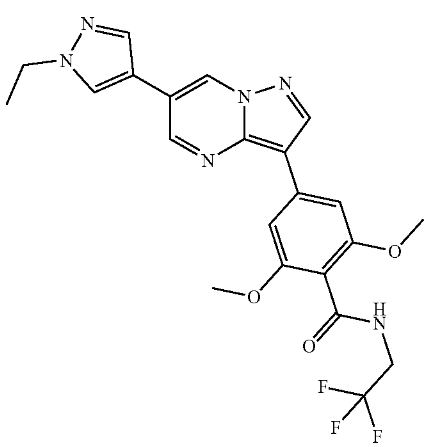 [SMILES: CCn1cc(-c2cnc3c(-c4cc(OC)c(C(=O)NCC(F)(F)F)c(OC)c4)cnn3c2)cn1] | 4-[6-(1-ethylpyrazol-4-yl)pyrazolo[1,5-a]pyrimidin-3-yl]-2,6-dimethoxy-N-(2,2,2-trifluoroethyl)benzamide | Int 30 + CAS# 373-88-6 | E1.2 | 474.4 | 475.4 |

TABLE III-continued

Illustrative compounds of the invention.

| Cpd # | Structure | Name | SM | Mtd | MW | MS Mes'd |
|---|---|---|---|---|---|---|
| 21 | 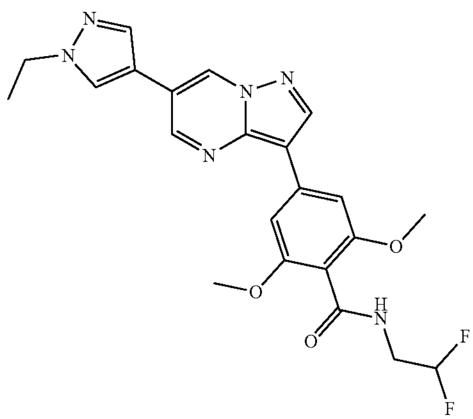 [SMILES: CCn1cc(-c2cnc3c(-c4cc(OC)c(C(=O)NCC(F)F)c(OC)c4)cnn3c2)cn1] | N-(2,2-difluoroethyl)-4-[6-(1-ethylpyrazol-4-yl)pyrazolo[1,5-a]pyrimidin-3-yl]-2,6-dimethoxy-benzamide | Int 30 + CAS# 430-67-1 | E1.2 | 456.4 | 457.2 |
| 22 | 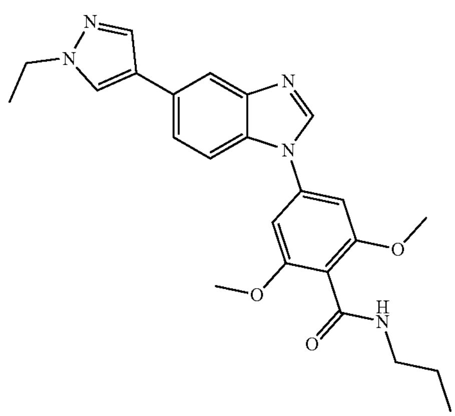 [SMILES: CCCNC(=O)c1c(OC)cc(-n2cnc3cc(-c4cnn(CC)c4)ccc32)cc1OC] | 4-[5-(1-ethylpyrazol-4-yl)benzimidazol-1-yl]-2,6-dimethoxy-N-propyl-benzamide | Int 44 + CAS# 107-10-8 + CAS# 847818-56-8 | E1.2 + E1.3 | 433.5 | 434.5 |
| 23 | 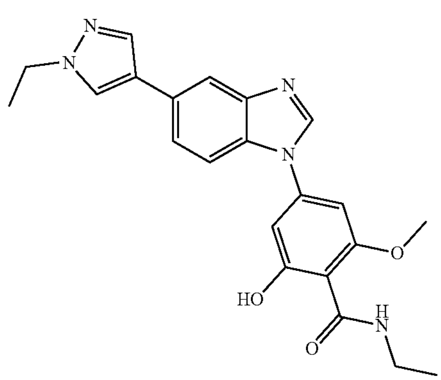 [SMILES: CCNC(=O)c1c(O)cc(-n2cnc3cc(-c4cnn(CC)c4)ccc32)cc1OC] | N-ethyl-4-[5-(1-ethylpyrazol-4-yl)benzimidazol-1-yl]-2-hydroxy-6-methoxy-benzamide | Cpd 1 | I | 405.4 | 406.3 |

TABLE III-continued

Illustrative compounds of the invention.

| Cpd # | Structure | Name | SM | Mtd | MW | MS Mes'd |
|---|---|---|---|---|---|---|
| 24 | 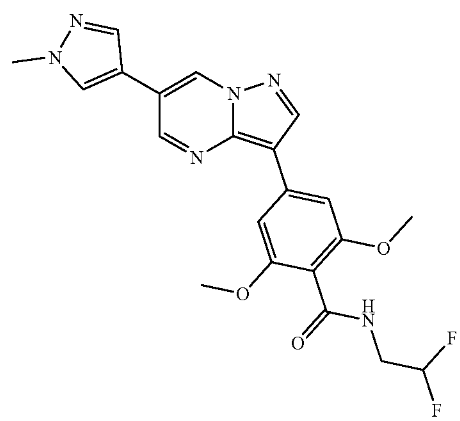 [SMILES: COc1cc(-c2cnn3cc(-c4cnn(C)c4)cnc23)cc(OC)c1C(=O)NCC(F)F] | N-(2,2-difluoroethyl)-2,6-dimethoxy-4-[6-(1-methylpyrazol-4-yl)pyrazolo[1,5-a]pyrimidin-3-yl]benzamide | Int 28 + CAS# 430-67-1 | E1.2 | 442.4 | 443.3 |
| 25 | 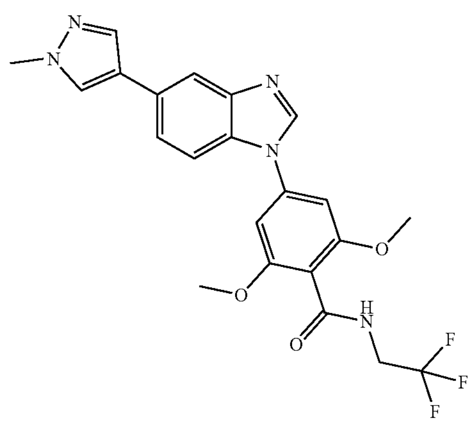 [SMILES: COc1cc(-n2cnc3cc(-c4cnn(C)c4)ccc32)cc(OC)c1C(=O)NCC(F)(F)F] | 2,6-dimethoxy-4-[5-(1-methylpyrazol-4-yl)benzimidazol-1-yl]-N-(2,2,2-trifluoroethyl)benzamide | Int 39 + CAS# 761446-44-0 | E1.3 | 459.4 | 460.6 |
| 26 | 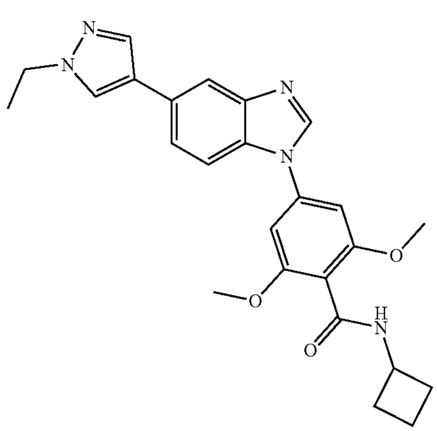 [SMILES: CCn1cc(-c2ccc3c(c2)ncn3-c2cc(OC)c(C(=O)NC3CCC3)c(OC)c2)cn1] | N-cyclobutyl-4-[5-(1-ethylpyrazol-4-yl)benzimidazol-1-yl]-2,6-dimethoxy-benzamide | Int 44 + CAS# 2516-34-9 + CAS# 847818-70-6 | E1.2 + E1.3 | 445.5 | 446.7 |

TABLE III-continued

Illustrative compounds of the invention.

| Cpd # | Structure | Name | SM | Mtd | MW | MS Mes'd |
|---|---|---|---|---|---|---|
| 27 | 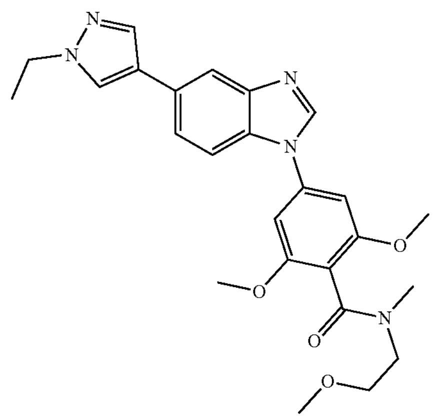 [SMILES: CCn1cc(-c2ccc3c(c2)ncn3-c2cc(OC)c(C(=O)N(C)CCOC)c(OC)c2)cn1] | 4-[5-(1-ethylpyrazol-4-yl)benzimidazol-1-yl]-2,6-dimethoxy-N-(2-methoxyethyl)-N-methyl-benzamide | Int 44 + CAS# 38256-93-8 + CAS# 847818-70-6 | E1.2 + E1.3 | 463.5 | 464.7 |
| 28 | 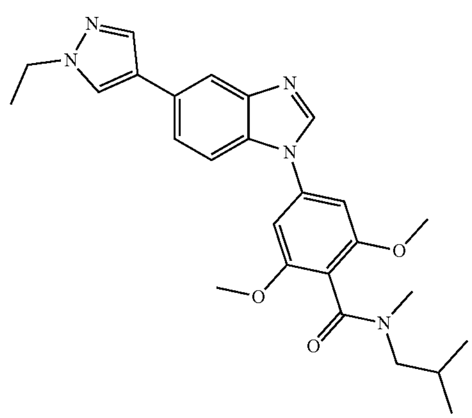 [SMILES: CCn1cc(-c2ccc3c(c2)ncn3-c2cc(OC)c(C(=O)N(C)CC(C)C)c(OC)c2)cn1] | 4-[5-(1-ethylpyrazol-4-yl)benzimidazol-1-yl]-N-isobutyl-2,6-dimethoxy-N-methyl-benzamide | Int 44 + CAS# 625-43-4 + CAS# 847818-70-6 | E1.2 + E1.3 | 461.6 | 462.7 |
| 29 | 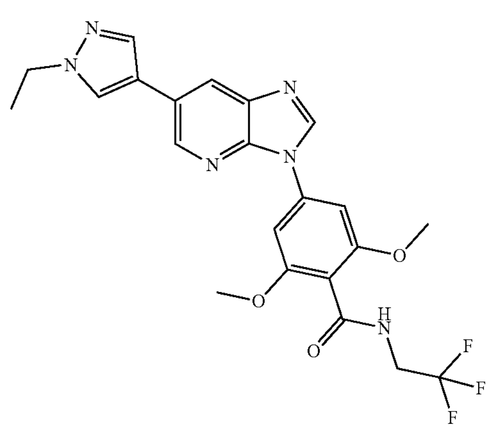 [SMILES: CCn1cc(-c2cnc3c(c2)ncn3-c2cc(OC)c(C(=O)NCC(F)(F)F)c(OC)c2)cn1] | 4-[6-(1-ethylpyrazol-4-yl)imidazo[4,5-b]pyridin-3-yl]-2,6-dimethoxy-N-(2,2,2-trifluoroethyl)benzamide | Int 74 + CAS# 373-88-6 | E1.1 + E1.2 | 474.4 | 475.3 |

TABLE III-continued

Illustrative compounds of the invention.

| Cpd # | Structure | Name | SM | Mtd | MW | MS Mes'd |
|---|---|---|---|---|---|---|
| 30 | 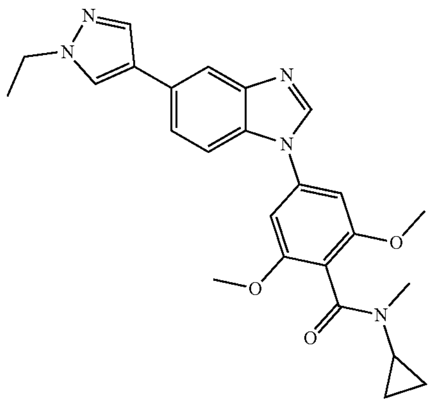 [SMILES: CCn1cc(-c2ccc3c(c2)ncn3-c2cc(OC)c(C(=O)N(C)C3CC3)c(OC)c2)cn1] | N-cyclopropyl-4-[5-(1-ethylpyrazol-4-yl)benzimidazol-1-yl]-2,6-dimethoxy-N-methyl-benzamide | Int 44 + CAS# 5163-20-2 + CAS# 847818-70-6 | E1.2 + E1.3 | 445.5 | 446.6 |
| 31 | 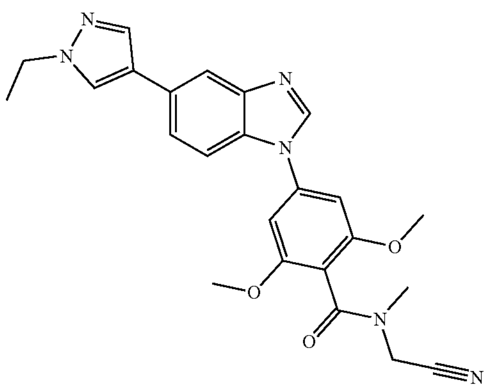 [SMILES: CCn1cc(-c2ccc3c(c2)ncn3-c2cc(OC)c(C(=O)N(C)CC#N)c(OC)c2)cn1] | N-(cyanomethyl)-4-[5-(1-ethylpyrazol-4-yl)benzimidazol-1-yl]-2,6-dimethoxy-N-methyl-benzamide | Int 44 + CAS# 25808-30-4 + CAS# 847818-70-6 | E1.2 + E1.3 | 444.5 | 445.5 |
| 32 | 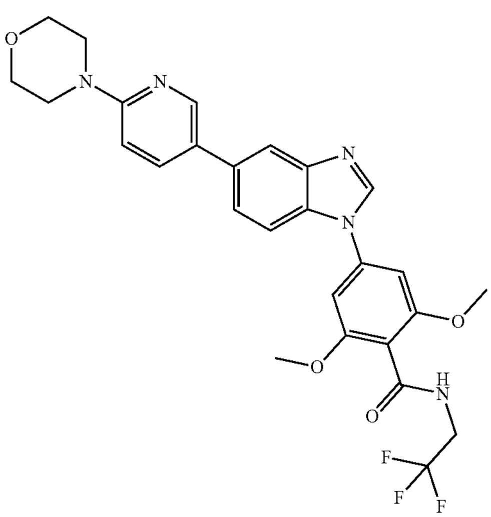 [SMILES: COc1cc(-n2cnc3cc(-c4ccc(N5CCOCC5)nc4)ccc32)cc(OC)c1C(=O)NCC(F)(F)F] | 2,6-dimethoxy-4-[5-(6-morpholino-3-pyridyl)benzimidazol-1-yl]-N-(2,2,2-trifluoroethyl)benzamide | Int 39 + CAS# 485799-04-0 | E1.3 | 541.5 | 542.5 |

TABLE III-continued

Illustrative compounds of the invention.

| Cpd # | Structure | Name | SM | Mtd | MW | MS Mes'd |
|---|---|---|---|---|---|---|
| 33 | 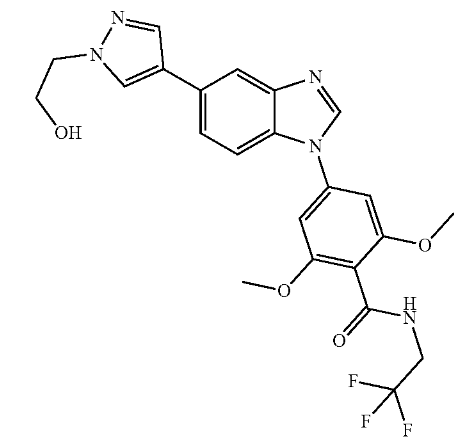 [SMILES: COc1cc(-n2cnc3cc(-c4cnn(CCO)c4)ccc32)cc(OC)c1C(=O)NCC(F)(F)F] | 4-[5-[1-(2-hydroxyethyl)pyrazol-4-yl]benzimidazol-1-yl]-2,6-dimethoxy-N-(2,2,2-trifluoroethyl)benzamide | Int 39 + CAS# 1040377-08-9 | E1.3 | 489.4 | 490.3 |
| 34 | 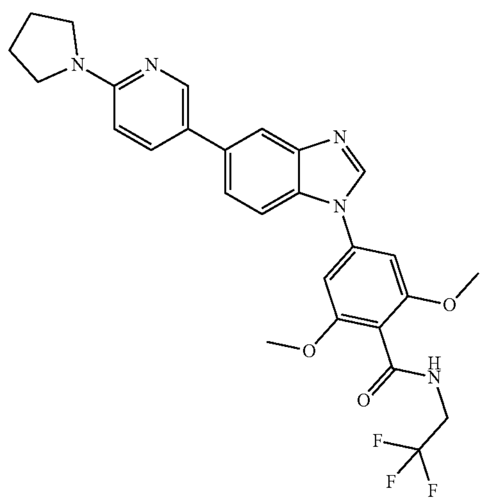 [SMILES: COc1cc(-n2cnc3cc(-c4ccc(N5CCCC5)nc4)ccc32)cc(OC)c1C(=O)NCC(F)(F)F] | 2,6-dimethoxy-4-[5-(6-pyrrolidin-1-yl-3-pyridyl)benzimidazol-1-yl]-N-(2,2,2-trifluoroethyl)benzamide | Int 39 + CAS# 933986-97-1 | E1.3 | 525.5 | 526.6 |
| 35 | 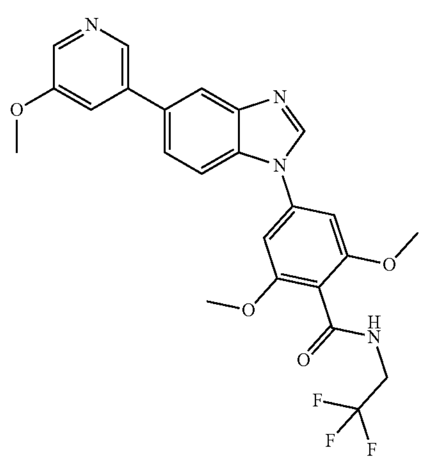 [SMILES: COc1cncc(-c2ccc3c(c2)ncn3-c2cc(OC)c(C(=O)NCC(F)(F)F)c(OC)c2)c1] | 2,6-dimethoxy-4-[5-(5-methoxy-3-pyridyl)benzimidazol-1-yl]-N-(2,2,2-trifluoroethyl)benzamide | Int 39 + CAS# 445264-60-8 | E1.3 | 486.4 | 487.6 |

TABLE III-continued

Illustrative compounds of the invention.

| Cpd # | Structure | Name | SM | Mtd | MW | MS Mes'd |
|---|---|---|---|---|---|---|
| 36 | 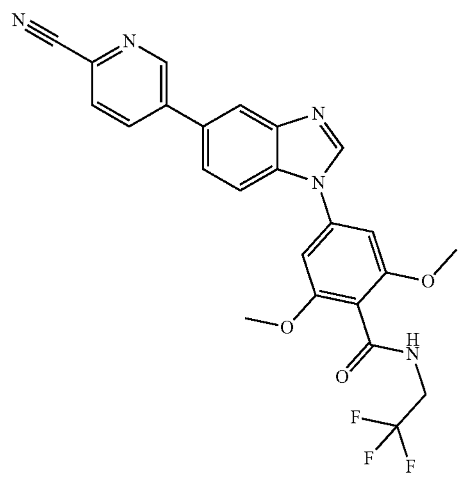 [SMILES: COc1cc(-n2cnc3cc(-c4ccc(C#N)nc4)ccc32)cc(OC)c1C(=O)NCC(F)(F)F] | 4-[5-(6-cyano-3-pyridyl) benzimidazol-1-yl]-2,6-dimethoxy-N-(2,2,2-trifluoroethyl) benzamide | Int 39 + CAS# 741709-63-7 | E1.3 | 481.4 | 482.5 |
| 37 | 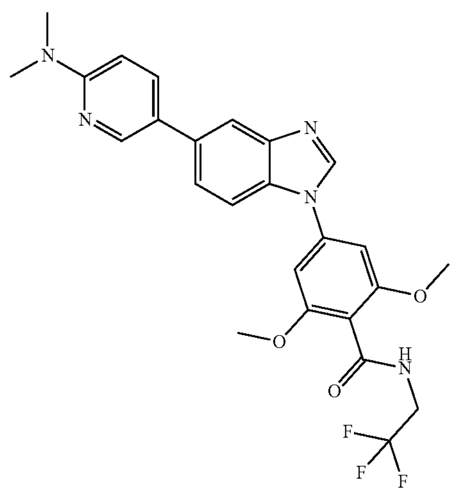 | 4-[5-[6-(dimethylamino)-3-pyridyl] benzimidazol-1-yl]-2,6-dimethoxy-N-(2,2,2-trifluoroethyl) benzamide | Int 39 + CAS# 1036991-24-8 | E1.3 | 499.5 | 500.6 |
| 38 | 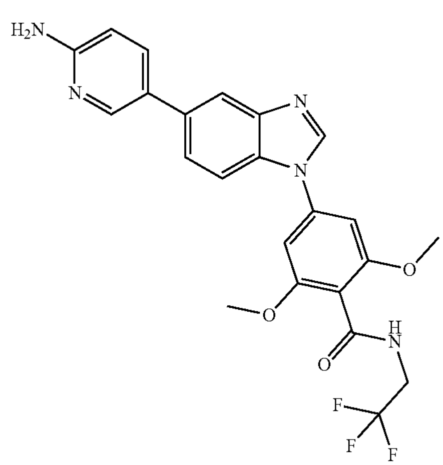 [SMILES: COc1cc(-n2cnc3cc(-c4ccc(N)nc4)ccc32)cc(OC)c1C(=O)NCC(F)(F)F] | 4-[5-(6-amino-3-pyridyl) benzimidazol-1-yl]-2,6-dimethoxy-N-(2,2,2-trifluoro-ethyl)benzamide | Int 39 + CAS# 827614-64-2 | E1.3 | 471.4 | 472.4 |

TABLE III-continued

Illustrative compounds of the invention.

| Cpd # | Structure | Name | SM | Mtd | MW | MS Mes'd |
|---|---|---|---|---|---|---|
| 39 | 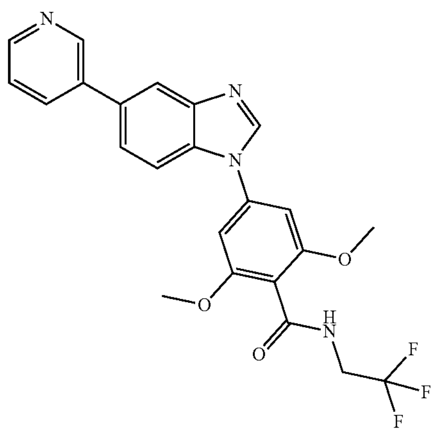 [SMILES: COc1cc(-n2cnc3cc(-c4cccnc4)ccc32)cc(OC)c1C(=O)NCC(F)(F)F] | 2,6-dimethoxy-4-[5-(3-pyridyl)benzimidazol-1-yl]-N-(2,2,2-trifluoroethyl)benzamide | Int 39 + CAS# 329214-79-1 | E1.3 | 456.4 | 457.6 |
| 40 | 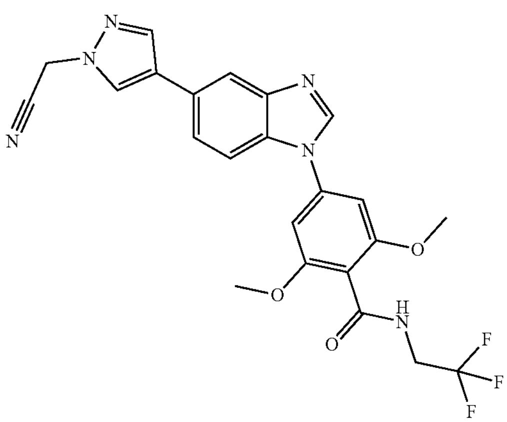 [SMILES: COc1cc(-n2cnc3cc(-c4cnn(CC#N)c4)ccc32)cc(OC)c1C(=O)NCC(F)(F)F] | 4-[5-[1-(cyanomethyl)pyrazol-4-yl]benzimidazol-1-yl]-2,6-dimethoxy-N-(2,2,2-trifluoroethyl)benzamide | Int 39 + CAS# 1093307-35-7 | E1.3 | 484.4 | 485.6 |
| 41 | 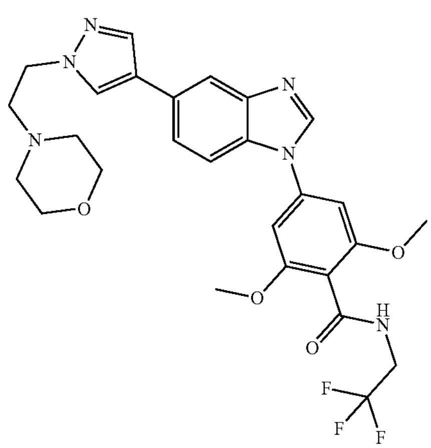 [SMILES: COc1cc(-n2cnc3cc(-c4cnn(CCN5CCOCC5)c4)ccc32)cc(OC)c1C(=O)NCC(F)(F)F] | 2,6-dimethoxy-4-[5-[1-(2-morpholinoethyl)pyrazol-4-yl]benzimidazol-1-yl]-N-(2,2,2-trifluoroethyl)benzamide | Int 39 + CAS# 864754-18-7 | E1.3 | 558.6 | 559.5 |

TABLE III-continued

Illustrative compounds of the invention.

| Cpd # | Structure | Name | SM | Mtd | MW | MS Mes'd |
|---|---|---|---|---|---|---|
| 42 | 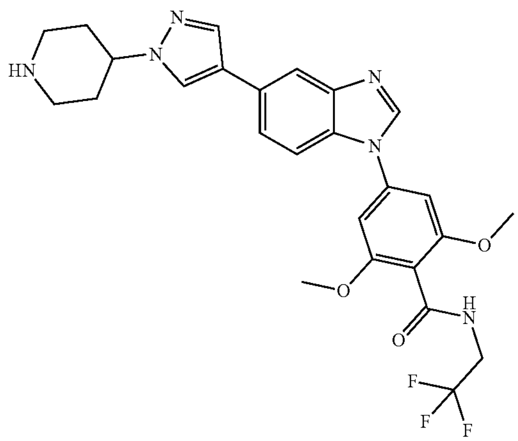 [SMILES: COc1cc(-n2cnc3cc(-c4cnn(C5CCNCC5)c4)ccc32)cc(OC)c1C(=O)NCC(F)(F)F] | 2,6-dimethoxy-4-[5-[1-(4-piperidyl)pyrazol-4-yl]benzimidazol-1-yl]-N-(2,2,2-trifluoroethyl)benzamide | Int 39 + CAS# 877399-74-1 | E1.3 + K | 528.5 | 529.4 |
| 43 | 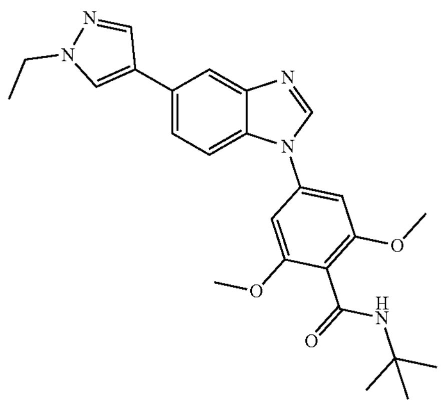 [SMILES: CCn1cc(-c2ccc3c(c2)ncn3-c2cc(OC)c(C(=O)NC(C)(C)C)c(OC)c2)cn1] | N-tert-butyl-4-[5-(1-ethylpyrazol-4-yl)benzimidazol-1-yl]-2,6-dimethoxy-benzamide | Int 44 + CAS# 75-64-9 + CAS# 847818-70-6 | E1.2 + E1.3 | 447.5 | 448.6 |
| 44 | 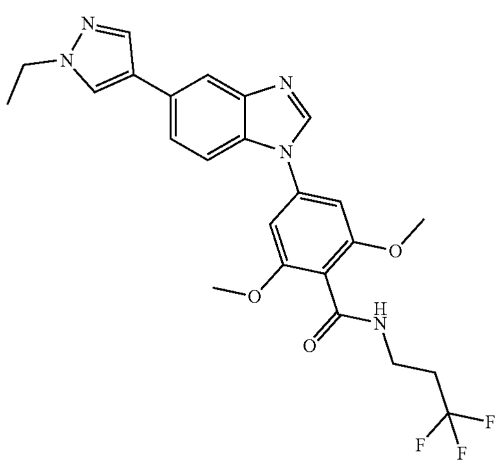 [SMILES: CCn1cc(-c2ccc3c(c2)ncn3-c2cc(OC)c(C(=O)NCCC(F)(F)F)c(OC)c2)cn1] | 4-[5-(1-ethylpyrazol-4-yl)benzimidazol-1-yl]-2,6-dimethoxy-N-(3,3,3-trifluoropropyl)benzamide | Int 44 + CAS# 460-39-9 + CAS# 847818-70-6 | E1.2 + E1.3 | 487.5 | 488.5 |

TABLE III-continued

Illustrative compounds of the invention.

| Cpd # | Structure | Name | SM | Mtd | MW | MS Mes'd |
|---|---|---|---|---|---|---|
| 45 | 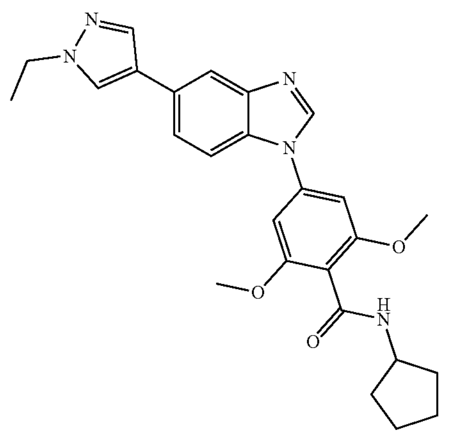 [SMILES: CCn1cc(-c2ccc3c(c2)ncn3-c2cc(OC)c(C(=O)NC3CCCC3)c(OC)c2)cn1] | N-cyclopentyl-4-[5-(1-ethylpyrazol-4-yl)benzimidazol-1-yl]-2,6-dimethoxy-benzamide | Int 44 + CAS# 1003-03-8 + CAS# 847818-70-6 | E1.2 + E1.3 | 459.5 | 460.6 |
| 46 | 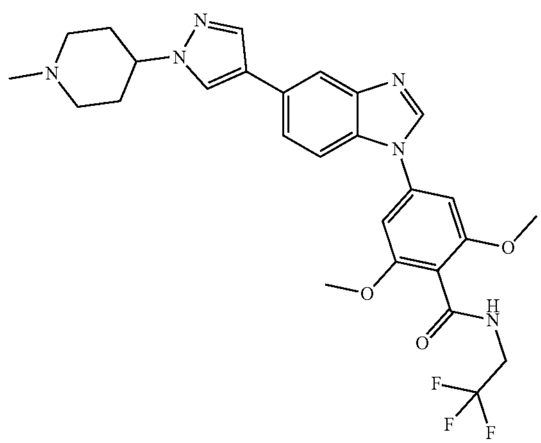 | 2,6-dimethoxy-4-[5-[1-(1-methyl-4-piperidyl)pyrazol-4-yl]benzimidazol-1-yl]-N-(2,2,2-trifluoroethyl)benzamide | Cpd 42 | L1ii | 542.6 | 543.4 |
| 47 | 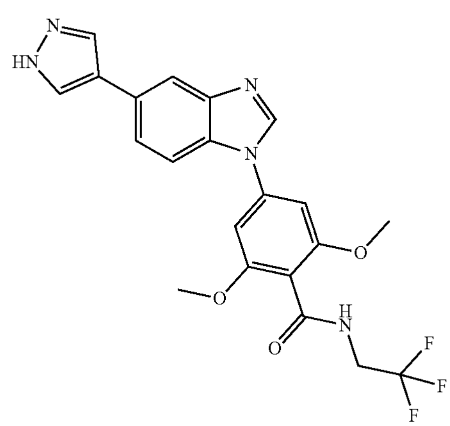 [SMILES: COc1cc(-n2cnc3cc(-c4cn[nH]c4)ccc32)cc(OC)c1C(=O)NCC(F)(F)F] | 2,6-dimethoxy-4-[5-(1H-pyrazol-4-yl)benzimidazol-1-yl]-N-(2,2,2-trifluoroethyl)benzamide | Int 39 + CAS# 269410-08-4 | E1.3 | 445.4 | 446.5 |

TABLE III-continued

Illustrative compounds of the invention.

| Cpd # | Structure | Name | SM | Mtd | MW | MS Mes'd |
|---|---|---|---|---|---|---|
| 48 | 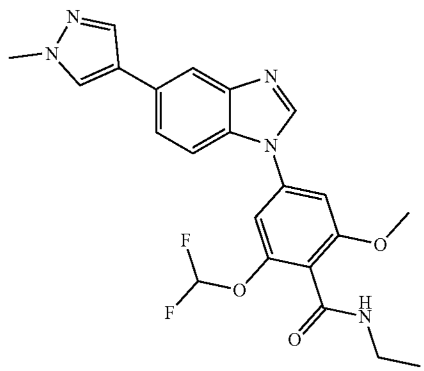 [SMILES: CCNC(=O)c1c(OC)cc(-n2cnc3cc(-c4cnn(C)c4)ccc32)cc1OC(F)F] | 2-(difluoromethoxy)-N-ethyl-6-methoxy-4-[5-(1-methylpyrazol-4-yl)benzimidazol-1-yl]benzamide | Int 57 | C2 | 441.4 | 442.3 |
| 49 | 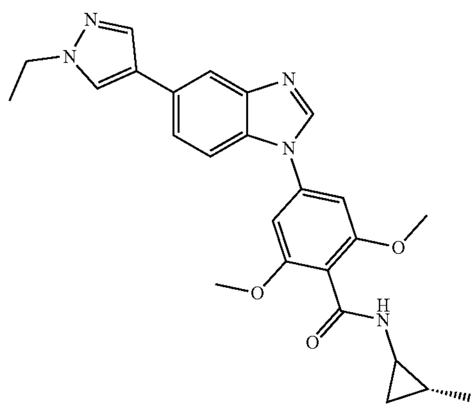 [SMILES: CCn1cc(-c2ccc3c(c2)ncn3-c2cc(OC)c(C(=O)NC3C[C@H]3C)c(OC)c2)cn1] | 4-[5-(1-ethylpyrazol-4-yl)benzimidazol-1-yl]-2,6-dimethoxy-N-[(2R)-2-methylcyclopropyl]benzamide | Int 44 + CAS# 97291-66-2 + CAS# 847818-70-6 | E1.2 + E1.3 | 445.5 | 446.4 |
| 50 | 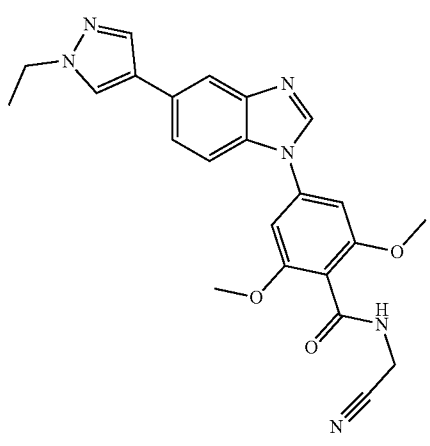 [SMILES: CCn1cc(-c2ccc3c(c2)ncn3-c2cc(OC)c(C(=O)NCC#N)c(OC)c2)cn1] | N-(cyanomethyl)-4-[5-(1-ethylpyrazol-4-yl)benzimidazol-1-yl]-2,6-dimethoxy-benzamide | Int 44 + CAS# 540-61-4 + CAS# 847818-70-6 | E1.2 + E1.3 | 430.5 | 431.5 |

TABLE III-continued

Illustrative compounds of the invention.

| Cpd # | Structure | Name | SM | Mtd | MW | MS Mes'd |
|---|---|---|---|---|---|---|
| 51 | 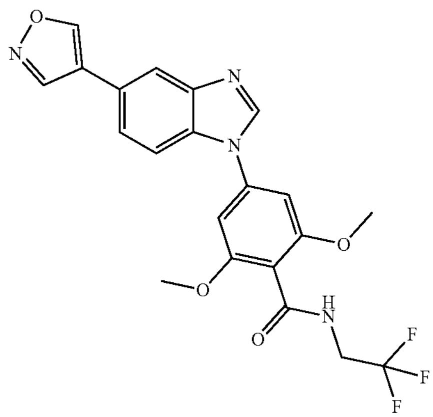 [SMILES: COc1cc(-n2cnc3cc(-c4cnoc4)ccc32)cc(OC)c1C(=O)NCC(F)(F)F] | 4-(5-isoxazol-4-ylbenzimidazol-1-yl)-2,6-dimethoxy-N-(2,2,2-trifluoroethyl)benzamide | Int 39 + CAS# 928664-98-6 | E1.3 | 446.4 | 447.3 |
| 52 | 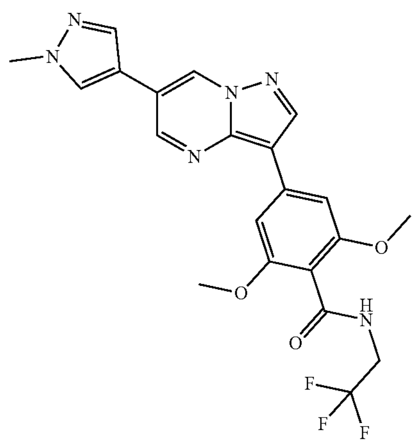 | 2,6-dimethoxy-4-[6-(1-methylpyrazol-4-yl)pyrazolo[1,5-a]pyrimidin-3-yl]-N-(2,2,2-trifluoroethyl)benzamide | Int 28 + CAS# 373-88-6 | E1.2 | 460.4 | 461.3 |
| 53 | 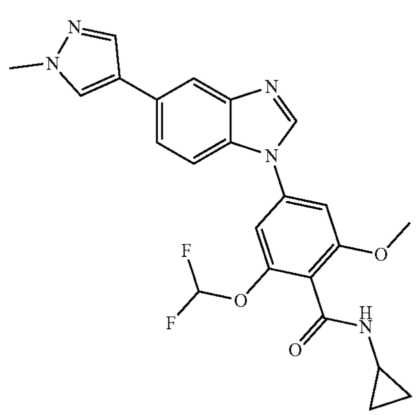 [SMILES: COc1cc(-n2cnc3cc(-c4cnn(C)c4)ccc32)cc(OC(F)F)c1C(=O)NC1CC1] | N-cyclopropyl-2-(difluoromethoxy)-6-methoxy-4-[5-(1-methylpyrazol-4-yl)benzimidazol-1-yl]benzamide | Int 55 | C3 | 453.4 | 454.5 |

TABLE III-continued

Illustrative compounds of the invention.

| Cpd # | Structure | Name | SM | Mtd | MW | MS Mes'd |
|---|---|---|---|---|---|---|
| 54 | 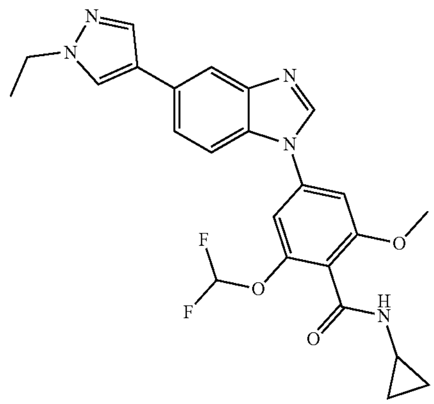 [SMILES: CCn1cc(-c2ccc3c(c2)ncn3-c2cc(OC)c(C(=O)NC3CC3)c(OC(F)F)c2)cn1] | N-cyclopropyl-2-(difluoromethoxy)-4-[5-(1-ethylpyrazol-4-yl)benzimidazol-1-yl]-6-methoxy-benzamide | Int 42 + CAS# 847818-70-6 | E1.3 | 467.5 | 468.5 |
| 55 | 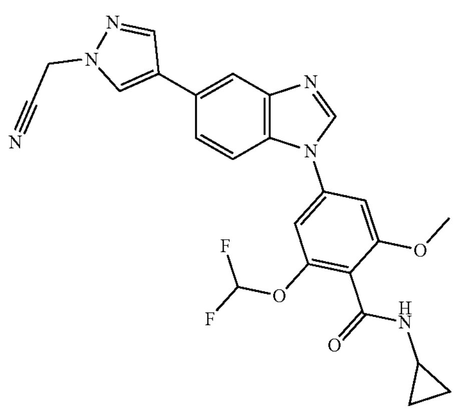 [SMILES: COc1cc(-n2cnc3cc(-c4cnn(CC#N)c4)ccc32)cc(OC(F)F)c1C(=O)NC1CC1] | 4-[5-[1-(cyanomethyl)pyrazol-4-yl]benzimidazol-1-yl]-N-cyclopropyl-2-(difluoromethoxy)-6-methoxy-benzamide | Int 42 + CAS# 1093307-35-7 | E1.3 | 478.5 | 479.3 |
| 56 | 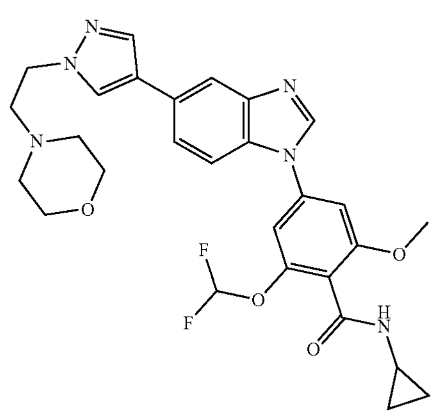 [SMILES: COc1cc(-n2cnc3cc(-c4cnn(CCN5CCOCC5)c4)ccc32)cc(OC(F)F)c1C(=O)NC1CC1] | N-cyclopropyl-2-(difluoromethoxy)-6-methoxy-4-[5-[1-(2-morpholinoethyl)pyrazol-4-yl]benzimidazol-1-yl]benzamide | Int 42 + CAS# 864754-18-7 | E1.3 | 552.6 | 553.4 |

TABLE III-continued

Illustrative compounds of the invention.

| Cpd # | Structure | Name | SM | Mtd | MW | MS Mes'd |
|---|---|---|---|---|---|---|
| 57 | 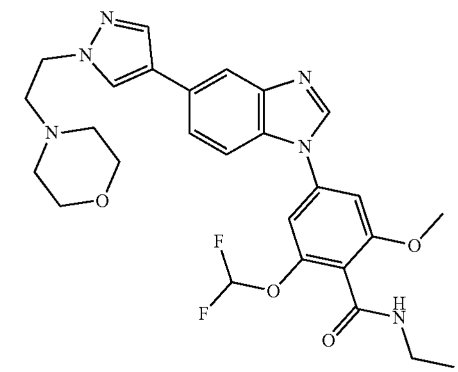 [SMILES: CCNC(=O)c1c(OC)cc(-n2cnc3cc(-c4cnn(CCN5CCOCC5)c4)ccc32)cc1OC(F)F] | 2-(difluoromethoxy)-N-ethyl-6-methoxy-4-[5-[1-(2-morpholinoethyl)pyrazol-4-yl]benzimidazol-1-yl]benzamide | Int 38 + CAS# 864754-18-7 | E1.3 | 540.6 | 541.3 |
| 58 | 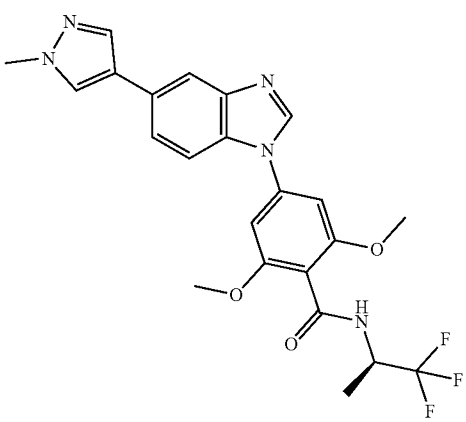 [SMILES: COc1cc(-n2cnc3cc(-c4cnn(C)c4)ccc32)cc(OC)c1C(=O)N[C@H](C)C(F)(F)F] | 2,6-dimethoxy-4-[5-(1-methylpyrazol-4-yl)benzimidazol-1-yl]-N-[(1R)-2,2,2-trifluoro-1-methyl-ethyl]benzamide | Int 50 + CAS# 125278-10-6 | E1.2 | 473.4 | 474.6 |
| 59 | 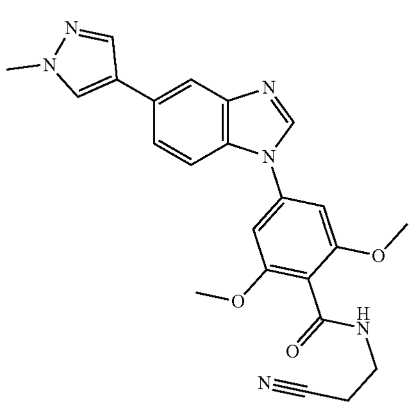 | N-(2-cyanoethyl)-2,6-dimethoxy-4-[5-(1-methylpyrazol-4-yl)benzimidazol-1-yl]benzamide | Int 50 + CAS# 151-18-8 | E1.2 | 430.5 | 431.4 |

TABLE III-continued

Illustrative compounds of the invention.

| Cpd # | Structure | Name | SM | Mtd | MW | MS Mes'd |
|---|---|---|---|---|---|---|
| 60 | 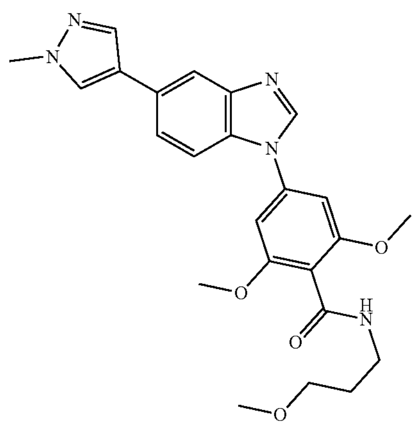 | 2,6-dimethoxy-N-(3-methoxypropyl)-4-[5-(1-methylpyrazol-4-yl)benzimidazol-1-yl]benzamide | Int 50 + CAS# 5332-73-0 | E1.2 | 449.5 | 450.4 |
| 61 | 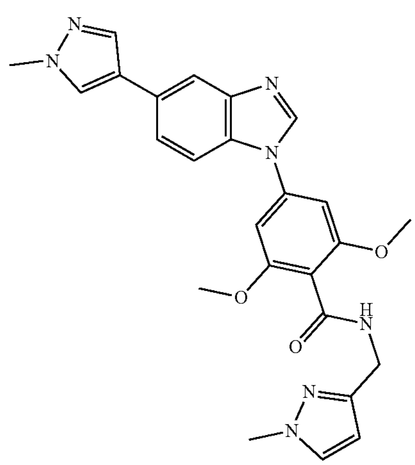 | 2,6-dimethoxy-4-[5-(1-methylpyrazol-4-yl)benzimidazol-1-yl]-N-[(1-methylpyrazol-3-yl)methyl]benzamide | Int 50 + CAS# 612511-81-6 | E1.2 | 471.5 | 472.4 |
| 62 | 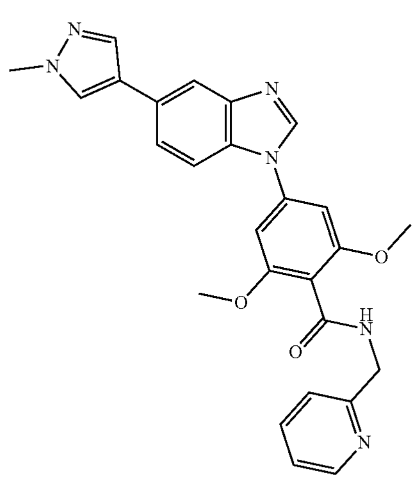 | 2,6-dimethoxy-4-[5-(1-methylpyrazol-4-yl)benzimidazol-1-yl]-N-(2-pyridylmethyl)benzamide | Int 50 + CAS# 3731-51-9 | E1.2 | 468.5 | 469.3 |

TABLE III-continued

Illustrative compounds of the invention.

| Cpd # | Structure | Name | SM | Mtd | MW | MS Mes'd |
|---|---|---|---|---|---|---|
| 63 | 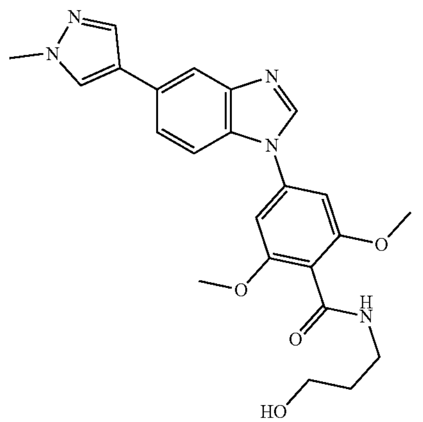 | N-(3-hydroxypropyl)-2,6-dimethoxy-4-[5-(1-methylpyrazol-4-yl)benzimidazol-1-yl]benzamide | Int 50 + CAS# 156-87-6 | E1.2 | 435.5 | 436.5 |
| 64 | 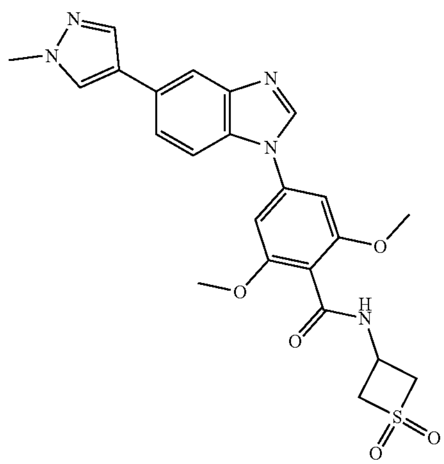 [SMILES: COc1cc(-n2cnc3cc(-c4cnn(C)c4)ccc32)cc(OC)c1C(=O)NC1CS(=O)(=O)C1] | N-(1,1-dioxothietan-3-yl)-2,6-dimethoxy-4-[5-(1-methylpyrazol-4-yl)benzimidazol-1-yl]benzamide | Int 50 + CAS# 88511-13-1 | E1.2 | 481.5 | 482.5 |
| 65 | 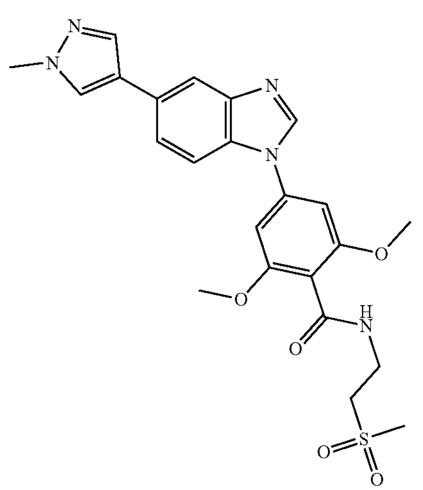 | 2,6-dimethoxy-4-[5-(1-methylpyrazol-4-yl)benzimiazol-1-yl]-N-(2-methylsulfonyl-ethyl)benzamide | Int 50 + CAS# 49773-20-8 | E1.2 | 483.5 | 484.6 |

TABLE III-continued

Illustrative compounds of the invention.

| Cpd # | Structure | Name | SM | Mtd | MW | MS Mes'd |
|---|---|---|---|---|---|---|
| 66 | 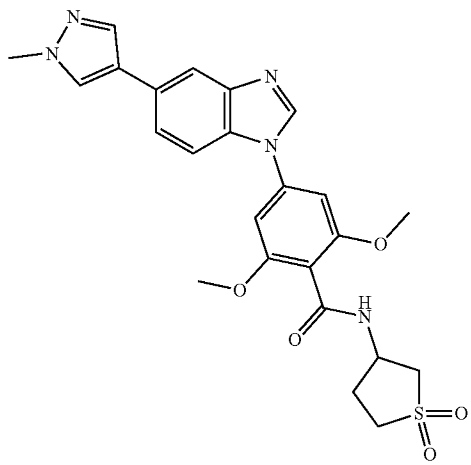 [SMILES: COc1cc(-n2cnc3cc(-c4cnn(C)c4)ccc32)cc(OC)c1C(=O)NC1CCS(=O)(=O)C1] | N-(1,1-dioxothiolan-3-yl)-2,6-dimethoxy-4-[5-(1-methylpyrazol-4-yl)benzimidazol-1-yl]benzamide | Int 50 + CAS# 6338-70-1 | E1.2 | 495.6 | 496.6 |
| 67 | 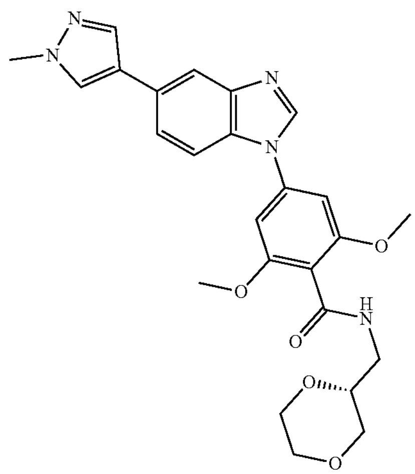 | N-[[(2R)-1,4-dioxan-2-yl]methyl]-2,6-dimethoxy-4-[5-(1-methylpyrazol-4-yl)benzimidazol-1-yl]benzamide | Int 50 + CAS# 1449010-18-7 | E1.2 | 477.5 | 478.4 |
| 68 | 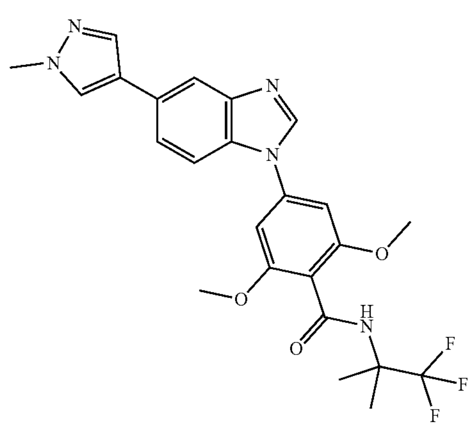 [SMILES: COc1cc(-n2cnc3cc(-c4cnn(C)c4)ccc32)cc(OC)c1C(=O)NC(C)(C)C(F)(F)F] | 2,6-dimethoxy-4-[5-(1-methylpyrazol-4-yl)benzimidazol-1-yl]-N-(2,2,2-trifluoro-1,1-dimethyl-ethyl)benzamide | Int 50 + CAS# 812-18-0 | E1.2 | 487.5 | 488.7 |

TABLE III-continued

Illustrative compounds of the invention.

| Cpd # | Structure | Name | SM | Mtd | MW | MS Mes'd |
|---|---|---|---|---|---|---|
| 69 | 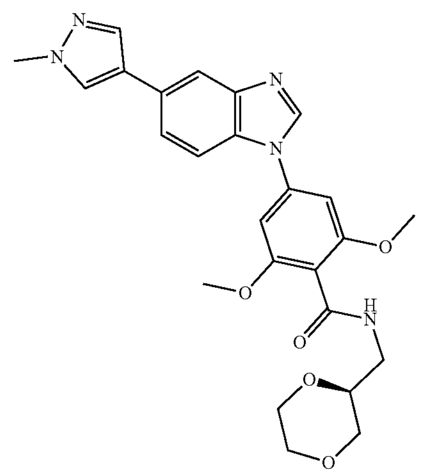 | N-[[(2S)-1,4-dioxan-2-yl]methyl]-2,6-dimethoxy-4-[5-(1-methylpyrazol-4-yl)benzimidazol-1-yl]benzamide | Int 50 + CAS# 1337470-52-6 | E1.2 | 477.5 | 478.4 |
| 70 | 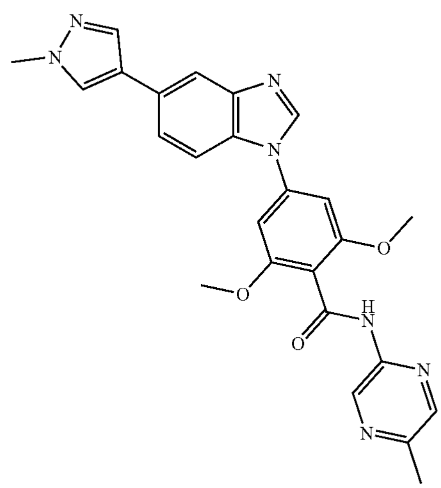 [SMILES: COc1cc(-n2cnc3cc(-c4cnn(C)c4)ccc32)cc(OC)c1C(=O)Nc1cnc(C)cn1] | 2,6-dimethoxy-N-(5-methylpyrazin-2-yl)-4-[5-(1-methylpyrazol-4-yl)benzimidazol-1-yl]benzamide | Int 50 + CAS# 5521-58-4 | E1.2 | 469.5 | 470.3 |
| 71 | 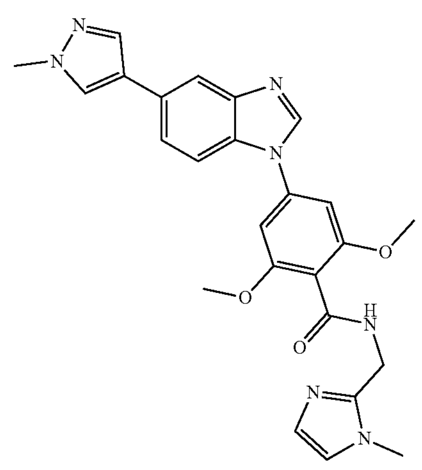 | 2,6-dimethoxy-N-[(1-methylimidazo-2-yl)methyl]-4-[5-(1-methylpyrazol-4-yl)benzimidazol-4-yl]benzamide | Int 50 + CAS# 124312-73-8 | E1.2 | 471.5 | 472.3 |

TABLE III-continued

Illustrative compounds of the invention.

| Cpd # | Structure | Name | SM | Mtd | MW | MS Mes'd |
|---|---|---|---|---|---|---|
| 72 | 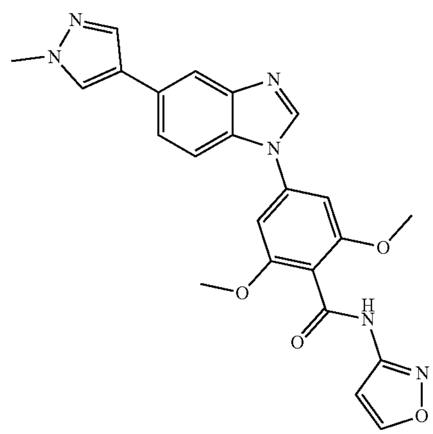 [SMILES: COc1cc(-n2cnc3cc(-c4cnn(C)c4)ccc32)cc(OC)c1C(=O)Nc1ccon1] | N-isoxazol-3-yl-2,6-dimethoxy-4-[5-(1-methylpyrazol-4-yl)benzimidazol-1-yl]benzamide | Int 50 + CAS# 1750-42-1 | E1.2 | 444.4 | 445.4 |
| 73 | 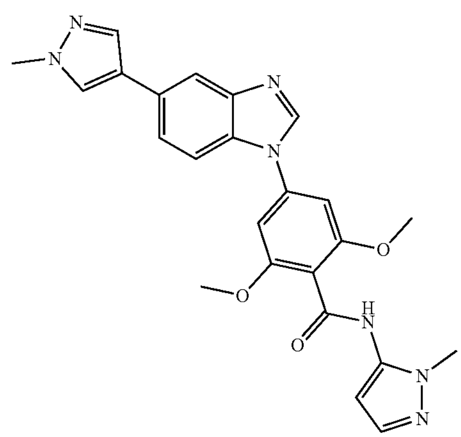 | 2,6-dimethoxy-N-(2-methylpyrazol-3-yl)-4-[5-(1-methylpyrazol-4-yl)benzimidazol-1-yl]benzamide | Int 50 + CAS# 1192-21-8 | E1.2 | 457.5 | 458.2 |
| 74 | 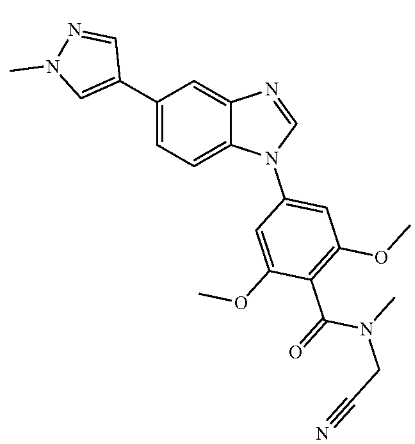 | N-(cyanomethyl)-2,6-dimethoxy-N-methyl-4-[5-(1-methylpyrazol-4-yl)benzimidazol-1-yl]benzamide | Int 50 + CAS# 5616-32-0 | E1.2 | 430.5 | 431.3 |

TABLE III-continued

Illustrative compounds of the invention.

| Cpd # | Structure | Name | SM | Mtd | MW | MS Mes'd |
|---|---|---|---|---|---|---|
| 75 | 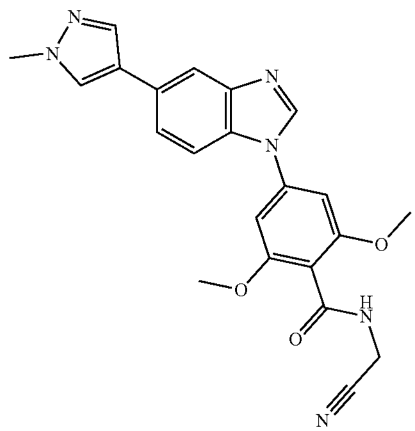 | N-(cyanomethyl)-2,6-dimethoxy-4-[5-(1-methylpyrazol-4-yl)benzimidazol-1-yl]benzamide | Int 50 + CAS# 540-61-4 | E1.2 | 416.4 | 417.3 |
| 76 | 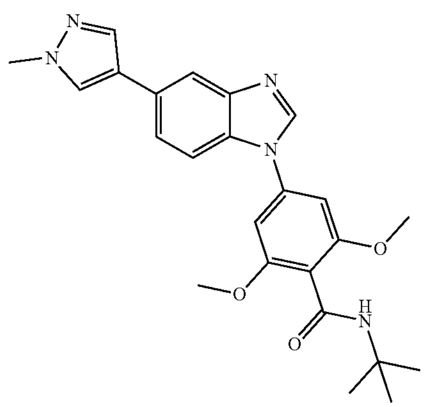 [SMILES: COc1cc(-n2cnc3cc(-c4cnn(C)c4)ccc32)cc(OC)c1C(=O)NC(C)(C)C] | N-tert-butyl-2,6-dimethoxy-4-[5-(1-methylpyrazol-4-yl)benzimidazol-1-yl]benzamide | Int 50 + CAS# 75-64-9 | E1.2 | 433.5 | 434.4 |
| 77 | 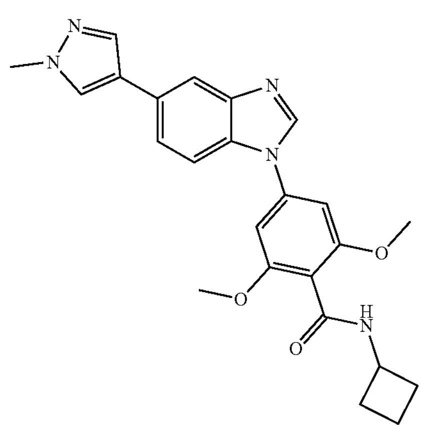 [SMILES: COc1cc(-n2cnc3cc(-c4cnn(C)c4)ccc32)cc(OC)c1C(=O)NC1CCC1] | N-cyclobutyl-2,6-dimethoxy-4-[5-(1-methylpyrazol-4-yl)benzimidazol-1-yl]benzamide | Int 50 + CAS# 2516-34-9 | E1.2 | 431.5 | 432.4 |

TABLE III-continued

Illustrative compounds of the invention.

| Cpd # | Structure | Name | SM | Mtd | MW | MS Mes'd |
|---|---|---|---|---|---|---|
| 78 | 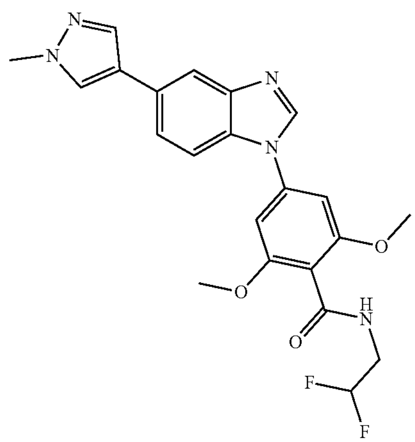 | N-(2,2-difluoroethyl)-2,6-dimethoxy-4-[5-(1-methylpyrazol-4-yl)benzimidazol-1-yl]benzamide | Int 50 + CAS# 430-67-1 | E1.2 | 441.4 | 442.3 |
| 79 | 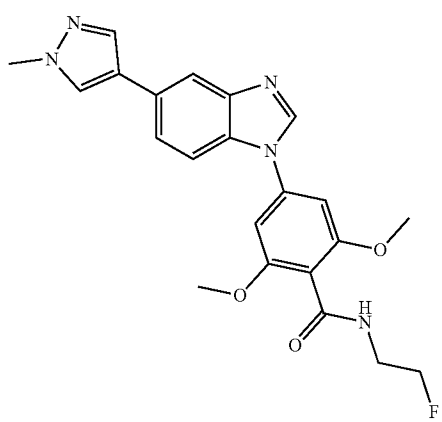 [SMILES: COc1cc(-n2cnc3cc(-c4cnn(C)c4)ccc32)cc(OC)c1C(=O)NCCF] | N-(2-fluoroethyl)-2,6-dimethoxy-4-[5-(1-methylpyrazol-4-yl)benzimidazol-1-yl]benzamide | Int 50 + CAS# 406-34-8 | E1.2 | 423.4 | 424.3 |
| 80 | 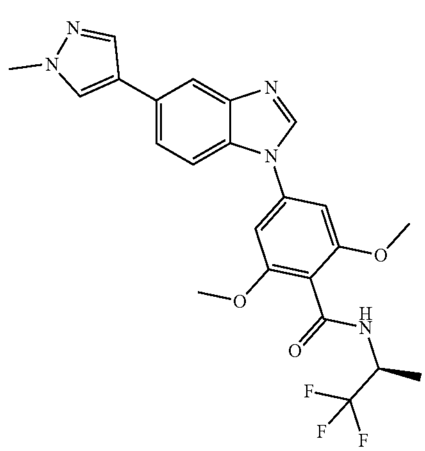 [SMILES: COc1cc(-n2cnc3cc(-c4cnn(C)c4)ccc32)cc(OC)c1C(=O)N[C@@H](C)C(F)(F)F] | 2,6-dimethoxy-4-[5-(1-methylpyrazol-4-yl)benzimidazol-1-yl]-N-[(1S)-2,2,2-trifluoro-1-methyl-ethyl]benzamide | Int 50 + CAS# 779303-24-1 | E1.2 | 473.4 | 474.3 |

TABLE III-continued

Illustrative compounds of the invention.

| Cpd # | Structure | Name | SM | Mtd | MW | MS Mes'd |
|---|---|---|---|---|---|---|
| 81 | 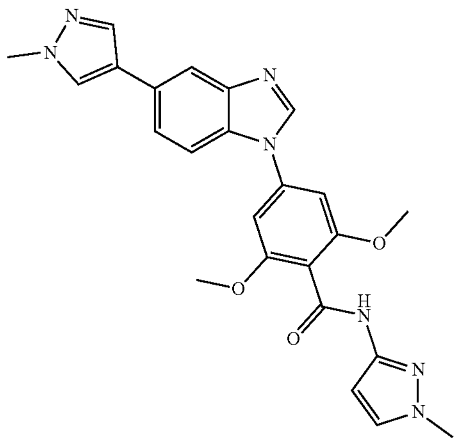 | 2,6-dimethoxy-N-(1-methylpyrazol-3-yl)-4-[5-(1-methylpyrazol-4-yl)benzimidazol-1-yl]benzamide | Int 50 + CAS# 1904-31-0 | E1.2 | 457.5 | 458.3 |
| 82 | 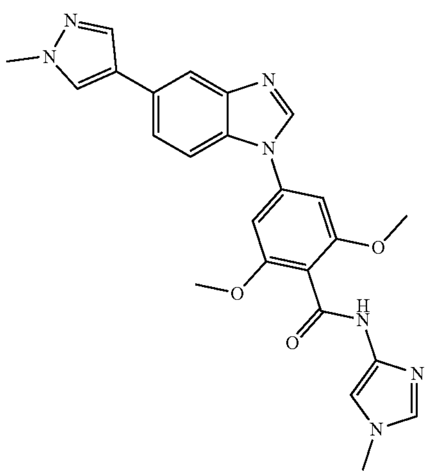 [SMILES: COc1cc(-n2cnc3cc(-c4cnn(C)c4)ccc32)cc(OC)c1C(=O)Nc1cn(C)cn1] | 2,6-dimethoxy-N-(1-methylimidazol-4-yl)-4-[5-(1-methylpyrazol-4-yl)benzimidazol-1-yl]benzamide | Int 50 + CAS# 79578-98-6 | E1.2 | 457.5 | 458.3 |
| 83 | 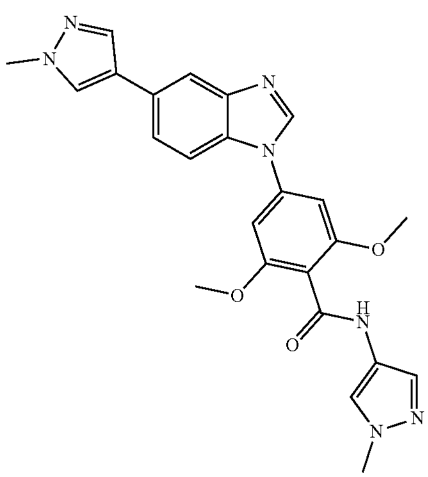 [SMILES: COc1cc(-n2cnc3cc(-c4cnn(C)c4)ccc32)cc(OC)c1C(=O)Nc1cnn(C)c1] | 2,6-dimethoxy-N-(1-methylpyrazol-4-yl)-4-[5-(1-methylpyrazol-4-yl)benzimidazol-1-yl]benzamide | Int 50 + CAS# 69843-13-6 | E1.2 | 457.5 | 458.3 |

TABLE III-continued

Illustrative compounds of the invention.

| Cpd # | Structure | Name | SM | Mtd | MW | MS Mes'd |
|---|---|---|---|---|---|---|
| 84 | 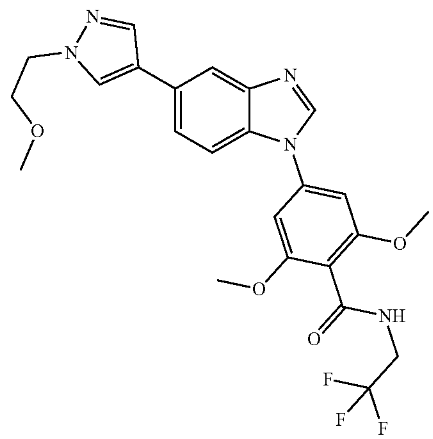 [SMILES: COCCn1cc(-c2ccc3c(c2)ncn3-c2cc(OC)c(C(=O)NCC(F)(F)F)c(OC)c2)cn1] | 2,6-dimethoxy-4-[5-[1-(2-methoxyethyl)pyrazol-4-yl]benzimidazol-1-yl]-N-(2,2,2-trifluoroethyl)benzamide | Int 39 + CAS# 847818-71-7 | E1.3 | 503.5 | 504.3 |
| 85 | 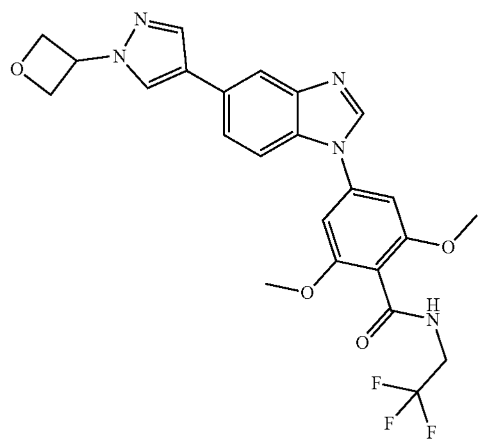 [SMILES: COc1cc(-n2cnc3cc(-c4cnn(C5COC5)c4)ccc32)cc(OC)c1C(=O)NCC(F)(F)F] | 2,6-dimethoxy-4-[5-(1-(oxetan-3-yl)pyrazol-4-yl]benzimidazol-1-yl]-N-(2,2,2-trifluoroethyl)benzamide | Int 39 + CAS# 1339890-99-1 | E1.3 | 501.5 | 502.3 |
| 86 | 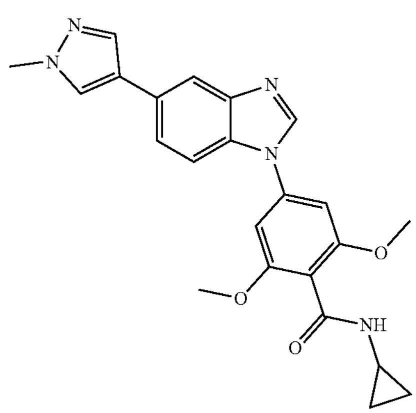 [SMILES: COc1cc(-n2cnc3cc(-c4cnn(C)c4)ccc32)cc(OC)c1C(=O)NC1CC1] | N-cyclopropyl-2,6-dimethoxy-4-[5-(1-methylpyrazol-4-yl)benzimidazol-1-yl]benzamide | Int 50 + CAS# 765-30-0 | E1.2 | 417.5 | 418.3 |

TABLE III-continued

Illustrative compounds of the invention.

| Cpd # | Structure | Name | SM | Mtd | MW | MS Mes'd |
|---|---|---|---|---|---|---|
| 87 | 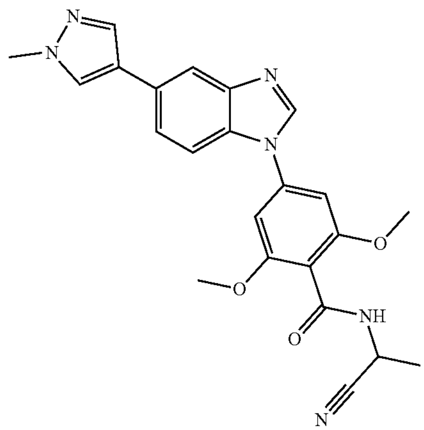 [SMILES: COc1cc(-n2cnc3cc(-c4cnn(C)c4)ccc32)cc(OC)c1C(=O)NC(C)C#N] | N-(1-cyanoethyl)-2,6-dimethoxy-4-[5-(1-methylpyrazol-4-yl)benzimidazol-1-yl]benzamide | Int 50 + CAS# 72187-91-8 | E1.2 | 430.5 | 431.3 |
| 88 | 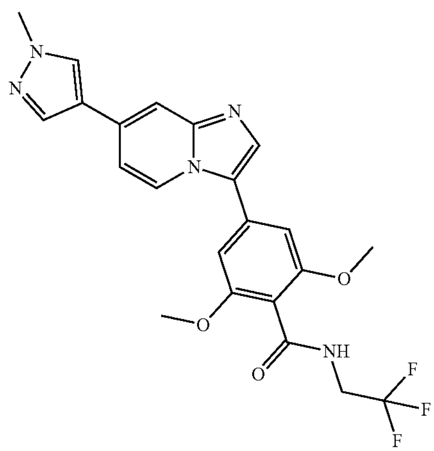 [SMILES: COc1cc(-c2cnc3cc(-c4cnn(C)c4)ccn23)cc(OC)c1C(=O)NCC(F)(F)F] | 2,6-dimethoxy-4-[7-(1-methylpyrazol-4-yl)imidazo[1,2-a]pyridin-3-yl]-N-(2,2,2-trifluoroethyl)benzamide | Int 52 + CAS# 753-90-2 | E1.2 | 459.4 | 460.4 |
| 89 | 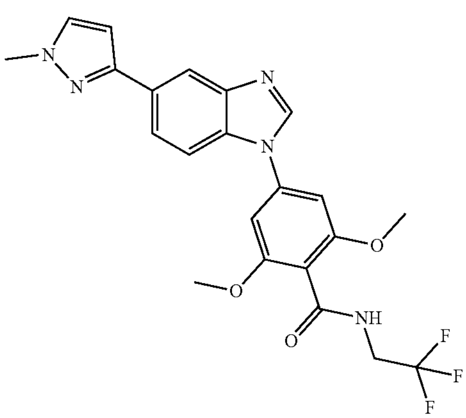 [SMILES: COc1cc(-n2cnc3cc(-c4ccn(C)n4)ccc32)cc(OC)c1C(=O)NCC(F)(F)F] | 2,6-dimethoxy-4-[5-(1-methylpyrazol-3-yl)benzimidazol-1-yl]-N-(2,2,2-trifluoroethyl)benzamide | Int 39 + CAS# 1020174-04-2 | E1.3 | 459.4 | 460.3 |

TABLE III-continued

Illustrative compounds of the invention.

| Cpd # | Structure | Name | SM | Mtd | MW | MS Mes'd |
|---|---|---|---|---|---|---|
| 90 | 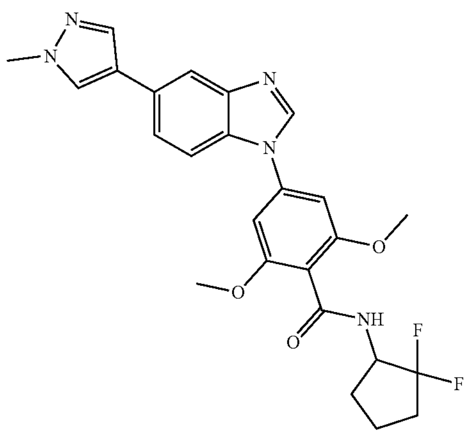 [SMILES: COc1cc(-n2cnc3cc(-c4cnn(C)c4)ccc32)cc(OC)c1C(=O)NC1CCCC1(F)F] | N-(2,2-difluorocyclopentyl)-2,6-dimethoxy-4-[5-(1-methylpyrazol-4-yl)benzimidazol-1-yl]benzamide | Int 50 + CAS# 921753-24-4 | E1.2 | 481.5 | 482.3 |
| 91 | 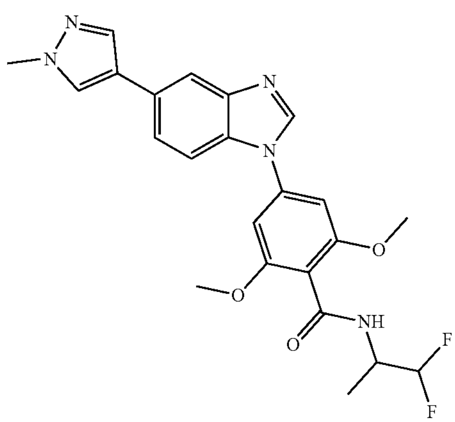 [SMILES: COc1cc(-n2cnc3cc(-c4cnn(C)c4)ccc32)cc(OC)c1C(=O)NC(C)C(F)F] | N-(2,2-difluoro-1-methyl-ethyl)-2,6-dimethoxy-4-[5-(1-methylpyrazol-4-yl)benzimidazol-1-yl]benzamide | Int 50 + CAS# 1384427-90-0 | E1.2 | 455.5 | 456.3 |
| 92 | 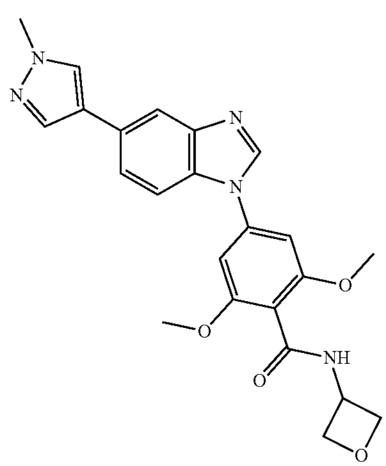 [SMILES: COc1cc(-n2cnc3cc(-c4cnn(C)c4)ccc32)cc(OC)c1C(=O)NC1COC1] | 2,6-dimethoxy-4-[5-(1-methylpyrazol-4-yl)benzimidazol-1-yl]-N-(oxetan-3-yl)benzamide | Int 50 + CAS# 21635-88-1 | E1.2 | 433.5 | 434.3 |

TABLE III-continued

Illustrative compounds of the invention.

| Cpd # | Structure | Name | SM | Mtd | MW | MS Mes'd |
|---|---|---|---|---|---|---|
| 93 | 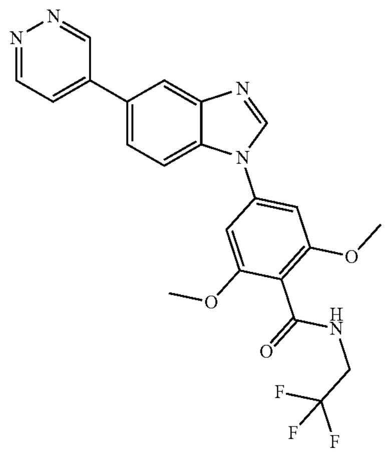 [SMILES: COc1cc(-n2cnc3cc(-c4ccnnc4)ccc32)cc(OC)c1C(=O)NCC(F)(F)F] | 2,6-dimethoxy-4-(5-pyridazin-4-ylbenzimidazol-1-yl)-N-(2,2,2-trifluoroethyl)benzamide | Int 39 + CAS# 863422-41-7 | E1.3 | 457.4 | 458.4 |
| 94 | 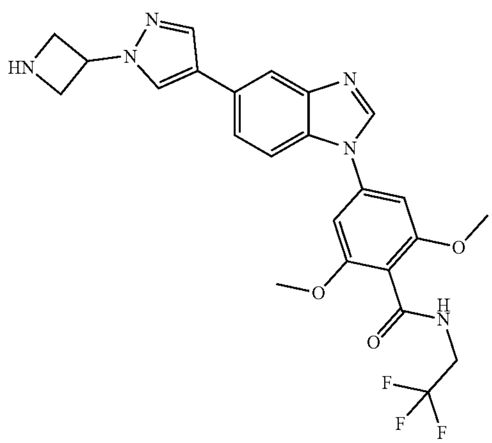 [SMILES: COc1cc(-n2cnc3cc(-c4cnn(C5CNC5)c4)ccc32)cc(OC)c1C(=O)NCC(F)(F)F] | 4-[5-[1-(azetidin-3-yl)pyrazol-4-yl]benzimidazol-1-yl]-2,6-dimethoxy-N-(2,2,2-trifluoroethyl)benzamide | Int 39 + CAS# 877399-35-4 | E1.3 + K | 500.5 | 501.3 |
| 95 | 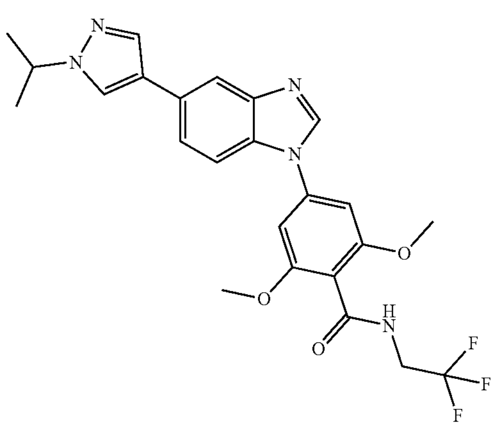 [SMILES: COc1cc(-n2cnc3cc(-c4cnn(C(C)C)c4)ccc32)cc(OC)c1C(=O)NCC(F)(F)F] | 4-[5-(1-isopropylpyrazol-4-yl)benzimidazol-1-yl]-2,6-dimethoxy-N-(2,2,2-trifluoroethyl)benzamide | Int 39 + CAS# 879487-10-2 | E1.3 | 487.5 | 488.5 |

TABLE III-continued

Illustrative compounds of the invention.

| Cpd # | Structure | Name | SM | Mtd | MW | MS Mes'd |
|---|---|---|---|---|---|---|
| 96 | 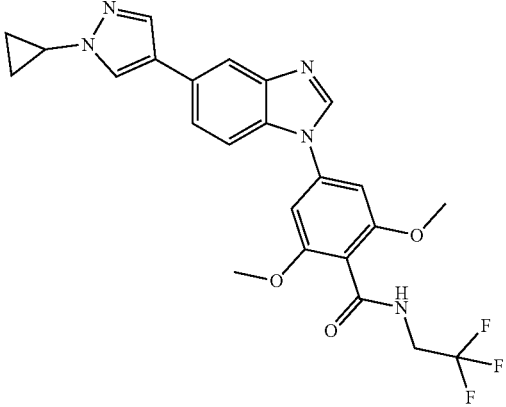 [SMILES: COc1cc(-n2cnc3cc(-c4cnn(C5CC5)c4)ccc32)cc(OC)c1C(=O)NCC(F)(F)F] | 4-[5-(1-cyclopropylpyrazol-4-yl)benzimidazol-1-yl]-2,6-dimethoxy-N-(2,2,2-trifluoro-ethyl)benzamide | Int 39 + CAS# 1151802-22-0 | E1.3 | 485.5 | 486.4 |
| 97 | 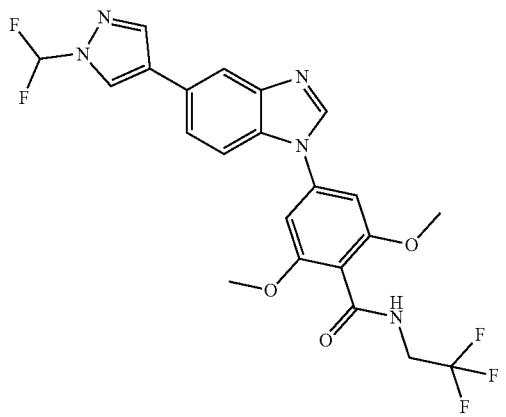 [SMILES: COc1cc(-n2cnc3cc(-c4cnn(C(F)F)c4)ccc32)cc(OC)c1C(=O)NCC(F)(F)F] | 4-[5-[1-(difluoromethyl) pyrazol-4-yl] benzimidazol-1-yl]-2,6-dimethoxy-N-(2,2,2-trifluoroethyl) benzamide | Int 39 + CAS# 1206640-82-5 | E1.3 | 495.4 | 496.5 |
| 98 | 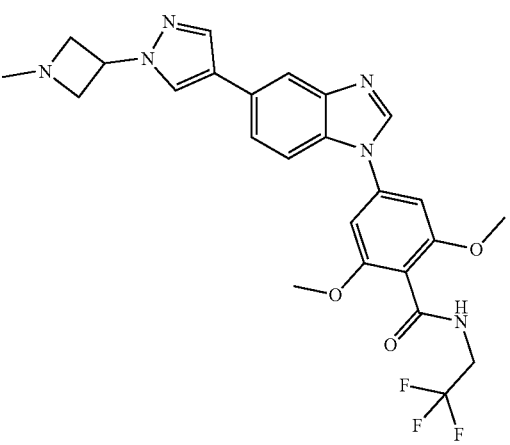 | 2,6-dimethoxy-4-[5-[1-(1-methylazetidin-3-yl)pyrazol-4-yl]benzimidazol-1-yl]-N-(2,2,2-trifluoroethyl) benzamide | Cpd 94 | L1i | 514.5 | 515.3 |

TABLE III-continued

Illustrative compounds of the invention.

| Cpd # | Structure | Name | SM | Mtd | MW | MS Mes'd |
|---|---|---|---|---|---|---|
| 99 | 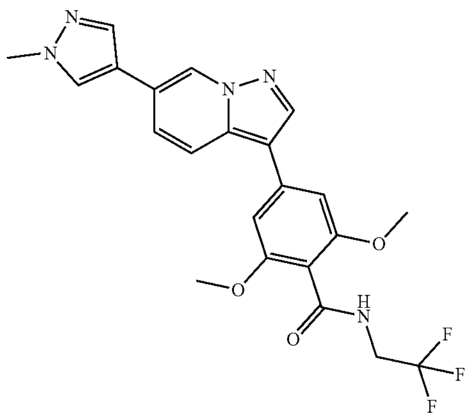 [SMILES: COc1cc(-c2cnn3cc(-c4cnn(C)c4)ccc23)cc(OC)c1C(=O)NCC(F)(F)F] | 2,6-dimethoxy-4-[6-(1-methylpyrazol-4-yl)pyrazolo[1,5-a]pyridin-3-yl]-N-(2,2,2-trifluoroethyl)benzamide | Int 34 + CAS# 761446-44-0 + CAS# 753-90-2 | E1.3 + E1.1 + E1.2 | 459.4 | 460.3 |
| 100 | 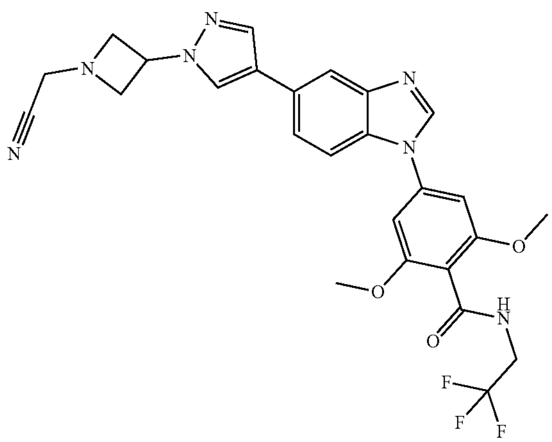 [SMILES: COc1cc(-n2cnc3cc(-c4cnn(C5CN(CC#N)C5)c4)ccc32)cc(OC)c1C(=O)NCC(F)(F)F] | 4-[5-[1-[1-(cyanomethyl)azetidin-3-yl]pyrazol-4-yl]benzimidazol-1-yl]-2,6-dimethoxy-N-(2,2,2-trifluoroethyl)benzamide | Cpd 94 + CAS# 590-17-0 | L2i | 539.5 | 540.5 |
| 101 | 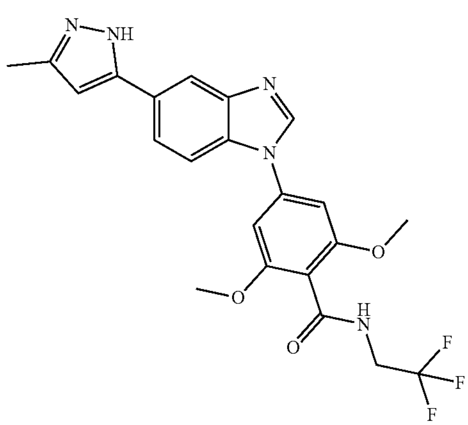 [SMILES: COc1cc(-n2cnc3cc(-c4cc(C)n[nH]4)ccc32)cc(OC)c1C(=O)NCC(F)(F)F] | 2,6-dimethoxy-4-[5-(3-methyl-1H-pyrazol-5-yl)benzimidazol-1-yl]-N-(2,2,2-trifluoroethyl)benzamide | Int 39 + CAS# 1888441-67-5 | E1.3 | 459.4 | 460.3 |

TABLE III-continued

Illustrative compounds of the invention.

| Cpd # | Structure | Name | SM | Mtd | MW | MS Mes'd |
|---|---|---|---|---|---|---|
| 102 | 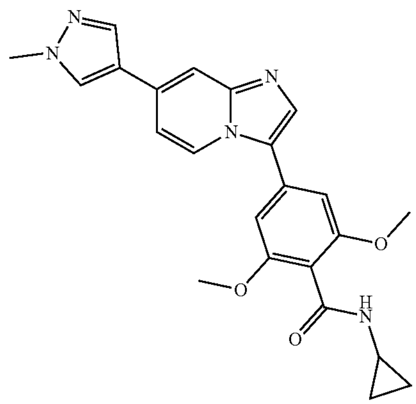 [SMILES: COc1cc(-c2cnc3cc(-c4cnn(C)c4)ccn23)cc(OC)c1C(=O)NC1CC1] | N-cyclopropyl-2,6-dimethoxy-4-[7-(1-methylpyrazol-4-yl)imidazo[1,2-a]pyridin-3-yl]benzamide | Int 52 + CAS# 765-30-0 | E1.2 | 417.5 | 418.3 |
| 103 | 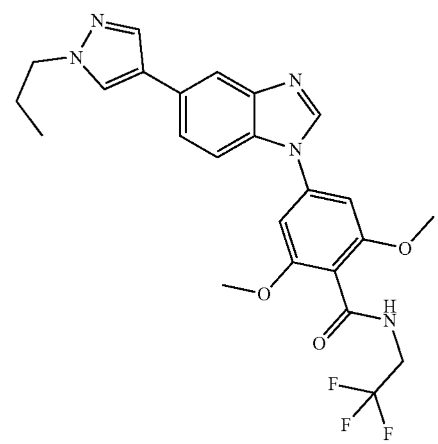 [SMILES: CCCn1cc(-c2ccc3c(c2)ncn3-c2cc(OC)c(C(=O)NCC(F)(F)F)c(OC)c2)cn1] | 2,6-dimethoxy-4-[5-(1-propylpyrazol-4-yl)benzimidazol-1-yl]-N-(2,2,2-trifluoroethyl)benzamide | Int 39 + CAS# 827614-69-7 | E1.3 | 487.5 | 488.6 |
| 104 | 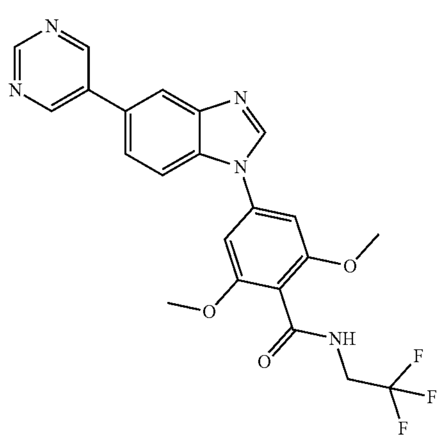 [SMILES: COc1cc(-n2cnc3cc(-c4cncnc4)ccc32)cc(OC)c1C(=O)NCC(F)(F)F] | 2,6-dimethoxy-4-(5-pyrimidin-5-ylbenzimidazol-1-yl)-N-(2,2,2-trifluoroethyl)benzamide | Int 39 + CAS# 109299-78-7 | E1.3 | 457.4 | 458.6 |

TABLE III-continued

Illustrative compounds of the invention.

| Cpd # | Structure | Name | SM | Mtd | MW | MS Mes'd |
|---|---|---|---|---|---|---|
| 105 | 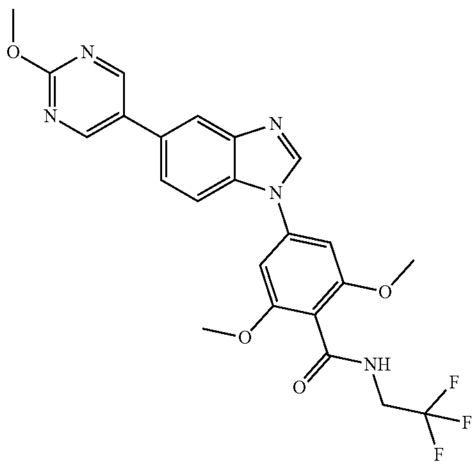 [SMILES: COc1ncc(-c2ccc3c(c2)ncn3-c2cc(OC)c(C(=O)NCC(F)(F)F)c(OC)c2)cn1] | 2,6-dimethoxy-4-[5-(2-methoxypyrimidin-5-yl)benzimidazol-1-yl]-N-(2,2,2-trifluoroethyl)benzamide | Int 39 + CAS# 628692-15-9 | E1.3 | 487.4 | 488.3 |
| 106 | 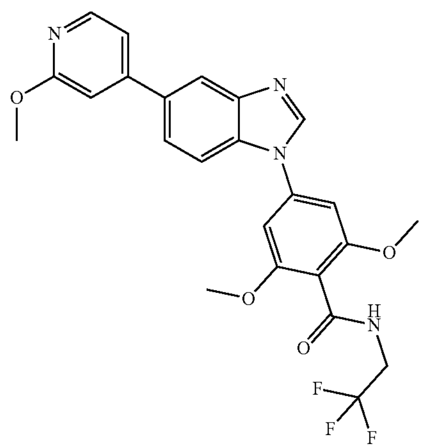 [SMILES: COc1cc(-c2ccc3c(c2)ncn3-c2cc(OC)c(C(=O)NCC(F)(F)F)c(OC)c2)ccn1] | 2,6-dimethoxy-4-[5-(2-methoxy-4-pyridyl)benzimidazol-1-yl]-N-(2,2,2-trifluoroethyl)benzamide | Int 39 + CAS# 762262-09-9 | E1.3 | 486.4 | 487.3 |
| 107 | 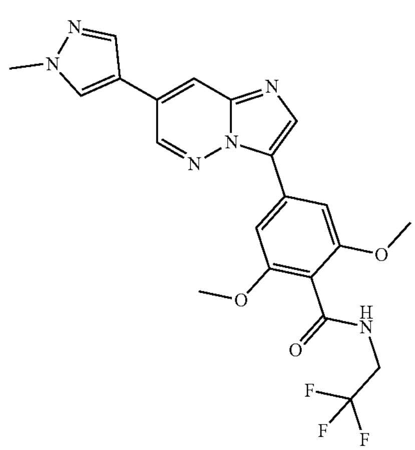 | 2,6-dimethoxy-4-[7-(1-methylpyrazol-4-yl)imidazo[1,2-a]pyridazin-3-yl]-N-(2,2,2-trifluoroethyl)benzamide | Int 33 + 753-90-2 | E1.2 | 460.4 | 461.2 |

TABLE III-continued

Illustrative compounds of the invention.

| Cpd # | Structure | Name | SM | Mtd | MW | MS Mes'd |
|---|---|---|---|---|---|---|
| 108 | 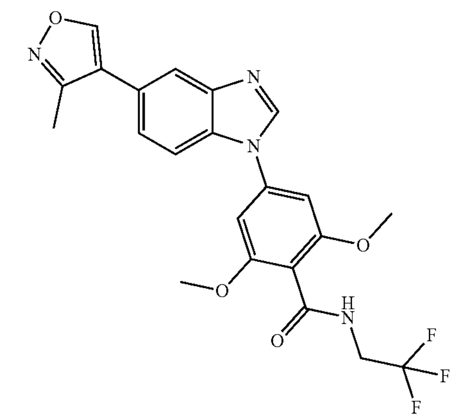 [SMILES: COc1cc(-n2cnc3cc(-c4conc4C)ccc32)cc(OC)c1C(=O)NCC(F)(F)F] | 2,6-dimethoxy-4-[5-(3-methylisoxazol-4-yl)benzimidazol-1-yl]-N-(2,2,2-trifluoroethyl)benzamide | Int 39 + CAS# 1421846-79-8 + CAS# 1346808-44-3 | E1.3 | 460.4 | 461.3 |
| 109 | 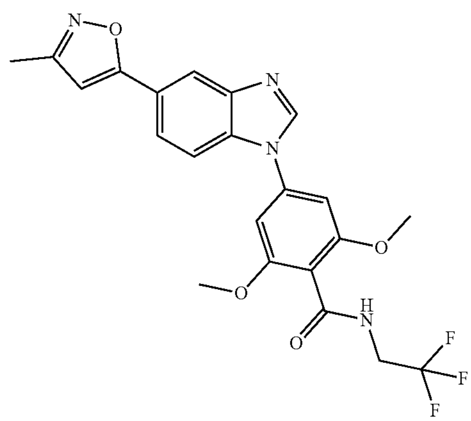 [SMILES: COc1cc(-n2cnc3cc(-c4cc(C)no4)ccc32)cc(OC)c1C(=O)NCC(F)(F)F] | 2,6-dimethoxy-4-[5-(3-methylisoxazol-5-yl)benzimidazol-1-yl]-N-(2,2,2-trifluoroethyl)benzamide | Int 39 + CAS# 1346808-44-3 | E1.3 | 460.4 | 461.4 |
| 110 | 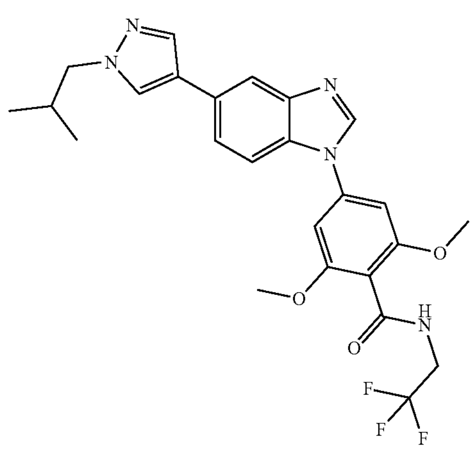 [SMILES: COc1cc(-n2cnc3cc(-c4cnn(CC(C)C)c4)ccc32)cc(OC)c1C(=O)NCC(F)(F)F] | 4-[5-(1-isobutylpyrazol-4-yl)benzimidazol-1-yl]-2,6-dimethoxy-N-(2,2,2-trifluoroethyl)benzamide | Cpd 47 + CAS# 78-77-3 | N1 | 501.5 | 502.3 |

TABLE III-continued

Illustrative compounds of the invention.

| Cpd # | Structure | Name | SM | Mtd | MW | MS Mes'd |
|---|---|---|---|---|---|---|
| 111 | 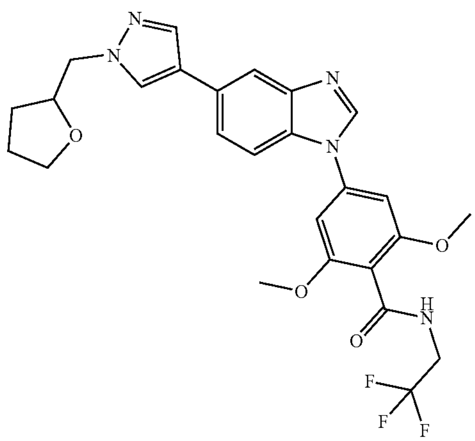 [SMILES: COc1cc(-n2cnc3cc(-c4cnn(CC5CCCO5)c4)ccc32)cc(OC)c1C(=O)NCC(F)(F)F] | 2,6-dimethoxy-4-[5-[1-(tetrahydrofuran-2-ylmethyl)pyrazol-4-yl]benzimidazol-1-yl]-N-(2,2,2-trifluoroethyl)benzamide | Cpd 47 + CAS# 1192-30-9 | N1 | 529.5 | 530.4 |
| 112 | 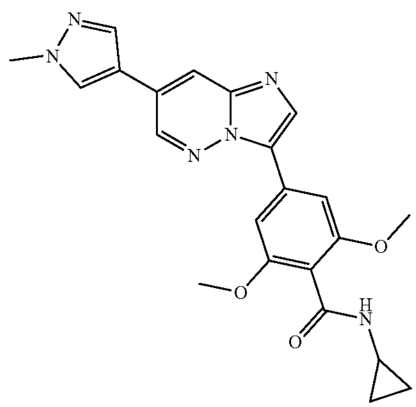 | N-cyclopropyl-2,6-dimethoxy-4-[7-(1-methylpyrazol-4-yl)imidazo[1,2-b]pyridazin-3-yl]benzamide | Int 33 + CAS# 765-30-0 | E1.2 | 418.4 | 419.3 |
| 113 | 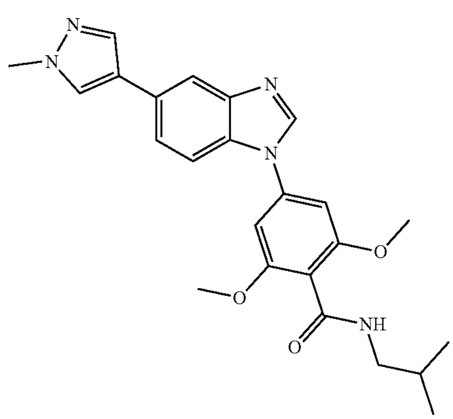 [SMILES: COc1cc(-n2cnc3cc(-c4cnn(C)c4)ccc32)cc(OC)c1C(=O)NCC(C)C] | N-isobutyl-2,6-dimethoxy-4-[5-(1-methylpyrazol-4-yl)benzimidazol-1-yl]benzamide | Int 44 + CAS# 78-81-9 + CAS# 761446-44-0 | E1.2 + E1.3 | 433.5 | 434.7 |

TABLE III-continued

Illustrative compounds of the invention.

| Cpd # | Structure | Name | SM | Mtd | MW | MS Mes'd |
|---|---|---|---|---|---|---|
| 114 | 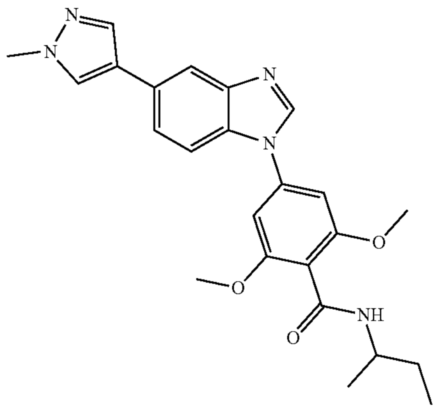 [SMILES: CCC(C)NC(=O)c1c(OC)cc(-n2cnc3cc(-c4cnn(C)c4)ccc32)cc1OC] | 2,6-dimethoxy-4-[5-(1-methylpyrazol-4-yl)benzimidazol-1-yl]-N-sec-butyl-benzamide | Int 44 + CAS# 13952-84-6 + CAS# 761446-44-0 | E1.2 + E1.3 | 433.5 | 434.7 |
| 115 | 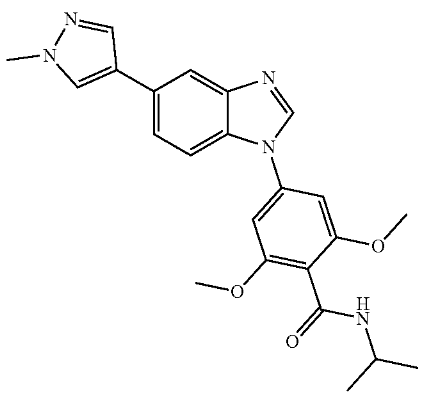 [SMILES: COc1cc(-n2cnc3cc(-c4cnn(C)c4)ccc32)cc(OC)c1C(=O)NC(C)C] | N-isopropyl-2,6-dimethoxy-4-[5-(1-methylpyrazol-4-yl)benzimidazol-1-yl]benzamide | Int 44 + CAS# 75-31-0 + CAS# 761446-44-0 | E1.2 + E1.3 | 419.5 | 420.7 |
| 116 | 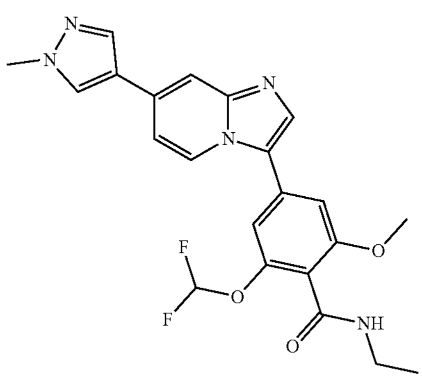 [SMILES: CCNC(=O)c1c(OC)cc(-c2cnc3cc(-c4cnn(C)c4)ccn23)cc1OC(F)F] | 2-(difluoromethoxy)-N-ethyl-6-methoxy-4-[7-(1-methylpyrazol-4-yl)imidazo[1,2-a]pyridin-3-yl]benzamide | Int 36 + CAS# 761446-44-0 | E1.3 | 441.4 | 442.6 |
| 117 | 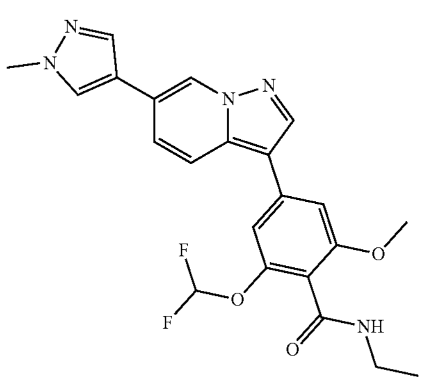 [SMILES: CCNC(=O)c1c(OC)cc(-c2cnn3cc(-c4cnn(C)c4)ccc23)cc1OC(F)F] | 2-(difluoromethoxy)-N-ethyl-6-methoxy-4-[6-(1-methylpyrazol-4-yl)pyrazolo[1,5-a]pyridin-3-yl]benzamide | Int 15 + Int 16 + CAS# 761446-44-0 | E1.3 + E1.3 | 441.4 | 442.5 |

TABLE III-continued

Illustrative compounds of the invention.

| Cpd # | Structure | Name | SM | Mtd | MW | MS Mes'd |
|---|---|---|---|---|---|---|
| 118 | 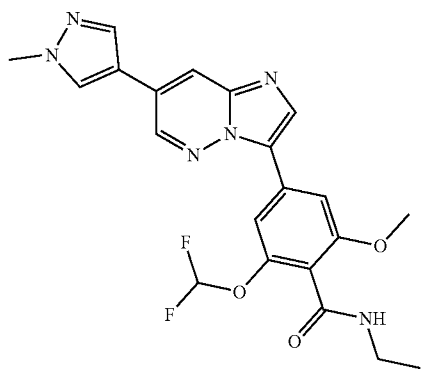 [SMILES: CCNC(=O)c1c(OC)cc(-c2cnc3cc(-c4cnn(C)c4)cnn23)cc1OC(F)F] | 2-(difluoromethoxy)-N-ethyl-6-methoxy-4-[7-(1-methylpyrazol-4-yl)imidazo[1,2-b]pyridazin-3-yl]benzamide | Int 16 + CAS# 1383481-13-7 + CAS# 761446-44-0 | E1.3 + E1.3 | 442.4 | 443.2 |
| 119 | 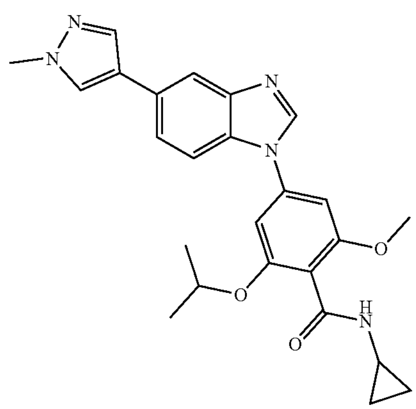 [SMILES: COc1cc(-n2cnc3cc(-c4cnn(C)c4)ccc32)cc(OC(C)C)c1C(=O)NC1CC1] | N-cyclopropyl-2-isopropoxy-6-methoxy-4-[5-(1-methylpyrazol-4-yl)benzimidazol-1-yl]benzamide | Cpd 86 + CAS# 75-30-9 | I + J1 | 445.5 | 446.8 |
| 120 | 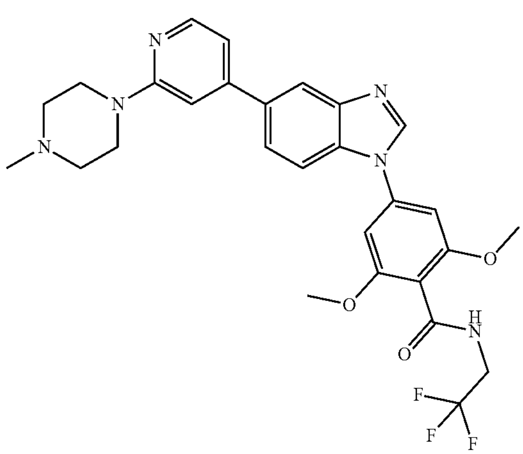 | 2,6-dimethoxy-4-[5-[2-(4-methylpiperazin-1-yl)-4-pyridyl]benzimidazol-1-yl]-N-(2,2,2-trifluoroethyl)benzamide | Int 39 + CAS# 832114-09-7 | E1.3 | 554.6 | 555.4 |

TABLE III-continued

Illustrative compounds of the invention.

| Cpd # | Structure | Name | SM | Mtd | MW | MS Mes'd |
|---|---|---|---|---|---|---|
| 121 | 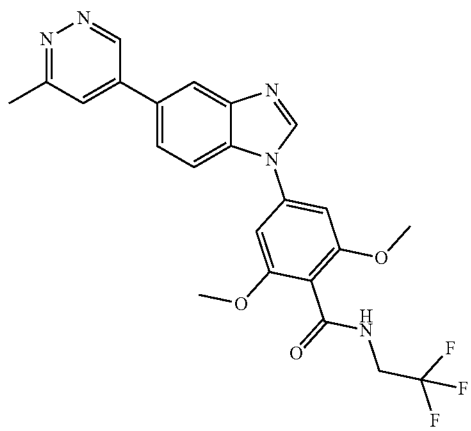 [SMILES: COc1cc(-n2cnc3cc(-c4cnnc(C)c4)ccc32)cc(OC)c1C(=O)NCC(F)(F)F] | 2,6-dimethoxy-4-[5-(6-methylpyridazin-4-yl)benzimidazol-1-yl]-N-(2,2,2-trifluoroethyl)benzamide | Int 39 + CAS# 1350543-95-1 | E1.3 | 471.4 | 472.6 |
| 122 | 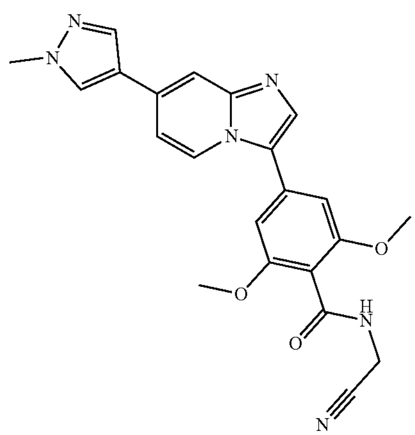 | N-(cyanomethyl)-2,6-dimethoxy-4-[7-(1-methylpyrazol-4-yl)imidazo[1,2-a]pyridin-3-yl]benzamide | Int 52 + CAS# 6011-14-9 | E1.2 | 416.4 | 417.5 |
| 123 | 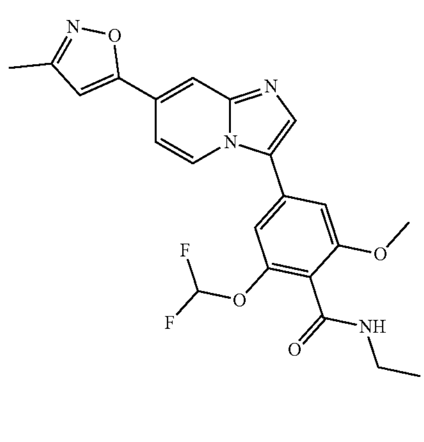 [SMILES: CCNC(=O)c1c(OC)cc(-c2cnc3cc(-c4cc(C)no4)ccn23)cc1OC(F)F] | 2-(difluoromethoxy)-N-ethyl-6-methoxy-4-[7-(3-methylisoxazol-5-yl)imidazo[1,2-a]pyridin-3-yl]benzamide | Int 36 + CAS# 1346808-44-3 | E1.3 | 442.4 | 443.3 |

TABLE III-continued

Illustrative compounds of the invention.

| Cpd # | Structure | Name | SM | Mtd | MW | MS Mes'd |
|---|---|---|---|---|---|---|
| 124 | 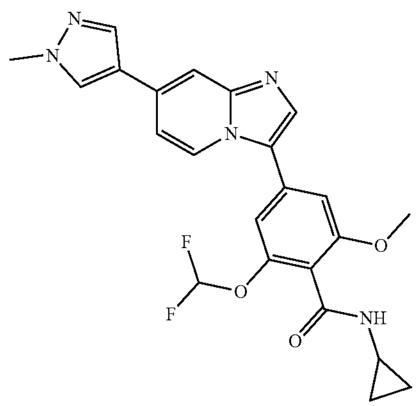 [SMILES: COc1cc(-c2cnc3cc(-c4cnn(C)c4)ccn23)cc(OC(F)F)c1C(=O)NC1CC1] | N-cyclopropyl-2-(difluoromethoxy)-6-methoxy-4-[7-(1-methylpyrazol-4-yl)imidazo[1,2-a]pyridin-3-yl]benzamide | Int 37 + CAS# 761446-44-0 | E1.3 | 453.4 | 454.3 |
| 125 | 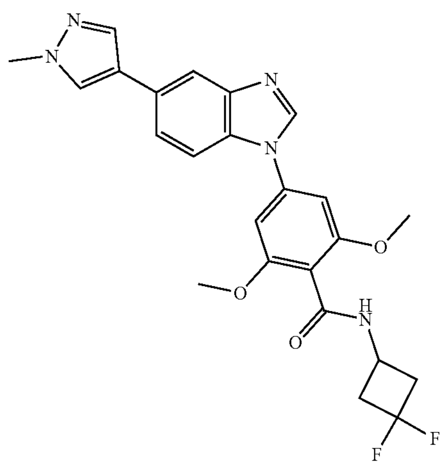 [SMILES: COc1cc(-n2cnc3cc(-c4cnn(C)c4)ccc32)cc(OC)c1C(=O)NC1CC(F)(F)C1] | N-(3,3-difluorocyclobutyl)-2,6-dimethoxy-4-[5-(1-methylpyrazol-4-yl)benzimidazol-1-yl]benzamide | Int 44 + CAS# 637031-93-7 + CAS# 761446-44-0 | E1.2 + E1.3 | 467.5 | 468.3 |
| 126 | 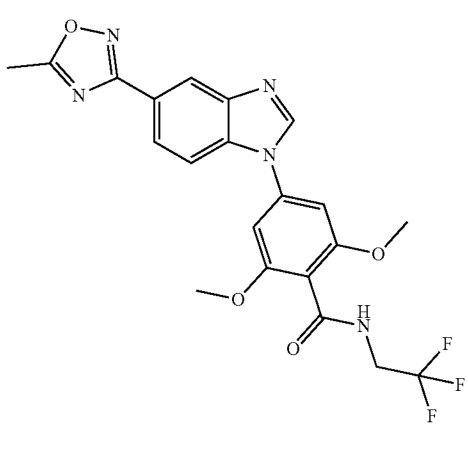 [SMILES: COc1cc(-n2cnc3cc(-c4noc(C)n4)ccc32)cc(OC)c1C(=O)NCC(F)(F)F] | 2,6-dimethoxy-4-[5-(5-methyl-1,2,4-oxadiazol-3-yl)benzimidazol-1-yl]-N-(2,2,2-trifluoroethyl)benzamide | Int 39 | E5.3 + E5.4i | 461.4 | 462.2 |

TABLE III-continued

Illustrative compounds of the invention.

| Cpd # | Structure | Name | SM | Mtd | MW | MS Mes'd |
|---|---|---|---|---|---|---|
| 127 | 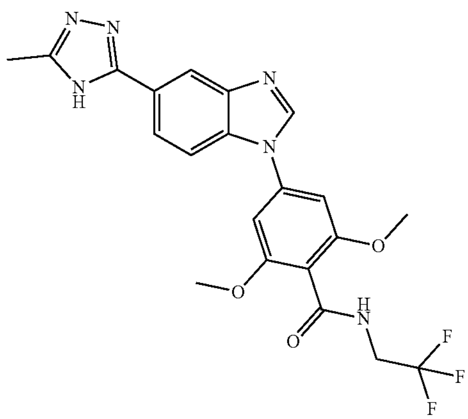 | 2,6-dimethoxy-4-[5-(5-methyl-4H-1,2,4-triazol-3-yl)benzimidazol-1-yl]-N-(2,2,2-trifluoroethyl)benzamide | Int 39 | E5.3 + E5.4ii | 460.4 | 461.3 |
| 128 | 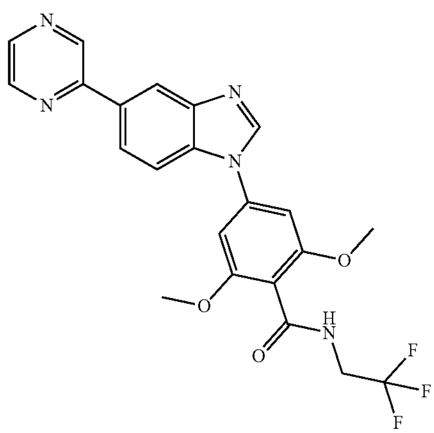 [SMILES: COc1cc(-n2cnc3cc(-c4cnccn4)ccc32)cc(OC)c1C(=O)NCC(F)(F)F] | 2,6-dimethoxy-4-(5-pyrazin-2-ylbenzimidazol-1-yl)-N-(2,2,2-trifluoroethyl)benzamide | Int 39 + CAS# 762263-64-9 | E1.3 | 457.4 | 458.3 |
| 129 | 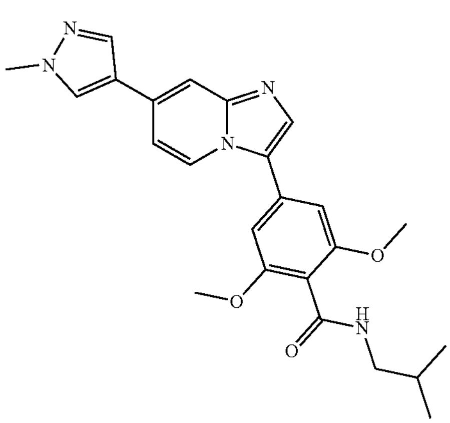 [SMILES: COc1cc(-c2cnc3cc(-c4cnn(C)c4)ccn23)cc(OC)c1C(=O)NCC(C)C] | N-isobutyl-2,6-dimethoxy-4-[7-(1-methylpyrazol-4-yl)imidazo[1,2-a]pyridin-3-yl]benzamide | Int 52 + CAS# 78-81-9 | E1.2 | 433.5 | 434.4 |

TABLE III-continued

Illustrative compounds of the invention.

| Cpd # | Structure | Name | SM | Mtd | MW | MS Mes'd |
|---|---|---|---|---|---|---|
| 130 | 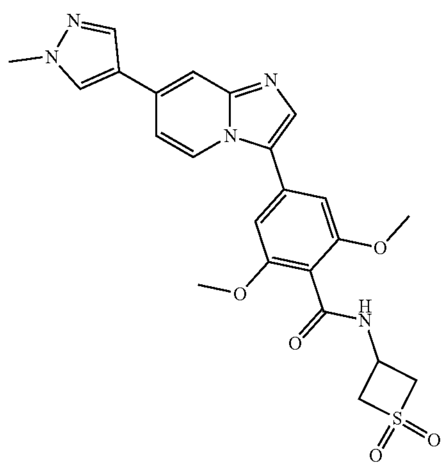 [SMILES: COc1cc(-c2cnc3cc(-c4cnn(C)c4)ccn23)cc(OC)c1C(=O)NC1CS(=O)(=O)C1] | N-(1,1-dioxothietan-3-yl)-2,6-dimethoxy-4-[7-(1-methylpyrazol-4-yl)imidazo[1,2-a]pyridin-3-yl]benzamide | Int 52 + CAS# 151-18-8 | E1.2 | 481.5 | 482.3 |
| 131 | 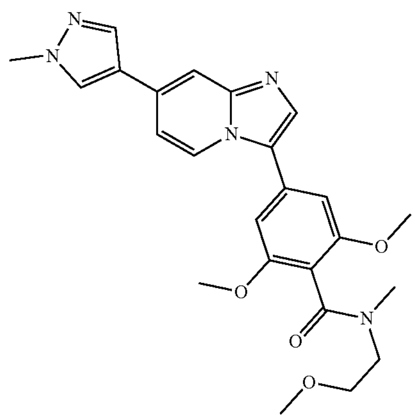 | 2,6-dimethoxy-N-(2-methoxyethyl)-N-methyl-4-[7-(1-methylpyrazol-4-yl)imidazo[1,2-a]pyridin-3-yl]benzamide | Int 52 + CAS# 38256-93-8 | E1.2 | 449.5 | 450.4 |
| 132 | 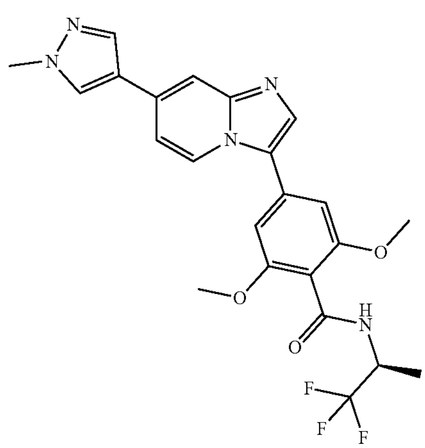 [SMILES: COc1cc(-c2cnc3cc(-c4cnn(C)c4)ccn23)cc(OC)c1C(=O)N[C@@H](C)C(F)(F)F] | 2,6-dimethoxy-4-[7-(1-methylpyrazol-4-yl)imidazo[1,2-a]pyridin-3-yl]-N-[(1S)-2,2,2-trifluoro-1-methyl-ethyl]benzamide | Int 52 + CAS# 125278-10-6 | E1.2 | 473.4 | 474.3 |

TABLE III-continued

Illustrative compounds of the invention.

| Cpd # | Structure | Name | SM | Mtd | MW | MS Mes'd |
|---|---|---|---|---|---|---|
| 133 | 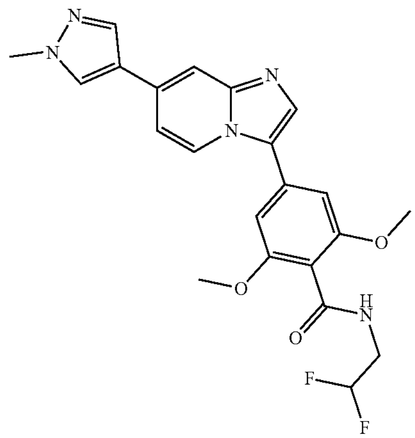 | N-(2,2-difluoroethyl)-2,6-dimethoxy-4-[7-(1-methylpyrazol-4-yl)imidazo[1,2-a]pyridin-3-yl]benzamide | Int 52 + CAS# 79667-91-7 | E1.2 | 441.4 | 442.4 |
| 134 | 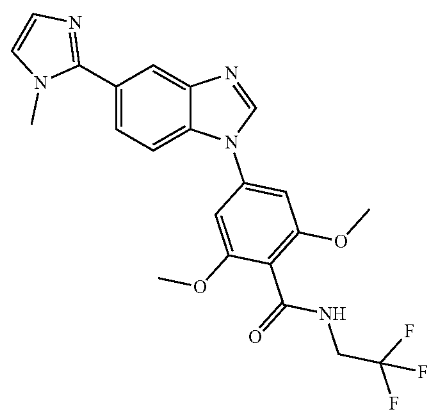 [SMILES: COc1cc(-n2cnc3cc(-c4nccn4C)ccc32)cc(OC)c1C(=O)NCC(F)(F)F] | 2,6-dimethoxy-4-[5-(1-methylimidazol-2-yl)benzimidazol-1-yl]-N-(2,2,2-trifluoroethyl)benzamide | Int 39 + CAS# 16681-59-7 | E4.3ii | 459.4 | 460.3 |
| 135 | 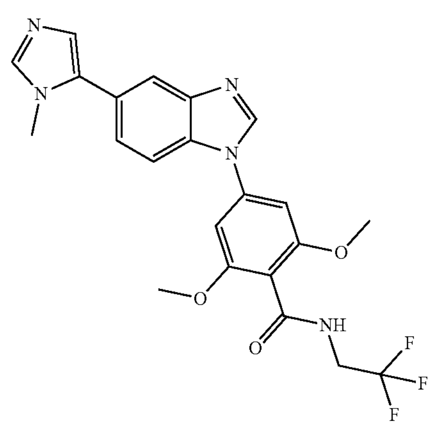 [SMILES: COc1cc(-n2cnc3cc(-c4cncn4C)ccc32)cc(OC)c1C(=O)NCC(F)(F)F] | 2,6-dimethoxy-4-[5-(3-methylimidazo-4-yl)benzimidazol-1-yl]-N-(2,2,2-trifluoroethyl)benzamide | Int 39 + CAS# 1003-21-0 | E4.3ii | 459.4 | 460.3 |

TABLE III-continued

Illustrative compounds of the invention.

| Cpd # | Structure | Name | SM | Mtd | MW | MS Mes'd |
|---|---|---|---|---|---|---|
| 136 | 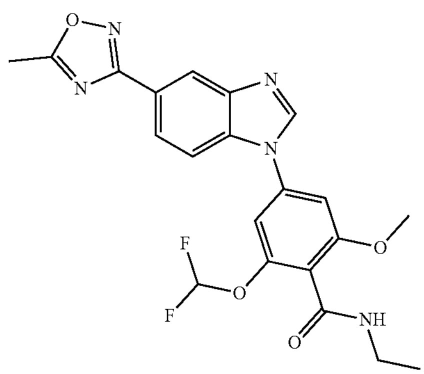 [SMILES: CCNC(=O)c1c(OC)cc(-n2cnc3cc(-c4noc(C)n4)ccc32)cc1OC(F)F] | 2-(difluoromethoxy)-N-ethyl-6-methoxy-4-[5-(5-methyl-1,2,4-oxadiazol-3-yl)benzimidazol-1-yl]benzamide | Int 12 + CAS# 1009-35-4 | B2 + C2 + E5.4i | 443.4 | 444.5 |
| 137 | 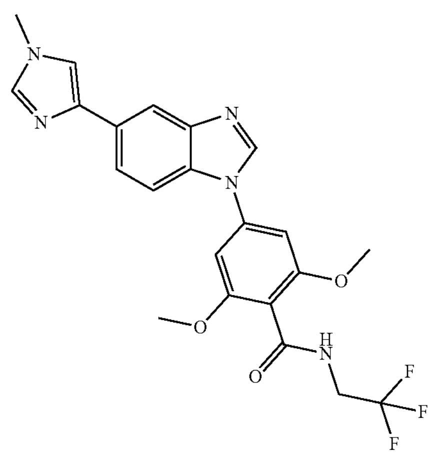 [SMILES: COc1cc(-n2cnc3cc(-c4cn(C)cn4)ccc32)cc(OC)c1C(=O)NCC(F)(F)F] | 2,6-dimethoxy-4-[5-(1-methylimidazol-4-yl)benzimidazol-1-yl]-N-(2,2,2-trifluoroethyl)benzamide | Int 39 + CAS# 25676-75-9 | E4.3ii | 459.4 | 460.3 |
| 138 | 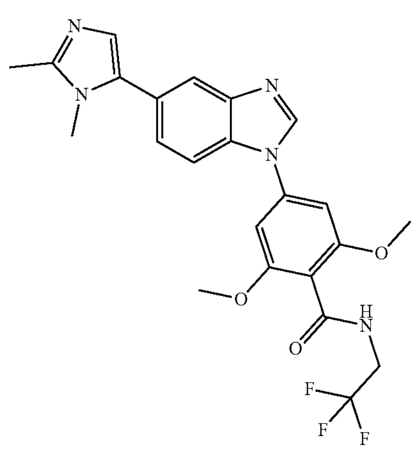 | 4-[5-(2,3-dimethylimidazol-4-yl)benzimidazol-1-yl]-2,6-dimethoxy-N-(2,2,2-trifluoroethyl)benzamide | Int 39 + CAS# 24134-09-6 | E4.3ii | 473.4 | 474.3 |

TABLE III-continued

Illustrative compounds of the invention.

| Cpd # | Structure | Name | SM | Mtd | MW | MS Mes'd |
|---|---|---|---|---|---|---|
| 139 | 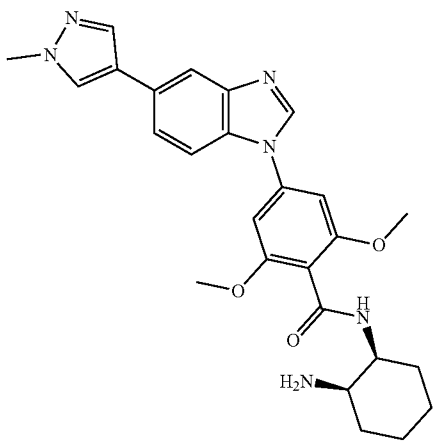 [SMILES: COc1cc(-n2cnc3cc(-c4cnn(C)c4)ccc32)cc(OC)c1C(=O)N[C@H]1CCCC[C@H]1N] | N-[(1R,2R)-2-aminocyclohexyl]-2,6-dimethoxy-4-[5-(1-methylpyrazol-4-yl)benzimidazol-1-yl]benzamide | Int 50 + CAS# 21436-03-3 | E1.2 | 474.6 | 475.4 |
| 140 | 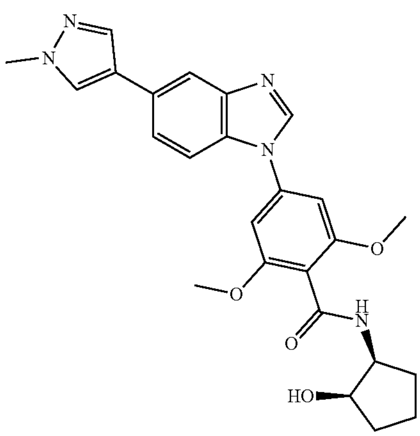 [SMILES: COc1cc(-n2cnc3cc(-c4cnn(C)c4)ccc32)cc(OC)c1C(=O)N[C@H]1CCC[C@H]1O] | N-[(1R,2R)-2-hydroxycyclopentyl]-2,6-dimethoxy-4-[5-(1-methylpyrazol-4-yl)benzimidazol-1-yl]benzamide | Int 50 + CAS# 31775-67-4 | E1.2 | 461.5 | 462.3 |
| 141 | 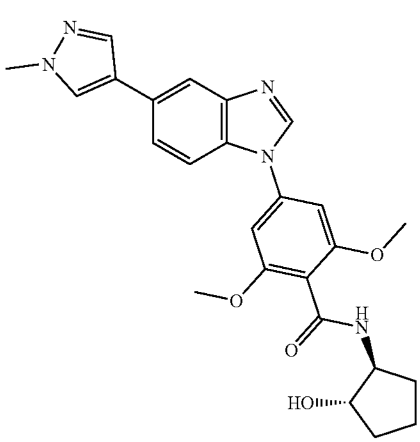 [SMILES: COc1cc(-n2cnc3cc(-c4cnn(C)c4)ccc32)cc(OC)c1C(=O)N[C@H]1CCC[C@@H]1O] | N-[(1R,2S)-2-hydroxycyclopentyl]-2,6-dimethoxy-4-[5-(1-methylpyrazol-4-yl)benzimidazol-1-yl]benzamide | Int 50 + CAS# 137254-03-6 | E1.2 | 461.5 | 462.3 |

TABLE III-continued

Illustrative compounds of the invention.

| Cpd # | Structure | Name | SM | Mtd | MW | MS Mes'd |
|---|---|---|---|---|---|---|
| 142 | 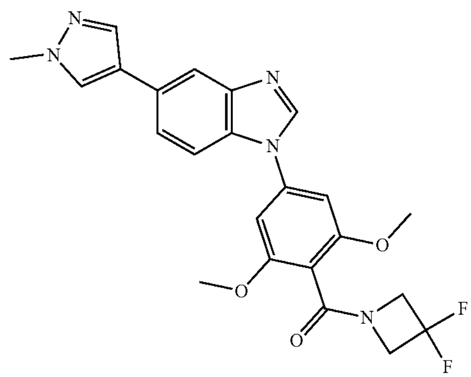 [SMILES: COc1cc(-n2cnc3cc(-c4cnn(C)c4)ccc32)cc(OC)c1C(=O)N1CC(F)(F)C1] | (3,3-difluoroazetidin-1-yl)-[2,6-dimethoxy-4-[5-(1-methylpyrazol-4-yl)benzimidazol-1-yl]phenyl]methanone | Int 50 + CAS# 288315-03-7 | E1.2 | 453.4 | 454.4 |
| 143 | 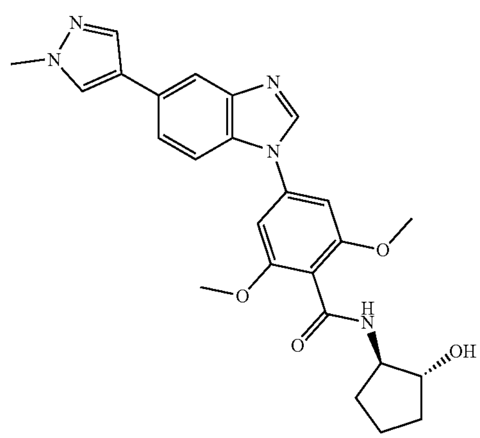 [SMILES: COc1cc(-n2cnc3cc(-c4cnn(C)c4)ccc32)cc(OC)c1C(=O)N[C@@H]1CCC[C@H]1O] | N-[(1R,2R)-2-hydroxycyclopentyl]-2,6-dimethoxy-4-[5-(1-methylpyrazol-4-yl)benzimidazol-1-yl]benzamide | Int 50 + CAS# 68327-11-7 | E1.2 | 461.5 | 462.4 |
| 144 | 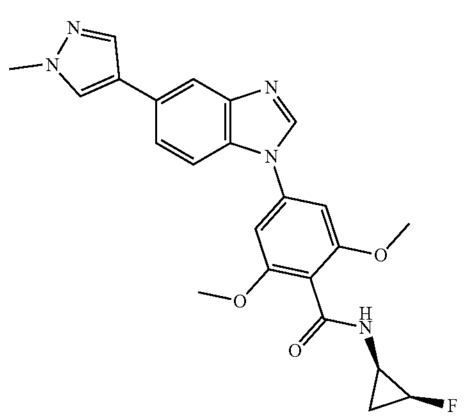 [SMILES: COc1cc(-n2cnc3cc(-c4cnn(C)c4)ccc32)cc(OC)c1C(=O)N[C@@H]1C[C@@H]1F] | N-[(1R,2S)-2-fluorocyclopropyl]-2,6-dimethoxy-4-[5-(1-methylpyrazol-4-yl)benzimidazol-1-yl]benzamide | Int 50 + CAS# 143062-84-4 | E1.2 | 435.5 | 436.4 |

TABLE III-continued

Illustrative compounds of the invention.

| Cpd # | Structure | Name | SM | Mtd | MW | MS Mes'd |
|---|---|---|---|---|---|---|
| 145 | 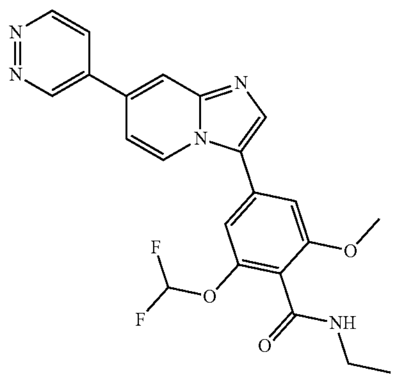 [SMILES: CCNC(=O)c1c(OC)cc(-c2cnc3cc(-c4ccnnc4)ccn23)cc1OC(F)F] | 2-(difluoromethoxy)-N-ethyl-6-methoxy-4-(7-pyridazin-4-ylimidazo[1,2-a]pyridin-3-yl)benzamide | Int 36 + CAS# 863422-41-7 | E1.3 | 439.4 | 440.4 |
| 146 | 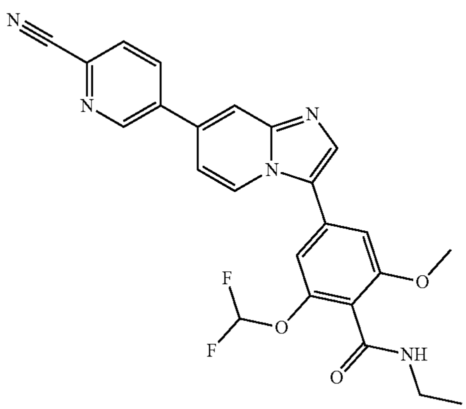 [SMILES: CCNC(=O)c1c(OC)cc(-c2cnc3cc(-c4ccc(C#N)nc4)ccn23)cc1OC(F)F] | 4-[7-(6-cyano-3-pyridyl)imidazo[1,2-a]pyridin-3-yl]-2-(difluoromethoxy)-N-ethyl-6-methoxy-benzamide | Int 36 + CAS# 741709-63-7 | E1.3 | 463.4 | 464.4 |
| 147 | 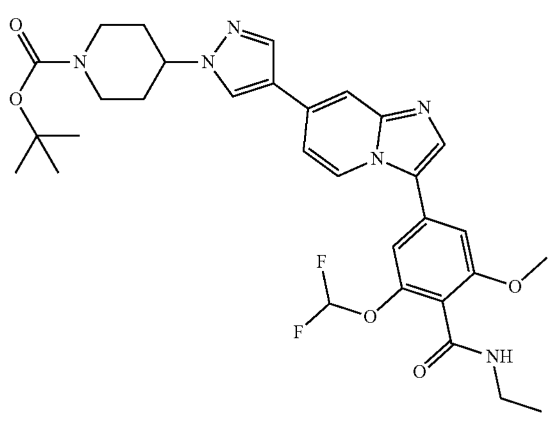 [SMILES: CCNC(=O)c1c(OC)cc(-c2cnc3cc(-c4cnn(C5CCN(C(=O)OC(C)(C)C)CC5)c4)ccn23)cc1OC(F)F] | tert-butyl 4-[4-[3-[3-(difluoromethoxy)-4-(ethylcarbamoyl)-5-methoxy-phenyl]imidazo[1,2-a]pyridin-7-yl]pyrazol-1-yl]piperidine-1-carboxylate | Int 36 + CAS# 877399-74-1 | E1.3 | 610.7 | 611.3 |

TABLE III-continued

Illustrative compounds of the invention.

| Cpd # | Structure | Name | SM | Mtd | MW | MS Mes'd |
|---|---|---|---|---|---|---|
| 148 | 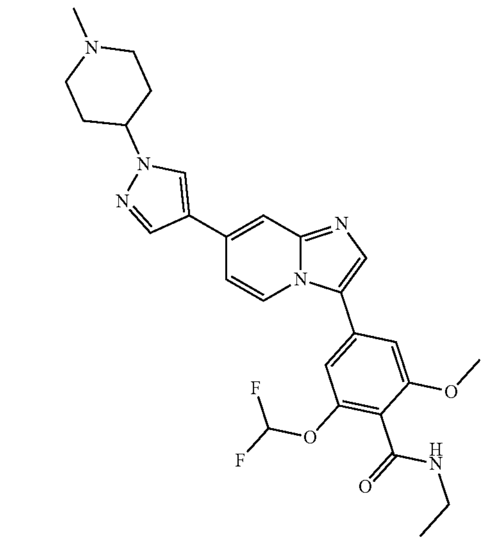 [SMILES: CCNC(=O)c1c(OC)cc(-c2cnc3cc(-c4cnn(C5CCN(C)CC5)c4)ccn23)cc1OC(F)F] | 2-(difluoromethoxy)-N-ethyl-6-methoxy-4-[7-[1-(1-methyl-4-piperidyl)pyrazol-4-yl]imidazo[1,2-a]pyridin-3-yl]benzamide | Cpd 149 | L1i | 524.6 | 525.3 |
| 149 | 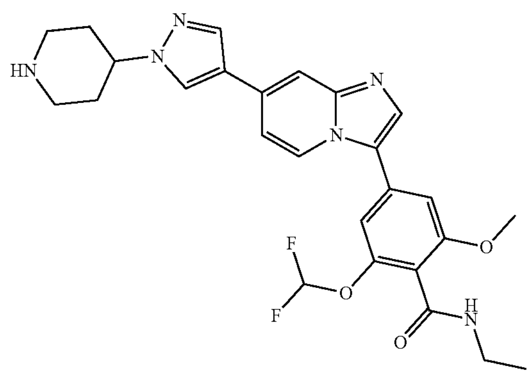 [SMILES: CCNC(=O)c1c(OC)cc(-c2cnc3cc(-c4cnn(C5CCNCC5)c4)ccn23)cc1OC(F)F] | 2-(difluoromethoxy)-N-ethyl-6-methoxy-4-[7-[1-(4-piperidyl)pyrazol-4-yl]imidazo[1,2-a]pyridin-3-yl]benzamide | Cpd 147 | K | 510.5 | 511.3 |
| 150 | 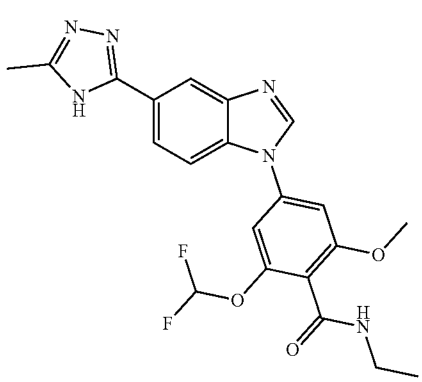 [SMILES: CCNC(=O)c1c(OC)cc(-n2cnc3cc(-c4nnc(C)[nH]4)ccc32)cc1OC(F)F] | 2-(difluoromethoxy)-N-ethyl-6-methoxy-4-[5-(5-methyl-4H-1,2,4-triazol-3-yl)benzimidazol-1-yl]benzamide | Int 12 + CAS# 1009-35-4 | B2 + C2 + E5.4ii | 442.4 | 443.6 |

TABLE III-continued

Illustrative compounds of the invention.

| Cpd # | Structure | Name | SM | Mtd | MW | MS Mes'd |
|---|---|---|---|---|---|---|
| 151 | 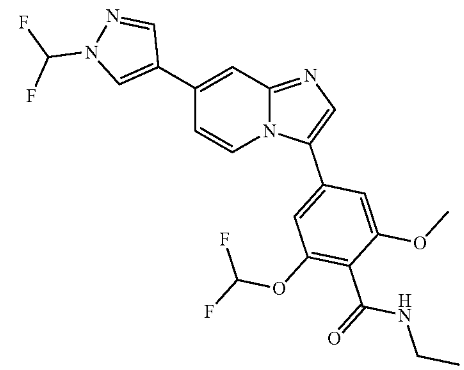 [SMILES: CCNC(=O)c1c(OC)cc(-c2cnc3cc(-c4cnn(C(F)F)c4)ccn23)cc1OC(F)F] | 2-(difluoromethoxy)-4-[7-[1-(difluoromethyl)pyrazol-4-yl]imidazo[1,2-a]pyridin-3-yl]-N-ethyl-6-methoxy-benzamide | Int 36 + CAS# 1206640-82-5 | E1.3 | 477.4 | 478.6 |
| 152 | 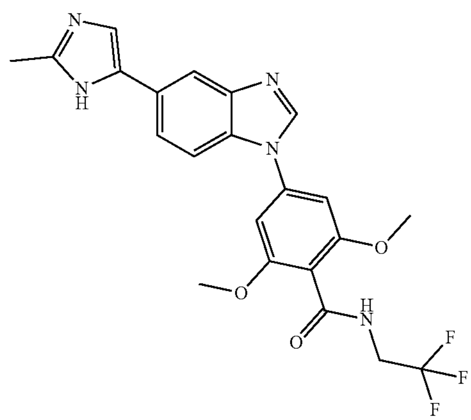 [SMILES: COc1cc(-n2cnc3cc(-c4cnc(C)[nH]4)ccc32)cc(OC)c1C(=O)NCC(F)(F)F] | 2,6-dimethoxy-4-[5-(2-methyl-1H-imidazol-5-yl)benzimidazol-1-yl]-N-(2,2,2-trifluoroethyl)benzamide | Int 39 + CAS# 16265-11-5 | E4.3ii | 459.4 | 460.2 |
| 153 | 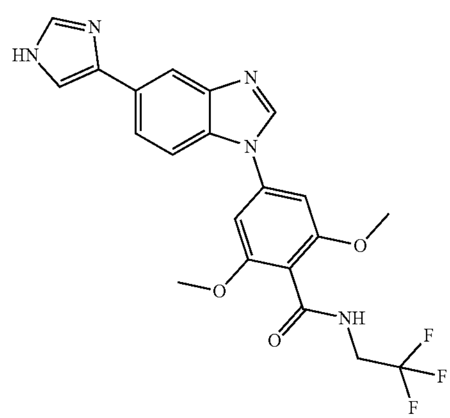 [SMILES: COc1cc(-n2cnc3cc(-c4c[nH]cn4)ccc32)cc(OC)c1C(=O)NCC(F)(F)F] | 4-[5-(1H-imidazol-4-yl)benzimidazol-1-yl]-2,6-dimethoxy-N-(2,2,2-trifluoroethyl)benzamide | Int 39 + CAS# 2302-25-2 | E4.3ii | 445.4 | 446.3 |

TABLE III-continued

Illustrative compounds of the invention.

| Cpd # | Structure | Name | SM | Mtd | MW | MS Mes'd |
|---|---|---|---|---|---|---|
| 154 | 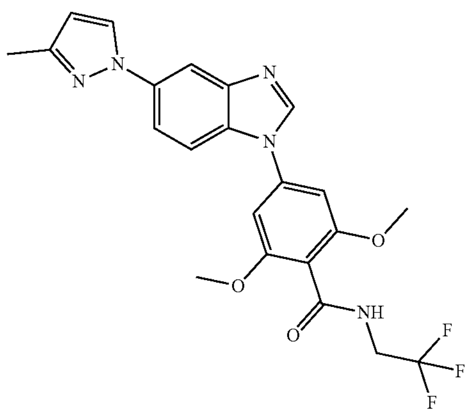 [SMILES: COc1cc(-n2cnc3cc(-n4ccc(C)n4)ccc32)cc(OC)c1C(=O)NCC(F)(F)F] | 2,6-dimethoxy-4-[5-(3-methylpyrazol-1-yl)benzimidazol-1-yl]-N-(2,2,2-trifluoroethyl)benzamide | Int 39 + CAS# 1453-58-3 | E2.3 | 459.3 | 460.3 |
| 155 | 85% + 15% | 2,6-dimethoxy-4-[5-(4-methylimidazol-1-yl)benzimidazol-1-yl]-N-(2,2,2-trifluoroethyl)benzamide | Int 39 + CAS# 822-36-6 | E3.3 | 459.4 | 460.3 |
| 156 | 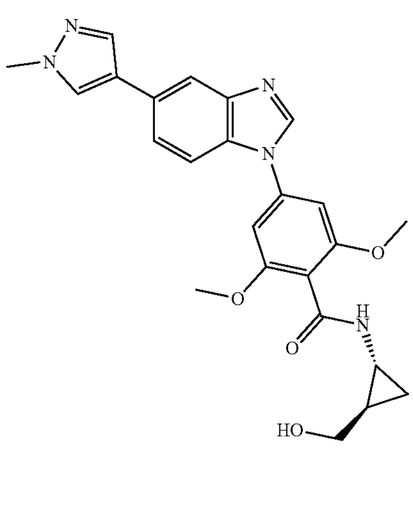 [SMILES: COc1cc(-n2cnc3cc(-c4cnn(C)c4)ccc32)cc(OC)c1C(=O)N[C@@H]1C[C@H]1CO] | N-[(1R,2R)-2-(hydroxymethyl)cyclopropyl]-2,6-dimethoxy-4-[5-(1-methylpyrazol-4-yl)benzimidazol-1-yl]benzamide | Int 50 + CAS# 873537-21-4 | E1.2 | 447.5 | 448.4 |

TABLE III-continued

Illustrative compounds of the invention.

| Cpd # | Structure | Name | SM | Mtd | MW | MS Mes'd |
|---|---|---|---|---|---|---|
| 157 | 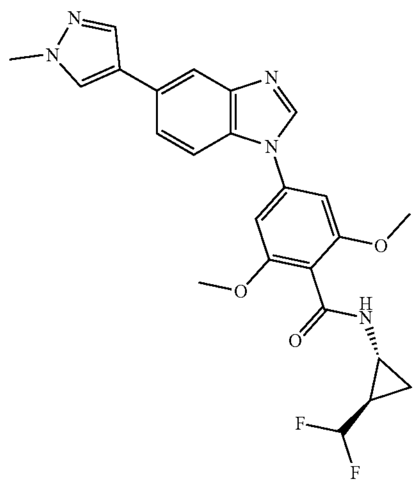 [SMILES: COc1cc(-n2cnc3cc(-c4cnn(C)c4)ccc32)cc(OC)c1C(=O)N[C@@H]1C[C@H]1C(F)F] | N-[(1R,2R)-2-(difluoromethyl)cyclopropyl]-2,6-dimethoxy-4-[5-(1-methylpyrazol-4-yl)benzimidazol-1-yl]benzamide | Int 50 + CAS# 2059915-48-7 | E1.2 | 467.5 | 468.1 |
| 158 | 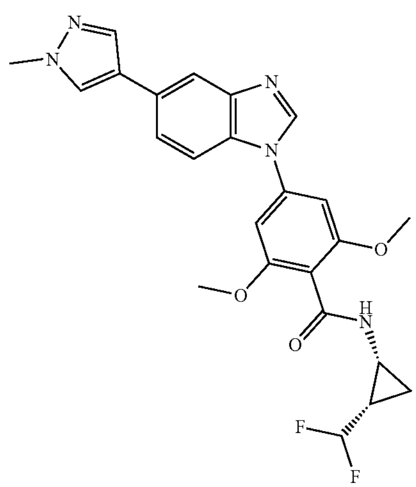 [SMILES: COc1cc(-n2cnc3cc(-c4cnn(C)c4)ccc32)cc(OC)c1C(=O)N[C@@H]1C[C@@H]1C(F)F] | N-[(1R,2S)-2-(difluoromethyl)cyclopropyl]-2,6-dimethoxy-4-[5-(1-methylpyrazol-4-yl)benzimidazol-1-yl]benzamide | Int 50 + CAS# 1909288-67-0 | E1.2 | 467.5 | 468.7 |
| 159 | 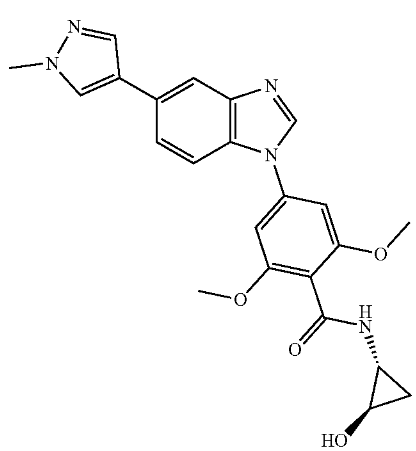 [SMILES: COc1cc(-n2cnc3cc(-c4cnn(C)c4)ccc32)cc(OC)c1C(=O)N[C@@H]1C[C@H]1O] | N-[(1R,2R)-2-hydroxycyclobutyl]-2,6-dimethoxy-4-[5-(1-methylpyrazol-4-yl)benzimidazol-1-yl]benzamide | Int 50 + CAS# 1609406-69-0 | E1.2 | 447.5 | 448.7 |

TABLE III-continued
Illustrative compounds of the invention.
| Cpd # | Structure | Name | SM | Mtd | MW | MS Mes'd |
|---|---|---|---|---|---|---|
| 160 | 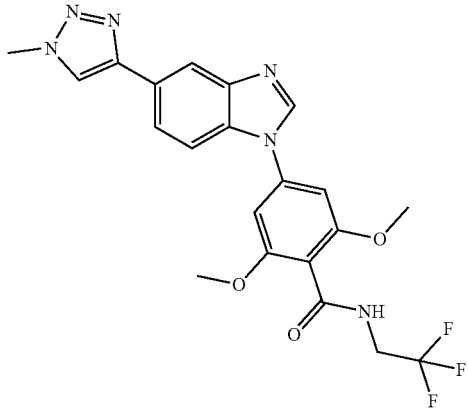 [SMILES: COc1cc(-n2cnc3cc(-c4cn(C)nn4)ccc32)cc(OC)c1C(=O)NCC(F)(F)F] | 2,6-dimethoxy-4-[5-(1-methyltriazol-4-yl)benzimidazol-1-yl]-N-(2,2,2-trifluoroethyl)benzamide | Int 39 + CAS# 13273-53-5 | E4.3ii | 460.4 | 461.5 |
| 161 | 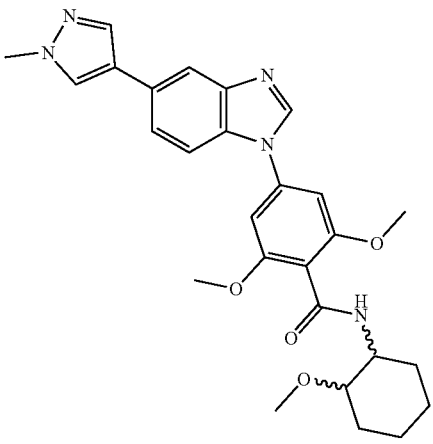 [SMILES: COc1cc(-n2cnc3cc(-c4cnn(C)c4)ccc32)cc(OC)c1C(=O)NC1CCCCC1OC] | 2,6-dimethoxy-N-(2-methoxy-cyclohexyl)-4-[5-(1-methylpyrazol-4-yl)benzimidazol-1-yl]benzamide | Int 50 + CAS# 4342-43-2 | E1.2 | 489.6 | 490.8 |
| 162 | 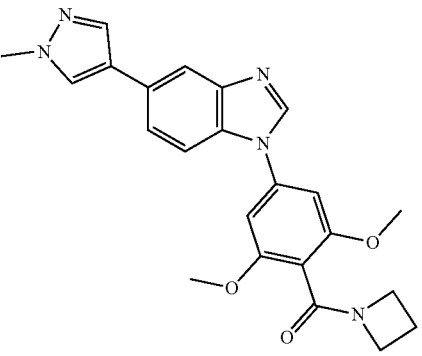 [SMILES: COc1cc(-n2cnc3cc(-c4cnn(C)c4)ccc32)cc(OC)c1C(=O)N1CCC1] | azetidin-1-yl-[2,6-dimethoxy-4-[5-(1-methylpyrazol-4-yl)benzimidazol-1-yl]phenyl]methanone | Int 50 + CAS# 503-29-7 | E1.2 | 417.5 | 418.7 |

TABLE III-continued

Illustrative compounds of the invention.

| Cpd # | Structure | Name | SM | Mtd | MW | MS Mes'd |
|---|---|---|---|---|---|---|
| 163 | 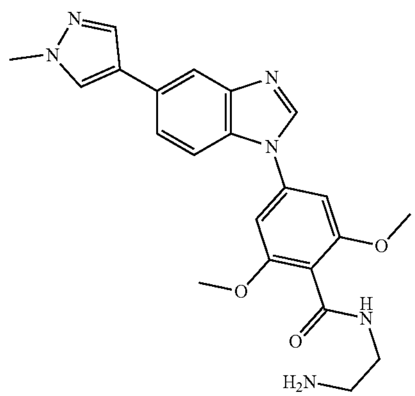 | N-(2-aminoethyl)-2,6-dimethoxy-4-[5-(1-methylpyrazol-4-yl)benzimidazol-1-yl]benzamide | Int 50 + CAS# 107-15-3 | E1.2 | 420.5 | 421.5 |
| 164 | 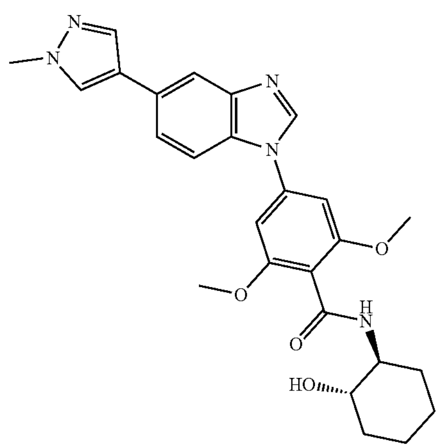 [SMILES: COc1cc(-n2cnc3cc(-c4cnn(C)c4)ccc32)cc(OC)c1C(=O)N[C@H]1CCCC[C@@H]1O] | N-[(1S,2S)-2-hydroxycyclohexyl]-2,6-dimethoxy-4-[5-(1-methylpyrazol-4-yl)benzimidazol-1-yl]benzamide | Int 50 + CAS# 13374-30-6 | E1.2 | 475.5 | 476.8 |
| 165 | 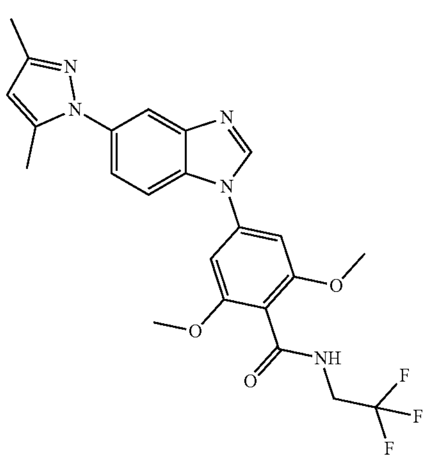 [SMILES: COc1cc(-n2cnc3cc(-n4nc(C)cc4C)ccc32)cc(OC)c1C(=O)NCC(F)(F)F] | 4-[5-(3,5-dimethylpyrazol-1-yl)benzimidazol-1-yl]-2,6-dimethoxy-N-(2,2,2-trifluoroethyl)benzamide | Int 39 | Ex. 2.39 | 473.4 | 474.3 |

TABLE III-continued

Illustrative compounds of the invention.

| Cpd # | Structure | Name | SM | Mtd | MW | MS Mes'd |
|---|---|---|---|---|---|---|
| 166 | 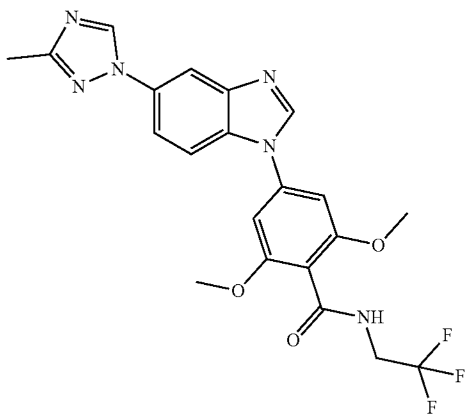 [SMILES: COc1cc(-n2cnc3cc(-n4cnc(C)n4)ccc32)cc(OC)c1C(=O)NCC(F)(F)F] | 2,6-dimethoxy-4-[5-(3-methyl-1,2,4-triazol-1-yl)benzimidazol-1-yl]-N-(2,2,2-trifluoroethyl)benzamide | Int 39 | Ex. 2.40 | 460.4 | 461.3 |
| 167 | 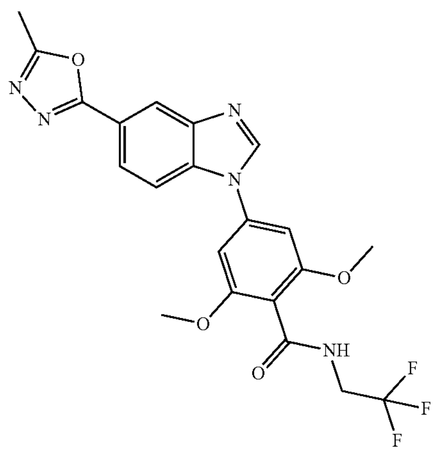 [SMILES: COc1cc(-n2cnc3cc(-c4nnc(C)o4)ccc32)cc(OC)c1C(=O)NCC(F)(F)F] | 2,6-dimethoxy-4-[5-(5-methyl-1,3,4-oxadiazol-2-yl)benzimidazol-1-yl]-N-(2,2,2-trifluoroethyl)benzamide | Int 39 | Ex. 2.41 | 461.4 | 462.7 |
| 168 | 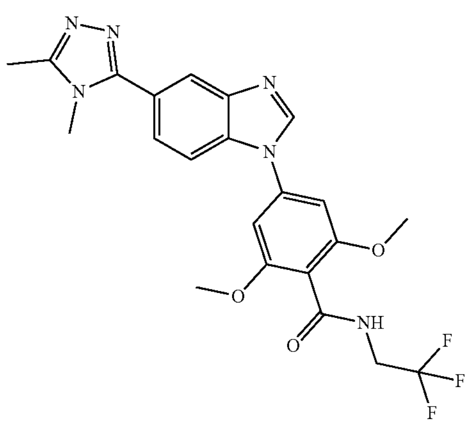 [SMILES: COc1cc(-n2cnc3cc(-c4nnc(C)n4C)ccc32)cc(OC)c1C(=O)NCC(F)(F)F] | 4-[5-(4,5-dimethyl-1,2,4-triazol-3-yl)benzimidazol-1-yl]-2,6-dimethoxy-N-(2,2,2-trifluoroethyl)benzamide | Int 39 | Ex. 2.42 | 474.4 | 475.7 |

TABLE III-continued

Illustrative compounds of the invention.

| Cpd # | Structure | Name | SM | Mtd | MW | MS Mes'd |
|---|---|---|---|---|---|---|
| 169 | 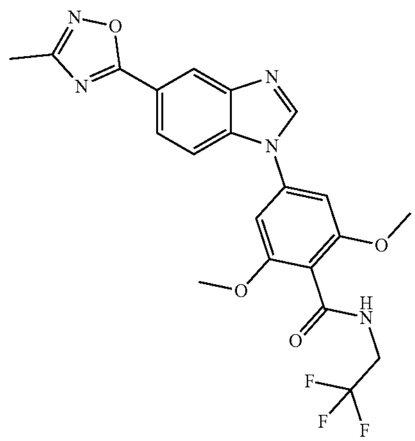 | 2,6-dimethoxy-4-[5-(3-methyl-1,2,4-oxadiazol-5-yl)benzimidazol-1-yl]-N-(2,2,2-trifluoroethyl)benzamide | Int 39 | Ex. 2.43 | 461.4 | 462.6 |
| 170 | 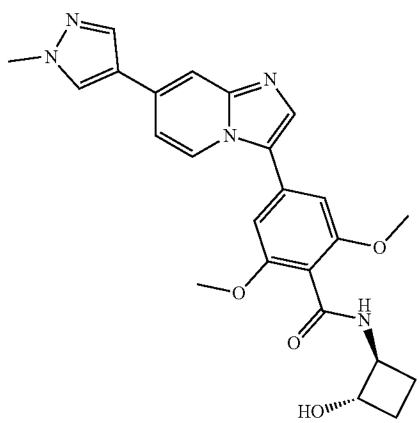 [SMILES: COc1cc(-c2cnc3cc(-c4cnn(C)c4)ccn23)cc(OC)c1C(=O)N[C@H]1CC[C@@H]1O] | N-[(1S,2S)-2-hydroxycyclobutyl]-2,6-dimethoxy-4-[7-(1-methylpyrazol-4-yl)imidazo[1,2-a]pyridin-3-yl]benzamide | Int 52 + CAS# 1820572-14-2 | E1.2 | 447.5 | 448.3 |
| 171 | 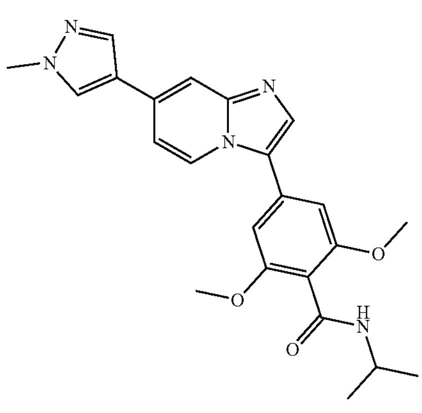 [SMILES: COc1cc(-c2cnc3cc(-c4cnn(C)c4)ccn23)cc(OC)c1C(=O)NC(C)C] | N-isopropyl-2,6-dimethoxy-4-[7-(1-methylpyrazol-4-yl)imidazo[1,2-a]pyridin-3-yl]benzamide | Int 52 + CAS# 75-31-0 | E1.2 | 419.5 | 420.4 |

TABLE III-continued

Illustrative compounds of the invention.

| Cpd # | Structure | Name | SM | Mtd | MW | MS Mes'd |
|---|---|---|---|---|---|---|
| 172 | 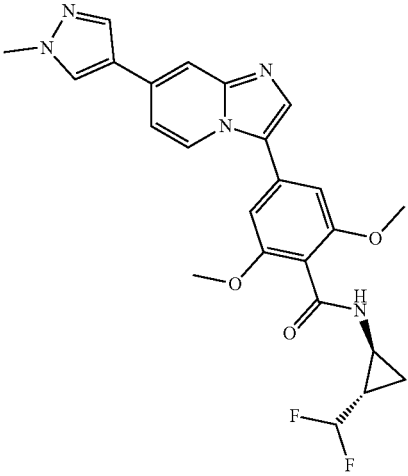 [SMILES: COc1cc(-c2cnc3cc(-c4cnn(C)c4)ccn23)cc(OC)c1C(=O)N[C@H]1C[C@@H]1C(F)F] | N-[(1S,2S)-2-(difluoromethyl)cyclopropyl]-2,6-dimethoxy-4-[7-(1-methylpyrazol-4-yl)imidazo[1,2-a]pyridin-3-yl]benzamide | Int 52 + CAS# 2059915-48-7 | E1.2 | 467.5 | 468.3 |
| 173 | 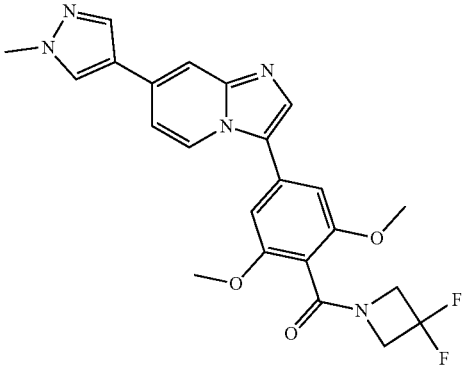 [SMILES: COc1cc(-c2cnc3cc(-c4cnn(C)c4)ccn23)cc(OC)c1C(=O)N1CC(F)(F)C1] | (3,3-difluoroazetidin-1-yl)-[2,6-dimethoxy-4-[7-(1-methylpyrazol-4-yl)imidazo[1,2-a]pyridin-3-yl]phenyl]methanone | Int 52 + CAS# 288315-03-7 | E1.2 | 453.4 | 454.3 |
| 174 | 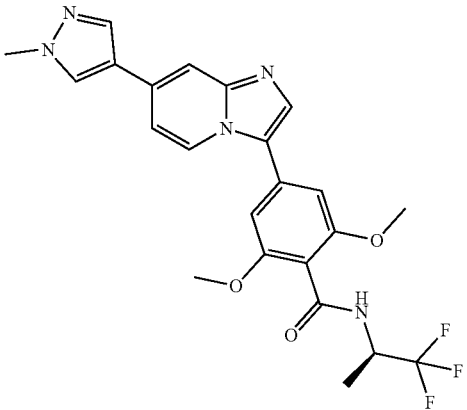 [SMILES: COc1cc(-c2cnc3cc(-c4cnn(C)c4)ccn23)cc(OC)c1C(=O)N[C@H](C)C(F)(F)F] | 2,6-dimethoxy-4-[7-(1-methylpyrazol-4-yl)imidazo[1,2-a]pyridin-3-yl]-N-[(1R)-2,2,2-trifluoro-1-methyl-ethyl]benzamide | Int 52 + CAS# 779303-24-1 | E1.2 | 473.4 | 474.3 |

TABLE III-continued

Illustrative compounds of the invention.

| Cpd # | Structure | Name | SM | Mtd | MW | MS Mes'd |
|---|---|---|---|---|---|---|
| 175 | 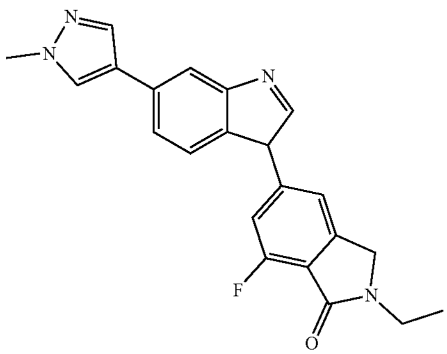 [SMILES: CCN1Cc2cc(C3C=Nc4cc(-c5cnn(C)c5)ccc43)cc(F)c2C1=O] | 2-ethyl-7-fluoro-5-[5-(1-methylpyrazol-4-yl)benzimidazol-1-yl]isoindolin-1-one | CAS# 4887-88-1 + CAS# 761446-44-0 + 5-bromo-2-ethyl-7-fluoro-isoindolin-1-one (cf. Ex. 2.16.1) | Ex. 2.46 | 375.4 | 376.7 |
| 176 | 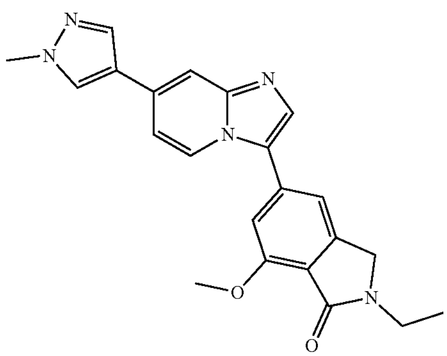 [SMILES: CCN1Cc2cc(-c3cnc4cc(-c5cnn(C)c5)ccn34)cc(OC)c2C1=O] | 2-ethyl-7-methoxy-5-[7-(1-methylpyrazol-4-yl)imidazo[1,2-a]pyridin-3-yl]isoindolin-1-one | CAS# 1246184-55-3 + Int 18 + CAS# 761446-44-9 | E1.3 + E1.3 | 387.4 | 388.8 |
| 177 | 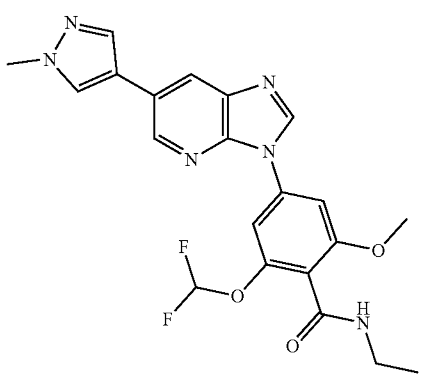 [SMILES: CCNC(=O)c1c(OC)cc(-n2cnc3cc(-c4cnn(C)c4)cnc32)cc1OC(F)F] | 2-(difluoromethoxy)-N-ethyl-6-methoxy-4-[6-(1-methylpyrazol-4-yl)imidazo[4,5-b]pyridin-3-yl]benzamide | CAS# 886372-98-1 + Int 12 + CAS# 761446-44-0 | B3 + C2 + E1.3 | 442.4 | 443.7 |
| 178 | 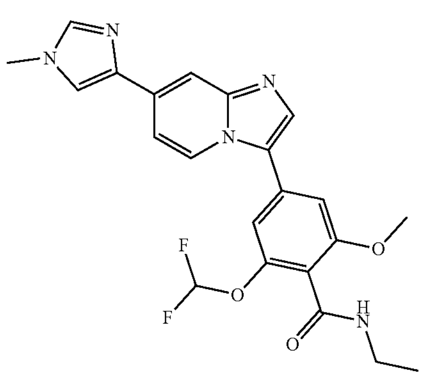 [SMILES: CCNC(=O)c1c(OC)cc(-c2cnc3cc(-c4cn(C)cn4)ccn23)cc1OC(F)F] | 2-(difluoromethoxy)-N-ethyl-6-methoxy-4-[7-(1-methylimidazol-4-yl)imidazo[1,2-a]pyridin-3-yl]benzamide | CAS# 1246184-55-3 + Int 16 + CAS# 1083180-01-1 | E1.3 + E1.3 | 441.4 | 443.3 |

TABLE III-continued

Illustrative compounds of the invention.

| Cpd # | Structure | Name | SM | Mtd | MW | MS Mes'd |
|---|---|---|---|---|---|---|
| 179 | 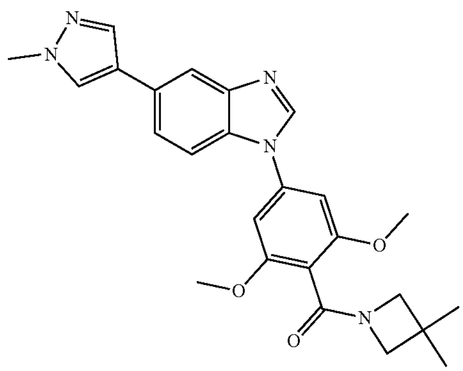 | [2,6-dimethoxy-4-[5-(1-methylpyrazol-4-yl)benzimidazol-1-yl]phenyl]-(3,3-dimethylazatidin-1-yl)methanone | Int 50 + CAS# 89381-03-3 | E1.2 | 445.5 | 446.4 |
| 180 | 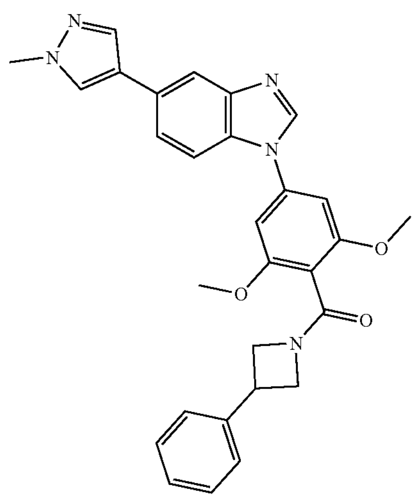 | [2,6-dimethoxy-4-[5-(1-methylpyrazol-4-yl)benzimidazol-1-yl]phenyl]-(3-phenylazetidin-1-yl)methanone | Int 50 + CAS# 4363-13-7 | E1.2 | 493.6 | 495.0 |
| 181 | 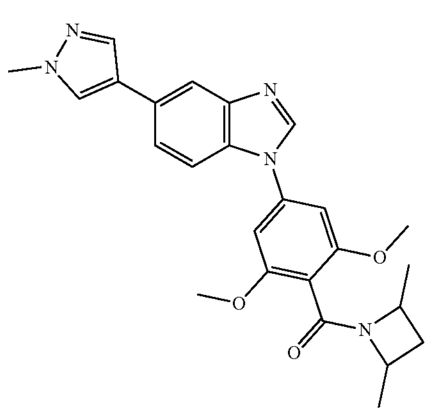 [SMILES: COc1cc(-n2cnc3cc(-c4cnn(C)c4)ccc32)cc(OC)c1C(=O)N1C(C)CC1C] | [2,6-dimethoxy-4-[5-(1-methylpyrazol-4-yl)benzimidazol-1-yl]phenyl]-(2,4-dimethylazetidin-1-yl)methanone | Int 50 + CAS# 1803606-22-5 | E1.2 | 445.5 | 447.0 |

TABLE III-continued

Illustrative compounds of the invention.

| Cpd # | Structure | Name | SM | Mtd | MW | MS Mes'd |
|---|---|---|---|---|---|---|
| 182 | 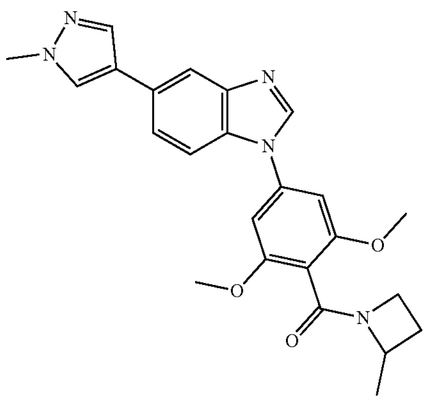 [SMILES: COc1cc(-n2cnc3cc(-c4cnn(C)c4)ccc32)cc(OC)c1C(=O)N1CCC1C] | [2,6-dimethoxy-4-[5-(1-methylpyrazol-4-yl)benzimidazol-1-yl]phenyl]-(2-methylazetidin-1-yl)methanone | Int 50 + CAS# 1152113-37-5 | E1.2 | 431.5 | 432.9 |
| 183 | 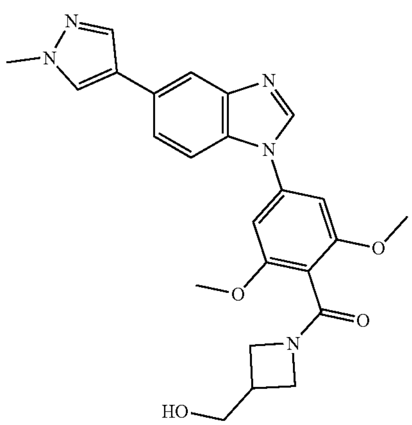 | [2,6-dimethoxy-4-[5-(1-methylpyrazol-4-yl)benzimidazol-1-yl]phenyl]-[3-(hydroxymethyl)azetidin-1-yl]methanone | Int 50 + CAS# 928038-44-2 | E1.2 | 447.5 | 449.0 |
| 184 | 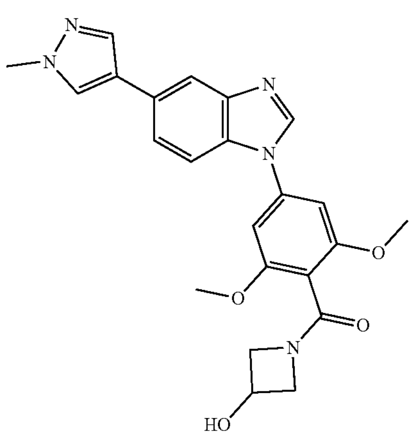 | [2,6-dimethoxy-4-[5-(1-methylpyrazol-4-yl)benzimidazol-1-yl]phenyl]-(3-hydroxyazetidin-1-yl)methanone | Int 50 + CAS# 18621-18-6 | E1.2 | 433.5 | 434.9 |

TABLE III-continued

Illustrative compounds of the invention.

| Cpd # | Structure | Name | SM | Mtd | MW | MS Mes'd |
|---|---|---|---|---|---|---|
| 185 | 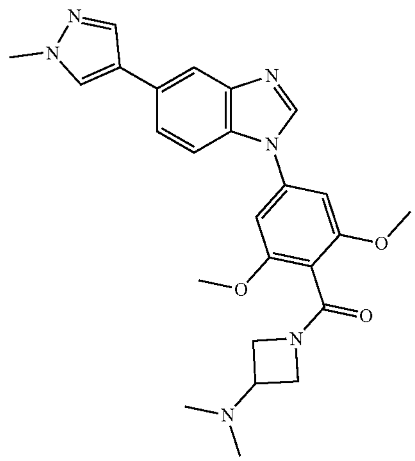 | [2,6-dimethoxy-4-[5-(1-methylpyrazol-4-yl)benzimidazol-1-yl]phenyl]-[3-(dimethylamino)azetidin-1-yl]methanone | Int 50 + CAS# 935670-07-8 | E1.2 | 460.5 | 461.9 |
| 186 | 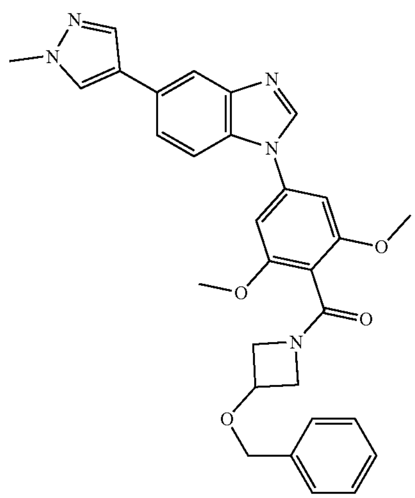 | (3-benzyloxyazetidin-1-yl)-2,6-dimethoxy-4-[5-(1-methylpyrazol-4-yl)benzimidazol-1-yl]phenyl]methanone | Int 50 + CAS# 897086-95-2 | E1.2 | 523.6 | 525.1 |
| 187 | 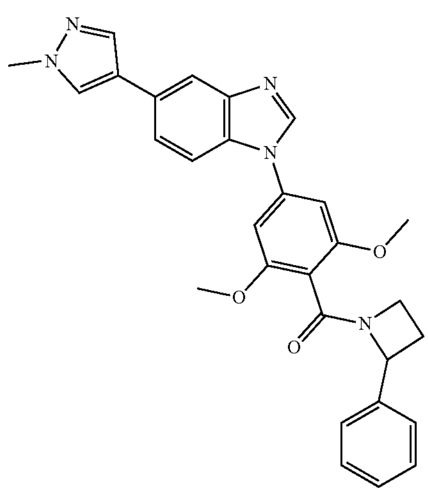 [SMILES: COc1cc(-n2cnc3cc(-c4cnn(C)c4)ccc32)cc(OC)c1C(=O)N1CCC1c1ccccc1] | [2,6-dimethoxy-4-[5-(1-methylpyrazol-4-yl)benzimidazol-1-yl]phenyl]-(2-phenylazetidin-1-yl)methanone | Int 50 + CAS# 22610-18-0 | E1.2 | 493.6 | 495.0 |

TABLE III-continued

Illustrative compounds of the invention.

| Cpd # | Structure | Name | SM | Mtd | MW | MS Mes'd |
|---|---|---|---|---|---|---|
| 188 | 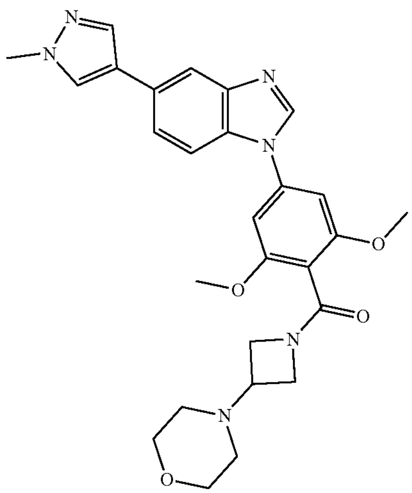 | [2,6-dimethoxy-4-[5-(1-methylpyrazol-4-yl)benzimidazol-1-yl]phenyl]-(3-morpholinoazetidin-1-yl)methanone | Int 50 + CAS# 302355-79-9 | E1.2 | 502.6 | 503.9 |
| 189 | 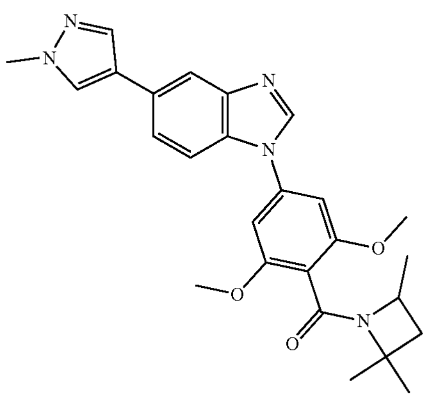 [SMILES: COc1cc(-n2cnc3cc(-c4cnn(C)c4)ccc32)cc(OC)c1C(=O)N1C(C)CC1(C)C] | [2,6-dimethoxy-4-[5-(1-methylpyrazol-4-yl)benzimidazol-1-yl]phenyl]-(2,2,4-trimethylazetidin-1-yl)methanone | Int 50 + CAS# 1197627-45-4 | E1.2 | 459.5 | 461.0 |
| 190 | 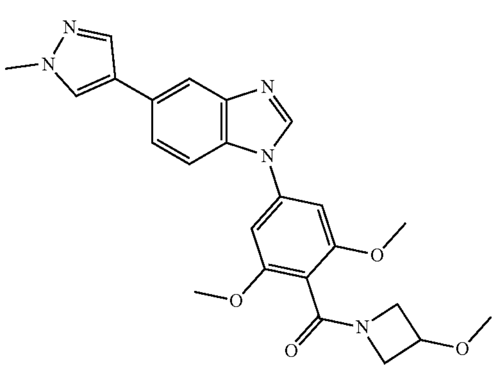 | [2,6-dimethoxy-4-[5-(1-methylpyrazol-4-yl)benzimidazol-1-yl]phenyl]-(3-methoxyazetidin-1-yl)methanone | Int 50 + CAS# 110925-17-2 | E1.2 | 447.5 | 448.9 |

TABLE III-continued

Illustrative compounds of the invention.

| Cpd # | Structure | Name | SM | Mtd | MW | MS Mes'd |
|---|---|---|---|---|---|---|
| 191 | 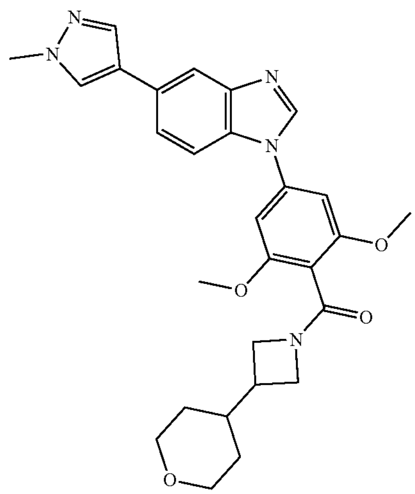 | [2,6-dimethoxy-4-[5-(1-methylpyrazol-4-yl)benzimidazol-1-yl]phenyl]-(3-tetrahydropyran-4-ylazetidin-1-yl)methanone | Int 50 + CAS# 550369-51-2 | E1.2 | 501.6 | 503.1 |
| 192 | 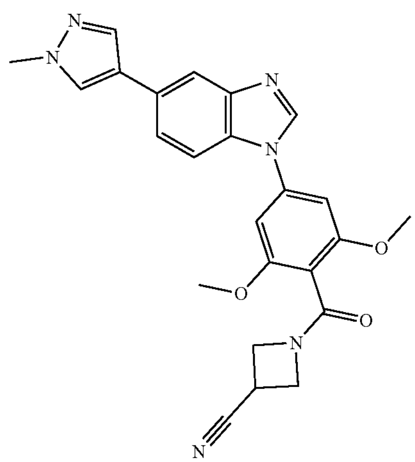 | 1-[2,6-dimethoxy-4-[5-(1-methylpyrazol-4-yl)benzimidazol-1-yl]benzoyl]azetidine-3-carbonitrile | Int 50 + CAS# 345954-83-8 | E1.2 | 442.5 | 443.3 |
| 193 | 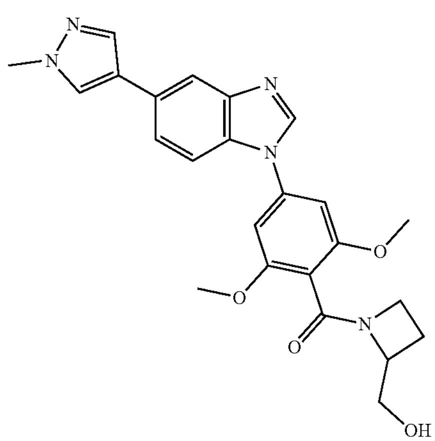 [SMILES: COc1cc(-n2cnc3cc(-c4cnn(C)c4)ccc32)cc(OC)c1C(=O)N1CCC1CO] | [2,6-dimethoxy-4-[5-(1-methylpyrazol-4-yl)benzimidazol-1-yl]phenyl]-[2-(hydroxymethyl)azetidin-1-yl]methanone | Int 50 + CAS# 250274-91-0 | E1.2 | 447.5 | 448.9 |

TABLE III-continued

Illustrative compounds of the invention.

| Cpd # | Structure | Name | SM | Mtd | MW | MS Mes'd |
|---|---|---|---|---|---|---|
| 194 | 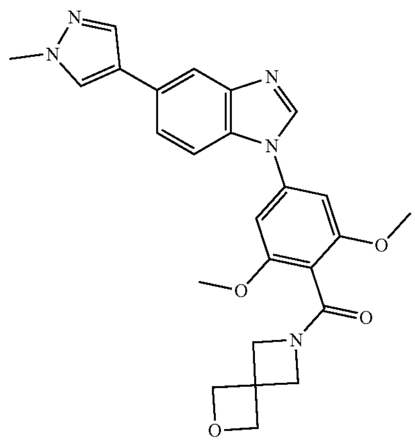 | [2,6-dimethoxy-4-[5-(1-methylpyrazol-4-yl)benzimidazol-1-yl]phenyl]-(2-oxa-6-azaspiro[3.3]heptan-6-yl)methanone | Int 50 + CAS# 1045709-32-7 | E1.2 | 459.5 | 461.0 |
| 195 | 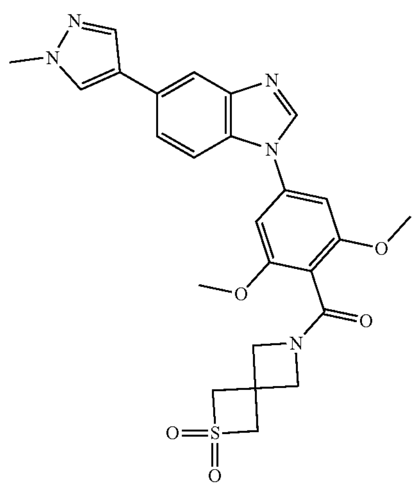 | [2,6-dimethoxy-4-[5-(1-methylpyrazol-4-yl)benzimidazol-1-yl]phenyl]-(2,2-dioxo-2λ$^6$-thia-6-azaspiro[3.3]heptan-6-yl)methanone | Int 50 + CAS# 1427388-39-3 | E1.2 | 507.6 | 509.0 |
| 196 | 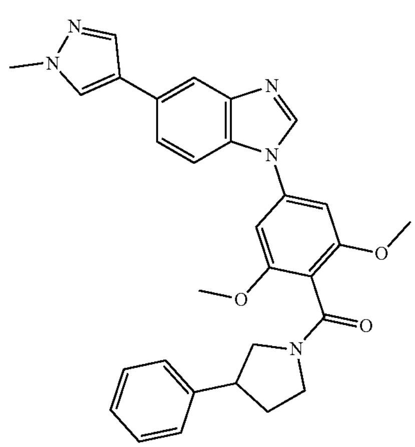 | [2,6-dimethoxy-4-[5-(1-methylpyrazol-4-yl)benzimidazol-1-yl]phenyl]-(3-phenylpyrrolidin-1-yl)methanone | Int 50 + CAS# 857281-02-8 | E1.2 | 507.6 | 509.0 |

TABLE III-continued

Illustrative compounds of the invention.

| Cpd # | Structure | Name | SM | Mtd | MW | MS Mes'd |
|---|---|---|---|---|---|---|
| 197 | 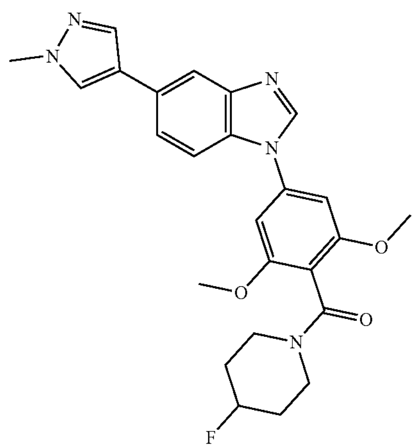 | [2,6-dimethoxy-4-[5-(1-methylpyrazol-4-yl)benzimidazol-1-yl]phenyl]-(4-fluoro-1-piperidyl)methanone | Int 50 + CAS# 57395-89-8 | E1.2 | 463.5 | 464.9 |
| 198 | 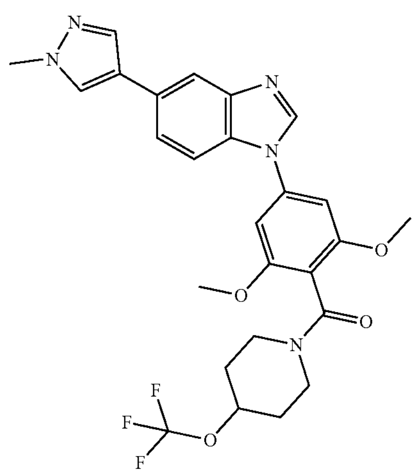 | [2,6-dimethoxy-4-[5-(1-methylpyrazol-4-yl)benzimidazol-1-yl]phenyl]-[4-(trifluoromethoxy)-1-piperidyl]methanone | Int 50 + CAS# 1612172-50-5 | E1.2 | 529.5 | 531.0 |
| 199 | 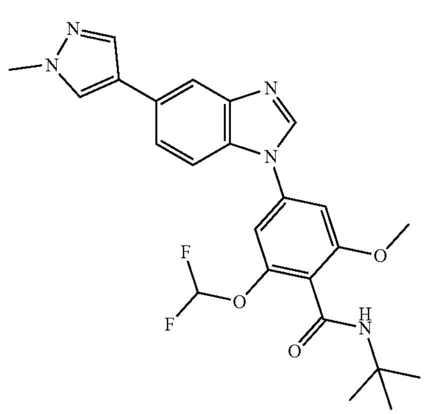 [SMILES: COc1cc(-n2cnc3cc(-c4cnn(C)c4)ccc32)cc(OC(F)F)c1C(=O)NC(C)(C)C] | N-tert-butyl-2-(difluoromethoxy)-6-methoxy-4-[5-(1-methylpyrazol-4-yl)benzimidazol-1-yl]benzamide | Int 58 + Int 11 | B2 + C2 | 469.5 | 470.8 |

TABLE III-continued

Illustrative compounds of the invention.

| Cpd # | Structure | Name | SM | Mtd | MW | MS Mes'd |
|---|---|---|---|---|---|---|
| 200 | 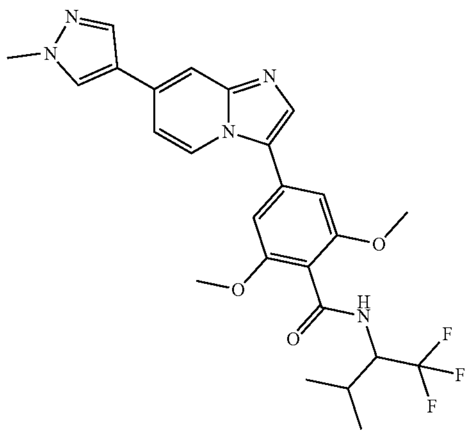 [SMILES: COc1cc(-c2cnc3cc(-c4cnn(C)c4)ccn23)cc(OC)c1C(=O)NC(C(C)C)C(F)(F)F] | 2,6-dimethoxy-4-[7-(1-methylpyrazol-4-yl)imidazo[1,2-a]pyridin-3-yl]-N-[2-methyl-1-(trifluoromethyl)propyl]benzamide | Int 52 + CAS# 1582-18-9 | E1.2 | 501.5 | 502.8 |
| 201 | 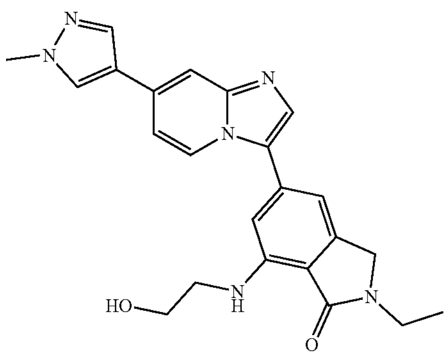 [SMILES: CCN1Cc2cc(-c3cnc4cc(-c5cnn(C)c5)ccn34)cc(NCCO)c2C1=O] | 2-ethyl-7-(2-hydroxyethyl-amino)-5-[7-(1-methylpyrazol-4-yl)imidazo[1,2-a]pyridin-3-yl]isoindolin-1-one | CAS# 1246184-55-3 + Int 19 + CAS# 761446-44-0 | E1.3 + E1.3 | 416.5 | 417.4 |
| 202 | 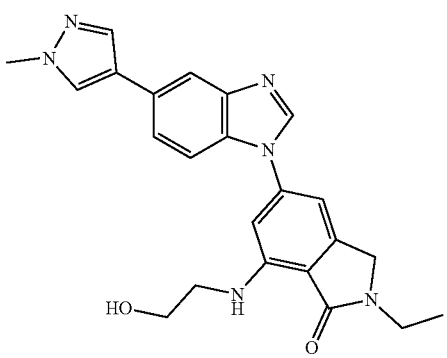 [SMILES: CCN1Cc2cc(-n3cnc4cc(-c5cnn(C)c5)ccc43)cc(NCCO)c2C1=O] | 2-ethyl-7-(2-hydroxyethyl-amino)-5-[5-(1-methylpyrazol-4-yl)benzimidazol-1-yl]isoindolin-1-one | Cpd 175 + CAS# 141-43-5 | Ex. 2.47 | 416.5 | 417.4 |
| 203 | 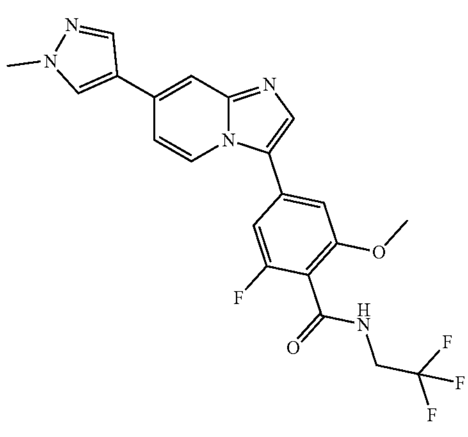 [SMILES: COc1cc(-c2cnc3cc(-c4cnn(C)c4)ccn23)cc(F)c1C(=O)NCC(F)(F)F] | 2-fluoro-6-methoxy-4-[7-(1-methylpyrazol-4-yl)imidazo[1,2-a]pyridin-3-yl]-N-(2,2,2-trifluoroethyl)benzamide | CAS# 1246184-55-3 + Int 20 + CAS# 761446-44-0 | E1.3 + E1.3 | 447.4 | 448.3 |

TABLE III-continued

Illustrative compounds of the invention.

| Cpd # | Structure | Name | SM | Mtd | MW | MS Mes'd |
|---|---|---|---|---|---|---|
| 204 | 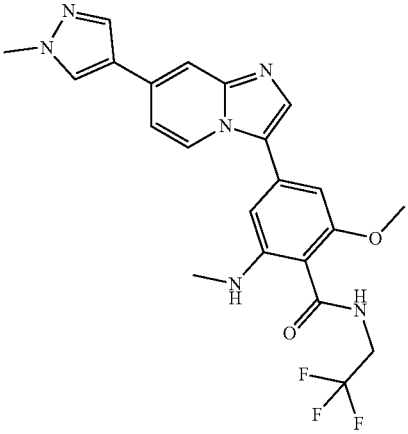 | 2-methoxy-6-(methylamino)-4-[7-(1-methylpyrazol-4-yl)imidazo[1,2-a]pyridin-3-yl]-N-(2,2,2-trifluoroethyl)benzamide | Cpd 203 + CAS# 74-89-5 | M1 | 458.4 | 459.4 |
| 205 | 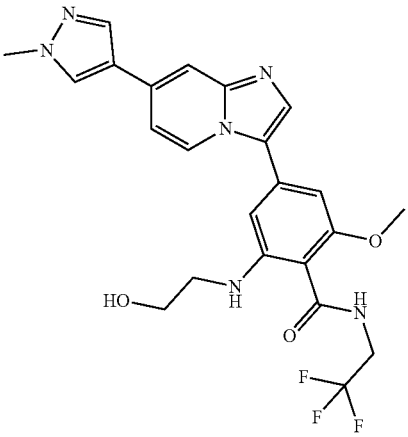 | 2-(2-hydroxy-ethylamino)-6-methoxy-4-[7-(1-methylpyrazol-4-yl)imidazo[1,2-a]pyridin-3-yl]-N-(2,2,2-trifluoroethyl)benzamide | Cpd 203 + CAS# 141-43-5 | M1 | 488.5 | 489.4 |
| 206 | 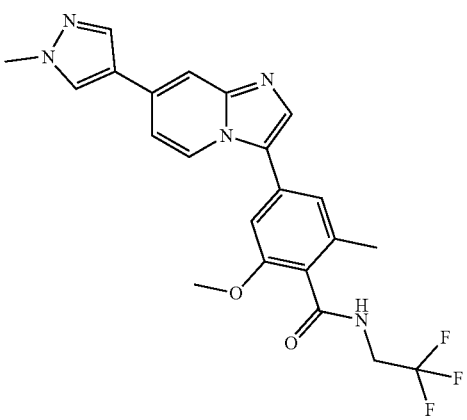 [SMILES: COc1cc(-c2cnc3cc(-c4cnn(C)c4)ccn23)cc(C)c1C(=O)NCC(F)(F)F] | 2-methoxy-6-methyl-4-[7-(1-methylpyrazol-4-yl)imidazo[1,2-a]pyridin-3-yl]-N-(2,2,2-trifluoroethyl)benzamide | CAS# 1246184-55-3 + Int 21 + CAS# 761446-44-0 + CAS# 753-90-2 | E1.3 + E1.3 + E1.1 + E1.2 | 443.4 | 444.4 |

TABLE III-continued

Illustrative compounds of the invention.

| Cpd # | Structure | Name | SM | Mtd | MW | MS Mes'd |
|---|---|---|---|---|---|---|
| 207 | 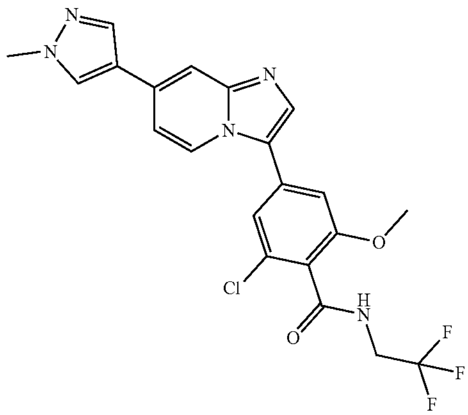 [SMILES: COc1cc(-c2cnc3cc(-c4cnn(C)c4)ccn23)cc(Cl)c1C(=O)NCC(F)(F)F] | 2-chloro-6-methoxy-4-[7-(1-methylpyrazol-4-yl)imidazo[1,2-a]pyridin-3-yl]-N-(2,2,2-trifluoroethyl)benzamide | CAS# 1246184-55-3 + Int 22 + CAS# 761446-44-0 + CAS# 753-90-2 | E1.3 + E1.3 + E1.1 + E1.2 | 463.8 | 464.3 |
| 208 | 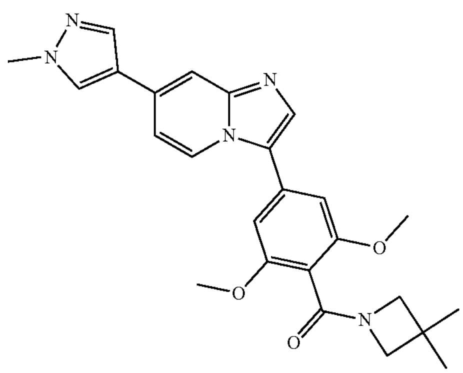 | [2,6-dimethoxy-4-[7-(1-methylpyrazol-4-yl)imidazo[1,2-a]pyridin-3-yl]phenyl]-(3,3-dimethylazetidin-1-yl)methanone | Int 52 + CAS# 89381-03-3 | E1.2 | 445.5 | 446.4 |
| 209 | 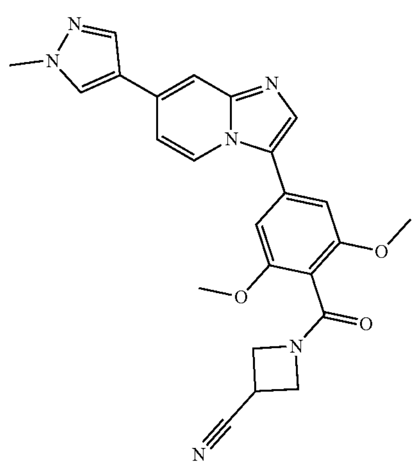 | 1-[2,6-dimethoxy-4-[7-(1-methylpyrazol-4-yl)imidazo[1,2-a]pyridin-3-yl]benzoyl]azetidine-3-carbonitrile | Int 52 + CAS# 345954-83-8 | E1.2 | 442.5 | 443.4 |

TABLE III-continued

Illustrative compounds of the invention.

| Cpd # | Structure | Name | SM | Mtd | MW | MS Mes'd |
|---|---|---|---|---|---|---|
| 210 | 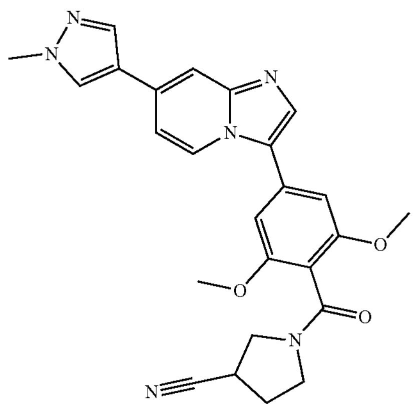 | 1-[2,6-dimethoxy-4-[7-(1-methylpyrazol-4-yl)imidazo[1,2-a]pyridin-3-yl]benzoyl] pyrrolidine-3-carbonitrile | Int 52 + CAS# 1187930-86-4 | E1.2 | 456.5 | 457.4 |
| 211 | 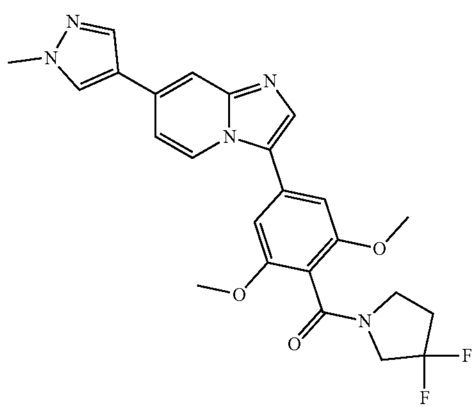 [SMILES: COc1cc(-c2cnc3cc(-c4cnn(C)c4)ccn23)cc(OC)c1C(=O)N1CCC(F)(F)C1] | (3,3-difluoropyrrolidin-1-yl)-[2,6-dimethoxy-4-[7-(1-methylpyrazol-4-yl)imidazo[1,2-a]pyridin-3-yl]phenyl] methanone | Int 52 + CAS# 163457-23-6 | E1.2 | 467.5 | 468.4 |
| 212 | 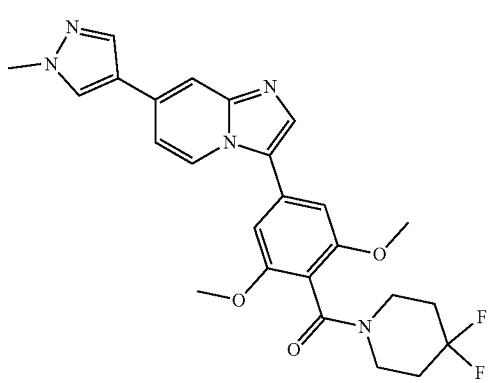 [SMILES: COc1cc(-c2cnc3cc(-c4cnn(C)c4)ccn23)cc(OC)c1C(=O)N1CCC(F)(F)CC1] | (4,4-difluoro-1-piperidyl)-[2,6-dimethoxy-4-[7-(1-methylpyrazol-4-yl)imidazo[1,2-a]pyridin-3-yl]phenyl] methanone | Int 52 + CAS# 144230-52-4 | E1.2 | 481.5 | 482.4 |

TABLE III-continued

Illustrative compounds of the invention.

| Cpd # | Structure | Name | SM | Mtd | MW | MS Mes'd |
|---|---|---|---|---|---|---|
| 213 | 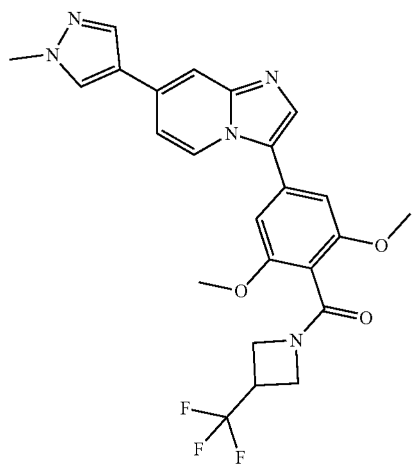 | [2,6-dimethoxy-4-[7-(1-methylpyrazol-4-yl)imidazo[1,2-a]pyridin-3-yl]phenyl]-[3-(trifluoromethyl)azetidin-1-yl]methanone | Int 52 + CAS# 1221272-90-7 | E1.2 | 485.5 | 486.8 |
| 215 | 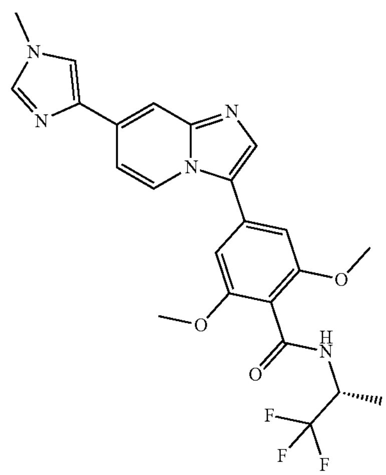 [SMILES: COc1cc(-c2cnc3cc(-c4cn(C)cn4)ccn23)cc(OC)c1C(=O)N[C@H](C)C(F)(F)F] | 2,6-dimethoxy-4-[7-(1-methylimidazol-4-yl)imidazo[1,2-a]pyridin-3-yl]-N-[(1R)-2,2,2-trifluoro-1-methyl-ethyl]benzamide | Int 35 + CAS# 1083180-01-1 + CAS# 779303-24-1 | E1.3 + E1.1 + E1.2 | 473.4 | 474.3 |
| 216 | 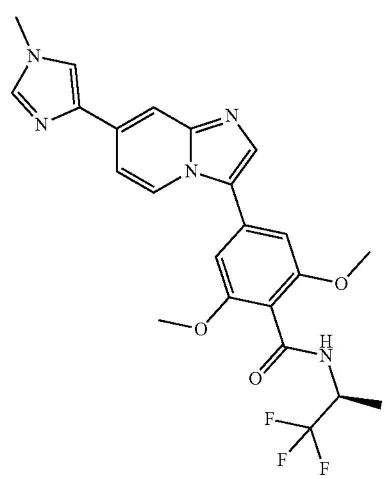 [SMILES: COc1cc(-c2cnc3cc(-c4cn(C)cn4)ccn23)cc(OC)c1C(=O)N[C@@H](C)C(F)(F)F] | 2,6-dimethoxy-4-[7-(1-methylimidazol-4-yl)imidazo[1,2-a]pyridin-3-yl]-N-[(1S)-2,2,2-trifluoro-1-methyl-ethyl]benzamide | Int 35 + CAS# 1083180-01-1 + CAS# 125278-10-6 | E1.3 + E1.1 + E1.2 | 473.4 | 474.3 |

TABLE III-continued

Illustrative compounds of the invention.

| Cpd # | Structure | Name | SM | Mtd | MW | MS Mes'd |
|---|---|---|---|---|---|---|
| 217 | 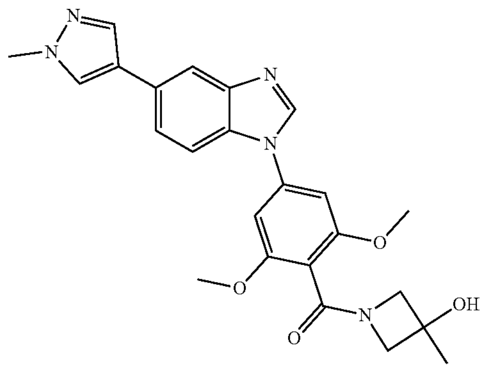 [SMILES: COc1cc(-n2cnc3cc(-c4cnn(C)c4)ccc32)cc(OC)c1C(=O)N1CC(C)(O)C1] | [2,6-dimethoxy-4-[5-(1-methylpyrazol-4-yl)benzimidazol-1-yl]phenyl]-(3-hydroxy-3-methyl-azetidin-1-yl)methanone | Int 50 + CAS# 124668-46-8 | E1.2 | 447.5 | 448.3 |
| 218 | 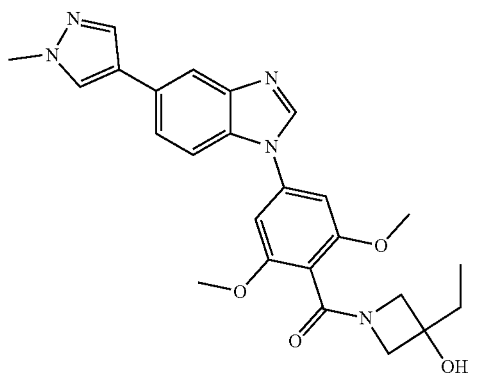 [SMILES: CCC1(O)CN(C(=O)c2c(OC)cc(-n3cnc4cc(-c5cnn(C)c5)ccc43)cc2OC)C1] | [2,6-dimethoxy-4-[5-(1-methylpyrazol-4-yl)benzimidazol-1-yl]phenyl]-(3-ethyl-3-hydroxy-azetidin-1-yl)methanone | Int 50 + CAS# 935668-00-1 | E1.2 | 461.5 | 462.4 |
| 219 | 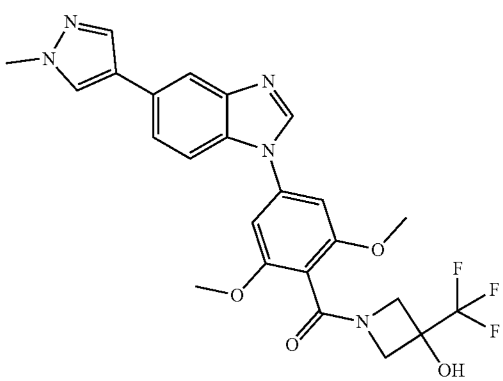 [SMILES: COc1cc(-n2cnc3cc(-c4cnn(C)c4)ccc32)cc(OC)c1C(=O)N1CC(O)(C(F)(F)F)C1] | [2,6-dimethoxy-4-[5-(1-methylpyrazol-4-yl)benzimidazol-1-yl]phenyl]-[3-hydroxy-3-(trifluoromethyl)azetidin-1-yl]methanone | Int 50 + CAS# 848192-96-1 | E1.2 | 501.5 | 502.3 |
| 220 | 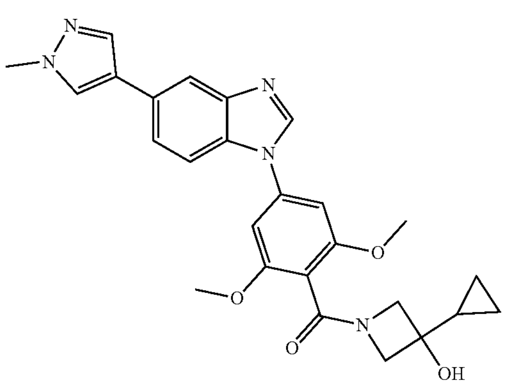 [SMILES: COc1cc(-n2cnc3cc(-c4cnn(C)c4)ccc32)cc(OC)c1C(=O)N1CC(O)(C2CC2)C1] | (3-cyclopropyl-3-hydroxy-azetidin-1-yl)-[2,6-dimethoxy-4-[5-(1-methylpyrazol-4-yl)benzimidazol-1-yl]phenyl]methanone | Int 50 + CAS# 848192-93-8 | E1.2 | 473.5 | 474.4 |

TABLE III-continued

Illustrative compounds of the invention.

| Cpd # | Structure | Name | SM | Mtd | MW | MS Mes'd |
|---|---|---|---|---|---|---|
| 221 | 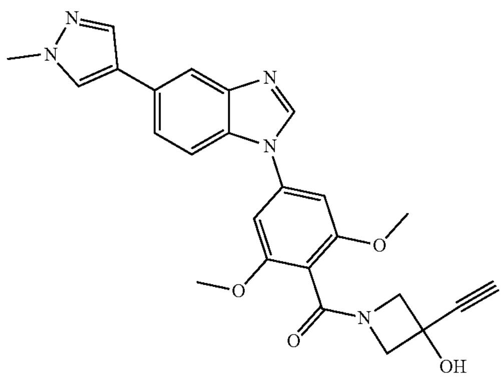 [SMILES: C#CC1(O)CN(C(=O)c2c(OC)cc(-n3cnc4cc(-c5cnn(C)c5)ccc43)cc2OC)C1] | [2,6-dimethoxy-4-[5-(1-methylpyrazol-4-yl)benzimidazol-1-yl]phenyl]-(3-ethynyl-3-hydroxy-azetidin-1-yl)methanone | Int 50 + CAS# 1408076-23-2 | E1.2 | 457.5 | 458.3 |
| 222 | 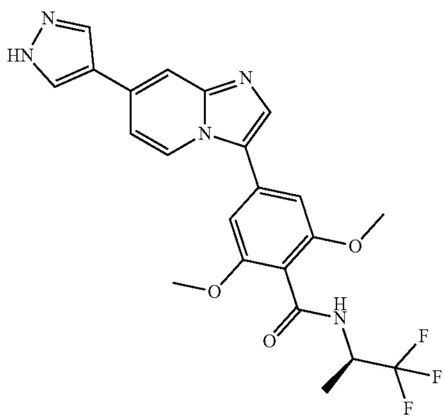 [SMILES: COc1cc(-c2cnc3cc(-c4cn[nH]c4)ccn23)cc(OC)c1C(=O)N[C@H](C)C(F)(F)F] | 2,6-dimethoxy-4-[7-(1H-pyrazol-4-yl)imidazo[1,2-a]pyridin-3-yl]-N-[(1R)-2,2,2-trifluoro-1-methyl-ethyl]benzamide | Int 35 + CAS# 269410-08-4 + CAS# 779303-24-1 | E1.3 + E1.1 + E1.2 | 459.4 | 460.3 |
| 223 | 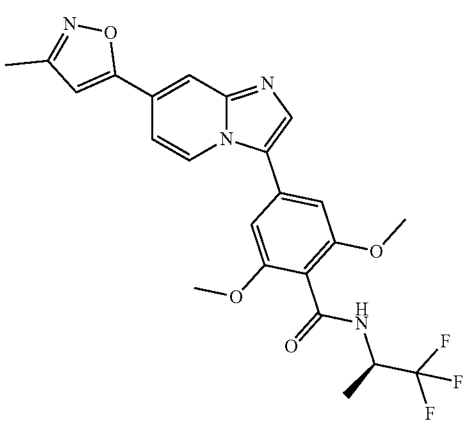 [SMILES: COc1cc(-c2cnc3cc(-c4cc(C)no4)ccn23)cc(OC)c1C(=O)N[C@H](C)C(F)(F)F] | 2,6-dimethoxy-4-[7-(3-methylisoxazol-5-yl)imidazo[1,2-a]pyridin-3-yl]-N-[(1R)-2,2,2-trifluoro-1-methyl-ethyl]benzamide | Int 54 + CAS# 779303-24-1 | E1.2 | 474.4 | 475.4 |

TABLE III-continued

Illustrative compounds of the invention.

| Cpd # | Structure | Name | SM | Mtd | MW | MS Mes'd |
|---|---|---|---|---|---|---|
| 224 | 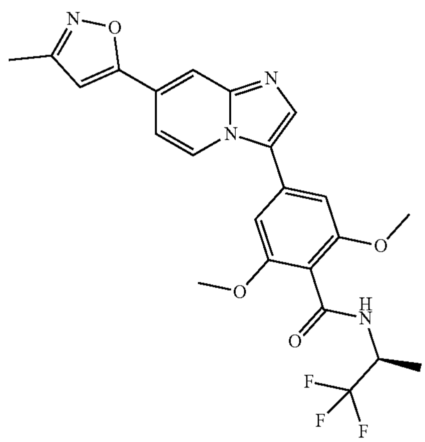 [SMILES: COc1cc(-c2cnc3cc(-c4cc(C)no4)ccn23)cc(OC)c1C(=O)N[C@@H](C)C(F)(F)F] | 2,6-dimethoxy-4-[7-(3-methylisoxazol-5-yl)imidazo[1,2-a]pyridin-3-yl]-N-[(1S)-2,2,2-trifluoro-1-methyl-ethyl]benzamide | Int 54 + CAS# 125278-10-6 | E1.2 | 474.4 | 475.3 |
| 225 | 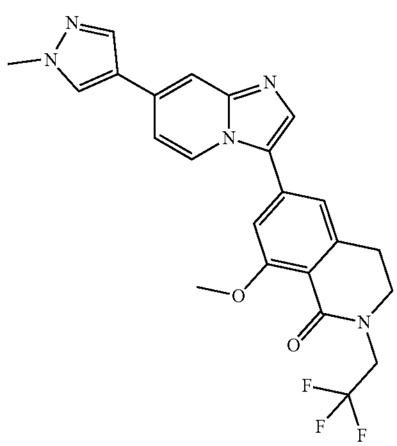 [SMILES: COc1cc(-c2cnc3cc(-c4cnn(C)c4)ccn23)cc2c1C(=O)N(CC(F)(F)F)CC2] | 8-methoxy-6-[7-(1-methylpyrazol-4-yl)imidazo[1,2-a]pyridin-3-yl]-2-(2,2,2-trifluoroethyl)-3,4-dihydroisoquinolin-1-one | Int 76 + CAS# 6226-25-1 | O | 455.4 | 456.4 |
| 226 | 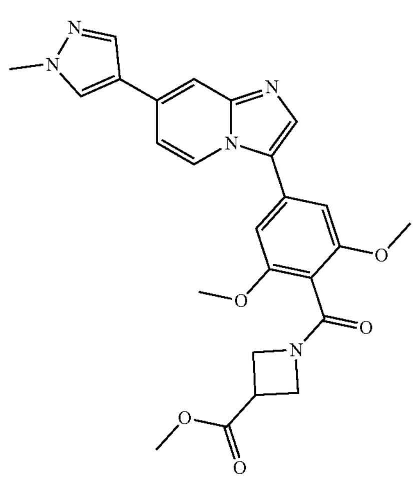 | methyl 1-[2,6-dimethoxy-4-[7-(1-methylpyrazol-4-yl)imidazo[1,2-a]pyridin-3-yl]benzoyl]azetidine-3-carboxylate | Int 52 + CAS# 100202-39-9 | E1.2 | 475.5 | 476.4 |

TABLE III-continued

Illustrative compounds of the invention.

| Cpd # | Structure | Name | SM | Mtd | MW | MS Mes'd |
|---|---|---|---|---|---|---|
| 227 | 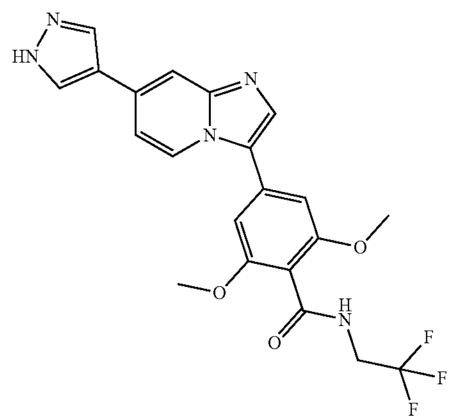 [SMILES: COc1cc(-c2cnc3cc(-c4cn[nH]c4)ccn23)cc(OC)c1C(=O)NCC(F)(F)F] | 2,6-dimethoxy-4-[7-(1H-pyrazol-4-yl)imidazo[1,2-a]pyridin-3-yl]-N-(2,2,2-trifluoroethyl)benzamide | Int 46 + CAS# 269410-08-4 | E1.3 | 445.4 | 446.3 |
| 228 | 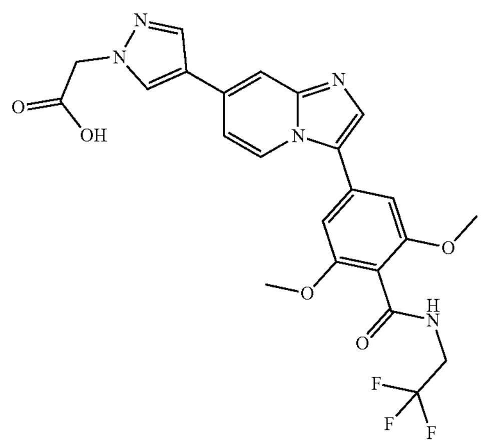 [SMILES: COc1cc(-c2cnc3cc(-c4cnn(CC(=O)O)c4)ccn23)cc(OC)c1C(=O)NCC(F)(F)F] | 2-[4-[3-[3,5-dimethoxy-4-(2,2,2-trifluoroethyl-carbamoyl)phenyl]imidazo[1,2-a]pyridin-7-yl]pyrazol-1-yl]acetic acid | Cpd-230 | E1.1 | 503.4 | 504.4 |
| 229 | 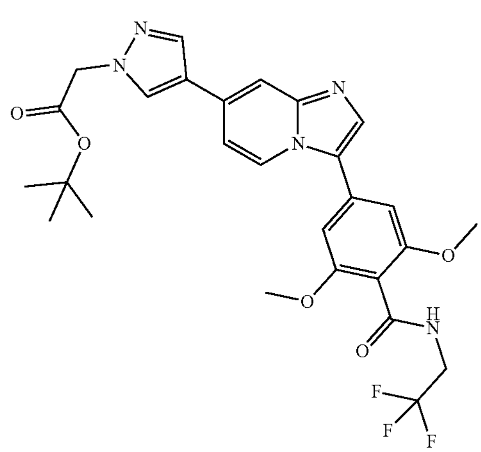 [SMILES: COc1cc(-c2cnc3cc(-c4cnn(CC(=O)OC(C)(C)C)c4)ccn23)cc(OC)c1C(=O)NCC(F)(F)F] | tert-butyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 227 + CAS# 107-59-5 | N2 | 559.5 | 560.4 |

TABLE III-continued

Illustrative compounds of the invention.

| Cpd # | Structure | Name | SM | Mtd | MW | MS Mes'd |
|---|---|---|---|---|---|---|
| 230 | 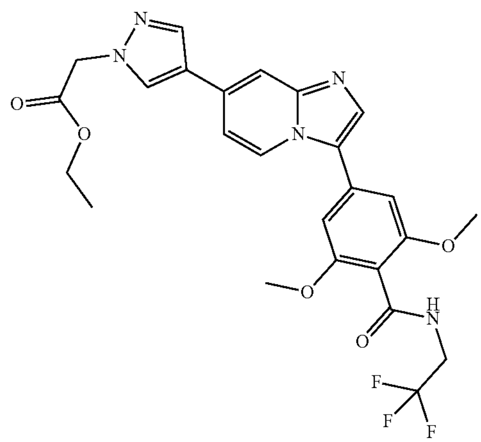 [SMILES: CCOC(=O)Cn1cc(-c2ccn3c(-c4cc(OC)c(C(=O)NCC(F)(F)F)c(OC)c4)cnc3c2)cn1] | ethyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Int 3 + Int 5 | H | 531.5 | 532.5 |
| 231 | 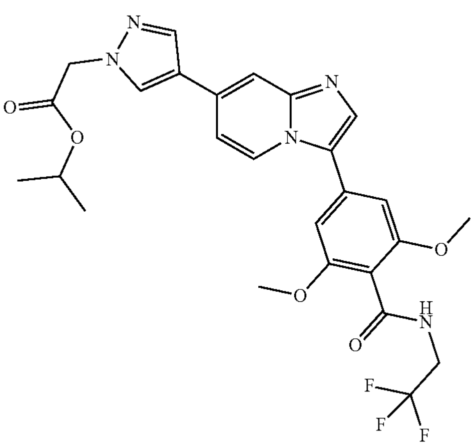 [SMILES: COc1cc(-c2cnc3cc(-c4cnn(CC(=O)OC(C)C)c4)ccn23)cc(OC)c1C(=O)NCC(F)(F)F] | isopropyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 229 + CAS# 67-63-0 | R | 545.5 | 546.4 |
| 232 | 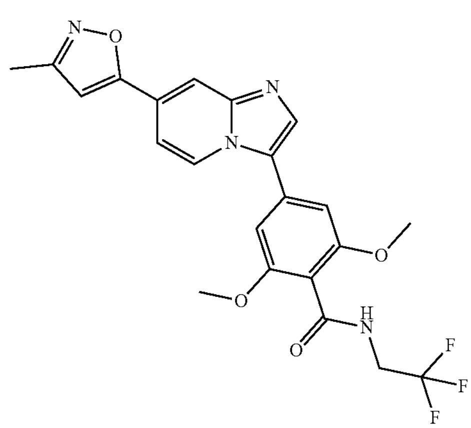 [SMILES: COc1cc(-c2cnc3cc(-c4cc(C)no4)ccn23)cc(OC)c1C(=O)NCC(F)(F)F] | 2,6-dimethoxy-4-[7-(3-methylisoxazol-5-yl)imidazo[1,2-a]pyridin-3-yl]-N-(2,2,2-trifluoroethyl)benzamide | Int 54 + CAS# 753-90-2 | E1.2 | 460.4 | 461.3 |

TABLE III-continued

Illustrative compounds of the invention.

| Cpd # | Structure | Name | SM | Mtd | MW | MS Mes'd |
|---|---|---|---|---|---|---|
| 233 | 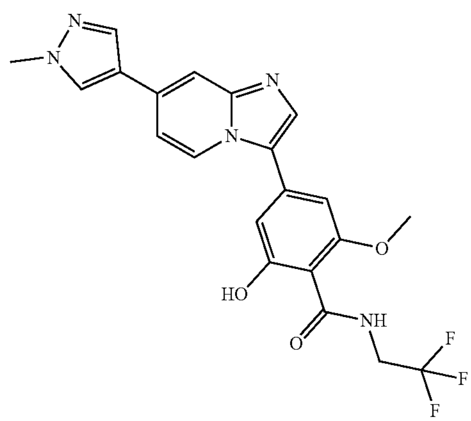 [SMILES: COc1cc(-c2cnc3cc(-c4cnn(C)c4)ccn23)cc(O)c1C(=O)NCC(F)(F)F] | 2-hydroxy-6-methoxy-4-[7-(1-methylpyrazol-4-yl)imidazo[1,2-a]pyridin-3-yl]-N-(2,2,2-trifluoroethyl)benzamide | Cpd 88 | I | 445.4 | 446.3 |
| 234 | 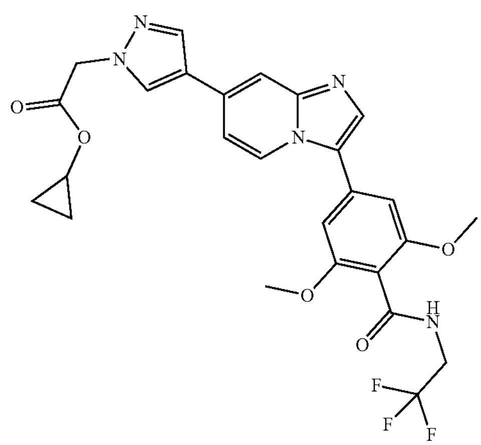 [SMILES: COc1cc(-c2cnc3cc(-c4cnn(CC(=O)OC5CC5)c4)ccn23)cc(OC)c1C(=O)NCC(F)(F)F] | cyclopropyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 + CAS# 16545-68-9 | Q1 | 543.5 | 544.4 |
| 235 | 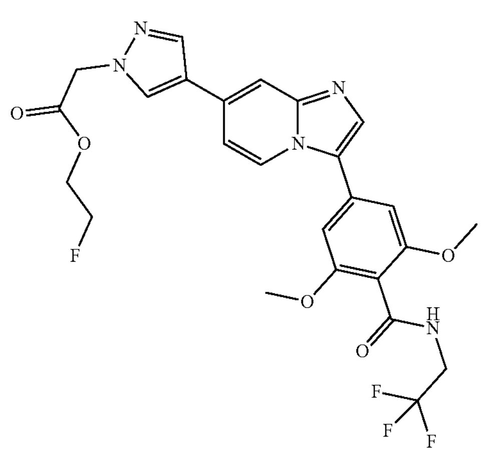 [SMILES: COc1cc(-c2cnc3cc(-c4cnn(CC(=O)OCCF)c4)ccn23)cc(OC)c1C(=O)NCC(F)(F)F] | 2-fluoroethyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 + CAS# 371-62-0 | Q1 | 549.5 | 550.3 |

TABLE III-continued

Illustrative compounds of the invention.

| Cpd # | Structure | Name | SM | Mtd | MW | MS Mes'd |
|---|---|---|---|---|---|---|
| 236 | 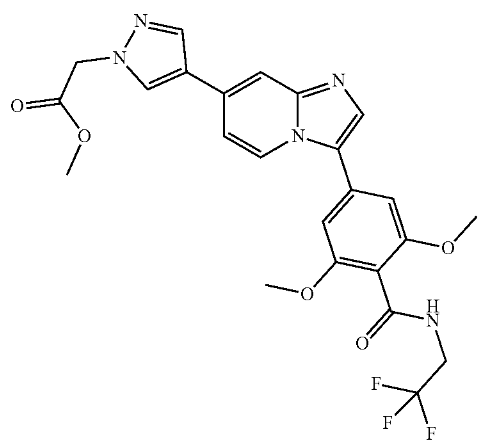 [SMILES: COC(=O)Cn1cc(-c2ccn3c(-c4cc(OC)c(C(=O)NCC(F)(F)F)c(OC)c4)cnc3c2)cn1] | methyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 + MeOH | Q2i | 517.5 | 518.3 |
| 237 | 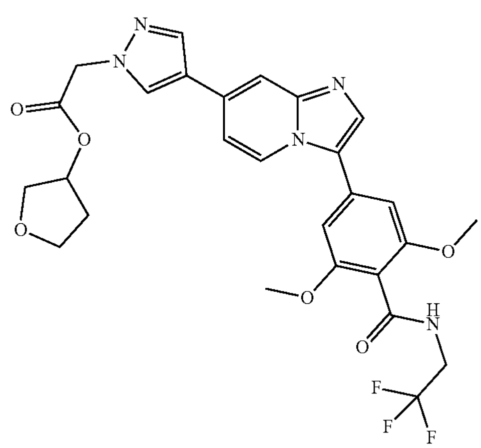 [SMILES: COc1cc(-c2cnc3cc(-c4cnn(CC(=O)OC5CCOC5)c4)ccn23)cc(OC)c1C(=O)NCC(F)(F)F] | tetrahydrofuran-3-yl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 + CAS# 453-20-3 | Q2ii | 573.5 | 574.4 |
| 238 | 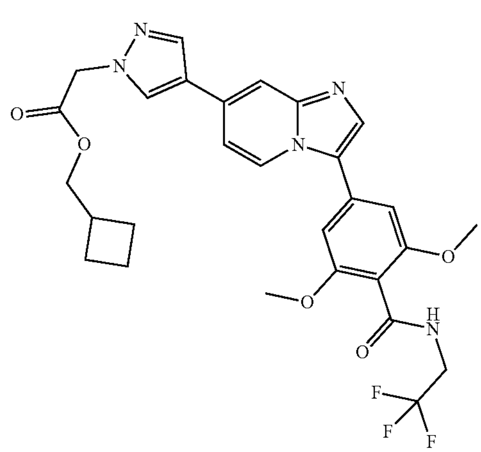 [SMILES: COc1cc(-c2cnc3cc(-c4cnn(CC(=O)OCC5CCC5)c4)ccn23)cc(OC)c1C(=O)NCC(F)(F)F] | cyclobutylmethyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 + CAS# 17247-58-4 | Q3 | 571.5 | 572.4 |

TABLE III-continued

Illustrative compounds of the invention.

| Cpd # | Structure | Name | SM | Mtd | MW | MS Mes'd |
|---|---|---|---|---|---|---|
| 239 | 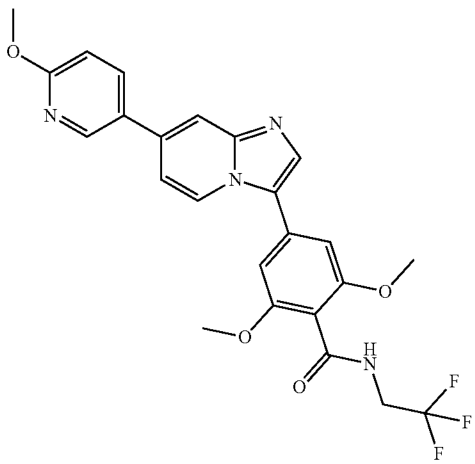 [SMILES: COc1ccc(-c2ccn3c(-c4cc(OC)c(C(=O)NCC(F)(F)F)c(OC)c4)cnc3c2)cn1] | 2,6-dimethoxy-4-[7-(6-methoxy-3-pyridyl)imidazo[1,2-a]pyridin-3-yl]-N-(2,2,2-trifluoroethyl)benzamide | Int 46 + CAS# 163105-89-3 | E1.3 | 486.4 | 487.6 |
| 240 | 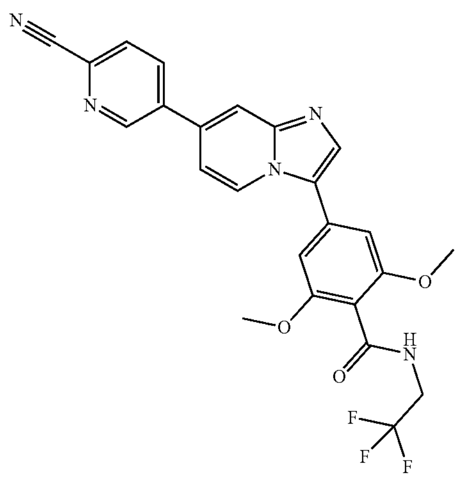 [SMILES: COc1cc(-c2cnc3cc(-c4ccc(C#N)nc4)ccn23)cc(OC)c1C(=O)NCC(F)(F)F] | 4-[7-(6-cyano-3-pyridyl)imidazo[1,2-a]pyridin-3-yl]-2,6-dimethoxy-N-(2,2,2-trifluoroethyl)benzamide | Int 46 + CAS# 741709-63-7 | E1.3 | 481.4 | 482.8 |
| 241 | 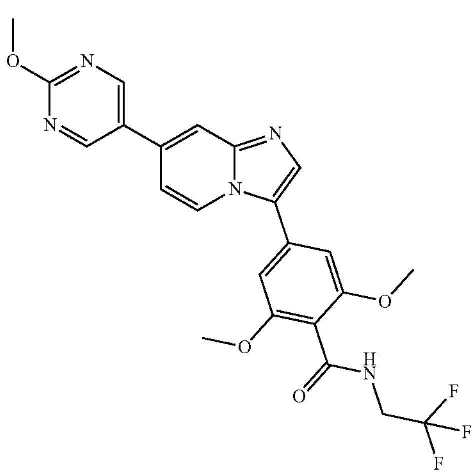 [SMILES: COc1ncc(-c2ccn3c(-c4cc(OC)c(C(=O)NCC(F)(F)F)c(OC)c4)cnc3c2)cn1] | 2,6-dimethoxy-4-[7-(2-methoxypyrimidin-5-yl)imidazo[1,2-a]pyridin-3-yl]-N-(2,2,2-trifluoroethyl)benzamide | Int 46 + CAS# 628692-15-9 | E1.3 | 487.4 | 488.7 |

TABLE III-continued

Illustrative compounds of the invention.

| Cpd # | Structure | Name | SM | Mtd | MW | MS Mes'd |
|---|---|---|---|---|---|---|
| 242 | 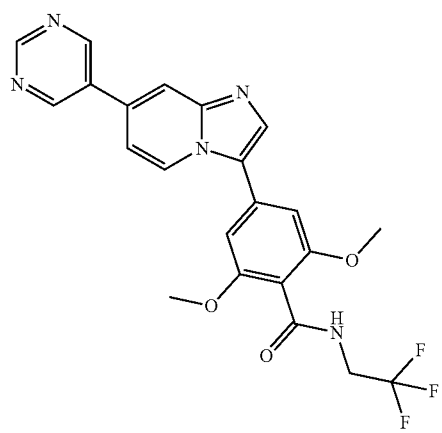 [SMILES: COc1cc(-c2cnc3cc(-c4cncnc4)ccn23)cc(OC)c1C(=O)NCC(F)(F)F] | 2,6-dimethoxy-4-(7-pyrimidin-5-ylimidazo[1,2-a]pyridin-3-yl)-N-(2,2,2-trifluoroethyl)benzamide | Int 46 + CAS# 109299-78-7 | E1.3 | 457.4 | 458.8 |
| 243 | 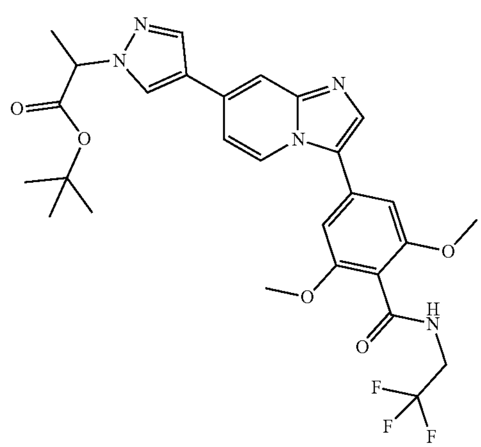 [SMILES: COc1cc(-c2cnc3cc(-c4cnn(C(C)C(=O)OC(C)(C)C)c4)ccn23)cc(OC)c1C(=O)NCC(F)(F)F] | tert-butyl 2-[4-[3-[3,5-dimethoxy-4-(2,2,2-trifluoroethyl-carbamoyl)phenyl]imidazo[1,2-a]pyridin-7-yl]pyrazol-1-yl]propanoate | Int 46 + Int 71 | E1.3 | 573.6 | 574.4 |
| 244 | 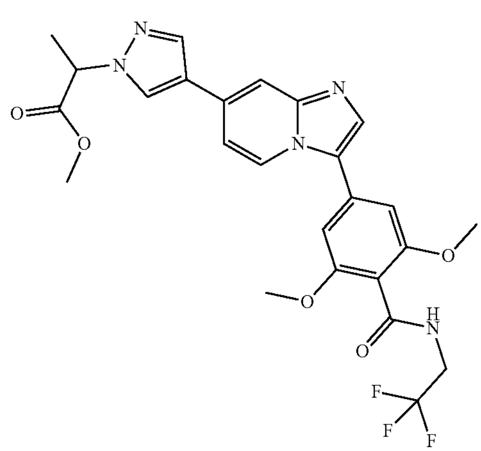 [SMILES: COC(=O)C(C)n1cc(-c2ccn3c(-c4cc(OC)c(C(=O)NCC(F)(F)F)c(OC)c4)cnc3c2)cn1] | methyl 2-[4-[3-[3,5-dimethoxy-4-(2,2,2-trifluoroethyl-carbamoyl)phenyl]imidazo[1,2-a]pyridin-7-yl]pyrazol-1-yl]propanoate | Cpd 243 + MeOH | R | 531.5 | 532.9 |

TABLE III-continued

Illustrative compounds of the invention.

| Cpd # | Structure | Name | SM | Mtd | MW | MS Mes'd |
|---|---|---|---|---|---|---|
| 245 | 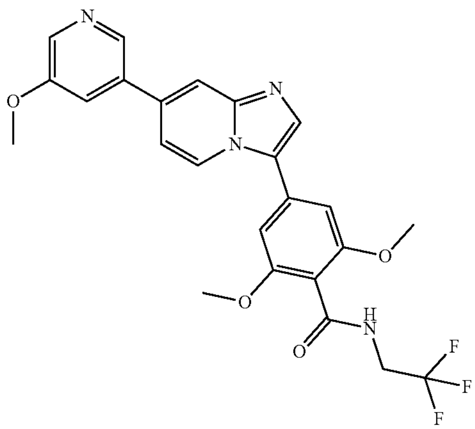 [SMILES: COc1cncc(-c2ccn3c(-c4cc(OC)c(C(=O)NCC(F)(F)F)c(OC)c4)cnc3c2)c1] | 2,6-dimethoxy-4-[7-(5-methoxy-3-pyridyl)imidazo[1,2-a]pyridin-3-yl]-N-(2,2,2-trifluoroethyl)benzamide | Int 46 + CAS# 850991-69-4 | E1.3 | 486.4 | 487.3 |
| 246 | 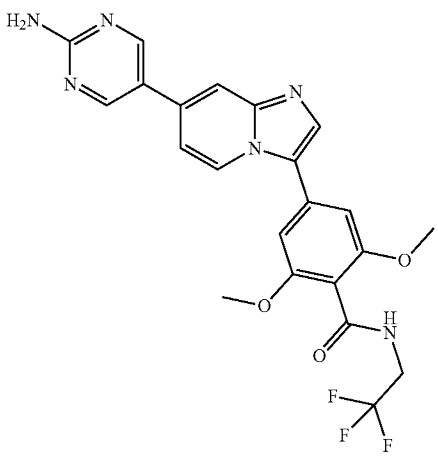 [SMILES: COc1cc(-c2cnc3cc(-c4cnc(N)nc4)ccn23)cc(OC)c1C(=O)NCC(F)(F)F] | 4-[7-(2-aminopyrimidin-5-yl)imidazo[1,2-a]pyridin-3-yl]-2,6-dimethoxy-N-(2,2,2-trifluoroethyl)benzamide | Int 46 + CAS# 936250-22-5 | E1.3 | 472.4 | 473.3 |
| 247 | 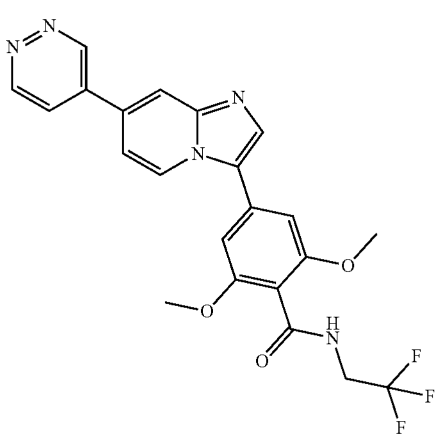 [SMILES: COc1cc(-c2cnc3cc(-c4ccnnc4)ccn23)cc(OC)c1C(=O)NCC(F)(F)F] | 2,6-dimethoxy-4-(7-pyridazin-4-ylimidazo[1,2-a]pyridin-3-yl)-N-(2,2,2-trifluoroethyl)benzamide | Int 46 + CAS# 863422-41-7 | E1.3 | 457.4 | 458.2 |

TABLE III-continued

Illustrative compounds of the invention.

| Cpd # | Structure | Name | SM | Mtd | MW | MS Mes'd |
|---|---|---|---|---|---|---|
| 248 | 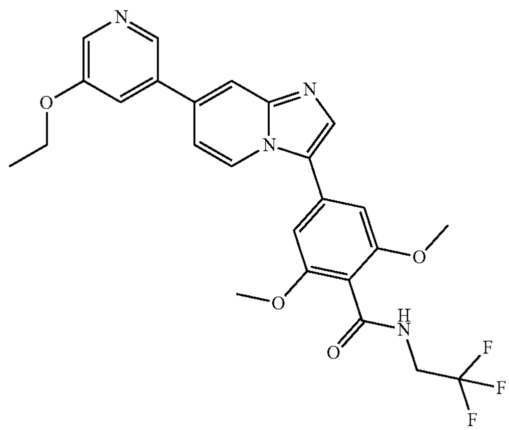 [SMILES: CCOc1cncc(-c2ccn3c(-c4cc(OC)c(C(=O)NCC(F)(F)F)c(OC)c4)cnc3c2)c1] | 4-[7-(5-ethoxy-3-pyridyl)imidazo[1,2-a]pyridin-3-yl]-2,6-dimethoxy-N-(2,2,2-trifluoroethyl)benzamide | Int 46 + CAS# 1224436-34-3 | E1.3 | 500.5 | 501.3 |
| 249 | 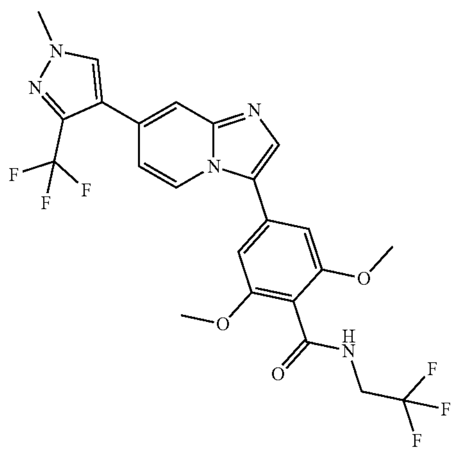 [SMILES: COc1cc(-c2cnc3cc(-c4cn(C)nc4C(F)(F)F)ccn23)cc(OC)c1C(=O)NCC(F)(F)F] | 2,6-dimethoxy-4-[7-[1-methyl-3-(trifluoromethyl)pyrazol-4-yl]imidazo[1,2-a]pyridin-3-yl]-N-(2,2,2-trifluoroethyl)benzamide | Int 46 + CAS# 1218790-53-4 | E1.3 | 527.4 | 528.3 |
| 250 | 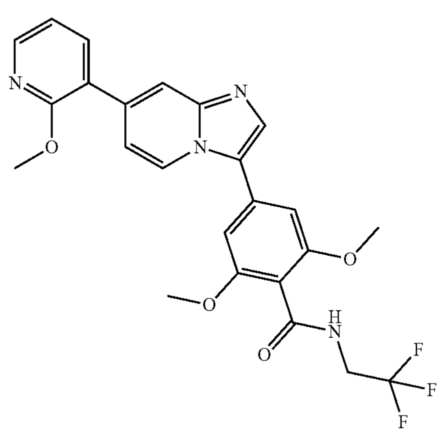 [SMILES: COc1cc(-c2cnc3cc(-c4cccnc4OC)ccn23)cc(OC)c1C(=O)NCC(F)(F)F] | 2,6-dimethoxy-4-[7-(2-methoxy-3-pyridyl)imidazo[1,2-a]pyridin-3-yl]-N-(2,2,2-trifluoroethyl)benzamide | Int 46 + CAS# 163105-90-6 | E1.3 | 486.4 | 487.3 |

TABLE III-continued

Illustrative compounds of the invention.

| Cpd # | Structure | Name | SM | Mtd | MW | MS Mes'd |
|---|---|---|---|---|---|---|
| 251 | 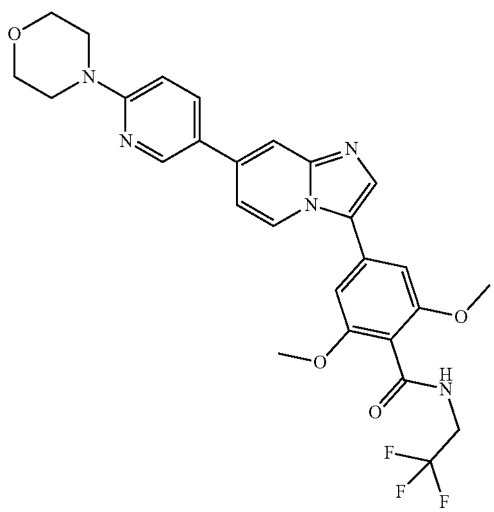 [SMILES: COc1cc(-c2cnc3cc(-c4ccc(N5CCOCC5)nc4)ccn23)cc(OC)c1C(=O)NCC(F)(F)F] | 2,6-dimethoxy-4-[7-(6-morpholino-3-pyridyl)imidazo[1,2-a]pyridin-3-yl]-N-(2,2,2-trifluoroethyl)benzamide | Int 46 + CAS# 904326-93-8 | E1.3 | 541.5 | 542.7 |
| 252 | 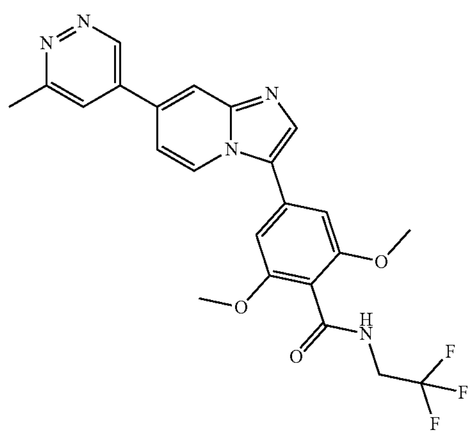 [SMILES: COc1cc(-c2cnc3cc(-c4cnnc(C)c4)ccn23)cc(OC)c1C(=O)NCC(F)(F)F] | 2,6-dimethoxy-4-[7-(6-methylpyridazin-4-yl)imidazo[1,2-a]pyridin-3-yl]-N-(2,2,2-trifluoroethyl)benzamide | Int 46 + CAS# 1350543-95-1 | E1.3 | 471.4 | 472.6 |
| 253 | 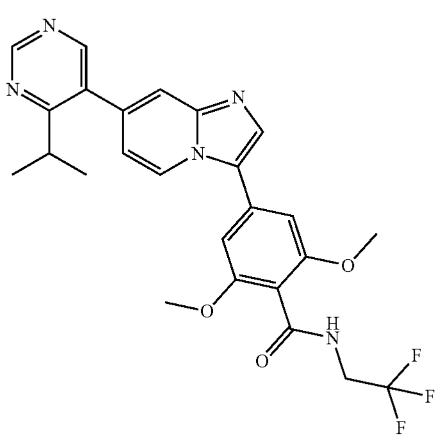 [SMILES: COc1cc(-c2cnc3cc(-c4cncnc4C(C)C)ccn23)cc(OC)c1C(=O)NCC(F)(F)F] | 4-[7-(4-isopropylpyrimidin-5-yl)imidazo[1,2-a]pyridin-3-yl]-2,6-dimethoxy-N-(2,2,2-trifluoroethyl)benzamide | Int 46 + CAS# 913835-27-5 | E1.3 | 499.5 | 500.8 |

TABLE III-continued

Illustrative compounds of the invention.

| Cpd # | Structure | Name | SM | Mtd | MW | MS Mes'd |
|---|---|---|---|---|---|---|
| 254 | 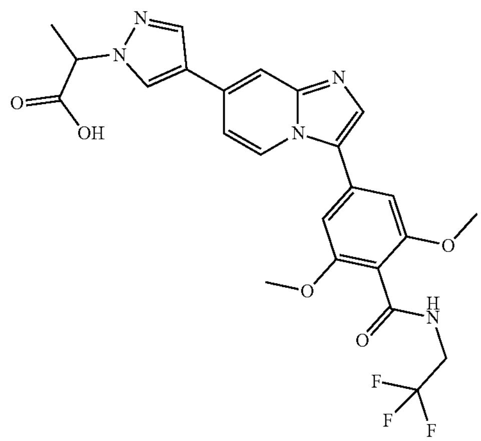 [SMILES: COc1cc(-c2cnc3cc(-c4cnn(C(C)C(=O)O)c4)ccn23)cc(OC)c1C(=O)NCC(F)(F)F] | 2-[4-[3-[3,5-dimethoxy-4-(2,2,2-trifluoroethyl-carbamoyl)phenyl]imidazo[1,2-a]pyridin-7-yl]pyrazol-1-yl]propanoic acid | Cpd 243 | P | 517.5 | 518.3 |
| 255 | 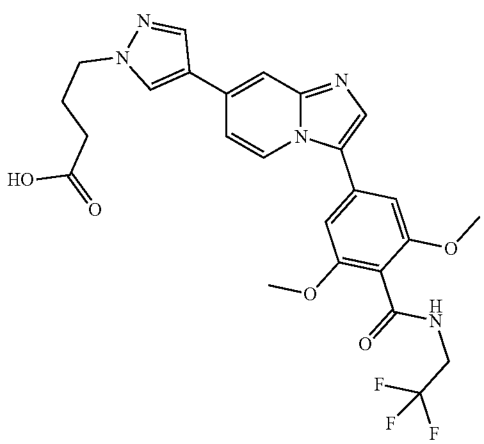 [SMILES: COc1cc(-c2cnc3cc(-c4cnn(CCCC(=O)O)c4)ccn23)cc(OC)c1C(=O)NCC(F)(F)F] | 4-[4-[3-[3,5-dimethoxy-4-(2,2,2-trifluoroethyl-carbamoyl)phenyl]imidazo[1,2-a]pyridin-7-yl]pyrazol-1-yl]butanoic acid | Int 46 + Int 72 | E1.3c | 531.5 | 532.3 |
| 256 | 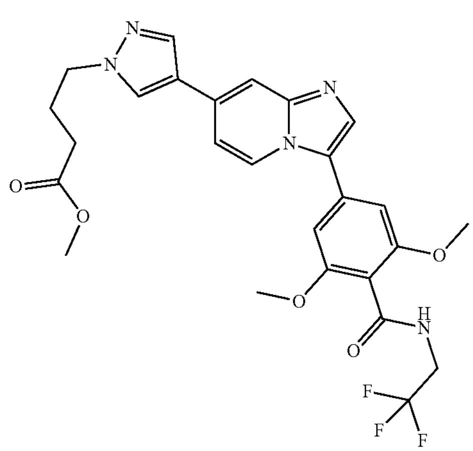 [SMILES: COC(=O)CCCn1cc(-c2ccn3c(-c4cc(OC)c(C(=O)NCC(F)(F)F)c(OC)c4)cnc3c2)cn1] | methyl 4-[4-[3-[3,5-dimethoxy-4-(2,2,2-trifluoroethyl-carbamoyl)phenyl]imidazo[1,2-a]pyridin-7-yl]pyrazol-1-yl]butanoate | Cpd 255 + MeOH | Q2i | 545.5 | 546.3 |

TABLE III-continued

Illustrative compounds of the invention.

| Cpd # | Structure | Name | SM | Mtd | MW | MS Mes'd |
|---|---|---|---|---|---|---|
| 257 | 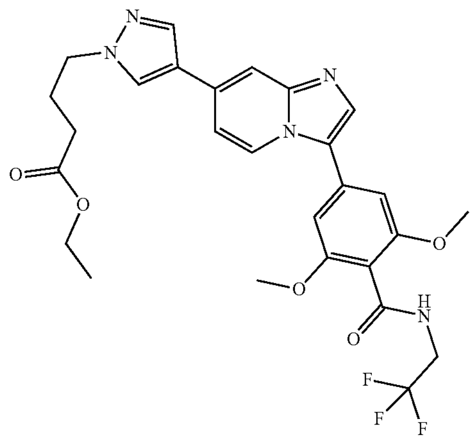 [SMILES: CCOC(=O)CCCn1cc(-c2ccn3c(-c4cc(OC)c(C(=O)NCC(F)(F)F)c(OC)c4)cnc3c2)cn1] | ethyl 4-[4-[3-[3,5-dimethoxy-4-(2,2,2-trifluoroethyl-carbamoyl)phenyl]imidazo[1,2-a]pyridin-7-yl]pyrazol-1-yl]butanoate | Cpd 255 + EtOH | Q2i | 559.5 | 560.3 |
| 258 | 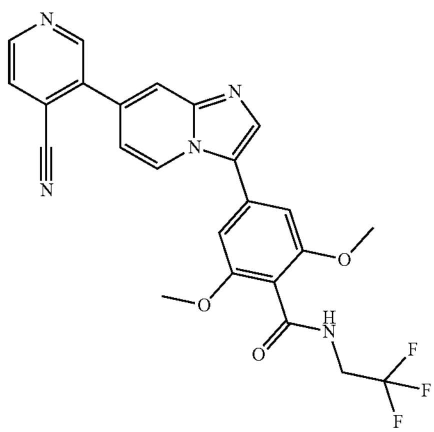 [SMILES: COc1cc(-c2cnc3cc(-c4cnccc4C#N)ccn23)cc(OC)c1C(=O)NCC(F)(F)F] | 4-[7-(4-cyano-3-pyridyl)imidazo[1,2-a]pyridin-3-yl]-2,6-dimethoxy-N-(2,2,2-trifluoroethyl)benzamide | Int 46 + CAS# 878194-91-3 | E1.3b | 481.4 | 482.0 |
| 259 | 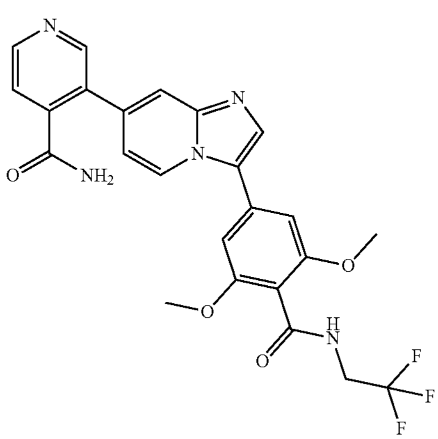 [SMILES: COc1cc(-c2cnc3cc(-c4cnccc4C(N)=O)ccn23)cc(OC)c1C(=O)NCC(F)(F)F] | 3-[3-[3,5-dimethoxy-4-(2,2,2-trifluoroethyl-carbamoyl)phenyl]imidazo[1,2-a]pyridin-7-yl]pyridine-4-carboxamide | Int 46 + CAS# 878194-91-3 | E1.3b | 499.4 | 500.2 |

TABLE III-continued

Illustrative compounds of the invention.

| Cpd # | Structure | Name | SM | Mtd | MW | MS Mes'd |
|---|---|---|---|---|---|---|
| 260 | 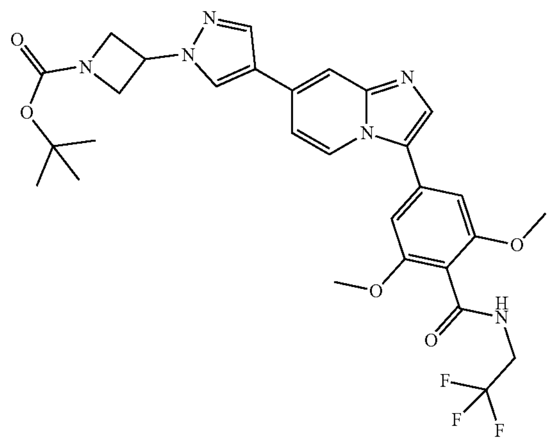 [SMILES: COc1cc(-c2cnc3cc(-c4cnn(C5CN(C(=O)OC(C)(C)C)C5)c4)ccn23)cc(OC)c1C(=O)NCC(F)(F)F] | tert-butyl 3-[4-[3-[3,5-dimethoxy-4-(2,2,2-trifluoroethyl-carbamoyl)phenyl]imidazo[1,2-a]pyridin-7-yl]pyrazol-1-yl]azetidine-1-carboxylate | Int 46 + CAS# 877399-35-4 | E1.3 | 600.6 | 601.4 |
| 261 | 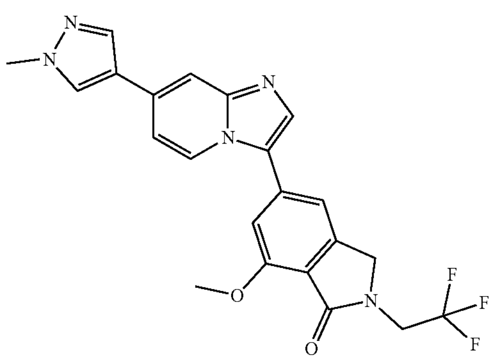 [SMILES: COc1cc(-c2cnc3cc(-c4cnn(C)c4)ccn23)cc2c1C(=O)N(CC(F)(F)F)C2] | 7-methoxy-5-[7-(1-methylpyrazol-4-yl)imidazo[1,2-a]pyridin-3-yl]-2-(2,2,2-trifluoroethyl)isoindolin-1-one | CAS# 1246184-55-3 + Int 25 + CAS# 761446-44-0 + CAS# 6226-25-1 | E1.3 + E1.3 + O | 441.4 | 442.3 |
| 262 | 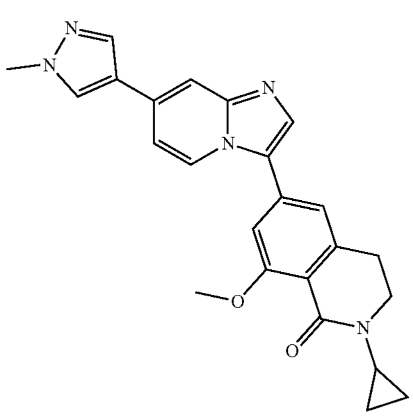 [SMILES: COc1cc(-c2cnc3cc(-c4cnn(C)c4)ccn23)cc2c1C(=O)N(C1CC1)CC2] | 2-cyclopropyl-8-methoxy-6-[7-(1-methylpyrazol-4-yl)imidazo[1,2-a]pyridin-3-yl]-3,4-dihydroisoquinolin-1-one | CAS# 1246184-55-3 + Int 24 + CAS# 761446-44-0 | E1.3 + E1.3 | 413.5 | 414.3 |

TABLE III-continued

Illustrative compounds of the invention.

| Cpd # | Structure | Name | SM | Mtd | MW | MS Mes'd |
|---|---|---|---|---|---|---|
| 263 | 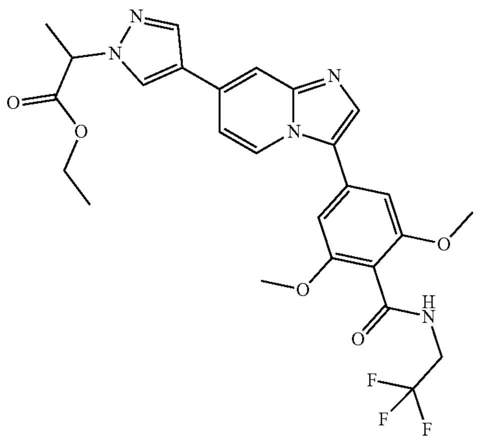 [SMILES: CCOC(=O)C(C)n1cc(-c2ccn3c(-c4cc(OC)c(C(=O)NCC(F)(F)F)c(OC)c4)cnc3c2)cn1] | ethyl 2-[4-[3-[3,5-dimethoxy-4-(2,2,2-trifluoroethyl-carbamoyl)phenyl]imidazo[1,2-a]pyridin-7-yl]pyrazol-1-yl]propanoate | Cpd 243 + EtOH | R | 545.5 | 546.3 |
| 264 | 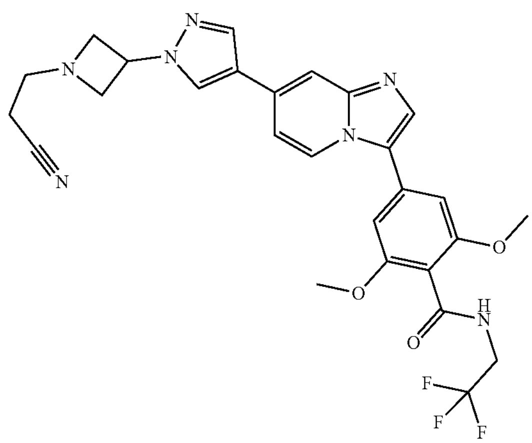 [SMILES: COc1cc(-c2cnc3cc(-c4cnn(C5CN(CCC#N)C5)c4)ccn23)cc(OC)c1C(=O)NCC(F)(F)F] | 4-[7-[1-[1-(2-cyanoethyl)azetidin-3-yl]pyrazol-4-yl]imidazo[1,2-a]pyridin-3-yl]-2,6-dimethoxy-N-(2,2,2-trifluoroethyl)benzamide | Cpd 260 | K + L2ii | 553.5 | 554.3 |
| 265 | 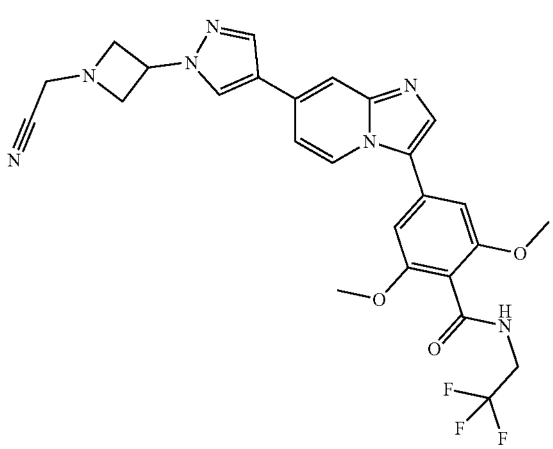 [SMILES: COc1cc(-c2cnc3cc(-c4cnn(C5CN(CC#N)C5)c4)ccn23)cc(OC)c1C(=O)NCC(F)(F)F] | 4-[7-[1-[1-(cyanomethyl)azetidin-3-yl]pyrazol-4-yl]imidazo[1,2-a]pyridin-3-yl]-2,6-dimethoxy-N-(2,2,2-trifluoroethyl)benzamide | Cpd 260 | K + L2i | 593.5 | 540.3 |

TABLE III-continued

Illustrative compounds of the invention.

| Cpd # | Structure | Name | SM | Mtd | MW | MS Mes'd |
|---|---|---|---|---|---|---|
| 266 | 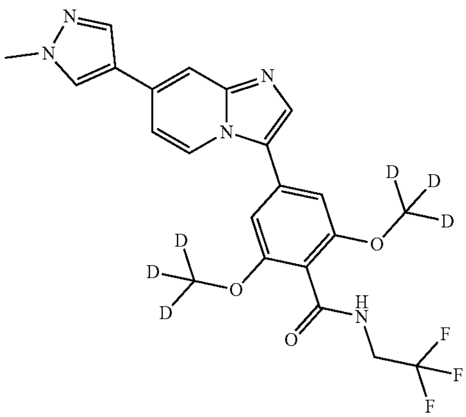 [SMILES: [2H]C([2H])([2H])Oc1cc(-c2cnc3cc(-c4cnn(C)c4)ccn23)cc(OC([2H])([2H])[2H])c1C(=O)NCC(F)(F)F] | 4-[7-(1-methylpyrazol-4-yl)imidazo[1,2-a]pyridin-3-yl]-2,6-bis(trideuterio-methoxy)-N-(2,2,2-trifluoroethyl)benzamide | Int 1 + Int 8 | H | 465.5 | 466.1 |
| 267 | 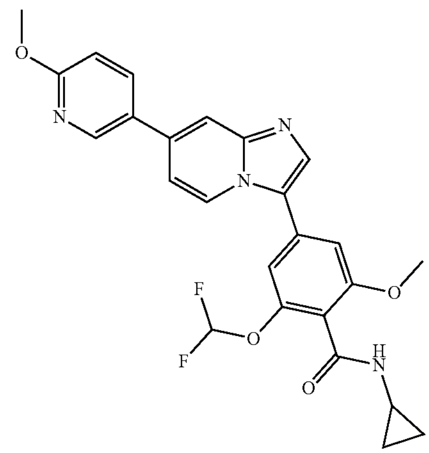 [SMILES: COc1ccc(-c2ccn3c(-c4cc(OC)c(C(=O)NC5CC5)c(OC(F)F)c4)cnc3c2)cn1] | N-cyclopropyl-2-(difluoromethoxy)-6-methoxy-4-[7-(6-methoxy-3-pyridyl)imidazo[1,2-a]pyridin-3-yl]benzamide | Int 37 + CAS# 163105-89-3 | E1.3 | 480.5 | 481.3 |
| 268 | 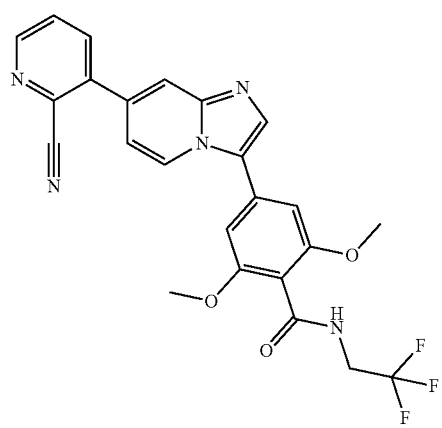 [SMILES: COc1cc(-c2cnc3cc(-c4cccnc4C#N)ccn23)cc(OC)c1C(=O)NCC(F)(F)F] | 4-[7-(2-cyano-3-pyridyl)imidazo[1,2-a]pyridin-3-yl]-2,6-dimethoxy-N-(2,2,2-trifluoroethyl)benzamide | Int 46 + CAS# 55758-02-6 | E4.3ii | 481.4 | 482.2 |

TABLE III-continued

Illustrative compounds of the invention.

| Cpd # | Structure | Name | SM | Mtd | MW | MS Mes'd |
|---|---|---|---|---|---|---|
| 269 | 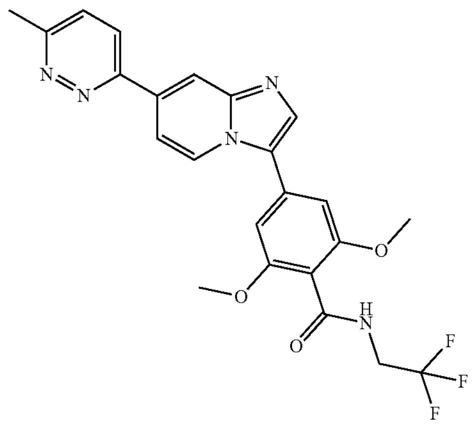 [SMILES: COc1cc(-c2cnc3cc(-c4ccc(C)nn4)ccn23)cc(OC)c1C(=O)NCC(F)(F)F] | 2,6-dimethoxy-4-[7-(6-methylpyridazin-3-yl)imidazo[1,2-a]pyridin-3-yl]-N-(2,2,2-trifluoroethyl)benzamide | Int 46 + CAS# 1121-79-5 | E4.3ii | 471.4 | 472.2 |
| 270 | 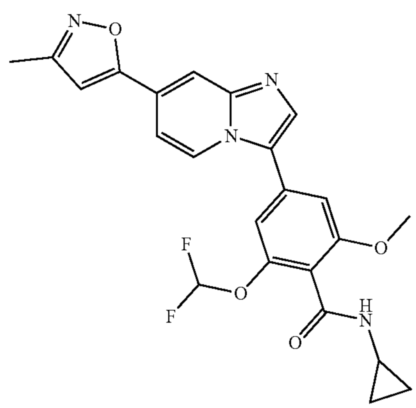 [SMILES: COc1cc(-c2cnc3cc(-c4cc(C)no4)ccn23)cc(OC(F)F)c1C(=O)NC1CC1] | N-cyclopropyl-2-(difluoromethoxy)-6-methoxy-4-[7-(3-methylisoxazol-5-yl)imidazo[1,2-a]pyridin-3-yl]benzamide | Int 37 + CAS# 1346808-44-3 | E1.3 | 454.4 | 455.2 |
| 271 | 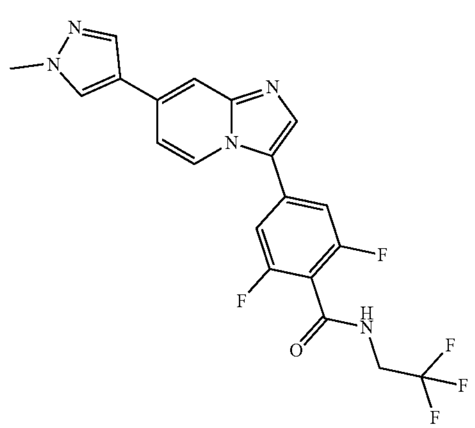 [SMILES: Cn1cc(-c2ccn3c(-c4cc(F)c(C(=O)NCC(F)(F)F)c(F)c4)cnc3c2)cn1] | 2,6-difluoro-4-[7-(1-methylpyrazol-4-yl)imidazo[1,2-a]pyridin-3-yl]-N-(2,2,2-trifluoroethyl)benzamide | Int 1 + Int 4 | H | 435.4 | 436.1 |

TABLE III-continued

Illustrative compounds of the invention.

| Cpd # | Structure | Name | SM | Mtd | MW | MS Mes'd |
|---|---|---|---|---|---|---|
| 272 | 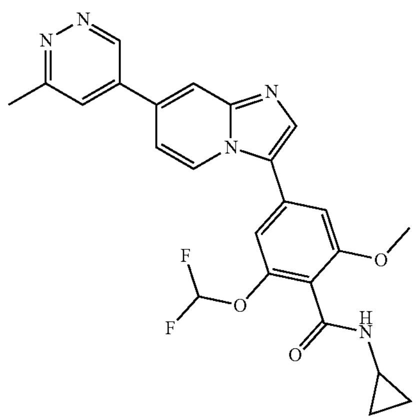 [SMILES: COc1cc(-c2cnc3cc(-c4cnnc(C)c4)ccn23)cc(OC(F)F)c1C(=O)NC1CC1] | N-cyclopropyl-2-(difluoromethoxy)-6-methoxy-4-[7-(6-methylpyridazin-4-yl)imidazo[1,2-a]pyridin-3-yl]benzamide | Int 37 + CAS# 1346808-44-3 | E1.3 | 465.5 | 466.2 |
| 273 | 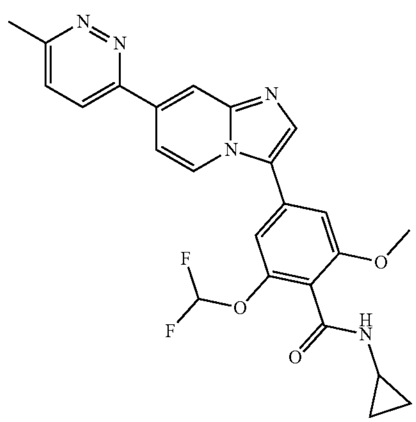 [SMILES: COc1cc(-c2cnc3cc(-c4ccc(C)nn4)ccn23)cc(OC(F)F)c1C(=O)NC1CC1] | N-cyclopropyl-2-(difluoromethoxy)-6-methoxy-4-[7-(6-methylpyridazin-3-yl)imidazo[1,2-a]pyridin-3-yl]benzamide | Int 37 + CAS# 1121-79-5 | E4.3i | 465.5 | 466.3 |
| 274 | 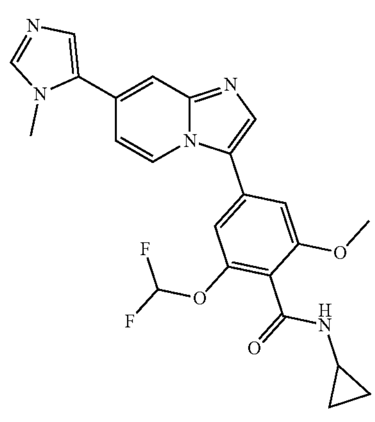 [SMILES: COc1cc(-c2cnc3cc(-c4cncn4C)ccn23)cc(OC(F)F)c1C(=O)NC1CC1] | N-cyclopropyl-2-(difluoromethoxy)-6-methoxy-4-[7-(3-methylimidazol-4-yl)imidazo[1,2-a]pyridin-3-yl]benzamide | Int 37 + CAS# 1003-21-0 | E4.3i | 453.4 | 454.3 |

TABLE III-continued

Illustrative compounds of the invention.

| Cpd # | Structure | Name | SM | Mtd | MW | MS Mes'd |
|---|---|---|---|---|---|---|
| 275 | 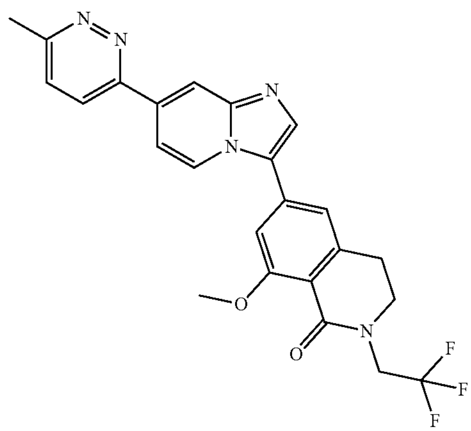 [SMILES: COc1cc(-c2cnc3cc(-c4ccc(C)nn4)ccn23)cc2c1C(=O)N(CC(F)(F)F)CC2] | 8-methoxy-6-[7-(6-methylpyridazin-3-yl)imidazo[1,2-a]pyridin-3-yl]-2-(2,2,2-trifluoroethyl)-3,4-dihydroisoquinolin-1-one | Int 2 + Int 7 | H | 467.4 | 468.3 |
| 276 | 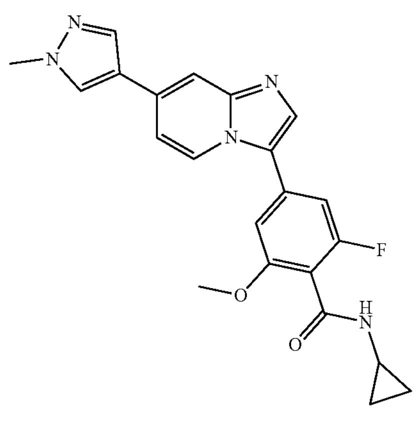 [SMILES: COc1cc(-c2cnc3cc(-c4cnn(C)c4)ccn23)cc(F)c1C(=O)NC1CC1] | N-cyclopropyl-2-fluoro-6-methoxy-4-[7-(1-methylpyrazol-4-yl)imidazo[1,2-a]pyridin-3-yl]benzamide | Int 1 + Int 6 | H | 405.4 | 406.2 |
| 277 | 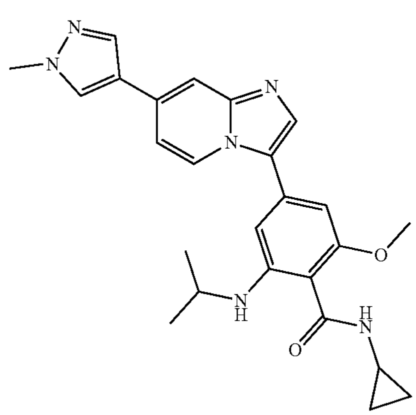 [SMILES: COc1cc(-c2cnc3cc(-c4cnn(C)c4)ccn23)cc(NC(C)C)c1C(=O)NC1CC1] | N-cyclopropyl-2-(isopropylamino)-6-methoxy-4-[7-(1-methylpyrazol-4-yl)imidazo[1,2-a]pyridin-3-yl]benzamide | Cpd 276 + CAS# 75-31-0 | M1 | 444.5 | 445.4 |

TABLE III-continued

Illustrative compounds of the invention.

| Cpd # | Structure | Name | SM | Mtd | MW | MS Mes'd |
|---|---|---|---|---|---|---|
| 278 | 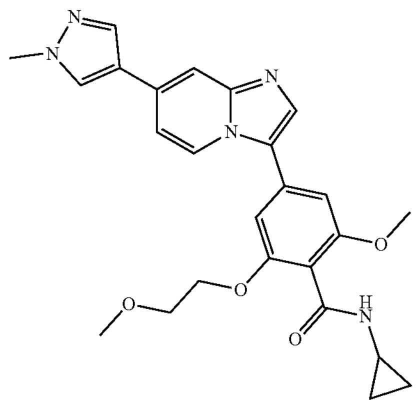 [SMILES: COCCOc1cc(-c2cnc3cc(-c4cnn(C)c4)ccn23)cc(OC)c1C(=O)NC1CC1] | N-cyclopropyl-2-methoxy-6-(2-methoxyethoxy)-4-[7-(1-methylpyrazol-4-yl)imidazo[1,2-a]pyridin-3-yl]benzamide | Cpd 276 + CAS# 109-86-4 | M2 | 461.5 | 462.3 |
| 279 | 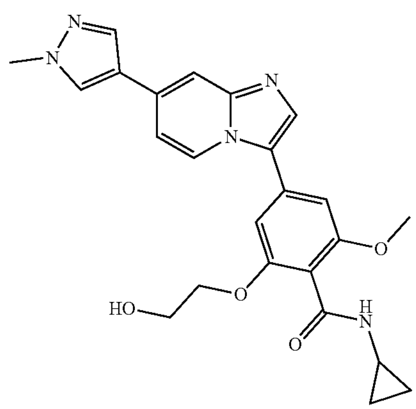 [SMILES: COc1cc(-c2cnc3cc(-c4cnn(C)c4)ccn23)cc(OCCO)c1C(=O)NC1CC1] | N-cyclopropyl-2-(2-hydroxyethoxy)-6-methoxy-4-[7-(1-methylpyrazol-4-yl)imidazo[1,2-a]pyridin-3-yl]benzamide | Cpd 276 + CAS# 107-21-1 | M2 | 447.5 | 448.4 |
| 280 | 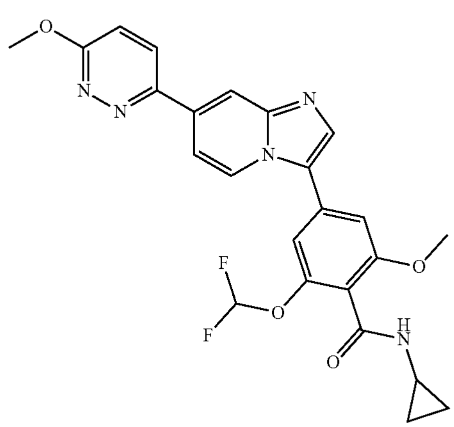 [SMILES: COc1ccc(-c2ccn3c(-c4cc(OC)c(C(=O)NC5CC5)c(OC(F)F)c4)cnc3c2)nn1] | N-cyclopropyl-2-(difluoromethyl)-6-methoxy-4-[7-(6-methoxypyridazin-3-yl)imidazo[1,2-a]pyridin-3-yl]benzamide | Int 37 + CAS# 17321-29-8 | E4.3i | 481.5 | 482.5 |

TABLE III-continued

Illustrative compounds of the invention.

| Cpd # | Structure | Name | SM | Mtd | MW | MS Mes'd |
|---|---|---|---|---|---|---|
| 281 | 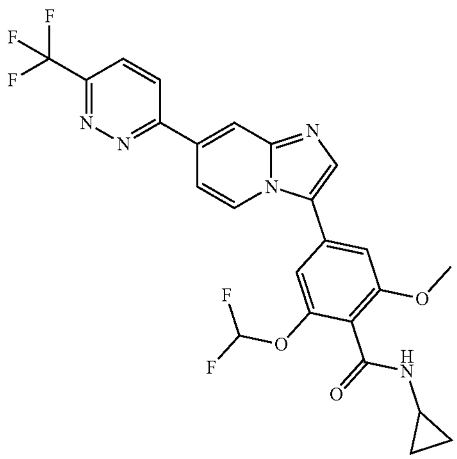 [SMILES: COc1cc(-c2cnc3cc(-c4ccc(C(F)(F)F)nn4)ccn23)cc(OC(F)F)c1C(=O)NC1CC1] | N-cyclopropyl-2-(difluoromethoxy)-6-methoxy-4-[7-[6-(trifluoromethyl)pyridazin-3-yl]imidazo[1,2-a]pyridin-3-yl]benzamide | Int 37 + CAS# 174607-37-5 | E4.3i | 519.4 | 520.4 |
| 282 | 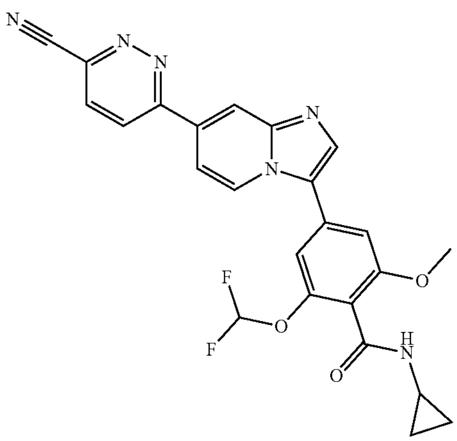 [SMILES: COc1cc(-c2cnc3cc(-c4ccc(C#N)nn4)ccn23)cc(OC(F)F)c1C(=O)NC1CC1] | 4-[7-(6-cyanopyridazin-3-yl)imidazo[1,2-a]pyridin-3-yl]-N-cyclopropyl-2-(difluoromethoxy)-6-methoxy-benzamide | Int 37 + CAS# 1027513-40-1 | E4.3i | 476.4 | 477.4 |
| 283 | 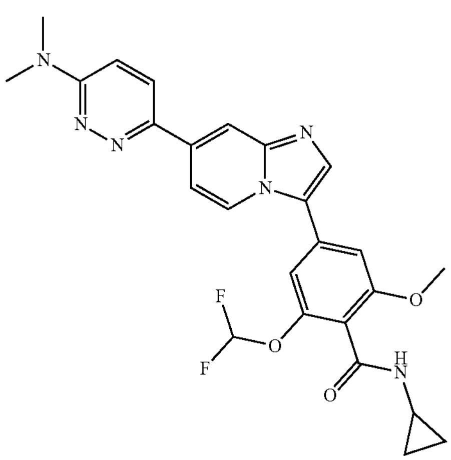 [SMILES: COc1cc(-c2cnc3cc(-c4ccc(N(C)C)nn4)ccn23)cc(OC(F)F)c1C(=O)NC1CC1] | N-cyclopropyl-2-(difluoromethoxy)-4-[7-[6-(dimethylamino)pyridazin-3-yl]imidazo[1,2-a]pyridin-3-yl]-6-methoxy-benzamide | Int 37 + CAS# 14959-33-2 | E4.3i | 494.5 | 495.4 |

TABLE III-continued

Illustrative compounds of the invention.

| Cpd # | Structure | Name | SM | Mtd | MW | MS Mes'd |
|---|---|---|---|---|---|---|
| 284 | 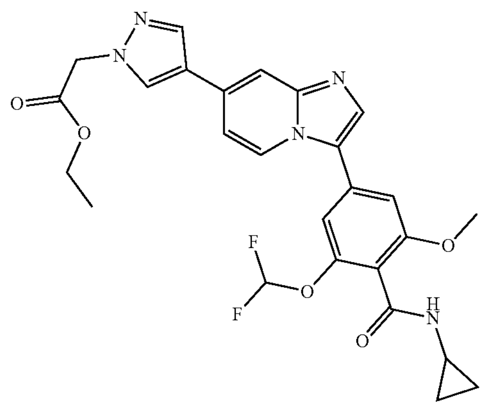 [SMILES: CCOC(=O)Cn1cc(-c2ccn3c(-c4cc(OC)c(C(=O)NC5CC5)c(OC(F)F)c4)cnc3c2)cn1] | ethyl 2-[4-[3-[4-(cyclopropyl-carbamoyl)-3-(difluoromethoxy)-5-methoxy-phenyl]imidazo[1,2-a]pyridin-7-yl]pyrazol-1-yl]acetate | Int 37 + CAS# 864754-16-5 | E1.3a | 525.4 | 526.4 |
| 285 | 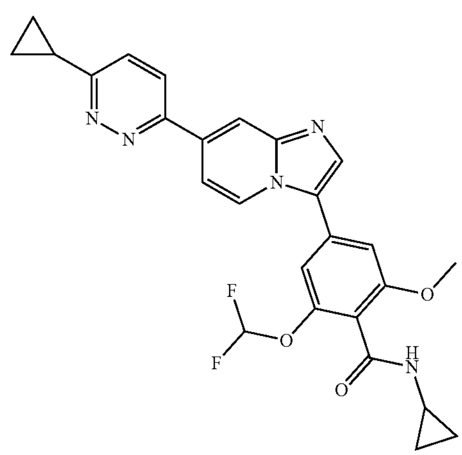 [SMILES: COc1cc(-c2cnc3cc(-c4ccc(C5CC5)nn4)ccn23)cc(OC(F)F)c1C(=O)NC1CC1] | N-cyclopropyl-4-[7-(6-cyclo-propylpyridazin-3-yl)imidazo[1,2-a]pyridin-3-yl]-2-(difluoromethoxy)-6-methoxy-benzamide | Int 37 + CAS# 1046816-38-9 | E4.3i | 491.5 | 492.4 |
| 286 | 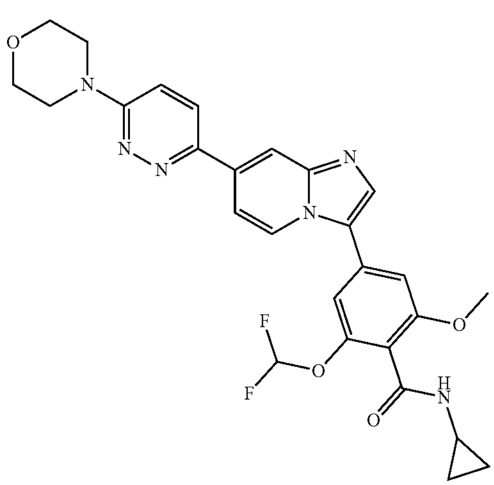 [SMILES: COc1cc(-c2cnc3cc(-c4ccc(N5CCOCC5)nn4)ccn23)cc(OC(F)F)c1C(=O)NC1CC1] | N-cyclopropyl-2-(difluoromethoxy)-6-methoxy-4-[7-(6-morpholino-pyridazin-3-yl)imidazo[1,2-a]pyridin-3-yl]benzamide | Int 37 + CAS# 927673-86-7 | E4.3i | 536.5 | 537.4 |

TABLE III-continued

Illustrative compounds of the invention.

| Cpd # | Structure | Name | SM | Mtd | MW | MS Mes'd |
|---|---|---|---|---|---|---|
| 291 | 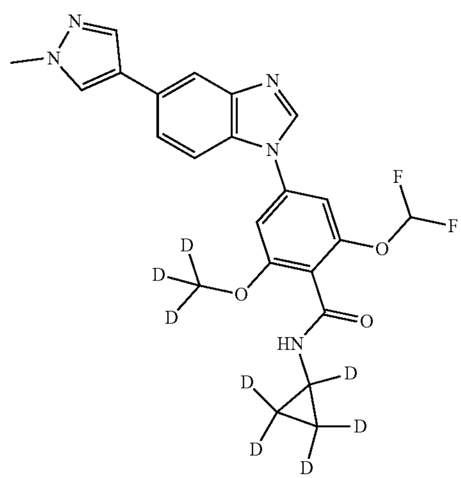 [SMILES: [2H]C([2H])([2H])Oc1cc(-n2cnc3cc(-c4cnn(C)c4)ccc32)cc(OC(F)F)c1C(=O)NC1([2H])C([2H])([2H])C1([2H])[2H]] | 2-(difluoromethoxy)-4-[5-(1-methylpyrazol-4-yl)benzimidazol-1-yl]-N-(1,2,2,3,3-pentadeutericyclopropyl)-6-(trideuteriomethoxy)benzamide | Int 69 | C3 (cf. Ex. 2.49) | 461.5 | 462.1 |
| 292 | 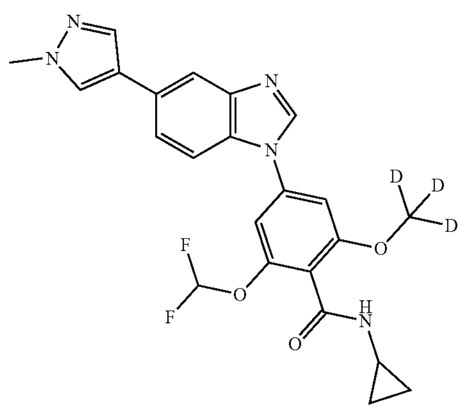 [SMILES: [2H]C([2H])([2H])Oc1cc(-n2cnc3cc(-c4cnn(C)c4)ccc32)cc(OC(F)F)c1C(=O)NC1CC1] | N-cyclopropyl-2-(difluoromethoxy)-4-[5-(1-methylpyrazol-4-yl)benzimidazol-1-yl]-6-(trideuteriomethoxy)benzamide | Int 70 + Int 56 | E2.3 + C3 (cf. Ex. 2.50) | 456.4 | 457.2 |
| 293 | 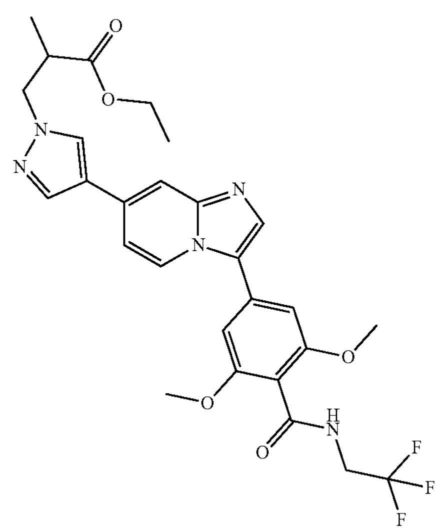 [SMILES: CCOC(=O)C(C)Cn1cc(-c2ccn3c(-c4cc(OC)c(C(=O)NCC(F)(F)F)c(OC)c4)cnc3c2)cn1] | ethyl 3-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate | Int 76 | Ex. 2.51 | 559.5 | 560.7 |

TABLE III-continued

Illustrative compounds of the invention.

| Cpd # | Structure | Name | SM | Mtd | MW | MS Mes'd |
|---|---|---|---|---|---|---|
| 294 | 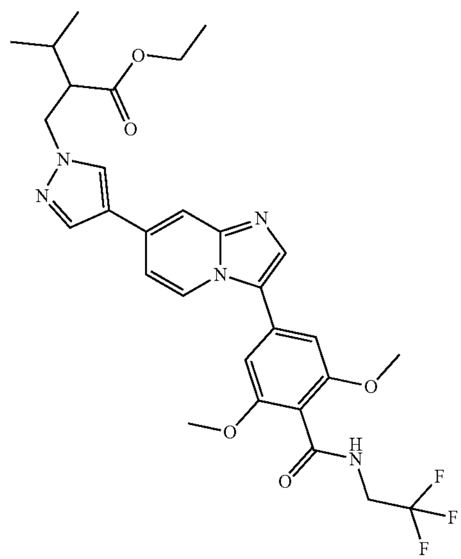 [SMILES: CCOC(=O)C(Cn1cc(-c2ccn3c(-c4cc(OC)c(C(=O)NCC(F)(F)F)c(OC)c4)cnc3c2)cn1)C(C)C] | ethyl 2-[[4-[3-[3,5-dimethoxy-4-(2,2,2-trifluoroethyl-carbamoyl)phenyl]imidazo[1,2-a]pyridin-7-yl]pyrazol-1-yl]methyl]-3-methyl-butanoate | Int 76 | Ex. 2.52 | 587.6 | 588.3 |
| 295 | 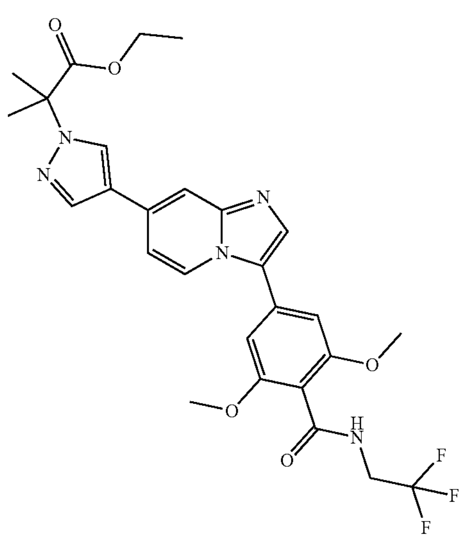 [SMILES: CCOC(=O)C(C)(C)n1cc(-c2ccn3c(-c4cc(OC)c(C(=O)NCC(F)(F)F)c(OC)c4)cnc3c2)cn1] | ethyl 2-[4-[3-[3,5-dimethoxy-4-(2,2,2-trifluoroethyl-carbamoyl)phenyl]imidazo[1,2-a]pyridin-7-yl]pyrazol-1-yl]-2-methyl-propanoate | Int 76 | Ex. 2.53 | 559.5 | 560.2 |

TABLE III-continued

Illustrative compounds of the invention.

| Cpd # | Structure | Name | SM | Mtd | MW | MS Mes'd |
|---|---|---|---|---|---|---|
| 296 | 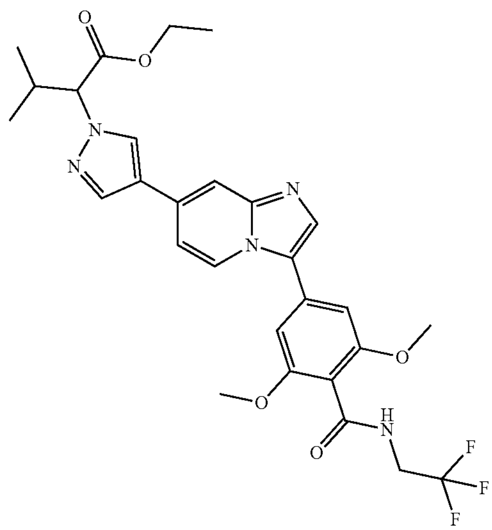 [SMILES: CCOC(=O)C(C(C)C)n1cc(-c2ccn3c(-c4cc(OC)c(C(=O)NCC(F)(F)F)c(OC)c4)cnc3c2)cn1] | ethyl 2-[4-[3-[3,5-dimethoxy-4-(2,2,2-trifluoroethyl-carbamoyl)phenyl]imidazo[1,2-a]pyridin-7-yl]pyrazol-1-yl]-3-methyl-butanoate | Int 76 | Ex. 2.54 | 573.6 | 574.2 |
| 297 | 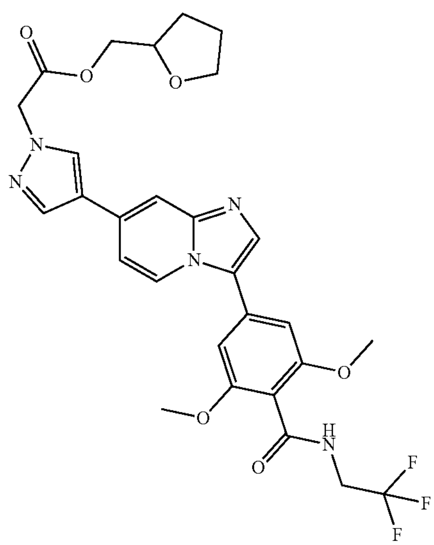 [SMILES: COc1cc(-c2cnc3cc(-c4cnn(CC(=O)OCC5CCCO5)c4)ccn23)cc(OC)c1C(=O)NCC(F)(F)F] | tetrahydrofuran-2-ylmethyl 2-[4-[3-[3,5-dimethoxy-4-(2,2,2-trifluoroethyl-carbamoyl)phenyl]imidazo[1,2-a]pyridin-7-yl]pyrazol-1-yl]acetate | Cpd 228 | Ex. 2.55 | 587.5 | 588.3 |
| 298 | 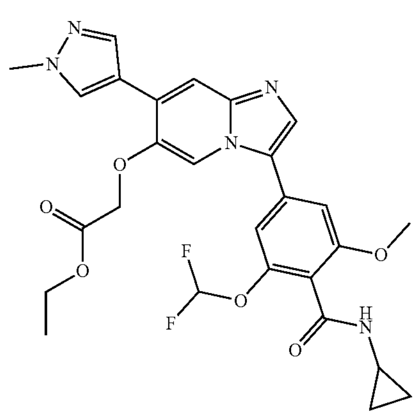 [SMILES: CCOC(=O)COc1cn2c(-c3cc(OC)c(C(=O)NC4CC4)c(OC(F)F)c3)cnc2cc1-c1cnn(C)c1] | ethyl 2-[3-[4-(cyclopropyl-carbamoyl)-3-(difluoromethoxy)-5-methoxy-phenyl]-7-(1-methylpyrazol-4-yl)imidazo[1,2-a]pyridin-6-yl]oxyacetate | Int 77 | Ex. 2.56 | 555.5 | 556.3 |

TABLE III-continued

Illustrative compounds of the invention.

| Cpd # | Structure | Name | SM | Mtd | MW | MS Mes'd |
|---|---|---|---|---|---|---|
| 299 | 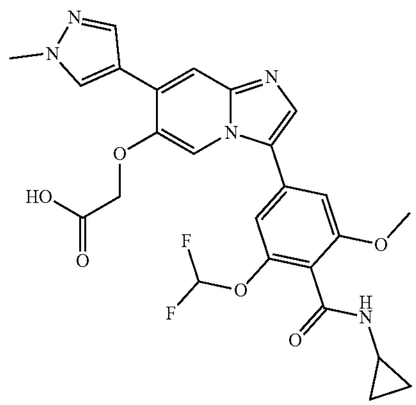 [SMILES: COc1cc(-c2cnc3cc(-c4cnn(C)c4)c(OCC(=O)O)cn23)cc(OC(F)F)c1C(=O)NC1CC1] | 2-[3-[4-(cyclopropyl-carbamoyl)-3-(difluoromethoxy)-5-methoxy-phenyl]-7-(1-methylpyrazol-4-yl)imidazo[1,2-a]pyridin-6-yl]oxyacetic acid | Cpd 298 | Ex. 2.57 | 527.5 | 528.2 |
| 300 | 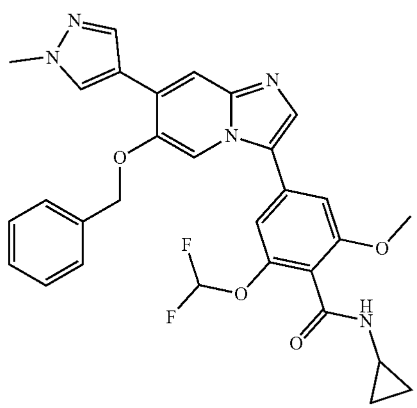 [SMILES: COc1cc(-c2cnc3cc(-c4cnn(C)c4)c(OCc4ccccc4)cn23)cc(OC(F)F)c1C(=O)NC1CC1] | 4-[6-benzyloxy-7-(1-methylpyrazol-4-yl)imidazo[1,2-a]pyridin-3-yl]-N-cyclopropyl-2-(difluoromethoxy)-6-methoxy-benzamide | Int 77 | Ex. 258 | 559.6 | 560.3 |
| 301 | 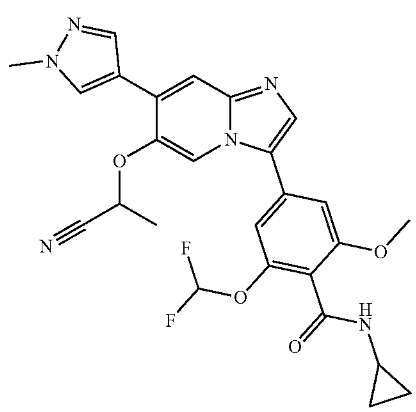 [SMILES: COc1cc(-c2cnc3cc(-c4cnn(C)c4)c(OC(C)C#N)cn23)cc(OC(F)F)c1C(=O)NC1CC1] | 4-[6-(1-cyano-methoxy)-7-(1-methylpyrazol-4-yl)imidazo[1,2-a]pyridin-3-yl]-N-cyclopropyl-2-(difluoromethoxy)-6-methoxy-benzamide | CAS# 942947-94-6 | Ex. 2.59 | 522.5 | 523.2 |

TABLE III-continued

Illustrative compounds of the invention.

| Cpd # | Structure | Name | SM | Mtd | MW | MS Mes'd |
|---|---|---|---|---|---|---|
| 302 | 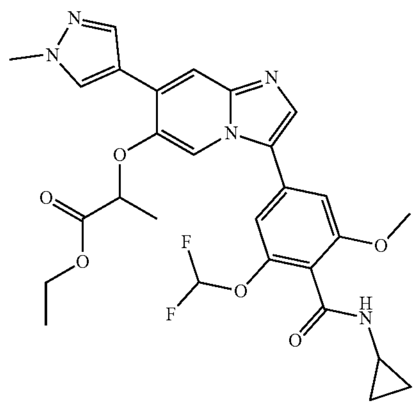 [SMILES: CCOC(=O)C(C)Oc1cn2c(-c3cc(OC)c(C(=O)NC4CC4)c(OC(F)F)c3)cnc2cc1-c1cnn(C)c1] | ethyl 2-[3-[4-(cyclopropyl-carbamoyl)-3-(difluoromethoxy)-5-methoxy-phenyl]-7-(1-methylpyrazol-4-yl)imidazo[1,2-a]pyridin-6-yl]oxypropanoate | Cpd 301 | Ex. 2.60 | 569.6 | 570.4 |
| 303 | 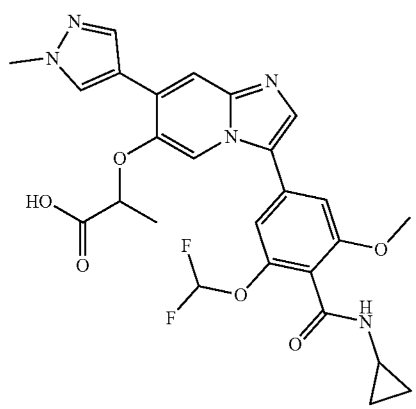 [SMILES: COc1cc(-c2cnc3cc(-c4cnn(C)c4)c(OC(C)C(=O)O)cn23)cc(OC(F)F)c1C(=O)NC1CC1] | 2-[3-[4-(cyclopropyl-carbamoyl)-3-(difluoromethoxy)-5-methoxy-phenyl]-7-(1-methylpyrazol-4-yl)imidazo[1,2-a]pyridin-6-yl]oxypropanoate acid | Cpd 302 | Ex. 2.61 | 541.5 | 542.3 |
| 304 | 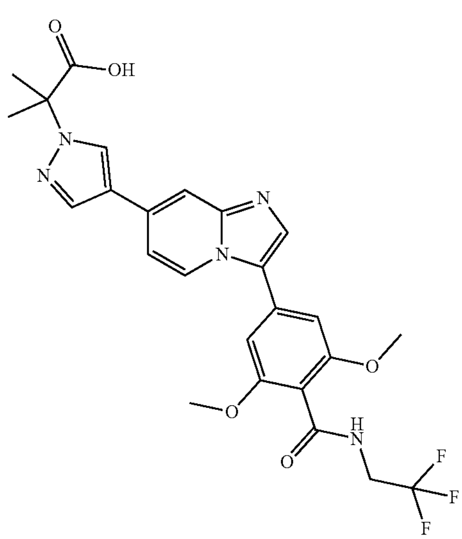 [SMILES: COc1cc(-c2cnc3cc(-c4cnn(C(C)(C)C(=O)O)c4)ccn23)cc(OC)c1C(=O)NCC(F)(F)F] | 2-[4-[3-[3,5-dimethoxy-4-(2,2,2-trifluoroethyl-carbamoyl)phenyl]imidazo[1,2-a]pyridin-7-yl]pyrazol-1-yl]-2-methyl-propanoic acid | Cpd 295 | Ex. 2.62 | 531.5 | 532.5 |

TABLE III-continued

Illustrative compounds of the invention.

| Cpd # | Structure | Name | SM | Mtd | MW | MS Mes'd |
|---|---|---|---|---|---|---|
| 305 | 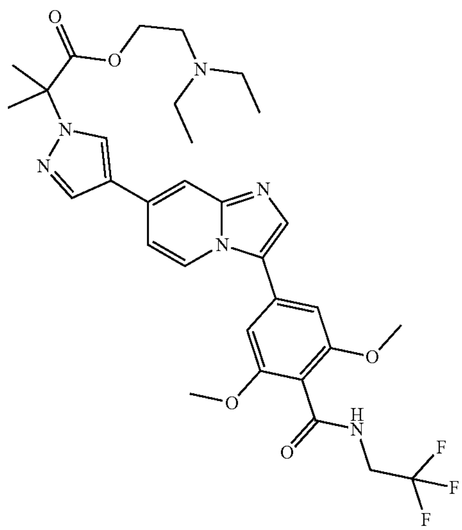 [SMILES: CCN(CC)CCOC(=O)C(C)(C)n1cc(-c2ccn3c(-c4cc(OC)c(C(=O)NCC(F)(F)F)c(OC)c4)cnc3c2)cn1] | 2-(diethylamino)ethyl 2-[4-[3-[3,5-dimethoxy-4-(2,2,2-trifluoroethyl-carbamoyl)phenyl]imidazo[1,2-a]pyridin-7-yl]pyrazol-1-yl]-2-methyl-propanoate | Cpd 304 | Ex. 2.63 | 630.7 | 631.7 |
| 306 | 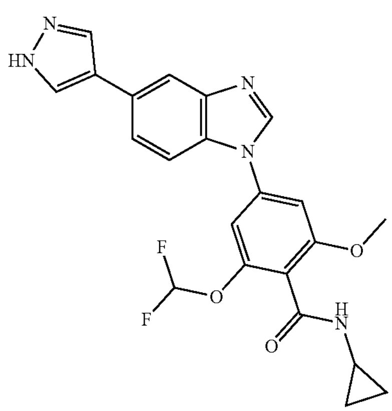 [SMILES: COc1cc(-n2cnc3cc(-c4cn[nH]c4)ccc32)cc(OC(F)F)c1C(=O)NC1CC1] | N-cyclopropyl-2-(difluoromethoxy)-6-methoxy-4-[5-(1H-pyrazol-4-yl)benzimidazol-1-yl]benzamide | Int 42 + CAS# 269410-08-4 | E1.3 | 439.4 | 440.3 |
| 307 | 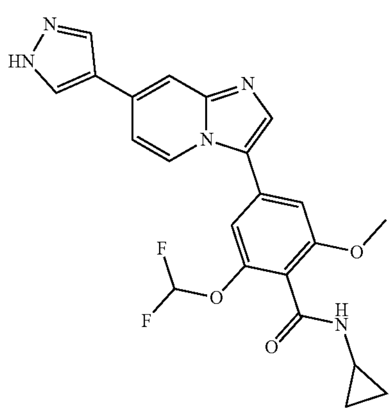 [SMILES: COc1cc(-c2cnc3cc(-c4cn[nH]c4)ccn23)cc(OC(F)F)c1C(=O)NC1CC1] | N-cyclopropyl-2-(difluoromethoxy)-6-methoxy-4-[7-(1H-pyrazol-4-yl)imidazo[1,2-a]pyridin-3-yl]benzamide | Int 37 + CAS# 269410-08-4 | E1.3 | 439.4 | 440.8 |

SM = Starting Material, Mtd = Method, MS Mes'd = Mesured mass

TABLE IV

NMR data of illustrative compounds of the invention.

| Cpd# | NMR data |
|---|---|
| 17 | $^1$H NMR (400 MHz, CDCl$_3$) δ 8.23 (s, 1H), 7.98 (s, 1H), 7.83 (s, 1H), 7.72 (s, 1H), 7.57-7.47 (m, 2H), 7.02 (s, 2H), 6.88-6.46 (m, 1H), 5.98 (t, 1H), 4.25 (q, 2H), 3.94 (s, 3H), 3.60-3.50 (m, 2H), 1.57 (t, 3H), 1.29 (t, 3H) |
| 25 | $^1$H NMR (400 MHz, DMSO-d$_6$) δ 8.88 (t, 1H), 8.61 (s, 1H), 8.19 (s, 1H), 7.98 (s, 1H), 7.93 (s, 1H), 7.71 (d, 1H), 7.58 (d, 1H), 7.02 (s, 2H), 4.07-3.96 (m, 2H), 3.88 (s, 3H), 3.84 (s, 6H) |
| 26 | $^1$H NMR (400 MHz, DMSO-d$_6$) δ 8.59 (s, 1H), 8.40 (d, 1H), 8.24 (s, 1H), 7.99 (s, 1H), 7.93 (s, 1H), 7.68 (d, 1H), 6.98 (s, 2H), 4.38-4.26 (m, 1H), 4.16 (q, 2H), 3.83 (s, 6H), 2.26-2.17 (m, 2H), 2.01-1.88 (m, 2H), 1.70-1.59 (m, 2H), 1.42 (t, 3H), 1.31-1.21 (m, 1H) |
| 48 | $^1$H NMR (400 MHz, DMSO-d$_6$) δ 7.99 (s, 1H), 7.94 (s, 1H), 7.69 (d, 1H), 7.59 (d, 1H), 7.33-7.06 (m, 3H), 8.62 (s, 1H), 8.35 (t, 1H), 8.19 (s, 1H), 3.89 (s, 6H), 3.28-3.14 (m, 2H), 1.10 (t, 3H) |
| 52 | $^1$H NMR (400 MHz, CDCl$_3$) δ 8.77-8.74 (m, 2H), 8.44 (s, 1H), 7.82 (s, 1H), 7.73 (s, 1H), 7.36 (s, 2H), 6.16 (t, 1H), 4.20-4.10 (m, 2H), 4.03 (s, 3H), 3.96 (s, 6H) |
| 53 | $^1$H NMR (400 MHz, DMSO-d$_6$) δ ppm 8.62 (1H, s), 8.42 (1H, d), 8.19 (1H, s), 7.99 (1H, s), 7.94 (1H, s), 7.69-7.59 (2H, m), 7.46-7.10 (2H, m), 7.15 (1H, s), 3.91 (3H, s), 3.88 (3H, s), 2.81 (1H, m), 0.70 (2H, m), 0.48 (2H, m) |
| 86 | $^1$H NMR (400 MHz, DMSO-d$_6$) δ 8.64 (s, 1H), 8.22-8.18 (m, 2H), 7.98 (s, 1H), 7.93 (d, 1H), 7.69 (d, 1H), 7.59 (dd, 1H), 6.98 (s, 2H), 3.88 (s, 3H), 3.83 (s, 6H), 2.83-2.77 (m, 1H), 0.69-0.62 (m, 2H), 0.48-0.43 (m, 2H) |
| 88 | $^1$H NMR (400 MHz, DMSO-d$_6$) δ 8.81 (t, 1H), 8.62 (d, 1H), 8.35 (s, 1H), 8.08 (s, 1H), 7.88 (s, 1H), 7.81 (s, 1H), 7.25 (d, 1H), 6.95 (s, 2H), 4.09-3.94 (m, 2H), 3.90 (s, 3H), 3.83 (s, 6H) |
| 124 | $^1$H NMR (400 MHz, CDCl$_3$) δ 8.27 (d, 1H), 7.86 (s, 1H), 7.72 (s, 3H), 7.11-6.99 (m, 2H), 7.02-6.94 (m, 1H), 6.86-6.44 (m, 1H), 6.04 (s, 1H), 4.00 (s, 3H), 3.92 (s, 3H), 3.00-2.92 (m, 1H), 0.96-0.87 (m, 2H), 0.71-0.62 (m, 2H) |
| 173 | $^1$H NMR (400 MHz, CDCl$_3$) δ 8.30 (d, 1H), 7.97 (s, 1H), 7.90 (s, 1H), 7.86 (s, 1H), 7.76 (s, 1H), 7.15 (d, 1H), 6.74 (s, 2H), 4.57 (t, 2H), 4.31 (t, 2H), 4.02 (s, 3H), 3.92 (s, 6H) |
| 174 | $^1$H NMR (400 MHz, DMSO-d$_6$) δ 8.69 (d, 1H), 8.60 (d, 1H), 8.35 (s, 1H), 8.08 (s, 1H), 7.87 (s, 1H), 7.80 (s, 1H), 7.25 (d, 1H), 6.95 (s, 2H), 4.78-4.67 (m, 1H), 3.90 (s, 3H), 3.83 (s, 6H), 1.28 (d, 3H) |
| 203 | $^1$H NMR (400 MHz, CDCl$_3$) δ 8.33 (s, 1H), 7.87 (s, 1H), 7.78-7.75 (m, 2H), 7.74 (s, 1H), 7.04 (dd, 2H), 6.93 (s, 1H), 6.61 (t, 1H), 4.23-4.12 (m, 2H), 3.99 (s, 6H) |
| 204 | $^1$H NMR (400 MHz, CDCl$_3$) δ 8.76 (d, 1H), 8.35 (d, 1H), 8.25 (t, 1H), 7.77 (s, 1H), 7.67 (s, 1H), 7.65 (s, 2H), 6.93 (d, 1H), 6.46 (s, 1H), 6.30 (s, 1H), 4.10-3.99 (m, 2H), 3.92 (s, 6H), 2.85 (d, 3H) |
| 206 | $^1$H NMR (400 MHz, DMSO-d$_6$) δ 8.97 (t, 1H), 8.58 (d, 1H), 8.35 (s, 1H), 8.08 (s, 1H), 7.87 (s, 1H), 7.77 (s, 1H), 7.24 (d, 1H), 7.16 (d, 2H), 4.14-4.00 (m, 2H), 3.90 (s, 3H), 3.84 (s, 3H), 2.27 (s, 3H) |
| 230 | $^1$H NMR (400 MHz, DMSO-d$_6$) δ 8.80 (t, 1H), 8.63 (d, 1H), 8.39 (s, 1H), 8.16 (s, 1H), 7.91 (s, 1H), 7.82 (s, 1H), 7.26 (d, 1H), 6.96 (s, 2H), 5.12 (s, 2H), 4.19 (q, 2H), 4.09-3.93 (m, 2H), 3.83 (s, 6H), 1.23 (t, 3H) |
| 266 | $^1$H NMR (400 MHz, DMSO-d$_6$) δ 8.81 (t, 1H), 8.62 (d, 1H), 8.35 (s, 1H), 8.08 (s, 1H), 7.88 (s, 1H), 7.81 (s, 1H), 7.25 (d, 1H), 6.95 (s, 2H), 4.07-3.95 (m, 2H), 3.90 (s, 3H) |
| 291 | $^1$H NMR (400 MHz, DMSO-d$_6$) δ 8.19 (s, 1H), 8.61 (s, 1H), 8.39 (s, 1H), 7.96 (s, 2H), 7.64 (dd, 2H), 7.46-7.06 (m, 3H), 3.88 (s, 3H) |

Biological Examples

Example 3. In Vitro Assays 3.1. Biochemical Assays 3.1.1. $^{33}$P Radioactive Kinase Assay 3.1.1.1. Overview The principle of the $^{33}$P radioactive kinase assay consists in measuring the incorporated $^{33}$P into the substrate AMARA peptide when phosphorylated by SIK1, SIK2 or SIK3 using [$^{33}$P]-g-ATP, which correlates with kinase activity.

3.1.1.2. Protocol

The test compounds are prepared as a serial dilution of 10 point dose responses with 1/5 dilution steps in 100% DMSO starting from 2 mM highest concentration, diluted 1/20 in water and 5 μL is transferred to the assay plates (Greiner, Cat #651201).

1% DMSO and 10 μM staurosporine final concentrations are used as negative and positive controls.

11 μL of enzyme-substrate mixture is added on the assay plates. The reactions are started by adding 9 μL ATP mixture, consisting of non-labeled and $^{33}$P-labeled ATP, on the assay plates. Plates are incubated at 30° C. for the time intervals indicated in Table V.

TABLE V

Conditions for human SIK kinase $^{33}$P radioactive assays

| Kinase, [Kinase] | Substrate, [Substrate] | ATP | Assay buffer | Incubation time |
|---|---|---|---|---|
| SIK1 (Carna Biosciences, Cat# 02-131), 0.4 ng/mL | AMARA (SignalChem, Cat# A11-58), 7 μM | 10 μM ATP + 0.25 μCi/25 μL [γ-$^{33}$P]ATP | 25 mM Tris pH 7.5 0.01% Triton X-100 0.5 mM EGTA 2.5 mM DTT 10 mM MgCl$_2$ | 120 min |
| SIK2 (ThermoFisher Scientific, Cat# PV4792), 0.0532 ng/mL | AMARA (SignalChem, Cat# A11-58), 5 μM | 10 μM ATP + 0.25 μCi/25 μL [γ-$^{33}$P]ATP | 25 mM Tris pH 7.5 0.01% Triton X-100 0.5 mM EGTA 5 mM MgCl$_2$ 2.5 mM DTT | 120 min |
| SIK3 (SignalChem, Cat# S12-11G-100), 0.4 ng/mL | AMARA (SignalChem, Cat# A11-58), 7 μM | 15 μM ATP + 0.50 μCi/25 μL [γ-$^{33}$P]ATP | 25 mM MOPS pH 7.5 0.01% Triton X-100 0.5 mM EGTA 5 mM MgCl$_2$ | 80 min |

The reactions are stopped by adding 25 μL phosphoric acid (150 mM) to the reactions.

The completely terminated kinase reactions are transferred using a harvester on pre-wetted UniFilter-96 plates (UniFilter-96 GF/B, PerkinElmer Inc., Cat #6005177).

After harvesting the kinase reactions, the filter plates are washed 6 times with phosphoric acid (75 mM). The back of the UniFilter-96 plates are sealed and 40 μL MicroScint-20 (PerkinElmer Inc., Cat #6013621) is added to each well. The top of the plates are sealed with TopSal-A. Read-out is performed with aTopCount instrument (PerkinElmer Inc.).

3.1.1.3. Data Analysis and Results

Raw data are generated following the read-out performed on the TopCount, plotted to generate dose response curves to calculate percentage inhibition (PIN) and average IC$_{50}$ for each SIK homologue which are reported in the table below.

TABLE VI $^{33}$P radioactive SIK kinase assay IC$_{50}$ of illustrative compounds of the invention

| Cpd# | SIK1 IC$_{50}$ | SIK2 IC$_{50}$ | SIK3 IC$_{50}$ |
|---|---|---|---|
| 1 | *** | *** | *** |
| 2 | ** | ** | *** |
| 3 | *** | *** | *** |
| 4 | *** | *** | *** |
| 5 | ** | *** | *** |
| 6 | *** | *** | *** |
| 7 | *** | *** | *** |
| 8 | ** | *** | ** |
| 9 | *** | *** | *** |
| 10 | *** | **** | **** |
| 11 | *** | **** | **** |
| 12 | *** | **** | **** |
| 13 | *** | *** | *** |
| 14 | *** | **** | *** |
| 15 | *** | **** | **** |
| 16 | *** | *** | *** |
| 17 | *** | **** | **** |
| 18 | *** | *** | *** |
| 19 | *** | **** | **** |
| 20 | *** | **** | *** |
| 21 | *** | **** | **** |
| 22 | *** | *** | *** |
| 23 | *** | *** | *** |
| 24 | *** | **** | *** |
| 25 | *** | **** | **** |
| 26 | *** | *** | *** |
| 27 | * | * | * |
| 28 | * | * | * |
| 29 | *** | *** | *** |
| 30 | * | * | * |
| 31 | ** | ** | *** |
| 32 | *** | *** | *** |
| 33 | **** | **** | **** |
| 34 | *** | **** | *** |
| 35 | ** | ** | *** |
| 36 | ** | *** | *** |
| 37 | ** | ** | ** |
| 38 | ** | *** | *** |
| 39 | ** | *** | *** |
| 40 | *** | **** | **** |
| 41 | *** | **** | **** |
| 42 | **** | **** | **** |
| 43 | * | * | * |
| 44 | *** | *** | *** |
| 45 | *** | *** | *** |
| 46 | **** | **** | **** |
| 47 | *** | *** | **** |
| 48 | *** | **** | **** |
| 49 | *** | *** | *** |
| 50 | *** | **** | **** |
| 51 | *** | *** | *** |
| 52 | *** | **** | *** |
| 53 | **** | **** | **** |
| 54 | *** | **** | **** |
| 55 | **** | **** | **** |
| 56 | **** | **** | **** |
| 57 | *** | **** | **** |
| 58 | *** | *** | *** |
| 59 | *** | *** | *** |
| 60 | *** | *** | ** |
| 61 | * | ** | * |
| 62 | ** | ** | ** |
| 63 | ** | *** | *** |
| 64 | ** | *** | *** |
| 65 | ** | *** | *** |
| 66 | ** | ** | ** |
| 67 | ** | ** | ** |
| 68 | * | * | ** |
| 69 | ** | ** | ** |
| 70 | ** | *** | ** |
| 71 | ** | *** | ** |
| 72 | *** | *** | *** |
| 73 | * | ** | ** |
| 74 | ** | ** | *** |
| 75 | *** | **** | **** |

TABLE VI-continued $^{33}$P radioactive SIK kinase assay IC$_{50}$ of illustrative compounds of the invention

| Cpd# | SIK1 IC$_{50}$ | SIK2 IC$_{50}$ | SIK3 IC$_{50}$ |
|---|---|---|---|
| 76 | * | * | * |
| 77 | *** | *** | *** |
| 78 | *** | **** | **** |
| 79 | *** | **** | **** |
| 80 | *** | **** | *** |
| 81 | ** | ** | ** |
| 82 | ** | ** | ** |
| 83 | ** | ** | ** |
| 84 | *** | **** | **** |
| 85 | *** | **** | **** |
| 86 | *** | **** | **** |
| 87 | *** | *** | *** |
| 88 | **** | **** | **** |
| 89 | *** | *** | *** |
| 90 | *** | *** | *** |
| 91 | *** | *** | *** |
| 92 | *** | *** | *** |
| 93 | ** | *** | *** |
| 94 | **** | **** | **** |
| 95 | *** | **** | **** |
| 96 | *** | **** | **** |
| 97 | *** | **** | **** |
| 98 | *** | **** | **** |
| 99 | **** | **** | **** |
| 100 | *** | **** | **** |
| 101 | *** | **** | **** |
| 102 | **** | **** | **** |
| 103 | **** | **** | **** |
| 104 | * | ** | ** |
| 105 | * | * | ** |
| 106 | ** | *** | *** |
| 107 | *** | **** | **** |
| 108 | ** | ** | ** |
| 109 | *** | *** | *** |
| 110 | *** | **** | **** |
| 111 | **** | **** | **** |
| 112 | **** | **** | **** |
| 113 | *** | *** | *** |
| 114 | ** | ** | ** |
| 115 | *** | *** | *** |
| 116 | **** | **** | **** |
| 117 | **** | **** | **** |
| 119 | ** | ** | ** |
| 120 | *** | *** | **** |
| 121 | * | ** | *** |
| 122 | **** | **** | **** |
| 123 | *** | **** | **** |
| 124 | **** | **** | **** |
| 125 | *** | *** | *** |
| 126 | * | * | * |
| 127 | * | ** | ** |
| 128 | * | * | ** |
| 129 | *** | **** | **** |
| 130 | *** | **** | *** |
| 131 | * | ** | ** |
| 132 | *** | *** | *** |
| 133 | **** | **** | **** |
| 134 | * | *** | ** |
| 135 | * | ** | ** |
| 136 | * | * | * |
| 137 | *** | **** | *** |
| 138 | * | ** | ** |
| 139 | **** | **** | **** |
| 140 | *** | *** | *** |
| 141 | *** | *** | *** |
| 142 | *** | *** | *** |
| 143 | ** | *** | *** |
| 144 | **** | **** | **** |
| 145 | *** | *** | *** |
| 146 | ** | *** | *** |
| 147 | **** | **** | **** |
| 148 | **** | **** | **** |
| 149 | **** | **** | **** |
| 150 | * | * | * |
| 151 | **** | **** | **** |
| 152 | *** | *** | *** |
| 153 | *** | *** | *** |
| 154 | ** | ** | ** |
| 155 | ** | *** | *** |
| 156 | *** | *** | *** |
| 157 | *** | *** | *** |
| 158 | *** | **** | **** |
| 159 | *** | *** | *** |
| 160 | *** | *** | *** |
| 161 | * | * | * |
| 162 | ** | ** | *** |
| 163 | *** | *** | *** |
| 164 | ** | ** | * |
| 165 | * | * | * |
| 166 | * | * | ** |
| 167 | * | * | ** |
| 168 | * | * | * |
| 169 | * | * | * |
| 170 | *** | **** | **** |
| 171 | *** | *** | *** |
| 172 | *** | **** | **** |
| 173 | *** | **** | **** |
| 174 | **** | **** | **** |
| 175 | * | ** | ** |
| 176 | *** | *** | *** |
| 177 | *** | *** | *** |
| 178 | *** | **** | **** |
| 179 | *** | *** | *** |
| 180 | *** | ** | ** |
| 181 | * | * | * |
| 182 | * | * | * |
| 183 | ** | ** | ** |
| 184 | ** | ** | ** |
| 185 | ** | ** | * |
| 186 | *** | ** | ** |
| 187 | * | * | * |
| 188 | * | * | * |
| 189 | * | * | * |
| 190 | *** | *** | ** |
| 191 | ** | ** | ** |
| 192 | *** | *** | *** |
| 193 | * | * | * |
| 194 | ** | *** | ** |
| 195 | ** | ** | ** |
| 196 | * | * | * |
| 197 | * | * | * |
| 198 | ** | * | ** |
| 199 | * | * | * |
| 200 | *** | *** | *** |
| 201 | * | *** | ** |
| 202 | ** | ** | * |
| 203 | *** | **** | **** |
| 204 | **** | **** | **** |
| 205 | *** | **** | **** |
| 206 | *** | **** | **** |
| 207 | *** | **** | **** |
| 208 | **** | **** | **** |
| 209 | **** | **** | **** |
| 210 | *** | *** | **** |
| 211 | *** | *** | *** |
| 212 | ** | *** | ** |
| 213 | **** | **** | **** |
| 215 | *** | **** | **** |
| 216 | ** | *** | *** |
| 217 | *** | *** | *** |
| 218 | *** | *** | ** |
| 219 | **** | **** | **** |
| 220 | *** | *** | *** |
| 221 | *** | *** | *** |
| 222 | **** | **** | **** |
| 223 | *** | *** | *** |
| 224 | ** | ** | ** |
| 225 | *** | **** | **** |

TABLE VI-continued $^{33}$P radioactive SIK kinase assay IC$_{50}$ of illustrative compounds of the invention

| Cpd# | SIK1 IC$_{50}$ | SIK2 IC$_{50}$ | SIK3 IC$_{50}$ |
|---|---|---|---|
| 226 | *** | *** | *** |
| 227 | **** | **** | **** |
| 228 | **** | **** | **** |
| 229 | **** | **** | **** |
| 230 | **** | **** | **** |
| 231 | **** | **** | **** |
| 232 | *** | **** | **** |
| 233 | *** | **** | **** |
| 234 | **** | **** | **** |
| 235 | **** | **** | **** |
| 236 | **** | **** | **** |
| 237 | **** | **** | **** |
| 238 | **** | **** | **** |
| 239 | *** | **** | **** |
| 240 | ** | *** | **** |
| 241 | ** | ** | *** |
| 242 | ** | ** | *** |
| 243 | **** | **** | **** |
| 244 | **** | **** | **** |
| 245 | *** | *** | **** |
| 246 | *** | *** | **** |
| 247 | *** | *** | **** |
| 248 | *** | **** | **** |
| 249 | ** | *** | *** |
| 250 | ** | *** | *** |
| 251 | **** | **** | **** |
| 252 | ** | *** | **** |
| 253 | * | * | ** |
| 254 | **** | **** | **** |
| 255 | **** | **** | **** |
| 256 | **** | **** | **** |
| 257 | **** | **** | **** |
| 258 | * | * | ** |
| 259 | * | * | ** |
| 260 | **** | **** | **** |
| 261 | *** | **** | **** |
| 262 | *** | **** | **** |
| 263 | **** | **** | **** |

\* >500 nM
\** >100-500 nM
\*** >10-100 nM
\**** 0.01-10 nM
NA not measured

3.1.2. ADP-Glo™ Kinase Assay

3.1.2.1. Overview

The ADP-Glom kinase assay is a luminescent technology assay which measures the ADP formed from a kinase reaction. In this specific study, the kinase reactions consisted of the phosphorylation of the AMARA peptide substrate (SignalChem, Cat #A11-58) by SIK1 (Carna Biosciences, Cat #02-131), SIK2 (ThermoFisher Scientific, Cat #PV4792) or SIK3 (SignalChem, Cat #S12-11G-100). In a second step the kinase reactions are terminated and all the remaining ATP is depleted. In a final step the ADP is converted into ATP and this newly synthesized ATP is measured by using a luciferase/luciferin reaction. The generated light is measured using an Envision plate reader, wherein the luminescent signal obtained positively correlates with the kinase activity.

3.1.2.2. Protocol

The test compounds are prepared as a serial dilution of 10 point dose responses with 1/5 dilution steps in 100% DMSO starting from 2 mM highest concentration, diluted 1/20 in water and 1 µL is transferred to the assay plates (PerkinElmer Inc., Cat #6007290).

1% DMSO and 10 µM staurosporine final concentrations are used as negative and positive controls.

2 µL enzyme-substrate mixture is added to the assay plates.

The reaction is started by adding 2 µL diluted ATP on the assay plates. Plates are centrifuged for a few seconds at 1000 rpm and gently shaken for 2 min followed by an incubation at RT for 120 min.

The reactions are stopped and the unconsumed ATP is depleted by adding 5 µL ADP-Glo Reagent (Promega, Cat #V912B) to the reaction. The plates are centrifuged for a few seconds at 1000 rpm and incubated at RT for 40 min (ATP depletion).

The ADP is converted to ATP and luciferase and luciferin is introduced to detect ATP by adding 10 µL Kinase Detection Reagent (Promega, Cat #V913B+V914B) to the reaction. The plates are centrifuged for a few seconds at 1000 rpm and incubated at RT for 30 min (ADP detection).

Luminescence is measured on an Envision plate reader (PerkinElmer Inc.).

TABLE VII

Conditions for human SIK kinase ADP-Glo ™ assays

| Kinase, [Kinase] | Substrate, [Substrate] | ATP | Assay buffer | Incubation time |
|---|---|---|---|---|
| SIK1 (Carna Biosciences, Cat# 02-131), 0.25 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 2.5 mM DTT 5 mM MgCl$_2$ | 120 min |
| SIK2 (ThermoFisher Scientific, Cat# PV4792), 0.0625 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 5 mM MgCl$_2$ 2.5 mM DTT | 120 min |
| SIK3 (SignalChem, Cat# S12-11G-100), 0.5 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 5 mM MgCl$_2$ 2.5 mM DTT | 120 min |

3.1.2.3. Data Analysis and Results

Raw data are generated following the read-out performed on the TopCount, plotted to generate dose response curves to calculate percentage inhibition (PIN) and average $IC_{50}$ for each SIK homologue which are reported in the table below.

TABLE VIII

ADP-Glo ™ SIK kinase assay $IC_{50}$ of illustrative compounds of the invention.

| Cpd# | SIK1 $IC_{50}$ | SIK2 $IC_{50}$ | SIK3 $IC_{50}$ |
|---|---|---|---|
| 53 | **** | **** | **** |
| 76 | * | * | * |
| 88 | **** | **** | **** |
| 98 | **** | **** | **** |
| 120 | *** | **** | **** |
| 133 | **** | **** | **** |
| 142 | *** | *** | *** |
| 172 | **** | **** | **** |
| 173 | **** | **** | **** |
| 174 | **** | **** | **** |
| 175 | * | ** | ** |
| 176 | *** | **** | **** |
| 177 | *** | **** | **** |
| 192 | *** | **** | **** |
| 201 | ** | *** | *** |
| 202 | ** | ** | ** |
| 204 | **** | **** | **** |
| 213 | **** | **** | **** |
| 215 | *** | **** | **** |
| 216 | ** | *** | *** |
| 225 | **** | **** | **** |
| 227 | **** | **** | **** |
| 230 | **** | **** | **** |
| 252 | ** | *** | **** |
| 258 | * | * | *** |
| 259 | * | * | *** |
| 260 | **** | **** | **** |
| 261 | **** | **** | **** |
| 262 | **** | **** | **** |
| 263 | **** | **** | **** |
| 264 | **** | **** | **** |
| 265 | **** | **** | **** |
| 266 | **** | **** | **** |
| 267 | **** | **** | **** |
| 268 | * | ** | *** |
| 269 | *** | **** | **** |
| 270 | **** | **** | **** |
| 271 | ** | **** | *** |
| 272 | *** | **** | **** |
| 273 | *** | **** | **** |
| 274 | *** | **** | **** |
| 275 | *** | **** | **** |
| 276 | *** | **** | **** |
| 277 | **** | **** | **** |
| 278 | *** | **** | **** |
| 279 | **** | **** | **** |
| 280 | **** | **** | **** |
| 281 | *** | **** | **** |
| 282 | **** | **** | **** |
| 283 | **** | **** | **** |
| 284 | **** | **** | **** |
| 285 | **** | **** | **** |
| 286 | **** | **** | **** |
| 291 | **** | **** | **** |
| 293 | **** | **** | **** |
| 294 | **** | **** | **** |
| 295 | **** | **** | **** |
| 296 | **** | **** | **** |
| 297 | **** | **** | **** |
| 298 | **** | **** | **** |
| 299 | *** | **** | *** |
| 300 | *** | **** | *** |
| 301 | **** | **** | **** |
| 302 | *** | *** | *** |
| 303 | *** | *** | *** |
| 304 | **** | *** | **** |
| 305 | **** | **** | **** |
| 306 | **** | **** | **** |
| 307 | **** | **** | **** |

\* >500 nM  
\*\* >100-500 nM  
\*\*\* >10-100 nM  
\*\*\*\* 0.01-10 nM  
NA not measured

3.2. Cellular Assays

3.2.1. PBMC Assay: LPS-Triggered TNFα (ELISA)

3.2.1.1. Overview

SIK inhibition inhibits TNFα and increase IL-10 release in LPS triggered monocyte derived macrophages (MdM) and dendritic cells (MdDCs) (Clark et al. 2012; Sundberg et al. 2014; Ozanne et al. 2015).

This assay measures the inhibition of LPS driven TNFα secretion by a test compound in Peripheral Blood Mononuclear Cells (PBMC), which in turn correlates with SIK inhibition.

3.2.1.2. Protocol

PBMCs are isolated from human blood samples (buffy coats). The buffy coat is aseptically transferred into a 50 mL Falcon™ tube, and diluted 1/2 in Phosphate Buffered Saline (PBS). Falcon tubes are filled with 20 mL Lymphoprep (Axis-Shield, Cat #1001967) and 25 mL of the buffy coat. The tubes are centrifuged for 35 min at 400×g in temperature controlled centrifuge, without brake, at 25° C. PBMCs are aspirated from the white interface layer between sample and Lymphoprep. PBMCs are washed five times in PBS. The cells are resuspended in RPMI 1640 complete medium supplemented with 10% FBS, 1% P/S, and cell density is determined using a hematologic analyzer (Sysmex XS-500i). The PBMCs are finally seeded at 400,000 PBMC/160 µL/96-well.

A compound dilution plate is made in 100% DMSO by 3-fold dilution of 10 mM stock solution of test compound. An intermediate dilution plate (10× final concentration) is made by diluting the compound dilution plate 50-fold in RPMI medium.

20 µL of the 10× final concentration compound is added to the cells and incubated for 1 hour at 37° C. before addition of trigger. No trigger conditions/trigger conditions are spiked with equal final DMSO concentrations of 0.2% DMSO. 20 µL of 10×LPS (final concentration 1 ng/mL) solution are added to all wells except for the 'no trigger wells' where 20 µL medium is added. Supernatant is collected after 18-20 h for IL-10 and TNFα determination using ELISA.

All wash steps for both TNFα (100 µL; 384-well plate) and IL-10 ELISA (200 µL/well; 96-well plate) are done by filling with Multidrop and tapping on absorbant paper; additions of antibodies/samples are done with Multichannel.

3.2.1.2.1 TNFα ELISA

A Lumitrac 600 Greiner 384-well plate is coated with 40 µL of capture antibody (BD Pharmingen, Cat #551220) reaching a final concentration of 1 µg/mL in 1×PBS and stored overnight at 4° C.

The plate is then washed once with PBST (PBS+0.05% Tween20) and once with PBS followed by the addition of 100 µL of blocking buffer (1% Bovine Serum Albumin (BSA)-5% Sucrose) and plates are sealed and incubated for at least 4 h at RT. After washing the plate once with PBST and once with PBS, 40 µL of standard or sample are added (TNFα standard curve is prepared using a 1/2 serial dilution starting from 16000 pg/mL; dilutions are made in dilution buffer (PBS+1% BSA)). Plates are washed twice with PBST, and once with PBS, after which 35 µL of the detection antibody is added (final concentration 0.25 µg/mL diluted in dilution buffer) and plates are incubated for at least 2 h at RT. Plates are washed twice with PBST, and once with PBS, where after 35 µL of Strep-HRP conjugate (0.5 µg/mL final concentration diluted in dilution buffer) is added. Plates are incubated in the dark, at RT for at least 45 min but no longer than 1 hour. Plates are washed twice with PBST, and once with PBS. Thereafter, 50 µL of luminol substrate is added to each well (prepared according to manufacturer's instructions), and incubated for 5 min at RT protected from light. Chemiluminescence is measured on the Envision 2104.

3.2.1.3. Data Analysis and Results

3.2.1.3.1 TNFα inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLUp - RLU\text{test compound})}{RLUp - RLUn} \times 100$$

Wherein RLU=Relative Chemiluminescent Light Units (background subtracted) and p and n subscripts refer to the average of positive and negative controls respectively.

PIN values are plotted in concentration-response and $EC_{50}$ values are derived using GraphPad Prism Software, applying 4-parameter nonlinear regression (sigmoidal) curve fitting. Because no clear bottom plateau is obtained, bottom of the curve is constrained to be equal to 0.

3.2.1.3.2 Results & Outcome

The data obtained when subjecting illustrative compounds of the invention are described in the table below.

TABLE IX

PBMC TNFα inhibition of illustrative compounds of the invention.

| Cpd# | TNFα EC50 (nM) |
|---|---|
| 1 | *** |
| 17 | **** |
| 25 | **** |

TABLE IX-continued

PBMC TNFα inhibition of illustrative compounds of the invention.

| Cpd# | TNFα EC50 (nM) |
|---|---|
| 48 | **** |
| 53 | **** |
| 56 | **** |
| 57 | **** |
| 78 | **** |
| 84 | **** |
| 85 | **** |
| 88 | **** |
| 94 | **** |
| 95 | **** |
| 96 | **** |
| 97 | **** |
| 98 | **** |
| 99 | **** |
| 100 | **** |
| 101 | **** |
| 102 | **** |
| 103 | **** |
| 107 | **** |
| 109 | *** |
| 110 | **** |
| 112 | **** |
| 116 | **** |
| 117 | **** |
| 120 | **** |
| 122 | **** |
| 123 | **** |
| 124 | **** |
| 132 | *** |
| 173 | **** |
| 174 | **** |
| 176 | **** |
| 177 | **** |
| 178 | **** |
| 179 | *** |
| 192 | *** |
| 203 | **** |

\* >5000 nM
\*\* >1000-5000 nM
\*\*\* >100-1000 nM
\*\*\*\* 0.1-100 nM
NA not measured

3.2.2. MdM Assay: LPS-Triggered TNFα/IL-10 (ELISA)

3.2.2.1. Overview

SIK inhibition inhibits TNFα and increases IL-10 release in LPS triggered monocyte-derived macrophages (MdM) and dendritic cells (MdDCs) (Clark et al. 2012; Sundberg et al. 2014; Ozanne et al. 2015). This assay evaluates illustrative compounds of the invention for their inhibition of LPS-induced TNFα and LPS triggered IL-10 secretion in monocyte-derived macrophages.

3.2.2.2. Protocols

PBMCs are isolated from human blood samples (buffy-coats). The buffy coat is aseptically transferred into a 50 mL Falcon tube, and diluted 1/2 in PBS. Falcon tubes are filled with 20 mL Lymphoprep™, on top of which 25 mL of the buffy coat is carefully added, tubes are centrifuged for 35 min at 400 g in temperature controlled centrifuge, without brake, at 25° C. PBMCs are aspirated from the white interface layer between sample and Lymphoprep™. PBMCs are washed five times in PBS. Cells are resuspended in RPMI 1640 complete medium supplemented with 10% FBS, 1% P/S, and cell density is determined using a hematologic analyzer (Sysmex XS-500i).

PBMCs are centrifuged at 300×g for 10 min and resuspended at a density of 1.0E07 cells/80 µL Miltenyi buffer (PBS, pH 7.4, 1% FBS, 2 mM EDTA). 3.2.2.2.1 Positive labelling of CD14+ monocytes.

Starting from this point of the protocol all steps are performed on ice. 20 µL of CD14+ micro-beads are added per 1.0E07 cells, the tube is mixed and incubated for 15 min in the fridge at 4° C. Cell suspension volume is adjusted to total volume of 100 mL using Miltenyi buffer, mixed gently and subsequently centrifuged for 10 min at 300×g. Supernantant is discarded and cell pellet is resuspended in 12 mL of Miltenyi buffer.

3.2.2.2.2 Magnetic Cell Sorting

Four LS columns are placed in the MACS Separator (magnet) from Miltenyi Biotec, and are prewet by rinsing with 3 mL of MACS buffer per column. Three mL of cell suspension is added onto the column (max $1*10^8$ of labelled cells/column), and columns are subsequently washed 3 times with 3 mL of Miltenyi buffer.

The columns are removed from the magnets, and 5 mL of Miltenyi buffer are added to the column to flush out the CD14+ fraction by pushing the plunger into the column. The flushed fractions are collected in a fresh 50 mL Falcon and volume is adjusted to 30 mL using Miltenyi buffer, cells are centrifuged for 10 min at 300×g. The obtained cell pellet is resuspended in 10 mL RPMI w/o FBS, and cell density is determined using a hematologic analyser (Sysmex XS-500i). 100 000 cells are seeded per well of a 96 well plate for differentiation to MdM in RPMI 1640 medium supplemented with 10% FBS, 1% P/S and 100 ng/mL rhM-CSF. On day 5 the medium is refreshed with 100 µL RPMI 1640 medium supplemented with 10% FBS, 1% P/S and 100 ng/mL rhM-CSF.

On day 10, MdMs are triggered and compound is added.

A compound dilution plate is made in 100% DMSO by 3-fold dilution of 10 mM stock solution. An intermediate dilution plate (10× final concentration) is made by diluting the compound dilution plate 50-fold in RPMI medium.

Medium is carefully removed from cell plates using multichannel pipette, and replaced by 80 µL fresh medium. 10 µL of the 10× final concentration compound is added to the cells and incubated for 1 hour at 37° C. before addition of trigger. No trigger conditions/trigger conditions are spiked with equal final DMSO concentrations of 0.2% DMSO. 10 µL of 10×LPS (final conc. 200 ng/mL) solution are added to all wells except for the no trigger wells' where 10 µL medium is added. Supernatant is collected after 2 h (IL-10 determination) and after 20 h (TNFα determination) of LPS triggering.

3.2.2.2.3 TNFα ELISA

A Lumitrac 600 Greiner 384 well plate is coated with 40 µL of capture antibody (BD Pharmingen, Cat #551220) reaching a final concentration of 1 µg/mL in 1×PBS and stored overnight at 4° C.

The plate is then washed once with PBST (PBS+0.05% Tween20) and once with PBS followed by the addition of 100 µL of blocking buffer (1% Bovine Serum Albumin (BSA)-5% Sucrose) and plates are sealed and incubated for at least 4 h at RT. After washing the plate once with PBST and once with PBS, 40 µL of standard or sample are added (TNFα standard curve is prepared using a 1/2 serial dilution starting from 16000 pg/mL; dilutions are made in dilution buffer (PBS+1% BSA)). Plates are washed twice with PBST, and once with PBS, after which 35 µL of the detection antibody is added (final concentration 0.25 µg/mL diluted in dilution buffer) and plates are incubated for at least 2 h at RT. Plates are washed twice with PBST, and once with PBS, where after 35 µL of Strep-HRP conjugate (0.5 µg/mL final concentration diluted in dilution buffer) is added. Plates are incubated in the dark, at RT for at least 45 min but no longer than 1 hour. Plates are washed twice with PBST, and once with PBS. Thereafter, 50 µL of luminol substrate is added to each well (prepared according to manufacturer's instructions), and incubated for 5 min at RT protected from light. Chemiluminescence is measured on the Envision 2104.

3.2.2.2.1 IL-10 ELISA

An Immulon 2HB 96 well plate (Thermo Electron Co., Cat #3455) is coated with 40 µL of capture antibody (final concentration of 2 µg/mL diluted in Tris buffer (50 mM Tris; 150 mM NaCl; pH 9 (adjusted with HCl)) and stored overnight at 4° C. The next day the plate is washed three times with PBST, and subsequently 200 µL blocking buffer (1% BSA+5% sucrose in PBS-T) is added. After an incubation of 30 min at 37° C., the plate is washed three times with PBST, and 100 µL of standard or sample are added (IL-10 standard curve samples are prepared using a 1/2 serial dilution starting from 1000 µg/mL; dilutions are made in dilution buffer: PBS+1% BSA). After 1 hour incubation at 37° C., plates are washed three times with PBST, after which 100 µL of the detection antibody (BD Pharmingen, Cat #554499) is added (final concentration 0.25 µg/mL diluted in Tris buffer) and plates are incubated for at least 2 h at RT. Plates are washed three times with PBST, where after 100 µL of Strep-HRP conjugate (0.5 µg/mL final concentration diluted in dilution buffer) is added. Plates are incubated in the dark, at 37° C. for 30 min. Plates are washed three times with PBST. A substrate solution is made, for a total volume of 20 mL, 18 mL $H_2O$; 2 mL citrate acetate buffer; 200 µL TMB mix (tetramethil benzidine (TMB) 101 mg, DMSO 10 mL stored at 4° C.); 2.5 µL 30% $H_2O_2$ are mixed. 100 µL of substrate solution is added to each well and incubated until brilliant blue color develops. The reaction is stopped by adding 50 µL of 1 M $H_2SO_4$, after which absorbance is measured at 450 nm on the SpectraMax i3, Molecular Devices.

3.2.2.3. Data Analysis and Results

3.2.2.3.1 TNFα Inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLUp - RLU\text{test compound})}{RLUp - RLUn} \times 100$$

Wherein RLU=Relative Chemiluminescent Light Units (background subtracted) and p and n subscripts refer to the average of positive and negative controls, respectively.

PIN values are plotted in concentration-response and $EC_{50}$ values are derived using GraphPad Prism Software, applying 4-parameter nonlinear regression (sigmoidal) curve fitting. Because no clear bottom plateau is obtained, bottom of the curve is constrained to be equal to 0.

3.2.2.3.2 IL-10 Induction Calculation

IL-10 is induced upon SIK inhibition. To quantify these inductions fold changes (FC) compared to 'LPS only' are calculated for each concentration tested and the maximal FC is calculated (IL-10 FC max):

$$IL-10FC\max = \frac{\max ABS \text{test compound}}{ABS \text{trigger}}$$

wherein ABS=Absorbance measured at 450 nm.

The median maximal FC for test compounds across two or more assays is reported (IL-10FC max median).

3.2.2.3.3 Results & Outcome

The data obtained when subjecting illustrative compounds of the invention are described in the table below.

TABLE X

MdM TNFα inhibition and IL-10 induction of illustrative compounds of the invention.

| Cpd# | TNFα $EC_{50}$ (nM) | IL-10 FCmax median |
|---|---|---|
| 1 | *** | ++ |
| 2 | ** | NA |
| 3 | *** | ++ |
| 4 | ** | ++ |
| 6 | *** | ++ |
| 7 | *** | ++ |
| 9 | *** | ++ |
| 10 | *** | ++ |
| 11 | *** | ++ |
| 12 | **** | ++ |
| 13 | *** | ++ |
| 14 | ** | NA |
| 15 | * | ++ |
| 16 | ** | ++ |
| 17 | *** | ++ |
| 18 | * | NA |
| 19 | *** | ++ |
| 20 | *** | ++ |
| 21 | *** | NA |
| 22 | *** | ++ |
| 24 | *** | ++ |
| 25 | **** | ++ |
| 26 | *** | NA |
| 29 | *** | ++ |
| 32 | *** | NA |
| 33 | * | ++ |
| 34 | *** | NA |
| 40 | **** | ++ |
| 41 | *** | ++ |
| 42 | *** | NA |
| 44 | *** | NA |
| 46 | **** | ++ |
| 48 | *** | ++ |
| 49 | * | ++ |
| 50 | *** | ++ |
| 51 | *** | ++ |

TABLE X-continued

MdM TNFα inhibition and IL-10 induction of illustrative compounds of the invention.

| Cpd# | TNFα $EC_{50}$ (nM) | IL-10 FCmax median |
|---|---|---|
| 52 | *** | NA |
| 53 | **** | ++ |
| 54 | **** | ++ |
| 55 | **** | NA |
| 56 | **** | ++ |
| 57 | *** | ++ |
| 58 | *** | NA |
| 76 | * | NA |
| 78 | *** | ++ |
| 80 | **** | ++ |
| 84 | **** | ++ |
| 85 | **** | ++ |
| 86 | **** | ++ |
| 88 | **** | ++ |
| 94 | *** | NA |
| 95 | **** | NA |
| 96 | **** | ++ |
| 97 | **** | NA |
| 98 | **** | ++ |
| 99 | **** | NA |
| 100 | *** | NA |
| 101 | **** | NA |
| 102 | **** | ++ |
| 103 | **** | NA |
| 107 | *** | NA |
| 109 | *** | NA |
| 110 | *** | NA |
| 112 | **** | + |
| 116 | **** | ++ |
| 117 | **** | NA |
| 120 | *** | ++ |
| 122 | **** | ++ |
| 123 | **** | ++ |
| 124 | **** | ++ |
| 125 | *** | NA |
| 126 | ** | NA |
| 127 | * | NA |
| 129 | *** | NA |
| 132 | *** | + |
| 133 | **** | ++ |
| 137 | *** | NA |
| 139 | ** | NA |
| 142 | *** | ++ |
| 144 | **** | ++ |
| 145 | ** | NA |
| 146 | *** | NA |
| 147 | **** | NA |
| 148 | **** | ++ |
| 149 | *** | NA |
| 151 | **** | NA |
| 152 | ** | NA |
| 155 | ** | NA |
| 156 | ** | NA |
| 157 | *** | NA |
| 158 | *** | ++ |
| 159 | *** | NA |
| 160 | *** | NA |
| 163 | * | NA |
| 171 | **** | NA |
| 173 | **** | ++ |
| 174 | **** | ++ |
| 176 | *** | NA |
| 177 | *** | NA |
| 178 | **** | ++ |
| 179 | *** | NA |
| 192 | *** | NA |
| 203 | **** | +++ |
| 204 | **** | ++ |
| 205 | **** | NA |
| 206 | *** | +++ |
| 207 | *** | ++ |
| 208 | *** | NA |
| 209 | *** | ++ |

TABLE X-continued

MdM TNFα inhibition and IL-10 induction of illustrative compounds of the invention.

| Cpd# | TNFα EC$_{50}$ (nM) | IL-10 FCmax median |
|---|---|---|
| 210 | *** | NA |
| 213 | **** | NA |
| 215 | *** | ++ |
| 216 | ** | NA |
| 219 | *** | ++ |
| 221 | *** | NA |
| 222 | **** | +++ |
| 223 | *** | +++ |
| 225 | **** | ++ |
| 274 | *** | NA |
| 275 | **** | ++ |
| 276 | **** | NA |
| 278 | *** | NA |
| 279 | *** | ++ |
| 280 | **** | ++ |
| 285 | **** | NA |
| 293 | **** | ++ |
| 294 | **** | NA |
| 227 | **** | +++ |
| 228 | * | ++ |
| 229 | *** | NA |
| 230 | **** | +++ |
| 231 | **** | NA |
| 232 | **** | NA |
| 233 | **** | NA |
| 234 | **** | NA |
| 235 | **** | NA |
| 236 | **** | NA |
| 237 | *** | NA |
| 238 | **** | NA |
| 239 | *** | ++ |
| 240 | *** | + |
| 241 | *** | NA |
| 242 | ** | NA |
| 243 | **** | NA |
| 244 | **** | NA |
| 248 | **** | NA |
| 251 | **** | NA |
| 252 | *** | NA |
| 254 | * | NA |
| 255 | ** | NA |
| 256 | **** | ++ |
| 257 | **** | + |
| 261 | **** | NA |
| 262 | **** | NA |
| 263 | **** | ++ |
| 264 | **** | ++ |
| 265 | **** | ++ |
| 267 | **** | NA |
| 270 | **** | NA |
| 272 | *** | ++ |
| 273 | **** | NA |
| 295 | **** | NA |
| 296 | **** | NA |
| 297 | *** | NA |
| 298 | ** | NA |
| 299 | * | NA |
| 305 | *** | NA |
| 306 | **** | NA |
| 307 | **** | NA |

\* >5000 nM
\*\* >1000-5000 nM
\*\*\* >100-1000 nM
\*\*\*\* 0.1-100 nM
+ ≤1.5
++ >1.5-4.5
+++ >4.5
NA not measured Example 4. In Vivo Assays 4.1. Inflammatory Bowel Disease 4.1.1. DSS Model (Mice)

The mouse chronic DSS-induced inflammatory bowel disease model (IBD) is a well validated disease model for inflammatory bowel disease (Wirtz et al. 2007; Sina et al. 2009).

To induce a chronic colitis, female BALB/c mice are fed with 4% dextran sodium sulfate (DSS) dissolved in drinking water for 4 days, followed by 3 days of regular drinking water. This cycle is repeated three times. This protocol allows inducing a strong colitis while avoiding high mortality rates. Animals are divided into several groups:
 a. intact water; vehicle alone, n=10),
 b. diseased (DSS; vehicle alone, n=10),
 c. sulfazalazine used as reference (DSS; 20 mg/kg/day, p.o., n=10) and
 d. the tested compound (DSS; 1, 3, 10, 30 mg/kg/day, p.o., n=10).

Clinical parameters are measured every other day. The disease activity index (DAI) is a composite measure combining of the individual scores for weight loss, stool consistency and rectal bleeding. Mice are sacrificed at day 20 of the experiment according to the protocol introduced by Sina et al. (Sina et al. 2009). At sacrifice time, the complete colon is removed and rinsed with sterile PBS. Segments of the distal colon are dissected for histological analysis, gene expression and protein level measurement.

4.2. CIA Model 4.2.1. Materials

Completed Freund's adjuvant (CFA) and incomplete Freund's adjuvant (IFA) were purchased from Difco. Bovine collagen type TT (CT), lipopolysaccharide (LPS), and Enbrel was obtained from Chondrex (Isle d'Abeau, France); Sigma (P4252, L'Isle d'Abeau, France), Whyett (25 mg injectable syringe, France), respectively. All other reagents used were of reagent grade and all solvents were of analytical grade.

4.2.2. Animals

DBA1/J mice (male, 7-8 weeks old) were obtained from Charles River Laboratories (France). Mice were kept on a 12 h light/dark cycle (07 h00-19 h00). Temperature was maintained at 22° C., and food and water were provided ad libitum.

4.2.3. Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.2 mL of the emulsion was injected intradermally at the base of the tail of each mouse on day 1, a second booster intradermal injection (CII solution at 2 mg/mL in CFA 0.1 mL saline) was performed on day 22. This immunization method was modified from published methods (Jou et al. 2005; Sims et al. 2004).

4.2.4. Study Design

The therapeutic effects of the compounds were tested in the mouse CIA model. Mice were randomly divided into equal groups and each group contained 10 mice. All mice were immunized on day 1 and boosted on day 22. The negative control group was treated with vehicle (MC 0.5%) and the positive control group with Enbrel (10 mg/kg, 3× week, s.c.). A compound of interest was typically tested at 3 doses per os (p.o.). At day 32, randomization between groups was performed with respect to clinical score and animals were therapeutically treated according to their group until day 47. Body weight and clinical score were recorded twice a week.

4.2.5. Clinical Assessment of Arthritis

Arthritis is scored according to the method of Khachigian 2006, Lin et al 2007 and Nishida et al. 2004 (Khachigian 2006; Lin et al. 2007; Nishida et al. 2004). The swelling of each of the four paws is ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al. 2004).

4.2.5.1. Change in Body Weight (%) after Onset of Arthritis

Clinically, body weight loss is associated with arthritis (Argilés & López-Soriano 1998; Rall & Roubenoff 2004; Shelton et al. 2005; Walsmith et al. 2004). Hence, changes in body weight after onset of arthritis can be used as a non-specific endpoint to evaluate the effect of therapeutics in the mouse model. The change in body weight (%) after onset of arthritis was calculated as follows:

$$\text{Mice}: \frac{\text{Body Weight}_{(week6)} - \text{Body Weight}_{(week5)}}{\text{Body Weight}_{(week5)}} \times 100\%$$

4.2.5.2. Radiology

X-ray photos were taken of the hind paws of each individual animal. A random blind identity number was assigned to each of the photos, and the severity of bone erosion was ranked by two independent scorers with the radiological Larsen's score system as follows: 0-normal with intact bony outlines and normal joint space; 1-slight abnormality with any one or two of the exterior metatarsal bones showing slight bone erosion; 2-definite early abnormality with any three to five of the exterior metatarsal bones showing bone erosion; 3-medium destructive abnormality with all the exterior metatarsal bones as well as any one or two of the interior metatarsal bones showing definite bone erosions; 4-severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from Salvemini et al., 2001; Bush et al., 2002; Sims et al., 2004; Jou et al., 2005 (Bush et al. 2002; Jou et al. 2005; Salvemini et al. 2001; Sims et al. 2004).

4.2.5.3. Steady State PK

At day 42, blood samples were collected at the retro-orbital sinus with lithium heparin as anti-coagulant at the following time points: predose, 1, 3 and 6 h. Whole blood samples were centrifuged and the resulting plasma samples were stored at −20° C. pending analysis. Plasma concentrations of each test compound were determined by an LC-MS/MS method in which the mass spectrometer was operated in positive electrospray mode.

4.2.6. Results

When tested in this protocol, the following data were obtained:

TABLE XI

| CIA clinical score | | | | | | | | | | | |
|---|---|---|---|---|---|---|---|---|---|---|---|
| Day | 32 | 33 | 34 | 35 | 36 | 39 | 40 | 41 | 42 | 43 | 46 |
| Disease vehicle | 2.5 | 2.7 | 3.7 | 3.6 | 4.2 | 5.0 | 4.8 | 5.8 | 6.0 | 7.2 | 8.2 |
| s.e.m. | 0.4 | 0.6 | 0.7 | 0.7 | 0.8 | 0.8 | 0.8 | 1.1 | 1.0 | 1.1 | 1.2 |
| P value | ns | ns | ns | ns | ns | ns | ns | ns | ns | ns | ns |
| Enbrel (10 mg/kg 3x/w) | 2.5 | 2.4 | 2.9 | 2.7 | 2.5 | 3.0 | 2.5 | 2.7 | 2.8 | 2.9 | 2.9 |
| s.e.m. | 0.3 | 0.3 | 0.5 | 0.4 | 0.4 | 0.4 | 0.4 | 0.5 | 0.4 | 0.5 | 0.6 |
| P value | ns | ns | ns | ns | ns | ns | ns | * | * | ** | ** |
| Cpd 53 (2 mg/kg bid) | 2.4 | 2.6 | 3.1 | 3.6 | 3.5 | 4.4 | 5.0 | 6.6 | 6.8 | 7.7 | 7.7 |
| s.e.m. | 0.3 | 0.4 | 0.6 | 0.7 | 0.7 | 1.0 | 0.9 | 1.1 | 1.0 | 1.2 | 1.3 |
| P value | ns | ns | ns | ns | ns | ns | ns | ns | ns | ns | ns |
| Cpd 53 (5 mg/kg bid) | 2.4 | 2.7 | 2.9 | 3.0 | 3.0 | 3.4 | 3.4 | 3.9 | 4.3 | 5.2 | 5.4 |
| s.e.m. | 0.4 | 0.4 | 0.4 | 0.4 | 0.5 | 0.5 | 0.5 | 0.7 | 0.6 | 0.7 | 1.0 |
| P value | ns | ns | ns | ns | ns | ns | ns | ns | ns | ns | ns |
| Cpd 53 (30 mg/kg bid) | 2.4 | 2.7 | 2.8 | 3.5 | 3.5 | 3.5 | 3.6 | 3.6 | 3.6 | 3.7 | 3.8 |
| s.e.m. | 0.3 | 0.4 | 0.5 | 0.7 | 0.7 | 0.7 | 0.7 | 0.8 | 0.6 | 0.7 | 0.7 |
| P value | ns | ns | ns | ns | ns | ns | ns | ns | ns | * | * | ns: not significant | p-values: * ($<0.001$)-p-values: * ($<0.01$)-p-values: *** ($<0.05$) vs disease vehicle group using ANOVA and Dunnett's test

4.3. Murine Model of Psoriatic-Like Epidermal Hyperplasia Induced by Topical Applications of Imiquimod, a TLR7/8 Agonist

4.3.1. Materials

Aldara® 5% imiquimod cream is obtained from MEDA. Anti mouse IL-12/IL-23 p40 purified antibody (C17.8) is obtained from eBioscience (cat no. 16 7123 85).

4.3.2. Animals

Balb/cJ mice (female, 18-20 g body weight) are obtained from Janvier Labs (France). Mice are kept on a 12 h light/dark cycle (07 h00-19 h00). Temperature is maintained at 22±2° C., food and water are provided ad libitum.

4.3.3. Study Design

The design of the study is adapted from Van der Fits L. et al. (van der Fits et al. 2009).

On the first day, the mice are shaved around the two ears under light anaesthesia with isoflurane.

30 mg of commercially available imiquimod cream (Aldara 5% cream) are applied on both internal and external surfaces of each ear for 4 consecutive days, corresponding to a daily dose of 1.5 mg of the active compound. Control animals received the same quantity of vaseline.

From day 1 to day 5, mice are dosed with test compound, 10 or 30 mg/kg, p.o., b.i.d. in methyl cellulose 0.5%, before application of imiquimod (on day 5, the mice are dosed only once, 2 h before euthanasia).

In a positive reference group, the animals receive two intraperitoneal injections of anti mouse IL-12/IL-23 p40 antibody, 10 mg/kg, on day 1 and 3 days before day 1.

4.3.4. Assessment of Disease

The thickness of both ears is measured daily with a thickness gage (Mitutoyo, Absolute Digimatic, 547 321). Body weight is assessed at initiation of the experiment and at sacrifice. At day 5,2 h after the last dosing, the mice are sacrificed. The pinnae of the ear are cut, excluding cartilage. The pinnae are weighed and then immersed in a vial containing 1 mL of RNAlater® solution to assess gene expression.

The results are expressed as mean SEM and statistical analysis is performed using one way ANOVA followed by Dunnett's post hoc test versus imiquimod vehicle group.

4.3.5. Gene Expression Analysis

Ears are removed from the RNAlater® solution and put in Trizol® after disruption with 1.4 mm ceramic beads in a Precellys device. Total RNA is then purified using Nucleo-Spin® RNA kit. cDNA is prepared and quantitative PCR is performed with gene-specific primers from Qiagen using SYBR Green technology in a ViiA7 real-time PCR system (Applied Biosystems). Expression levels of each gene (are calculated relative to the cyclophilin A housekeeping gene expression level. Data are expressed as mean±SEM of the relative quantity. The statistical test used is ANOVA analysis of variance with Dunnett's post-hoc test versus imiquimod vehicle group.

4.4. Murine Model of Psoriatic-Like Epidermal Hyperplasia Induced by Intradermal Injections of IL-23

4.4.1. Materials

Mouse recombinant IL-23, carrier free (14-8231,) is provided by e-Bioscience.

4.4.2. Animals

Balb/c mice (female, 18-20 g body weight) are obtained from CERJ (France). Mice are kept on a 12 h light/dark cycle (07:00-19:00). Temperature is maintained at 22° C., food and water are provided ad libitum.

4.4.3. Study Design

The design of the study is adapted from Rizzo H L. et al. (Rizzo et al. 2011).

On the first day (D1), the mice are shaved around the two ears.

For 4 consecutive days (D1 to D4), the mice receive a daily intradermal dose of mouse recombinant IL-23 (1 µg/20 µL in PBS/0.1% BSA) in the right pinna ear and 20 µL of PBS/0.1% BSA in the left pinna ear under anesthesia induced by inhalation of isoflurane.

From D1 to D5, mice are dosed with test-compound or with vehicle, 1 h prior IL-23 injection.

4.4.4. Assessment of Disease

The thickness of both ears is measured daily with an automatic caliper. Body weight is assessed at initiation and at sacrifice. On fifth day, 2 h after the last dosing, the mice are sacrificed. The pinnae of the ear are cut, excluding cartilage. The pinnae, placed in a vial containing 1 mL of RNAlater® solution.

At D4, blood samples are also collected from the retro-orbital sinus for PK profiling just before dosing (T0) and 1 h, 3 h, 6 h post-dosing.

There are 8 mice per group. The results are expressed as mean SEM and statistical analysis is performed using one-way ANOVA followed by Dunnett's post-hoc test versus IL-23 vehicle groups.

4.4.5. Gene Expression Analysis

Half ears are removed from RNAlater® solution and put in Trizol® after disruption with 1.4 mm ceramic beads in a Precellys device. Total RNA is then purified using Nucleo-Spin® RNA kit. cDNA is prepared and quantitative PCR is performed with gene-specific primers from Qiagen using SYBR Green technology in a ViiA7 real-time PCR system (Applied Biosystems). Expression levels of each gene are calculated relative to the cyclophilin A housekeeping gene expression level. Data are expressed as mean±SEM of the relative quantity. The statistical test used is ANOVA analysis of variance with Dunnett's post-hoc test versus the IL-23 vehicle group.

4.5. Murine Model of Systemic Lupus Erythematosus Induced by Epicutaneous Applications of Imiquimod

4.5.1. Materials

Aldara® 5% imiquimod cream is obtained from MEDA.
Mouse anti-double-stranded DNA antibodies ELISA kits are obtained from Alpha Diagnostic International (Cat no. 5120). Mouse urinary albumin ELISA kits are obtained from Abcam (cat no. ab108792). Urine creatinine assay kits are obtained from Abnova (cat no. KA4344).

4.5.2. Animals

BALB/cJ mice (female, 18-20 g body weight) are obtained from Janvier Labs (France). Mice are kept on a 12 h light/dark cycle (07:00-19:00). Temperature is maintained at 22±2° C., food and water are provided ad libitum.

4.5.3. Study Design

The design of the study is adapted from Yokogawa M. et al. (Yokogawa et al. 2014).

On the first day (D1), the mice are shaved around the right ears.

The mice receive an epicutaneous application of 1.25 mg of imiquimod 3 times per week on the right pinna ear for 12 consecutive weeks (D1 to D86). The control group receives the same quantity of vaseline.

From D1 to D86, mice are dosed with test compound (30 mg/kg, p.o., q.d. in methylcellulose 0.5%) or with vehicle (10 mL/kg).

4.5.4. Assessment of Disease

The thickness of the ears is measured once a week with an automatic gage (Mitutoyo, Absolute Digimatic, 547-321).

Body weight is assessed at initiation and once a week until sacrifice. At necropsy, the spleen weight is also measured. The mice are sacrificed 2 h after the last dosing.

At different time points (e.g., on days D28, D56 and D84), the mice are individually placed in a metabolic cage to perform urinalysis and assess proteinuria (albumin to creatinine ratio).

Serums are collected at different time points (e.g., on D28, D56 and D86) to assess anti-double stranded-DNA IgG levels.

At D13, blood samples are also collected from the retroorbital sinus for PK profiling just before dosing (T0) and 1 h, 3 h, 6 h post-dosing.

There are 8-19 mice per group. The results are expressed as mean SEM and statistical analysis is performed using one-way ANOVA followed by Dunnett's post-hoc test versus imiquimod vehicle groups.

4.5.5. Quantification of Compound Levels in Plasma

Plasma concentrations of each test compound are determined by an LC-MS/MS method in which the mass spectrometer is operated in positive or negative electrospray mode.

4.5.5.1. Histopathology

In each glomerulus, 4 different readouts including mesangioproliferation, endocapillary proliferation, mesangial matrix expansion and segmental sclerosis are graded on a scale of 0 to 2 and then summed. For each kidney, about 50 glomeruli are scored and then averaged giving one glomerular lesion score (Yokogawa et al. 2014). Data are expressed as mean SEM and statistical analysis is performed using the Kruskal-Wallis test followed by Dunn's post-hoc test versus imiquimod vehicle group.

4.5.5.2. Cellular Quantifications

For each cell type, immunohistochemical analysis is performed using image analysis (CaloPix software, TRIBVN Healthcare) on the whole tissue section at a magnification of ×20. Data are expressed as mean SEM and statistical analysis is performed using one-way ANOVA followed by Dunnett's post-hoc test versus imiquimod vehicle group.

4.5.5.3. Gene Expression Analysis

At sacrifice, the second part of the left kidneys is placed in tubes containing 1.4 mm ceramic beads and disrupted in 1% DTT RLT lysis buffer (Qiagen, cat no. 79216) with a Bertin Instruments Precellys® homogenizer. Total RNA is then purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene of interest (GOI=CD3, CD68, CD20, OAS1, Mx1, IFIT1, CXCL11 and Usp18) are calculated relative to the cyclophilin, GAPDH and β-actin housekeeping gene expression levels.

At sacrifice, one-third of the spleen is placed into tubes containing 1.4 mm ceramic beads and disrupted in Trizol® with a Bertin Instruments Precellys® homogenizer. Total RNA is extracted using a phenol/chloroform process and then purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene of interest are calculated relative to the cyclophilin, GAPDH and β-actin housekeeping gene expression levels.

4.6. Murine Model of Psoriatic Arthritis Induced by Overexpression of IL-23

4.6.1. Materials

Mouse IL-23 enhanced episomal expression vector (EEV) is obtained from System Biosciences (cat no. EEV651A-1). Mouse IL-23 Quantikine ELISA Kits are obtained from R&D Systems (cat no. M2300). ProSense® 680 and OsteoSense® 750EX are obtained from PerkinElmer (cat no. NEV10003 and NEV10053EX). RNAlater® is obtained from Ambion (cat no. AM7021). Imalgene® 1000 (Merial) and Rompun® 2% (Bayer) are obtained from Centravet (cat no. IMA004-6827812 and ROM001-6835444).

4.6.2. Animals

B10.RIII mice (male, 8-week old) are obtained from Charles River (France). Mice are kept on a 12 h light/dark cycle (07:00-19:00). Temperature is maintained at 22±2° C., food and water are provided ad libitum.

4.6.3. Study Design

The design of the study is adapted from Sherlock J P. et al. (Sherlock et al. 2012).

On the first day (D1), the mice undergo a hydrodynamic injection of Ringer or IL-23 EEV in Ringer into the tail vein.

As of D5, twice a week, the mice are scored for clinical symptoms until the end of the experiment.

On D5, blood is collected by puncture in the submandibular vein to assess the serum IL-23 concentration.

On D9, mice from all groups receive ProSense® 680 probe (0.8 nmol/10 g, IP). On D10, the mice are anesthetized with an intraperitoneal injection of Imalgene and Rompun (Granulocyte infiltration is then measured using in vivo molecular imaging (Bruker In-Vivo Xtreme imaging system).

On D11, randomization is performed according to ProSense® 680 molecular imaging and scoring.

As of D12, mice are dosed with test compound or with vehicle.

On D19, blood is sampled at time T0, T1 h, T3 h and T6 h after last dosing. Plasma is separated and kept at 20° C. until bioanalysis.

On D36, mice from all groups are sacrificed 2 h after last administration of compound.

Total blood is collected in a serum blood tube and mixed by gentle inversion 8-10 times. After clotting, blood samples are centrifuged 10 min at 1800×g. After centrifugation, serum is stored at −80 C.

4.6.4. Assessment of Disease

Body weight is assessed at initiation of the study, then twice a week and at sacrifice.

Twice weekly, clinical signs of inflammation are scored: 0 for normal paw; 1 if swelling of one digit; 2 if swelling of two or more digits; 3 if swelling of the entire paw. The scores of all limbs are summed up to produce a global score.

On D32, mice from all groups receive ProSense® 680 probe (0.8 nmol/10 g, IP) and OsteoSense® 750EX probe (0.8 nmol/10 g, IP). On D33, the mice are anesthetized with an intraperitoneal injection of Imalgene and Rompun. Granulocyte infiltration and bone remodelling are measured using in vivo molecular imaging (Bruker In-Vivo Xtreme imaging system).

There are 10 mice per group. The results are expressed as mean SEM and statistical analysis is performed using one-way ANOVA followed by Dunnett's post-hoc test versus diseased vehicle group for scoring and imaging analysis, versus sham vehicle group for body weight.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Argilés J M, López-Soriano F J. 1998. Catabolic proinflammatory cytokines. *Curr. Opin. Clin. Nutr. Metab. Care* 1, 245-251.
Ashour Ahmed A et al. 2010. SIK2 is a centrosome kinase required for bipolar mitotic spindle formation that provides a potential target for therapy in ovarian cancer. *Cancer Cell* 18, 109-121.
Bundgaard H. 1985. *Design of prodrugs*, Elsevier.
Bush K A et al. 2002. Reduction of joint inflammation and bone erosion in rat adjuvant arthritis by treatment with interleukin-17 receptor IgG1 Fc fusion protein. *Arthritis Rheum.* 46, 802-805.
Charoenfuprasert S et al. 2011. Identification of salt-inducible kinase 3 as a novel tumor antigen associated with tumorigenesis of ovarian cancer. *Oncogene* 30, 3570-3584.
Clark K et al. 2012. Phosphorylation of CRTC3 by the salt-inducible kinases controls the interconversion of classically activated and regulatory macrophages. *Proc. Natl. Acad. Sci. U.S.A.* 109, 16986-16991.
Darling N J et al. 2017. Inhibition of SIK2 and SIK3 during differentiation enhances the anti-inflammatory phenotype of macrophages. *Biochem. J.* 474, 521-537.
van der Fits L et al. 2009. Imiquimod-induced psoriasis-like skin inflammation in mice is mediated via the IL-23/IL-17 axis. *J. Immunol.* 182, 5836-5845.
Jou I-M et al. 2005. Thrombospondin 1 as an effective gene therapeutic strategy in collagen-induced arthritis. *Arthritis Rheum.* 52, 339-344.
Katoh Y et al. 2004. Salt-inducible kinase (SIK) isoforms: their involvement in steroidogenesis and adipogenesis. *Mol. Cell. Endocrinol.* 217, 109-112.
Khachigian L M. 2006. Collagen antibody-induced arthritis. *Nat. Protoc.* 1, 2512-2516.
Kumagai A et al. 2011. A Potent Inhibitor of SIK2,3,3',7-Trihydroxy-4'-Methoxyflavon (4'-O-Methylfisetin), Promotes Melanogenesis in B16F10 Melanoma Cells. *PLoS ONE* 6.
Lin H-S et al. 2007. Anti-rheumatic activities of histone deacetylase (HDAC) inhibitors in vivo in collagen-induced arthritis in rodents. *Br. J. Pharmacol.* 150, 862-872.
Liu J Z et al. 2013. Dense genotyping of immune-related disease regions identifies nine new risk loci for primary sclerosing cholangitis. *Nat. Genet.* 45, 670-675.
Nishida K et al. 2004. Histone deacetylase inhibitor suppression of autoantibody-mediated arthritis in mice via regulation of p16INK4a and p21WAF1/Cip1 expression. *Arthritis Rheum.* 50, 3365-3376.
Nixon M et al. 2016. Skeletal muscle salt inducible kinase 1 promotes insulin resistance in obesity. *Mol. Metab.* 5, 34-46.
Ozanne J, Prescott A R, Clark K. 2015. The clinically approved drugs dasatinib and bosutinib induce anti-inflammatory macrophages by inhibiting the salt-inducible kinases. *Biochem. J.* 465, 271-279.
Rall L C, Roubenoff R. 2004. Rheumatoid cachexia: metabolic abnormalities, mechanisms and interventions. *Rheumatology* 43, 1219-1223.
Rizzo H L et al. 2011. IL-23-mediated psoriasis-like epidermal hyperplasia is dependent on IL-17a. *J. Immunol.* 186, 1495-1502.
Salvemini D et al. 2001. Amelioration of joint disease in a rat model of collagen-induced arthritis by M40403, a superoxide dismutase mimetic. *Arthritis Rheum.* 44, 2909-2921.
Sasaki T et al. 2011. SIK2 is a key regulator for neuronal survival after ischemia via TORC1-CREB. *Neuron* 69, 106-119.
Shelton D L et al. 2005. Nerve growth factor mediates hyperalgesia and cachexia in auto-immune arthritis. *Pain* 116, 8-16.
Sherlock J P et al. 2012. IL-23 induces spondyloarthropathy by acting on ROR-γt+CD3+CD4−CD8− entheseal resident T cells. *Nat. Med.* 18, 1069-1076.

Sims N A et al. 2004. Targeting osteoclasts with zoledronic acid prevents bone destruction in collagen-induced arthritis. *Arthritis Rheum.* 50, 2338-2346.

Sina C et al. 2009. G Protein-Coupled Receptor 43 Is Essential for Neutrophil Recruitment during Intestinal Inflammation. *J. Immunol.* 183, 7514-7522.

Sundberg T B et al. 2014. Small-molecule screening identifies inhibition of salt-inducible kinases as a therapeutic strategy to enhance immunoregulatory functions of dendritic cells. *Proc. Natl. Acad. Sci. U.S.A.* 111, 12468-12473.

Walsmith J et al. 2004. Tumor necrosis factor-alpha production is associated with less body cell mass in women with rheumatoid arthritis. *J. Rheumatol.* 31, 23-29.

Wein M N et al. 2016. SKs control osteocyte responses to parathyroid hormone. *Nat. Commun.* 7, 13176.

Wirtz S et al. 2007. Chemically induced mouse models of intestinal inflammation. *Nat. Protoc.* 2, 541-546.

Wuts P G M, Greene T W. 2006. *Greene's Protective Groups in Organic Synthesis* 4th ed., Wiley-Interscience.

Yao C et al. 2013. Prostaglandin $E_2$ promotes Th1 differentiation via synergistic amplification of IL-12 signalling by cAMP and PI3-kinase. *Nat. Commun.* 4, 1685.

Yokogawa M et al. 2014. Epicutaneous application of toll-like receptor 7 agonists leads to systemic autoimmunity in wild-type mice: a new model of systemic lupus erythematosus. *Arthritis Rheumatol.* 66, 694-706.

Yu J et al. 2013. Salt-inducible kinase 1 is involved in high glucose-induced mesangial cell proliferation mediated by the ALK5 signaling pathway. *Int. J. Mol. Med.* 32, 151-157.

The invention claimed is:
1. A compound according to Formula I:

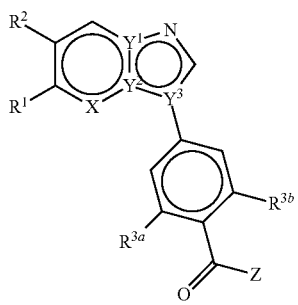

I wherein,
X is N or $CR^4$;
$Y_1$ is C;
one of $Y_2$ and $Y_3$ is N and the other is C;
Z is
 —$NR^{5a}R^{5b}$,
 —$NR^{5c}$—, wherein the N atom and $R^{3b}$ together with the atoms onto which they are attached form a fused 5-6 membered heterocycloalkenyl comprising one double bond and further comprising zero, one, or two additional heteroatoms independently selected from N, O, and S, or
 N-linked 4-7 membered heterocycloalkyl further comprising zero, one, or two additional heteroatoms independently selected from N, O, and S, optionally substituted with one, two or three independently selected $R^6$ groups;

$R^1$ is H, halo, $C_{1-4}$ alkyl, or $C_{1-4}$ alkoxy optionally substituted with $C_{1-4}$ alkoxy, phenyl, —CN, —C(=O)OH, or —C(=O)—$C_{1-4}$ alkoxy;

$R^2$ is 5-6 membered monocyclic heteroaryl comprising one, two or three heteroatoms independently selected from N, O, and S, which heteroaryl is optionally substituted with one or more independently selected $R^7$ groups;

$R^{3a}$ and $R^{3b}$ are independently selected from
 halo,
 $C_{1-4}$ alkyl,
 $C_{1-4}$ alkoxy optionally substituted with one or more independently selected halo, —OH or $C_{1-4}$ alkoxy,
 —$NR^{8a}R^{8b}$, and
 —OH;

$R^4$ is H or $C_{1-4}$ alkyl;
$R^{5a}$ is H or $C_{1-4}$ alkyl;
$R^{5b}$ is selected from
 $C_{1-6}$ alkyl optionally substituted with one or more independently selected $R^9$,
 $C_{3-7}$ cycloalkyl optionally substituted with one or more independently selected $R^{10}$,
 4-7 membered monocyclic heterocycloalkyl comprising one, two or three heteroatoms independently selected from N, O, and S, which heterocycloalkyl is optionally substituted with one or more oxo, and
 5-6 membered monocyclic heteroaryl comprising one, two or three heteroatoms independently selected from N, O, and S, which heteroaryl is optionally substituted with one or more independently selected $C_{1-4}$ alkyl;

$R^{5c}$ is selected from $C_{3-7}$ cycloalkyl, and $C_{1-6}$ alkyl optionally substituted with one or more independently selected halo;

each $R^6$ is independently selected from
 oxo,
 halo,
 —CN,
 —OH,
 —$NR^{11a}R^{11b}$
 phenyl,
 $C_{3-7}$ cycloalkyl,
 $C_{2-4}$ alkynyl,
 —C(=O)—$C_{1-4}$ alkoxy,
 —$C_{1-4}$ alkoxy optionally substituted with one or more halo or phenyl,
 $C_{1-4}$ alkyl optionally substituted with one or more halo, —OH, or $C_{1-4}$ alkoxy, and
 4-7 membered monocyclic heterocycloalkyl comprising one, two or three heteroatoms independently selected from N, O, and S;

each $R^7$ is selected from
 halo,
 —CN,
 $C_{1-6}$ alkyl optionally substituted with one or more independently selected
  halo,
  —CN,
  —OH,
  $C_{1-4}$ alkoxy optionally substituted with one or more independently selected halo,
  $NR^{11c}R^{11d}$,
  —C(=O)$R^{12}$, or
  4-6 membered monocyclic heterocycloalkyl comprising one, two or three heteroatoms independently selected from N, O, and S,
 $C_{1-4}$ alkoxy, C$_{3-7}$ cycloalkyl,
4-6 membered monocyclic heterocycloalkyl comprising one, two or three heteroatoms independently selected from N, O, and S, which heterocycloalkyl is optionally substituted with —C(=O)C$_{1-4}$ alkoxy or C$_{1-4}$ alkyl optionally substituted with —CN,
—NR$^{13a}$R$^{13b}$, and
—C(=O)NR$^{13c}$R$^{13d}$;

each R$^{8a}$ and R$^{8b}$ is independently selected from H and C$_{1-4}$ alkyl optionally substituted with one —OH or C$_{1-4}$ alkoxy;

each R$^9$ is independently selected from
halo,
—CN,
—NR$^{11e}$R$^{11f}$
—OH,
C$_{1-4}$ alkoxy,
—S(=O)$_2$-C$_{1-4}$ alkyl,
4-7 membered monocyclic heterocycloalkyl comprising one, two or three heteroatoms independently selected from N, O, and S, and
5-6 membered monocyclic heteroaryl comprising one, two or three heteroatoms independently selected from N, O, and S, which heteroaryl is optionally substituted with one or more independently selected C$_{1-4}$ alkyl;

each R$^{10}$ is independently selected from
halo,
C$_{1-4}$ alkyl optionally substituted with one or more independently selected halo, —OH, or C$_{1-4}$ alkoxy,
—OH,
C$_{1-4}$ alkoxy, and
—NR$^{11g}$R$^{11h}$;

each R$^{11a}$, R$^{11b}$, R$^{11c}$, R$^{11d}$, R$^{11e}$, R$^{11f}$, R$^{11g}$, and R$^{11h}$ is independently selected from H and C$_{1-4}$ alkyl; each R$^{12}$ is
—NR$^{14a}$R$^{14b}$ wherein each R$^{14a}$ and R$^{14b}$ is independently selected from H and C$_{1-4}$ alkyl,
—OH,
C$_{1-4}$ alkoxy optionally substituted with one or more independently selected C$_{3-7}$ cycloalkyl, halo, —NR$^{15a}$R$^{15b}$ or 4-6 membered monocyclic heterocycloalkyl comprising one, two or three heteroatoms independently selected from N, O, and S,
—O-(4-6 membered monocyclic heterocycloalkyl comprising one, two or three heteroatoms independently selected from N, O, and S), or
—O-(C$_{3-7}$ monocyclic cycloalkyl);

each R$^{13a}$, R$^{13b}$, R$^{13c}$, and R$^{13d}$, is independently selected from H and C$_{1-4}$ alkyl; and each R$^{15a}$ and R$^{15b}$ is independently selected from H and C$_{1-4}$ alkyl;
or a pharmaceutically acceptable salt thereof.

2. A compound or pharmaceutically acceptable salt thereof, according to claim 1, wherein R$^1$ is H, halo, C$_{1-4}$ alkyl, or C$_{1-4}$ alkoxy optionally substituted with C$_{1-4}$ alkoxy;
each R$^7$ is selected from
halo,
—CN,
C$_{1-4}$ alkyl optionally substituted with one or more independently selected
halo,
—CN,
—OH,
C$_{1-4}$ alkoxy optionally substituted with one or more independently selected halo,
NR$^{11c}$R$^{11d}$, —C(=O)R$^{12}$, or
4-6 membered monocyclic heterocycloalkyl comprising one, two or three heteroatoms independently selected from N, O, and S,
C$_{1-4}$ alkoxy,
C$_{3-7}$ cycloalkyl,
4-6 membered monocyclic heterocycloalkyl comprising one, two or three heteroatoms independently selected from N, O, and S, which heterocycloalkyl is optionally substituted with —C(=O)C$_{1-4}$ alkoxy or C$_{1-4}$ alkyl optionally substituted with —CN,
—NR$^{13a}$R$^{13b}$), and
C(=O)NR$^{13c}$R$^{13d}$, and each R$^{12}$ is
—NR$^{14a}$R$^{14b}$) wherein each R$^{14a}$ and R$^{14b}$) is independently selected from H and C$_{1-4}$ alkyl,
—OH,
C$_{1-4}$ alkoxy optionally substituted with one or more independently selected C$_{3-7}$ cycloalkyl, or halo,
—O-(4-6 membered monocyclic heterocycloalkyl comprising one, two or three heteroatoms independently selected from N, O, and S), or
—O—(C$_{3-7}$ monocyclic cycloalkyl).

3. A compound or pharmaceutically acceptable salt thereof, according to claim 1, wherein R$^2$ is imidazolyl, pyrazolyl, triazolyl, thiazolyl, oxazolyl, isoxazolyl, oxadiazolyl, pyridinyl, pyridazinyl, pyrimidinyl, or pyrazinyl, each of which is optionally substituted with one or more independently selected R$^7$ groups.

4. A compound or pharmaceutically acceptable salt thereof, according to claim 1, wherein the compound is according to any one of Formulae Vb, Vc, Ve, and Vf:

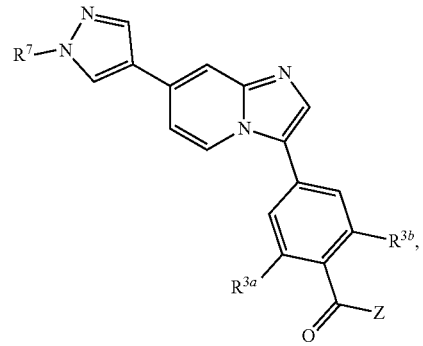

Vb

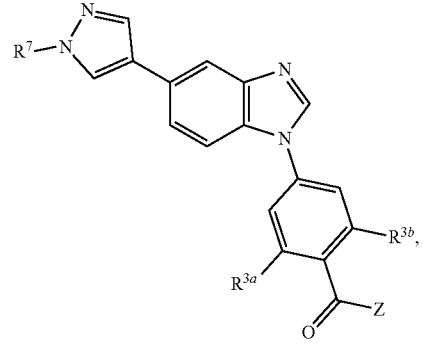

Vc

531

-continued

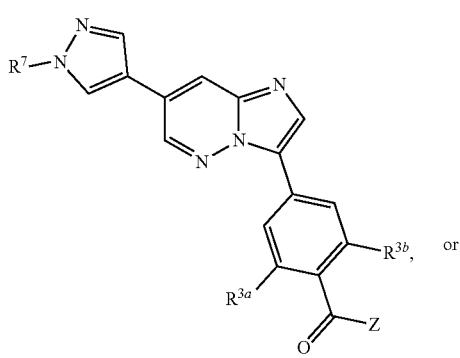
Ve or

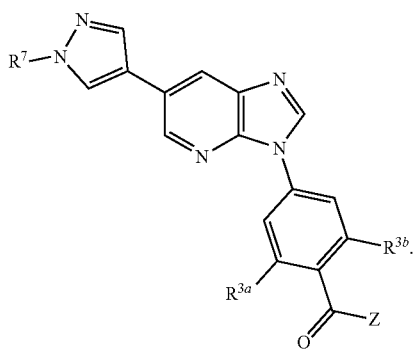
Vf

5. A compound or pharmaceutically acceptable salt thereof, according to claim 1, wherein $R^7$ is $C_{1-4}$ alkyl.

6. A compound or pharmaceutically acceptable salt thereof, according to claim 1, wherein $R^{3b}$ is —O—$CH_3$, —O—$CH_2CH_3$, or —O—CH($CH_3$)$_2$, each of which is optionally substituted with one or more independently selected halo, —OH or $C_{1-4}$ alkoxy.

7. A compound or pharmaceutically acceptable salt thereof, according to claim 1, wherein $R^{3a}$ is halo, —OH, $C_{1-4}$ alkoxy, or $C_{1-4}$ alkoxy substituted with one or more independently selected halo, —OH or $C_{1-4}$ alkoxy.

8. A compound or pharmaceutically acceptable salt thereof, according to claim 1, wherein the compound is according to any one of Formulae VIIIa-VIIId:

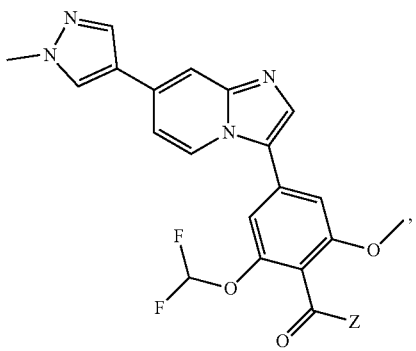
VIIIa

532

-continued

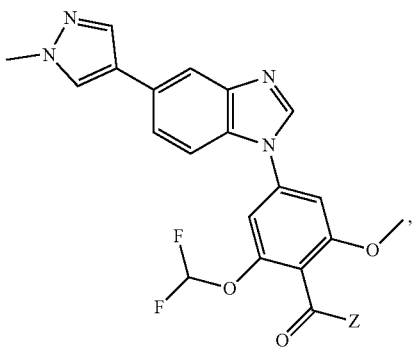
VIIIb

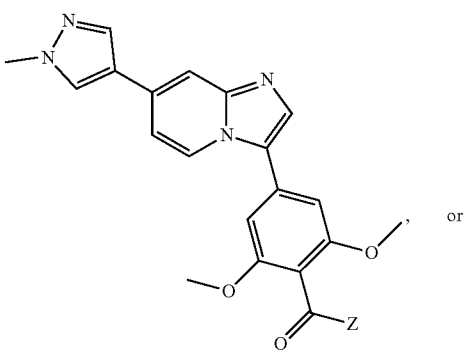
VIIIc or

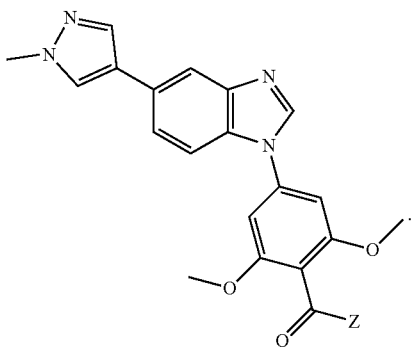
VIIId

9. A compound or pharmaceutically acceptable salt thereof, according to claim 1, wherein Z is —$NR^{5a}R^{5b}$.

10. A compound or pharmaceutically acceptable salt thereof, according to claim 1, wherein $R^{5a}$ is H, —$CH_3$, —$CH_2CH_3$, or —CH($CH_3$)$_2$.

11. A compound or pharmaceutically acceptable salt thereof, according to claim 1, wherein $R^{5b}$ is cyclopropyl, cyclobutyl, cyclopentyl, or cyclohexyl.

12. A compound or pharmaceutically acceptable salt thereof, according to claim 1, wherein $R^{5b}$ is —$CH_3$, —$CH_2CH_3$, —$CH_2CH_2CH_3$, —CH($CH_3$)$_2$, —$CH_2CH$ ($CH_3$)$_2$, —C($CH_3$)$_3$, —CH($CH_3$)$CH_2CH_3$, or —CH($CH_3$) CH($CH_3$)$_2$, each of which is substituted with one or more independently selected $R^9$.

13. A compound or pharmaceutically acceptable salt thereof, according to claim 12, wherein $R^9$ is F, Cl, —CN, —OH, —O—$CH_3$, —O—$CH_2CH_3$, —O—CH ($CH_3$)$_2$, —S(=O)$_2$—$CH_3$, —S(=O)$_2$—$CH_2CH_3$, or —S(=O)$_2$—CH($CH_3$)$_2$.

14. A pharmaceutical composition comprising a pharmaceutically acceptable carrier and a pharmaceutically effective amount of a compound or pharmaceutically acceptable salt thereof according to claim 1.

15. A method for inhibiting salt-inducible kinase (SIK) or tumor necrosis factor-alpha (TNF-α) activity or treating diseases associated with SIK or TNF-α activity, comprising administering an effective amount of the compound or pharmaceutically acceptable salt thereof, according to claim 1, to a subject in need thereof.

16. A method for inhibiting salt-inducible kinase (SIK) or tumor necrosis factor-alpha (TNF-α) activity or treating diseases associated with SIK or TNF-α activity, comprising administering the pharmaceutical composition according to claim 14, to a subject in need thereof.

17. The compound of claim 1, wherein the compound is
N-ethyl-4-[5-(1-ethylpyrazol-4-yl)benzimidazol-1-yl]-2,6-dimethoxy-benzamide,
N-ethyl-2,6-dimethoxy-4-[5-(3-pyridyl)benzimidazol-1-yl]benzamide,
N-ethyl-2,6-dimethoxy-4-[5-(6-morpholino-3-pyridyl)benzimidazol-1-yl]benzamide,
N-ethyl-2,6-dimethoxy-4-[5-[1-(2-morpholinoethyl)pyrazol-4-yl]benzimidazol-1-yl]benzamide,
4-[5-(1-ethylpyrazol-4-yl)benzimidazol-1-yl]-N-(2-hydroxyethyl)-2,6-dimethoxy-benzamide,
4-[5-(1-ethylpyrazol-4-yl)benzimidazol-1-yl]-2,6-dimethoxy-N-methyl-benzamide,
N-ethyl-2,6-dimethoxy-4-[5-(1-methylpyrazol-4-yl)benzimidazol-1-yl]benzamide,
4-[5-(1,3-dimethylpyrazol-4-yl)benzimidazol-1-yl]-N-ethyl-2,6-dimethoxy-benzamide,
4-[5-(1-ethylpyrazol-4-yl)benzimidazol-1-yl]-N-(2-fluoroethyl)-2,6-dimethoxy-benzamide,
N-(2,2-difluoroethyl)-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2,2,2-trifluoroethyl)benzamide,
N-ethyl-2,6-dimethoxy-4-[5-[1-(2-methoxyethyl)pyrazol-4-yl]benzimidazol-1-yl]benzamide,
N-ethyl-2,6-dimethoxy-4-[5-(1-tetrahydropyran-4-ylpyrazol-4-yl)benzimidazol-1-yl]benzamide,
4-[5-[1-(cyanomethyl)pyrazol-4-yl]benzimidazol-1-yl]-N-ethyl-2,6-dimethoxy-benzamide,
N-ethyl-4-[5-[1-(2-hydroxyethyl)pyrazol-4-yl]benzimidazol-1-yl]-2,6-dimethoxy-benzamide,
2-(difluoromethoxy)-N-ethyl-4-[5-(1-ethylpyrazol-4-yl)benzimidazol-1-yl]-6-methoxy-benzamide,
4-[5-[1-(2-amino-2-oxo-ethyl)pyrazol-4-yl]benzimidazol-1-yl]-N-ethyl-2,6-dimethoxy-benzamide,
N-cyclopropyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-propyl-benzamide,
N-ethyl-4-[5-(1-ethylpyrazol-4-yl)benzimidazol-1-yl]-2-hydroxy-6-methoxy-benzamide,
2,6-dimethoxy-4-[5-(1-methylpyrazol-4-yl)benzimidazol-1-yl]-N-(2,2,2-trifluoroethyl)benzamide,
N-cyclobutyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(2-methoxyethyl)-N-methyl-benzamide,
4-[5-(1-ethylpyrazol-4-yl)benzimidazol-1-yl]-N-isobutyl-2,6-dimethoxy-N-methyl-benzamide,
4-[6-(1-ethylpyrazol-4-yl)imidazo[4,5-b]pyridin-3-yl]-2,6-dimethoxy-N-(2,2,2-trifluoroethyl)benzamide,
N-cyclopropyl-4-[5-(1-ethylpyrazol-4-yl)benzimidazol-1-yl]-2,6-dimethoxy-N-methyl-benzamide,
N-(cyanomethyl)-4-[5-(1-ethylpyrazol-4-yl)benzimidazol-1-yl]-2,6-dimethoxy-N-methyl-benzamide,
2,6-dimethoxy-4-[5-(6-morpholino-3-pyridyl)benzimidazol-1-yl]-N-(2,2,2-trifluoroethyl)benzamide,
4-[5-[1-(2-hydroxyethyl)pyrazol-4-yl]benzimidazol-1-yl]-2,6-dimethoxy-N-(2,2,2-trifluoroethyl)benzamide,
2,6-dimethoxy-4-[5-(6-pyrrolidin-1-yl-3-pyridyl)benzimidazol-1-yl]-N-(2,2,2-trifluoroethyl)benzamide,
2,6-dimethoxy-4-[5-(5-methoxy-3-pyridyl)benzimidazol-1-yl]-N-(2,2,2-trifluoroethyl)benzamide,
4-[5-(6-cyano-3-pyridyl)benzimidazol-1-yl]-2,6-dimethoxy-N-(2,2,2-trifluoroethyl)benzamide,
4-[5-[6-(dimethylamino)-3-pyridyl]benzimidazol-1-yl]-2,6-dimethoxy-N-(2,2,2-trifluoroethyl)benzamide,
4-[5-(6-amino-3-pyridyl)benzimidazol-1-yl]-2,6-dimethoxy-N-(2,2,2-trifluoroethyl)benzamide,
2,6-dimethoxy-4-[5-(3-pyridyl)benzimidazol-1-yl]-N-(2,2,2-trifluoroethyl)benzamide,
4-[5-[1-(cyanomethyl)pyrazol-4-yl]benzimidazol-1-yl]-2,6-dimethoxy-N-(2,2,2-trifluoroethyl)benzamide,
2,6-dimethoxy-4-[5-[1-(2-morpholinoethyl)pyrazol-4-yl]benzimidazol-1-yl]-N-(2,2,2-trifluoroethyl)benzamide,
2,6-dimethoxy-4-[5-[1-(4-piperidyl)pyrazol-4-yl]benzimidazol-1-yl]-N-(2,2,2-trifluoroethyl)benzamide,
N-tert-butyl-4-[5-(1-ethylpyrazol-4-yl)benzimidazol-1-yl]-2,6-dimethoxy-benzamide,
4-[5-(1-ethylpyrazol-4-yl)benzimidazol-1-yl]-2,6-dimethoxy-N-(3,3,3-trifluoropropyl)benzamide,
N-cyclopentyl-4-[5-(1-ethylpyrazol-4-yl)benzimidazol-1-yl]-2,6-dimethoxy-benzamide,
2,6-dimethoxy-4-[5-[1-(1-methyl-4-piperidyl)pyrazol-4-yl]benzimidazol-1-yl]-N-(2,2,2-trifluoroethyl)benzamide,
2,6-dimethoxy-4-[5-(1H-pyrazol-4-yl)benzimidazol-1-yl]-N-(2,2,2-trifluoroethyl)benzamide,
2-(difluoromethoxy)-N-ethyl-6-methoxy-4-[5-(1-methylpyrazol-4-yl)benzimidazol-1-yl]benzamide,
4-[5-(1-ethylpyrazol-4-yl)benzimidazol-1-yl]-2,6-dimethoxy-N-[(2R)-2-methylcyclopropyl]benzamide,
N-(cyanomethyl)-4-[5-(1-ethylpyrazol-4-yl)benzimidazol-1-yl]-2,6-dimethoxy-benzamide,
4-(5-isoxazol-4-ylbenzimidazol-1-yl)-2,6-dimethoxy-N-(2,2,2-trifluoroethyl)benzamide,
N-cyclopropyl-2-(difluoromethoxy)-6-methoxy-4-[5-(1-methylpyrazol-4-yl)benzimidazol-1-yl]benzamide,
N-cyclopropyl-2-(difluoromethoxy)-4-[5-(1-ethylpyrazol-4-yl)benzimidazol-1-yl]-6-methoxy-benzamide,
4-[5-[1-(cyanomethyl)pyrazol-4-yl]benzimidazol-1-yl]-N-cyclopropyl-2-(difluoromethoxy)-6-methoxy-benzamide,
N-cyclopropyl-2-(difluoromethoxy)-6-methoxy-4-[5-[1-(2-morpholinoethyl)pyrazol-4-yl]benzimidazol-1-yl]benzamide,
2-(difluoromethoxy)-N-ethyl-6-methoxy-4-[5-[1-(2-morpholinoethyl)pyrazol-4-yl]benzimidazol-1-yl]benzamide,
2,6-dimethoxy-4-[5-(1-methylpyrazol-4-yl)benzimidazol-1-yl]-N-[(1R)-2,2,2-trifluoro-1-methyl-ethyl]benzamide,
N-(2-cyanoethyl)-2,6-dimethoxy-4-[5-(1-methylpyrazol-4-yl)benzimidazol-1-yl]benzamide,
2,6-dimethoxy-N-(3-methoxypropyl)-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1-methylpyrazol-3-yl)methyl]benzamide,
2,6-dimethoxy-4-[5-(1-methylpyrazol-4-yl)benzimidazol-1-yl]-N-(2-pyridylmethyl)benzamide, N-(3-hydroxypropyl)-2,6-dimethoxy-4-[5-(1-methylpyrazol-4-yl)benzimidazol-1-yl]benzamide,
N-(1,1-dioxothietan-3-yl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2-methyl sulfonyl ethyl)benzamide,
N-(1,1-dioxothiolan-3-yl)-2,6-dimethoxy-4-[5-(1-methylpyrazol-4-yl)benzimidazol-1-yl]benzamide,
N-[[(2R)-1,4-dioxan-2-yl]methyl]-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(2,2,2-trifluoro-1,1-dimethyl-ethyl)benzamide,
N-[[(2 S)-1,4-dioxan-2-yl]methyl]-2,6-dimethoxy-4-[5-(1-methylpyrazol-4-yl)benzimidazol-1-yl]benzamide,
2,6-dimethoxy-N-(5-methylpyrazin-2-yl)-4-[ 5-(1-methylpyrazol-4-yl)benzimidazol-1-yl]benzamide,
2,6-dimethoxy-N-[(1-methylimidazol-2-yl)methyl]-4-[5-(1-methylpyrazol-4-yl)benzimidazol-1-yl]benzamide,
N-isoxazol-3-yl-2,6-dimethoxy-4-[5-(1-methylpyrazol-4-yl)benzimidazol-1-yl]benzamide,
2,6-dimethoxy-N-(2-methylpyrazol-3-yl)-4-[ 5-(1-methylpyrazol-4-yl)benzimidazol-1-yl]benzamide,
N-(cyanomethyl)-2,6-dimethoxy-N-methyl-4-[5-(1-methylpyrazol-4-yl)benzimidazol-1-yl]benzamide,
N-(cyanomethyl)-2,6-dimethoxy-4-[5-(1-methylpyrazol-4-yl)benzimidazol-1-yl]benzamide,
N-tert-butyl-2,6-dimethoxy-4-[5-(1-methylpyrazol-4-yl)benzimidazol-1-yl]benzamide,
N-cyclobutyl-2,6-dimethoxy-4-[5-(1-methylpyrazol-4-yl)benzimidazol-1-yl]benzamide,
N-(2,2-difluoroethyl)-2,6-dimethoxy-4-[5-(1-methylpyrazol-4-yl)benzimidazol-1-yl]benzamide,
N-(2-fluoroethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-[(1 S)-2,2,2-trifluoro-1-methyl-ethyl]benzamide,
2,6-dimethoxy-N-(1-methylpyrazol-3-yl)-4-[ 5-(1-methylpyrazol-4-yl)benzimidazol-1-yl]benzamide,
2,6-dimethoxy-N-(1-methylimidazol-4-yl)-4-[5-(1-methylpyrazol-4-yl)benzimidazol-1-yl]benzamide,
2,6-dimethoxy-N-(1-methylpyrazol-4-yl)-4-[5-(1-methylpyrazol-4-yl)benzimidazol-1-yl]benzamide,
2,6-dimethoxy-4-[5-[1-(2-methoxyethyl)pyrazol-4-yl]benzimidazol-1-yl]-N-(2,2,2-trifluoroethyl)benzamide,
2,6-dimethoxy-4-[5-[1-(oxetan-3-yl)pyrazol-4-yl]benzimidazol-1-yl]-N-(2,2,2-trifluoroethyl)benzamide,
N-cyclopropyl-2,6-dimethoxy-4-[5-(1-methylpyrazol-4-yl)benzimidazol-1-yl]benzamide,
N-(1-cyanoethyl)-2,6-dimethoxy-4-[5-(1-methylpyrazol-4-yl)benzimidazol-1-yl]benzamide,
2,6-dimethoxy-4-[7-(1-methylpyrazol-4-yl)imidazo[1,2-a]pyridin-3-yl]-N-(2,2,2-trifluoroethyl)benzamide,
2,6-dimethoxy-4-[5-(1-methylpyrazol-3-yl)benzimidazol-1-yl]-N-(2,2,2-trifluoroethyl)benzamide,
N-(2,2-difluorocyclopentyl)-2,6-dimethoxy-4-[5-(1-methylpyrazol-4-yl)benzimidazol-1-yl]benzamide,
N-(2,2-difluoro-1-methyl-ethyl)-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-(oxetan-3-yl)benzamide,
2,6-dimethoxy-4-(5-pyridazin-4-ylbenzimidazol-1-yl)-N-(2,2,2-trifluoroethyl)benzamide,
4-[5-[1-(azetidin-3-yl)pyrazol-4-yl]benzimidazol-1-yl]-2,6-dimethoxy-N-(2,2,2-trifluoroethyl)benzamide,
4-[5-(1-isopropylpyrazol-4-yl)benzimidazol-1-yl]-2,6-dimethoxy-N-(2,2,2-trifluoroethyl)benzamide,
4-[5-(1-cyclopropylpyrazol-4-yl)benzimidazol-1-yl]-2,6-dimethoxy-N-(2,2,2-trifluoroethyl)benzamide,
4-[5-[1-(difluoromethyl)pyrazol-4-yl]benzimidazol-1-yl]-2,6-dimethoxy-N-(2,2,2-trifluoroethyl)benzamide,
2,6-dimethoxy-4-[5-[1-(1-methylazetidin-3-yl)pyrazol-4-yl]benzimidazol-1-yl]-N-(2,2,2-trifluoroethyl)benzamide,
4-[5-[1-[1-(cyanomethyl)azetidin-3-yl]pyrazol-4-yl]benzimidazol-1-yl]-2,6-dimethoxy-N-(2,2,2-trifluoroethyl)benzamide,
2,6-dimethoxy-4-[5-(3-methyl-1H-pyrazol-5-yl)benzimidazol-1-yl]-N-(2,2,2-trifluoroethyl)benzamide,
N-cyclopropyl-2,6-dimethoxy-4-[7-(1-methylpyrazol-4-yl)imidazo[1,2-a]pyridin-3-yl]benzamide,
2,6-dimethoxy-4-[5-(1-propylpyrazol-4-yl)benzimidazol-1-yl]-N-(2,2,2-trifluoroethyl)benzamide,
2,6-dimethoxy-4-(5-pyrimidin-5-ylbenzimidazol-1-yl)-N-(2,2,2-trifluoroethyl)benzamide,
2,6-dimethoxy-4-[5-(2-methoxypyrimidin-5-yl)benzimidazol-1-yl]-N-(2,2,2-trifluoroethyl)benzamide,
2,6-dimethoxy-4-[5-(2-methoxy-4-pyridyl)benzimidazol-1-yl]-N-(2,2,2-trifluoroethyl)benzamide,
2,6-dimethoxy-4-[7-(1-methylpyrazol-4-yl)imidazo[1,2-b]pyridazin-3-yl]-N-(2,2,2-trifluoroethyl)benzamide,
2,6-dimethoxy-4-[5-(3-methylisoxazol-4-yl)benzimidazol-1-yl]-N-(2,2,2-trifluoroethyl)benzamide,
2,6-dimethoxy-4-[5-(3-methylisoxazol-5-yl)benzimidazol-1-yl]-N-(2,2,2-trifluoroethyl)benzamide,
4-[5-(1-isobutylpyrazol-4-yl)benzimidazol-1-yl]-2,6-dimethoxy-N-(2,2,2-trifluoroethyl)benzamide,
2,6-dimethoxy-4-[5-[1-(tetrahydrofuran-2-ylmethyl)pyrazol-4-yl]benzimidazol-1-yl]-N-(2,2,2-trifluoroethyl)benzamide,
N-cyclopropyl-2,6-dimethoxy-4-[7-(1-methylpyrazol-4-yl)imidazo[1,2-b]pyridazin-3-yl]benzamide,
N-isobutyl-2,6-dimethoxy-4-[5-(1-methylpyrazol-4-yl)benzimidazol-1-yl]benzamide,
2,6-dimethoxy-4-[5-(1-methylpyrazol-4-yl)benzimidazol-1-yl]-N-sec-butyl-benzamide,
N-isopropyl-2,6-dimethoxy-4-[5-(1-methylpyrazol-4-yl)benzimidazol-1-yl]benzamide,
2-(difluoromethoxy)-N-ethyl-6-methoxy-4-[7-(1-methylpyrazol-4-yl)imidazo[1,2-a]pyridin-3-yl]benzamide,
2-(difluoromethoxy)-N-ethyl-6-methoxy-4-[7-(1-methylpyrazol-4-yl)imidazo[1,2-b]pyridazin-3-yl]benzamide,
N-cyclopropyl-2-isopropoxy-6-methoxy-4-[5-(1-methylpyrazol-4-yl)benzimidazol-1-yl]benzamide,
2,6-dimethoxy-4-[5-[2-(4-methylpiperazin-1-yl)-4-pyridyl]benzimidazol-1-yl]-N-(2,2,2-trifluoroethyl)benzamide,
2,6-dimethoxy-4-[5-(6-methylpyridazin-4-yl)benzimidazol-1-yl]-N-(2,2,2-trifluoroethyl)benzamide,
N-(cyanomethyl)-2,6-dimethoxy-4-[7-(1-methylpyrazol-4-yl)imidazo[1,2-a]pyridin-3-yl]benzamide,
2-(difluoromethoxy)-N-ethyl-6-methoxy-4-[7-(3-methylisoxazol-5-yl)imidazo[1,2-a]pyridin-3-yl]benzamide,
N-cyclopropyl-2-(difluoromethoxy)-6-methoxy-4-[7-(1-methylpyrazol-4-yl)imidazo[1,2-a]pyridin-3-yl]benzamide,
N-(3,3-difluorocyclobutyl)-2,6-dimethoxy-4-[5-(1-methylpyrazol-4-yl)benzimidazol-1-yl]benzamide,
2,6-dimethoxy-4-[5-(5-methyl-1,2,4-oxadiazol-3-yl)benzimidazol-1-yl]-N-(2,2,2-trifluoroethyl)benzamide, 2,6-dimethoxy-4-[5-(5-methyl-4H-1,2,4-triazol-3-yl)benzimidazol-1-yl]-N-(2,2,2-trifluoroethyl)benzamide,
2,6-dimethoxy-4-(5-pyrazin-2-ylbenzimidazol-1-yl)-N-(2,2,2-trifluoroethyl)benzamide,
N-isobutyl-2,6-dimethoxy-4-[7-(1-methylpyrazol-4-yl)imidazo[1,2-a]pyridin-3-yl]benzamide,
N-(1,1-dioxothietan-3-yl)-2,6-dimethoxy-4-[7-(1-methylpyrazol-4-yl)imidazo[1,2-a]pyridin-3-yl]benzamide,
2,6-dimethoxy-N-(2-methoxyethyl)-N-methyl-4-[7-(1-methylpyrazol-4-yl)imidazo[1,2-a]pyridin-3-yl]benzamide,
2,6-dimethoxy-4-[7-(1-methylpyrazol-4-yl)imidazo[1,2-a]pyridin-3-yl]-N-[(1S)-2,2,2-trifluoro-1-methyl-ethyl]benzamide,
N-(2,2-difluoroethyl)-2,6-dimethoxy-4-[7-(1-methylpyrazol-4-yl)imidazo[1,2-a]pyridin-3-yl]benzamide,
2,6-dimethoxy-4-[5-(1-methylimidazol-2-yl)benzimidazol-1-yl]-N-(2,2,2-trifluoroethyl)benzamide,
2,6-dimethoxy-4-[5-(3-methylimidazol-4-yl)benzimidazol-1-yl]-N-(2,2,2-trifluoroethyl)benzamide,
2-(difluoromethoxy)-N-ethyl-6-methoxy-4-[5-(5-methyl-1,2,4-oxadiazol-3-yl)benzimidazol-1-yl]benzamide,
2,6-dimethoxy-4-[5-(1-methylimidazol-4-yl)benzimidazol-1-yl]-N-(2,2,2-trifluoroethyl)benzamide,
4-[5-(2,3-dimethylimidazol-4-yl)benzimidazol-1-yl]-2,6-dimethoxy-N-(2,2,2-trifluoroethyl)benzamide,
N-[(1R,2R)-2-aminocyclohexyl]-2,6-dimethoxy-4-[5-(1-methylpyrazol-4-yl)benzimidazol-1-yl]benzamide,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-hydroxycyclopentyl]-2,6-dimethoxy-4-[5-(1-methylpyrazol-4-yl)benzimidazol-1-yl]benzamide,
(3,3-difluoroazetidin-1-yl)-[2,6-dimethoxy-4-[5-(1-methylpyrazol-4-yl)benzimidazol-1-yl]phenyl]methanone,
N-[(1R,2R)-2-hydroxycyclopentyl]-2,6-dimethoxy-4-[5-(1-methylpyrazol-4-yl)benzimidazol-1-yl]benzamide,
N-[(1R,2S)-2-fluorocyclopropyl]-2,6-dimethoxy-4-[5-(1-methylpyrazol-4-yl)benzimidazol-1-yl]benzamide,
2-(difluoromethoxy)-N-ethyl-6-methoxy-4-(7-pyridazin-4-ylimidazo[1,2-a]pyridin-3-yl)benzamide,
4-[7-(6-cyano-3-pyridyl)imidazo[1,2-a]pyridin-3-yl]-2-(difluoromethoxy)-N-ethyl-6-methoxy-benzamide,
tert-butyl 4-[4-[3-[3-(difluoromethoxy)-4-(ethylcarbamoyl)-5-methoxy-phenyl]imidazo[1,2-a]pyridin-7-yl]pyrazol-1-yl]piperidine-1-carboxylate,
2-(difluoromethoxy)-N-ethyl-6-methoxy-4-[7-[1-(1-methyl-4-piperidyl)pyrazol-4-yl]imidazo[1,2-a]pyridin-3-yl]benzamide,
2-(difluoromethoxy)-N-ethyl-6-methoxy-4-[7-[1-(4-piperidyl)pyrazol-4-yl]imidazo[1,2-a]pyridin-3-yl]benzamide,
2-(difluoromethoxy)-N-ethyl-6-methoxy-4-[5-(5-methyl-4H-1,2,4-triazol-3-yl)benzimidazol-1-yl]benzamide,
2-(difluoromethoxy)-4-[7-[1-(difluoromethyl)pyrazol-4-yl]imidazo[1,2-a]pyridin-3-yl]-N-ethyl-6-methoxy-benzamide,
2,6-dimethoxy-4-[5-(2-methyl-1H-imidazol-5-yl)benzimidazol-1-yl]-N-(2,2,2-trifluoroethyl)benzamide,
4-[5-(1H-imidazol-4-yl)benzimidazol-1-yl]-2,6-dimethoxy-N-(2,2,2-trifluoroethyl)benzamide,
2,6-dimethoxy-4-[5-(3-methylpyrazol-1-yl)benzimidazol-1-yl]-N-(2,2,2-trifluoroethyl)benzamide,
2,6-dimethoxy-4-[5-(4-methylimidazol-1-yl)benzimidazol-1-yl]-N-(2,2,2-trifluoroethyl)benzamide,
N-[(1R,2R)-2-(hydroxymethyl)cyclopropyl]-2,6-dimethoxy-4-[5-(1-methylpyrazol-4-yl)benzimidazol-1-yl]benzamide,
N-[(1R,2R)-2-(difluoromethyl)cyclopropyl]-2,6-dimethoxy-4-[5-(1-methylpyrazol-4-yl)benzimidazol-1-yl]benzamide,
N-[(1R,2S)-2-(difluoromethyl)cyclopropyl]-2,6-dimethoxy-4-[5-(1-methylpyrazol-4-yl)benzimidazol-1-yl]benzamide,
N-[(1R,2R)-2-hydroxycyclobutyl]-2,6-dimethoxy-4-[5-(1-methylpyrazol-4-yl)benzimidazol-1-yl]benzamide,
2,6-dimethoxy-4-[5-(1-methyltriazol-4-yl)benzimidazol-1-yl]-N-(2,2,2-trifluoroethyl)benzamide,
2,6-dimethoxy-N-(2-methoxycyclohexyl)-4-[5-(1-methylpyrazol-4-yl)benzimidazol-1-yl]benzamide,
azetidin-1-yl-[2,6-dimethoxy-4-[5-(1-methylpyrazol-4-yl)benzimidazol-1-yl]phenyl]m ethanone,
N-(2-aminoethyl)-2,6-dimethoxy-4-[5-(1-methylpyrazol-4-yl)benzimidazol-1-yl]benzamide,
N-[(1S,2S)-2-hydroxycyclohexyl]-2,6-dimethoxy-4-[5-(1-methylpyrazol-4-yl)benzimidazol-1-yl]benzamide,
4-[5-(3,5-dimethylpyrazol-1-yl)benzimidazol-1-yl]-2,6-dimethoxy-N-(2,2,2-trifluoroethyl)benzamide,
2,6-dimethoxy-4-[5-(3-methyl-1,2,4-triazol-1-yl)benzimidazol-1-yl]-N-(2,2,2-trifluoroethyl)benzamide,
2,6-dimethoxy-4-[5-(5-methyl-1,3,4-oxadiazol-2-yl)benzimidazol-1-yl]-N-(2,2,2-trifluoroethyl)benzamide,
4-[5-(4,5-dimethyl-1,2,4-triazol-3-yl)benzimidazol-1-yl]-2,6-dimethoxy-N-(2,2,2-trifluoroethyl)benzamide,
2,6-dimethoxy-4-[5-(3-methyl-1,2,4-oxadiazol-5-yl)benzimidazol-1-yl]-N-(2,2,2-trifluoroethyl)benzamide,
N-[(1S,2S)-2-hydroxycyclobutyl]-2,6-dimethoxy-4-[7-(1-methylpyrazol-4-yl)imidazo[1,2-a]pyridin-3-yl]benzamide,
N-isopropyl-2,6-dimethoxy-4-[7-(1-methylpyrazol-4-yl)imidazo[1,2-a]pyridin-3-yl]benzamide,
N-[(1S,2S)-2-(difluoromethyl)cyclopropyl]-2,6-dimethoxy-4-[7-(1-methylpyrazol-4-yl)imidazo[1,2-a]pyridin-3-yl]benzamide,
(3,3-difluoroazetidin-1-yl)-[2,6-dimethoxy-4-[7-(1-methylpyrazol-4-yl)imidazo[1,2-a]pyridin-3-yl]phenyl]methanone,
2,6-dimethoxy-4-[7-(1-methylpyrazol-4-yl)imidazo[1,2-a]pyridin-3-yl]-N-[(1R)-2,2,2-trifluoro-1-methyl-ethyl]benzamide,
2-ethyl-7-fluoro-5-[5-(1-methylpyrazol-4-yl)benzimidazol-1-yl]isoindolin-1-one,
2-ethyl-7-methoxy-5-[7-(1-methylpyrazol-4-yl)imidazo[1,2-a]pyridin-3-yl]isoindolin-1-one,
2-(difluoromethoxy)-N-ethyl-6-methoxy-4-[6-(1-methylpyrazol-4-yl)imidazo[4,5-b]pyridin-3-yl]benzamide,
2-(difluoromethoxy)-N-ethyl-6-methoxy-4-[7-(1-methylimidazol-4-yl)imidazo[1,2-a]pyridin-3-yl]benzamide,
[2,6-dimethoxy-4-[5-(1-methylpyrazol-4-yl)benzimidazol-1-yl]phenyl]-(3,3-dimethylazetidin-1-yl)methanone,
[2,6-dimethoxy-4-[5-(1-methylpyrazol-4-yl)benzimidazol-1-yl]phenyl]-(3-phenylazetidin-1-yl) methanone,
[2,6-dimethoxy-4-[5-(1-methylpyrazol-4-yl)benzimidazol-1-yl]phenyl]-(2,4-dimethylazetidin-1-yl) methanone,
[2,6-dimethoxy-4-[5-(1-methylpyrazol-4-yl)benzimidazol-1-yl]phenyl]-(2-methylazetidin-1-yl) methanone,
[2,6-dimethoxy-4-[5-(1-methylpyrazol-4-yl)benzimidazol-1-yl]phenyl]-3-(hydroxymethyl)azetidin-1-yl]methanone,
[2,6-dimethoxy-4-[5-(1-methylpyrazol-4-yl)benzimidazol-1-yl]phenyl]-(3-hydroxyazetidin-1-yl) methanone,

[2,6-dimethoxy-4-[5-(1-methylpyrazol-4-yl)benzimidazol-1-yl]phenyl]-[3-(dimethylamino)azetidin-1-yl] methanone,
(3-benzyloxyazetidin-1-yl)-[2,6-dimethoxy-4-[5-(1-methylpyrazol-4-yl)benzimidazol-1-yl]phenyl]methanone,
[2,6-dimethoxy-4-[5-(1-methylpyrazol-4-yl)benzimidazol-1-yl]phenyl]-(2-phenylazetidin-1-yl) methanone,
[2,6-dimethoxy-4-[5-(1-methylpyrazol-4-yl)benzimidazol-1-yl]phenyl]-(3-morpholinoazetidin-1-yl) methanone,
[2,6-dimethoxy-4-[5-(1-methylpyrazol-4-yl)benzimidazol-1-yl]phenyl]-(2,2,4-trimethylazetidin-1-yl) methanone,
[2,6-dimethoxy-4-[5-(1-methylpyrazol-4-yl)benzimidazol-1-yl]phenyl]-(3-methoxyazetidin-1-yl) methanone,
[2,6-dimethoxy-4-[5-(1-methylpyrazol-4-yl)benzimidazol-1-yl]phenyl]-(3-tetrahydropyran-4-ylazetidin-1-yl) methanone,
1-[2,6-dimethoxy-4-[5-(1-methylpyrazol-4-yl)benzimidazol-1-yl]benzoyl]azetidine-3-carbonitrile,
[2,6-dimethoxy-4-[5-(1-methylpyrazol-4-yl)benzimidazol-1-yl]phenyl]-[2-(hydroxymethyl)azetidin-1-yl] methanone,
[2,6-dimethoxy-4-[5-(1-methylpyrazol-4-yl)benzimidazol-1-yl]phenyl]-(2-oxa-6-azaspiro[3.3]heptan-6-yl) methanone,
[2,6-dimethoxy-4-[5-(1-methylpyrazol-4-yl)benzimidazol-1-yl]phenyl]-(2,2-dioxo-2$\lambda^6$-thia-6-azaspiro[3.3]heptan-6-yl)methanone,
[2,6-dimethoxy-4-[5-(1-methylpyrazol-4-yl)benzimidazol-1-yl]phenyl]-(3-phenylpyrrolidin-1-yl)methanone,
[2,6-dimethoxy-4-[5-(1-methylpyrazol-4-yl)benzimidazol-1-yl]phenyl]-(4-fluoro-1-piperidyl)methanone,
[2,6-dimethoxy-4-[5-(1-methylpyrazol-4-yl)benzimidazol-1-yl]phenyl]-[4-(trifluoromethoxy)-1-piperidyl] methanone,
N-tert-butyl-2-(difluoromethoxy)-6-methoxy-4-[5-(1-methylpyrazol-4-yl)benzimidazol-1-yl]benzamide,
2,6-dimethoxy-4-[7-(1-methylpyrazol-4-yl)imidazo[1,2-a]pyridin-3-yl]-N-[2-methyl-1-(trifluoromethyl)propyl]benzamide,
2-ethyl-7-(2-hydroxyethylamino)-5-[7-(1-methylpyrazol-4-yl)imidazo[1,2-a]pyridin-3-yl]isoindolin-1-one,
2-ethyl-7-(2-hydroxyethylamino)-5-[5-(1-methylpyrazol-4-yl)benzimidazol-1-yl]isoindolin-1-one,
2-fluoro-6-methoxy-4-[7-(1-methylpyrazol-4-yl)imidazo[1,2-a]pyridin-3-yl]-N-(2,2,2-trifluoroethyl)benzamide,
2-methoxy-6-(methylamino)-4-[7-(1-methylpyrazol-4-yl)imidazo[1,2-a]pyridin-3-yl]-N-(2,2,2-trifluoroethyl)benzamide,
2-(2-hydroxyethylamino)-6-methoxy-4-[7-(1-methylpyrazol-4-yl)imidazo[1,2-a]pyridin-3-yl]-N-(2,2,2-trifluoroethyl)benzamide,
2-methoxy-6-methyl-4-[7-(1-methylpyrazol-4-yl)imidazo[1,2-a]pyridin-3-yl]-N-(2,2,2-trifluoroethyl)benzamide,
2-chloro-6-methoxy-4-[7-(1-methylpyrazol-4-yl)imidazo[1,2-a]pyridin-3-yl]-N-(2,2,2-trifluoroethyl)benzamide,
[2,6-dimethoxy-4-[7-(1-methylpyrazol-4-yl)imidazo[1,2-a]pyridin-3-yl]phenyl]-(3,3-dimethylazetidin-1-yl) methanone,
1-[2,6-dimethoxy-4-[7-(1-methylpyrazol-4-yl)imidazo[1,2-a]pyridin-3-yl]benzoyl]azetidine-3-carbonitrile,
1-[2,6-dimethoxy-4-[7-(1-methylpyrazol-4-yl)imidazo[1,2-a]pyridin-3-yl]benzoyl]pyrrolidine-3-carbonitrile,
(3,3-difluoropyrrolidin-1-yl)-[2,6-dimethoxy-4-[7-(1-methylpyrazol-4-yl)imidazo[1,2-a]pyridin-3-yl]phenyl]methanone,
(4,4-difluoro-1-piperidyl)-[2,6-dimethoxy-4-[7-(1-methylpyrazol-4-yl)imidazo[1,2-a]pyridin-3-yl]phenyl] methanone,
[2,6-dimethoxy-4-[7-(1-methylpyrazol-4-yl)imidazo[1,2-a]pyridin-3-yl]phenyl]-[3-(trifluoromethyl)azetidin-1-yl]methanone,
8-methoxy-6-[7-(1-methylpyrazol-4-yl)imidazo[1,2-a]pyridin-3-yl]-3,4-dihydro-2H-isoquinolin-1-one,
2,6-dimethoxy-4-[7-(1-methylimidazol-4-yl)imidazo[1,2-a]pyridin-3-yl]-N-[(1R)-2,2,2-trifluoro-1-methyl-ethyl]benzamide,
2,6-dimethoxy-4-[7-(1-methylimidazol-4-yl)imidazo[1,2-a]pyridin-3-yl]-N-[(1S)-2,2,2-trifluoro-1-methyl-ethyl]benzamide,
[2,6-dimethoxy-4-[5-(1-methylpyrazol-4-yl)benzimidazol-1-yl]phenyl]-(3-hydroxy-3-methyl-azetidin-1-yl) methanone,
[2,6-dimethoxy-4-[5-(1-methylpyrazol-4-yl)benzimidazol-1-yl]phenyl]-(3-ethyl-3-hydroxy-azetidin-1-yl) methanone,
[2,6-dimethoxy-4-[5-(1-methylpyrazol-4-yl)benzimidazol-1-yl]phenyl]-[3-hydroxy-3-(trifluoromethyl)azetidin-1-yl]methanone,
(3-cyclopropyl-3-hydroxy-azetidin-1-yl)-[2,6-dimethoxy-4-[5-(1-methylpyrazol-4-yl)benzimidazol-1-yl] phenyl]methanone,
[2,6-dimethoxy-4-[5-(1-methylpyrazol-4-yl)benzimidazol-1-yl]phenyl]-(3-ethynyl-3-hydroxy-azetidin-1-yl) methanone,
2,6-dimethoxy-4-[7-(1H-pyrazol-4-yl)imidazo[1,2-a]pyridin-3-yl]-N-[(1R)-2,2,2-trifluoro-1-methyl-ethyl] benzamide,
2,6-dimethoxy-4-[7-(3-methylisoxazol-5-yl)imidazo[1,2-a]pyridin-3-yl]-N-[(1R)-2,2,2-trifluoro-1-methyl-ethyl]benzamide,
2,6-dimethoxy-4-[7-(3-methylisoxazol-5-yl)imidazo[1,2-a]pyridin-3-yl]-N-[(1S)-2,2,2-trifluoro-1-methyl-ethyl] benzamide,
8-methoxy-6-[7-(1-methylpyrazol-4-yl)imidazo[1,2-a]pyridin-3-yl]-2-(2,2,2-trifluoroethyl)-3,4-dihydroisoquinolin-1-one,
methyl 1-[2,6-dimethoxy-4-[7-(1-methylpyrazol-4-yl)imidazo[1,2-a]pyridine-3-yl]benzoyl]azetidine-3-carboxylate,
2,6-dimethoxy-4-[7-(1H-pyrazol-4-yl)imidazo[1,2-a]pyridin-3-yl]-N-(2,2,2-trifluoroethyl)benzamide,
2-[4-[3-[3,5-dimethoxy-4-(2,2,2-trifluoroethylcarbamoyl)phenyl]imidazo[1,2-a]pyridin-7-yl]pyrazol-1-yl] acetic acid,
tert-butyl 2-[4-[3-[3,5-dimethoxy-4-(2,2,2-trifluoroethylcarbamoyl)phenyl]imidazo[1,2-a]pyridin-7-yl]pyrazol-1-yl]acetate,
ethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
isopropyl 2-[4-[3-[3,5-dimethoxy-4-(2,2,2-trifluoroethylcarbamoyl)phenyl]imidazo[1,2-a]pyridin-7-yl]pyrazol-1-yl]acetate,
2,6-dimethoxy-4-[7-(3-methylisoxazol-5-yl)imidazo[1,2-a]pyridin-3-yl]-N-(2,2,2-trifluoroethyl)benzamide, 2-hydroxy-6-methoxy-4-[7-(1-methylpyrazol-4-yl)imidazo[1,2-a]pyridin-3-yl]-N-(2,2,2-trifluoroethyl)benzamide, cyclopropyl 2-[4-[3-[3,5-dimethoxy-4-(2,2,2-trifluoroethylcarbamoyl)phenyl]imidazo[1,2-a]pyridin-7-yl]pyrazol-1-yl]acetate, 2-fluoroethyl 2-[4-[3-[3,5-dimethoxy-4-(2,2,2-trifluoroethylcarbamoyl)phenyl]imidazo[1,2-a]pyridin-7-yl]pyrazol-1-yl]acetate, methyl 2-[4-[3-[3,5-dimethoxy-4-(2,2,2-trifluoroethylcarbamoyl)phenyl]imidazo[1,2-a]pyridin-7-yl]pyrazol-1-yl]acetate, tetrahydrofuran-3-yl 2-[4-[3-[3,5-dimethoxy-4-(2,2,2-trifluoroethylcarbamoyl)phenyl]imidazo[1,2-a]pyridin-7-yl]pyrazol-1-yl]acetate, cyclobutylmethyl 2-[4-[3-[3,5-dimethoxy-4-(2,2,2-trifluoroethylcarbamoyl)phenyl]imidazo[1,2-a]pyridin-7-yl]pyrazol-1-yl]acetate, 2,6-dimethoxy-4-[7-(6-methoxy-3-pyridyl)imidazo[1,2-a]pyridin-3-yl]-N-(2,2,2-trifluoroethyl)benzamide, 4-[7-(6-cyano-3-pyridyl)imidazo[1,2-a]pyridin-3-yl]-2,6-dimethoxy-N-(2,2,2-trifluoroethyl)benzamide, 2,6-dimethoxy-4-[7-(2-methoxypyrimidin-5-yl)imidazo[1,2-a]pyridin-3-yl]-N-(2,2,2-trifluoroethyl)benzamide, 2,6-dimethoxy-4-(7-pyrimidin-5-ylimidazo[1,2-a]pyridin-3-yl)-N-(2,2,2-trifluoroethyl)benzamide, tert-butyl 2-[4-[3-[3,5-dimethoxy-4-(2,2,2-trifluoroethylcarbamoyl)phenyl]imidazo[1,2-a]pyridin-7-yl]pyrazol-1-yl]propanoate, methyl 2-[4-[3-[3,5-dimethoxy-4-(2,2,2-trifluoroethylcarbamoyl)phenyl]imidazo[1,2-a]pyridin-7-yl]pyrazol-1-yl]propanoate, 2,6-dimethoxy-4-[7-(5-methoxy-3-pyridyl)imidazo[1,2-a]pyridin-3-yl]-N-(2,2,2-trifluoroethyl)benzamide, 4-[7-(2-aminopyrimidin-5-yl)imidazo[1,2-a]pyridin-3-yl]-2,6-dimethoxy-N-(2,2,2-trifluoroethyl)benzamide, 2,6-dimethoxy-4-(7-pyridazin-4-ylimidazo[1,2-a]pyridin-3-yl)-N-(2,2,2-trifluoroethyl)benzamide, 4-[7-(5-ethoxy-3-pyridyl)imidazo[1,2-a]pyridin-3-yl]-2,6-dimethoxy-N-(2,2,2-trifluoroethyl)benzamide, 2,6-dimethoxy-4-[7-[1-methyl-3-(trifluoromethyl)pyrazol-4-yl]imidazo[1,2-a]pyridin-3-yl]-N-(2,2,2-trifluoroethyl)benzamide, 2,6-dimethoxy-4-[7-(2-methoxy-3-pyridyl)imidazo[1,2-a]pyridin-3-yl]-N-(2,2,2-trifluoroethyl)benzamide, 2,6-dimethoxy-4-[7-(6-morpholino-3-pyridyl)imidazo[1,2-a]pyridin-3-yl]-N-(2,2,2-trifluoroethyl)benzamide, 2,6-dimethoxy-4-[7-(6-methylpyridazin-4-yl)imidazo[1,2-a]pyridin-3-yl]-N-(2,2,2-trifluoroethyl)benzamide, 4-[7-(4-isopropylpyrimidin-5-yl)imidazo[1,2-a]pyridin-3-yl]-2,6-dimethoxy-N-(2,2,2-trifluoroethyl)benzamide, 2-[4-[3-[3,5-dimethoxy-4-(2,2,2-trifluoroethylcarbamoyl)phenyl]imidazo[1,2-a]pyridin-7-yl]pyrazol-1-yl]propanoic acid, 4-[4-[3-[3,5-dimethoxy-4-(2,2,2-trifluoroethylcarbamoyl)phenyl]imidazo[1,2-a]pyridin-7-yl]pyrazol-1-yl]butanoic acid, methyl 4-[4-[3-[3,5-dimethoxy-4-(2,2,2-trifluoroethylcarbamoyl)phenyl]imidazo[1,2-a]pyridin-7-yl]pyrazol-1-yl]butanoate, ethyl 4-[4-[3-[3,5-dimethoxy-4-(2,2,2-trifluoroethylcarbamoyl)phenyl]imidazo[1,2-a]pyridin-7-yl]pyrazol-1-yl]butanoate, 4-[7-(4-cyano-3-pyridyl)imidazo[1,2-a]pyridin-3-yl]-2,6-dimethoxy-N-(2,2,2-trifluoroethyl)benzamide, 3-[3-[3,5-dimethoxy-4-(2,2,2-trifluoroethylcarbamoyl)phenyl]imidazo[1,2-a]pyridin-7-yl]pyridine-4-carboxamide, tert-butyl 3-[4-[3-[3,5-dimethoxy-4-(2,2,2-trifluoroethylcarbamoyl)phenyl]imidazo[1,2-a]pyridin-7-yl]pyrazol-1-yl]azetidine-1-carboxylate, 7-methoxy-5-[7-(1-methylpyrazol-4-yl)imidazo[1,2-a]pyridin-3-yl]-2-(2,2,2-trifluoroethyl)isoindolin-1-one, 2-cyclopropyl-8-methoxy-6-[7-(1-methylpyrazol-4-yl)imidazo[1,2-a]pyridin-3-yl]-3,4-dihydroisoquinolin-1-one, ethyl 2-[4-[3-[3,5-dimethoxy-4-(2,2,2-trifluoroethylcarbamoyl)phenyl]imidazo[1,2-a]pyridin-7-yl]pyrazol-1-yl]propanoate, 4-[7-[1-[1-(2-cyanoethyl)azetidin-3-yl]pyrazol-4-yl]imidazo[1,2-a]pyridin-3-yl]-2,6-dimethoxy-N-(2,2,2-trifluoroethyl)benzamide, 4-[7-[14-[1-(cyanomethyl)azetidin-3-yl]pyrazol-4-yl]imidazo[1,2-a]pyridin-3-yl]-2,6-dimethoxy-N-(2,2,2-trifluoroethyl)benzamide, 4-[7-(1-methylpyrazol-4-yl)imidazo[1,2-a]pyridin-3-yl]-2,6-bis(trideuteriomethoxy)-N-(2,2,2-trifluoroethyl)benzamide, N-cyclopropyl-2-(difluoromethoxy)-6-methoxy-4-[7-(6-methoxy-3-pyridyl)imidazo[1,2-a]pyridin-3-yl]benzamide, 4-[7-(2-cyano-3-pyridyl)imidazo[1,2-a]pyridin-3-yl]-2,6-dimethoxy-N-(2,2,2-trifluoroethyl)benzamide, 2,6-dimethoxy-4-[7-(6-methylpyridazin-3-yl)imidazo[1,2-a]pyridin-3-yl]-N-(2,2,2-trifluoroethyl)benzamide, N-cyclopropyl-2-(difluoromethoxy)-6-methoxy-4-[7-(3-methylisoxazol-5-yl)imidazo[1,2-a]pyridin-3-yl]benzamide, 2,6-difluoro-4-[7-(1-methylpyrazol-4-yl)imidazo[1,2-a]pyridin-3-yl]-N-(2,2,2-trifluoroethyl)benzamide, N-cyclopropyl-2-(difluoromethoxy)-6-methoxy-4-[7-(6-methylpyridazin-4-yl)imidazo[1,2-a]pyridin-3-yl]benzamide, N-cyclopropyl-2-(difluoromethoxy)-6-methoxy-4-[7-(6-methylpyridazin-3-yl)imidazo[1,2-a]pyridin-3-yl]benzamide, N-cyclopropyl-2-(difluoromethoxy)-6-methoxy-4-[7-(3-methylimidazol-4-yl)imidazo[1,2-a]pyridin-3-yl]benzamide, 8-methoxy-6-[7-(6-methylpyridazin-3-yl)imidazo[1,2-a]pyridin-3-yl]-2-(2,2,2-trifluoroethyl)-3,4-dihydroisoquinolin-1-one, N-cyclopropyl-2-fluoro-6-methoxy-4-[7-(1-methylpyrazol-4-yl)imidazo[1,2-a]pyridin-3-yl]benzamide, N-cyclopropyl-2-(isopropylamino)-6-methoxy-4-[7-(1-methylpyrazol-4-yl)imidazo[1,2-a]pyridin-3-yl]benzamide, N-cyclopropyl-2-methoxy-6-(2-methoxyethoxy)-4-[7-(1-methylpyrazol-4-yl)imidazo[1,2-a]pyridin-3-yl]benzamide, N-cyclopropyl-2-(2-hydroxyethoxy)-6-methoxy-4-[7-(1-methylpyrazol-4-yl)imidazo[1,2-a]pyridin-3-yl]benzamide, N-cyclopropyl-2-(difluoromethoxy)-6-methoxy-4-[7-(6-methoxypyridazin-3-yl)imidazo[1,2-a]pyridin-3-yl]benzamide, N-cyclopropyl-2-(difluoromethoxy)-6-methoxy-4-[7-[6-(trifluoromethyl)pyridazin-3-yl]imidazo[1,2-a]pyridin-3-yl]benzamide, 4-[7-(6-cyanopyridazin-3-yl)imidazo[1,2-a]pyridin-3-yl]-N-cyclopropyl-2-(difluoromethoxy)-6-methoxybenzamide, N-cyclopropyl-2-(difluoromethoxy)-4-[7-[6-(dimethyl-amino)pyridazin-3-yl]imidazo[1,2-a]pyridin-3-yl]-6-methoxy-benzamide,
ethyl 2-[4-[3-[4-(cyclopropylcarbamoyl)-3-(difluoromethoxy)-5-methoxy-phenyl]imidazo[1,2-a]pyridin-7-yl]pyrazol-1-yl]acetate,
N-cyclopropyl-4-[7-(6-cyclopropylpyridazin-3-yl)imidazo[1,2-a]pyridin-3-yl]-2-(difluoromethoxy)-6-methoxy-benzamide,
N-cyclopropyl-2-(difluoromethoxy)-6-methoxy-4-[7-(6-morpholinopyridazin-3-yl)imidazo[1,2-a]pyridin-3-yl]benzamide,
7-[5-(5-fluoro-3-pyridyl)benzimidazol-1-yl]-5-methoxy-2,3-dihydro-1,3-benzoxazin-4-one,
5-methoxy-7-[5-(5-methoxy-3-pyridyl)benzimidazol-1-yl]-2,3-dihydro-1,3-benzoxazin-4-one,
7-[5-(3-fluoro-2-pyridyl)benzimidazol-1-yl]-5-methoxy-2,3-dihydro-1,3-benzoxazin-4-one,
7-[5-(2-isopropylthiazol-4-yl)benzimidazol-1-yl]-5-methoxy-2,3-dihydro-1,3-benzoxazin-4-one,
ethyl 3-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
ethyl 2-[[4-[3-[3,5-dimethoxy-4-(2,2,2-trifluoroethylcarbamoyl)phenyl]imidazo[1,2-a]pyridin-7-yl]pyrazol-1-yl]methyl]-3-methyl-butanoate,
ethyl 2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
ethyl 2-[4-[3-[3,5-dimethoxy-4-(2,2,2-trifluoroethylcarbamoyl)phenyl]imidazo[1,2-a]pyridin-7-yl]pyrazol-1-yl]-3-methyl-butanoate,
tetrahydrofuran-2-ylmethyl 2-[4-[3-[3,5-dimethoxy-4-(2,2,2-trifluoroethylcarbamoyl)phenyl]imidazo[1,2-a]pyridin-7-yl]pyrazol-1-yl]acetate,
ethyl 2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxyacetate,
2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxyacetic acid,
4-[6-benzyloxy-7-(1-methylpyrazol-4-yl)imidazo[1,2-a]pyridin-3-yl]-N-cyclopropyl-2-(difluoromethoxy)-6-methoxy-benzamide,
4-[6-(1-cyanoethoxy)-7-(1-methylpyrazol-4-yl)imidazo[1,2-a]pyridin-3-yl]-N-cyclopropyl-2-(difluoromethoxy)-6-methoxy-benzamide,
ethyl 2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxypropanoate,
2-[3-[4-(cyclopropylcarbamoyl)-3-(difluoromethoxy)-5-methoxy-phenyl]-7-(1-methylpyrazol-4-yl)imidazo[1,2-a]pyridin-6-yl]oxypropanoic acid,
2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoic acid,
2-(diethylamino)ethyl 2-[4-[3-[3,5-dimethoxy-4-(2,2,2-trifluoroethylcarbamoyl)phenyl]imidazo[1,2-a]pyridin-7-yl]pyrazol-1-yl]-2-methyl-propanoate,
N-cyclopropyl-2-(difluoromethoxy)-6-methoxy-4-[5-(1H-pyrazol-4-yl)benzimidazol-1-yl]benzamide, or
N-cyclopropyl-2-(difluoromethoxy)-6-methoxy-4-[7-(1H-pyrazol-4-yl)imidazo[1,2-a]pyridin-3-yl]benzamide.

18. A pharmaceutical composition comprising a pharmaceutically acceptable carrier and a pharmaceutically effective amount of a compound of claim 17 or pharmaceutically acceptable salt thereof.

19. A method of treating inflammatory bowel disease, collagen-induced arthritis, psoriatic-like epidermal hyperplasia, systemic lupus erythematosus, and psoriatic arthritis, comprising administering an effective amount of the compound or pharmaceutically acceptable salt thereof, according to claim 1, to a subject in need thereof.

20. A method of treating inflammatory bowel disease, collagen-induced arthritis, psoriatic-like epidermal hyperplasia, systemic lupus erythematosus, and psoriatic arthritis, comprising administering the pharmaceutical composition according to claim 14, to a subject in need thereof.

* * * * *